United States Patent
Schönbrunn et al.

(10) Patent No.: US 11,643,396 B2
(45) Date of Patent: May 9, 2023

(54) BRD4-KINASE INHIBITORS AS CANCER THERAPEUTICS

(71) Applicant: H. LEE MOFFITT CANCER CENTER AND RESEARCH INSTITUTE, INC., Tampa, FL (US)

(72) Inventors: Ernst Schönbrunn, Tampa, FL (US); Nicholas J. Lawrence, Tampa, FL (US); Harshani R. Lawrence, Tampa, FL (US)

(73) Assignee: H. LEE MOFFITT CANCER CENTER AND RESEARCH INSTITUTE, INC., Tampa, FL (US)

(*) Notice: Subject to any disclaimer, the term of this patent is extended or adjusted under 35 U.S.C. 154(b) by 0 days.

(21) Appl. No.: 16/894,010

(22) Filed: Jun. 5, 2020

(65) Prior Publication Data

US 2020/0407328 A1 Dec. 31, 2020

Related U.S. Application Data

(63) Continuation of application No. 15/767,676, filed as application No. PCT/US2016/056811 on Oct. 13, 2016, now Pat. No. 10,738,016.

(60) Provisional application No. 62/240,871, filed on Oct. 13, 2015.

(51) Int. Cl.
| | |
|---|---|
| C07D 239/48 | (2006.01) |
| C07D 491/048 | (2006.01) |
| C07D 405/14 | (2006.01) |
| C07D 403/12 | (2006.01) |
| C07D 405/12 | (2006.01) |
| C07D 403/14 | (2006.01) |
| C07D 401/14 | (2006.01) |
| C07D 403/04 | (2006.01) |
| A61P 35/00 | (2006.01) |
| A61K 45/06 | (2006.01) |

(52) U.S. Cl.
CPC ............ *C07D 239/48* (2013.01); *A61P 35/00* (2018.01); *C07D 401/14* (2013.01); *C07D 403/04* (2013.01); *C07D 403/12* (2013.01); *C07D 403/14* (2013.01); *C07D 405/12* (2013.01); *C07D 405/14* (2013.01); *C07D 491/048* (2013.01); *A61K 45/06* (2013.01)

(58) Field of Classification Search
CPC ....... A61K 45/06; A61P 35/00; C07D 239/48; C07D 401/14; C07D 403/04; C07D 403/12; C07D 403/14; C07D 405/12; C07D 405/14; C07D 491/048
See application file for complete search history.

(56) References Cited

U.S. PATENT DOCUMENTS

| | | | |
|---|---|---|---|
| 4,559,157 | A | 12/1985 | Smith |
| 4,608,392 | A | 8/1986 | Jacquet et al. |
| 4,820,508 | A | 4/1989 | Wortzman |
| 4,938,949 | A | 7/1990 | Borch |
| 4,992,478 | A | 2/1991 | Geria |
| 5,167,649 | A | 12/1992 | Zook |
| 6,960,648 | B2 | 11/2005 | Bonny |
| 7,378,417 | B2 | 5/2008 | Goetschi et al. |
| 7,449,456 | B2 | 11/2008 | Nagashima |
| 7,964,592 | B2 | 6/2011 | Garcia-Echeverria |
| 8,563,542 | B2 | 10/2013 | Hollick et al. |
| 2002/0035243 | A1 | 3/2002 | Imfeld |
| 2002/0120100 | A1 | 8/2002 | Bonny |
| 2003/0032594 | A1 | 2/2003 | Bonny |
| 2005/0256125 | A1 | 11/2005 | Kath et al. |
| 2007/0254884 | A1 | 11/2007 | Chen et al. |
| 2009/0270418 | A1 | 10/2009 | Sloss et al. |
| 2010/0099658 | A1 | 4/2010 | Kondoh et al. |
| 2011/0212077 | A1* | 9/2011 | Noronha ............ A61K 31/4545 544/323 |
| 2012/0149737 | A1 | 6/2012 | Corcoran et al. |
| 2012/0157500 | A1 | 6/2012 | Tao et al. |
| 2013/0017194 | A1 | 1/2013 | Holmes et al. |
| 2015/0005281 | A1 | 1/2015 | Hobson et al. |
| 2017/0226065 | A1 | 8/2017 | Shönbrunn et al. |
| 2019/0055203 | A1 | 2/2019 | Shönbrunn et al. |

FOREIGN PATENT DOCUMENTS

| | | |
|---|---|---|
| WO | 03055866 | 7/2003 |
| WO | 2004046118 | 6/2004 |
| WO | 2005013996 | 2/2005 |
| WO | 2005042518 | 5/2005 |
| WO | 2006033631 | 3/2006 |
| WO | 2007008541 | 1/2007 |
| WO | 2007053452 | 5/2007 |
| WO | 2008122667 | 10/2008 |
| WO | 2011039735 | 4/2011 |
| WO | 2011119704 | 9/2011 |

(Continued)

OTHER PUBLICATIONS

Aliagas-Martin, et al., A class of 2,4-bisanilinopyrimidine Aurora A inhibitors with unusually high selectivity against Aurora B. J. Med. Chem. 2009, 52, 3300-7.

(Continued)

*Primary Examiner* — Erich A Leeser

(74) *Attorney, Agent, or Firm* — Meunier Carlin & Curfman LLC

(57) ABSTRACT

Disclosed herein are compounds that are inhibitors of BDR4 and their use in the treatment of cancer. Methods of screening for selective inhibitors of BDR4 are also disclosed. In certain aspects, disclosed are compounds of Formula I through IV.

10 Claims, 4 Drawing Sheets

(56) References Cited

FOREIGN PATENT DOCUMENTS

| WO | 2011120026 | 9/2011 |
|---|---|---|
| WO | 2013123401 | 8/2013 |

OTHER PUBLICATIONS

Altenbach, et al., Synthesis and structure-activity studies on N-[5-(1H-imidazol-4-yl)-5,6,7,8-tetrahydro-1-naphthalenyl]methanesulfonamide, an imidazole-containing alpha(1A)-adrenoceptor agonist. J. Med. Chem. 2004, 47, 3220-35.
Campbell, et al., Derivatives of the lower aliphatic amines. Proc. Indiana Acad. Sci. 1948, 57, 97-100.
Chi, et al., Pyrimidine Research: The Molecular Rearrangement of 2-Ethylmercapto-4,5-dimethyl-6-thiocyanopyrimidine. J. Am. Chem. Soc. 1936, 58, 769-771.
Ciceri et al., Dual kinase-bromodomain inhibitors for rationally designed polypharmacology. Nat. Chem. Biol. 2014, 305-312.
Delmore et al., BET bromodomain inhibition as a therapeutic strategy to target c-Myc. Cell 2011, 146, 904-17.
Ember et al., The acetyl-lysine binding site of bromodomain-containing protein 4 (BRD4) interacts with diverse kinase inhibitors. Chem. Biol. 2014, 9, 1160-71.
Filippakopoulos et al., Benzodiazepines and benzotriazepines as protein interaction inhibitors targeting bromodomains of the BET family. Bioorg. Med. Chem. 2012, 20, 1878-86.
Filippakopoulos et al., Selective inhibition of BET bromodomains. Nature. 2010, 468, 1067-731.
Fish et al., Identification of a chemical probe for bromo and extra C-terminal bromodomain inhibition through optimization of a fragment-derived hit. J. Med. Chem. 2012, 55, 9831-7.
Goldfarb, et al., New Compounds. Derivatives of 2,5-Diaminobenzenesulfonamide. J. Am. Chem. Soc. 1943, 65, 738-9.
Gunawan, et al., Construction of functionalized tricyclic dihydropyrazino-quinazolinedione chemotypes via an Ugi/N-acyliminium ion cyclization cascade. Tet. Lett. 2013, 54, 4467-70.
Hewings et al., Progress in the development and application of small molecule inhibitors of bromodomain-acetyl-lysine interactions. J. Med. Chem. 2012, 55, 9393-413.
Lawrence et al., Development of o-chlorophenyl substituted pyrimidines as exceptionally potent aurora kinase inhibitors. J. Med. Chem. 2012, 55, 7392-416.
Lawrence, et al., Synthesis and biological evaluation of naphthoquinone analogs as a novel class of proteasome inhibitors. Bioorg. Med. Chem. 2010, 18, 5576-92.
Lawrence, et al., Development of novel ACK1/TNK2 inhibitors using a fragment-based approach. J. Med. Chem. 2015, 58, 2746-63.
Liu, et al., Discovery of a new class of 4-anilinopyrimidines as potent c-Jun N-terminal kinase inhibitors: Synthesis and SAR studies. Bioorg. Med. Chem. Lett. 2007, 17, 668-72.
Martin et al., Cyclin-dependent kinase inhibitor dinaciclib interacts with the acetyl-lysine recognition site of bromodomains. Chem. Biol. 2013, 8, 2360-.
Matzuk et al., Small-Molecule Inhibition of BRDT for Male Contraception. Cell 2012, 150, 673-84.
McIver, et al., Synthesis and structure-activity relationships of a novel series of pyrimidines as potent inhibitors of TBK1/IKKepsilon kinases. Bioorg. Med. Chem. Lett. 2012, 22, 7169-73.
Mertz et al., Targeting MYC dependence in cancer by inhibiting BET bromodomains. Proc. Nat. Acad. Sci. USA 2011, 108, 16669-74.
Mirguet et al., Discovery of epigenetic regulator I-BET762: lead optimization to afford a clinical candidate inhibitor of the BET bromodomains. J. Med. Chem. 2013, 56, 7501-15.
Mirguet et al., Naphthyridines as Novel BET Family Bromodomain Inhibitors. Chem. Med. Chem. 2014, 9, 580-9.
Muller et al., Bromodomains as therapeutic targets. Expert. Rev. Mol. Med. 2011, 13, e29.
Ott et al., BET bromodomain inhibition targets both c-Myc and IL7R in high-risk acute lymphoblastic leukemia. Blood 2012, 120, 2843-52.
Prinjha et al., Place your BETs: the therapeutic potential of bromodomains. Trends Pharmacol. Sci. 2012, 33, 146-53.
Puissant et al., Targeting MYCN in neuroblastoma by BET bromodomain inhibition. Cancer Discov. 2013, 3, 308-23.
Qin, et al., Synthesis and biological evaluation of 2,4-diaminopyrimidines as selective Aurora A kinase inhibitors. Eur. J. Med. Chem. 2015, 95, 174-84.
Richter, et al., Selective addition of amines to 5-trifluoromethyl-2,4-dichloropyrimidine induced by Lewis acids. Tetrahedron Lett. 2013, 54, 4610-2.
Rodríguez, et al., New Bis(2-aminoimidazoline) and Bisguanidine DNA Minor Groove Binders with Potent in Vivo Antitrypanosomal and Antiplasmodial Activity. J. Med. Chem. 2008, 51, 909-23.
Sanchez et al., The role of human bromodomains in chromatin biology and gene transcription. Current opinion in drug discovery & development 2009, 12, 659-65.
Seal et al., Identification of a novel series of BET family bromodomain inhibitors binding mode and profile of I-BET151 (GSK1210151A). Bioorg. Med. Chem. Lett. 2012, 22, 2968-72.
Siu et al., 2-Amino-[1,2,4]triazolo[1,5-a]pyridines as JAK2 inhibitors. Bioorg. Med. Chem. Lett. 2013, 23, 5014-21.
Smith et al., Validation of ITD mutations in FLT3 as a therapeutic target in human acute myeloid leukaemia. Nature 2012, 485, 260-3.
Sun, et al., tert-Butylsulfonyl (Bus), a New Protecting Group for Amines. J. Org. Chem. 1997, 62, 8604-8.
Tangallapally, et al., Synthesis and evaluation of cyclic secondary amine substituted phenyl and benzyl nitrofuranyl amides as novel antituberculosis agents. J. Med. Chem. 2005, 48, 8261-9.
Toyoizumi, et al., Combined therapy with chemotherapeutic agents and herpes simplex virus type IICP34.5 mutant (HSV-1716) in human non-small cell lung cancer. Human Gene Therapy, 1999, 10(18):3013-29.
Ueda, et al., Copper-catalyzed synthesis of benzoxazoles via a regioselective C-H functionalization/C-O bond formation under an air atmosphere. J. Org. Chem. 2009, 74, 4272-7.
Xu, et al., Oxidative cyclization of N-alkyl-o-methyl-arenesulfonamides to biologically important saccharin derivatives. Tetrahedron 2006, 62, 7902-10.
Zhang, et al., Design and synthesis of pyrimidinone and pyrimidinedione inhibitors of dipeptidyl peptidase IV. J. Med. Chem. 2011, 54, 510-24.
International Preliminary Report on Patentability issued for Application No. PCT/US2016/056811, dated Apr. 26, 2018.
International Search Report and Written Opinion issued for Application No. PCT/US2016/056811, dated Feb. 21, 2017.
Simone, Oncology: Introduction, Cecil Textbook of Medicine, 2oth Edition, vol. 1, pp. 1004-1010, 1996.
Gura, Systems for identifying New Drugs Are Often Faulty, Cancer Models, Science, vol. 278, No. 5340, pp. 1041-1042, Nov. 1997.
Johnson et al., Relationships between drug activity in NCI preclinical in vitro and in vivo models and early clinical trials, British J. Cancer 2001, 64(10), 1424-31.
Pearce et al., Failure modes in anticancer drug discovery and development, Cancer Drug Design and Discovery Edited by Stephen Neidle, 2008, Ch. 18, pp. 424-435.
Shi et al., The mechanisms behind the therapeutic activity of BET Bromodomain inhibition, Molecular Cell, 2014, 54, 728-36.
Pardanani, JAK2 inhibitor therapy in myeloproliferative disorders: rationale, preclinical studies and ongoing clinical trials. Leukemia 2008, 22, 22-30.
International Search Report and Written Opinion issued in International Application No. PCT/US2015/43389, dated Nov. 6, 2015.
International Preliminary Report on Patentability issued for Application No. PCT/US2015/43389, dated Feb. 16, 2017.
ChemSpider (ChemZoo, INC.) Registry Search pp. 15-16, 2008.
Mollard, et al., Design, Synthesis, and Biological Evaluation of a Series of Novel AXL Kinase Inhibitor, ACS Med Chem Letters, 2011, 2, 907-912.

* cited by examiner

R[1]: Partly solvent exposed; possible interactions with KL flank, ZA channel or Ile146
R[2]: Partly solvent exposed; possible interactions with KL flank
R[3]: Partly solvent exposed; possible interactions with ASN rim and/or KL flank
R[4]: Directed towards deep hydrophobic pocket

|  | Estimated IC$_{50}$ (uM) for reduction of: | | Cell survival IC$_{50}$ (uM) |
| --- | --- | --- | --- |
|  | pSTAT3 | c-Myc |  |
| TG101209 | <1 | <3 | 1.6 |
| SG1-180 | <0.3 | <1 | 0.45 |
| SG1-183 | <0.3 | <0.3 | 0.42 |
| SG2-70-1 | <3 | <0.1 | 1.1 |
| MA2-14 | <0.3 | <0.1 | 0.4 |
| MA2-32 | <10 | <0.3 | 0.9 |
| RJ1-36-1 | <1 | <1 | 0.6 |
| RJ1-41-1 | <3 | <1 | 2.6 |
| RJ1-45-1 | <3 | <3 | 1.2 |
| RJ1-53-1 | <3 | <10 | 0.9 |

FIG. 2B

BRD4-KINASE INHIBITORS AS CANCER THERAPEUTICS

CROSS REFERENCE TO RELATED APPLICATIONS

This application is a continuation of U.S. application Ser. No. 15/767,676, filed Apr. 12, 2018, which is a U.S. National Phase of International Application PCT/US2016/056811, filed Oct. 13, 2016, and which claims the benefit of priority to U.S. Provisional Application 62/240,871, filed Oct. 13, 2015, which is incorporated by reference herein in its entirety.

FIELD

The subject matter disclosed herein relates generally to cancer therapy and to anti-cancer compounds. More specifically, the subject matter disclosed herein relates to inhibitors of BDR4 and their use in the treatment of cancer. Methods of screening for selective inhibitors of BDR4 are also disclosed.

BACKGROUND

Bromodomain (BRD)-containing proteins are essential for the recognition of acetylated lysine (KAc) residues of histones during transcriptional activation (Sanchez et al., The role of human bromodomains in chromatin biology and gene transcription. *Current opinion in drug discovery & development* 2009, 12, 659-65). BRDs have emerged as promising drug targets for a number of disease pathways that are characterized by changes in the epigenetic cell signature (Id.; Filippakopoulos et al., Selective inhibition of BET bromodomains. *Nature* 2010, 468, 1067-731). To date, only a few structurally diverse BRD inhibitors have been reported, all of which specifically target the KAc recognition sites of the bromodomain and extra terminal (BET) family of proteins (BRD2, BRD3, BRD4, and BRDT), each containing two tandem BRDs (Hewings et al., Progress in the development and application of small molecule inhibitors of bromodomain-acetyl-lysine interactions. *J Med Chem* 2012, 55, 9393-413; Muller et al., Bromodomains as therapeutic targets. *Expert Rev Mol Med* 2011, 13, e29; Prinjha et al., Place your BETs: the therapeutic potential of bromodomains. *Trends Pharmacol Sci* 2012, 33, 146-53). BET-inhibitors exert a broad spectrum of desirable biological effects such as anticancer and anti-inflammatory properties (Delmore et al., BET bromodomain inhibition as a therapeutic strategy to target c-Myc. *Cell* 2011, 146, 904-17; Matzuk et al., Small-Molecule Inhibition of BRDT for Male Contraception. *Cell* 2012, 150, 673-684; Mertz et al., Targeting MYC dependence in cancer by inhibiting BET bromodomains. *Proc Nat Acad Sci USA* 2011, 108, 16669-74; Ott et al., BET bromodomain inhibition targets both c-Myc and IL7R in high-risk acute lymphoblastic leukemia. *Blood* 2012, 120, 2843-52; Puissant et al., Targeting MYCN in neuroblastoma by BET bromodomain inhibition. *Cancer Discov* 2013, 3, 308-23). Of these, I-BET-762 (GSK525762) has recently entered clinical trials for the treatment of NUT midline carcinoma (Mirguet et al., Discovery of epigenetic regulator I-BET762: lead optimization to afford a clinical candidate inhibitor of the BET bromodomains. *J Med Chem* 2013, 56, 7501-15). Intense efforts are currently underway to discover new chemical scaffolds for hit-to-lead development campaigns of BET inhibitors as novel therapeutics (Filippakopoulos et al., Benzodiazepines and benzotriazepines as protein interaction inhibitors targeting bromodomains of the BET family. *Bioorg Med Chem* 2012, 20, 1878-86; Fish et al., Identification of a chemical probe for bromo and extra C-terminal bromodomain inhibition through optimization of a fragment-derived hit. *J Med Chem* 2012, 55, 9831-7; Mirguet et al., Naphthyridines as Novel BET Family Bromodomain Inhibitors. *Chem Med Chem* 2014, 9, 580-9; Seal et al., Identification of a novel series of BET family bromodomain inhibitors: binding mode and profile of I-BET151 (GSK1210151A). *Bioorg & Med Chem Lett* 2012, 22, 2968-72). Recently, BETs were discovered that interact with diverse kinase inhibitors (Martin et al., Cyclin-dependent kinase inhibitor dinaciclib interacts with the acetyl-lysine recognition site of bromodomains. *Chem Biol* 2013, 8, 2360; Ember et al., The acetyl-lysine binding site of bromodomain-containing protein 4 (BRD4) interacts with diverse kinase inhibitors. *Chem Biol* 2014; Ciceri et al., Dual kinase-bromodomain inhibitors for rationally designed polypharmacology. *Nat Chem Biol* 2014). Among these, the PLK1 inhibitor BI2536 and the JAK2/FLT3 inhibitors TG101348 and TG101209 inhibited the binding of KAc peptide to BRD4 with ICso values of 0.03 and 0.13 µM, respectively, and showed strong downregulation of c-Myc in MM.1S cells. These activities were similar to that of the prototypic BET inhibitor JQ1, the most potent BRD4 inhibitor described to date. Furthermore, TG101348, but not JAK2 inhibitors that lack BET and FLT3 activity, potently inhibited proliferation of MV4-11 AML cells ($IC_{50}$=79 nM) (Id.). AML is often driven by BETs and mutant FLT38 (Smith et al., Validation of ITD mutations in FLT3 as a therapeutic target in human acute myeloid leukaemia. *Nature* 2012, 485, 260-3) and the findings by Knapp and colleagues provided compelling evidence of an oncology indication that could be exploited through dual targeting of kinases and bromodomains. What are thus needed are new BRD inhibitors, for example, those with dual targeting activity, and uses of such inhibitors to treat various cancers. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds. More specifically, the subject matter disclosed herein relates to inhibitors of BDRs, e.g., BDR4, and their use in the treatment of cancer. Methods of screening for new BDR inhibitors are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 2B shows $IC_{50}$ values for cell survival were determined by MTT assay after 72 hours compound exposure. Increased anti-proliferative effects are correlated with an early, strong reduction of both pSTAT2 and c-Myc levels. The inhibitors highlighted are the most promising equipotent dual BET-JAK2 inhibitors of this series. JQ1 and the BET-inactive JAK2 inhibitor NVP-BSK805 served as controls.

DETAILED DESCRIPTION

Figure 1A:
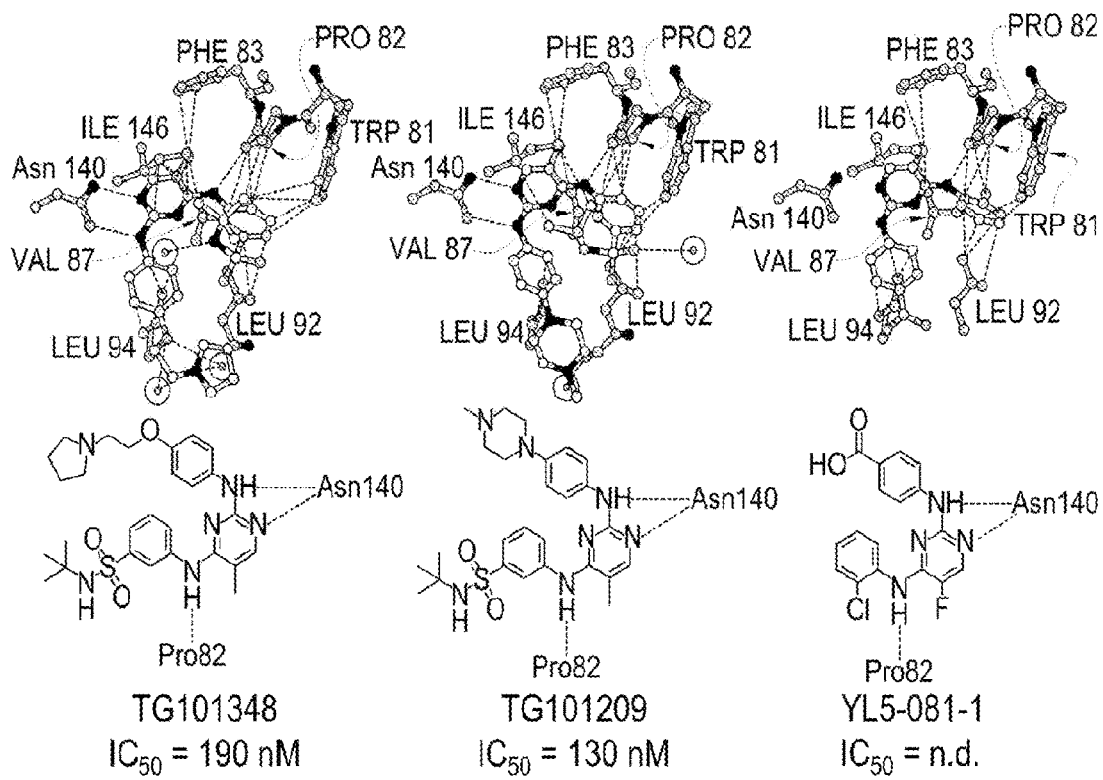
FIG. 1A shows the Jak2/Flt3 inhibitors TG101348 and TG101209 bind to the KAc site of BRD4-1 through multiple VDW (dotted lines) and H-bonding interactions (PDB entries 4O76 and 4O73 from Ember et al., The acetyl-lysine binding site of bromodomain-containing protein 4 (BRD4) interacts with diverse kinase inhibitors. The bottom panel shows the H-bonding interactions of the kinase-hinge binding atoms with Asn140 and Pro82 of the WPF shelf.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substitutent in the definitions below.

The term "alkoxy" as used herein is an alkyl group bound through a single, terminal ether linkage; that is, an "alkoxy" group can be defined as $-OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C.

Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN

The term "azido" as used herein is represted by the formula —N$_3$.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective. Reference will now be made in detail to specific aspects of the disclosed materials, compounds, compositions, articles, and methods, examples of which are illustrated in the accompanying Examples and Figures.

Compounds

Figure 1B:
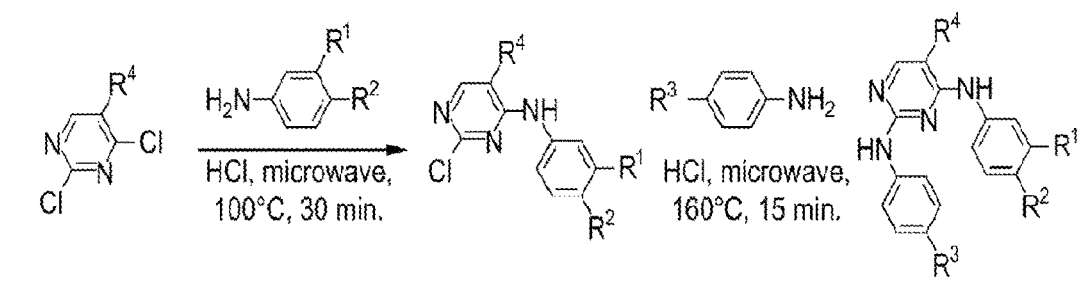
FIG. 1B shows the architecture of the KAc site of BRD4-1 (liganded with TG101348), design and synthesis of bisanilinopyrimidine-based inhibitors for structure-activity relationship (SAR) studies.
Figure 1B:
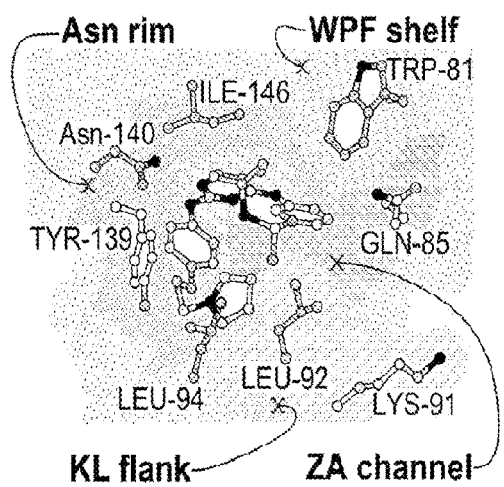
Figure 2A:
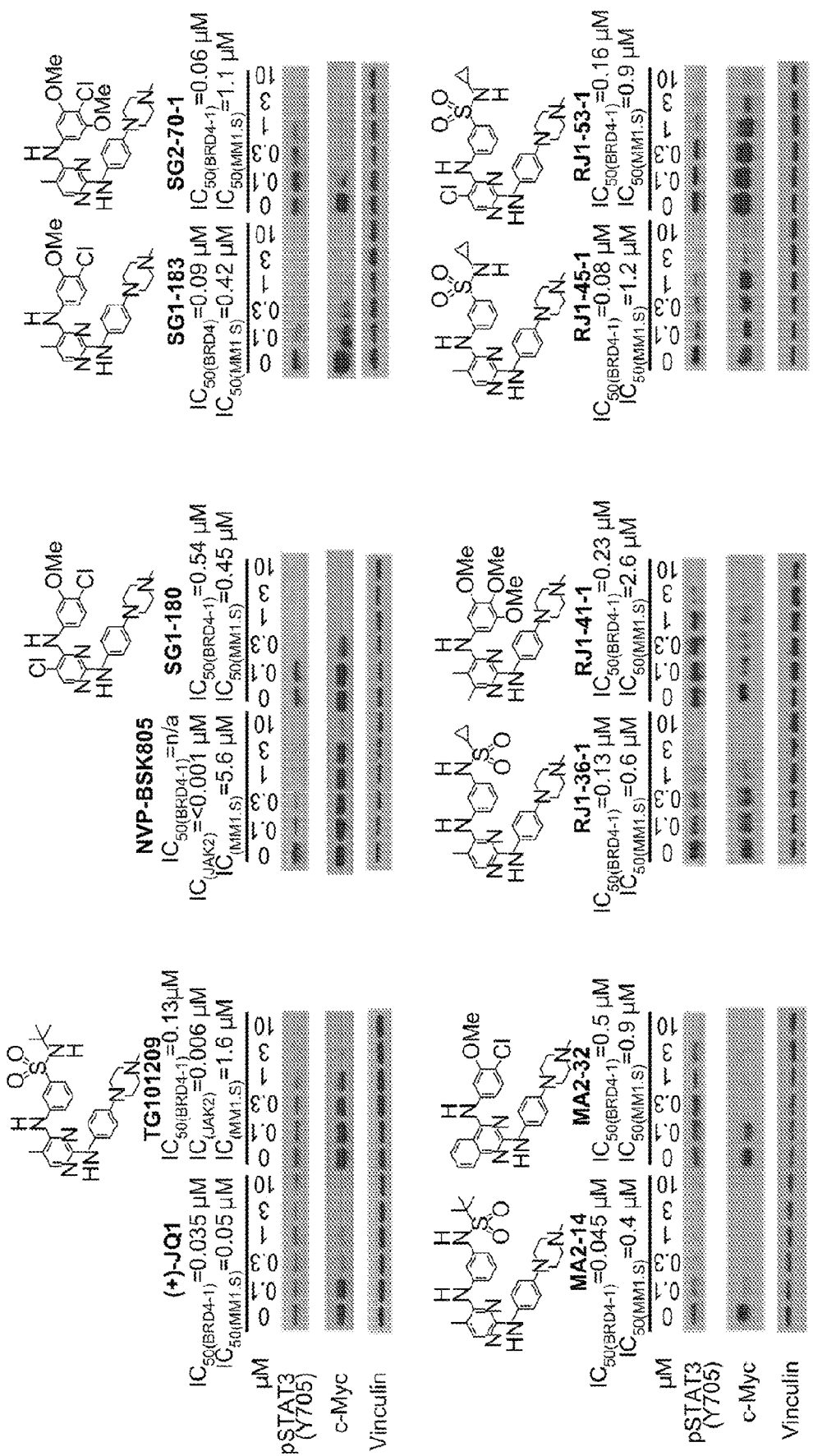
FIG. 2A shows SAR studies of analogues of TG101209. MM1.S cells were exposed for 6 hours to compounds that showed sub-micromolar binding potential for BRD4 by DSF. Cellular levels of pSTAT3 (JAK2 activity) and c-Myc (BRD4 activity) were determined by Western blotting.
Figure 3:
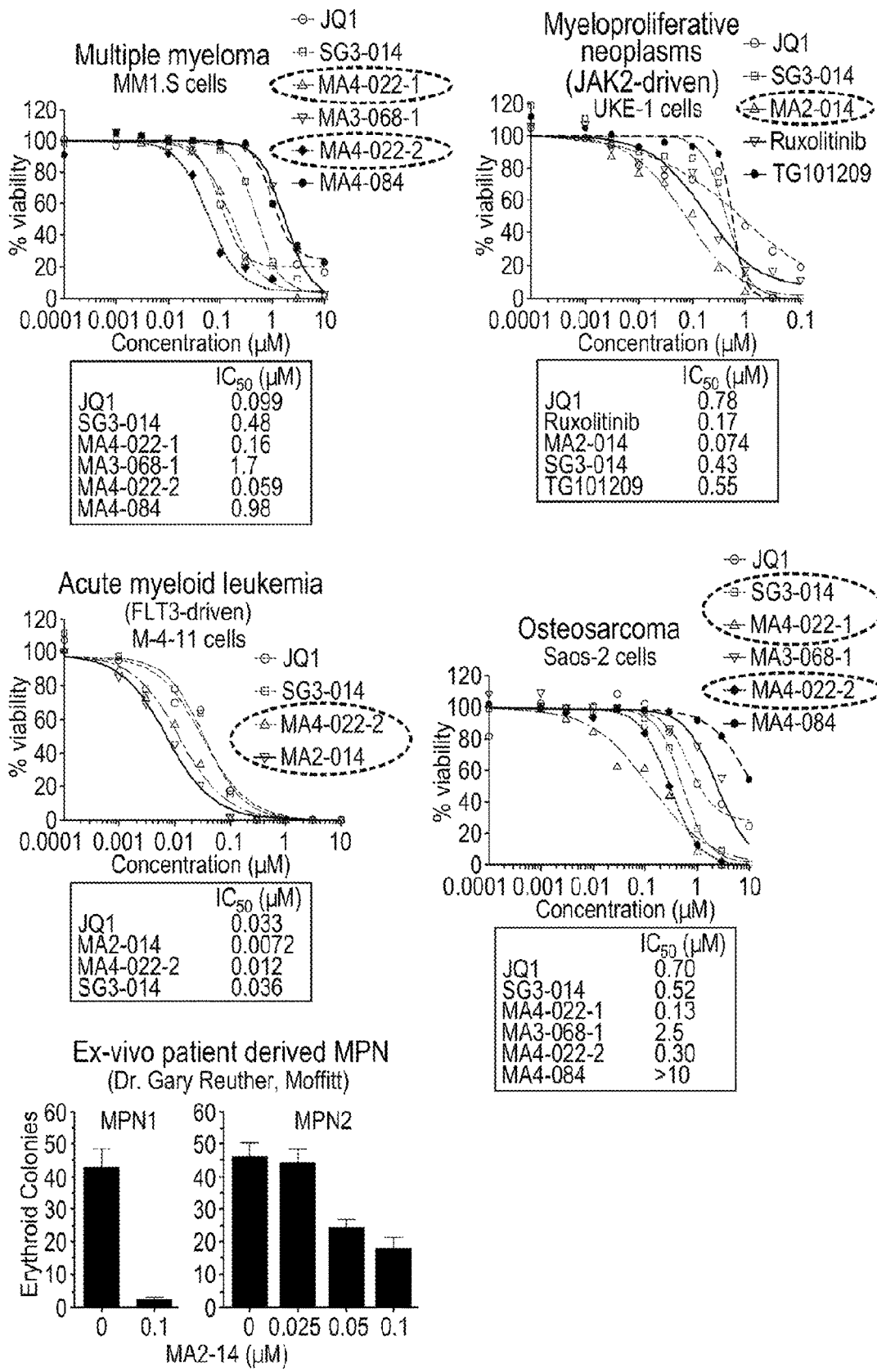
FIG. 3 shows the activity of several compounds disclosed herein in various cancer cell lines.

TG101348 and TG101209 contain a bisanilinopyrimidine scaffold which is critical for the interaction with the hinge-region of the ATP site of JAK2 and FLT3 (Siu et al., 2-Amino-[1,2,4]triazolo[1,5-a]pyridines as JAK2 inhibitors. *Bioorg & Med Chem Lett* 2013, 23, 5014-21). In BRD4, this scaffold directly interacts with Asn140 and Pro82, residues critical for the interaction with KAc residues in all BETs (FIG. 1A and FIG. 1B). This binding mode in the KAc site indicates that other bisanilinopyrimidine-containing compounds can interact with BRD4 in the same manner. Bisanilinopyrimidines were developed as potent inhibitors of Aurora A (Lawrence et al., Development of o-chlorophenyl substituted pyrimidines as exceptionally potent aurora kinase inhibitors. *J Med Chem* 2012, 55, 7392-416). Initial cocrystallization screening of BRD4 against five such Aurora inhibitors revealed that one compound, YL5-081-1, indeed interacted with the KAc site of BRD4 as expected from the structures with TG101348/TG101209 (FIG. 1A and FIG. 1B). The new structural information provided by this work led to the hypothesis of this proposal that bisanilinopyrimidine-containing compounds can be tailored to potently inhibit BRD4 with simultaneous activity against JAK2, FLT3 or Aurora kinases.

Thus, disclosed are compounds that are BDR4 inhibitors. These disclosed compounds can be used in various compositions as anti-cancer therapeutics.

In certain embodiments, the disclosed compounds have the chemical structure shown in Formula I.

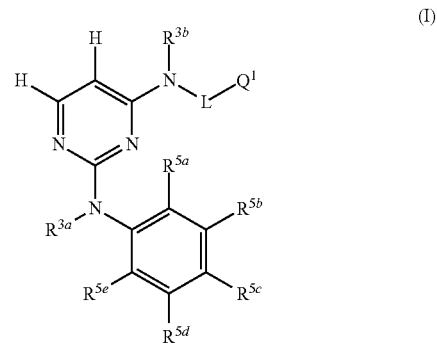

(I)

wherein $R^{3a}$ and $R^{3b}$ are independently selected from hydrogen and substituted or unsubstituted $C_1$-$C_6$ alkyl;

$L^1$ is selected from a $(CH_2)_n$, $(CH_2)_nC(O)$, $(CH_2)_nC(O)O$, $(CH_2)_nC(O)(NR^{3c})$, $(CH_2)_nSO_2$, and $(CH_2)_nP(O)(NR^{3c})$;

$Q^1$ is selected from substituted or unsubstituted alkyl, substituted or unsubstituted aryl, substituted or unsubstituted cycloalkyl, substituted or unsubstituted heteroaryl, substituted or unsubstituted heterocycloalkyl, and poly(ethylene oxide), or wherein, when substituted, one or more substituents on $Q^1$ forms a ring with $R^{3b}$;

$R^{5a}$, $R^{5b}$, $R^{5c}$, $R^{5d}$, and $R^{5e}$ are independently selected from hydrogen, $C_1$-$C_6$ alkyl, $C_1$-$C_6$ alkoxy, $C_3$-$C_{10}$ cycloalkyl, halogen, hydroxy, carboxyl, amino, nitro, cyano, isocyano, -$L^2Q^2$; wherein said $C_1$-$C_6$ alkyl, $C_1$-$C_6$ alkoxy and $C_3$-$C_{10}$ cycloalkyl groups are optionally substituted one or more times with a group selected from halogen, hydroxy, carboxyl, amino, nitro, cyano, isocyano, and combinations thereof;

or wherein any two of $R^{5a}$, $R^{5b}$, $R^{5c}$, $R^{5d}$, $R^{5e}$, and $R^{3a}$, together form a ring;

$L^2$ is selected from $(CH_2)_n$, $(CH_2)_nO$, $(CH_2)_nS$, $(CH_2)_nS(O)$, $(CH_2)_nSO_2$, $(CH_2)_nN(R^{3c})$, $(CH_2)_nC(O)$, $(CH_2)_nN(R^{3c})C(O)$, $(CH_2)_nOC(O)$, $(CH_2)_nC(O)O$, $(CH_2)_nC(O)N(R^{3c})$, $(CH_2)_nN(R^{3c})C(O)N(R^{3c})$, $(CH_2)_nSO_2N(R^3)$, $(CH_2)_nN(R^{3c})SO_2$, $(CH_2)_nN(R^{3c})P(O)(R^{3c})$, and $(CH_2)_nP(O)N(R^{3c})$;

$R^{3c}$ is in each case independently selected from hydrogen and substituted or unsubstituted $C_1$-$C_6$ alkyl;

$Q^2$ is selected from substituted or unsubstituted alkyl, substituted or unsubstituted aryl, substituted or unsubstituted cycloalkyl, substituted or unsubstituted heteroaryl, and substituted or unsubstituted heterocyclyl or poly(ethylene oxide); or wherein two or more substituents on $Q^2$ form a ring may together with $R^{3a}$ form a ring; and n in each case is independently selected from 0, 1, 2, 3, 4, 5, 6, 7, 8, 9 and 10;

or a salt thereof.

In certain embodiments $Q^1$ is selected from:

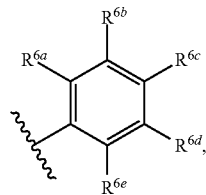
a)

wherein
$R^{6a}$, $R^{6b}$, $R^{6c}$, $R^{6d}$, $R^{6e}$ are independently selected from hydrogen, halogen, hydroxyl, amino, nitro, cyano, isocyano, carboxyl, $(CH_2)_nOR^{3d}$, $(CH_2)_nSR^{3d}$, $(CH_2)_nS(O)R^{3d}$, $(CH_2)_nSO_2R^{3d}$, $(CH_2)_nN(R^{3c})R^{3d}$, $(CH_2)_nC(O)R^{3d}$, $(CH_2)_nN(R^{3c})C(O)R^{3d}$, $(CH_2)_nOC(O)R^{3d}$, $(CH_2)_nC(O)OR^{3d}$, $(CH_2)_nC(O)N(R^{3c})R^{3d}$, $(CH_2)_nN(R^{3c})C(O)N(R^{3c})R^{3d}$, $(CH_2)_nSO_2N(R^{3c})R^{3d}$, $(CH_2)_nN(R^{3c})SO_2R^{3d}$, $(CH_2)_nN(R^{3c})P(O)(R^{3d})_2$, $(CH_2)_nP(O)(N(R^{3c}R^{3d}))_2$, and poly(ethylene oxide);
$R^{3d}$ is in each case independently selected from hydrogen, substituted or unsubstituted $C_1$-$C_{10}$ alkyl, substituted or unsubstituted $C_3$-$C_{10}$ cycloalkyl, substituted or unsubstituted $C_6$-$C_{12}$ aryl, and substituted or unsubstituted $C_2$-$C_{10}$ heteroaryl; or wherein any two or more of $R^{3b}$, $R^{6a}$, $R^{6b}$, $R^{6c}$, $R^{6d}$, $R^{6e}$, $R^{3c}$ and $R^{3d}$ together form one or more rings;

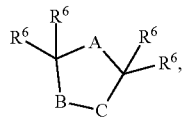
b)

wherein
A, B, and C are independently selected from a bond, O, $-C(R^6)_2-$, $-C(R^6)_2-C(R^6)_2-$, $-C(R^6)_2-N(R^6)-$, $-C(R^6)_2-O-$, $NR^6$, S, SO, and $SO_2$;

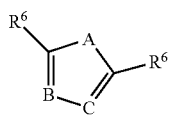
c)

wherein
A is O, $NR^6$, S, SO, $SO_2$, $-C(R^6)=C(R^6)-$, or $-C(R^6)=N-$; and
B and C are either N or $CR^6$;

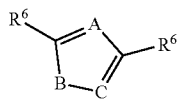
d)

wherein
B is O, $NR^6$, S, SO, $SO_2$, $-C(R^6)=C(R^6)-$, or $-C(R^6)=N-$; and
A and C are either N or $CR^6$,

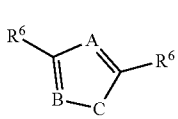
e)

C is O, $NR^6$, S, SO, $SO_2$, $-C(R^6)=C(R^6)-$, or $-C(R6)=N-$;
A and B are either N or $CR^6$,
one $R^6$ group represents a bond to $L^1$, and the remaining $R^6$ groups are independently selected from hydrogen, halogen, hydroxyl, amino, nitro, cyano, isocyano, carboxyl, $(CH_2)_nOR^{3d}$, $(CH_2)_nSR^{3d}$, $(CH_2)_nS(O)R^{3d}$, $(CH_2)_nSO_2R^{3d}$, $(CH_2)_nN(R^{3c})R^{3d}$, $(CH_2)_nC(O)R^{3d}$, $(CH_2)_nN(R^{3c})C(O)R^{3d}$, $(CH_2)_nOC(O)R^{3d}$, $(CH_2)_nC(O)OR^{3d}$, $(CH_2)_nC(O)N(R^{3c})R^{3d}$, $(CH_2)_nN(R^{3c})C(O)N(R^{3c})R^{3d}$, $(CH_2)_nSO_2N(R^{3c})R^{3d}$, $(CH_2)_nN(R^{3c})SO_2R^{3d}$; poly(ethylene oxide); or two adjacent $R^6$ groups form a double or triple bond, or two geminal $R^6$ groups together form a carbonyl; or any two $R^6$ groups together form a ring, or $R^{3b}$ and one or more $R^6$ groups together form a ring; and
n in each case is independently selected from 0, 1, 2, 3, 4, 5, 6, 7, 8, 9 and 10;

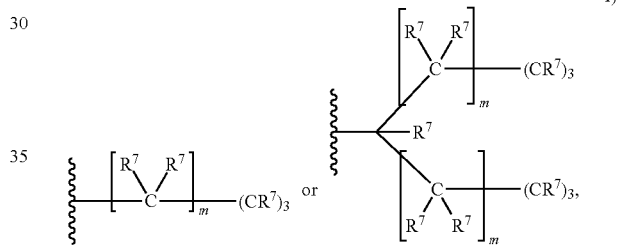
f)

wherein
m is independently selected from 0, 1, 2, 3, 4, 5, 6, 7, 8, 9, and 10; and
$R^7$ is in each case independently selected from hydrogen, halogen, hydroxyl, amino, nitro, cyano, isocyano, $(CH_2)_nOR^{3d}$, $(CH_2)_nSR^{3d}$, $(CH_2)_nS(O)R^{3d}$, $(CH_2)_nSO_2R^{3d}$, $(CH_2)_nN(R^{3c})R^{3d}$, $(CH_2)_nC(O)R^{3d}$, $(CH_2)_nN(R^{3c})C(O)R^{3d}$, $(CH_2)_nOC(O)R^{3d}$, $(CH_2)_nC(O)OR^{3d}$, $(CH_2)_nC(O)N(R^{3c})R^{3d}$, $(CH_2)_nN(R^{3c})C(O)N(R^{3c})R^{3d}$, $(CH_2)_nSO_2N(R^{3c})R^{3d}$, $(CH_2)_nN(R^{3c})SO_2R^{3d}$, and poly(ethylene oxide); or two geminal $R^7$ groups together form a carbonyl; or $R^7$ groups on adjacent carbon atoms form a double or triple bond; or any two or more $R^7$ groups together form a ring, or $R^{3b}$ and one or more $R^7$ groups together for a ring. In certain embodiments, $Q^1$ is substituted or unsubstituted cyclopropyl, cyclobutyl cyclopentyl, cyclohexyl, imidazolyl, oxazolyl, thiazolyl, a heterocycle, or

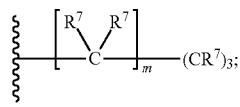

wherein m is selected from 1, 2, 3 and 4. In some instances, $Q^1$ can be a moiety selected from

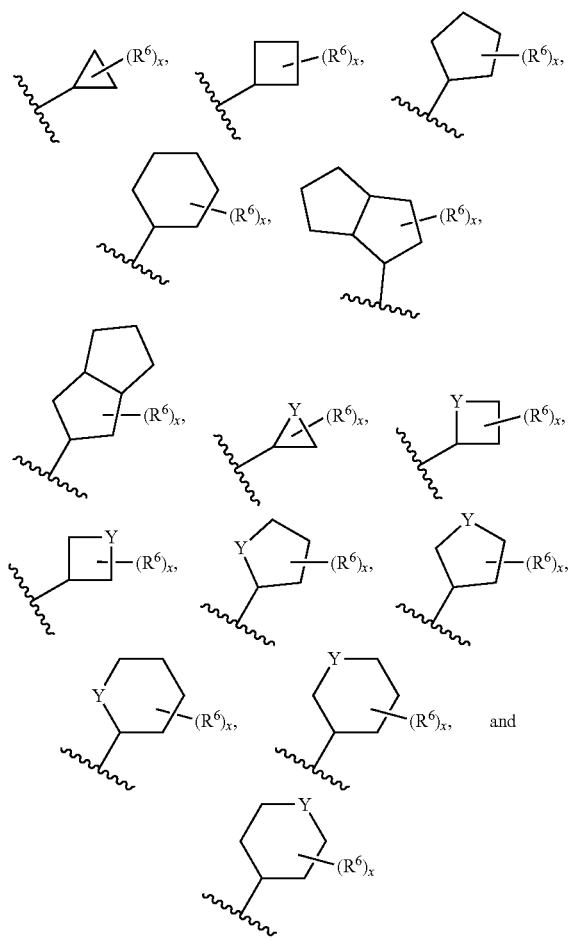

wherein x is any chemically permissible integer, preferably 0, 1, 2 or 3, $R^6$ is independently selected from the substituents defined above, Y can be O, S or $NR^6$. Oxazolyl, imidazolyl and thiazolyl rings can be unsubstituted, or substituted one or two times by $R^6$ groups, which may be the same or different.

In certain embodiments $Q^1$ has the formula:

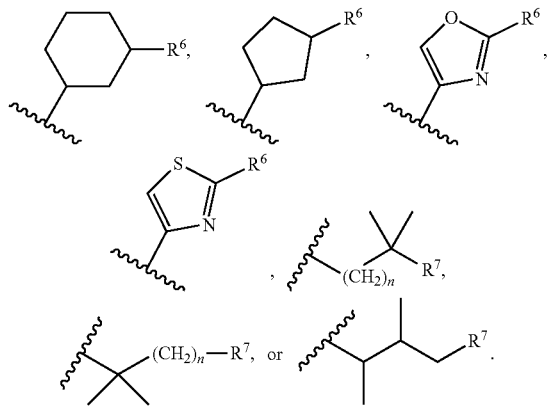

For certain embodiments, the compounds of Formula (I) are compounds in which $L^1$ is a bond or $CH_2$. In certain preferred embodiments of the compounds of Formula (I), at least one of $R^6$ or $R^7$ are $NHSO_2R^{3d}$, in which $R^{3d}$ is as defined above. Preferred $R^{3d}$ groups include methyl, tert-butyl, cyclopropyl, 1-methylcyclopropyl, s-butyl isopropyl, propyl, $C(CH_3)_2CH_2OH$, and phenyl.

In certain instances, $R^{3a}$ and $R^{3b}$ are both hydrogen.

In other examples $R^{5a}$ and $R^{5e}$ are both hydrogen.

In other examples, $R^{5b}$ and $R^{5d}$ are hydrogen or halogen. In certain preferred embodiments, $R^{5a}$, $R^{5e}$, $R^{3a}$ and $R^{3b}$ are each hydrogen.

In some instance the compound of Formula (I) is characterized $R^{5c}$ is $-L^2Q^2$. In some cases, $Q^2$ is substituted or unsubstituted heterocyclyl, or poly(ethylene oxide). Exemplary heterocycles include

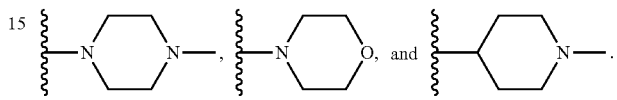

Exemplary $L^2$ groups include $(CH_2)_n$, $(CH_2)_nC(O)N(R^3)$, $(CH_2)_nN(R^{3c})$, $(CH_2)_nC(O)$, and $(CH_2)_nN(R^{3c})C(O)$, and in some cases n is either 0 or 1.

Also provided herein are compounds of Formula (II)

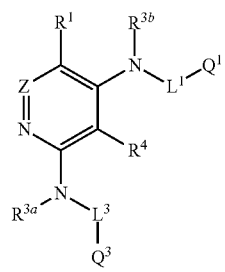

(II)

wherein
Z is selected from $CR^2$ and N;
$R^1$ and $R^2$ are independently selected from hydrogen, halogen, hydroxyl, carboxyl, amino, nitro, cyano, isocyano, substituted or unsubstituted $C_1$-$C_6$ alkyl, substituted or unsubstituted $C_1$-$C_6$ alkoxy, and substituted or unsubstituted $C_1$-$C_6$ alkenyl; or wherein $R^1$ and $R^2$ together form a ring;
$R^{3a}$ and $R^{3b}$ are independently selected from hydrogen and substituted or unsubstituted $C_1$-$C_6$ alkyl;
$R^4$ is selected from hydrogen, halogen, hydroxyl, carboxyl, amino, nitro, cyano, isocyano, substituted or unsubstituted $C_1$-$C_6$ alkyl, substituted or unsubstituted $C_1$-$C_6$ alkoxy, substituted or unsubstituted $C_1$-$C_6$ alkylamino, substituted or unsubstituted $C_2$-$C_6$ alkenyl, and substituted or unsubstituted $C_2$-$C_6$ alkynyl; or $R^4$ forms a ring with any of $R^{3a}$, $R^{3b}$ and $R^{3c}$.
$L^1$ and $L^3$ are independently selected from $(CR^{3e}_2)_n$, $(CR^{3e}_2)_n$ $C(O)$, $(CR^{3e}_2)_nC(O)O$, $(CR^{3e}_2)_nC(O)(NR^{3c})$, $SO_2$, $(CR^{3c}_2)_nN(R^{3c})P(O)(R^{3c})$, and $(CR^{3c}_2)_nP(O)N(R^{3c})$;
$R^{3c}$ is in each case independently selected from hydrogen and substituted or unsubstituted $C_1$-$C_6$ alkyl;
$R^{3e}$ is in each case independently selected from hydrogen, halogen, hydroxyl, carboxyl, amino, nitro, cyano, isocyano, substituted or unsubstituted $C_1$-$C_6$ alkyl, substituted or unsubstituted $C_1$-$C_6$ alkoxy, substituted or unsubstituted $C_1$-$C_6$ alkylamino substituted or unsubstituted $C_2$-$C_6$ alkenyl, and substituted or unsubstituted $C_2$-$C_6$ alkynyl; or two geminal $R^{3e}$ groups together form a carbonyl; or $R^{3e}$ groups on adjacent carbon atoms form a double or triple bond; or any two or more $R^{3c}$ groups together form a ring; or $R^{3e}$ forms a ring with any, some or all of $R^{3a}$, $R^{3b}$, $R^{3c}$ and $R^4$;

n in each case is independently selected from 0, 1, 2, 3, 4, 5, 6, 7, 8, 9 and 10;

$Q^1$ and $Q^3$ are independently selected from substituted or unsubstituted alkyl, substituted or unsubstituted aryl, substituted or unsubstituted cycloalkyl, substituted or unsubstituted heteroaryl, substituted or unsubstituted heterocyclyl, and poly(ethylene oxide); or one or more substituents on $Q^3$ form a ring with $R^{3a}$, $R^{3c}$, $R^{3e}$ or $R^4$; or one or more substituents on $Q^1$ form a ring with $R^{3b}$, $R^{3c}$, $R^{3e}$ or $R_4$ groups;

or a salt thereof.

In some examples, $Q^1$ and $Q^3$ are independently selected from:

a)
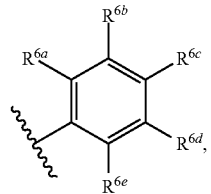

wherein $R^{6a}$, $R^{6b}$, $R^{6c}$, $R^{6d}$, $R^{6e}$ are independently selected from hydrogen, halogen, hydroxyl, amino, $(CH_2)_n R^{3d}$, $(CH_2)_n OR^{3d}$, $(CH_2)_n SR^{3d}$, $(CH_2)_n S(O)R^{3d}$, $(CH_2)_n SO_2 R^{3d}$, $(CH_2)_n N(R^{3c})R^{3d}$, $(CH_2)_n C(O)R^{3d}$, $(CH_2)_n N(R^{3c})C(O)R^{3d}$, $(CH_2)_n OC(O)R^{3d}$, $(CH_2)_n C(O)OR^{3d}$, $(CH_2)_n C(O)N(R^{3c})R^{3d}$, $(CH_2)_n N(R^{3c})C(O)N(R^{3c})R^{3d}$, $(CH_2)_n SO_2 N(R^{3c})R^{3d}$, $(CH_2)_n N(R^{3c})SO_2 R^{3d}$, $(CH_2)_n SO_2 N(R^{3c})R^{3d}$, $(CH_2)_n N(R^{3c})SO_2 R^{3d}$, $(CH_2)_n N(R^{3c})P(O)(R^{3d})_2$, $(CH_2)_n P(O)(N(R^{3c}R^{3d}))_2$, and poly(ethylene oxide);

$R^{3d}$ is independently selected from hydrogen, substituted or unsubstituted $C_1$-$C_6$ alkyl, and substituted or unsubstituted $C_3$-$C_{10}$ cycloalkyl;

or two of $R^{3b}$, $R^{6a}$, $R^{6b}$, $R^{6c}$, $R^{6d}$, $R^{6e}$, $R^{3c}$, $R^{3e}$ and $R^{3d}$ together form a ring;

b)
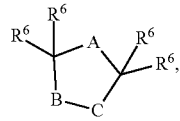

wherein A, B and C are independently selected from a bond, O, $-C(R^6)_2-$, $-C(R^6)_2-C(R^6)_2-$, $-C(R^6)_2-N(R^6)-$, $-C(R^6)_2-O-$, $NR^6$, S, SO, and $SO_2$;

c)
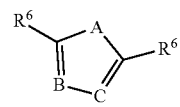

wherein
A is O, $NR^6$, S, SO, $SO_2$, $-C(R^6)=C(R^6)-$, or $-C(R^6)=N-$; and

B and C are either N or $CR^6$, d)
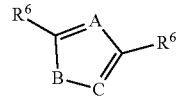

wherein
B is O, $NR^6$, S, SO, $SO_2$, $-C(R^6)=C(R^6)-$, or $-C(R^6)=N-$; and
A and C are either N or $CR^6$, e)
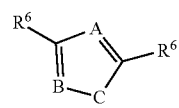

wherein
C is O, $NR^6$, S, SO, $SO_2$, $-C(R^6)=C(R^6)-$, or $-C(R^6)=N-$;
A and B are either N or $CR^6$, one $R^6$ group represents a bond to $L^1$, and the remaining $R^6$ groups are independently selected from hydrogen, halogen, hydroxyl, amino, nitro, cyano, isocyano, carboxyl, $(CH_2)_n OR^{3d}$, $(CH_2)_n SR^{3d}$, $(CH_2)_n S(O)R^{3d}$, $(CH_2)_n SO_2 R^{3d}$, $(CH_2)_n N(R^{3c})R^{3d}$, $(CH_2)_n C(O)R^{3d}$, $(CH_2)_n N(R^{3c})C(O)R^{3d}$, $(CH_2)_n OC(O)R^{3d}$, $(CH_2)_n C(O)OR^{3d}$, $(CH_2)_n C(O)N(R^{3c})R^{3d}$, $(CH_2)_n N(R^{3c})C(O)N(R^{3c})R^{3d}$, $(CH_2)_n SO_2 N(R^{3c})R^{3d}$, $(CH_2)_n N(R^{3c})SO_2 R^{3d}$, $(CH_2)_n N(R^{3c})P(O)(R^{3d})_2$, $(CH_2)_n P(O)(N(R^{3c}R^{3d}))_2$, and poly(ethylene oxide), wherein two geminal $R^6$ groups may together form a carbonyl; or any two or more $R^6$ groups together form a ring, or $R^{3b}$ and one or more $R^6$ groups together for a ring; and n in each case is independently selected from 0, 1, 2, 3, 4, 5, 6, 7, 8, 9 and 10;

f)
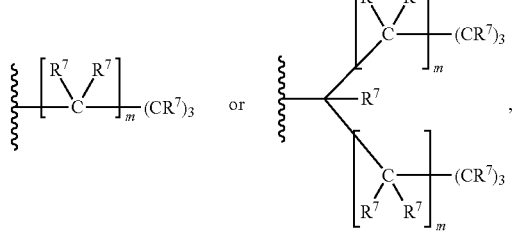

wherein
m is independently selected from 0, 1, 2, 3, 4, 5, 6, 7, 8, 9, and 10;

$R^7$ is in each case independently selected from hydrogen, halogen, hydroxyl, amino, nitro, cyano, isocyano, $(CH_2)_n OR^{3d}$, $(CH_2)_n SR^{3d}$, $(CH_2)_n S(O)R^{3d}$, $(CH_2)_n SO_2 R^{3d}$, $(CH_2)_n N(R^{3c})R^{3d}$, $(CH_2)_n C(O)R^{3d}$, $(CH_2)_n N(R^{3c})C(O)R^{3d}$, $(CH_2)_n OC(O)R^{3d}$, $(CH_2)_n C(O)OR^{3d}$, $(CH_2)_n C(O)N(R^{3c})R^{3d}$, $(CH_2)_n N(R^{3c})C(O)N(R^{3c})R^{3d}$, $(CH_2)_n SO_2 N(R^{3c})R^{3d}$, $(CH_2)_n N(R^{3c})SO_2 R^{3d}$, $(CH_2)_n N(R^{3c})P(O)(R^{3d})_2$, $(CH_2)_n P(O)(N(R^{3c}R^{3d}))_2$, and poly(ethylene oxide); or two geminal $R^7$ groups together form a carbonyl; or $R^7$ groups on adjacent carbon atoms form a double or triple bond; or any two or more R⁷ groups together form a ring, or R³ᵇ and one or more R⁷ groups together form a ring.

In certain examples, the compound of Formula (II) is a fused ring system, for instance having the formula:

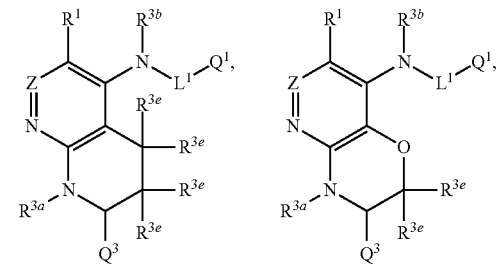

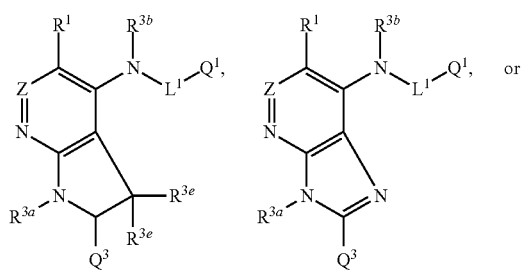

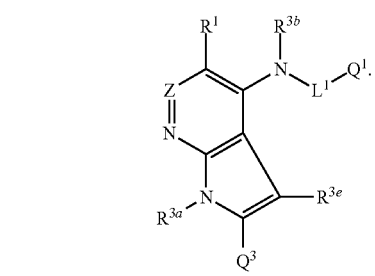

In certain embodiments, the above compounds are characterized wherein in each case $R^{3e}$ is hydrogen, and in other embodiments, Z is $CR^2$.

$Q^1$ can be substituted or unsubstituted cyclopropyl, cyclobutyl, cyclopentyl, cyclohexyl, a heterocycle, or a group of formula:

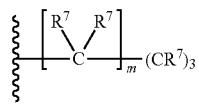

wherein m is 1, 2, 3 or 4. $Q^1$ may be as defined above for the compound of Formula (I), such as a moiety selected from

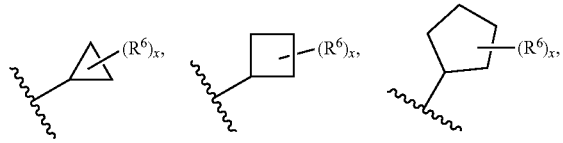

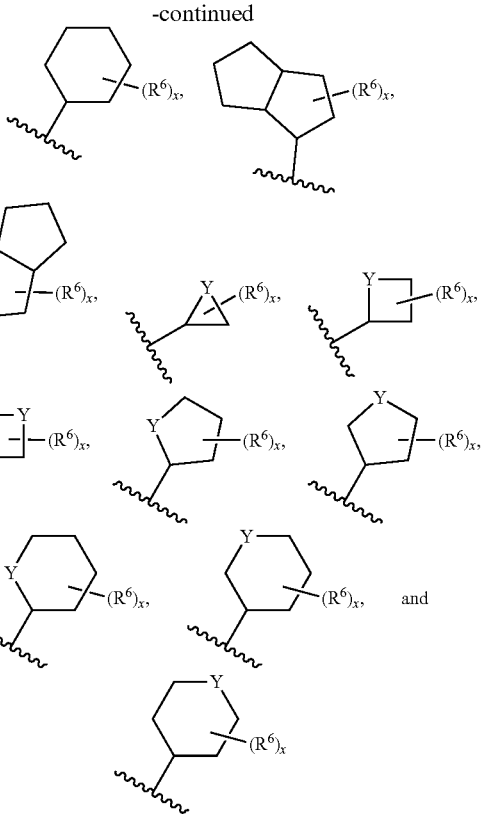

wherein x is any chemically permissible integer, preferably 0, 1, 2 or 3, $R^6$ is independently selected from the substituents defined above, Y can be O, S or $NR^6$. Oxazolyl, imidazolyl and thiazolyl rings can be unsubstituted, or substituted one or two times by $R^6$ groups, which may be the same or different.

In certain examples $Q^1$ has the formula:

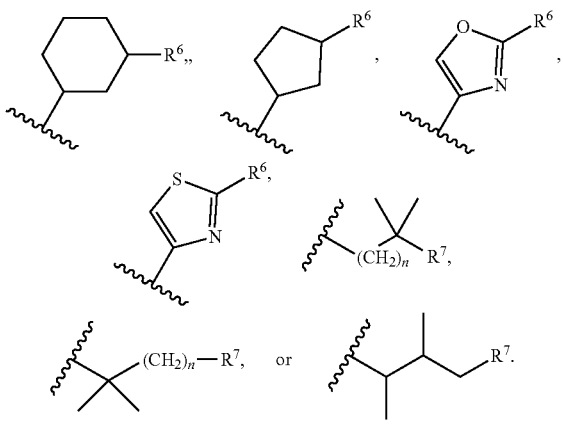

For certain embodiments, the compounds of Formula (II) are compounds in which $L^1$ is a bond or $CH_2$. In certain preferred embodiments of the compounds of Formula (I), at least one of $R^6$ or $R^7$ are $NHSO_2R^{3d}$, in which $R^{3d}$ is as defined above. Preferred $R^{3d}$ groups include methyl, tert-butyl, cyclopropyl, 1-methylcyclopropyl, s-butyl isopropyl, propyl, $C(CH_3)_2CH_2OH$, and phenyl.

Also provided herein are compounds of the formula (III):

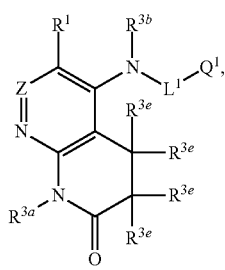
(III)

wherein
Z is selected from $CR^2$ and N;
$R^1$ and $R^2$ are independently selected from hydrogen, halogen, hydroxyl, carboxyl, amino, nitro, cyano, isocyano, substituted or unsubstituted $C_1$-$C_6$ alkyl, substituted or unsubstituted $C_1$-$C_6$ alkoxy, and substituted or unsubstituted $C_1$-$C_6$ alkenyl; or wherein $R^1$ and $R^2$ together form a ring;
$R^{3a}$ and $R^{3b}$ are independently selected from hydrogen and substituted or unsubstituted $C_1$-$C_6$ alkyl;
$L^1$ is independently selected from $(CR^{3e}_2)_n$, $(CR^{3e}_2)_nC(O)$, $(CR^{3e}_2)C(O)O$, $(CR^{3e}_2)_nC(O)(NR^{3c})$, $SO_2$, $(CR^{3e}_2)_nN(R^{3c})P(O)(R^{3c})$, and $(CR^{3e}_2)_nP(O)N(R^{3c})$;
$R^{3c}$ is in each case independently selected from hydrogen and substituted or unsubstituted $C_1$-$C_6$ alkyl;
$R^{3e}$ is in each case independently selected from hydrogen, halogen, hydroxyl, carboxyl, amino, nitro, cyano, isocyano, substituted or unsubstituted $C_1$-$C_6$ alkyl, substituted or unsubstituted $C_1$-$C_6$ alkoxy, substituted or unsubstituted $C_1$-$C_6$ alkylamino substituted or unsubstituted $C_2$-$C_6$ alkenyl, and substituted or unsubstituted $C_2$-$C_6$ alkynyl; or two geminal $R^{3e}$ groups together form a carbonyl; or $R^{3e}$ groups on adjacent carbon atoms form a double or triple bond; or any two or more $R^{3e}$ groups together form a ring; or $R^{3c}$ forms a ring with either or both of $R^{3a}$ and $R^{3b}$ or a substituent on $Q^1$.
n in each case is independently selected from 0, 1, 2, 3, 4, 5, 6, 7, 8, 9 and 10;
$Q^1$ is selected from substituted or unsubstituted alkyl, substituted or unsubstituted aryl, substituted or unsubstituted cycloalkyl, substituted or unsubstituted heteroaryl, substituted or unsubstituted heterocyclyl, and poly(ethylene oxide); or one or more substituents on $Q^1$ form a ring with $R^{3b}$, $R^{3c}$, $R^{3e}$ or $R^4$ groups;
or a salt thereof.
In certain examples, the compound of Formula (III) contains a $Q^1$ group such as:

a)

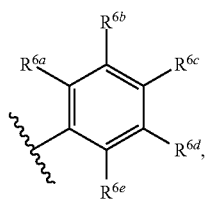

wherein
$R^{6a}$, $R^{6b}$, $R^{6c}$, $R^{6d}$, $R^{6e}$ are independently selected from hydrogen, halogen, hydroxyl, amino, $(CH_2)_nR^{3d}$, $(CH_2)_nOR^{3d}$, $(CH_2)_nSR^{3d}$, $(CH_2)_nS(O)R^{3d}$, $(CH_2)_nSO_2R^{3d}$, $(CH_2)_nN(R^{3c})R^{3d}$, $(CH_2)_nC(O)R^{3d}$, $(CH_2)_nN(R^{3c})C(O)R^{3d}$, $(CH_2)_nOC(O)R^{3d}$, $(CH_2)_nC(O)OR^{3d}$, $(CH_2)_nC(O)N(R^{3c})R^{3d}$, $(CH_2)_nN(R^{3c})C(O)N(R^{3c})R^{3d}$, $(CH_2)_nSO_2N(R^{3c})R^{3d}$, $(CH_2)_nN(R^{3c})SO_2R^{3d}$, $(CH_2)_nSO_2N(R^{3c})R^{3d}$, $(CH_2)_nN(R^{3c})SO_2R^{3d}$, $(CH_2)_nN(R^{3c})P(O)(R^{3d})_2$, $(CH_2)_nP(O)(N(R^{3c}R^{3d}))_2$, and poly(ethylene oxide);
$R^{3d}$ is independently selected from hydrogen, substituted or unsubstituted $C_1$-$C_6$ alkyl, and substituted or unsubstituted $C_3$-$C_{10}$ cycloalkyl;
or two of $R^{3b}$, $R^{6a}$, $R^{6b}$, $R^{6c}$, $R^{6d}$, $R^{6e}$, $R^{3c}$ and $R^{3d}$ together form a ring;

b)

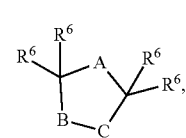

wherein A, B and C are independently selected from a bond, O, $-C(R^6)_2-$, $-C(R^6)_2-C(R^6)_2-$, $-C(R^6)_2-N(R^6)-$, $-C(R^6)_2-O-$, $NR^6$, S, SO, and $SO_2$;

c)

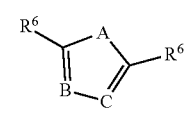

wherein
A is O, $NR^6$, S, SO, $SO_2$, $-C(R^6)=C(R^6)-$, or $-C(R^6)=N-$; and
B and C are either N or $CR^6$, d)

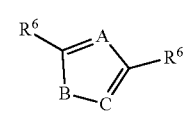

wherein
B is O, $NR^6$, S, SO, $SO_2$, $-C(R^6)=C(R^6)-$, or $-C(R^6)=N-$; and
A and C are either N or $CR^6$, e)

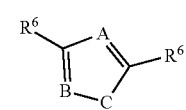

wherein
C is O, $NR^6$, S, SO, $SO_2$, $-C(R^6)=C(R^6)-$, or $-C(R^6)=N-$;
A and B are either N or $CR^6$,
one $R^6$ group represents a bond to $L^1$, and the remaining $R^6$ groups are independently selected from hydrogen, halogen, hydroxyl, amino, nitro, cyano, isocyano, carboxyl, $(CH_2)_nOR^{3d}$, $(CH_2)_nSR^{3d}$, $(CH_2)_nS(O)R^{3d}$, $(CH_2)_nSO_2R^{3d}$, $(CH_2)_nN(R^{3c})R^{3d}$, $(CH_2)_nC(O)R^{3d}$, $(CH_2)_nN(R^{3c})C(O)R^{3d}$, $(CH_2)_nOC(O)R^{3d}$, $(CH_2)_nC(O)OR^{3d}$, $(CH_2)_nC(O)N(R^{3c})R^{3d}$, $(CH_2)_nN(R^{3c})C(O)N(R^{3c})R^{3d}$, $(CH_2)_nSO_2N(R^{3c})R^{3d}$, $(CH_2)_nN(R^{3c})SO_2R^{3d}$, $(CH_2)_nN(R^{3c})P(O)(R^{3d})_2$, $(CH_2)_nP(O)(N(R^{3c}R^{3d}))_2$, and poly(ethylene oxide), wherein two geminal $R^6$ groups may together form a carbonyl; or any two or more $R^6$ groups together form a ring, or $R^{3b}$ and one or more $R^6$ groups together for a ring; and n in each case is independently selected from 0, 1, 2, 3, 4, 5, 6, 7, 8, 9 and 10;

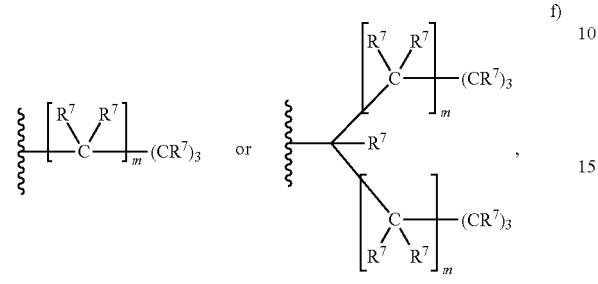

wherein m is independently selected from 0, 1, 2, 3, 4, 5, 6, 7, 8, 9, and 10;

$R^7$ is in each case independently selected from hydrogen, halogen, hydroxyl, amino, nitro, cyano, isocyano, $(CH_2)_nOR^{3d}$, $(CH_2)_nSR^{3d}$, $(CH_2)_nS(O)R^{3d}$, $(CH_2)_nSO_2R^{3d}$, $(CH_2)_nN(R^{3c})R^{3d}$, $(CH_2)_nC(O)R^{3d}$, $(CH_2)_nN(R^{3c})C(O)R^{3d}$, $(CH_2)_nOC(O)R^{3d}$, $(CH_2)_nC(O)OR^{3d}$, $(CH_2)_nC(O)N(R^{3c})R^{3d}$, $(CH_2)_nN(R^{3c})C(O)N(R^{3c})R^{3d}$, $(CH_2)_nSO_2N(R^{3c})R^{3d}$, $(CH_2)_nN(R^{3c})SO_2R^{3d}$, $(CH_2)_nN(R^{3c})P(O)(R^{3d})_2$, $(CH_2)_nP(O)(N(R^{3c}R^{3d}))_2$, and poly(ethylene oxide); or two geminal $R^7$ groups together form a carbonyl; or $R^7$ groups on adjacent carbon atoms form a double or triple bond; or any two or more $R^7$ groups together form a ring, or $R^{3b}$ and one or more $R^7$ groups together form a ring.

In some embodiments, each case $R^{3e}$ can be hydrogen.

$Q^1$ can be substituted or unsubstituted cyclopropyl, cyclobutyl, cyclopentyl, cyclohexyl, a heterocycle, or a group of formula:

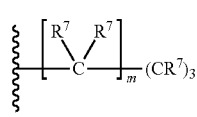

wherein m is 1, 2, 3 or 4. For instance $Q^1$ may be as defined above for the compound of Formula (I), such as a moiety selected from

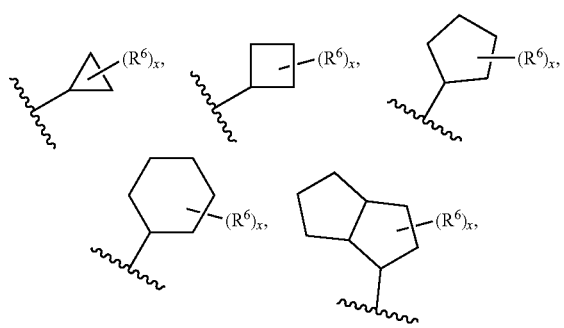

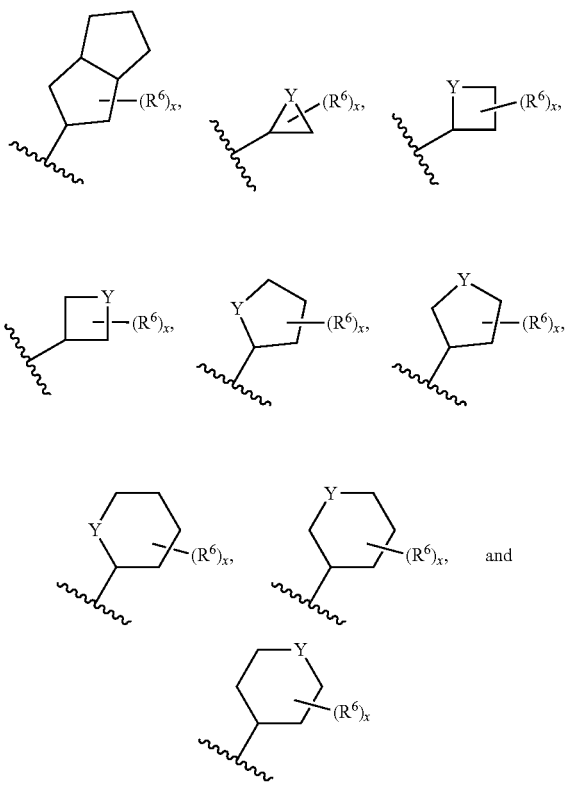

wherein x is any chemically permissible integer, preferably 0, 1, 2 or 3, $R^6$ is independently selected from the substituents defined above, Y can be O, S or $NR^6$. Oxazolyl, imidazolyl and thiazolyl rings can be unsubstituted, or substituted one or two times by $R^6$ groups, which may be the same or different.

In certain examples $Q^1$ has the formula:

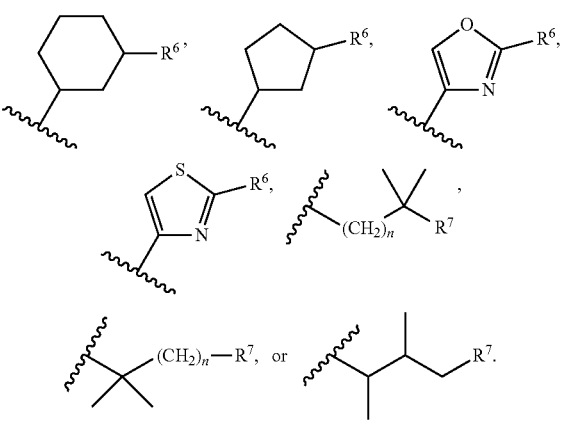

For certain embodiments, the compounds of Formula (III) are compounds in which $L^1$ is a bond or $CH_2$. In certain preferred embodiments of the compounds of Formula (I), at least one of $R^6$ or $R^7$ are $NHSO_2R^{3d}$, in which $R^{3d}$ is as defined above. Preferred $R^{3d}$ groups include methyl, tert-butyl, cyclopropyl, 1-methylcyclopropyl, s-butyl isopropyl, propyl, $C(CH_3)_2CH_2OH$, and phenyl.

Also provided herein are compounds of formula (IV):

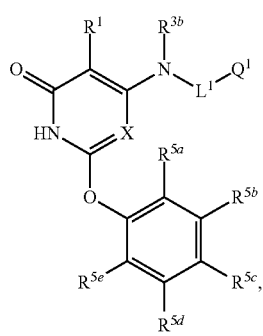

(IV)

wherein
X is N or CR$^4$
R$^1$ is selected from hydrogen, halogen, hydroxyl, carboxyl, amino, nitro, cyano, isocyano, substituted or unsubstituted C$_1$-C$_6$ alkyl, substituted or unsubstituted C$_1$-C$_6$ alkoxy, and substituted or unsubstituted C$_1$-C$_6$ alkenyl;
R$^4$ is selected from hydrogen, halogen, hydroxyl, carboxyl, amino, nitro, cyano, isocyano, substituted or unsubstituted C$_1$-C$_6$ alkyl, substituted or unsubstituted C$_1$-C$_6$ alkoxy, substituted or unsubstituted C$_1$-C$_6$ alkylamino, substituted or unsubstituted C$_2$-C$_6$ alkenyl, and substituted or unsubstituted C$_2$-C$_6$ alkynyl; or R$^4$ forms a ring with either or both of R$^{5a}$ and R$^{3b}$.
L$^1$ is selected from (CR$^{3e}{}_2$)$_n$, (CR$^{3e}{}_2$)$_n$C(O), (CR$^{3e}{}_2$)$_n$C(O)O, (CR$^{3e}{}_2$)$_n$C(O)(NR$^{3c}$), SO$_2$, (CR$^{3e}{}_2$)$_n$N(R$^{3c}$)P(O)(R$^{3c}$), and (CR$^{3e}{}_2$)$_n$P(O)N(R$^{3c}$);
R$^{3b}$ and R$^{3c}$ are in each case independently selected from hydrogen and substituted or unsubstituted C$_1$-C$_6$ alkyl;
R$^{3e}$ is in each case independently selected from hydrogen, halogen, hydroxyl, carboxyl, amino, nitro, cyano, isocyano, substituted or unsubstituted C$_1$-C$_6$ alkyl, substituted or unsubstituted C$_1$-C$_6$ alkoxy, substituted or unsubstituted C$_1$-C$_6$ alkylamino substituted or unsubstituted C$_2$-C$_6$ alkenyl, and substituted or unsubstituted C$_2$-C$_6$ alkynyl; or two geminal R$^{3e}$ groups together form a carbonyl; or R$^{3e}$ groups on adjacent carbon atoms form a double or triple bond; or any two or more R$^{3e}$ groups together form a ring; or R$^{3e}$ forms a ring with any, some or all of R$^{3b}$, R$^{3c}$ and R$^4$;
n in each case is independently selected from 0, 1, 2, 3, 4, 5, 6, 7, 8, 9 and 10;
Q$^1$ is selected from substituted or unsubstituted alkyl, substituted or unsubstituted aryl, substituted or unsubstituted cycloalkyl, substituted or unsubstituted heteroaryl, substituted or unsubstituted heterocyclyl, and poly(ethylene oxide); or one or more substituents on Q$^1$ form a ring with R$^{3b}$, R$^{3c}$, R$^{3e}$ or R$^4$;
R$^{5a}$, R$^{5b}$, R$^{5c}$, R$^{5d}$, and R$^{5e}$ are independently selected from hydrogen, C$_1$-C$_6$alkyl, C$_1$-C$_6$alkoxy, C$_3$-C$_{10}$ cycloalkyl, halogen, hydroxy, carboxyl, amino, nitro, cyano, isocyano, -L$^2$Q$^2$; wherein said C$_1$-C$_6$ alkyl and C$_3$-C$_{10}$ cycloalkyl groups are optionally substituted one or more times with a group selected from halogen, hydroxy, carboxyl, amino, nitro, cyano, isocyano, and combinations thereof;
or wherein any two of R$^{5a}$, R$^{5b}$, R$^{5c}$, R$^{5d}$, R$^{5e}$, R$^4$, together form a ring;
or a salt thereof.

In certain examples, Q$^1$ and Q$^3$ can be:

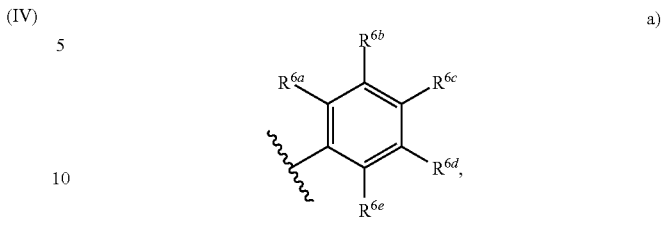

a)

wherein
R$^{6a}$, R$^{6b}$, R$^{6c}$, R$^{6d}$, R$^{6e}$ are independently selected from hydrogen, halogen, hydroxyl, amino, (CH$_2$)$_n$R$^{3d}$, (CH$_2$)$_n$OR$^{3d}$, (CH$_2$)$_n$SR$^{3d}$, (CH$_2$)$_n$S(O)R$^{3d}$, (CH$_2$)$_n$SO$_2$R$^{3d}$, (CH$_2$)$_n$N(R$^{3c}$)R$^{3d}$, (CH$_2$)$_n$C(O)R$^{3d}$, (CH$_2$)$_n$N(R$^{3c}$)C(O)R$^{3d}$, (CH$_2$)$_n$OC(O)R$^{3d}$, (CH$_2$)$_n$C(O)OR$^{3d}$, (CH$_2$)$_n$C(O)N(R$^{3c}$)R$^{3d}$, (CH$_2$)$_n$N(R$^{3c}$)C(O)N(R$^{3c}$)R$^{3d}$, (CH$_2$)$_n$SO$_2$N(R$^{3c}$)R$^{3d}$, (CH$_2$)$_n$N(R$^{3c}$)SO$_2$R$^{3d}$, (CH$_2$)$_n$SO$_2$N(R$^{3c}$)R$^{3d}$, (CH$_2$)$_n$N(R$^{3c}$)SO$_2$R$^{3d}$, (CH$_2$)$_n$N(R$^{3c}$)P(O)(R$^{3d}$)$_2$, (CH$_2$)$_n$P(O)(N(R$^{3c}$R$^{3d}$))$_2$, and poly(ethylene oxide);
R$^{3d}$ is independently selected from hydrogen, substituted or unsubstituted C$_1$-C$_6$ alkyl, and substituted or unsubstituted C$_3$-C$_{10}$ cycloalkyl;
or two of R$^{3b}$, R$^{6a}$, R$^{6b}$, R$^{6c}$, R$^{6d}$, R$^{6e}$, R$^{3e}$, R$^{3c}$ and R$^{3d}$ together form a ring;

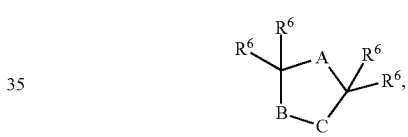

b)

wherein A, B and C are independently selected from a bond, O, —C(R$^6$)$_2$—, —C(R$^6$)$_2$—C(R$^6$)$_2$—, —C(R$^6$)$_2$—N(R$^6$)—, —C(R$^6$)$_2$—O—, NR$^6$, S, SO, and SO$_2$;

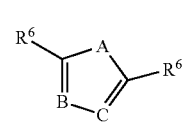

c)

wherein
A is O, NR$^6$, S, SO, SO$_2$, —C(R$^6$)=C(R$^6$)—, or —C(R$^6$)=N—; and
B and C are either N or CR$^6$,

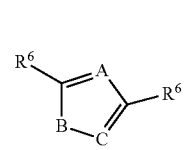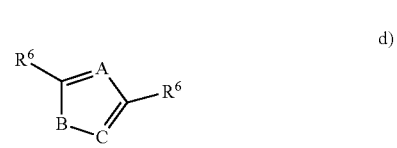

d)

wherein
B is O, NR$^6$, S, SO, SO$_2$, —C(R$^6$)=C(R$^6$)—, or —C(R$^6$)=N—; and
A and C are either N or CR$^6$,

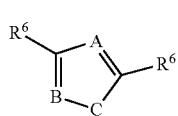

e)

wherein

C is O, NR$^6$, S, SO, SO$_2$, —C(R$^6$)=C(R$^6$)—, or —C(R$^6$)=N—;

A and B are either N or CR$^6$, one R$^6$ group represents a bond to L$^1$, and the remaining R$^6$ groups are independently selected from hydrogen, halogen, hydroxyl, amino, nitro, cyano, isocyano, carboxyl, (CH$_2$)$_n$OR$^{3d}$, (CH$_2$)$_n$SR$^{3d}$, (CH$_2$)$_n$S(O)R$^{3d}$, (CH$_2$)$_n$SO$_2$R$^{3d}$, (CH$_2$)$_n$N(R$^{3c}$)R$^{3d}$, (CH$_2$)$_n$C(O)R$^{3d}$, (CH$_2$)$_n$N(R$^{3c}$)C(O)R$^{3d}$, (CH$_2$)$_n$OC(O)R$^{3d}$, (CH$_2$)$_n$C(O)OR$^{3d}$, (CH$_2$)$_n$C(O)N(R$^{3c}$)R$^{3d}$, (CH$_2$)$_n$N(R$^{3c}$)C(O)N(R$^{3c}$)R$^{3d}$, (CH$_2$)$_n$SO$_2$N(R$^{3c}$)R$^{3d}$, (CH$_2$)$_n$N(R$^{3c}$)SO$_2$R$^{3d}$, (CH$_2$)$_n$N(R$^{3c}$)P(O)(R$^{3d}$)$_2$, (CH$_2$)$_n$P(O)(N(R$^{3c}$R$^{3d}$))$_2$, and poly(ethylene oxide), wherein two geminal R$^6$ groups may together form a carbonyl; or any two or more R$^6$ groups together form a ring, or R$^{3b}$ and one or more R$^6$ groups together for a ring; and n in each case is independently selected from 0, 1, 2, 3, 4, 5, 6, 7, 8, 9 and 10;

f)

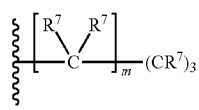

wherein m is independently selected from 0, 1, 2, 3, 4, 5, 6, 7, 8, 9, and 10;

R$^7$ is in each case independently selected from hydrogen, halogen, hydroxyl, amino, nitro, cyano, isocyano, (CH$_2$)$_n$OR$^{3d}$, (CH$_2$)$_n$SR$^{3d}$, (CH$_2$)$_n$S(O)R$^{3d}$, (CH$_2$)$_n$SO$_2$R$^{3d}$, (CH$_2$)$_n$N(R$^{3c}$)R$^{3d}$, (CH$_2$)$_n$C(O)R$^{3d}$, (CH$_2$)$_n$N(R$^{3c}$)C(O)R$^{3d}$, (CH$_2$)$_n$OC(O)R$^{3d}$, (CH$_2$)$_n$C(O)OR$^{3d}$, (CH$_2$)$_n$C(O)N(R$^{3c}$)R$^{3d}$, (CH$_2$)$_n$N(R$^{3c}$)C(O)N(R$^{3c}$)R$^{3d}$, (CH$_2$)$_n$SO$_2$N(R$^{3c}$)R$^{3d}$, (CH$_2$)$_n$N(R$^{3c}$)SO$_2$R$^{3d}$, (CH$_2$)$_n$N(R$^{3c}$)P(O)(R$^{3d}$)$_2$, (CH$_2$)$_n$P(O)(N(R$^{3c}$R$^{3d}$))$_2$, and poly(ethylene oxide); or two geminal R$^7$ groups together form a carbonyl; or R$^7$ groups on adjacent carbon atoms form a double or triple bond; or any two or more R$^7$ groups together form a ring, or R$^{3b}$ and one or more R$^7$ groups together form a ring.

Q$^1$ can be substituted or unsubstituted cyclopropyl, cyclobutyl, cyclopentyl, cyclohexyl, a heterocycle, or a group of formula:

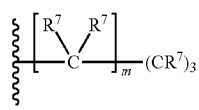

wherein m is 1, 2, 3 or 4. Q$^1$ may be as defined above for the compound of Formula (I), such as a moiety selected from

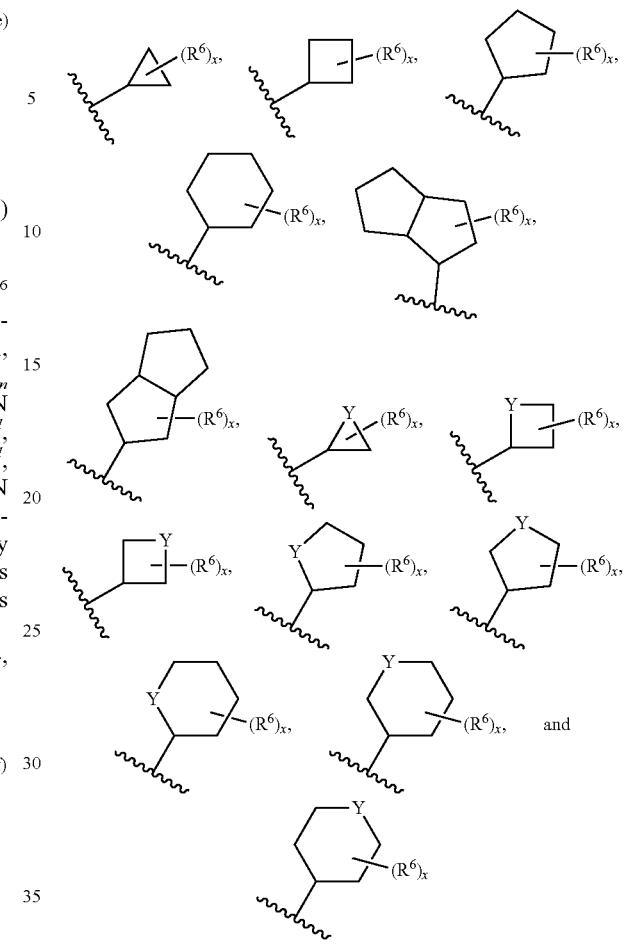

wherein x is any chemically permissible integer, preferably 0, 1, 2 or 3, R$^6$ is independently selected from the substituents defined above, Y can be O, S or NR$^6$. Oxazolyl, imidazolyl and thiazolyl rings can be unsubstituted, or substituted one or two times by R$^6$ groups, which may be the same or different.

In certain examples Q$^1$ has the formula:

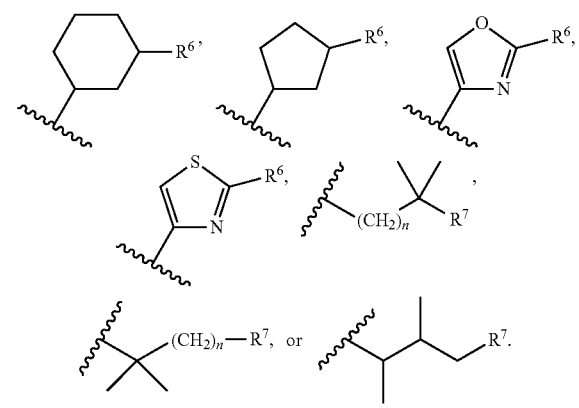

For certain examples, the compounds of Formula (IV) are compounds in which L$^1$ is a bond or CH$_2$. In certain preferred embodiments of the compounds of Formula (I), at least one of R$^6$ or R$^7$ are NHSO$_2$R$^{3d}$, in which R$^{3d}$ is as defined above. Preferred R$^{3d}$ groups include methyl, tert-butyl, cyclopropyl, 1-methylcyclopropyl, s-butyl isopropyl, propyl, C(CH$_3$)$_2$CH$_2$OH, and phenyl.

Specific examples of compounds disclosed herein are in table 1.

TABLE 1

| Name<br>Molecular Wt (Amt. Supplied mg) | Co-crystal | DSF ΔTm (° C.) | Estimated BRD4 IC$_{50}$ (μM) | Comments |
|---|---|---|---|---|
| 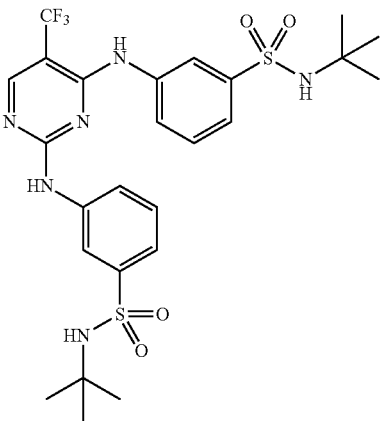<br>SG1-171-02<br>M.W. = 600.68 | No | Not determined | N/A | |
| 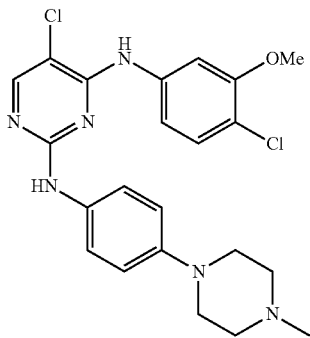 [SMILES: COc1cc(Nc2nc(Nc3ccc(N4CCN(C)CC4)cc3)ncc2Cl)ccc1Cl]<br>SG1-180<br>M.W. = 459.37 | Yes (1.3 Å) | 4.8 ± 0.058 | 0.54 | HEK293 (IC$_{50}$ = 1.4 (μM) MM.1S (IC$_{50}$ = 0.45 μM) |
| 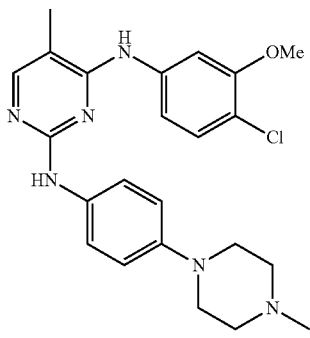 [SMILES: COc1cc(Nc2nc(Nc3ccc(N4CCN(C)CC4)cc3)ncc2C)ccc1Cl]<br>SG1-183<br>M.W. = 438.95 | Yes (1.3 Å) | 5.6 ± 0.082 | 0.29 (IC$_{50}$ RB = 0.617) | HEK293 (IC$_{50}$ = 0.38 μM) MM.1S (IC$_{50}$ = 0.42 μM) BRD2 IC$_{50}$ = 2.80 × 10$^3$ nM BRD3 IC$_{50}$ = 1.14 × 10$^3$ nM BRD4 IC$_{50}$ = 617 nM BRDT IC$_{50}$ = 1.40 × 10$^3$ nM JAK1 IC$_{50}$ = 1.83 nM JAK2 IC$_{50}$ = 0.690 nM JAK3 IC$_{50}$ = 9.06 nM |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 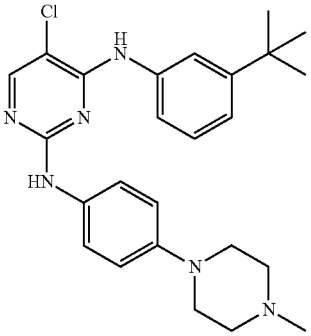 [SMILES: CN1CCN(c2ccc(Nc3ncc(Cl)c(Nc4cccc(C(C)(C)C)c4)n3)cc2)CC1]<br>SG1-184<br>M.W. = 451.01 | No | 0.12 ± 0.053 | 19.78 | |
| 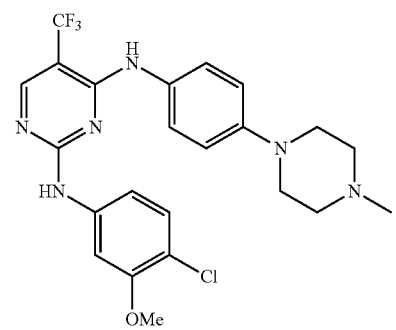<br>SG2-002<br>M.W. = 492.92 | No | 0.56 ± 0.37 | 14.10 | |
| 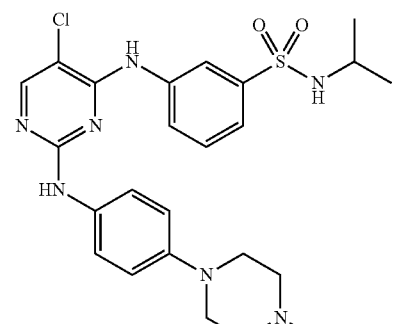<br>SG2-004<br>M.W. = 516.06 | Partial (1.65 Å) | 4.6 ± 0.12 | 0.63 | |
| 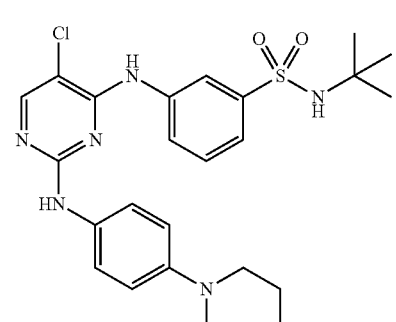<br>SG2-005-01<br>M.W. = 517.04 | No | −.071 ± 0.042 | 22.91 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 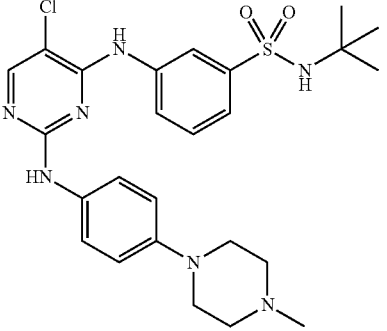 [SMILES: CN1CCN(c2ccc(Nc3ncc(Cl)c(Nc4cccc(S(=O)(=O)NC(C)(C)C)c4)n3)cc2)CC1]<br>SG2-015-01<br>M.W. = 530.09 | Yes<br>(2.6 Å) | 5.7 ± 0.054 | 0.27 | |
| 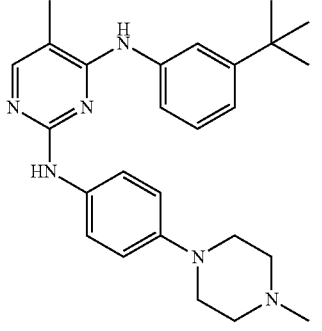 [SMILES: Cc1cnc(Nc2ccc(N3CCN(C)CC3)cc2)nc1Nc1cccc(C(C)(C)C)c1]<br>SG2-016<br>M.W. = 430.59 | No | 2.9 ± 0.12 | 2.33 | |
| 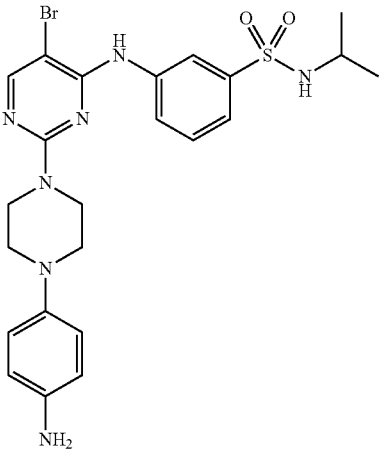<br>MA1-014<br>M.W. = 546.48 | No | 0.16 | 19.18 | |

TABLE 1-continued
| Name<br>Molecular Wt (Amt. Supplied mg) | Co-crystal | DSF ΔTm (° C.) | Estimated BRD4 IC$_{50}$ (μM) | Comments |
| --- | --- | --- | --- | --- |
| 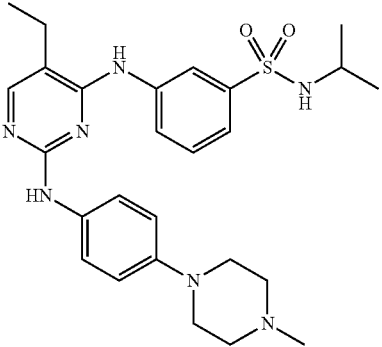 [SMILES: CCc1cnc(Nc2ccc(N3CCN(C)CC3)cc2)nc1Nc1cccc(S(=O)(=O)NC(C)C)c1]<br>MA1-020<br>M.W. = 509.67 | No | 2.2 | 3.99 | |
| 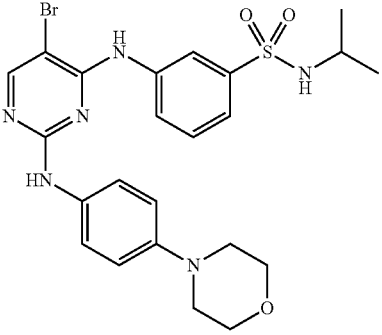 [SMILES: CC(C)NS(=O)(=O)c1cccc(Nc2nc(Nc3ccc(N4CCOCC4)cc3)ncc2Br)c1]<br>MA1-021<br>M.W. = 547.47 | No | −0.79 | 39.83 | |
| 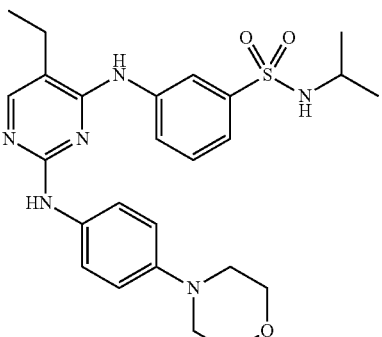<br>MA1-022<br>M.W. = 496.62 | No | −0.29 | 27.11 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 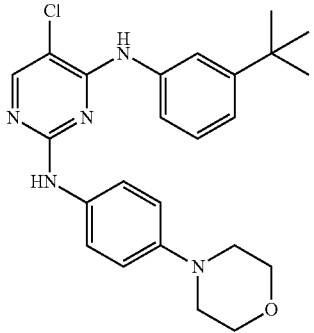 [SMILES: CC(C)(C)c1cccc(Nc2nc(Nc3ccc(N4CCOCC4)cc3)ncc2Cl)c1]<br>MA1-023<br>M.W. = 437.97 | No | −0.34 | 28.18 | |
| 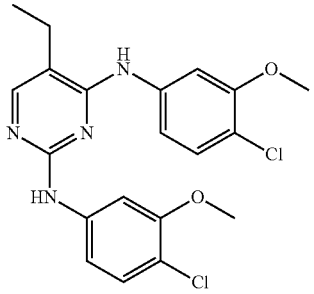<br>MA1-025B<br>M.W. = 419.30 | No | Not determined | N/A | |
| 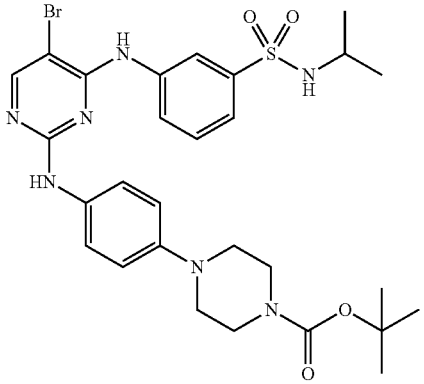<br>MA1-027<br>M.W. = 646.60 | No | Not determined | N/A | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 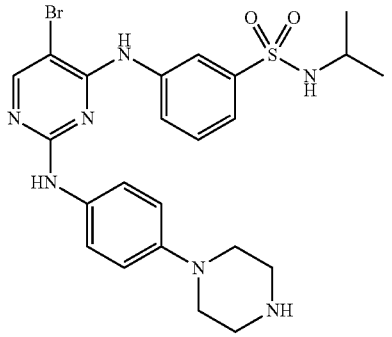 [SMILES: CC(C)NS(=O)(=O)c1cccc(Nc2nc(Nc3ccc(N4CCNCC4)cc3)ncc2Br)c1]<br>MA1-027-2<br>M.W. = 546.48 | Yes | 5.0 | 0.46 | |
| 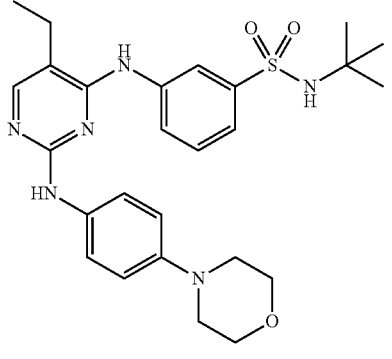 [SMILES: CCc1cnc(Nc2ccc(N3CCOCC3)cc2)nc1Nc1cccc(S(=O)(=O)NC(C)(C)C)c1]<br>MA1-028<br>M.W. = 510.65 | No | −0.0084 | 21.83 | |
| 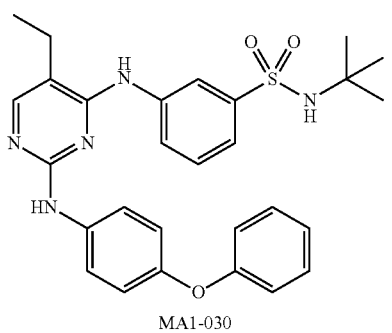<br>MA1-030<br>M.W. = 517.64 | No | Not determined | N/A | |
| 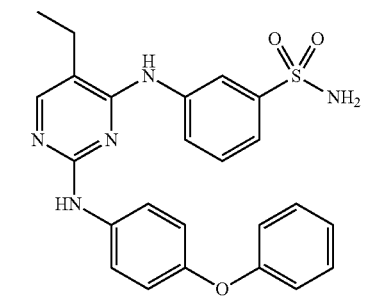<br>MA1-030B<br>M.W. = 461.54 | No | Not determined | N/A | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 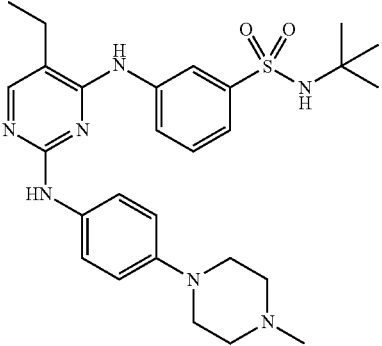 [SMILES: CCc1cnc(Nc2ccc(N3CCN(C)CC3)cc2)nc1Nc1cccc(S(=O)(=O)NC(C)(C)C)c1]<br>MA1-032<br>M.W. = 523.69 | No | 3.2 | 1.85 | |
| 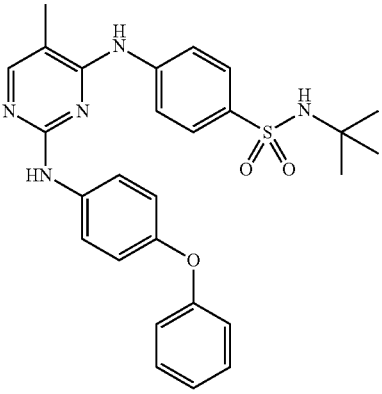 [SMILES: Cc1cnc(Nc2ccc(Oc3ccccc3)cc2)nc1Nc1ccc(S(=O)(=O)NC(C)(C)C)cc1]<br>MA1-033<br>M.W. = 503.62 | No | Not determined | N/A | |
| Dinaciclib | Yes | 0.53 | 17.22 | BRD4 IC$_{50}$ = 19 KM (RB) |
| TG101209 | Yes | 6.83 ± 0.129<br>7.55 ± 0.154 | 0.13<br>0.186 | BRD4 IC$_{50}$ = 0.13 μM (RB)<br>BRD2 IC$_{50}$ = 2.35 × 10$^3$ nM<br>BRD3 IC$_{50}$ = 477 nM<br>BRD4 IC$_{50}$ = 518 nM<br>BRDT IC$_{50}$ = 840 nM (RB)<br>JAK1 IC$_{50}$ = 2.63 nM<br>JAK2 IC$_{50}$ = 0.508 nM<br>JAK3 IC$_{50}$ = 97.6 nM (RB) |

TABLE 1-continued
| Name<br>Molecular Wt (Amt. Supplied mg) | Co-crystal | DSF ΔTm (° C.) | Estimated BRD4 IC$_{50}$ (μM) | Comments |
| --- | --- | --- | --- | --- |
| 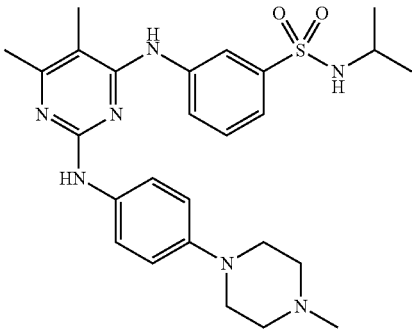 [SMILES: Cc1nc(Nc2ccc(N3CCN(C)CC3)cc2)nc(Nc2cccc(S(=O)(=O)NC(C)(C)C)c2)c1C]<br>RJ1-014<br>M.W. = 523.69 | No | 5.3 ± 0.064 | 0.37 | HEK293 (IC$_{50}$ = 120 μM) |
| 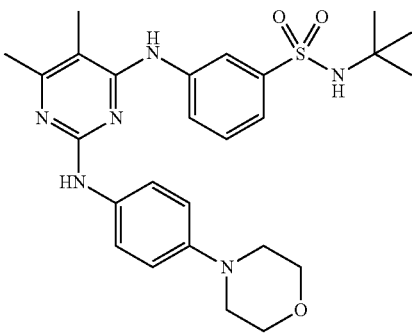 [SMILES: Cc1nc(Nc2ccc(N3CCOCC3)cc2)nc(Nc2cccc(S(=O)(=O)NC(C)(C)C)c2)c1C]<br>RJ1-024-01<br>M.W. = 510.65 | No | 1.9 ± 0.17 | 5.03 | |
| 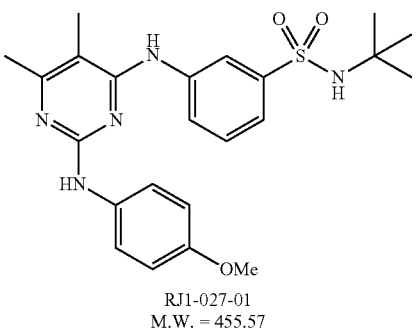<br>RJ1-027-01<br>M.W. = 455.57 | No | 0.22 ± 0.20 | 18.31 | |
| 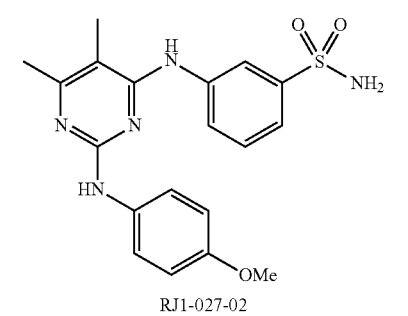<br>RJ1-027-02<br>M.W. = 399.47 | No | 0.12 ± 0.13 | 19.78 | |

TABLE 1-continued

| Name<br>Molecular Wt (Amt. Supplied mg) | Co-crystal | DSF ΔTm (° C.) | Estimated BRD4 IC$_{50}$ (μM) | Comments |
|---|---|---|---|---|
| RJ1-030-01<br>M.W. = 512.62 | No | Not determined | N/A | |
| RJ1-036-01<br>M.W. = 493.62 | Yes<br>(1.97 Å) | 6.7 ± 0.11 | 0.13 | HEK293<br>(IC$_{50}$ = 1.0 μM)<br>MM.1S<br>(IC$_{50}$ = 0.60 μM) |
| RJ1-040-01<br>M.W. = 452.98 | No | 4.1 ± 0.14 | 0.93 | JAK2<br>(IC$_{50}$ RB = 14 μM)<br>HEK293<br>(IC$_{50}$ = 0.84 μM) |
| RJ1-041-01<br>M.W. = 478.59 | Yes<br>(1.35 Å) | 5.9 ± 0.14 | 0.23 | HEK293<br>0050 = 1.4 μM<br>MM.1S<br>(IC$_{50}$ = 5.6 μM) |

TABLE 1-continued
| Name<br>Molecular Wt (Amt. Supplied mg) | Co-crystal | DSF ΔTm<br>(° C.) | Estimated<br>BRD4 IC$_{50}$<br>(μM) | Comments |
|---|---|---|---|---|
| 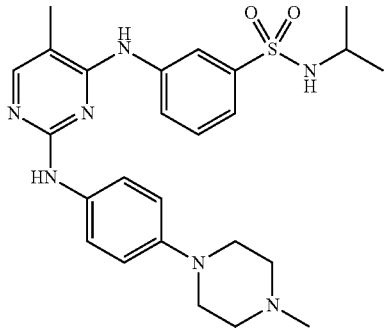<br>SG2-021-03<br>M.W. = 495.64 | Partial<br>(1.52 Å) | 6.0 ± 0.10 | 0.21 | |
| 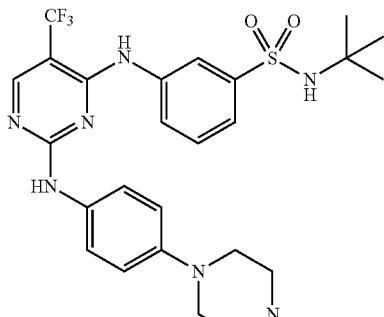<br>SG2-029-01<br>M.W. = 563.64 | No | 0.20 ± 0.082 | 18.60 | |
| 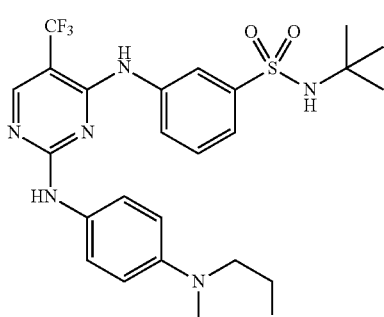<br>SG2-033-01-1<br>M.W. = 549.61 | No | 2.9 ± 0.031 | 2.33 | |

TABLE 1-continued
| Name<br>Molecular Wt (Amt. Supplied mg) | Co-crystal | DSF ΔTm (° C.) | Estimated BRD4 IC$_{50}$ (μM) | Comments |
| --- | --- | --- | --- | --- |
| 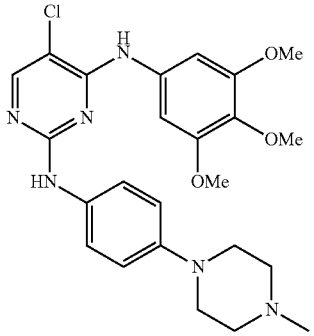 [SMILES: COc1cc(Nc2nc(Nc3ccc(N4CCN(C)CC4)cc3)ncc2C(F)(F)F)cc(OC)c1OC]<br>SG2-054-01<br>M.W. = 484.98 | No | 5.2 ± 0.020 | 0.40 | HEK293 (IC$_{50}$ = 2.0 μM) |
| 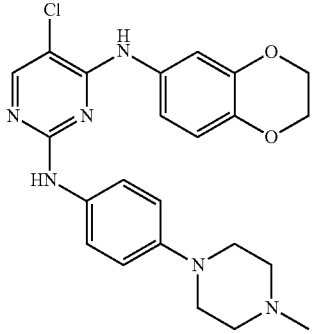 [SMILES: CN1CCN(c2ccc(Nc3ncc(Cl)c(Nc4ccc5c(c4)OCCO5)n3)cc2)CC1]<br>SG2-055-01<br>M.W. = 452.94 | No | 2.6 ± 0.15 | 2.94 | |
| 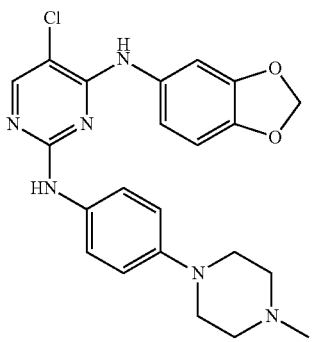 [SMILES: CN1CCN(c2ccc(Nc3ncc(Cl)c(Nc4ccc5c(c4)OCO5)n3)cc2)CC1]<br>SG2-056<br>M.W. = 438.94 | No | 0.073 ± 0.083 | 20.51 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 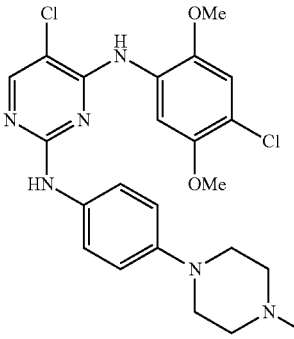<br>SG2-060-01<br>M.W. = 489.40 | No | 0.073 ± 0.13 | 20.51 | |
| 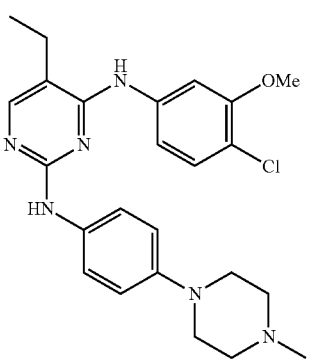<br>MA1-057<br>M.W. = 452.98 | No | 1.3 ± 0.11 | 7.98 | |
| 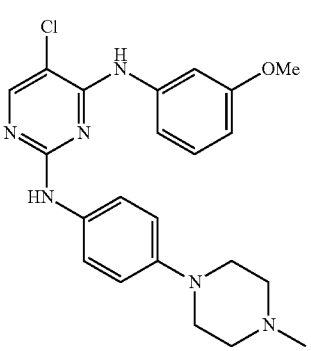 [SMILES: CCOc1cccc(Nc2nc(Nc3ccc(N4CCN(C)CC4)cc3)ncc2Cl)c1]<br>MA1-063<br>M.W. = 424.93 | No | 1.68 ± 0.078 | 5.96 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 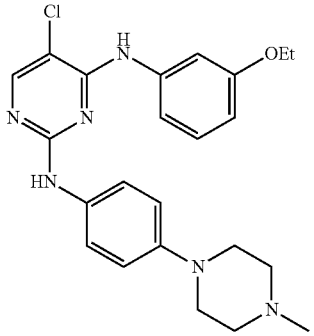<br>0.76 mg submitted on 07/03/2014<br>MA1-064<br>M.W. = 438.95 | Yes<br>(1.75 Å) | 4.3 ± 0.12 | 0.79 | |
| 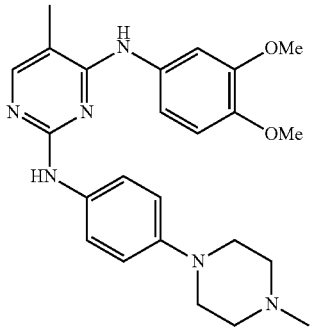 [SMILES: COc1ccc(Nc2nc(Nc3ccc(N4CCN(C)CC4)cc3)ncc2C)cc1OC]<br>MA1-065<br>M.W. = 434.53 | Yes<br>(1.75 Å) | 5.6 ± 0.059 | 0.29 | |
| 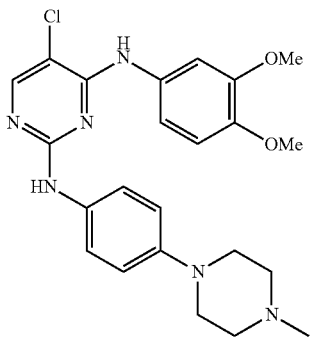<br>MA1-066<br>M.W. = 454.95 | No | 5.1 ± 0.039 | 0.43 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 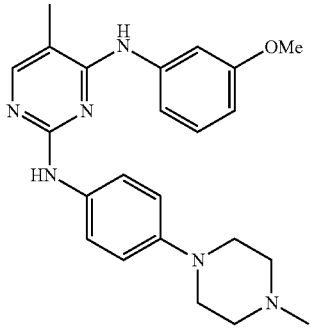<br>MA1-067<br>M.W. = 404.51 | Yes<br>(1.75 Å) | 3.2 ± 0.083 | 1.85 | |
| 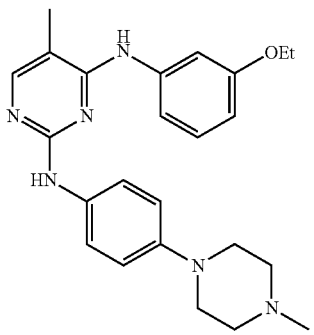<br>MA1-068<br>M.W. = 418.53 | Yes<br>(1.88Å) | 5.4 ± 0.15 | 0.34 | |
| 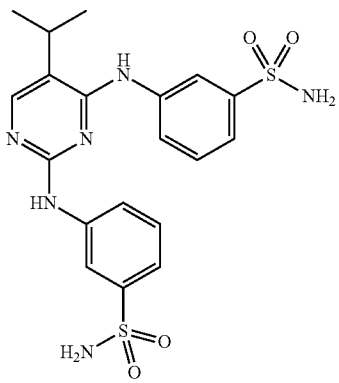<br>MA1-036B<br>M.W. = 462.55 | No | Not determined. | N/A | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 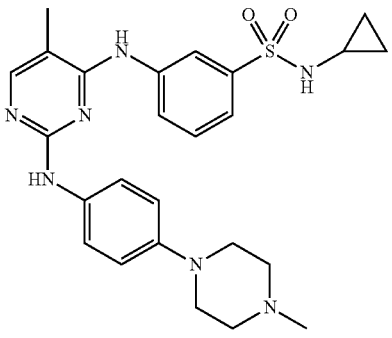 [SMILES: Cc1cnc(Nc2ccc(N3CCN(C)CC3)cc2)nc1Nc1cccc(S(=O)(=O)NC2CC2)c1]<br>RJ1-045-01<br>M.W. = 493.62 | Yes<br>(1.70 Å) | 7.3 ± 0.099 | 0.079 | HEK293<br>(IC$_{50}$ = 1.2 μM)<br>MM.1S<br>(IC$_{50}$ = 1.2 μM) |
| 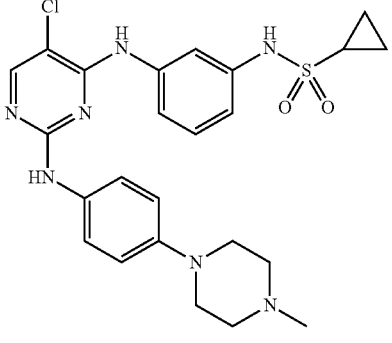<br>RJ1-051-01<br>M.W. = 514.04 | Yes<br>(1.84 Å) | 6.9 ± 0.15 | 0.11 | HEK293<br>(IC$_{50}$ = 3.6 μM) |
| 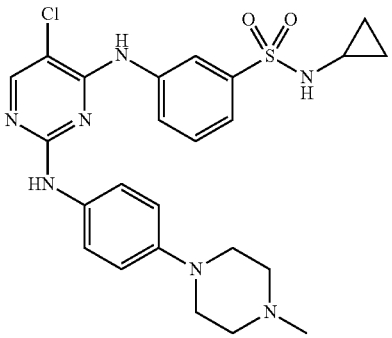 [SMILES: CN1CCN(c2ccc(Nc3ncc(Cl)c(Nc4cccc(S(=O)(=O)NC5CC5)c4)n3)cc2)CC1]<br>RJ1-053-01<br>M.W. = 514.04 | Yes<br>(1.93 Å) | 6.4 ± 0.15 | 0.16 | HEK293<br>(IC$_{50}$ = 1.8 μM)<br>MM.1S<br>(IC$_{50}$ = 0.88 μM) |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 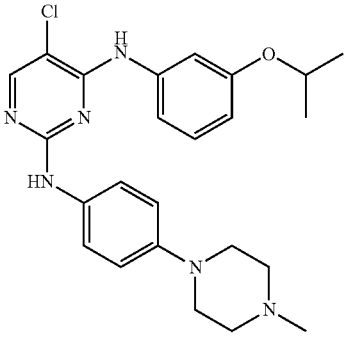 [SMILES: CC(C)Oc1cccc(Nc2nc(Nc3ccc(N4CCN(C)CC4)cc3)ncc2Cl)c1]<br>RJ1-057-01<br>M.W. = 452.98 | Yes<br>(1.70 Å) | 4.8 ± 0.12 | 0.54 | |
| 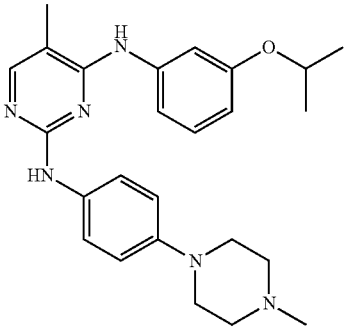<br>RJ1-060-01<br>M.W. = 432.56 | Yes<br>(1.78 Å) | 6.6 ± 0.10 | 0.14 | |
| 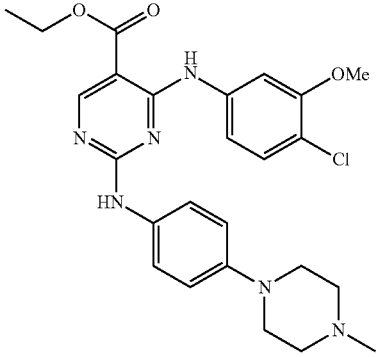<br>RJ1-064-01<br>M.W. = 496.99 | No | 0.24 ± 0.13 | 18 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 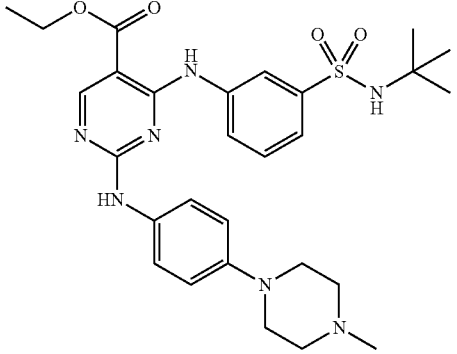<br>RJ1-066-01<br>M.W. = 567.70 | No | −0.0056 ± 0.24 | >20 | |
| 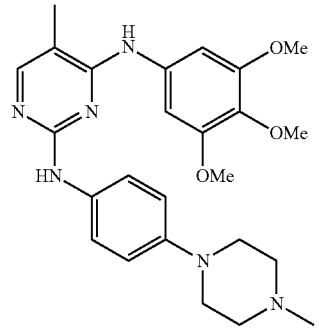 [SMILES: COc1cc(Nc2nc(Nc3ccc(N4CCN(C)CC4)cc3)ncc2C)cc(OC)c1OC]<br>SG2-063-01<br>M.W. = 464.56 | | 6.9 ± 0.10 | 0.11 | HEK293 (IC$_{50}$ = 0.97 μM) |
| 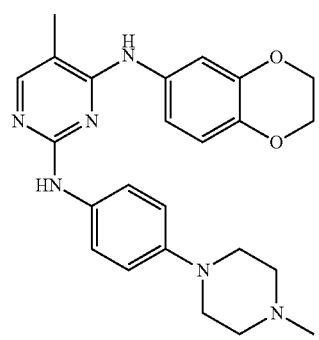 [SMILES: Cc1cnc(Nc2ccc(N3CCN(C)CC3)cc2)nc1Nc1ccc2c(c1)OCCO2]<br>SG2-064-01<br>M.W. = 432.52 | Partial (1.70 Å) | 4.4 ± 0.11 | 0.74 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 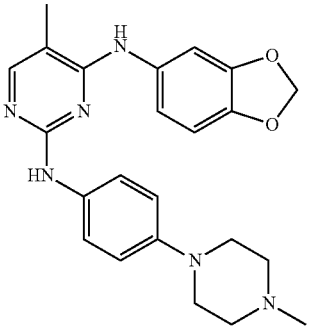 [SMILES: Cc1cnc(Nc2ccc(N3CCN(C)CC3)cc2)nc1Nc1ccc2c(c1)OCO2]<br>SG2-065-01<br>M.W. = 418.49 | No | 0.79 ± 0.079 | 12 | |
| 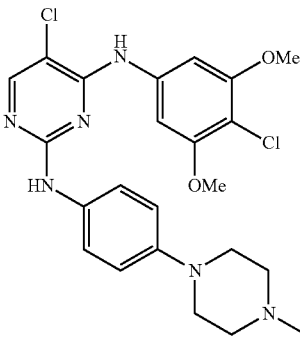<br>SG2-069-01<br>M.W. = 489.40 | | 2 ± 0.42 | 4.7 | |
| 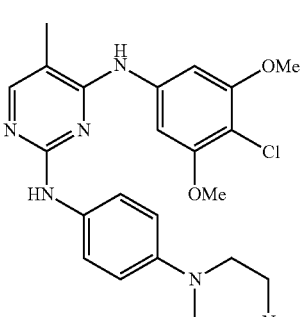<br>SG2-070-01<br>M.W. = 468.89 | Yes<br>(1.54 Å) | 7.6 ± 0.15 | 0.063 | MM.1S<br>(IC$_{50}$ = 1.1 μM) |
| 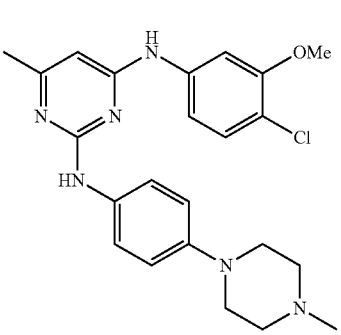<br>SG2-071-01<br>M.W. = 438.95 | | 2.6 ± 0.095 | 2.9 | |

TABLE 1-continued
| Name Molecular Wt (Amt. Supplied mg) | Co-crystal | DSF ΔTm (° C.) | Estimated BRD4 IC$_{50}$ (μM) | Comments |
|---|---|---|---|---|
| 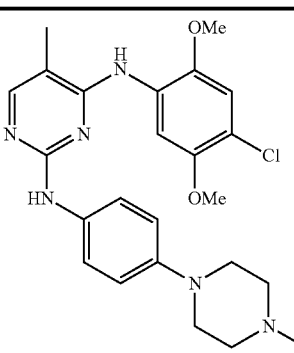 SG2-072-01 M.W. = 468.98 | | 0.57 ± 0.25 | 14 | |
| 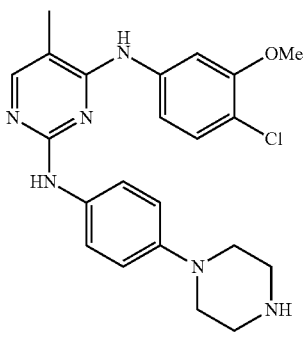 [SMILES: COc1cc(Nc2nc(Nc3ccc(N4CCNCC4)cc3)ncc2C)ccc1Cl] SG2-081-01 M.W. = 424.93 | Yes (1.50 Å) | 7.1 ± 0.15 | 0.092 | |
| 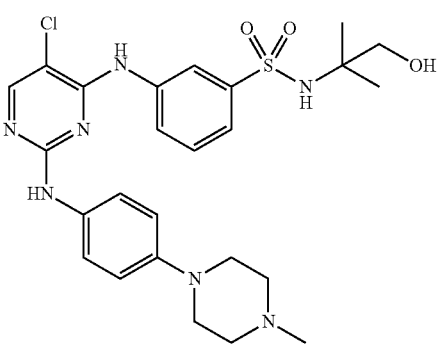 [SMILES: CN1CCN(c2ccc(Nc3ncc(Cl)c(Nc4cccc(S(=O)(=O)NC(C)(C)CO)c4)n3)cc2)CC1] SG2-085-01 M.W. = 546.08 | | 6.1 ± 0.15 | 0.2 | HEK293 (IC$_{50}$ = 1.5 μM) |
| 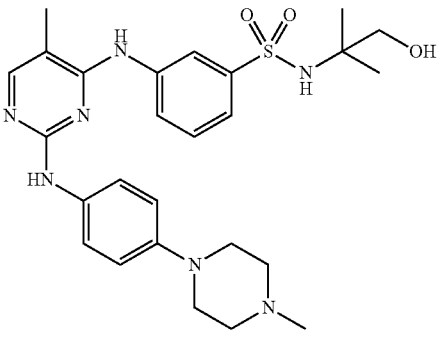 [SMILES: Cc1cnc(Nc2ccc(N3CCN(C)CC3)cc2)nc1Nc1cccc(S(=O)(=O)NC(C)(C)CO)c1] SG2-087-01 M.W. = 525.67 | | 6.5 ± 0.18 | 0.15 | HEK293 (IC$_{50}$ = 3.6 μM) |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 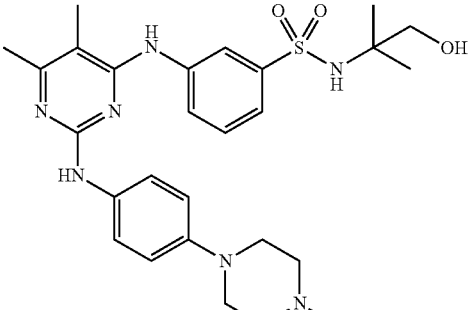<br>SG2-088-01<br>M.W. = 539.69 | | 5.5 ± 0.17 | 0.32 | HEK293 (IC$_{50}$ = 4.3 μM) |
| 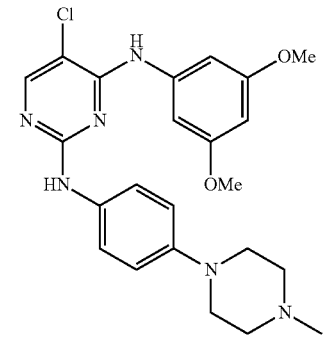<br>MA1-070<br>M.W. = 454.95 | | 3.5 ± 0.17 | 1.5 | |
| 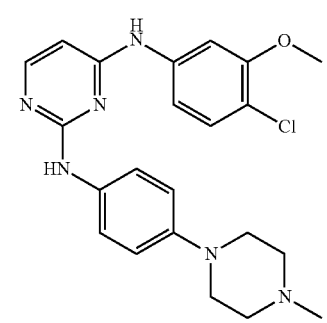 [SMILES: COc1cc(Nc2ccnc(Nc3ccc(N4CCN(C)CC4)cc3)n2)ccc1Cl]<br>MA1-094B<br>M.W. = 424.93 | No | 2.5 ± 0.069 | 3.2 | |
| 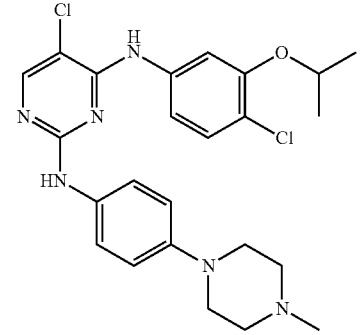 [SMILES: CC(C)Oc1cc(Nc2nc(Nc3ccc(N4CCN(C)CC4)cc3)ncc2Cl)ccc1Cl]<br>MA1-096-1<br>M.W. = 487.42 | Yes (1.42 Å) | Not determined | n/a | |

TABLE 1-continued
| Name<br>Molecular Wt (Amt. Supplied mg) | Co-crystal | DSF ΔTm (° C.) | Estimated BRD4 IC$_{50}$ (μM) | Comments |
| --- | --- | --- | --- | --- |
| 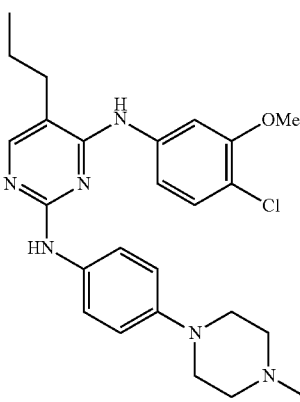<br>MA1-096-2<br>M.W. = 467.01 | Yes (1.60 Å) | 3.1 ± 0.075 | 2.0 | |
| 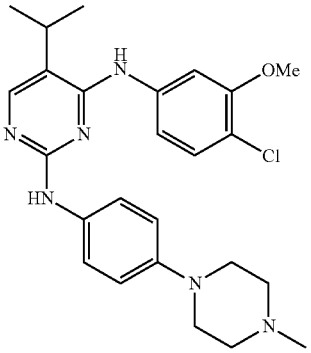 [SMILES: COc1cc(Nc2nc(Nc3ccc(N4CCN(C)CC4)cc3)ncc2C(C)C)ccc1Cl]<br>MA1-096-3<br>M.W. = 467.01 | No | 1.4 ± 0.11 | 7.4 | |
| 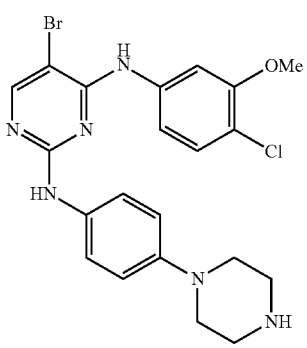 [SMILES: COc1cc(Nc2nc(Nc3ccc(N4CCNCC4)cc3)ncc2Br)ccc1Cl]<br>MA1-012<br>M.W. = 489.79 | Yes (1.60 Å) | 4.5 ± 0.10 | 0.68 | |

TABLE 1-continued
| Name Molecular Wt (Amt. Supplied mg) | Co-crystal | DSF ΔTm (° C.) | Estimated BRD4 IC$_{50}$ (μM) | Comments |
|---|---|---|---|---|
| 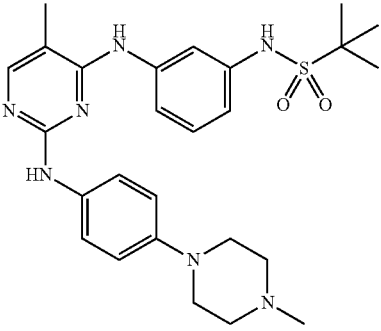 [SMILES: Cc1cnc(Nc2ccc(N3CCN(C)CC3)cc2)nc1Nc1cccc(NS(=O)(=O)C(C)(C)C)c1]<br>MA2-014<br>M.W. = 509.67 | Yes (1.76 Å) | 8.54 ± 0.088 | 0.025 | JAK2 (IC$_{50}$ RB = 0.4 nM) HEK293 (IC$_{50}$ = 1.2 μM) MM.1S (IC$_{50}$ = 0.40 μM) BRD2 IC$_{50}$ = 625 nM BRD3 IC$_{50}$ = 12.5 nM BRD4 IC$_{50}$ = 10.2 nM BRDT IC$_{50}$ = 29.1 nM (RB)<br><br>JAK1 IC$_{50}$ = 4.58 nM<br>JAK2 IC$_{50}$ = 2.70 nM<br>JAK3 IC$_{50}$ = 91.4 nM (RB) |
| 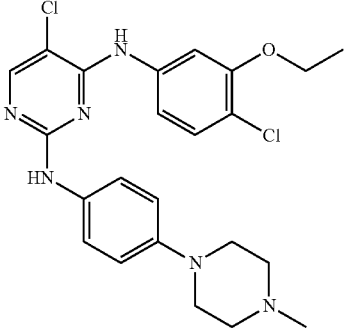 [SMILES: CCOc1cc(Nc2nc(Nc3ccc(N4CCN(C)CC4)cc3)ncc2Cl)ccc1Cl]<br>MA2-024-1<br>M.W. = 473.40 | Yes (1.42 Å) | 3.7 ± 0.12 | 1.3 | |
| 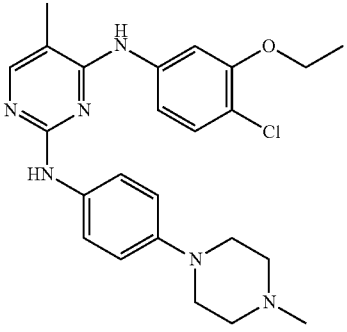 [SMILES: CCOc1cc(Nc2nc(Nc3ccc(N4CCN(C)CC4)cc3)ncc2C)ccc1Cl]<br>MA2-024-2<br>M.W. = 452.98 | Yes (1.55 Å) | 6.4 ± 0.0066 | 0.16 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 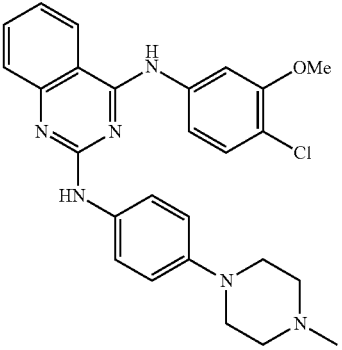 [SMILES: COc1cc(Nc2nc(Nc3ccc(N4CCN(C)CC4)cc3)nc3ccccc23)ccc1Cl]<br>MA2-032<br>M.W. = 474.99 | Partial (1.57 Å) | 4.9 ± 0.13 | 0.5 | HEK293 (IC$_{50}$ = 1.7 μM) |
| 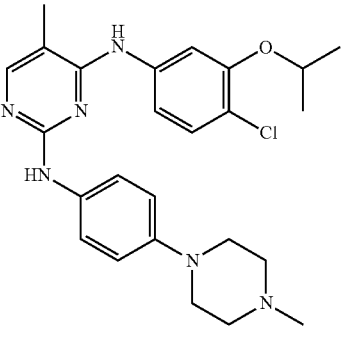 [SMILES: Cc1cnc(Nc2ccc(N3CCN(C)CC3)cc2)nc1Nc1ccc(Cl)c(OC(C)C)c1]<br>MA2-031<br>M.W. = 467.00 | Yes | 6.3 ± 0.10 | 0.17 | |
| 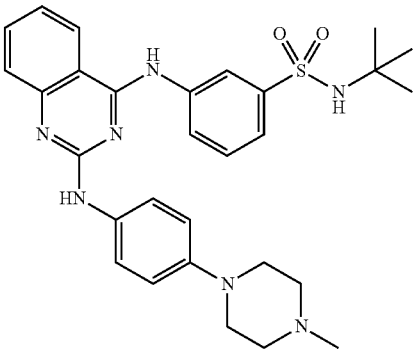 [SMILES: CN1CCN(c2ccc(Nc3nc(Nc4cccc(S(=O)(=O)NC(C)(C)C)c4)c4ccccc4n3)cc2)CC1]<br>MA2-034<br>M.W. = 545.69 | | 2.6 ± 0.081 | 2.9 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 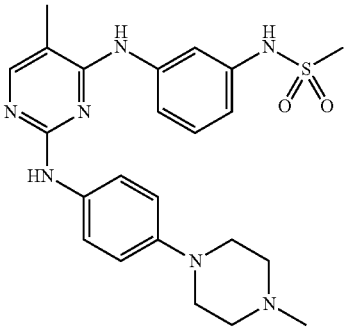 [SMILES: Cc1cnc(Nc2ccc(N3CCN(C)CC3)cc2)nc1Nc1cccc(NS(C)(=O)=O)c1]<br>MA2-046<br>M.W. = 467.58 | | 4.6 ± 0.13 | 0.63 | |
| 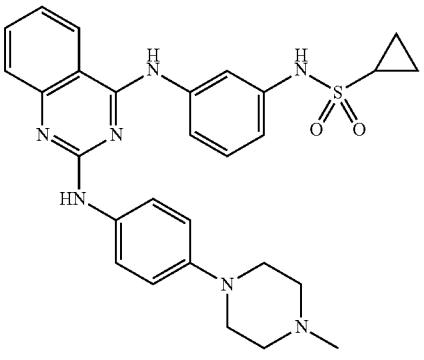 [SMILES: CN1CCN(c2ccc(Nc3nc(Nc4cccc(NS(=O)(=O)C5CC5)c4)c4ccccc4n3)cc2)CC1]<br>MA2-047<br>M.W. = 529.66 | | 5.8 ± 0.11 | 0.26 | |
| 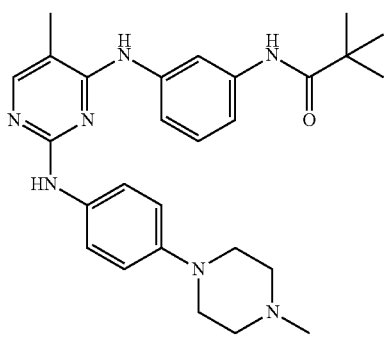 [SMILES: Cc1cnc(Nc2ccc(N3CCN(C)CC3)cc2)nc1Nc1cccc(NC(=O)C(C)(C)C)c1]<br>MA2-052-1<br>M.W. = 473.61 | | 3.5 ± 0.19 | 1.5 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 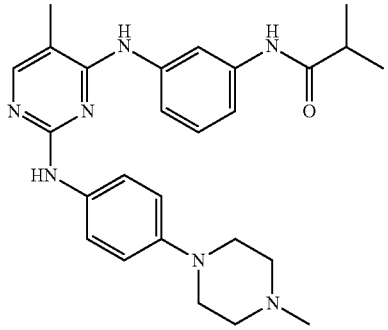<br>MA2-052-2<br>M.W. = 459.58 | | 4.1 ± 0.12 | 0.90 | |
| 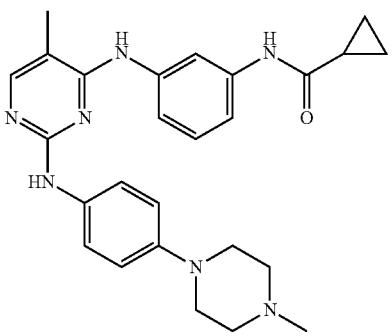<br>MA2-052-3<br>M.W. = 457.57 | | 4.6 ± 0.21 | 0.63 | |
| 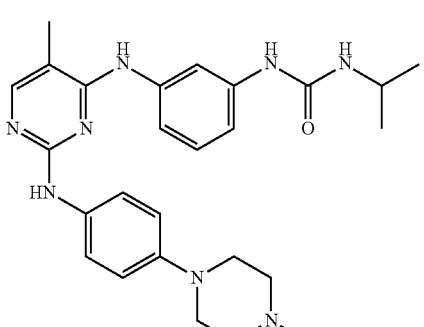<br>MA2-082-2<br>M.W. = 474.60 | | 2.1 ± 0.10 | 4.3 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 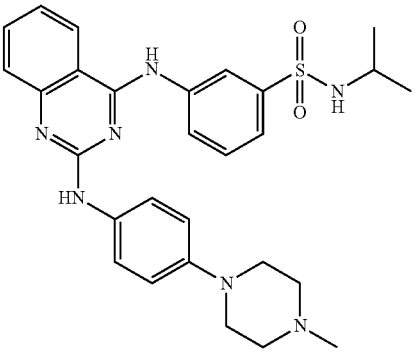<br>1.02 mg submitted on 09/05/2014<br>MA2-085<br>M.W. = 531.67 | | 5.0 ± 0.13 | 0.48 | |
| 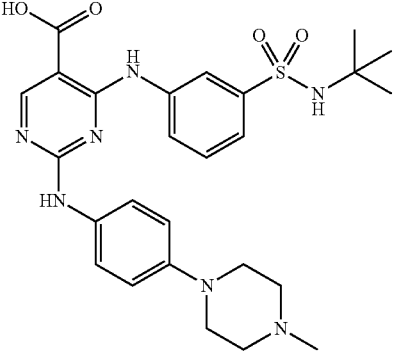 [SMILES: CN1CCN(c2ccc(Nc3ncc(C(=O)O)c(Nc4cccc(S(=O)(=O)NC(C)(C)C)c4)n3)cc2)CC1]<br>SG2-086-01<br>M.W. = 539.65 | | −0.20 ± 0.20 | 25 | |
| 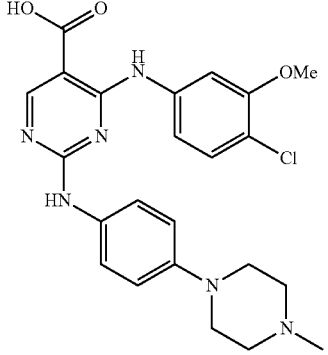 [SMILES: COc1cc(Nc2nc(Nc3ccc(N4CCN(C)CC4)cc3)ncc2C(=O)O)ccc1Cl]<br>SG2-102<br>M.W. = 468.94 | | 0.0094 ± 0.11 | 22 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 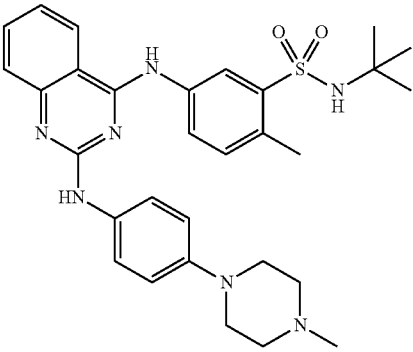 [SMILES: Cc1ccc(Nc2nc(Nc3ccc(N4CCN(C)CC4)cc3)nc3ccccc23)cc1S(=O)(=O)NC(C)(C)C]<br>SG2-120<br>M.W. = 559.73 | | 6.1 ± 0.032 | 0.20 | |
| 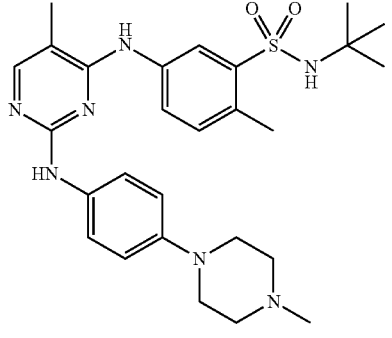 [SMILES: Cc1ccc(Nc2nc(Nc3ccc(N4CCN(C)CC4)cc3)ncc2C)cc1S(=O)(=O)NC(C)(C)C]<br>SG2-121<br>M.W. = 523.69 | Yes | 8.6 ± 0.090 | 0.030 | |
| 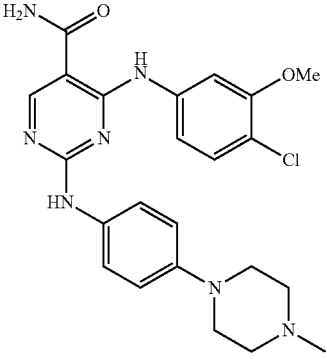 [SMILES: COc1cc(Nc2nc(Nc3ccc(N4CCN(C)CC4)cc3)ncc2C(N)=O)ccc1Cl]<br>SG2-135<br>M.W. = 467.95 | | Not determined | N/A | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 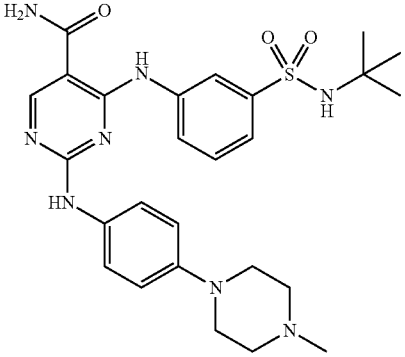 [SMILES: CN1CCN(c2ccc(Nc3ncc(C(N)=O)c(Nc4cccc(S(=O)(=O)NC(C)(C)C)c4)n3)cc2)CC1]<br>SG2-142-01<br>M.W. = 538.66 | | 2.7 ± 0.0089 | 2.7 | |
| 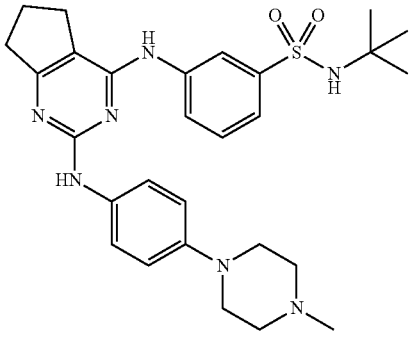 [SMILES: CN1CCN(c2ccc(Nc3nc4c(c(Nc5cccc(S(=O)(=O)NC(C)(C)C)c5)n3)CCC4)cc2)CC1]<br>MA3-006-1<br>M.W. = 535.70 | | 4.9 ± 0.11 | 0.50 | |
| 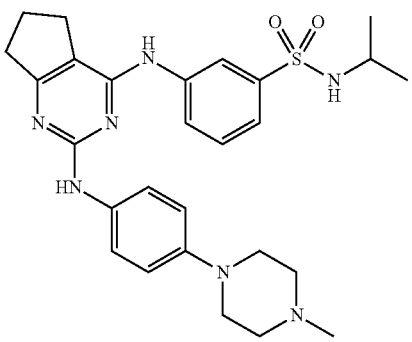<br>MA3-006-2<br>M.W. = 521.68 | | 3.8 ± 0.056 | 1.2 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 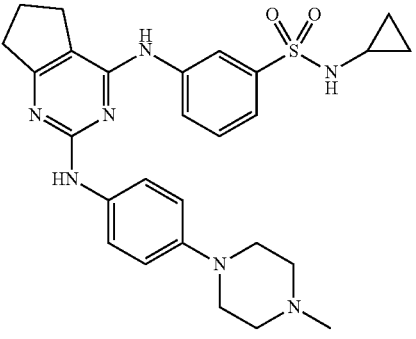 [SMILES: CN1CCN(c2ccc(Nc3nc4c(c(Nc5cccc(S(=O)(=O)NC6CC6)c5)n3)CCC4)cc2)CC1]<br>MA3-006-3<br>M.W. = 519.66 | | 4.9 ± 0.099 | 0.52 | |
| 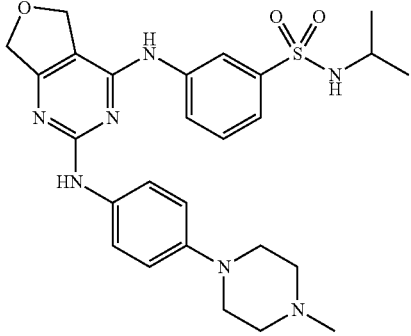 [SMILES: CC(C)NS(=O)(=O)c1cccc(Nc2nc(Nc3ccc(N4CCN(C)CC4)cc3)nc3c2COC3)c1]<br>MA3-012-2<br>M.W. = 523.65 | | 0.60 ± 0.14 | 14 | |
| 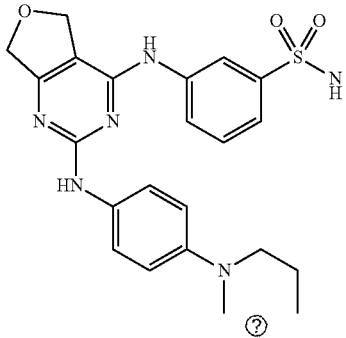<br>MA3-012-3<br>M.W. = 521.63 | | 2.9 ± 0.084 | 2.3 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 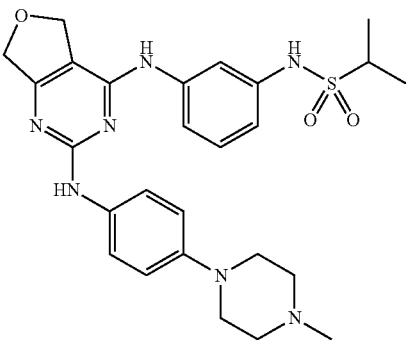 [SMILES: CC(C)S(=O)(=O)Nc1cccc(Nc2nc(Nc3ccc(N4CCN(C)CC4)cc3)nc3c2COC3)c1]<br>MA3-018<br>M.W. = 523.65 | | 3.9 ± 0.24 | 1.0 | |
| 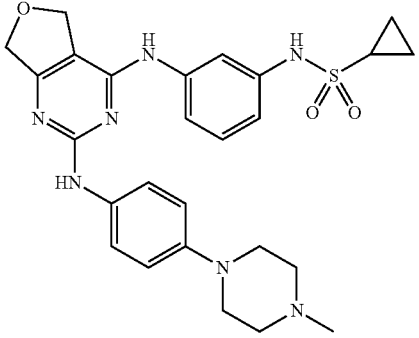 [SMILES: CN1CCN(c2ccc(Nc3nc4c(c(Nc5cccc(NS(=O)(=O)C6CC6)c5)n3)COC4)cc2)CC1]<br>MA3-022<br>M.W. = 521.63 | | 1.3 ± 0.12 | 7.9 | |
| 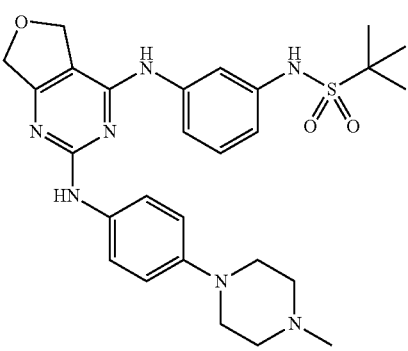 [SMILES: CN1CCN(c2ccc(Nc3nc4c(c(Nc5cccc(NS(=O)(=O)C(C)(C)C)c5)n3)COC4)cc2)CC1]<br>MA3-023<br>M.W. = 537.68 | | 6.0 ± 0.13 | 0.22 | |

TABLE 1-continued
| Name<br>Molecular Wt (Amt. Supplied mg) | Co-crystal | DSF ΔTm (° C.) | Estimated BRD4 IC$_{50}$ (μM) | Comments |
| --- | --- | --- | --- | --- |
| 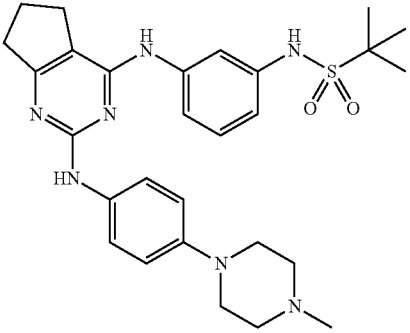 [SMILES: CN1CCN(c2ccc(Nc3nc4c(c(Nc5cccc(NS(=O)(=O)C(C)(C)C)c5)n3)CCC4)cc2)CC1]<br>MA3-024-1<br>M.W. = 535.70 | | 6.4 ± 0.12 | 0.15 | |
| 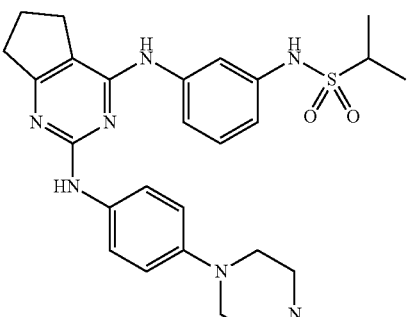<br>MA3-024-2<br>M.W. = 521.68 | | 4.3 ± 0.14 | 0.77 | |
| 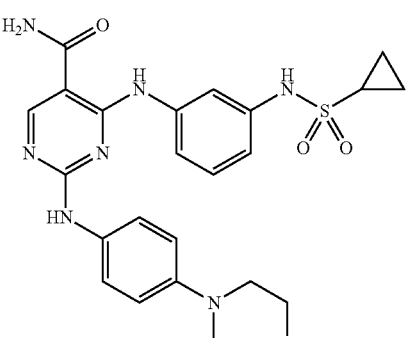<br>SG2-147<br>M.W. = 522.62 | | 2.3 ± 0.073 | 3.8 | |

TABLE 1-continued
| Name<br>Molecular Wt (Amt. Supplied mg) | Co-crystal | DSF ΔTm (° C.) | Estimated BRD4 IC$_{50}$ (μM) | Comments |
| --- | --- | --- | --- | --- |
| 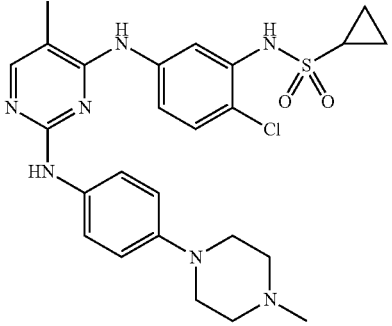 [SMILES: Cc1cnc(Nc2ccc(N3CCN(C)CC3)cc2)nc1Nc1ccc(Cl)c(NS(=O)(=O)C2CC2)c1]<br>SG2-180<br>M.W. = 528.07 | Yes | 7.0 ± 0.14 | 0.10 | |
| 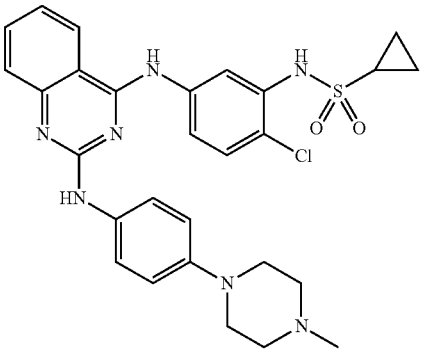 [SMILES: CN1CCN(c2ccc(Nc3nc(Nc4ccc(Cl)c(NS(=O)(=O)C5CC5)c4)c4ccccc4n3)cc2)CC1]<br>SG2-181<br>M.W. = 564.10 | | Not determined | N/A | |
| 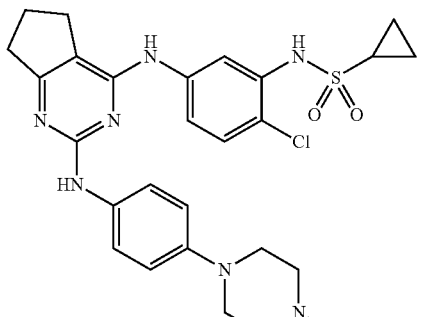<br>SG2-182<br>M.W. = 554.11 | | 4.6 ± 0.050Δ | 0.62 | |

TABLE 1-continued

| Name Molecular Wt (Amt. Supplied mg) | Co-crystal | DSF ΔTm (° C.) | Estimated BRD4 IC$_{50}$ (μM) | Comments |
|---|---|---|---|---|
| 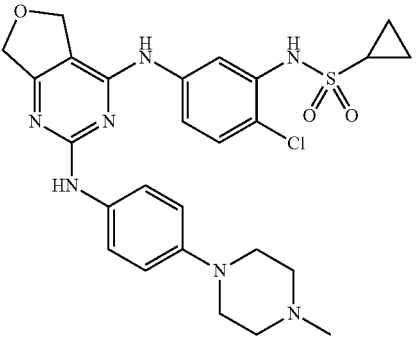 [SMILES: CN1CCN(c2ccc(Nc3nc4c(c(Nc5ccc(Cl)c(NS(=O)(=O)C6CC6)c5)n3)COC4)cc2)CC1]<br>SG2-183<br>M.W. = 556.08 | | 5.4 ± 0.20 | 0.35 | |
| 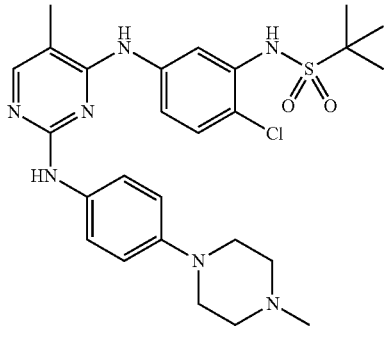<br>SG3-014<br>M.W. = 544.11 | Yes | 9.57 ± 0.086 | 0.010 | MM.1S IC$_{50}$ = 0.074 μM MM1.S (IC$_{50}$ = 0.142 μM) BRD2 IC$_{50}$ = 81.4 nM BRD3 IC$_{50}$ = 16.5 nM BRD4 IC$_{50}$ = 4.04 nM BRDT IC$_{50}$ = 27.8 nM (RB) JAK1 IC$_{50}$ = n.d. JAK2 IC$_{50}$ = 11.2 nM JAK3 IC$_{50}$ = n.d. (RB) Solubility 650 uM in PBS buffer (~9.3% DMSO) = 0.416 mg SG3-014B2.MSA in 1 mL PBS buffer (~9.3% DMSO) Solubility > 14.4 mg SG3-014B2.MSA in 1 mL PBS buffer (15% HPCD) |
| 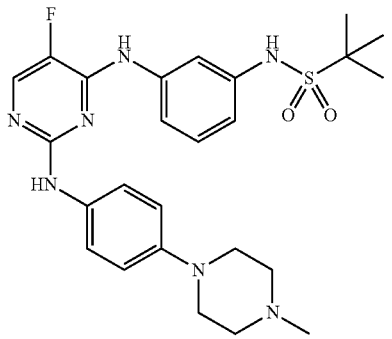 [SMILES: CN1CCN(c2ccc(Nc3ncc(F)c(Nc4cccc(NS(=O)(=O)C(C)(C)C)c4)n3)cc2)CC1]<br>MA3-066<br>M.W. = 513.63 | | 5.2 ± 0.15 | 0.40 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 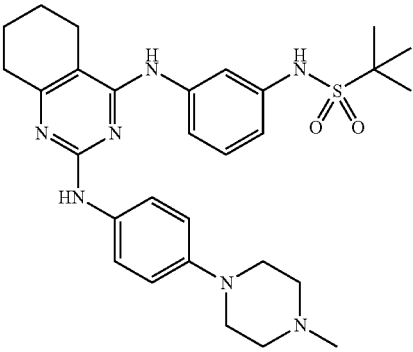 [SMILES: CN1CCN(c2ccc(Nc3nc4c(c(Nc5cccc(NS(=O)(=O)C(C)(C)C)c5)n3)CCCC4)cc2)CC1]<br>MA3-068-1<br>M.W. = 549.73 | | 6.9 ± 0.038 | 0.11 | MM1.S (IC$_{50}$ = 1.7 μM)<br>Saos-2 (IC$_{50}$ = 2.5 μM) |
| 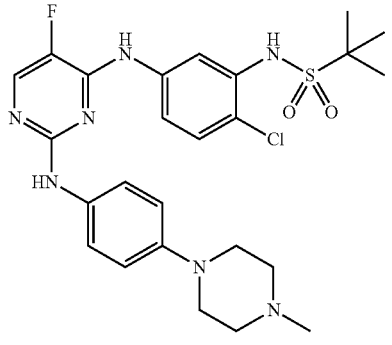 [SMILES: CN1CCN(c2ccc(Nc3ncc(F)c(Nc4ccc(Cl)c(NS(=O)(=O)C(C)(C)C)c4)n3)cc2)CC1]<br>MA3-072<br>M.W. = 548.08 | | 7.2 ± 0.17 | 0.085 | |
| 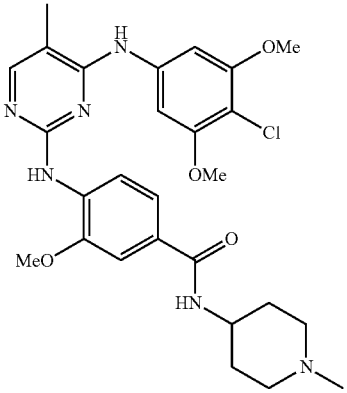 [SMILES: COc1cc(C(=O)NC2CCN(C)CC2)ccc1Nc1ncc(C)c(Nc2cc(OC)c(Cl)c(OC)c2)n1]<br>SG3-026-02<br>M.W. = 541.04 | | 3.0 ± 0.11 | 2.2 | |

TABLE 1-continued
| Name Molecular Wt (Amt. Supplied mg) | Co-crystal | DSF ΔTm (° C.) | Estimated BRD4 IC$_{50}$ (μM) | Comments |
|---|---|---|---|---|
| 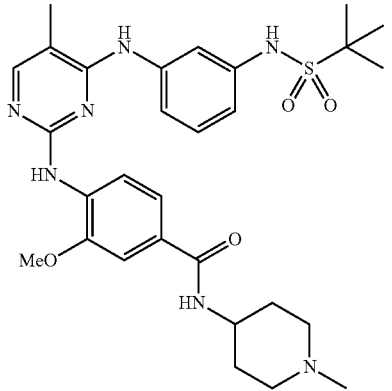 [SMILES: COc1cc(C(=O)NC2CCN(C)CC2)ccc1Nc1ncc(C)c(Nc2cccc(NS(=O)(=O)C(C)(C)C)c2)n1]<br>SG3-059-01<br>M.W. = 581.73 | | NA | NA | |
| 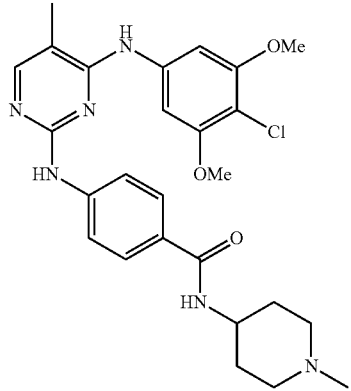 [SMILES: COc1cc(Nc2nc(Nc3ccc(C(=O)NC4CCN(C)CC4)cc3)ncc2C)cc(OC)c1Cl]<br>SG3-064<br>M.W. = 511.02 | | 5.9 ± 0.063 | 2.3 | |
| 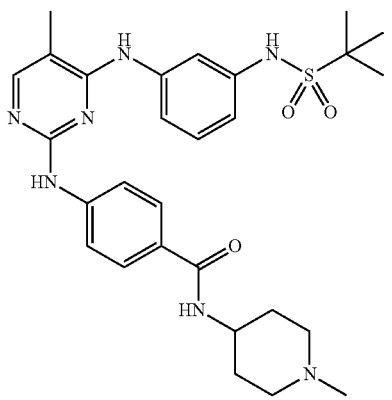 [SMILES: Cc1cnc(Nc2ccc(C(=O)NC3CCN(C)CC3)cc2)nc1Nc1cccc(NS(=O)(=O)C(C)(C)C)c1]<br>SG3-065<br>M.W. = 551.70 | | 7.6 ± 0.047 | 0.062 | |

TABLE 1-continued
| Name Molecular Wt (Amt. Supplied mg) | Co-crystal | DSF ΔTm (° C.) | Estimated BRD4 IC$_{50}$ (μM) | Comments |
|---|---|---|---|---|
| 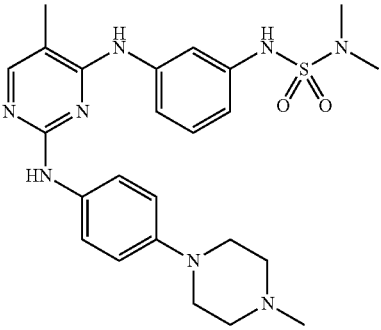 [SMILES: Cc1cnc(Nc2ccc(N3CCN(C)CC3)cc2)nc1Nc1cccc(NS(=O)(=O)N(C)C)c1]SG3-043A M.W. = 496.63 | | 3.3 ± 0.36 | 1.8 | |
| 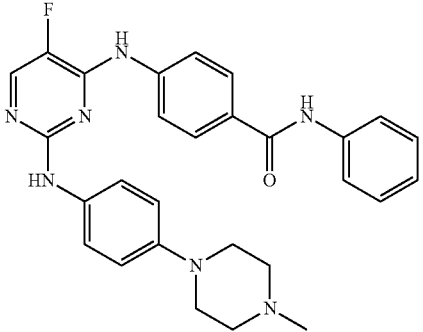 [SMILES: CN1CCN(c2ccc(Nc3ncc(F)c(Nc4ccc(C(=O)Nc5ccccc5)cc4)n3)cc2)CC1]SG3-073 M.W. = 497.57 | | 0.35 ± 0.068 | 17 | |
| 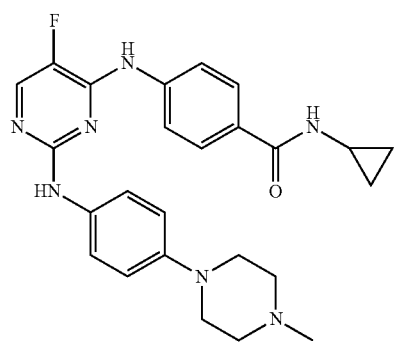 [SMILES: CN1CCN(c2ccc(Nc3ncc(F)c(Nc4ccc(C(=O)NC5CC5)cc4)n3)cc2)CC1]SG3-081 M.W. = 461.53 | | 3.4 ± 0.27 | 1.6 | |
| 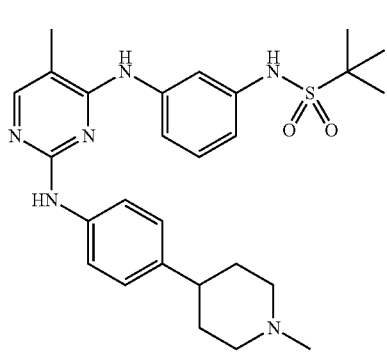SG3-082 M.W. = 508.68 | | 7.6 ± 0.28 | 0.061 | |

TABLE 1-continued
| Name<br>Molecular Wt (Amt. Supplied mg) | Co-crystal | DSF ΔTm (° C.) | Estimated BRD4 IC$_{50}$ (μM) | Comments |
| --- | --- | --- | --- | --- |
| 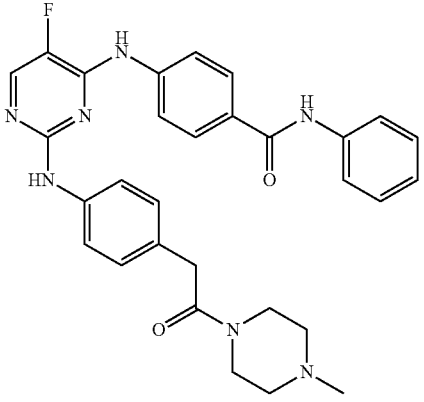 [SMILES: CN1CCN(C(=O)Cc2ccc(Nc3ncc(F)c(Nc4ccc(C(=O)Nc5ccccc5)cc4)n3)cc2)CC1]<br>SG3-075<br>M.W. = 539.60 | | Not determined | n/a | |
| 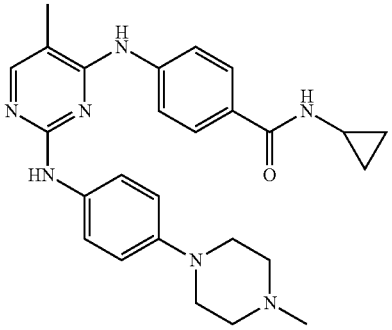 [SMILES: Cc1cnc(Nc2ccc(N3CCN(C)CC3)cc2)nc1Nc1ccc(C(=O)NC2CC2)cc1]<br>SG3-087-01<br>M.W. = 457.57 | | 6.5 ± 0.11 | 0.15 | |
| 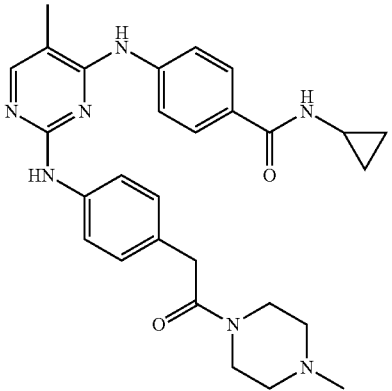 [SMILES: Cc1cnc(Nc2ccc(CC(=O)N3CCN(C)CC3)cc2)nc1Nc1ccc(C(=O)NC2CC2)cc1]<br>SG3-092<br>M.W. = 499.61 | | 6.8 ± 0.15 | 0.11 | |

| Name Molecular Wt (Amt. Supplied mg) | Co-crystal | DSF ΔTm (° C.) | Estimated BRD4 IC$_{50}$ (μM) | Comments |
|---|---|---|---|---|
| 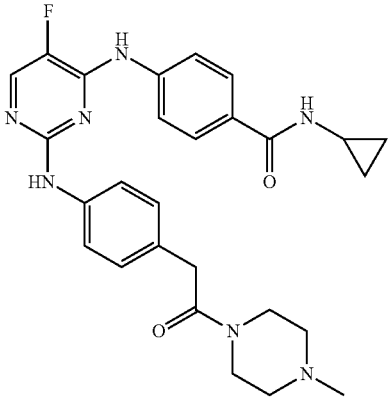 [SMILES: CN1CCN(C(=O)Cc2ccc(Nc3ncc(F)c(Nc4ccc(C(=O)NC5CC5)cc4)n3)cc2)CC1]<br>SG3-094<br>M.W. = 503.57 | | 4.2 ± 0.20 | 0.85 | |
| 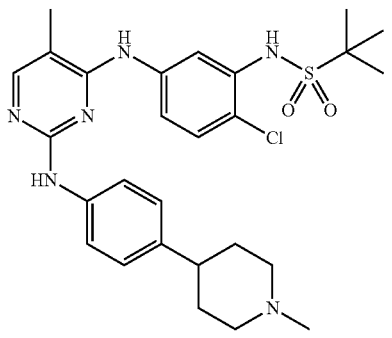 [SMILES: Cc1cnc(Nc2ccc(C3CCN(C)CC3)cc2)nc1Nc1ccc(Cl)c(NS(=O)(=O)C(C)(C)C)c1]<br>SG3-111<br>M.W. = 543.12 | yes | 10 ± 0.11<br>10 ± 0.11 | 0.0074<br>0.0099 | UKE-1<br>(IC$_{50}$ = 0.47 μM)<br>MV-4-11<br>(IC$_{50}$ = 0.098 μM) |
| 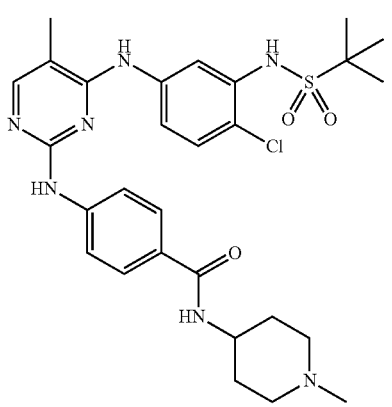 [SMILES: Cc1cnc(Nc2ccc(C(=O)NC3CCN(C)CC3)cc2)nc1Nc1ccc(Cl)c(NS(=O)(=O)C(C)(C)C)c1]<br>SG3-112<br>M.W. = 586.15 | Yes | 11 ± 0.12<br>11 ± 0.12 | 0.0061<br>0.0046 | UKE-1<br>(IC$_{50}$ = 1.6 μM)<br>MV-4-11<br>(IC$_{50}$ = 0.071 μM) |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 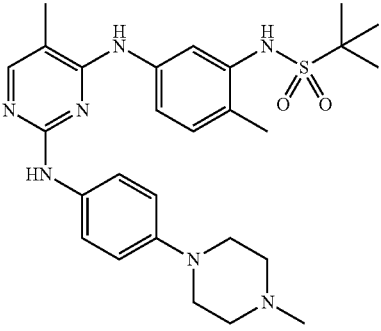 [SMILES: Cc1ccc(Nc2nc(Nc3ccc(N4CCN(C)CC4)cc3)ncc2C)cc1NS(=O)(=O)C(C)(C)C]<br>SG3-127<br>M.W. = 523.69 | | 9.2 ± 0.12 | 0.018 | |
| 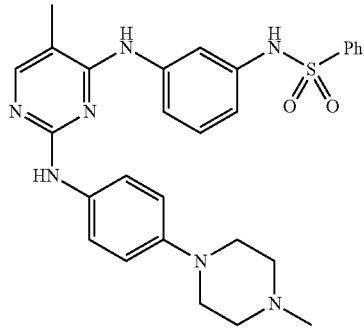 [SMILES: Cc1cnc(Nc2ccc(N3CCN(C)CC3)cc2)nc1Nc1cccc(NS(=O)(=O)c2ccccc2)c1]<br>MA4-012-1<br>M.W. = 529.66 | | 4.1 ± 0.07 | 0.900 | |
| 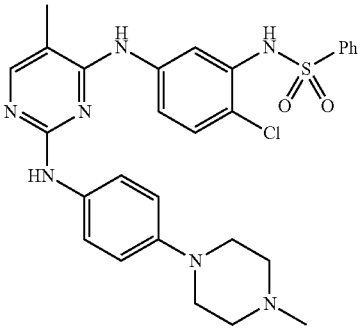 [SMILES: Cc1cnc(Nc2ccc(N3CCN(C)CC3)cc2)nc1Nc1cccc(NS(=O)(=O)c2ccccc2)c1]<br>MA4-012-2<br>M.W. = 564.10 | | 4.1 ± 0.10 | 0.960 | |
| 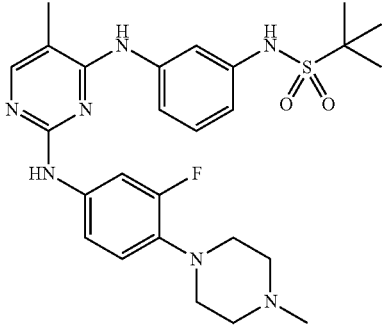 [SMILES: Cc1cnc(Nc2ccc(N3CCN(C)CC3)c(F)c2)nc1Nc1cccc(NS(=O)(=O)C(C)(C)C)c1]<br>MA4-022-1<br>M.W. = 527.66 | Yes | 9.5 ± 0.14<br>11.2 ± 0.15 | 0.014<br>0.0039 | MM1.S<br>(IC$_{50}$ = 0.16 μM)<br>(IC$_{50}$ = 0.146 μM)<br>Saos-2<br>(IC$_{50}$ = 0.133 μM)<br>NCI-H2052<br>(IC$_{50}$ = 1.4 μM)<br>UKE-1<br>(IC$_{50}$ = 0.200 μM)<br>MV-4-11<br>(IC$_{50}$ = 0.0268 μM) |

TABLE 1-continued
| Name Molecular Wt (Amt. Supplied mg) | Co-crystal | DSF ΔTm (° C.) | Estimated BRD4 IC$_{50}$ (μM) | Comments |
|---|---|---|---|---|
| 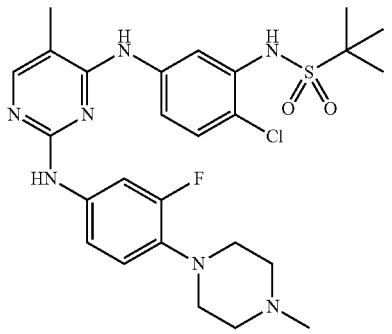 [SMILES: Cc1cnc(Nc2ccc(N3CCN(C)CC3)c(F)c2)nc1Nc1ccc(Cl)c(NS(=O)(=O)C(C)(C)C)c1]<br>MA4-022-2<br>M.W. = 562.10 | Yes | 11 ± 0.04<br>12.6 ± 0.069 | 0.0048<br>0.0013 | MM1.S<br>(IC$_{50}$ = 0.059 μM)<br>(IC$_{50}$ = 0.064 μM)<br>(IC$_{50}$ = 0.066 μM)<br>Saos-2<br>(IC$_{50}$ = 0.320 μM)<br>NCI-H2052<br>(IC$_{50}$ = 2.5 μM)<br>UKE-1<br>(IC$_{50}$ = 0.294 μM)<br>MV-4-11<br>(IC$_{50}$ = 0.0532 μM) |
| 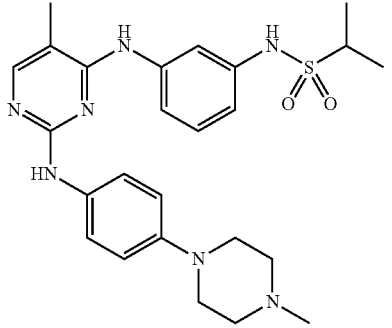 [SMILES: Cc1cnc(Nc2ccc(N3CCN(C)CC3)cc2)nc1Nc1cccc(NS(=O)(=O)C(C)C)c1]<br>MA4-026<br>M.W. = 495.65 | | 7.5 ± 0.14 | 0.066 | |
| 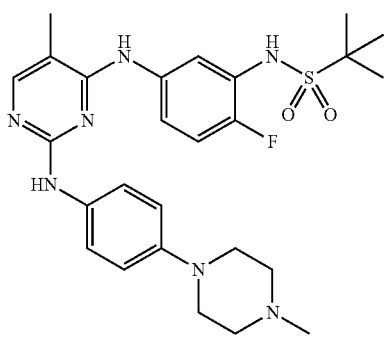 [SMILES: Cc1cnc(Nc2ccc(N3CCN(C)CC3)cc2)nc1Nc1ccc(F)c(NS(=O)(=O)C(C)(C)C)c1]<br>MA4-034<br>M.W. = 527.66 | | 9.5 ± 0.07 | 0.014 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 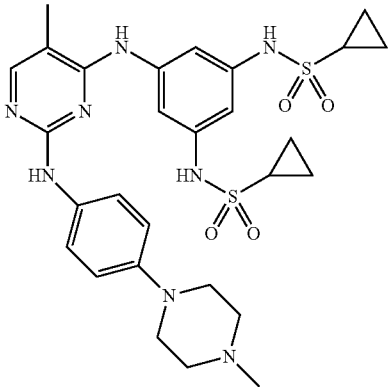 [SMILES: Cc1cnc(Nc2ccc(N3CCN(C)CC3)cc2)nc1Nc1cc(NS(=O)(=O)C2CC2)cc(NS(=O)(=O)C2CC2)c1]<br>MA4-084<br>M.W. = 612.77 | | 5.3 ± 0.041 | 0.370 | |
| 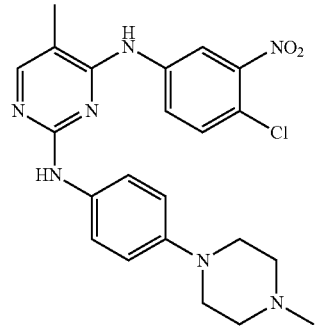<br>SG3-155<br>M.W. = 453.92 | | 2.0 ± 0.05 | 4.70 | |
| 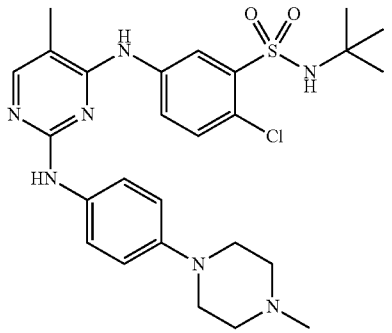 [SMILES: Cc1cnc(Nc2ccc(N3CCN(C)CC3)cc2)nc1Nc1ccc(Cl)c(S(=O)(=O)NC(C)(C)C)c1]<br>SG3-158<br>M.W. = 544.11 | | 8.4 ± 0.13 | 0.034 | |

| Name Molecular Wt (Amt. Supplied mg) | Co-crystal | DSF ΔTm (° C.) | Estimated BRD4 IC$_{50}$ (μM) | Comments |
|---|---|---|---|---|
| 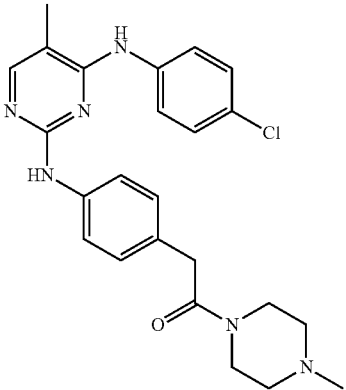<br>SG3-166<br>M.W. = 450.96 | | 4.1 ± 0.21 | 0.930 | |
| 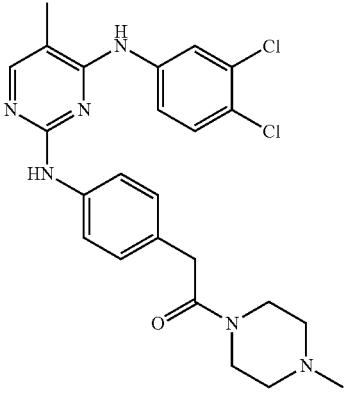<br>SG3-167<br>M.W. = 485.41 | | 4.7 ± 0.14 | 0.580 | |
| 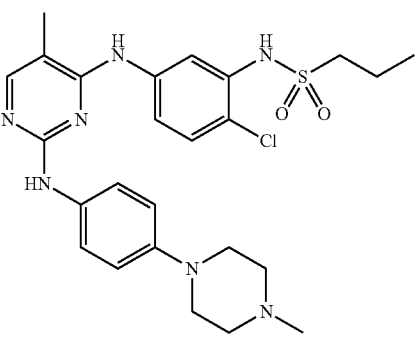<br>SG3-170<br>M.W. = 530.09 | | 6.7 ± 0.15 | 0.130 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 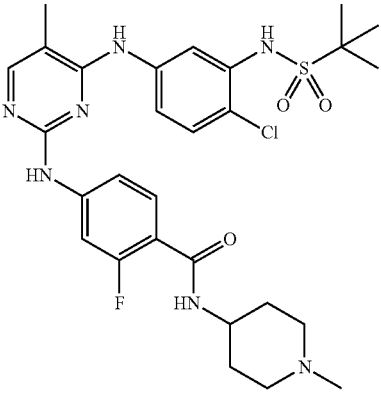 [SMILES: Cc1cnc(Nc2ccc(C(=O)NC3CCN(C)CC3)c(F)c2)nc1Nc1ccc(Cl)c(NS(=O)(=O)C(C)(C)C)c1]<br>SG3-179<br>M.W. = 604.14 | Yes | 12.5 ± 0.165 | 0.0013 | MM 1.S (IC$_{50}$ = 0.057 μM, n = 2)<br>NCI-H2052 (IC$_{50}$ = >10 μM)<br>UKE-1 (IC$_{50}$ = 0.22 μM)<br>MV-4-11 (IC$_{50}$ = 0.038 μM) |
| 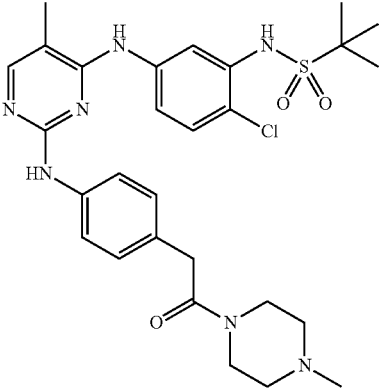<br>SG3-180<br>M.W. = 586.15 | | 9.8 ± 0.03 | 0.012 | |
| 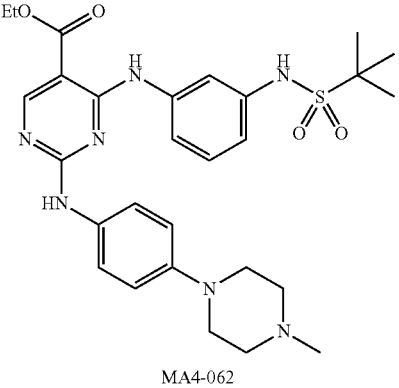<br>MA4-062<br>M.W. = 567.71 | | 3.4 ± 0.12 | 1.60 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 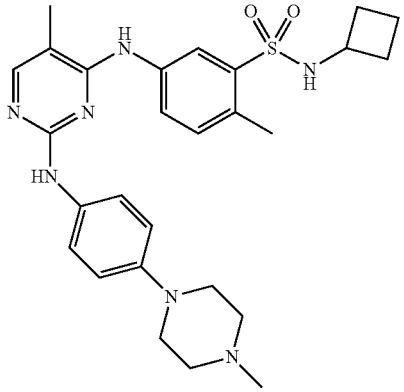<br>MA4-088<br>M.W. = 521.68 | | 6.7 ± 0.13 | 0.130 | |
| 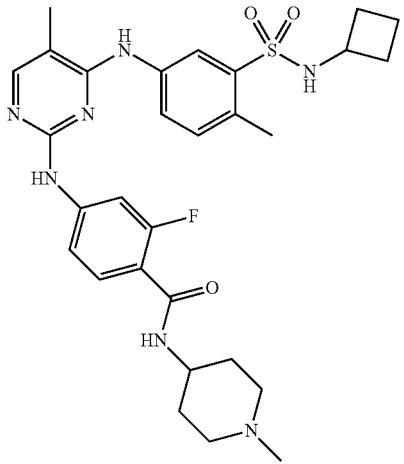<br>MA4-089<br>M.W. = 581.71 | | 7.8 ± 0.15 | 0.054 | |
| 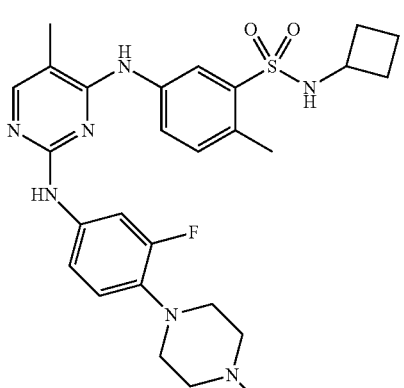<br>MA4-090<br>M.W. = 539.67 | | 6.8 ± 0.01 | 0.120 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 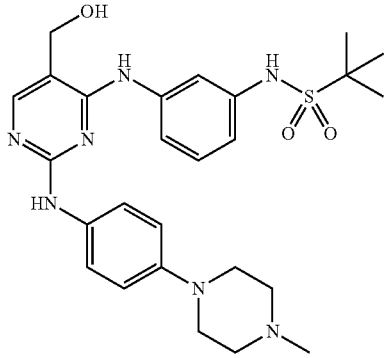<br>MA2-094<br>M.W. = 525.67 | | 3.1 ± 0.08 | 2.00 | |
| 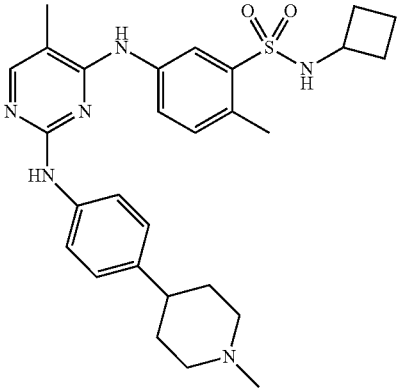<br>MA4-100<br>M.W. = 520.70 | | 7.7 ± 0.17 | 0.058 | |
| 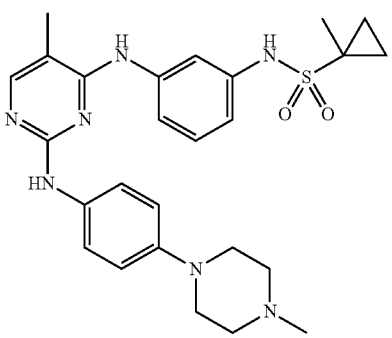<br>MA4-102<br>M.W. = 507.66 | | 7.5 ± 0.23 | 0.068 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 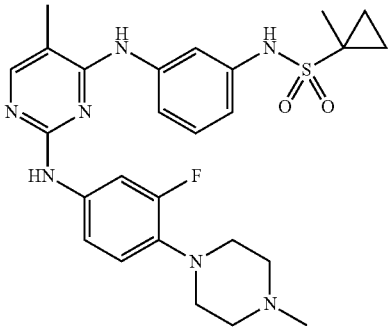<br>MA4-103<br>M.W. = 525.65 | | 9.1 ± 0.05 | 0.020 | |
| 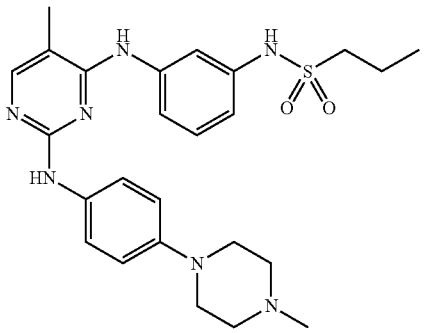<br>MA4-108<br>M.W. = 495.65 | | 6.70 ± 0.157 | 0.321 | |
| 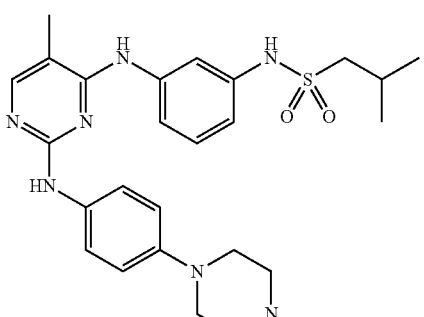<br>MA4-116<br>M.W. = 509.67 | | 6.58 ± 0.103 | 0.347 | |
| 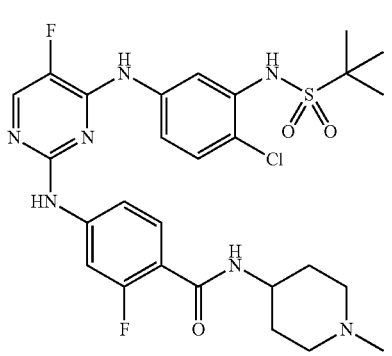<br>MA4-144-1<br>M.W. = 608.11 | | 9.91 ± 0.039 | 0.0405 | MM1.S (IC$_{50}$ = 0.12 μM) |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 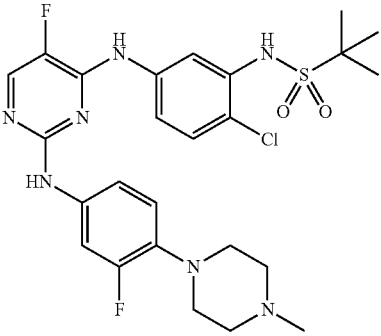<br>MA4-144-2<br>M.W. = 566.07 | | 0.570 ± 0.124<br>Precipitation observed in DSF buffer | 16.8 | MM1.S<br>(IC$_{50}$ = 0.16 μM) |
| 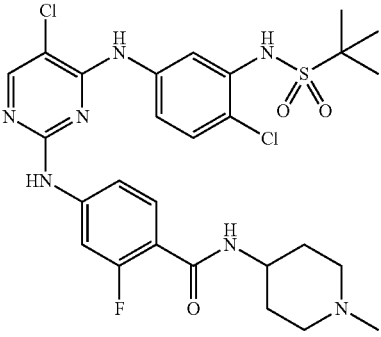<br>MA4-146-1<br>M.W. = 624.56 | | 12.0 ± 0.50 | 0.0105 | MM1.S<br>(IC$_{50}$ = 0.090 μM) |
| 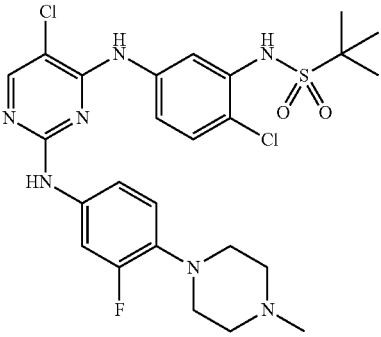<br>MA4-146-2<br>M.W. = 582.52 | | 5.22 ± 0.065<br>Precipitation observed in DSF buffer | 0.835 | MM1.S<br>(IC$_{50}$ = 0.11 μM) |

TABLE 1-continued
| Name Molecular Wt (Amt. Supplied mg) | Co-crystal | DSF ΔTm (° C.) | Estimated BRD4 IC$_{50}$ (μM) | Comments |
|---|---|---|---|---|
| 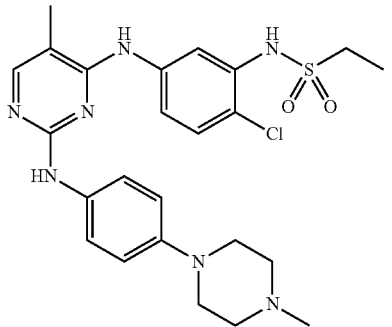 SG4-013 M.W. = 516.06 | | 7.93 ± 0.183 | 0.145 | |
| 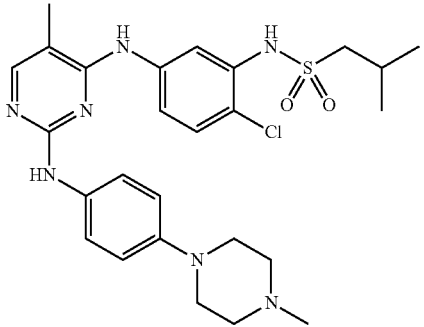 SG4-025 M.W. = 544.11 | | 7.28 ± 0.091 | 0.221 | |
| 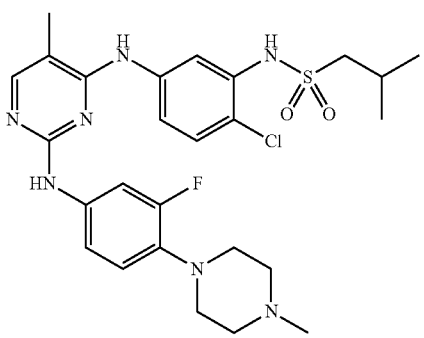 SG4-027 M.W. = 562.10 | | 8.89 ± 0.044 | 0.0748 | |

TABLE 1-continued
| Name Molecular Wt (Amt. Supplied mg) | Co-crystal | DSF ΔTm (° C.) | Estimated BRD4 IC$_{50}$ (μM) | Comments |
|---|---|---|---|---|
| 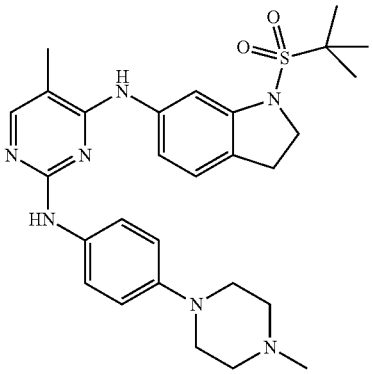 SG4-031 M.W. = 535.70 | | 9.97 ± 0.080 | 0.039 | |
| 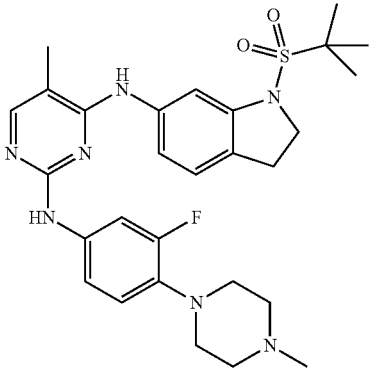 SG4-032 M.W. = 553.69 | | 12.1 ± 0.105 | 0.0098 | |
| 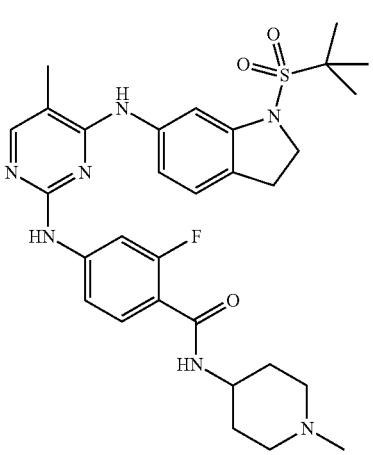 SG4-033 M.W. = 595.73 | | 12.3 ± 0.116 | 0.0086 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 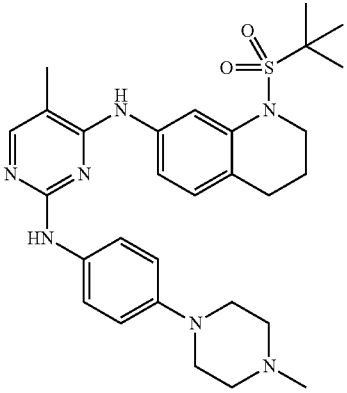<br>SG4-038<br>M.W. = 549.73 | | 8.72 ± 0.141 | 0.0873 | |
| 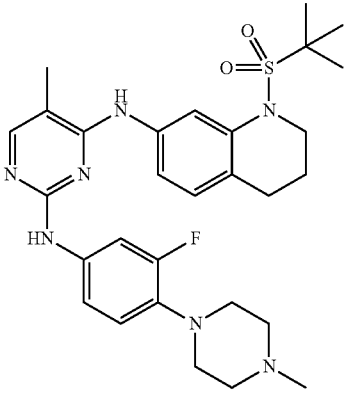<br>SG4-039-01<br>M.W. = 567.72 | | 10.5 ± 0.150 | 0.0277 | |
| 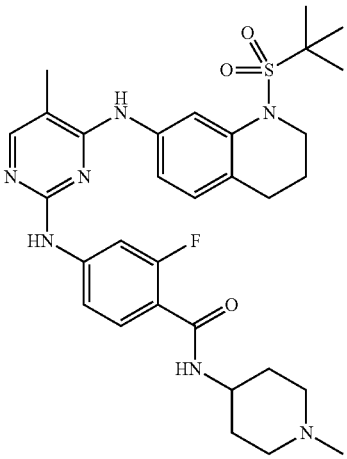<br>SG4-043<br>M.W. = 609.76 | | 11.4 ± 0.103 | 0.0155 | |

TABLE 1-continued
| Name<br>Molecular Wt (Amt. Supplied mg) | Co-crystal | DSF ΔTm<br>(° C.) | Estimated<br>BRD4 IC$_{50}$<br>(μM) | Comments |
|---|---|---|---|---|
| 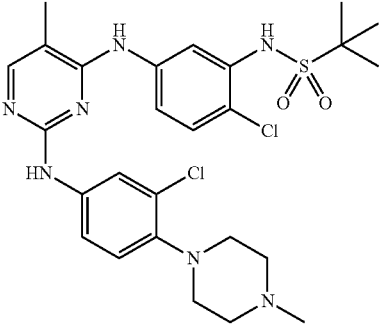<br>SG4-046<br>M.W. = 578.56 | | 9.54 ± 0.163 | 0.0514 | |
| 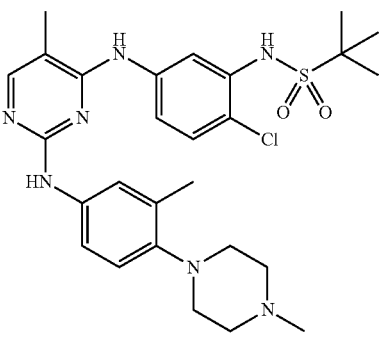<br>SG4-047<br>M.W. = 558.14 | | 10.4 ± 0.151 | 0.0295 | |
| 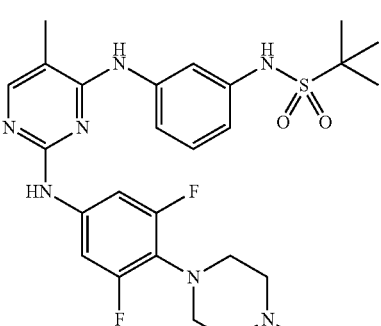<br>MA5-006-1<br>M.W. = 545.65 | | 12.8 ± 0.058 | 0.00628 | |
| 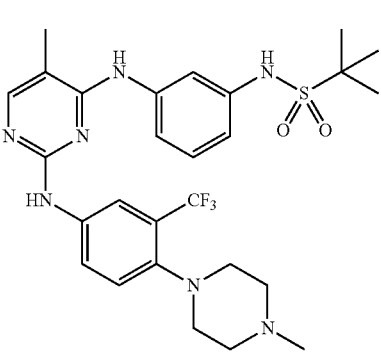<br>MA5-006-2<br>M.W. = 577.66 | | 8.12 ± 0.044 | 0.129 | |

TABLE 1-continued
| Name Molecular Wt (Amt. Supplied mg) | Co-crystal | DSF ΔTm (° C.) | Estimated BRD4 IC$_{50}$ (μM) | Comments |
|---|---|---|---|---|
| 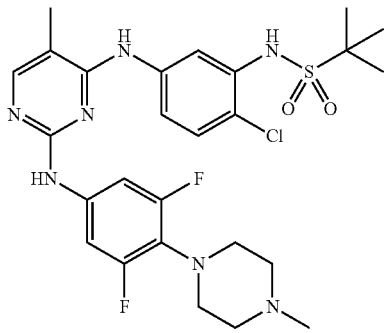<br>MA5-008-1<br>M.W. = 580.09 | | 13.8 ± 0.191 | 0.00329 | |
| 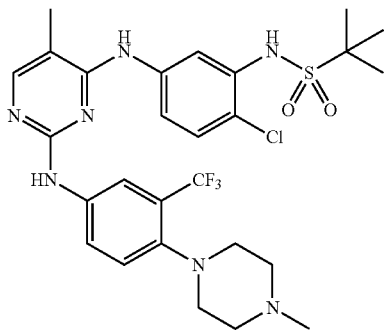<br>MA5-008-2<br>M.W. = 612.11 | | 2.46 ± 0.111 | 4.95 | Precipitation interferes with the assay |
| 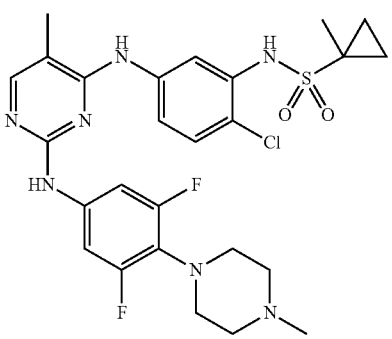<br>MA5-016-1<br>M.W. = 578.08 | | 12.3 ± 0.167 | 0.0086 | |

TABLE 1-continued
| Name<br>Molecular Wt (Amt. Supplied mg) | Co-crystal | DSF ΔTm (° C.) | Estimated BRD4 IC$_{50}$ (μM) | Comments |
|---|---|---|---|---|
| 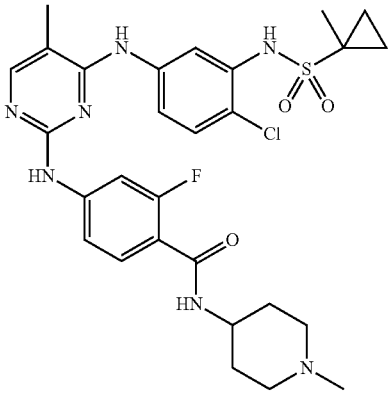<br>MA5-018<br>M.W. = 602.12 | | 10.9 ± 0.22 | 0.021 | |
| 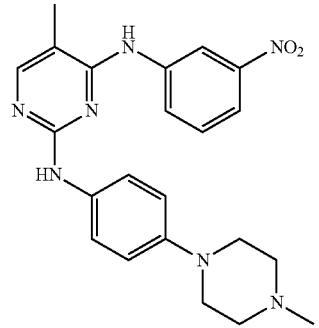<br>MA4-104<br>M.W. = 419.48 | | 3.17 ± 0.142 | 3.13 | |
Further Examples are shown in Tables 2 and 3:
TABLE 2
| Name, Structure | MW | Co-crystal | DSF ΔT$_m$ (° C.) | BRD4 IC$_{50}$ |
|---|---|---|---|---|
| 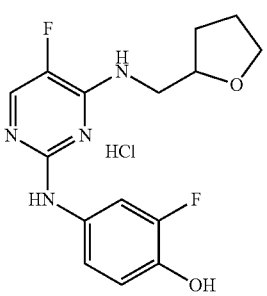<br>YL7-164 | 358.8 | No | Not Determined | Not Determined |

TABLE 2-continued
| Name, Structure | MW | Co-crystal | DSF ΔT$_m$ (° C.) | BRD4 IC$_{50}$ |
|---|---|---|---|---|
| 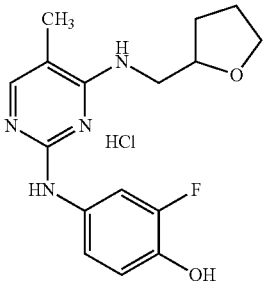 YL7-164 | 354.4 | No | Not Determined | Not Determined |
| 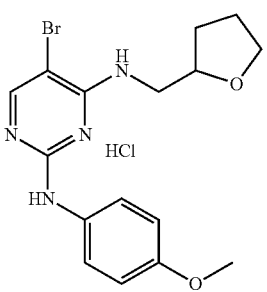 SK1-022 | 415.7 | No | Not Determined | Not Determined |
Additional examples are shown in Table 3.
TABLE 3
| Compound Code(Structure) | MW | Co-crystal |
|---|---|---|
| 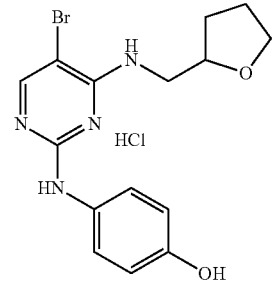 SK1-028 | 401.7 | No |
| 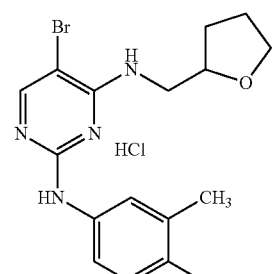 SK1-040 | 415.7 | No |

135 136
TABLE 3-continued
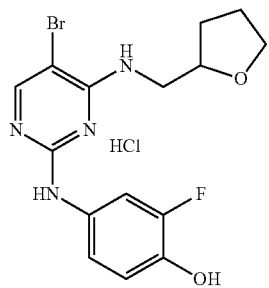
SK1-044B2
419.7   No
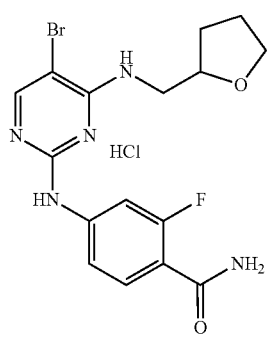
YL7-172-5
428.7   No
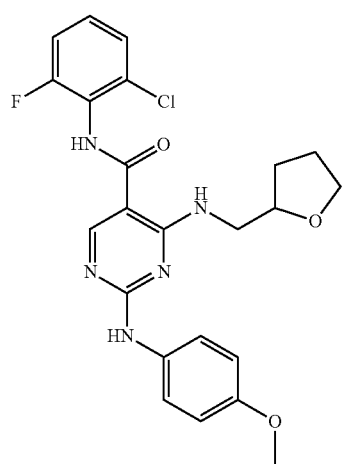
YL7-104-1
471.9   No TABLE 3-continued
| | | |
|---|---|---|
| 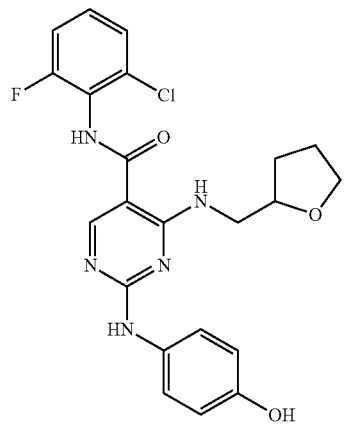<br>YL7-104-2 | 457.9 | No |
| 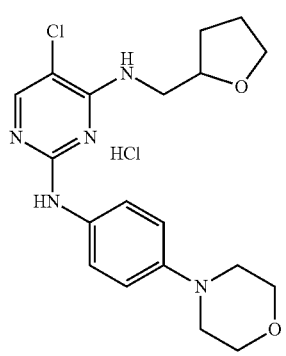<br>MH1-006-3 | 426.3 | No |
| 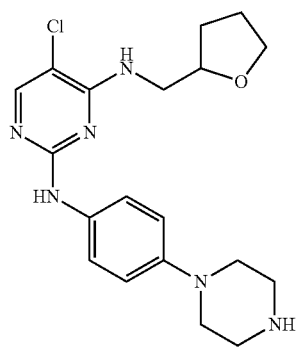<br>MH1-007-3 | 388.9 | No |
| 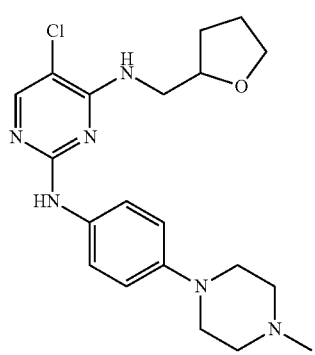<br>MH1-022-5 | 402.9 | No |

TABLE 3-continued
| | | |
|---|---|---|
| 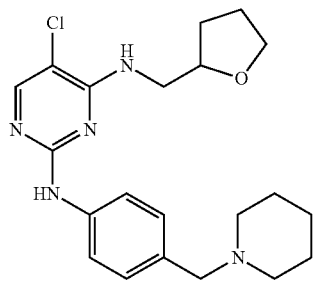 MH1-035-3 | 401.9 | No |
| 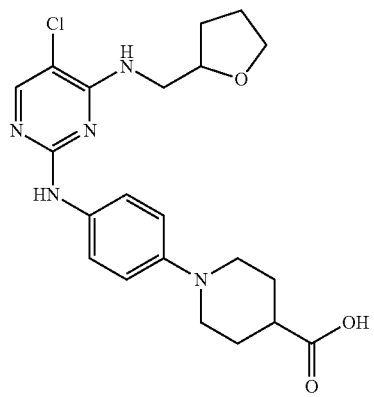 YL8-050B2 | 431.9 | No |
| 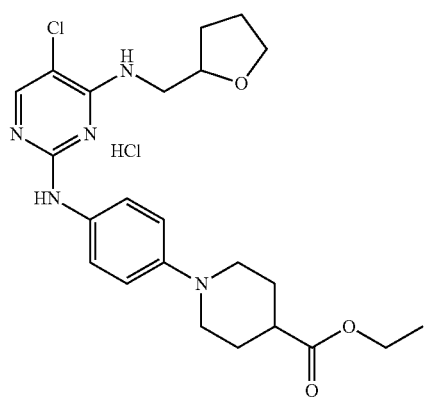 DZ1-070 | 406.4 | No |
| 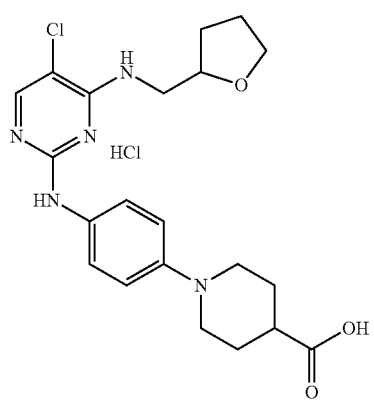 DZ1-072 | 431.9 | No |

TABLE 3-continued
| Compound Code(Structure) | MW | Co-crystal | DSF ΔTm (° C.) |
|---|---|---|---|
| DZ1-074 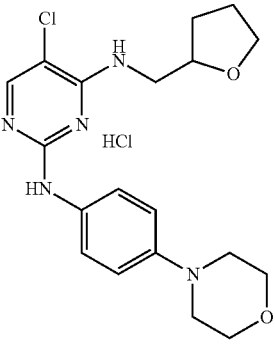 | 426.3 | No | Not Determined |
| DZ1-077 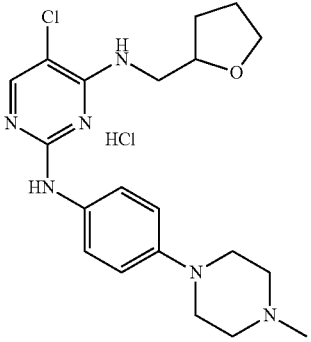 | 402.9 | No | Not Determined |
Additional examples are shown in Table 4.
TABLE 4
| Structure | BRD4, DSF: ΔTm (° C.) | IC$_{50}$ BRD4 (nM) (Est. by DSF) | Alpha Screen IC$_{50}$ (nM) (Reaction Biology data) BRD2-1 BRD3-1 BRD4-1 BRDT-1 (BRD4-2) | HotSpot Kinase assay IC$_{50}$(nM) (Reaction Biology data) JAK1 JAK2 JAK3 FLT3 | Cellular IC$_{50}$(nM) MM.1S MV-4-11 SAOS-2 UKE-1 |
|---|---|---|---|---|---|
| SG3-179 | 12.5 ± 0.16 | 1.3 | 9.55   22.5   11.6 | 31.5   57.0 | 38.3   225 |

TABLE 4-continued

| Structure | DSF: BRD4 ΔTm (° C.) | BRD4, IC$_{50}$ (nM) (Est. by DSF) | Alpha Screen IC$_{50}$ (nM) (Reaction Biology data) BRD2-1 BRD3-1 BRD4-1 BRDT-1 (BRD4-2) | | | | HotSpot Kinase assay IC$_{50}$(nM) (Reaction Biology data) JAK1 JAK2 JAK3 FLT3 | | | | Cellular IC$_{50}$(nM) MM.1S MV-4-11 SAOS-2 UKE-1 | | | |
|---|---|---|---|---|---|---|---|---|---|---|---|---|---|---|
| MA4-022-2 | 11.0 ± 0.04<br>12.6 ± 0.06 | 4.8<br>1.3 | | | 11.2 (17.5) | 19.0 | 3.36 | 10.7 | | | 66.0 | 53.2 | 320 | 294 |
| MA4-022-1 | 9.50 ± 0.04<br>11.2 ± 0.15 | 14<br>3.9 | | | 24.3 (22.0) | 41.3 | 1.14 | 1.10 | 146 | | 26.8 | 133 | 200 | |
| SG3-014 | 9.57 ± 0.08 | 10 | 81.4 | 16.5 | 25.0 (27.3) | 27.8 | 11.2 | 9.71 | 142 | | 186 | 567 | 512 | |
| MA2-014 | 8.54 ± 0.88 | 25 | 625 | 12.5 | 10.2 (23.6) | 29.1 | 4.58 | 2.70 | 91.4 | 0.917 | 399 | 56.7 | 184 | 260 |
| TG101209 | 6.83 ± 0.12 | 130 | 680 | 130 | 120 (172) | 290 | 2.63 | 0.51 | 97.6 | 1.53 | 1.58 | 122 | 425 | 689 |

DSF = Differential Scanning Fluorimetry; provides a measure of the increased stability of BRD4 upon ligand binding The DSF experiment was run at 100 μM protein, 4 μM compound and 2% DMSO.

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Ban Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Method of Screening

Also disclosed herein are methods of identifying a putative anti-cancer compound comprising contacting BDR4 with a target compound and determining whether the compound binds the BDR4, wherein the compound that binds BDR4 is identified as a putative anti-cancer compound.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

First, a set of 2-chloro-4-anilinopyrimidines 2 is be prepared by reaction of the 5-substituted dichloropyrimidine 1 ($R^4$=Me, Et, $CF_3$, Cl, F, Br, CN, CCH) with appropriate aniline bearing $R^1$ and $R^2$ groups. Reaction of building blocks 2 with a set of anilines bearing the $R^3$ group will provide the target set of dianilinopyrimidines 3. This modular two-step synthesis will provide rapid access to libraries for analysis of both BRD4 and kinase inhibitory properties.

Cellular activity of promising compounds is assessed using MM.1S and MV4-11 AML cells using c-Myc levels as biomarker (6-12 hr treatment) and antiproliferative activity (48-72 hr treatment) as described (Ciceri et al., Dual kinase-bromodomain inhibitors for rationally designed polypharmacology. *Nat Chem Biol* 2014). The most potent BRD4 inhibitors are profiled against representative panels of kinases and BRDs to assess potency and specificity using commercial services.

| Compound Code(Structure) | MW | Co-crystal | DSF ΔTm (° C.) |
|---|---|---|---|
| 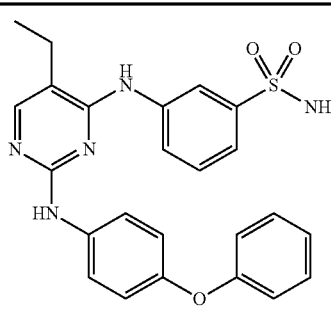<br>MA1-030B | 461.5 | No | High background |
| 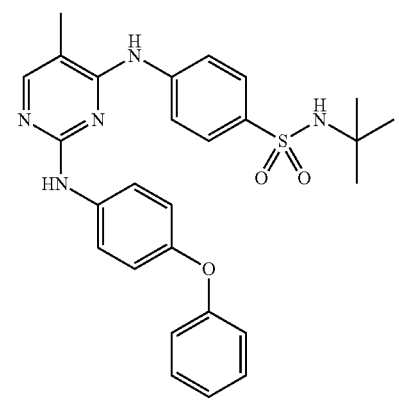<br>MA1-033 | 503.5 | No | High background |

-continued

| Compound Code(Structure) | MW | Co-crystal | DSF ΔTm (° C.) |
|---|---|---|---|
| RJ1-030-01 | 512.6 | No | High background |
| MA1-036B | 462.5 | No | High background |

The dianilinopyrimidines were prepared according to Scheme 1, using methods previously reported,[1,2] by reaction of a substituted 2,4-dichloropyrimidine 1 with A-ring aniline 2 to form the 4-anilino-pyrimidine intermediate 3. This intermediate 3, upon reaction with a second set of B-ring anilines 4 under more forcing conditions, generated the final dianilinopyrimidine library 5. Alternatively the reaction of the 4-anilino-pyrimidine intermediate 3 and the B-ring aniline may be effected by palladium catalysis. An alternative approach to certain sulfonamide substituted B-rings involves sulfonylation of dianilinopyrimidine (Scheme 1B). When the pyrimidine has a trifluoromethyl group at position 5, the target dianilinopyrimidine is prepared by the route shown in Scheme 1C. Regioselective reaction[3] of an aniline with 5-(trifluoromethyl)-2,4-dichlorpyrimidine (6) provides the 4-chloropyrimidine 7. Reaction with the B-ring aniline provides SG2-029-01 a precursor to SG2-033-01-1.

The intermediate 2,4-dichloropyrimidines 1 were prepared from the corresponding pyrimidine-2,4(1H,3H)-dione 8 (prepared using reported methods[4] shown in Scheme 2A) by treatment with phosphorus oxychloride (Scheme 2). The 2,4-dichloro-5,6-dimethylpyrimidine was prepared according to the route[5] shown in Schemes 2B. The preparation of 2,4-dichloropyrimidines in which the 5 and 6 positions are part of a further ring (MA2-092, MA2-096, MA2-028 and MA3-034)[6] is shown in Schemes 2C and 2D.

The A-ring anilines with an amide, urea or alkoxy group were synthesized from nitroaniline and nitroisocyanate precursors via standard methods[7-9] according to the routes shown in Schemes 3A and 3B. The anilines MA1-086 and MA1-087 were prepared by O-alkylation of 2-chloro-5-aminophenol (Scheme 3C).[10] The synthetic routes to the A-ring anilines bearing a sulfonamide group are shown in Schemes 4A-D. Those shown in Scheme 4A were prepared by reaction of nitrophenylsulfonyl chlorides and amines, followed by reduction of the nitro group.[11] A similar approach is shown for those B-ring anilines prepared from nitroaniline or mono-BOC diaminobenzene derivatives as shown in Scheme 4B.[12] The B-ring aniline bearing a tert-butylsulfonamide (MA3-098, MA3-010, SG3-105, SG3-124, SG4-020 and SG4-023) were prepared by tert-butylsulfinylation followed by oxidation of the intermediate tert-butylsulfinamides by standard methods as shown in Scheme 4C.[13] The synthesis of the aniline MA4-044 was prepared according to the method shown in Scheme 4D. In this way 3,5-dinitroaniline was acetylated and reduced with hydrazine hydrate and palladium on carbon[14] to give MA4-042. Sulfonylation of MA4-042 followed by hydrolysis of the acetamide gives the A-ring aniline MA4-044. The B-ring anilines were synthesized according to the routes shown in Schemes 5.[15-17]

Scheme 1
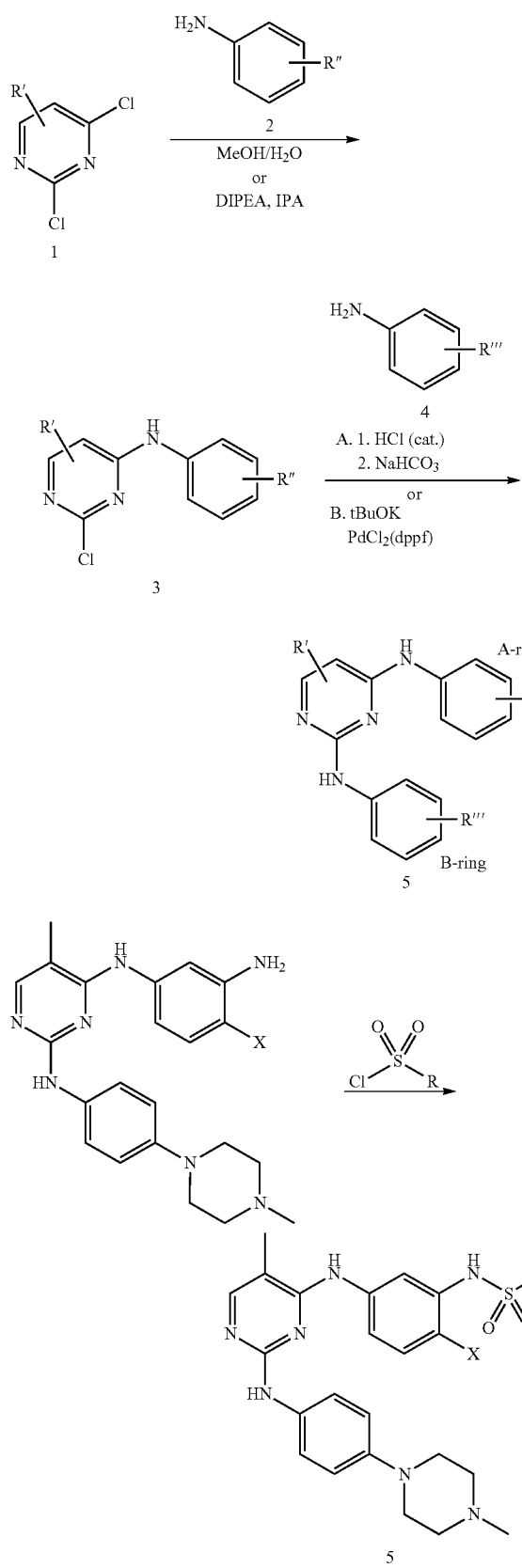
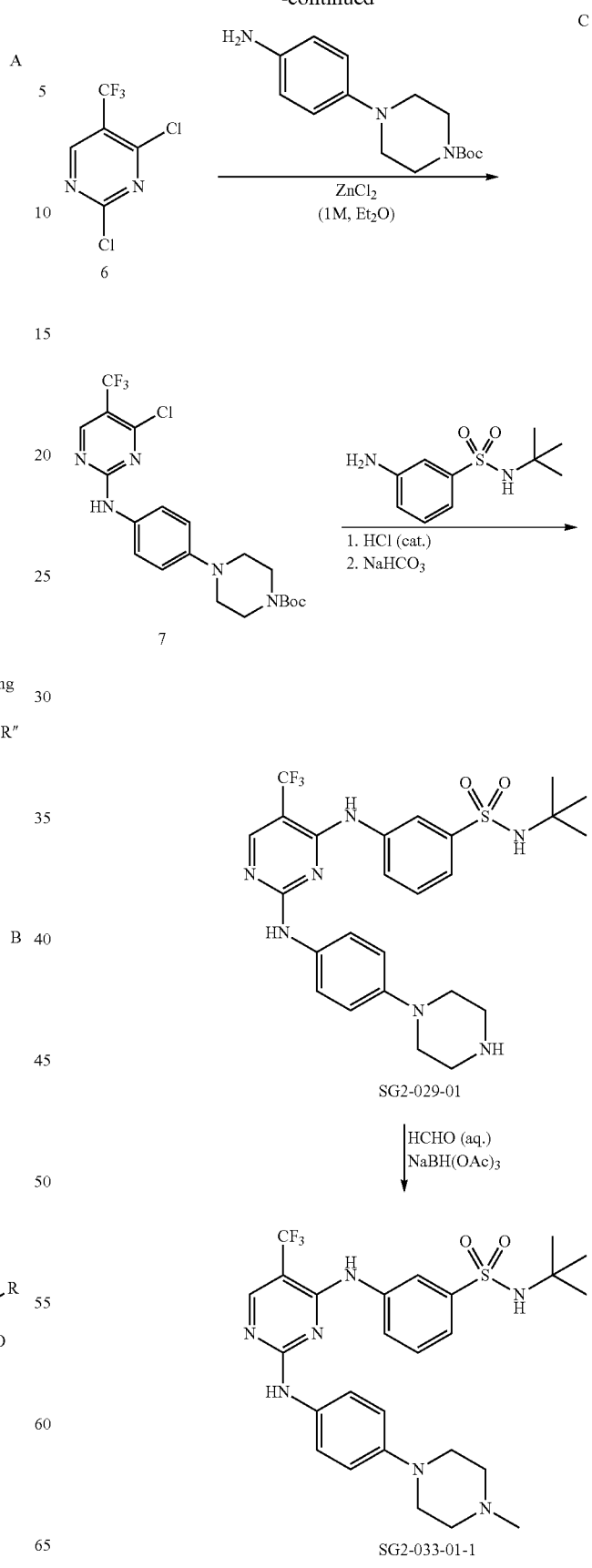

Scheme 2 Synthesis of the Dichloropyrimidine intermediates 1
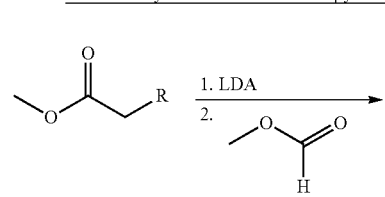
3.
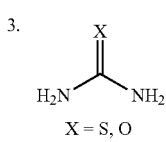
X = S, O
4. When X = S
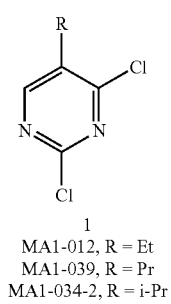
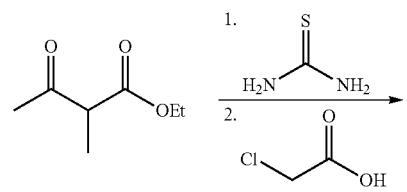
1
MA1-012, R = Et
MA1-039, R = Pr
MA1-034-2, R = i-Pr
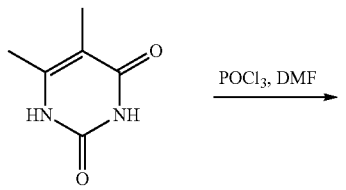
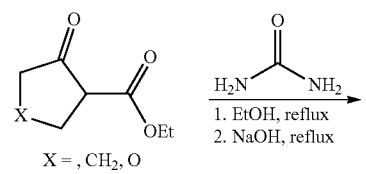
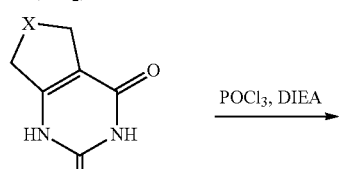
X = , CH₂, O
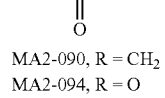
MA2-090, R = CH₂
MA2-094, R = O
MA2-092, R = CH₂
MA2-096, R = O
-continued
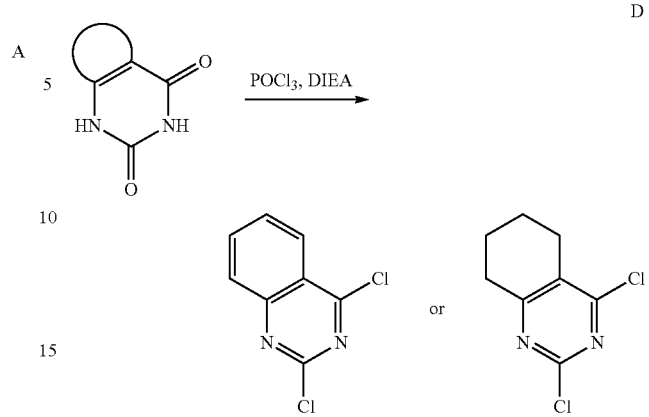
MA2-028    MA3-034
Scheme 3 Synthesis of 3-urea, 3-amido, 3-alkoxy substituted A-ring anilines
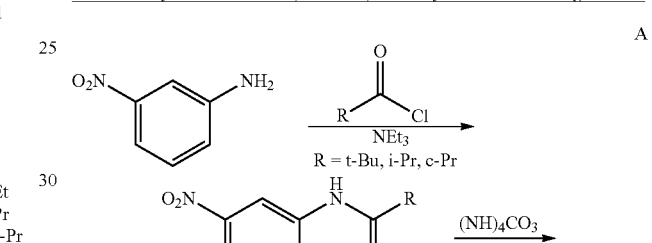
MA2-036-1, R = t-Bu
MA2-036-2, R = i-Pr
MA2-036-3, R = c-Pr
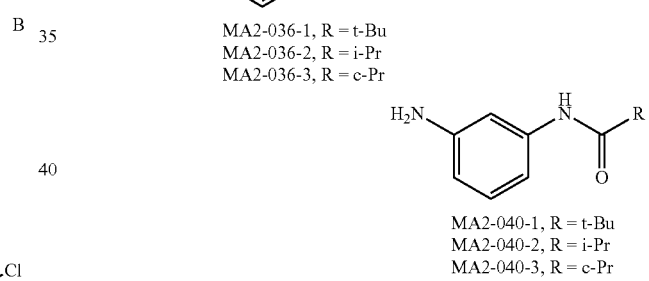
MA2-040-1, R = t-Bu
MA2-040-2, R = i-Pr
MA2-040-3, R = c-Pr
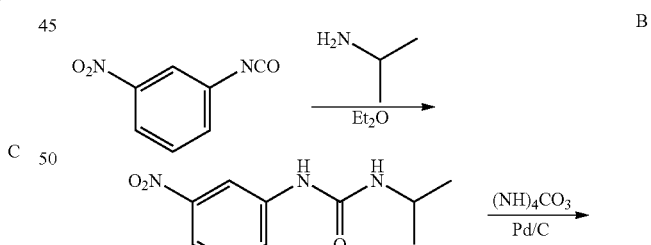
MA2-054-2
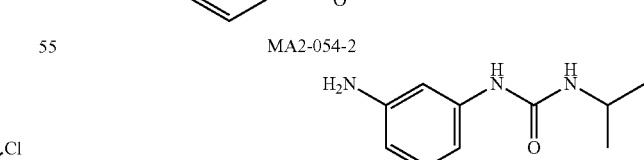
MA2-056-2
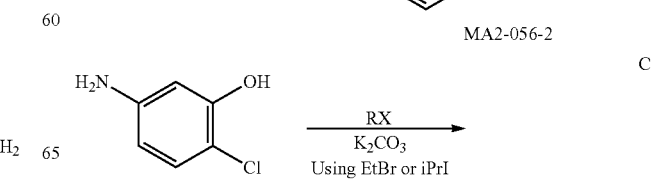

-continued

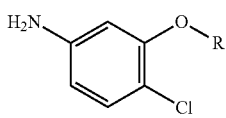

MA1-086, R = iPr
MA1-087, R = Et

Scheme 4 Synthesis of A-ring anilines with sulfonamides

A

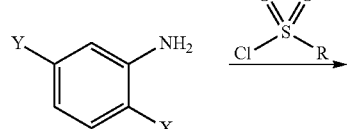

SG1-137: 3-NH₂, R' = H, R'' = t-Bu
SG1-147: 3-NH₂, R' = H, R'' = i-Pr
SG1-177: 4-NH₂, R' = H, R'' = t-Bu
RJ1-042: 3-NH₂, R' = H, R'' = Cyclopropyl
SG2-079: 3-NH₂, R' = H, R'' = 1-OH-2-methylpropan-2-yl
SG2-100: 3-NH₂, R' = 6-Me, R'' = t-Bu
MA4-080: 3-NH₂, R' = H, R'' = i-Pr
SG3-142: 3-NH₂, R' = 6-Cl, R'' = t-Bu

B

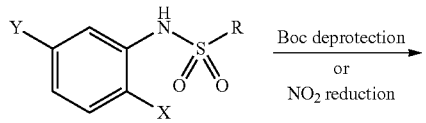

X = H, F, or Cl
Y = NHBoc or NO₂

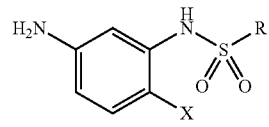

RJ1-025: X = H, R = Cyclopropyl
SG2-159: X = Cl, R = Cyclopropyl
SG4-009: X = Cl, R = Et
SG4-016: X = Cl, R = i-Bu
MA3-004: X = H, R = i-Pr
MA3-092: X = H, R = Ph
MA4-002: X = Cl, R = Ph
MA4-096: X = H, R = Cyclopropyl-methyl
MA5-010: X = Cl, R = Cyclopropyl-methyl -continued

C

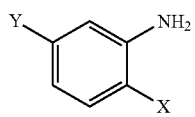

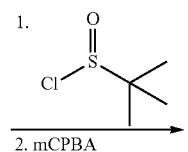

X = H, F, or Cl
Y = NHBoc or NO₂

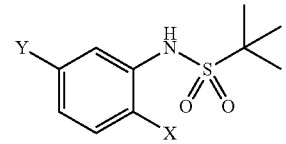

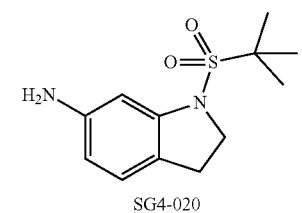

SG4-020           SG4-023

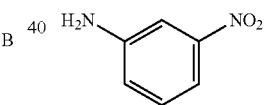

MA3-098: X = F
MA3-010: X = H
SG3-105: X = Cl
SG3-124: X = Me

D

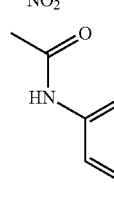

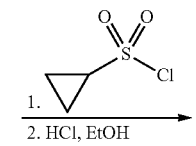

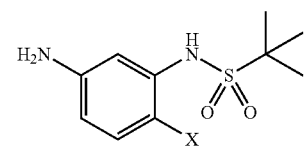

MA4-042

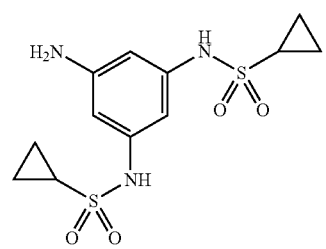

MA4-044

Scheme 5 Synthesis of the B-ring anilines 4

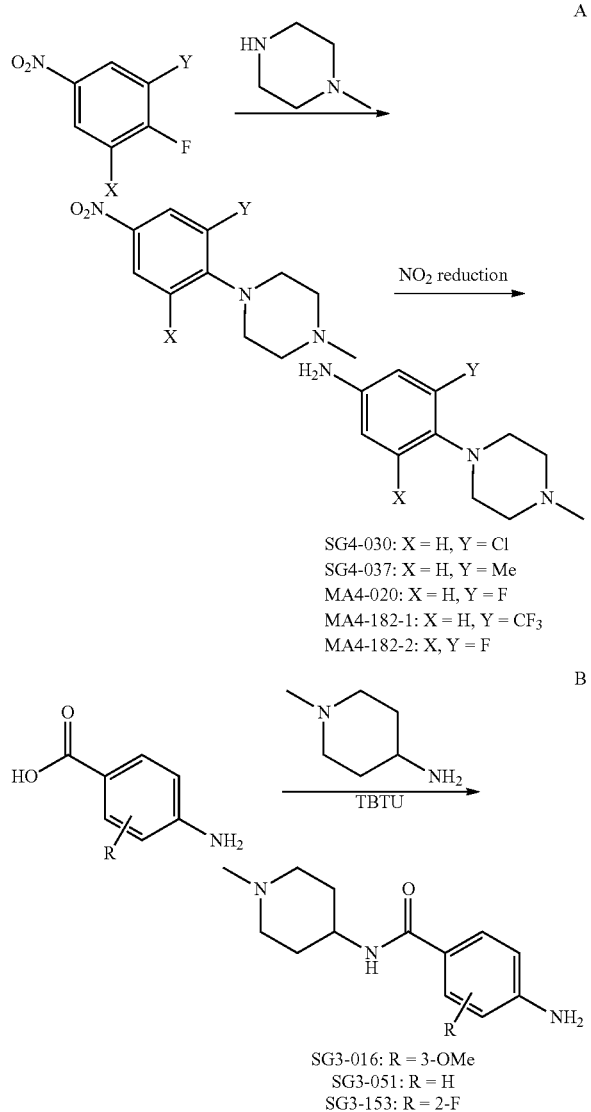

REFERENCES

1. Lawrence, H. R.; Mahajan, K.; Luo, Y.; Zhang, D.; Tindall, N.; Huseyin, M.; Gevariya, H.; Kazi, S.; Ozcan, S.; Mahajan, N. P.; Lawrence, N. J. Development of novel ACK1/TNK2 inhibitors using a fragment-based approach. *J Med Chem* 2015, 58, 2746-63.
2. Lawrence, H. R.; Martin, M. P.; Luo, Y.; Pireddu, R.; Yang, H.; Gevariya, H.; Ozcan, S.; Zhu, J. Y.; Kendig, R.; Rodriguez, M.; Elias, R.; Cheng, J. Q.; Sebti, S. M.; Schonbrunn, E.; Lawrence, N. J. Development of o-chlorophenyl substituted pyrimidines as exceptionally potent aurora kinase inhibitors. *J. Med. Chem.* 2012, 55, 7392-416.
3. Richter, D. T.; Kath, J. C.; Luzzio, M. J.; Keene, N.; Berliner, M. A.; Wessel, M. D. Selective addition of amines to 5-trifluoromethyl-2,4-dichloropyrimidine induced by Lewis acids. *Tetrahedron Letters* 2013, 54, 4610-4612.
4. McIver, E. G.; Bryans, J.; Birchall, K.; Chugh, J.; Drake, T.; Lewis, S. J.; Osborne, J.; Smiljanic-Hurley, E.; Tsang, W.; Kamal, A.; Levy, A.; Newman, M.; Taylor, D.; Arthur, J. S.; Clark, K.; Cohen, P. Synthesis and structure-activity relationships of a novel series of pyrimidines as potent inhibitors of TBK1/IKKepsilon kinases. *Bioorg Med Chem Lett* 2012, 22, 7169-73.
5. Zhang, Z.; Wallace, M. B.; Feng, J.; Stafford, J. A.; Skene, R. J.; Shi, L.; Lee, B.; Aertgeerts, K.; Jennings, A.; Xu, R.; Kassel, D. B.; Kaldor, S. W.; Navre, M.; Webb, D. R.; Gwaltney, S. L. Design and synthesis of pyrimidinone and pyrimidinedione inhibitors of dipeptidyl peptidase IV. *J Med Chem* 2011, 54, 510-24.
6. Kath, J.; Luzzio, M. Pyrimidine derivatives for the treatment of abnormal cell growth. US Pat. Appl. US2005/0256125A1, 2005.
7. Moore, M.; Moorhouse, A. D.; Moses, J. E.; Neidle, S. Ureylene derivatives. WO2008/122667A3, 2008.
8. Ueda, S.; Nagasawa, H. Copper-catalyzed synthesis of benzoxazoles via a regioselective C—H functionalization/C—O bond formation under an air atmosphere. *J Org Chem* 2009, 74, 4272-7.
9. Radi, M.; Botta, M.; Falchi, F.; Maga, G.; Baldanti, F.; Paolucci, S. Compounds with ddx3 inhibitory activity and uses thereof. WO2011/039735A3, 2011.
10. Brooks, C. A.; Cheung, M.; Eidam, H. S.; Fox, R. M.; Hilfker, M. A.; Manas, E. S.; Ye, G. Antagonistes de trpv4. WO2011/119704A1, 2011.
11. Lawrence, H. R.; Kazi, A.; Luo, Y.; Kendig, R.; Ge, Y.; Jain, S.; Daniel, K.; Santiago, D.; Guida, W. C.; Sebti, S. M. Synthesis and biological evaluation of naphthoquinone analogs as a novel class of proteasome inhibitors. *Bioorg Med Chem* 2010, 18, 5576-92.
12. Altenbach, R. J.; Khilevich, A.; Kolasa, T.; Rohde, J. J.; Bhatia, P. A.; Patel, M. V.; Searle, X. B.; Yang, F.; Bunnelle, W. H.; Tietje, K.; Bayburt, E. K.; Carroll, W. A.; Meyer, M. D.; Henry, R.; Buckner, S. A.; Kuk, J.; Daza, A. V.; Milicic, I. V.; Cain, J. C.; Kang, C. H.; Ireland, L. M.; Carr, T. L.; Miller, T. R.; Hancock, A. A.; Nakane, M.; Esbenshade, T. A.; Brune, M. E.; O'Neill, A. B.; Gauvin, D. M.; Katwala, S. P.; Holladay, M. W.; Brioni, J. D.; Sullivan, J. P. Synthesis and structure-activity studies on N-[5-(1H-imidazol-4-yl)-5,6,7,8-tetrahydro-1-naphthalenyl]methanesulfonamide, an imidazole-containing alpha (1A)-adrenoceptor agonist. *J Med Chem* 2004, 47, 3220-35.
13. Sun, P.; Weinreb, S. M.; Shang, M. tert-Butylsulfonyl (Bus), a New Protecting Group for Amines. *J Org Chem* 1997, 62, 8604-8608.
14. Gunawan, S., Hulme, C. Construction of functionalized tricyclic dihydropyrazino-quinazolinedione chemotypes via an Ugi/N-acyliminium ion cyclization cascade. *Tet. Lett.* 2013, 54, 4467-4470.
15. Tangallapally, R. P.; Yendapally, R.; Lee, R. E.; Lenaerts, A. J. Synthesis and evaluation of cyclic secondary amine substituted phenyl and benzyl nitrofuranyl amides as novel antituberculosis agents. *J Med Chem* 2005, 48, 8261-9.
16. Casillas, L. N.; Chakravorty, S. J.; Eidam, P.; Haile, P. A.; Hughes, T. V.; Lakdawala, S. A.; Leister, L. K.; Miller, N. A.; Rahman, A.; Sehon, C. A. Pyrazolyl-pyrimidines as kinase inhibitors. WO2011/120026A1, 2011.
17. Hollick, J. J.; Jones, S. D.; Flynn, C. J.; Thomas, M. G. Pyrimidine derivatives as protein kinase inhibitors. U.S. Pat. No. 8,563,542B2, 2013.

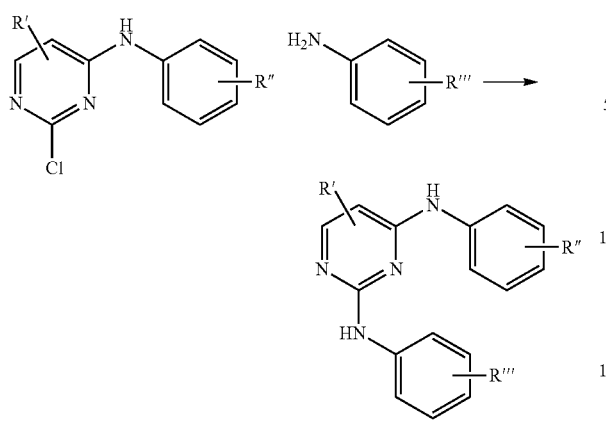

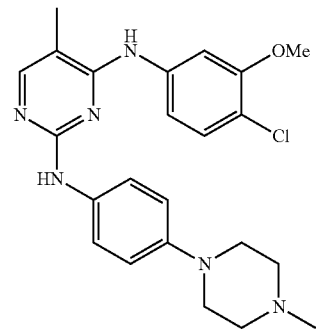

Method x: A mixture of 4-anilino-pyrimidine intermediate 3 (50 mg, 1.0 equiv.), the corresponding aniline B-ring aniline (1.0 equiv.), 2 drops of 4 M HCl, and EtOH (1 mL) was heated in a microwave reactor at 160° C. for 15 minutes. The reaction mixture was diluted with EtOAc (20 mL) and washed with saturated NaHCO$_3$ (20 mL). The aqueous layer was then re-extracted with EtOAc (20 mL). The combined organic layers were dried over Na$_2$SO$_4$ and concentrated under reduced pressure. Unless otherwise mentioned, all products were purified via column chromatography using DCM/MeOH (0-10%).

Method y: A mixture of 4-anilino-pyrimidine intermediate 3 (50 mg, 1.0 equiv.), the corresponding aniline B-ring aniline (1.0 equiv.), 2 drops of 4 M HCl, and EtOH (1 mL) was heated in a microwave reactor at 100° C. for 1 h. Sodium bicarbonate (ca. 100 mg) was added to the mixture, stirred for 30 min at room temperature, and concentrated under reduced pressure. Unless otherwise mentioned, all products were purified via column chromatography using DCM/MeOH (0-10%).

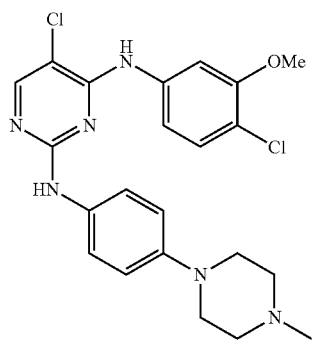

5-Chloro-N$^4$-(4-chloro-3-methoxyphenyl)-N$^2$-[4-(4-methylpiperazin-1-yl)phenyl]pyrimidine-2,4-diamine (SG1-180): This was prepared from SG1-168 (50 mg) and 4-(4-methylpiperazino)aniline (31 mg) using the general method x. The crude reaction mixture was triturated using EtOAc/hexanes to give the title compound as a light brown solid (50 mg, 66%). Mp: 232° C. (dec). HPLC: 96% [t$_R$=5.8 min, 40% MeOH, 60% water (with 0.1% TFA), 20 min]. $^1$H NMR (400 MHz, DMSO-d$_6$): δ 9.10 (s, 1H, disappeared on D$_2$O shake), 8.82 (s, 1H, disappeared on D$_2$O shake), 8.09 (s, 1H), 7.46-7.26 (m, 5H), 6.78 (d, J=8.6 Hz, 2H), 3.70 (s, 3H), 3.06-2.98 (m, 4H), 2.46-2.41 (m, 4H), 2.21 (s, 3H). HPLC-MS (ESI+): m/z 461.2 [60%, (M$^{35}$Cl$^{37}$Cl+H)$^+$], 459.2 (100%, M$^{35}$Cl$^{35}$Cl+H)$^+$], 231.1 [60%, (M$^{35}$Cl$^{37}$Cl+2H)$^{2+}$], 230.1 [90%, M$^{35}$Cl$^{35}$Cl+2H)$^{2+}$]. LC-MS (ESI+): 461.1 [70%, (M$^{35}$Cl$^{37}$Cl+H)$^+$], 459.1 [100%, (M$^{35}$Cl$^{35}$Cl+H)$^4$]. HRMS (ESI+): m/z calcd for C$_{22}$H$_{24}$Cl$_2$N$_6$O (M+H)$^+$ 459.1461, found 459.1458.

5-Methyl-N$^4$-(4-chloro-3-methoxyphenyl)-N$^2$-[4-(4-methylpiperazin-1-yl)phenyl]pyrimidine-2,4-diamine (SG1-183): This was prepared from SG1-173-01 (50 mg) and 4-(4-methylpiperazino)aniline (34 mg) using the general method x. The crude reaction mixture was triturated using EtOAc/hexanes to give the title compound as a light brown solid (49 mg, 64%), mp 257° C. (dec). HPLC: 98% [t$_R$=8.9 min, 35% MeOH, 65% water (with 0.1% TFA), 20 min]. $^1$H NMR (400 MHz, DMSO-d$_6$): δ 8.73 (s, 1H, disappeared on D$_2$O shake), 8.28 (s, 1H, disappeared on D$_2$O shake), 7.85 (s, 1H), 7.50-7.39 (m, 4H), 7.26 (d, J=8.6 Hz, 1H), 6.77 (d, J=8.7 Hz, 2H), 3.71 (s, 3H), 3.04-2.96 (m, 4H), 2.45-2.40 (m, 4H), 2.20 (s, 3H), 2.07 (s, 3H). HPLC-MS (ESI+): m/z 439.2 [20%, (M$^{35}$Cl+H)$^+$], 221.0 [40%, (M$^{37}$Cl+H, 40%)$^{2+}$], 220.2 [100%, (M$^{35}$Cl+2H)$^2$]. LC-MS (ESI+): 439.2 [100%, (M$^{35}$Cl+H)$^+$], 220.1 [50%, (M$^{35}$Cl+2H)$^{2+}$]. HRMS (ESI+): m/z calcd for C$_{23}$H$_{27}$ClN$_6$O (M+H)$^+$ 439.2007, found 439.2007.

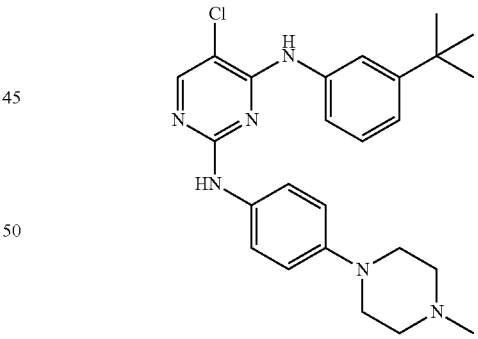

5-Chloro-N$^4$-[3-(1,1-dimethylethyl)]phenyl-N$^2$-[4-(4-methylpiperazin-1-yl)phenyl]pyrimidine-2,4-diamine (SG1-184): This was prepared from SG1-175 (50 mg) and 4-(4-methylpiperazino)aniline (32 mg) using the general method x. The crude reaction mixture was triturated using EtOAc/hexanes to give the title compound as a light brown solid (22 mg, 29%). Mp: 212° C. (dec). HPLC: 95% [t$_R$=5.9 min, 50% MeOH, 50% water (with 0.1% TFA), 20 min]. $^1$H NMR (400 MHz, DMSO-d$_6$): δ 9.03 (s, 1H, disappeared on D$_2$O shake), 8.67 (s, 1H, disappeared on D$_2$O shake), 8.05 (s, 1H), 7.65 (d, J=6.4 Hz, 1H), 7.45 (s, 1H), 7.39 (d, J=8.7 Hz, 2H), 7.25 (t, J=7.8 Hz, 1H), 7.13 (d, J=7.6 Hz, 1H), 6.74 (d, J=8.6 Hz, 2H), 3.04-2.95 (m, 4H), 2.44-2.38 (m, 4H), 2.19 (s, 3H), 1.24 (s, 9H). HPLC-MS (ESI+): m/z 453.3 [20%, $(M^{37}Cl+H)^+$], 451.3 [70%, $(M^{35}Cl+H)^+$], 227.1 [30%, $(M^{37}Cl+2H)^{2+}$], 226.3 [100%, $(M^{35}Cl+2H)^{2+}$]. LC-MS (ESI+): 451.2 [100%, $(M^{35}Cl+H)^+$]. HRMS (ESI+): m/z calcd for $C_{25}H_{31}ClN_6$ (M+H)$^+$ 451.2371, found 451.2372.

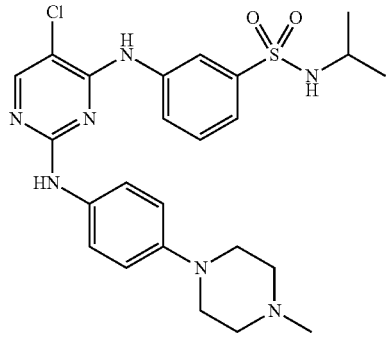

5-Chloro-$N^4$-(3-[N-(1-methylethyl)sulfamoyl]phenyl)-$N^2$-[4-(4-methylpiperazin-1-yl)phenyl]pyrimidine-2,4-diamine (SG2-004): This was prepared from SG2-003 (50 mg) and 4-(4-methylpiperazino)aniline (26 mg) using the general method x. The crude reaction mixture was triturated using EtOAc/hexanes to give the title compound as a light brown solid (49 mg, 66%). Mp: 195° C. (dec). HPLC: 95% [$t_R$=9.9 min, 35% MeOH, 65% water (with 0.1% TFA), 20 min]. $^1$H NMR (400 MHz, DMSO-$d_6$): δ 9.08 (s, 2H, disappeared on D$_2$O shake), 8.11 (s, 1H), 8.08-7.95 (m, 2H), 7.62-7.47 (m, 3H; 1H disappeared on D$_2$O shake), 7.37 (d, J=7.6 Hz, 2H), 6.78 (d, J=7.6 Hz, 2H), 3.23 (m, 1H), 3.06-2.94 (m, 4H), 2.45-2.36 (m, 4H), 2.19 (s, 3H), 0.94 (d, J=5.7 Hz, 6H). HPLC-MS (ESI+): m/z 516.2 [80%, $(M^{35}Cl+H)^+$], 259.4 [50%, $(M^{37}Cl+2H)^{2+}$], 258.7 [100%, $(M^{35}Cl+2H)^{2+}$]. LC-MS (ESI+): 516.1 [100%, $(M^{35}Cl+H)^+$]. HRMS (ESI+): m/z calcd for $C_{24}H_{30}ClN_7O_2S$ (M+H)$^+$ 516.1943, found 516.1924.

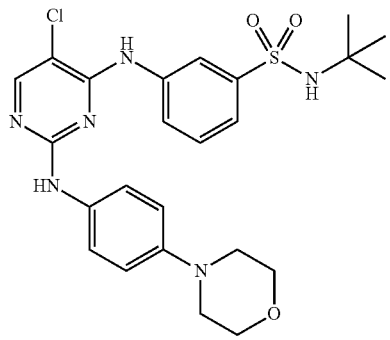

5-Chloro-$N^4$-(3-[N-(1,1-dimethylethyl)sulfamoyl]phenyl)-$N^2$-[4-morpholinophenyl]pyrimidine-2,4-diamine (SG2-005-01): This was prepared from SG1-149 (50 mg) and 4-morpholinoaniline (24 mg) using the general method x. The crude reaction product was purified via flash chromatography using hexanes/EtOAc (30-40%) to give the title compound as a brown solid (18 mg, 26%). Mp: 236° C. (dec). HPLC: 90% [$t_R$=9.3 min, 50% MeOH, 50% water (with 0.1% TFA), 20 min]. $^1$H NMR (400 MHz, DMSO-$d_6$): δ 9.10 (s, 1H, disappeared on D$_2$O shake), 9.08 (s, 1H, disappeared on D$_2$O shake), 8.12 (s, 1H), 8.09-7.96 (m, 2H), 7.56 (s, 1H, disappeared on D$_2$O shake), 7.54 (d, J=7.9 Hz, 1H), 7.49 (t, J=7.8 Hz, 1H), 7.41 (d, J=8.7 Hz, 2H), 6.80 (d, J=9.0 Hz, 2H), 3.74-3.66 (m, 4H), 3.03-2.93 (m, 4H), 1.09 (s, 9H). HPLC-MS (ESI+): m/z 517.2 [100%, $(M^{35}Cl+H)^+$], 259.1 [10%, $(M^{35}Cl+2H)^{2+}$]. LC-MS (ESI+): 539.2 [45%, $(M^{35}Cl+Na)^+$], 517.2 [100%, $(M^{35}Cl+H)^+$]. HRMS (ESI+): m/z calcd for $C_{24}H_{29}ClN_6O_3S$ (M+H)$^+$ 517.1783, found 517.1775.

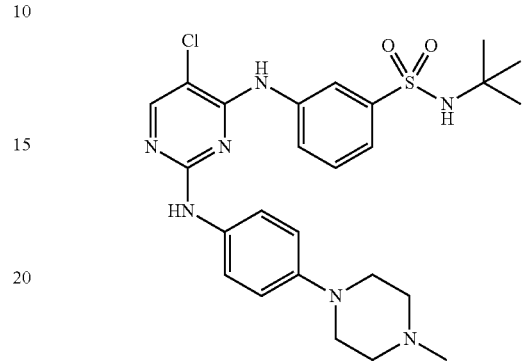

5-Chloro-$N^4$-(3-[N-(1,1-dimethylethyl)sulfamoyl]phenyl)-$N^2$-[4-(4-methylpiperazin-1-yl)phenyl]pyrimidine-2,4-diamine (SG2-015-01): This was obtained as a light yellow solid (50 mg, 35%) from SG1-149 (100 mg) and 4-(4-methylpiperazino)aniline (51 mg) using the general method x. Mp: 208° C. (dec). HPLC: 90% [$t_R$=4.8 min, 45% MeOH, 55% water (with 0.1% TFA), 20 min]. $^1$H NMR (400 MHz, DMSO-$d_6$): δ 9.08 (s, 1H, disappeared on D$_2$O shake), 9.07 (s, 1H, disappeared on D$_2$O shake), 8.11 (s, 1H), 8.08-7.95 (m, 2H), 7.57-7.54 (m, 2H; 1H disappeared on D$_2$O shake), 7.49 (t, J=7.9 Hz, 1H), 7.38 (d, J=8.4 Hz, 1H), 6.78 (d, J=8.8 Hz, 1H), 3.06-2.96 (m, 4H), 2.49-2.42 (m, 4H), 2.22 (s, 3H), 1.09 (s, 9H). HPLC-MS (ESI+): m/z 530.3 [60%, $(M^{35}Cl+H)^+$], 266.3 [30%, $(M^{37}Cl+2H)^{2+}$], 265.7 [100%, $(M^{35}Cl+2H)^{2+}$]. LC-MS (ESI+): 530.2 [100%, $(M^{35}Cl+H)^+$]. HRMS (ESI+): m/z calcd for $C_{25}H_{32}ClN_7O_2S$ (M+H)$^+$ 530.2099, found 530.2092.

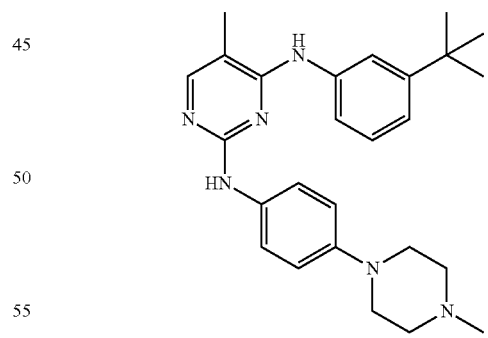

5-Methyl-$N^4$-[3-(1,1-dimethylethyl)]phenyl-$N^2$-[4-(4-methylpiperazin-1-yl)phenyl]pyrimidine-2,4-diamine (SG2-016): This was prepared from SG2-013 (50 mg) and 4-(4-methylpiperazino)aniline (35 mg) using the general method x. The crude reaction mixture was triturated using EtOAc/hexanes to give the title compound as a light brown solid (38 mg, 49%). Mp: 221° C. (dec). HPLC: 98% [$t_R$=11.3 min, 45% MeOH, 55% water (with 0.1% TFA), 20 min]. $^1$H NMR (400 MHz, DMSO-$d_6$): δ 8.65 (s, 1H, disappeared on D$_2$O shake), 8.12 (s, 1H, disappeared on D$_2$O shake), 7.80

(s, 1H), 7.76 (d, J=8.1 Hz, 1H), 7.46 (d, J=9.0 Hz, 2H), 7.43 (t, J=1.8 Hz, 1H), 7.22 (t, J=7.9 Hz, 1H), 7.06 (d, J=7.8 Hz, 1H), 6.74 (d, J=9.0 Hz, 2H), 3.02-2.94 (m, 4H), 2.44-2.38 (m, 4H), 2.19 (s, 3H), 2.07 (s, 3H), 1.25 (s, 9H). HPLC-MS (ESI+): m/z 431.3 [30%, (M+H)$^+$], 216.3 [100%, (M+2H)$^{2+}$]. LC-MS (ESI+): 431.3 [100%, (M+H)$^+$]. HRMS (ESI+): m/z calcd for $C_{26}H_{34}N_6$ (M+H)$^+$ 431.2918, found 431.2913.

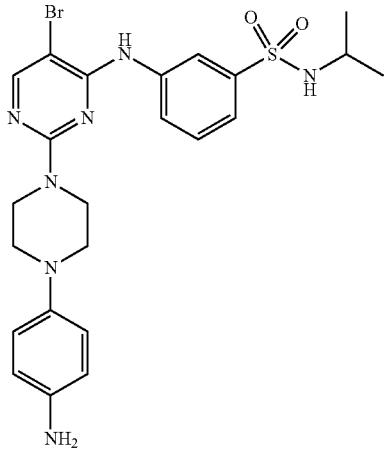

3-(2-[4-(4-Aminophenyl)piperazin-1-yl]-5-bromopyrimidin-4-yl)amino)-N-isopropylbenzenesulfonamide (MA1-014): This was obtained as a gray solid (51 mg, 78%) from MA1-001 (50 mg) and 4-(4-methylpiperazino)aniline (23 mg) using the general method x. Mp: 275° C. (dec). HPLC: 99% [$t_R$=14.0 min, 40% MeOH, 60% water (with 0.1% TFA), 20 min]. $^1$H NMR (400 MHz, DMSO-d$_6$): δ 8.81 (s, 1H, disappeared on D$_2$O shake), 8.40 (t, J=1.9 Hz, 1H), 8.18 (s, 1H), 7.75 (ddd, J=7.9, 1.9, 1.3 Hz, 1H), 7.52 (d, J=7.3 Hz, 1H disappeared on D$_2$O shake), 7.51 (t, J=7.9 Hz, 1H), 7.46 (dt, J=7.9, 1.3 Hz, 1H), 6.69 (d, J=8.8 Hz, 2H), 6.48 (d, J=8.8 Hz, 2H), 4.60 (s, 2H, disappeared on D$_2$O shake), 3.78-3.71 (m, 4H), 3.26-3.18 (m, 1H), 2.93-2.87 (m, 4H), 0.93 (d, J=6.5 Hz, 6H). HPLC-MS (ESI+): m/z 548.1 [100%, (M$^{81}$Br+H)$^+$], 546.2 [97%, (M$^{79}$Br)$^+$], 273.3 [10%, (M$^{79}$Br+2H)$^{2+}$]. LC-MS (ESI+): 548.1 [100%, (M$^{81}$Br+H)$^+$], 546.1 [90%, (M$^{79}$Br+H)$^+$]. HRMS (ESI+): m/z calcd for $C_{23}H_{28}BrN_7O_2S$ (M+H)$^+$ 546.1281, found 546.1263.

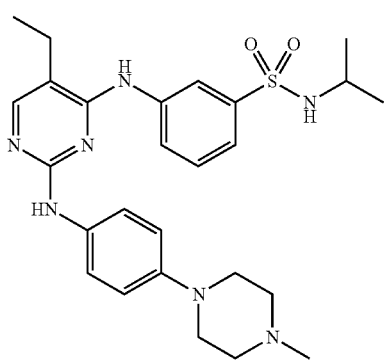

5-Ethyl-N$^4$-(3-[N-(1,1-dimethylethyl)sulfamoyl]phenyl)-N$^2$-[4-(4-methylpiperazin-1-yl)phenyl]pyrimidine-2,4-diamine (MA1-020): This was obtained as a gray solid (26 mg, 38%) from MA1-013 (50 mg) and 4-(4-methylpiperazino)aniline (32 mg) using the general method x. Mp: 244° C. (dec). HPLC: 93% [$t_R$=7.9 min, 40% MeOH, 60% water (with 0.1% TFA), 20 min]. $^1$H NMR (400 MHz, DMSO-d$_6$): δ 8.75 (s, 1H, disappeared on D$_2$O shake), 8.57 (s, 1H, disappeared on D$_2$O shake), 8.19 (d, J=8.0 Hz, 1H), 8.03 (brs, 1H), 7.90 (s, 1H), 7.61 (d, J=7.1 Hz, 1H, disappeared on D$_2$O shake), 7.54-7.42 (m, 4H), 6.80 (d, J=9.1 Hz, 2H), 3.30-3.18 (m, 1H), 3.11-2.98 (m, 4H), 2.57 (q, J=7.4 Hz, 2H), 2.50-2.43 (m, 4H, overlapped with the residual DMSO signal) 2.25 (s, 3H), 1.16 (t, J=7.4 Hz, 3H), 0.97 (d, J=6.6 Hz, 6H). HPLC-MS (ESI+): m/z 510.3 [25%, (M+H)$^+$], 255.7 [100%, (M+2H)$^{2+}$]. LC-MS (ESI+): m/z 510.3 [100%, (M+H)$^+$], 255.6 [15%, (M+2H)$^{2+}$]. HRMS (ESI+): m/z calcd for $C_{28}H_{35}N_7O_2S$ (M+H)$^+$ 510.2646, found 510.2631.

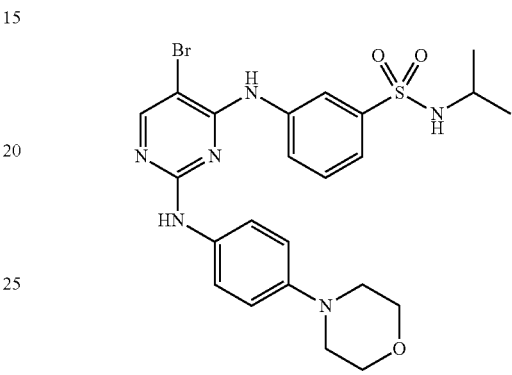

5-Bromo-N$^4$-(3-[N-(1-methylethyl)sulfamoyl]phenyl)-N$^2$-[4-morpholinophenyl]pyrimidine-2,4-diamine (MA1-021): This was obtained as a white solid (46 mg, 70%) from MA1-001 (50 mg) and 4-morpholinoaniline (21 mg) using the general method x. Mp: 220° C. (dec). HPLC: 99% [$t_R$=5.4 min, 50% MeOH, 50% water (with 0.1% TFA), 20 min]. $^1$H NMR (400 MHz, DMSO-d$_6$): δ 9.12 (s, 1H, disappeared on D$_2$O shake), 8.86 (s, 1H, disappeared on D$_2$O shake), 8.19 (s, 1H), 7.96 (brs, 2H), 7.58 (d, J=7.1 Hz, 1H, disappeared on D$_2$O shake), 7.55-7.51 (m, 2H), 7.38 (d, J=8.8 Hz, 2H), 6.77 (d, J=8.8 Hz, 2H), 3.74-3.68 (m, 4H), 3.21 (septet, J=6.5 Hz, 1H), 3.00-2.95 (m, 4H), 0.93 (d, J=6.5 Hz, 6H). HPLC-MS (ESI+): m/z 549.1 [100%, (M$^{81}$Br+H)$^+$], 548.2 [30%, (M$^{81}$Br+H)$^+$], 547.2 [97%, (M$^{79}$Br+H)$^+$]. LC-MS (ESI+): 549.1 [100%, (M$^{81}$Br+H)$^+$], 547.1 [90%, (M$^{79}$Br+H)$^+$]. HRMS (ESI+): m/z calcd for $C_{23}H_{27}BrN_6O_3S$ (M+H)$^+$ 547.1121, found 547.1102.

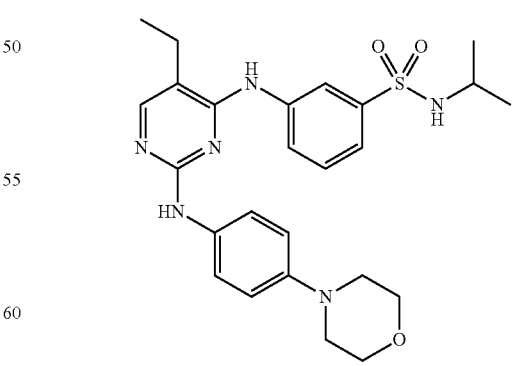

5-Ethyl-N$^4$-(3-[N-(1-methylethyl)sulfamoyl]phenyl)-N$^2$-[4-morpholinophenyl]pyrimidine-2,4-diamine (MA1-022): This was obtained as a gray solid (26 mg, 38%) from MA1-013 (50 mg) and 4-morpholinoaniline (25 mg) using the general method x. Mp: 235° C. (dec). HPLC: 99% [$t_R$=6.2 min, 50% MeOH, 50% water (with 0.1% TFA), 20 min]. $^1$H NMR (400 MHz, DMSO-$d_6$): δ 8.75 (s, 1H, disappeared on D$_2$O shake), 8.55 (s, 1H, disappeared on D$_2$O shake), 8.17 (d, J=7.7 Hz, 1H), 8.01 (s, 1H), 7.89 (s, 1H), 7.59 (d, J=7.1 Hz, 1H, disappeared on D$_2$O shake), 7.51-7.42 (m, 4H), 6.79 (d, J=9.1 Hz, 2H), 3.74-3.67 (m, 4H), 3.25-3.18 (m, 1H), 3.02-2.93 (m, 4H), 2.55 (q, J=7.4 Hz, 2H), 1.14 (t, J=7.4 Hz, 3H), 0.95 (d, J=6.5 Hz, 6H). HPLC-MS (ESI+): m/z 497.3 [100%, (M+H)$^+$], 249.1 [49%, (M+2H)$^{2+}$]. LC-MS (ESI+): 497.2 [100%, (M+H)$^+$]. HRMS (ESI+): m/z calcd for $C_{25}H_{32}N_6O_3S$ (M+H)$^+$ 497.2329, found 497.2322.

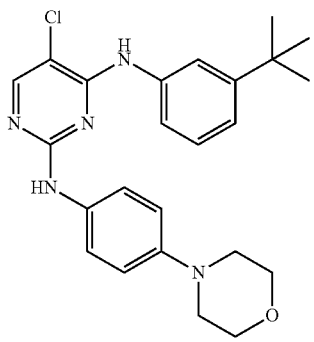

5-Chloro-N$^4$-[3-(1,1-dimethylethyl)phenyl]-N$^2$-[4-morpholinophenyl]pyrimidine-2,4-diamine (MA1-023): This was prepared from SG1-175 (50 mg) and 4-morpholinoaniline (32 mg) using the general method x. No purification was required to get the final product as a white solid (78 mg, 99%). Mp: 189° C. (dec). HPLC: 99% [$t_R$=13.0 min, 65% MeOH, 35% water (with 0.1% TFA), 20 min]. $^1$H NMR (400 MHz, DMSO-$d_6$): δ 9.05 (s, 1H, disappeared on D$_2$O shake), 8.68 (s, 1H, disappeared on D$_2$O shake), 8.06 (s, 1H), 7.65 (d, J=7.5 Hz, 1H), 7.46 (t, J=1.9 Hz, 1H), 7.42 (d, J=9.0 Hz, 2H), 7.26 (t, J=7.9 Hz, 1H), 7.14 (ddd, J=7.9, 1.6, 0.9 Hz, 1H), 6.75 (d, 9.0 Hz, 2H), 3.72-3.68 (m, 4H), 2.99-2.95 (m, 4H), 1.25 (s, 9H). HPLC-MS (ESI+): m/z 440.2 [35%, (M$^{37}$Cl+H)$^+$], 438.2 [100%, (M$^{35}$Cl+H)$^+$]. LC-MS (ESI+): 440.2 [30%, (M$^{37}$Cl+H)$^+$], 438.2 [100%, (M$^{35}$Cl+H)$^+$]. HRMS (ESI+): m/z calcd for $C_{24}H_{28}ClN_5O$ (M+H)$^+$ 438.2055, found 438.2074.

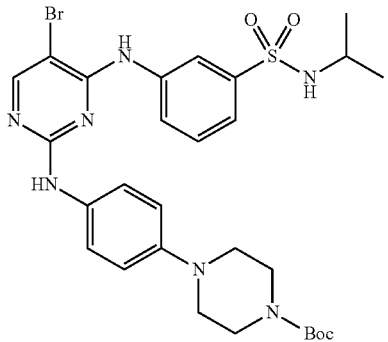

5-Bromo-N$^4$(3-[N-(1-Methylethyl)sulfamoyl]phenyl)-N$^2$-[4-(4-tert-butoxycarbonylpiperazin-1-yl)phenyl]pyrimidine-2,4-diamine (MA1-027): This was obtained by stirring MA1-001 (90 mg) and 4-(4-tert-butoxycarbonylpiperazino) aniline (62 mg) in isopropanol (2 mL) at 80° C. (oil bath) for 2 days. The reaction mixture was allowed to cool to room temperature and diluted with ethyl acetate (30 mL). The mixture was washed with NaHCO$_3$ (sat. aq. solution, 20 mL), brine (20 mL) and water (20 mL). The organic layer was dried (Na$_2$SO$_4$), and the solvent evaporated under reduced pressure. The residue was purified by column chromatography (SiO$_2$) eluting with ethyl acetate and hexane to provide MA1-027 as a dark grey solid (64 mg, 45%). Mp: 196-197° C. HPLC: 99% [$t_R$=12.8 min, 60% MeOH, 40% water (with 0.1% TFA), 30 min]. $^1$H NMR (400 MHz, DMSO-$d_6$) δ 9.13 (s, 1H, disappeared on D$_2$O shake), 8.86 (s, 1H, disappeared on D$_2$O shake), 8.19 (s, 1H), 8.02-7.92 (brs, 2H), 7.58 (d, J=7.1 Hz, 1H, disappeared on D$_2$O shake), 7.55-7.50 (m, 2H), 7.38 (d, J=8.8 Hz, 2H), 6.78 (d, J=8.8 Hz, 2H), 3.45-3.38 (m, 4H), 3.21 (septet, J=6.5 Hz, 1H), 2.98-2.91 (m, 4H), 1.40 (s, 9H), 0.93 (d, J=6.5 Hz, 6H). HPLC-MS (ESI+): m/z 648.2 [100%, (M$^{81}$Br+H)$^+$], 646.2 [84%, (M$^{79}$Br+2H)$^+$]. LC-MS (ESI+): δ 70.2 [30%, (M$^{81}$Br+H)$^+$], 668.2 [30%, (M$^{79}$Br+2H)$^+$], 648.2 [100%, (M$^{81}$Br+H)$^+$], 646.2 [90%, (M$^{79}$Br+2H)$^+$]. HRMS (ESI+): m/z calcd for $C_{28}H_{36}BrN_7O_4S$ (M+H)$^+$ 646.1806, found 646.1787.

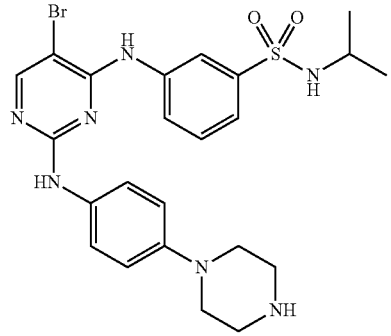

5-Bromo-N$^4$-(3-[N-(1-methylethyl)sulfamoyl]phenyl)-N$^2$-[4-(piperazin-1-yl)phenyl]pyrimidine-2,4-diamine (MA1-027-2): This was prepared by overnight stirring of MA1-027 (41 mg) in 20% TFA/DCE (1.2 mL) at 80° C. Upon cooling to room temperature, the reaction mixture was poured into aq. NaHCO$_3$ and extracted with ethyl acetate (2×40 mL). Column chromatography with DCM/MeOH (0-15%) yielded MA1-027-2 as a golden white solid (22 mg, 64%). Mp: 233° C. (dec). HPLC: 99% [$t_R$=5.2 min, 40% MeOH, 60% water (with 0.1% TFA), 20 min]. $^1$H NMR (400 MHz, DMSO-$d_6$): δ 9.09 (s, 1H, disappeared on D$_2$O shake), 8.85 (s, 1H, disappeared on D$_2$O shake), 8.18 (s, 1H), 7.96 (brs, 2H), 7.58 (d, J=7.1 Hz, 1H, disappeared on D$_2$O shake), 7.55-7.50 (m, 2H), 7.35 (d, J=8.9 Hz, 2H), 6.75 (d, J=8.9 Hz, 2H), 3.22 (septet, J=6.5 Hz, 1H), 2.97-2.90 (m, 4H), 2.86-2.78 (m, 4H), 0.93 (d, J=6.5 Hz, 6H). HPLC-MS (ESI+): m/z 546.2 [100%, (M$^{79}$Br+H, 100%)$^+$], 274.6 [97%, (M$^{81}$Br+H)$^{2+}$], 273.6 [100%, (M$^{79}$Br+2H)$^{+2}$]. LC-MS (ESI+): 570.1 [20%, (M$^{81}$Br+Na)$^+$], 568.1 [20%, (M$^{79}$Br+Na)$^+$], 548.1 [100%, (M$^{81}$Br+H)$^+$], 546.1 [100%, (M$^{79}$Br+H)$^+$]. HRMS (ESI+): m/z calcd for $C_{23}H_{28}BrN_7O_2S$ (M+H)$^+$ 546.1281, found 546.1276.

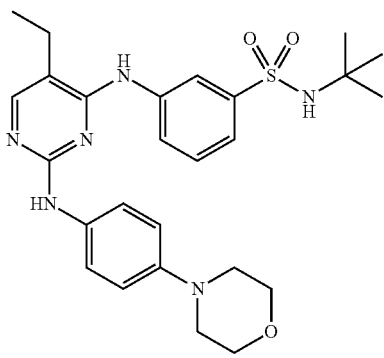

5-Ethyl-$N^4$-(3-[N-(1,1-dimethylethyl)sulfamoyl]phenyl)-$N^2$-[4-morpholinophenyl]pyrimidine-2,4-diamine (MA1-028): This was obtained as gray solid (25 mg, 38%) from MA1-017 (50 mg) and 4-morpholinoaniline (23 mg) using the general method x. Mp: 214° C. (dec). HPLC: 99% [$t_R$=9.4 min, 50% MeOH, 50% water (with 0.1% TFA), 20 min]. $^1$H NMR (400 MHz, DMSO-$d_6$): δ 8.74 (s, 1H, disappeared on D$_2$O shake), 8.54 (s, 1H, disappeared on D$_2$O shake), 8.15-8.06 (m, 2H), 7.89 (s, 1H), 7.56 (s, 1H, disappeared on D$_2$O shake), 7.50-7.44 (m, 4H), 6.80 (d, J=9.1 Hz, 2H), 3.73-3.68 (m, 4H), 3.00-2.95 (m, 4H), 2.55 (q, J=7.4 Hz, 2H), 1.14 (t, J=7.4 Hz, 3H), 1.10 (s, 9H). HPLC-MS (ESI+): m/z 511.3 [100%, (M+H)$^+$ 1, 256.2 [55%, (M+H)$^{2+}$]. LC-MS (ESI+): 511.2 [100%, (M+H)$^+$]. HRMS (ESI+): m/z calcd for $C_{26}H_{34}N_6O_3S$ (M+H)$^+$ 511.2486, found 511.2470.

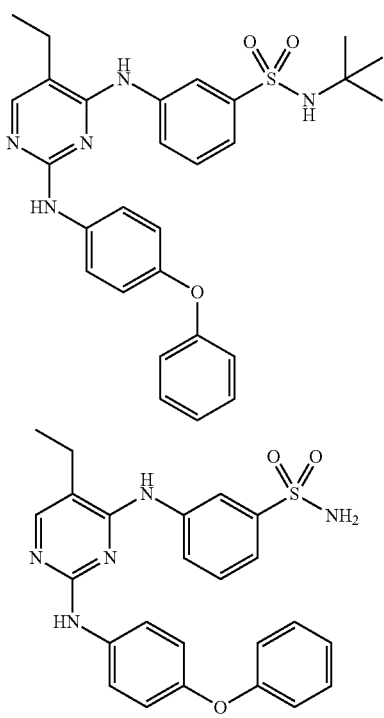

5-Ethyl-$N^4$-(3-[$N^4$-(3-[N-(1,1-Dimethylethyl)sulfamoyl]phenyl)-$N^2$-[4-phenoxyphenyl]pyrimidine-2,4-diamine (MA1-030) and 5-ethyl-$N^4$-[(3-sulfamoyl)phenyl]-$N^2$-[4-phenoxyphenyl]pyrimidine-2,4-diamine (MA1-030B): This was prepared from MA1-017 (50 mg) and 4-morpholinoaniline (25 mg) using the general method x. The residue was purified via flash chromatography eluting with ethyl acetate-hexane to provide MA1-030 (30 mg, 43%) as a white solid. Mp: 256° C. (dec). HPLC: 99% [$t_R$=9.0 min, 55% MeOH, 45% water (with 0.1% TFA), 20 min]. $^1$H NMR (400 MHz, DMSO-$d_6$): δ 9.05 (s, 1H, disappeared on D$_2$O shake), 8.64 (s, 1H, 65% reduced on D$_2$O shake), 8.12-8.08 (m, 1H), 8.05 (s, 1H), 7.95 (s, 1H), 7.65 (d, J=9.0 Hz, 2H), 7.56 (s, 1H, disappeared on D$_2$O shake), 7.50-7.47 (m, 2H), 7.37-7.31 (m, 2H), 7.09-7.03 (m, 1H), 6.94-6.90 (m, 2H), 6.87 (d, J=9.0 Hz, 2H), 2.59 (q, J=7.4 Hz, 2H), 1.15 (t, J=7.4 Hz, 3H), 1.10 (s, 9H). HPLC-MS (ESI+): m/z 518.3 [100%, (M+H)$^+$]. LC-MS (ESI+): 518.2 [100%, (M+H)$^+$]. HRMS (ESI+): m/z calcd for $C_{28}H_{31}N_5O_3S$ (M+H)$^+$ 518.2220, found 518.2215. Further elution gave the sulfonamide MA1-030B (18 mg, 28%) as a white solid Mp: 281° C. (dec). HPLC: 99% [$t_R$=9.0 min, 55% MeOH, 45% water (with 0.1% TFA), 20 min]. $^1$H NMR (400 MHz, DMSO-$d_6$): δ 9.03 (s, 1H, disappeared on D$_2$O shake), 8.65 (s, 1H, disappeared on D$_2$O shake), 8.13-8.07 (m, 1H), 7.99 (brs, 1H), 7.93 (s, 1H), 7.64 (d, J=9.0 Hz, 2H), 7.48-7.44 (m, 2H), 7.35-7.30 (m, 4H; 2H disappeared on D$_2$O shake), 7.04 (tt, J=7.7, 1.1 Hz, 1H), 6.93-6.86 (m, 4H), 2.56 (q, J=7.4 Hz, 2H), 1.15 (t, J=7.4 Hz, 3H). HPLC-MS (ESI+): m/z 462.1 [100%, (M+H)$^+$]. LC-MS (ESI+): 462.2 [100%, (M+H)$^+$]. HRMS (ESI+): m/z calcd for $C_{24}H_{23}N_5O_3S$ (M+H)$^+$ 462.1594, found 462.1589.

5-Ethyl-$N^4$-(3-[N-(1,1-dimethylethyl)sulfamoyl]phenyl)-$N^2$-[4-(4-methylpiperazin-1-yl)phenyl]pyrimidine-2,4-diamine (MA1-032): This was obtained as a light green solid (29 mg, 41%) from MA1-017 (50 mg) and 4-(4-methylpiperazino)aniline (26 mg) using the general method x. Mp: 220° C. (dec). HPLC: 90% [$t_R$=12.5 min, 40% MeOH, 60% water (with 0.1% TFA), 20 min]. $^1$H NMR (400 MHz, DMSO-$d_6$): δ 8.72 (s, 1H, disappeared on D$_2$O shake), 8.53 (s, 1H, disappeared on D$_2$O shake), 8.15-8.10 (m, 1H), 8.08 (s, 1H), 7.88 (s, 1H), 7.56 (s, 1H, disappeared on D$_2$O shake), 7.48-7.42 (m, 4H), 6.78 (d, J=9.1 Hz, 2H), 3.04-2.94 (m, 4H), 2.55 (q, J=7.4 Hz, 2H), 2.45-2.36 (m, 4H), 2.19 (s, 3H), 1.14 (t, J=7.4 Hz, 3H), 1.10 (s, 9H). HPLC-MS (ESI+): m/z 524.3 [30%, (M+H)$^+$], 262.7 [100%, (M+H)$^{2+}$]. LC-MS (ESI+): 524.3 [100%, (M+H)$^+$]. HRMS (ESI+): m/z calcd for $C_{27}H_{37}N_7O_2S$ (M+H)$^+$ 524.2802, found 524.2787.

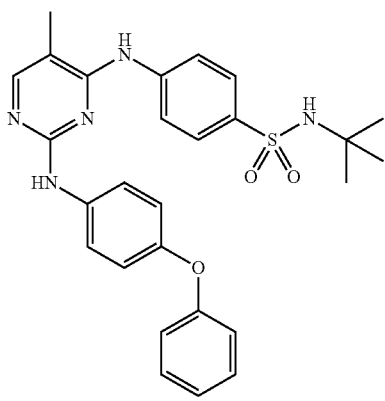

5-Methyl-N[4]-(4-[N-(1,1-Dimethylethyl)sulfamoyl]phenyl)-N[2]-[4-phenoxyphenyl]pyrimidine-2,4-diamine (MA1-033): This was prepared from SG2-007 (50 mg) and 4-phenoxyaniline (26 mg) using the general method x. The residue was purified via chromatography eluting with ethyl acetate-hexane (1:5-1:0, v/v) to provide MA1-033 (15 mg, 21%) as beige solid. Mp: 276° C. (dec). HPLC: 94% [$t_R$=9.8 min, 50% MeOH, 50% water (with 0.1% TFA), 20 min]. $^1$H NMR (400 MHz, DMSO-$d_6$) δ 9.14 (s, 1H, disappeared on $D_2O$ shake), 8.58 (s, 1H, disappeared on $D_2O$ shake), 7.95 (s, 1H), 7.92 (d, J=8.8 Hz, 2H), 7.75-7.66 (m, 4H), 7.38 (s, 1H, disappeared on $D_2O$ shake), 7.36-7.29 (m, 2H), 7.03 (t, J=7.4 Hz, 1H), 6.96-6.86 (m, 4H), 2.12 (s, 3H), 1.03 (s, 9H). HPLC-MS (ESI+): m/z 504.3 [100%, (M+H)$^+$]. LC-MS (ESI+): 504.2 [100%, (M+H)$^+$]. HRMS (ESI+): m/z calcd for $C_{27}H_{29}N_5O_3S$ (M+H)$^+$ 504.2064, found 504.2047.

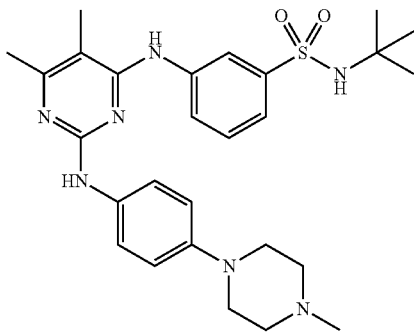

5,6-Dimethyl-N[4]-(3-[N-(1,1-dimethylethyl)sulfamoyl]phenyl)-N[2]-[4-(4-methylpiperazin-1-yl)phenyl]pyrimidine-2,4-diamine (RJ1-014): A mixture of RJ1-010 (0.050 g, 0.136 mmol), 4-(4-methyl-1-piperazinyl)-aniline (0.026 g, 0.136 mmol), EtOH (1 mL, 0.027 mol) and 4 M HCl (2 drops) was heated in a microwave reactor at 160° C. for 15 minutes. The reaction mixture was dissolved in EtOAc (20 mL) and washed with saturated $NaHCO_3$ (20 mL). The aqueous layer was then re-extracted with EtOAc (20 mL). The combined organic layers were washed with water (20 mL), brine (20 mL), dried over $Na_2SO_4$, and concentrated. The residue was then triturated with hexanes and EtOAc to provide RJ1-014 (0.041 g, 58%) as a powdery, off-white solid. Mp: 201° C. (dec). HPLC: 90% [$t_R$=8.8 min, 40% MeOH, 60% water (with 0.1% TFA), 20 min]. $^1$H NMR (400 MHz, DMSO-$d_6$): δ 8.66 (s, 1H, disappeared on $D_2O$ shake), 8.44 (s, 1H, disappeared on $D_2O$ shake), 8.05-7.94 (m, 2H), 7.54 (s, 1H), 7.49-7.41 (m, 4H), 6.76 (d, J=9.0 Hz, 2H), 3.04-2.93 (m, 4H), 2.45-2.38 (m, 4H), 2.25 (s, 3H), 2.19 (s, 3H), 2.09 (s, 3H), 1.10 (s, 9H). HPLC-MS (ESI+): m/z 524.2 [90%, (M+H)$^+$], 262.8 [100%, (M+2H)$^{2+}$]. LC-MS (ESI+): 524.3 [100%, (M+H)+], 262.6 [10%, (M+2H)$^{2+}$], 234.6 [40%, (M+2H-tBu)$^{2+}$]. HRMS (ESI+): m/z calcd for $C_{27}H_{37}N_7O_2S$ (M+H)$^+$ 524.2802, found 524.2791.

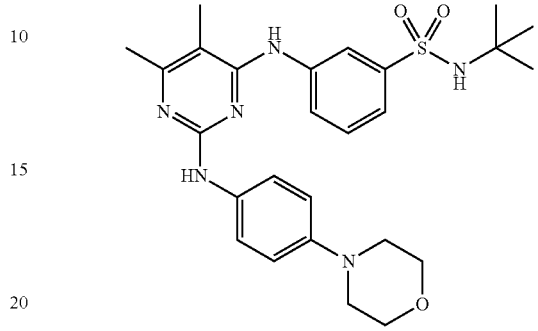

5,6-Dimethyl-N[4]-(3-[N-(1,1-dimethylethyl)sulfamoyl]phenyl)-N[2]-[4-morpholinophenyl]pyrimidine-2,4-diamine (RJ1-024-01): A mixture of RJ1-010 (0.100 g, 0.271 mmol), 4-morpholinoaniline (0.048 g, 0.271 mmol), EtOH (2 mL), and 4M HCl (3 drops) was allowed to react and worked up following the same procedure as used for RJ1-014. The residue was purified via flash chromatography eluting with DCM (with 2% MeOH) to provide RJ1-024-01 (0.037 g, 27%) as a pale lilac solid. Mp: 222° C. (dec). HPLC 99.9% [$t_R$=8.2 min, 45% MeOH (with 0.1% TFA), 20 min]. $^1$H NMR (400 MHz, DMSO-$d_6$): δ 8.69 (s, 1H, disappeared on $D_2O$ shake), 8.44 (s, 1H, disappeared on $D_2O$ shake), 8.05-7.97 (m, 2H), 7.54 (s, 1H, disappeared on $D_2O$ shake), 7.47 (d, J=9.0 Hz, 2H), 7.45-7.42 (m, 2H), 6.78 (d, J=9.0 Hz, 2H), 3.74-3.65 (m, 4H), 3.00-2.93 (m, 4H), 2.26 (s, 3H), 2.09 (s, 3H), 1.10 (s, 9H). HPLC-MS (ESI+): m/z 511.3 [100%, (M+H)$^+$], 256.3 [90%, (M+2H)$^{2+}$]. LC-MS (ESI+): m/z 511.3 (M+H)$^+$; HRMS (ESI+): m/z calcd for $C_{26}H_{34}N_6O_3S$ (M+H)$^+$ 511.2486, found 511.2485.

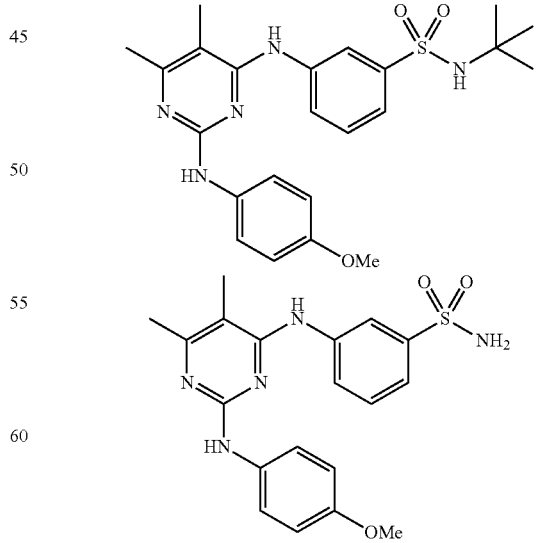

5,6-Dimethyl-N[4]-(3-[N-(1,1-dimethylethyl)sulfamoyl]phenyl)-N[2]-(4-methoxyphenyl)pyrimidine-2,4-diamine (RJ1-027-01) and 5,6-dimethyl-N$^4$-[3-(sulfamoyl)phenyl]-N$^2$-[4-methoxyphenyl]pyrimidine-2,4-diamine (RJ1-027-02): A mixture of RJ1-010 (0.100 g, 0.271 mmol), p-anisidine (0.033 g, 0.271 mmol), EtOH (2 mL), and 4M HCl (3 drops) was allowed to react and worked up following the same procedure as with RJ1-014. The residue was then purified via flash chromatography, eluting with DCM (with 2% MeOH) to provide RJ1-027-01, as a white solid (0.041 g, 33%). Mp: 224° C. (dec). HPLC 95% [t$_R$=10.6 min, 45% MeOH, 55% water (with 0.1% TFA), 20 min]. $^1$H NMR (400 MHz, DMSO-d$_6$): δ 8.73 (s, 1H, disappeared on D$_2$O shake), 8.46 (s, 1H, disappeared on D$_2$O shake), 8.04-7.98 (m, 2H), 7.55-7.43 (m, 5H), 6.74 (d, J=9.0 Hz, 2H), 3.67 (s, 3H), 2.26 (s, 3H), 2.09 (s, 3H), 1.09 (s, 9H). HPLC-MS (ESI+): m/z 456.2 (100%, M+H)$^+$]. LC-MS (ESI+): m/z 456.3 (M+H)$^+$. HRMS (ESI+): m/z calcd for C$_{23}$H$_{29}$N$_5$O$_3$S (M+H)$^+$ 456.2064, found 456.2059. Further elution from the column using DCM (with 3-4% MeOH) gave RJ1-027-02 as a white solid, (0.006 g, 5%). Mp: 216° C. (dec). HPLC 94% [t$_R$=7.4 min, 35% MeOH, 65% water (with 0.1% TFA), 20 min]. $^1$H NMR (400 MHz, DMSO-d$_6$): δ 8.73 (s, 1H, disappeared on D$_2$O shake), 8.49 (s, 1H, disappeared on D$_2$O shake), 8.08-7.99 (m, 1H), 7.96 (brs, 1H), 7.52 (d, J=9.0 Hz, 2H), 7.47-7.43 (m, 2H), 7.32 (s, 2H, disappeared on D$_2$O shake), 6.75 (d, J=9.0 Hz, 2H), 3.67 (s, 3H), 2.26 (s, 3H), 2.09 (s, 3H). HPLC-MS (ESI+): m/z 400.2 (100%, M+H)$^+$ 1. LC-MS (ESI+): m/z 400.1 [100%, (M+H)+]. HRMS (ESI+): m/z calcd for C$_{19}$H$_{21}$N$_5$O$_3$S (M+H)+ 400.1438, found 400.1446.

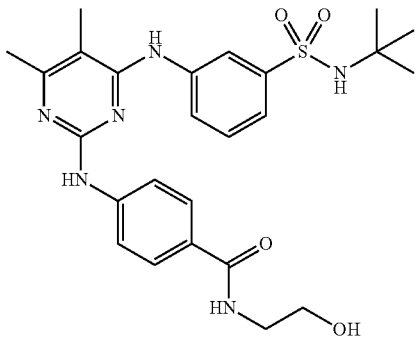

5,6-Dimethyl-N$^4$-(3-[N-(1,1-dimethylethyl)sulfamoyl]phenyl)-N$^2$-[4-(2-hydroxyethylcarbamoyl)phenyl]pyrimidine-2,4-diamine (RJ1-030-01): A mixture of RJ1-010 (0.100 g, 0.271 mmol, N-(4-aminobenzoyl)aminoethanol (0.033 g, 0.271 mmol), EtOH (2 mL), and 4M HCl (3 drops) was allowed to react and worked up following the same procedure used to make RJ1-014. The residue was then purified via flash chromatography eluting with DCM (with 6% MeOH) to provide RJ1-030-01 as a white foam (0.030 g, 22%). Mp: 174° C. (decomposed). HPLC 97% [t$_R$=6.0 min, 40% MeOH, 60% water (with 0.1% TFA), 20 min]. $^1$H NMR (400 MHz, DMSO-d$_6$): δ 9.25 (s, 1H, disappeared on D$_2$O shake), 8.60 (s, 1H, disappeared on D$_2$O shake), 8.15 (t, J=5.5 Hz, 1H, disappeared on D$_2$O shake), 8.05-7.96 (m, 2H), 7.70 (d, J=8.8 Hz, 2H), 7.64 (d, J=8.8 Hz, 2H), 7.57-7.45 (m, 3H), 4.71 (t, J=5.3 Hz, 1H, disappeared on D$_2$O shake), 3.49-3.42 (m, 2H), 3.30-3.23 (m, 2H), 2.31 (s, 3H), 2.12 (s, 3H), 1.10 (s, 9H). HPLC-MS (ESI+): m/z 535.2 [100%, (M+1-1)$^+$]. LC-MS (ESI+): m/z 535.2 [40%, (M+Na)$^+$], 513.2 [100%, (M+H)$^+$]. HRMS (ESI+): m/z calcd for C$_{25}$H$_{32}$N$_6$O$_4$S (M+H)$^+$ 513.2279, found 513.2291.

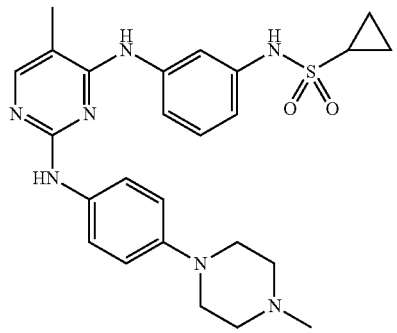

5-Methyl-N$^4$-(3-Cyclopropylsulfonamido)phenyl-N$^2$-[4-(4-methylpiperazin-1-yl)phenyl]pyrimidine-2,4-diamine (RJ1-036-01): A mixture of RJ1-032 (0.100 g, 0.295 mmol), 4-(4-methyl-1-piperazinyl)aniline (0.056 g, 0.295 mmol), EtOH (2 mL), and 4M HCl (3 drops) was reacted and worked up following the same procedure as with RJ1-014. The residue was then purified via flash chromatography eluting with MeOH (6-7%) in DCM to give the product RJ1-036-01 as a beige-colored solid, (0.052 g, 36%). Mp: 124° C. (dec). HPLC 99% [t$_R$=9.7 min, 30% MeOH, 70% water (with 0.1% TFA), 20 min]. $^1$H NMR (400 MHz, DMSO-d$_6$): δ 9.70-9.60 (brs, 1H, disappeared on D$_2$O shake), 8.58 (s, 1H, disappeared on D$_2$O shake), 8.30 (s, 1H, disappeared on D$_2$O shake), 7.83 (d, J=0.7 Hz, 1H), 7.52 (d, J=7.2 Hz, 2H), 7.46 (d, J=9.0 Hz, 2H), 7.22 (t, J=8.3 Hz, 1H), 6.94-6.85 (m, 1H), 6.77 (d, J=9.1 Hz, 2H), 3.02-2.96 (m, 4H), 2.63-2.54 (m, 1H), 2.46-2.36 (m, 4H), 2.19 (s, 3H), 2.07 (s, 3H), 0.92 (m, 4H). HPLC-MS (ESI+): m/z 494.3 [20%, (M+H)]$^+$; 247.8 [100%, (M+2H)$^{2+}$], LC-MS (ESI+): m/z 494.2 [100%, (M+H)$^+$], 247.6 [25%, (M+2H)$^{2+}$]. HRMS (ESI+): m/z calcd for C$_{25}$H$_{31}$N$_7$O$_2$S (M+H)$^+$ 494.2333, found 494.2331.

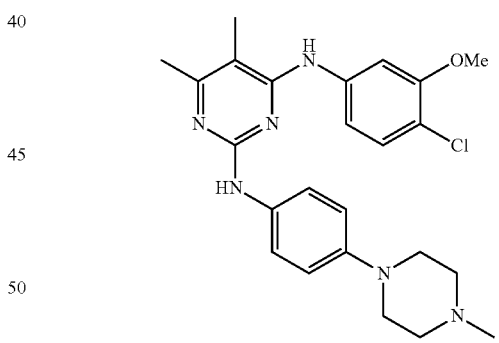

N$^4$-(4-Chloro-3-methoxyphenyl)-5,6-dimethyl-N$^2$-(4-(4-methylpiperazin-1-yl)phenyl)pyrimidine-2,4-diamine (RJ1-040-01): A mixture of RJ1-034 (0.050 g, 0.168 mmol), 4-(4-methyl-1-piperazinyl)aniline (0.032 g, 0.168 mmol), EtOH (1 mL), and 4M HCl (2 drops) was allowed to react and worked up following the same procedure used to prepare RJ1-014. The residue was purified via flash chromatography eluting with MeOH (4%) in DCM to provide the desired product as an off-white solid, RJ1-040-01 (0.012 g, 16%). Mp: 157° C. (dec). HPLC 99.8% [t$_R$=8.4 min, 40% MeOH, 60% water (with 0.1% TFA), 20 min]. $^1$H NMR (400 MHz, DMSO-d$_6$): δ 8.69 (s, 1H, disappeared on D$_2$O shake), 8.21 (s, 1H, disappeared on D$_2$O shake), 7.45 (d, J=9.0 Hz, 2H), 7.41 (d, J=2.2 Hz, 1H), 7.33 (dd, J=8.6, 2.2

Hz, 1H), 7.25 (d, J=8.6 Hz, 1H), 6.74 (d, J=9.1 Hz, 2H), 3.68 (s, 3H), 3.02-2.97 (m, 4H), 2.46-2.40 (m, 4H), 2.24 (s, 3H), 2.19 (s, 3H), 2.07 (s, 3H). HPLC-MS (ESI+): m/z 453.2 [15%, (M$^{35}$Cl+H)$^+$], 227.9 [40%, (M$^{37}$Cl+2H)$^{2+}$]. 227.2 [100%, (M$^{35}$Cl+2H)$^{2+}$]. LC-MS (ESI+): m/z 455.2 [35%, (M$^{37}$Cl+H)$^+$], 453.2 [100%, (M$^{35}$Cl+H)$^+$], 227.1 [25%, (M$^{35}$Cl+2H)$^{2+}$]. HRMS (ESI+): m/z calcd for C$_{24}$H$_{29}$ClN$_6$O (M+H)$^+$ 453.2164, found 453.2155.

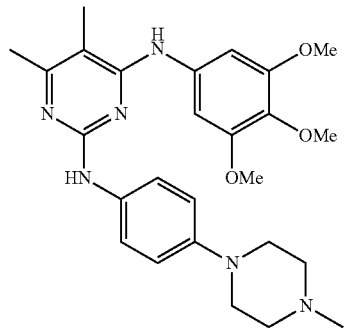

5,6-Dimethyl-N$^2$-(4-(4-methylpiperazin-1-yl)phenyl)-N$^4$-(3,4,5-trimethoxyphenyl)pyrimidine-2,4-diamine (RJ1-041-01): A mixture of RJ1-037 (0.100 g, 0.309 mol), 4-(4-methyl-1-piperazinyl)aniline (0.059 g, 0.309 mol), EtOH (2 mL), and 4M HCl (3 drops) was allowed to react and worked up following the same procedure for RJ1-014. The residue was then purified via flash chromatography eluting with MeOH (5-6%) in DCM to gibe the desired product as a champagne-colored solid, RJ1-041-01 (0.054 g, 36%). Mp: 137° C. (dec). HPLC 99% [t$_R$=5.5 min, 40% MeOH, 60% water (with 0.1% TFA), 20 min]. $^1$H NMR (400 MHz, DMSO-d$_6$): δ 8.66 (s, 1H, disappeared on D$_2$O shake), 8.05 (s, 1H, disappeared on D$_2$O shake), 7.48 (d, J=9.0 Hz, 2H), 6.90 (s, 2H), 6.70 (d, J=9.0 Hz, 2H), 3.63 (s, 9H), 3.00-2.91 (m, 4H), 2.44-2.40 (m, 4H), 2.23 (s, 3H), 2.19 (s, 3H), 2.05 (s, 3H). HPLC-MS (ESI+): m/z 479.3 [15%, (M+H)$^+$], 240.3 [100%, (M+2H)$^{2+}$]. LC-MS (ESI+): m/z 479.3 [100%, (M+H)$^+$], 240.1 [40%, (M+2H)$^{2+}$], HRMS (ESI+): m/z calcd for C$_{26}$H$_{34}$N$_6$O$_3$ (M+H)$^+$ 479.2765, found 479.2768.

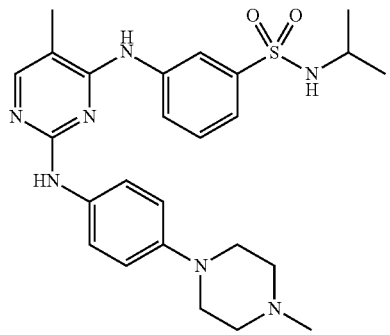

5-Methyl-N$^4$-(3-[N-(1-methylethyl)sulfamoyl]phenyl)-N$^2$-[4-(4-methylpiperazin-1-yl)phenyl]pyrimidine-2,4-diamine (SG2-021-03): This was obtained as a tangerine-colored solid (24 mg, 33%) from SG2-014 (50 mg) and 4-(4-methylpiperazino)aniline (28 mg) using the general method x. Mp: 192° C. (dec). HPLC: 99% [t$_R$=7.8 min, 35% MeOH, 65% water (with 0.1% TFA), 20 min]. $^1$H NMR (400 MHz, DMSO-d$_6$): δ 8.72 (s, 1H, disappeared on D$_2$O shake), 8.52 (s, disappeared on D$_2$O shake), 8.19 (d, J=8.3 Hz, 1H), 8.03 (s, 1H), 7.87 (s, 1H), 7.59 (d, J=7.1 Hz, 1H), 7.52-7.38 (m, 4H; 1H disappeared on D$_2$O shake), 6.79 (d, J=9.0 Hz, 2H), 3.22 (septet, J=6.4 Hz, 1H), 3.03-2.96 (m, 4H), 2.46-2.41 (m, 4H), 2.20 (s, 3H), 2.09 (s, 3H), 0.95 (d, J=6.5 Hz, 6H). HPLC-MS (ESI+): m/z 496.3 [20%, (M+H)$^+$], 248.7 [100%, (M+2H)$^{2+}$]. LC-MS (ESI+): 496.2 [100%, (M+H)$^+$]. HRMS (ESI+): m/z calcd for C$_{25}$H$_{33}$N$_7$O$_2$S (M+H)+496.2489, found 496.2474.

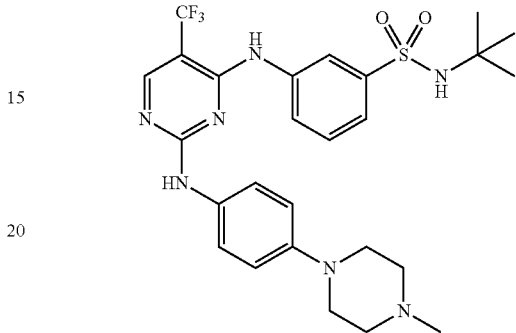

5-Trifluoromethyl-N$^4$-(3-[N-(1,1-dimethylethyl)sulfamoyl]phenyl)-N$^2$-[4-(4-methylpiperazin-1-yl)phenyl]pyrimidine-2,4-diamine (SG2-029-01) (2 TFA salt): The 4-chloropyrimidine SG2-022 was prepared using the previously reported method.[1] A solution of 2,4-dichloro-5-trifluoromethylpyrimidine (120 mg, 0.550 mmol) in t-BuOH/DCM (1:1, 4 mL) was cooled to 0° C. Zinc chloride (1 M in diethyl ether, 0.633 mL, 0.633 mmol) was added dropwise over 10 minutes at 0° C. and the solution stirred at the same temperature for 30 minutes. A solution of tert-butyl 4-(4-aminophenyl)piperazine-1-carboxylate (145 mg, 0.523 mmol) in t-BuOH/DCM (1:1, 2 mL) was added dropwise over 10 minutes at 0° C. followed by Et$_3$N (0.089 mL, 0.633 mmol) in t-BuOH/DCM (1:1, 2 mL). The mixture was warmed to room temperature and stirred for 24 hours. The solvent was removed under reduced pressure and water (20 mL) was added. The suspension was sonicated for 30 minutes and the precipitate was filtered, dried to provide SG2-022 (0.210 g) which was used in the next step without purification. The 4-chloropyrimidine SG2-022 (50 mg, 0.109 mmol) and SG1-137 (25 mg, 0.109 mmol) and HCl (aq. 37%, 0.067 mL, 0.818 mmol) were mixed in EtOH (1 mL) and stirred at 85° C. for 2 hours. The reaction mixture was diluted with EtOAc (20 mL) and washed with saturated NaHCO$_3$ (20 mL). The aqueous layer was then re-extracted with EtOAc (20 mL). The combined organic layers were washed with water and brine (20 mL each), dried over Na$_2$SO$_4$, and concentrated under reduced pressure. The residue was triturated with hexanes/EtOAc and provided SG2-024 (0.046 g) as an off-white solid which was used in the next step without purification. To a solution of SG2-024 (40 mg, 0.073 mmol) in dry MeOH (1 mL) was added formaldehyde (37% aq. solution, 0.024 ml, 0.328 mmol) and sodium triacetoxyborohydride (0.077 mg, 0.364 mmol). The reaction mixture was stirred at room temperature for 2 hours. The solvent was removed under reduced pressure and the residue was diluted with EtOAc (10 mL) and washed with saturated NaHCO$_3$ (15 mL). The aqueous layer was then re-extracted with EtOAc (10 mL). The combined organic layers were washed with water and brine (10 mL each), dried over Na$_2$SO$_4$, and concentrated under reduced pressure. The resulting crude oil was purified via HPLC eluting with 35%

MeCN and 65% water (with 0.1% TFA) to provide the title compound SG2-029-01 as light brown thin film (8 mg, 20%). HPLC: 99% [$t_R$=6.6 min, 50% MeOH, 50% water (with 0.1% TFA), 20 min]. $^1$H NMR at 80° C. (400 MHz, DMSO-$d_6$): δ 9.22 (s, 1H, disappeared on D$_2$O shake), 8.62 (s, 1H, disappeared on D$_2$O shake), 8.32 (s, 1H), 7.89 (s, 1H), 7.77 (d, J=8.1 Hz, 1H), 7.64 (d, J=8.1 Hz, 1H), 7.51 (t, J=8.1 Hz, 1H), 7.37 (d, J=9.0 Hz, 2H), 7.18 (s, 1H, disappeared on D$_2$O shake), 6.80 (d, J=9.0 Hz, 2H), 2.85 (s, 3H), 1.13 (s, 9H). $^{19}$F NMR (376 MHz, DMSO-$d_6$): δ −58.61 (s, 3F), −73.54 (s, 6F). HPLC-MS (ESI+): m/z 564.3 [100%, (M+H)$^+$], 282.7 [40%, (M+2H)$^{2+}$]. LC-MS (ESI+): 564.2 [100%, (M+H)$^+$]. HRMS (ESI+): m/z calcd for C$_{26}$H$_{32}$F$_3$N$_7$O$_2$S (M+H)$^+$ 564.2363, found 564.2370.

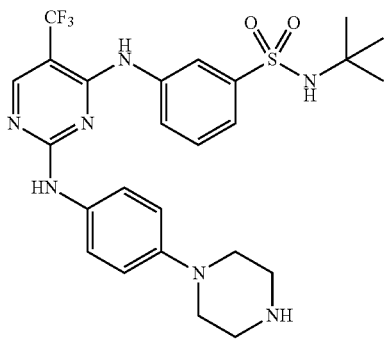

5-Trifluoromethyl-N$^4$-(3-[N-(1,1-dimethylethyl)sulfamoyl]phenyl)-N$^2$[4-(piperazin-1-yl)phenyl]pyrimidine-2,4-diamine (SG2-033-01-1) (3 TFA salt): To a solution of SG2-022 (100 mg, 0.218 mmol) and SG1-137 (50 mg, 0.218 mmol) in EtOH (1 mL) was added 3 drops of 4 M HCl (aq). The mixture was stirred at 85° C. for 2 hours. The solution was diluted with EtOAc (40 mL) and washed with saturated NaHCO$_3$ (40 mL). The aqueous layer was then re-extracted with EtOAc (40 mL). The combined organic layers were washed with water and brine (40 mL each), dried over Na$_2$SO$_4$, and concentrated under reduced pressure to provide a crude oil. The crude oil was purified via HPLC eluting with 30% MeCN and 70% water (with 0.1% TFA) to provide the title compound SG2-033-01-1 as a yellow solid (35 mg, 29%). Mp: 183° C. (dec). HPLC: 99% [$t_R$=6.8 min, 50% MeOH, 50% water (with 0.1% TFA), 20 min]. $^1$H NMR at 80° C. (400 MHz, DMSO-$d_6$): δ 9.22 (s, 1H, disappeared on D$_2$O shake), 8.62 (s, 1H, disappeared on D$_2$O shake), 8.60 (br s, 1H, disappeared on D$_2$O shake), 8.33 (s, 1H), 7.89 (s, 1H), 7.77 (d, J=8.0 Hz, 1H), 7.65 (d, J=8.0 Hz, 1H), 7.50 (t, J=8.0 Hz, 1H), 7.37 (d, J=8.7 Hz, 2H), 7.18 (s, 1H, disappeared on D$_2$O shake), 6.79 (d, J=8.7 Hz, 2H), 1.13 (s, 9H). $^{19}$F NMR (376 MHz, DMSO-$d_6$): δ −59.20 (3F), −74.25 (9F). HPLC-MS (ESI+): m/z 550.3 [100%, (M+H)$^+$], 275.7 [50%, (M+2H)$^{2+}$]. LC-MS (ESI+): 572.2 [15%, (M+Na)$^+$], 550.2 [100%, (M+H)$^+$]. HRMS (ESI+): m/z calcd for C$_{25}$H$_{30}$F$_3$N$_7$O$_2$S (M+H)$^+$ 550.2207, found 550.2194.

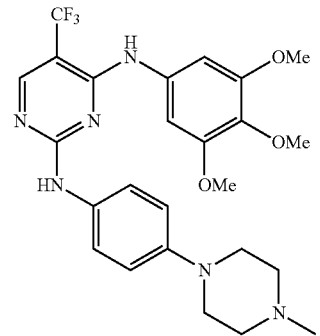

5-Chloro-N$^4$-(3,4,5-trimethoxyphenyl)-N$^2$-[4-(4-methylpiperazin-1-yl)phenyl]pyrimidine-2,4-diamine (SG2-054-01): This was obtained as a light yellow oil (30 mg, 41%) from SG2-047 (50 mg) and 4-(4-methylpiperazino)aniline (29 mg) using the general method x. HPLC: 96% [$t_R$=8.6 min, 35% MeOH, 65% water (with 0.1% TFA), 20 min]. $^1$H NMR (400 MHz, DMSO-$d_6$): δ 9.06 (s, 1H, disappeared on D$_2$O shake), 8.66 (s, 1H, disappeared on D$_2$O shake), 8.05 (s, 1H), 7.41 (d, J=9.0 Hz, 2H), 6.94 (s, 1H), 6.73 (d, J=8.9 Hz, 2H), 3.64 (s, 9H), 3.04-2.94 (m, 4H), 2.44-2.39 (m, 4H), 2.19 (s, 3H). HPLC-MS (ESI+): m/z 485.3 [40%, (M$^{35}$Cl+H)$^+$], 244.2 [40%, (M$^{37}$Cl+2H)$^{2+}$], 243.2 [100%, (M$^{35}$Cl+2H)$^{2+}$]. LC-MS (ESI+): 485.2 [100%, (M$^{35}$Cl+H)$^+$]. HRMS (ESI+): m/z calcd for C$_{24}$H$_{29}$ClN$_6$O$_3$ (M+H)$^+$ 485.2062, found 485.2058.

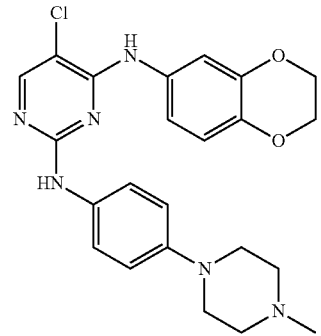

5-Chloro-N$^4$-(2,3-dihydrobenzo[b][1,4]dioxin-6-yl)-N$^2$-[4-(4-methylpiperazin-1-yl)phenyl]pyrimidine-2,4-diamine (SG2-055-01): This was obtained as a brown-yellow solid (29 mg, 38%) from SG2-048 (50 mg) and 4-(4-methylpiperazino)aniline (32 mg) using the general method x. Mp: 220° C. (dec). HPLC: 99% [$t_R$=8.6 min, 35% MeOH, 65% water (with 0.1% TFA), 20 min]. $^1$H NMR (400 MHz, DMSO-$d_6$): δ 9.03 (s, 1H, disappeared on D$_2$O shake), 8.57 (s, 1H, disappeared on D$_2$O shake), 8.01 (s, 1H), 7.41 (d, J=9.0 Hz, 2H), 7.19 (d, J=2.0 Hz, 1H), 7.05 (dd, J=8.7, 2.0 Hz, 1H), 6.79 (d, J=8.7 Hz, 1H), 6.76 (d, J=9.0 Hz, 2H), 4.27-4.17 (m, 4H), 3.10-2.96 (m, 4H), 2.46-2.37 (m, 4H), 2.19 (s, 3H). HPLC-MS (ESI+): m/z 453.2 [40%, (M$^{35}$Cl+H)$^+$]; 228.2 [40%, (M$^{37}$Cl+2H)$^{2+}$], 227.2 [100%, (M$^{35}$Cl+2H)$^{2+}$]. LC-MS (ESI+): 453.2 [100%, (M$^{35}$Cl+H)$^+$]. HRMS (ESI+): m/z calcd for C$_{23}$H$_{25}$ClN$_6$O$_2$ (M+H)$^+$ 453.1800, found 453.1812.

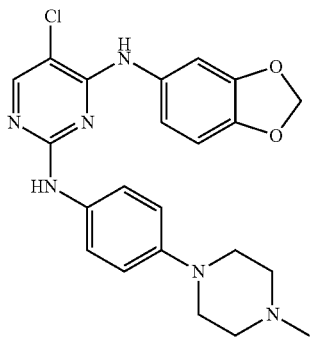

5-Chloro-N⁴-(benzo[d][1,3]dioxol-5-yl)-N²-[4-(4-methylpiperazin-1-yl)phenyl]pyrimidine-2,4-diamine (SG2-056): This was obtained as a light magenta solid (45 mg, 58%) from SG2-049 (50 mg) and 4-(4-methylpiperazino)aniline (34 mg) using the general method x. Mp: 175° C. (dec). HPLC: 86% [$t_R$=7.8 min, 35% MeOH, 65% water (with 0.1% TFA), 20 min]. ¹H NMR (400 MHz, DMSO-$d_6$): δ 9.04 (s, 1H, disappeared on $D_2O$ shake), 8.64 (s, 1H, disappeared on $D_2O$ shake), 8.02 (s, 1H), 7.40 (d, J=8.8 Hz, 2H), 7.29 (s, 1H), 7.02 (d, J=8.4 Hz, 1H), 6.87 (d, J=8.4 Hz, 1H), 6.76 (d, J=8.8 Hz, 2H), 6.01 (s, 2H), 3.05-2.98 (m, 4H), 2.47-2.41 (m, 4H), 2.20 (s, 3H). HPLC-MS (ESI+): m/z 441.2 [20%, $(M^{37}Cl+H)^+$], 439.2 [50%, $(M^{35}Cl+H)^+$], 221.1 [40%, $(M^{37}Cl+2H)^{2+}$], 220.2 [100%, $(M^{35}Cl+2H)^{2+}$]. LC-MS (ESI+): 439.1 [100%, $(M^{35}Cl+H)^+$]. HRMS (ESI+): m/z calcd for $C_{22}H_{23}ClN_6O_2$ (M+H)⁺ 439.1643, found 439.1637.

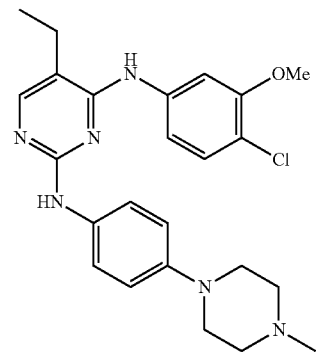

5-Ethyl-N⁴-[4-chloro-3-methoxyphenyl]-N²-[4-(4-methylpiperazin yl)phenyl]pyrimidine-2,4-diamine (MA1-057): This was obtained as a white solid (18 mg, 16%) from MA1-025 (74 mg) and 4-(4-methylpiperazino)aniline (50 mg) using the general method x. Mp: 244° C. (dec). HPLC: 100% [$t_R$=10.1 min, 40% MeOH, 60% water (with 0.1% TFA), 20 min]. ¹H NMR (400 MHz, DMSO-$d_6$): δ 8.77 (s, 1H, disappeared on $D_2O$ shake), 8.33 (s, 1H, disappeared on $D_2O$ shake), 7.88 (s, 1H), 7.48 (d, J=2.2 Hz, 1H), 7.46 (d, J=9.1 Hz), 7.42 (dd, J=8.6, 2.2 Hz, 1H), 7.28 (d, J=8.6 Hz, 1H), 6.79 (d, J=9.1 Hz, 2H), 3.72 (s, 3H), 3.07-3.01 (s, 4H), 2.55 (q, J=7.4 Hz, 2H), 2.53-2.45 (m, 4H), 2.28 (s, 3H), 1.16 (t, J=7.4 Hz, 3H). HPLC-MS (ESI+): m/z 453.3 [20%, (M+H)⁺], 227.2 [100%, $(M^{35}Cl+2H)^{2+}$], 227.9 [40%, $(M^{35}Cl^{37}Cl+2H)^{2+}$]. LC-MS (ESI+): 455.2 [35%, (M+H)⁺], 453.2 [100%, (M+H)⁺]. HRMS (ESI+): m/z calcd for $C_{24}H_{29}ClN_6O$ (M+H)⁺ 453.2164, found 453.2154.

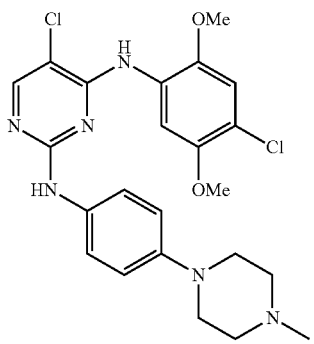

5-Chloro-N⁴-(4-chloro-2,5-dimethoxyphenyl)-N²-[4-(4-methylpiperazin-1-yl)phenyl]pyrimidine-2,4-diamine (SG2-060-01): This was obtained as an off-white solid (40 mg, 55%) from SG2-059 (50 mg) and 4-(4-methylpiperazino)aniline (28 mg) using the general method x. Mp: 232° C. (dec). HPLC: 99% [$t_R$=10.5 min, 45% MeOH, 55% water (with 0.1% TFA), 20 min]. ¹H NMR (400 MHz, DMSO-$d_6$): δ 9.08 (s, 1H, disappeared on $D_2O$ shake), 8.15 (s, 1H, disappeared on $D_2O$ shake), 8.09 (s, 1H), 7.63 (brs, 1H), 7.29 (d, J=8.5 Hz, 2H), 7.20 (s, 1H), 6.74 (d, J=8.5 Hz, 2H), 3.78 (s, 314), 3.60 (s, 3H), 3.03-2.95 (m, 4H), 2.45-2.38 (m, 4H), 2.20 (s, 4H). HPLC-MS (ESI+): m/z 491.2 [70%, $(M^{35}Cl^{37}Cl+H)^+$], 489.2 [100%, $(M^{35}Cl^{35}Cl+H)^+$], 246.2 [70%, $(M^{35}Cl^{37}Cl+2H)^{2+}$], 245.2 [100%, $(M^{35}Cl^{35}Cl+2H)^{2+}$]. LC-MS (ESI+): 489.1 $(M^{35}Cl^{35}Cl+H)^+$. HRMS (ESI+): m/z calcd for $C_{23}H_{26}Cl_2N_6O_2$ (M+H)⁺ 489.1567, found 489.1552.

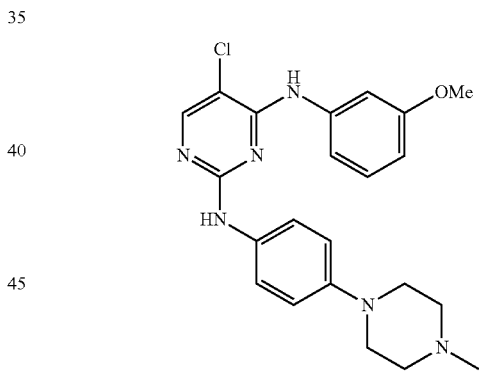
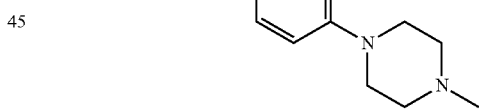

5-Chloro-N⁴-(3-methoxyphenyl)-N²-[4-(4-methylpiperazin-1-yl)phenyl]pyrimidine-2,4-diamine (MA1-063): This was obtained as a light gray solid (39 mg, 50%) from MA1-055-1 (50 mg) and 4-(4-methylpiperazino)aniline (37 mg) using the general method x. Mp: 149° C. (dec). HPLC: 99% [$t_R$=9.7 min, 35% MeOH, 65% water (with 0.1% TFA), 20 min]. ¹H NMR (400 MHz, DMSO-$d_6$): δ 9.11 (s, 1H, disappeared on $D_2O$ shake), 8.69 (s, 1H, disappeared on $D_2O$ shake), 8.09 (s, 1H), 7.45 (d, J=9.0 Hz, 2H), 7.32 (brd, J=7.9 Hz, 1H), 7.27 (t, J=1.9 Hz, 1H), 7.23 (t, J=8.2 Hz, 1H), 6.79 (d, J=9.0 Hz, 2H), 6.69 (ddd, J=8.2, 2.5, 0.8 Hz, 1H), 3.71 (s, 3H), 3.05 (brs, 4H), 2.47 (brs, 4H, appeared from the solvent signal on $D_2O$ shake) 2.26 (s, 3H). HPLC-MS (ESI+): m/z 425.3 [50%, $(M^{35}Cl+H)^+$], 214.2 [100%, $(M^{37}Cl+2H)^{2+}$], 213.2 [40%, $(M^{35}Cl+2H)^{2+}$]. LC-MS (ESI+): 425.2 [100%, $(M^{35}Cl+H)^+$]. HRMS (ESI+): m/z calcd for $C_{22}H_{25}ClN_6O$ (M+H)⁺ 425.1838, found 425.1851.

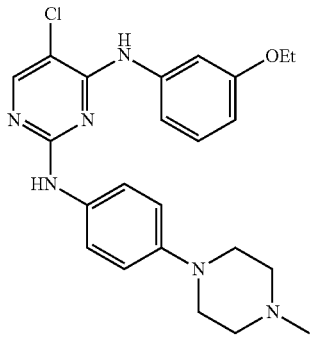

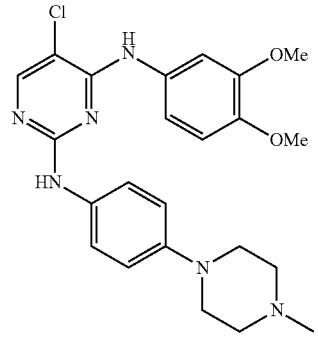

5-Chloro-N⁴-(3-ethoxyphenyl)-N²-[4-(4-methylpiperazin-1-yl)phenyl]pyrimidine-2,4-diamine (MA1-064): This was obtained as a white solid (28 mg, 36%) from MA1-058 (50 mg) and 4-(4-methylpiperazino)aniline (33.6 mg) using the general method x. Mp: 133-139° C. HPLC: 96% [$t_R$=8.7 min, 40% MeOH, 60% water (with 0.1% TFA), 20 min]. $^1$H NMR (400 MHz, DMSO-$d_6$): δ 9.09 (s, 1H, disappeared on D$_2$O shake), 8.66 (s, 1H, disappeared on D$_2$O shake), 8.07 (s, 1H), 7.43 (d, J=9.0 Hz, 2H), 7.26 (s, 1H), 7.23 (d, J=2.1 Hz, 1H), 7.20 (t, J=8.1 Hz, 1H), 6.76 (d, J=9.1 Hz, 2H), 6.66 (dd, J=8.6, 2.0 Hz, 1H), 3.93 (q, J=6.9 Hz, 2H), 3.04-2.95 (m, 4H), 2.47-2.39 (m, 4H), 2.20 (s, 3H), 1.29 (t, J=7.0 Hz, 3H). HPLC-MS (ESI+): m/z 441.3 [20%, (M$^{37}$Cl+H)$^+$], 439.3 [50%, (M$^{35}$Cl+H)$^+$], 221.2 [100%, (M$^{37}$Cl+2H)$^2$], 220.2 [100%, (M$^{35}$Cl+2H)$^{2+}$]. LC-MS (ESI+): 439.2 [100%, (M$^{35}$Cl+H)$^4$]. HRMS (ESI+): m/z calcd for C$_{23}$H$_{27}$ClN$_6$O (M+H)$^+$ 439.2008, found 439. 2007.

5-Chloro-N⁴-(3,4-dimethoxyphenyl)-N²-[4-(4-methylpiperazin yl)phenyl]pyrimidine-2,4-diamine (MA1-066): This was obtained as a dark grey solid (46 mg, 61%) from MA1-059 (50 mg) and 4-(4-methylpiperazino)aniline (31.9 mg) using the general method x. Mp: 163° C. (dec). HPLC: 99% [$t_R$=6.2 min, 35% MeOH, 65% water (with 0.1% TFA), 20 min]. $^1$H NMR (400 MHz, DMSO-$d_6$): δ 9.03 (s, 1H, disappeared on D$_2$O shake), 8.65 (s, 1H, disappeared on D$_2$O shake), 8.03 (s, 1H), 7.41 (d, J=9.0 Hz, 2H), 7.21-7.14 (m, 2H), 6.91 (d, J=8.6 Hz, 1H), 6.75 (d, J=9.0 Hz, 2H), 3.76 (s, 3H), 3.66 (s, 3H), 3.0-2.99 (m, 4H), 2.47-2.42 (m, 4H), 2.21 (s, 3H). HPLC-MS (ESI+): m/z 457.3 [15%, (M$^{37}$Cl+H)$^+$], 455.2 [40%, (M$^{35}$Cl+H)$^+$], 229.0 [100%, (M$^{37}$Cl+2H)$^{2+}$], 228.2 [100%, (M$^{35}$Cl+2H)$^{2+}$]. LC-MS (ESI+): 455.2 [100%, (M$^{35}$Cl+H)$^+$]. HRMS (ESI+): m/z calcd for C$_{23}$H$_{27}$ClN$_6$O$_2$ (M+H)$^+$ 455.1957, found 455.1933.

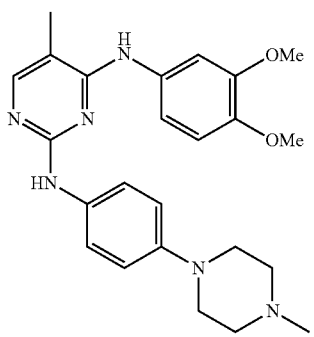

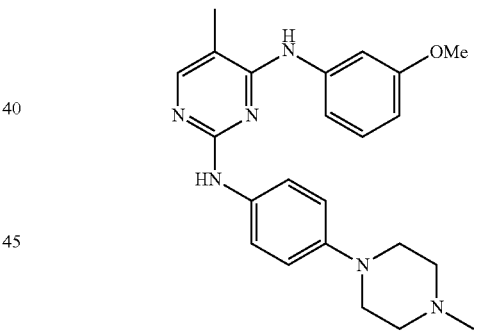

5-Methyl-N⁴-(3,4-Dimethoxyphenyl)-N²-[4-(4-methylpiperazin-1-yl)phenyl]pyrimidine-2,4-diamine (MA1-065): This was obtained as a white solid (36 mg, 46%) from MA1-062 (50 mg) and 4-(4-methylpiperazino)aniline (34 mg) using the general method x. Mp: 157-163° C. HPLC: 100% [$t_R$=6.9 min, 35% MeOH, 65% water (with 0.1% TFA), 20 min]. $^1$H NMR (400 MHz, DMSO-$d_6$): δ 8.66 (s, 1H, disappeared on D$_2$O shake), 8.10 (s, 1H, disappeared on D$_2$O shake), 7.79 (s, 1H), 7.48 (d, J=9.0 Hz, 2H), 7.25-7.20 (m, 2H), 6.89 (d, J=8.4 Hz, 1H), 6.75 (d, J=9.0 Hz, 2H), 3.75 (s, 3H), 3.66 (s, 3H), 3.05-2.99 (m, 4H), 2.53-2.45 (m, 4H), 2.26 (s, 3H), 2.06 (s, 3H). HPLC-MS (ESI+): m/z 435.3 [20%, (M+H)$^+$], 218.3 [100%, (M+2H)$^{2+}$]. LC-MS (ESI+): 435.2 [100%, (M+H)$^+$]. HRMS (ESI+): m/z calcd for C$_{24}$H$_{30}$N$_6$O$_2$ (M+H)$^+$ 435.2503, found 435.2516.

5-Methyl-N⁴-(3-methoxyphenyl)-N²-[4-(4-methylpiperazin-1-yl)phenyl]pyrimidine-2,4-diamine (MA1-067): This was obtained as a gray solid (38 mg, 47%) from MA1-060 (50 mg) and 4-(4-methylpiperazino)aniline (38.3 mg) using the general method x. Mp: 139° C. (dec). HPLC: 98% [$t_R$=8.7 min, 40% MeOH, 60% water (with 0.1% TFA), 20 min]. $^1$H NMR (400 MHz, DMSO-$d_6$): δ 8.72 (s, 1H, disappeared on D$_2$O shake), 8.14 (s, 1H, disappeared on D$_2$O shake), 7.82 (s, 1H), 7.49 (d, J=9.1 Hz, 2H), 7.35 (d, J=8.2 Hz, 1H), 7.30 (t, J=2.2 Hz, 1H), 7.18 (t, J=8.2 Hz, 1H), 6.77 (d, J=9.1 Hz, 2H), 6.60 (ddd, J=8.2, 2.5, 0.8 Hz, 1H), 3.69 (s, 3H), 3.05-2.97 (m, 4H), 2.50-2.45 (m, 4H, appeared from the solvent signal on D$_2$O Shake), 2.23 (s, 3H), 2.07 (s, 3H). HPLC-MS (ESI+): m/z 405.3 [20%, (M+H)$^+$], 203.2 [100%, (M+2H)$^{2+}$]. LC-MS (ESI+): 405.2 [100%, (M+H)$^+$]. HRMS (ESI+): m/z calcd for C$_{23}$H$_{28}$N$_6$O (M+H)$^+$ 405.2397, found 405.2417.

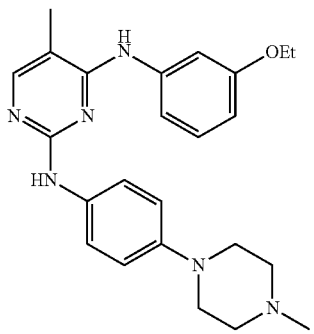

5-Methyl-$N^4$-[3-ethoxyphenyl]-$N^2$-[4-(4-methylpiperazin-1-yl)phenyl]pyrimidine-2,4-diamine (MA1-068): This was obtained as a white solid (26 mg, 33%) from MA1-061 (50 mg) and 4-(4-methylpiperazino)aniline (36 mg) using the general method x. Mp: 201° C. (dec). HPLC: 100% [$t_R$=3.5 min, 45% MeOH, 55% water (with 0.1% TFA), 20 min]. $^1$H NMR (400 MHz, DMSO-$d_6$): δ 8.72 (s, 1H, disappeared on D$_2$O shake), 8.12 (s, 1H, disappeared on D$_2$O shake), 7.82 (s, 1H), 7.49 (d, J=9.0 Hz, 2H), 7.31 (d, J=8.1 Hz, 1H), 7.28 (d, J=1.8 Hz, 1H), 7.17 (t, J=8.1 Hz, 1H), 6.76 (d, J=9.0 Hz, 2H), 6.58 (dd, J=8.1, 2.0 Hz, 1H), 3.93 (q, J=6.9 Hz, 2H), 3.04-2.98 (m, 4H), 2.50-2.45 (m, 4H, overlapped by the residual solvent signal), 2.23 (s, 3H), 2.07 (s, 3H), 1.28 (t, J=6.9 Hz, 3H). HPLC-MS (ESI+): m/z 419.2 [20%, (WW)], 210.3 [100%, (M+2H)$^{2+}$]. LC-MS (ESI+): 419.2 [100%, (M+H)$^+$], 210.3 [15%, (M+2H)$^{2+}$]. HRMS (ESI+): m/z calcd for $C_{24}H_{30}N_6O$ (M+H)$^+$ 419.2554, found 419.2567.

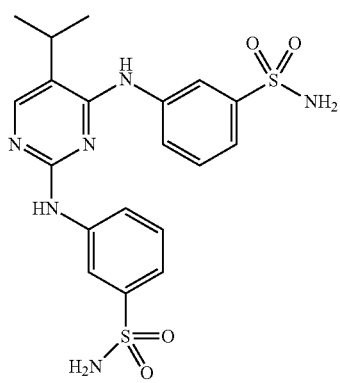

5-Isopropyl-$N^4$,$N^2$-bis-[3-(sulfamoyl)phenyl]pyrimidine-2,4-diamine (MA1-036B): A mixture of SG1-137 (57 mg) and MA1-034-2 (47 mg) in dry MeOH (2 mL) in a 5 mL microwave vial were heated in microwave at 150° C. for 15 minutes. Upon cooling to room temperature, and evaporation of the methanol the crude material was directly purified using column chromatography (ethyl acetate-hexane) to provide the title compound as a solid (20 mg, 17%). Mp: 291° C. (dec). HPLC: 99% [$t_R$=7.5 min, 35% MeOH, 65% water (with 0.1% TFA), 20 min]. δ 10.27 (brs, 1H, disappeared on D$_2$O shake), 9.80 (brs, 1H, disappeared on D$_2$O shake), 7.95 (s, 1H), 7.91-7.86 (m, 2H), 7.79 (d, J=8.0 Hz, 1H), 7.74 (brs, 1H), 7.66 (d, J=7.6 Hz, 1H), 7.58 (t, J=7.9 Hz, 1H), 7.50 (d, J=7.3 Hz, 1H), 7.45-7.35 (m, 5H, 4H disappeared on D$_2$O shake), 3.21 (septet, J=6.7 Hz, 1H, partially overlapped by residual DMSO signal), 1.25 (d, J=6.7 Hz, 6H). HPLC-MS (ESI+): m/z 463.2 [100%, (M+H)$^+$]. LC-MS (ESI+): 463.1 [100%, (M+H)$^+$], 485.1 [30%, (M+Na)$^+$]. HRMS (ESI+): m/z calcd for $C_{19}H_{22}N_6O_4S_2$ (M+H)$^+$ 463.1217, found 463.1214.

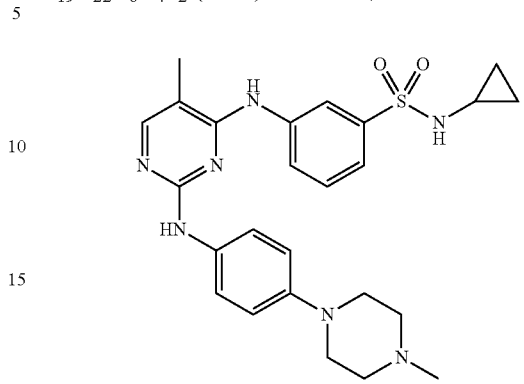

5-Methyl-$N^4$-(3-[N-(cyclopropyl)sulfamoyl]phenyl)-$N^2$-[4-(4-methylpiperazin-1-yl)phenyl]pyrimidine-2,4-diamine (RJ1-045-01): A mixture of RJ1-046 (0.100 g, 0.295 mmol), 4-(4-methyl-1-piperazinyl)aniline (0.056 g, 0.295 mmol), EtOH (2 mL) and 4M HCl (3 drops) was allowed to react and worked up following the same procedure used for RJ1-014. The residue was then purified via flash chromatography eluting with DCM (with 6% MeOH) to provide the product RJ1-045-01 as a white, flaky solid (0.057 g, 39%). Mp: 201° C. (dec). HPLC 98% [$t_R$=14.5 min, gradient 5-95% MeOH and water (with 0.1% TFA), 20 min]. $^1$H NMR (400 MHz, DMSO-$d_6$): δ 8.73 (s, 1H, disappeared on D$_2$O shake), 8.59 (s, 1H, disappeared on D$_2$O shake), 8.28 (brd, J=8.1 Hz, 1H), 7.99 (s, 1H), 7.93 (d, J=2.2 Hz, 1H, disappeared on D$_2$O shake), 7.89 (s, 1H), 7.53 (t, J=7.9 Hz, 1H), 7.48-7.43 (m, 3H), 6.81 (d, J=9.0 Hz, 2H), 3.04-2.99 (m, 4H), 2.47-2.39 (m, 4H), 2.21 (s, 3H), 2.11 (s, overlapping 3H and 1H), 0.53-0.35 (m, 4H). HPLC-MS (ESI+): m/z 494.2 [10%, (M+H)$^+$], 247.7 [100%, (M+2H)$^{2+}$]. LC-MS (ESI+): m/z 494.2 [100%, (M+H)$^+$], 247.6 [15%, (M+2H)$^{2+}$]. HRMS (ESI+): m/z calcd for $C_{25}H_{31}N_7O_2S$ (M+H)$^+$ 494.2333, found 494.2332.

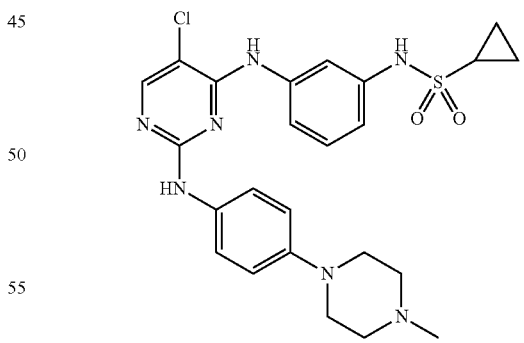

5-Chloro-$N^4$-(3-Cyclopropylsulfonamido)phenyl-$N^2$-[4-(4-methylpiperazin-1-yl)phenyl]pyrimidine-2,4-diamine (RJ1-051-01): A mixture of RJ1-050 (0.500 g, 0.139 mmol), 4-(4-methyl-1-piperazinyl)aniline (0.027 g, 0.139 mmol), EtOH (1 mL), and 4M HCl (2 drops) was allowed to react and worked up following the same procedure used for RJ1-014. The residue was then purified via flash chromatography eluting with DCM (with 4% MeOH) to provide the product RJ1-051-01 as an off-white flaky solid (0.031 g, 43%). Mp: 178° C. (dec). HPLC 99.7% [$t_R$=12.3 min, 30% MeOH, 70% water (with 0.1% TFA), 20 min]. $^1$H NMR (400 MHz, DMSO-$d_6$): δ 9.80-9.65 (brs, 1H, disappeared on D$_2$O shake), 9.05-8.95 (brs, 1H, disappeared on D$_2$O shake), 8.85 (s, 1H, disappeared on D$_2$O shake), 8.07 (s, 1H), 7.51-7.35 (m, 4H), 7.26 (t, J=8.3 Hz, 1H), 6.98 (d, J=7.6 Hz, 1H), 6.77 (d, J=8.8 Hz, 2H), 3.06-2.95 (s, 4H), 2.69-2.55 (m, 1H), 2.47-2.35 (m, 4H), 2.19 (s, 3H), 0.98-0.80 (m, 4H). HPLC-MS (ESI+): m/z 516.1 [30%, (M$^{37}$Cl+H)$^+$], 514.2 [100%, (M$^{37}$Cl+H)$^+$], 258.4 [40%, (M$^{37}$Cl+2H)$^{2+}$], 257.6 [90%, (M$^{35}$Cl+2H)$^{2+}$]. LC-MS (ESI+): m/z 516.2 [100%, (M$^{37}$Cl+H)$^+$], 514.1 [35%, (M$^{35}$Cl+H)$^+$]. HRMS (ESI+): m/z calcd for C$_{24}$H$_{28}$ClN$_7$O$_2$S (M+H)$^+$ 514.1787, found 514.1801.

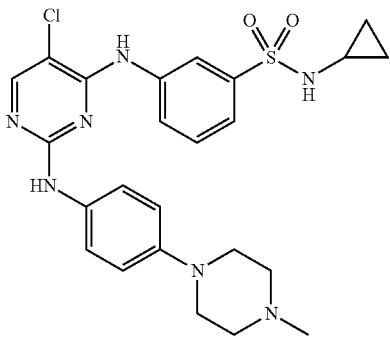

5-Chloro-N$^4$-(3-[N-(cyclopropyl)sulfamoyl]phenyl)-N$^2$-[4-(4-methylpiperazin-1-yl)phenyl]pyrimidine-2,4-diamine (RJ1-053-01): A mixture of RJ1-052 (0.500 g, 0.139 mmol), 4-(4-methyl-1-piperazinyl)aniline (0.027 g, 0.139 mmol), EtOH (1 mL), and 4M HCl (2 drops) was allowed to react and worked up following the same procedure used for RJ1-014. The residue was then purified via flash chromatography eluting with DCM (with 4% MeOH) to provide the product RJ1-053-01 as a light beige solid (0.019 g, 26%). Mp: 205° C. (dec). HPLC 99% [$t_R$=6.7 min, 35% MeOH, 65% water (with 0.1% TFA), 20 min]. $^1$H NMR (400 MHz, DMSO-$d_6$): δ 9.15 (s, 1H, disappeared on D$_2$O shake), 9.10 (s, 1H, disappeared on D$_2$O shake), 8.15-8.05 (brs, 1H, disappeared on D$_2$O shake), 8.13 (s, 1H), 7.98 (s, 1H), 7.95 (d, J=2.2 Hz, 1H), 7.61-7.49 (m, 2H), 7.39 (d, J=8.9 Hz, 2H), 6.80 (d, J=8.9 Hz, 2H), 3.06-2.95 (m, 4H), 2.47-2.39 (m, 4H), 2.21 (s, 3H), 2.16-2.07 (m, 1H), 0.54-0.32 (m, 4H). HPLC-MS (ESI+): m/z 516.2 [30%, (M$^{37}$Cl+H)$^+$], 514.2 [100%, (M$^{35}$Cl+H)$^+$], 258.4 [20%, (M$^{37}$Cl+2H)$^{2+}$], 257.6 [20%, (M$^{35}$Cl+2H)$^{2+}$]. LC-MS (ESI+): m/z 516.2 [100%, (M$^{37}$Cl+H)$^+$], 514.1 [40%, (M$^{35}$Cl+H)$^+$]. (ESI+): m/z calcd for C$_{24}$H$_{28}$ClN$_7$O$_2$S (M+H)$^+$ 514.1787, found 514.1786.

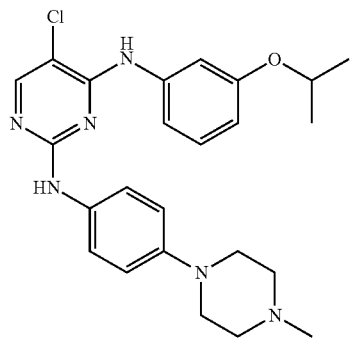

5-Chloro-N$^4$-[3-(1-methylethoxy)phenyl]-N$^2$-(4-(4-methylpiperazin yl)phenyl)pyrimidine-2,4-diamine (RJ1-057-01): A mixture of RJ1-048 (0.500 g, 0.168 mmol), 4-(4-methyl-1-piperazinyl)aniline (0.027 g, 0.168 mmol), EtOH (1 mL), and 4M HCl (2 drops) was allowed to react and worked up following the same procedure as used for RJ1-014. The residue was then purified via flash chromatography eluting with DCM (with 3-4% MeOH) to provide the product RJ1-057-01 as a foamy, champagne-colored solid (0.038 g, 50%). Mp: 135-137° C. HPLC 98% [$t_R$=10.4 min, 40% MeOH, 60% water (with 0.1% TFA), 20 min]. $^1$H NMR (400 MHz, DMSO-$d_6$): δ 9.09 (s, 1H, disappeared on D$_2$O shake), 8.64 (s, 1H, disappeared on D$_2$O shake), 8.07 (s, 1H), 7.43 (d, J=9.0 Hz, 2H), 7.29 (d, J=7.9 Hz, 1H), 7.23-7.13 (m, 2H), 6.76 (d, J=9.0 Hz, 2H), 6.65 (dd, J=8.2, 2.4 Hz, 1H), 4.52 (sept, J=6.0 Hz, 1H), 3.05-2.94 (m, 4H), 2.46-2.37 (m, 4H), 2.19 (s, 3H), 1.23 (d, J=6.0 Hz, 6H). HPLC-MS (ESI+): m/z 455.3 [20%, (M$^{37}$Cl+H)$^+$], 453.2 [60%, (M$^{35}$Cl+H)$^+$], 228.2 [20%, (M$^{37}$Cl+2H)$^{2+}$], 227.2 [20%, (M$^{35}$Cl+2H)$^{2+}$]. LC-MS (ESI+): m/z 455.2 [40%, (M$^{37}$Cl+H)$^+$], 453.2 [100%, (M$^{35}$Cl+H)$^+$]. HRMS (ESI+): m/z calcd for C$_{24}$H$_{29}$ClN$_6$O (M+H)$^+$ 453.2164, found 453.2175.

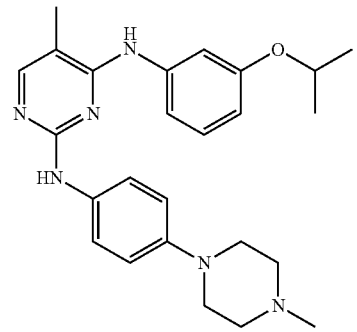

5-Methyl-N$^4$-[3-(1-methylethoxy)phenyl]-N$^2$-(4-(4-methylpiperazin-1-yl)phenyl)pyrimidine-2,4-diamine RJ1-060-01): A mixture of RJ1-058 (0.050 g, 0.180 mmol), 4-(4-methyl-1-piperazinyl)aniline (0.034 g, 0.180 mol), EtOH (1 mL), and 4M HCl (2 drops) was allowed to react and worked up following the same procedure as used for RJ1-014. The residue was then purified via flash chromatography eluting with DCM (with 4% MeOH) to provide the product RJ1-060-01 as a yellow-tan solid (0.028 g, 36%). Mp: 135-137° C. HPLC 97% [$t_R$=8.3 min, 40% MeOH, 60% water (with 0.1% TFA), 20 min]. $^1$H NMR (400 MHz, DMSO-$d_6$): δ 8.70 (s, 1H, disappeared on D$_2$O shake), 8.08 (s, 1H, disappeared on D$_2$O shake), 7.82 (s, 1H), 7.49 (d, J=9.0 Hz, 2H), 7.35 (d, J=8.0 Hz, 1H), 7.22 (t, J=2.2 Hz, 1H), 7.16 (t, J=8.0 Hz, 1H), 6.76 (d, J=9.0 Hz, 2H), 6.57 (dd, J=8.0, 2.1 Hz, 1H), 4.51 (sept, J=6.0 Hz, 1H), 3.05-2.91 (m, 4H), 2.45-2.38 (m, 4H), 2.19 (s, 3H), 2.07 (s, 3H), 1.23 (d, J=6.0 Hz, 6H). HPLC-MS (ESI+): m/z 433.3 [20%, (M+H)$^+$], 217.3 [100%, (M+2H)$^{2+}$]. LC-MS (ESI+): m/z 217.1 [10%, (M+2H)$^{2+}$], 433.3 [100%, (M+H)$^+$]. HRMS (ESI+): m/z calcd for C$_{25}$H$_{32}$N$_6$O (M+H)$^+$ 433.2710, found 433.2708.

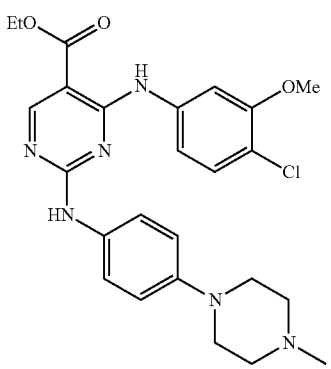

5-Carboethoxy-N⁴-(4-Chloro-3-methoxyphenyl)-N²-(4-(4-methylpiperazin-1-yl)phenyl)pyrimidine-2,4-diamine (RJ1-064-01): A mixture of RJ1-061 (0.200 g, 0.584 mmol), 4-(4-methyl-1-piperazinyl)aniline (0.112 g, 0.584 mmol), EtOH (4 mL), and 4M HCl (8 drops) and was reacted following the same procedure as used for RJ1-014. The residue was then purified via flash chromatography eluting with DCM (with 4% MeOH) to provide the product RJ1-064-01 as an off-white solid (0.116 g, 40%). Mp: 203° C. (dec). HPLC 97% [$t_R$=8.0 min, 60% MeOH, 40% water (with 0.1% TFA), 20 min]. ¹H NMR (400 MHz, DMSO-$d_6$): δ 10.12 (s, 1H, 50% reduced on D₂O shake), 9.37 (s, 1H, disappeared on D₂O shake), 8.68 (s, 1H), 7.30-7.26 (d, J=9.0 Hz, 2H, overlapping s, 1H), 7.28 (d, J=8.5 Hz, 2H), 6.82 (d, J=9.0 Hz, 2H), 4.32 (q, J=7.0 Hz, 2H), 3.71 (s, 3H), 3.13-3.06 (m, 4H), 2.50-2.44 (m, 4H, partly overlapped by residual DMSO solvent signal), 2.23 (s, 3H), 1.34 (t, J=7.0 Hz, 3H). HPLC-MS (ESI+): m/z 499.2 [30%, (M³⁷Cl+H)⁺], 497.2 [100%, (M³⁵Cl+H)⁺], 250.2 [30%, (M³⁷Cl+2H)²⁺], 249.2 [60%, (M³⁵Cl+2H)²⁺]. LC-MS (ESI+): m/z 249.1 [10%, (M³⁵Cl+2H)²⁺], 499.2 [40%, (M³⁷Cl+H)⁺], 497.2 [100%, (M³⁵Cl+H)⁺]. HRMS (ESI+): m/z calcd for C₂₅H₂₉ClN₆O₃ (M+H)⁺ 497.2062, found 497.2063.

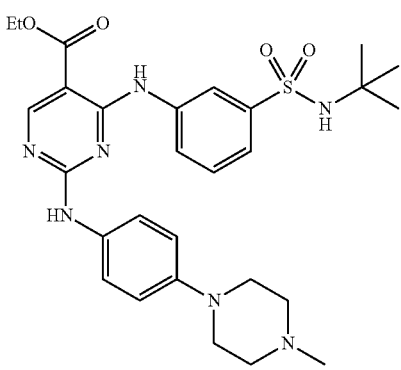

5-Carboethoxy-N⁴-(3-[N-(1,1-dimethylethyl)sulfamoyl]phenyl)-N²-[4-(4-methylpiperazin-1-yl)phenyl]pyrimidine-2,4-diamine (RJ1-066-01): A mixture of RJ1-063-01 (0.150 g, 0.363 mmol), 4-(4-methyl-1-piperazinyl)aniline (0.069 g, 0.363 mmol), EtOH (3 mL), and 4M HCl (6 drops) and was reacted following the same procedure used for RJ1-014. The residue was then purified via flash chromatography eluting with DCM (with 4% MeOH) to provide the product RJ1-066-01 as an off-white solid (0.093 g, 45%). Mp: 202° C. (dec). HPLC 95% [$t_R$=6.2 min, 60% MeOH, 40% water (with 0.1% TFA), 20 min]. ¹H NMR (400 MHz, DMSO-$d_6$): δ 10.27 (s, 1H, 75% reduced on D₂O shake), 9.38 (s, 1H, disappeared on D₂O shake), 8.70 (s, 1H), 8.05 (d, J=8.0 Hz, 1H), 7.90 (s, 1H), 7.57 (d, J=8.0 Hz, 1H), 7.47 (t, J=8.0 Hz, 1H), 7.42 (d, J=8.8 Hz, 2H), 7.22 (s, 1H), 6.85 (d, J=8.8 Hz, 2H), 4.34 (q, J=6.9 Hz, 2H), 3.12-3.06 (m, 4H), 2.48-2.42 (m, 4H, partly overlapped by residual DMSO solvent signal), 2.23 (s, 3H), 1.35 (t, J=6.9 Hz, 3H), 1.13 (s, 9H). HPLC-MS (ESI+): m/z 568.3 [80%, (M+H)⁺], 284.7 [100%, (M+2H)²⁺]. LC-MS (ESI+): m/z 284.6 [10%, (M+2H)²⁺], 568.3 [100%, (M+H)⁺]. HRMS (ESI+): m/z calcd for C₂₈H₃₇N₇O₄S (M+H)⁺ 568.2701, found 568.2677.

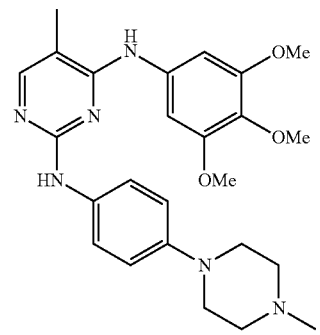

5-Methyl-N⁴-(3,4,5-trimethoxyphenyl)-N²-[4-(4-methylpiperazin-1-yl)phenyl]pyrimidine-2,4-diamine (SG2-063-01): This was obtained as a light brown solid (30 mg, 40%) from SG2-050 (50 mg) and 4-(4-methylpiperazino)aniline (31 mg) using the general method x. Mp: 248° C. (dec). HPLC: 99% [$t_R$=7.6 min, 35% MeOH, 65% water (with 0.1% TFA), 20 min]. ¹H NMR (400 MHz, DMSO-$d_6$): δ 8.68 (s, 1H, disappeared on D₂O shake), 8.13 (s, 1H, disappeared on D₂O shake), 7.81 (s, 1H), 7.46 (d, J=9.0 Hz, 2H), 6.97 (s, 2H), 6.73 (d, J=9.0 Hz, 2H), 3.65 (s, 6H), 3.63 (s, 3H), 3.01-2.94 (m, 4H), 2.45-2.39 (m, 4H), 2.19 (s, 3H), 2.05 (s, 3H). HPLC-MS (ESI+): m/z 465.3 [20%, (M+H)⁺], 233.2 [80%, (M+2H)²⁺]. LC-MS (ESI+): 465.2 [100%, (M+H)⁺], 233.1 [20%, (M+2H)²⁺]. HRMS (ESI+): m/z calcd for C₂₅H₃₂N₆O₃ (M+H)⁺ 465.2609, found 465.2601.

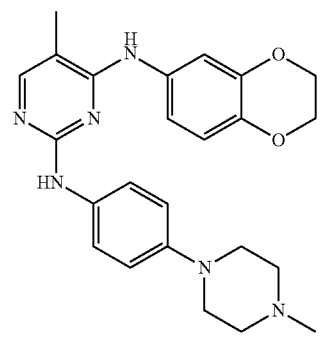

5-Methyl-N⁴-(2,3-dihydrobenzo[b][1,4]dioxin-6-yl)-N²-[4-(4-methylpiperazin yl)phenyl]pyrimidine-2,4-diamine (SG2-064-01): This was obtained as a brown oil (23 mg, 30%) from SG2-051 (50 mg) and 4-(4-methylpiperazino)aniline (34 mg) using the general method x. HPLC: 98% [$t_R$=8.3 min, 35% MeOH, 65% water (with 0.1% TFA), 20 min]. ¹H NMR (400 MHz, DMSO-$d_6$): δ 8.65 (s, 1H, disappeared on D₂O shake), 8.01 (s, 1H, disappeared on D₂O shake), 7.76 (s, 1H), 7.47 (d, J=9.0 Hz, 2H), 7.25 (d, J=2.4 Hz, 1H), 7.09 (dd, J=8.7, 2.4 Hz, 1H), 6.77 (d, J=8.7 Hz, 1H), 6.76 (d, J=9.0 Hz, 2H), 4.25-4.19 (m, 4H), 3.01-2.96 (m, 4H), 2.45-2.41 (m, 4H), 2.19 (s, 3H), 2.03 (s, 3H). HPLC-MS (ESI+): m/z 433.3 (M+H, 20%)$^+$, 217.1 [100%, (M+2H)$^{2+}$]. LC-MS (ESI+): 433.2 [100%, (M+H)$^+$], 217.2 [20%, (M+2H)$^{2+}$]. HRMS (ESI+): m/z calcd for $C_{24}H_{28}N_6O_2$ (M+H)$^+$ 433.2347, found 433.2341.

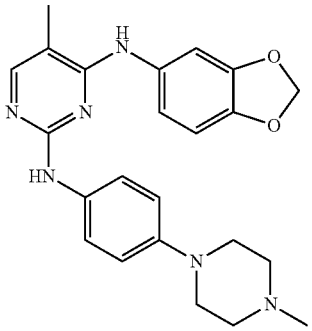

5-Methyl-N$^4$-(benzo[d][1,3]dioxol-5-yl)-N$^2$-[4-(4-methylpiperazin-1-yl)phenyl]pyrimidine-2,4-diamine (SG2-065-01): This was obtained as a red solid (25 mg, 32%) from SG2-052 (50 mg) and 4-(4-methylpiperazino)aniline (36 mg) using the general method x. Mp: 236° C. (dec). HPLC: 99% [t$_R$=8.8 min, 35% MeOH, 65% water (with 0.1% TFA), 20 min]. $^1$H NMR (400 MHz, DMSO-d$_6$): δ 8.67 (s, 1H, disappeared on D$_2$O shake), 8.08 (s, 1H, disappeared on D$_2$O shake), 7.77 (s, 1H), 7.46 (d, J=9.0 Hz, 2H), 7.38 (d, J=2.0 Hz, 1H), 7.05 (dd, J=8.4, 2.0 Hz, 1H), 6.84 (d, J=8.4 Hz, 1H), 6.76 (d, J=9.0 Hz, 2H), 5.99 (s, 2H), 3.04-2.96 (m, 4H), 2.45-2.40 (m, 4H), 2.19 (s, 3H), 2.04 (s, 3H). HPLC-MS (ESI+): m/z 419.2 [20%, (M+H)$^+$], 210.2 [100%, (M+2H)$^{2+}$]. LC-MS (ESI+): 419.2 [100%, (M+H)$^+$], 210.1 [10%, (M+2H)$^{2+}$]. HRMS (ESI+): m/z calcd for $C_{23}H_{26}N_6O_2$ (M+H)$^+$ 419.2190, found 419.2193.

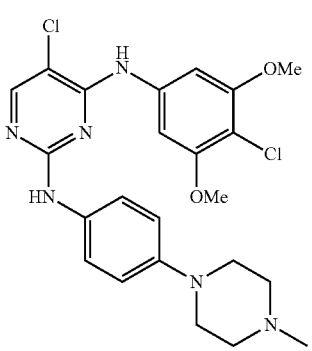

5-Chloro-N$^4$-(4-chloro-3,5-dimethoxyphenyl)-N$^2$-[4-(4-methylpiperazin yl)phenyl]pyrimidine-2,4-diamine (SG2-069-01): This was obtained as an off-white solid (46 mg, 63%) from SG2-066 (50 mg) and 4-(4-methylpiperazino)aniline (29 mg) using the general method x. Mp: 231° C. (dec). HPLC: 96% [t$_R$=6.6 min, 40% MeOH, 60% water (with 0.1% TFA), 20 min]. $^1$H NMR (400 MHz, DMSO-d$_6$): δ 9.10 (s, 1H, disappeared on D$_2$O shake), 8.80 (s, 1H, disappeared on D$_2$O shake), 8.10 (s, 1H), 7.38 (d, J=8.9 Hz, 2H), 7.14 (s, 2H), 6.75 (d, J=8.9 Hz, 2H), 3.68 (s, 6H), 3.04-2.97 (m, 4H), 2.45-2.39 (m, 4H), 2.19 (s, 3H). HPLC-MS (ESI+): m/z 491.2 [60%, (M$^{35}$Cl$^{37}$Cl+H)$^+$], 489.2 [90%, M$^{35}$Cl$^{35}$Cl+H)$^+$], 246.1 [70%, (M$^{35}$Cl$^{37}$Cl+2H)$^{2+}$], 245.1 [100%, M$^{35}$Cl$^{35}$Cl+2H)$^{2+}$]. LC-MS (ESI+): 491.2 [60%, (M$^{35}$Cl$^{37}$Cl+H)$^+$], 489.2 [100%, (M$^{35}$Cl$^{35}$Cl+H)$^+$]. HRMS (ESI+): m/z calcd for $C_{23}H_{26}Cl_2N_6O_2$ (M+H)$^+$ 489.1567, found 489.1561.

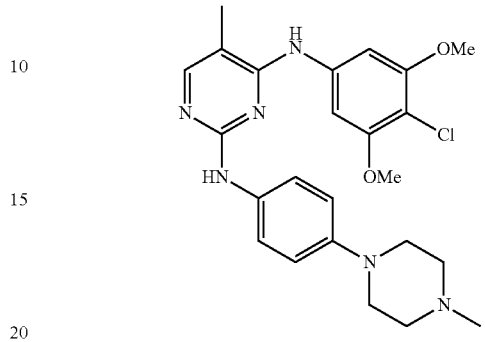

5-Methyl-N$^4$-(4-chloro-3,5-dimethoxyphenyl)-N$^2$-[4-(4-methylpiperazin-1-yl)phenyl]pyrimidine-2,4-diamine (SG2-070-01): This was obtained as a light green solid (40 mg, 53%) from SG2-067 (50 mg) and 4-(4-methylpiperazino)aniline (31 mg) using the general method x. Mp: 223° C. (dec). HPLC: 98% [t$_R$=11.3 min, 35% MeOH, 65% water (with 0.1% TFA), 20 min]. $^1$H NMR (400 MHz, DMSO-d$_6$): δ 8.73 (s, 1H, disappeared on D$_2$O shake), 8.27 (s, 1H, disappeared on D$_2$O shake), 7.86 (s, 1H), 7.43 (d, J=9.1 Hz, 2H), 7.18 (s, 2H), 6.75 (d, J=9.1 Hz, 2H), 3.69 (s, 6H), 3.02-2.96 (m, 4H), 2.45-2.39 (m, 4H), 2.19 (s, 3H), 2.08 (s, 3H). HPLC-MS (ESI+): m/z 469.2 [20%, (M$^{35}$Cl+H)$^+$], 235.2 [100%, (M$^{35}$Cl+2H)$^{2+}$]. LC-MS (ESI+): 471.2 [30%, (M$^{35}$Cl+H)$^+$], 469.2 [100%, (M$^{35}$Cl+H)$^+$]. HRMS (ESI+): m/z calcd for $C_{24}H_{1}$-129ClN$_6$O$_2$ (M+H)$^+$ 469.2113, found 469.2114.

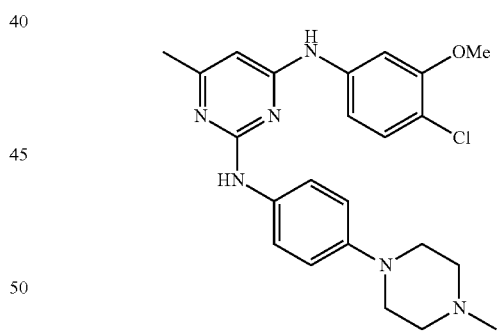

6-Methyl-N$^4$-(4-chloro-3-methoxyphenyl)-N$^2$-[4-(4-methylpiperazin yl)phenyl]pyrimidine-2,4-diamine (SG2-071-01): This was obtained as a yellow oil (32 mg, 42%) from SG2-053 (50 mg) and 4-(4-methylpiperazino)aniline (34 mg) using the general method x. HPLC: 95% [t$_R$=7.7 min, 40% MeOH, 60% water (with 0.1% TFA), 20 min]. $^1$H NMR (400 MHz, DMSO-d$_6$): δ 9.28 (s, 1H, disappeared on D$_2$O shake), 8.86 (s, 1H, disappeared on D$_2$O shake), 7.47 (d, J=9.0 Hz, 2H), 7.40 (d, J=2.1 Hz, 1H), 7.34-7.26 (m, 1H), 7.23 (d, J=8.6 Hz, 1H), 6.82 (d, J=9.0 Hz, 2H), 6.00 (s, 1H), 3.67 (s, 3H), 3.06-2.99 (m, 4H), 2.45-2.40 (m, 4H), 2.20 (s, 3H), 2.17 (s, 314). HPLC-MS (ESI+): m/z 439.2 [30%, (M$^{35}$Cl+H)$^+$], 221.2 [30%, (M$^{37}$Cl+2H)$^{2+}$], 220.2 [100%, (M$^{35}$Cl+2H)$^{2+}$]. LC-MS (ESI+): 441.2 [30%, (M$^{37}$Cl+H)$^+$], 439.2 [100%, (M$^{35}$Cl+H)$^+$]. HRMS (ESI+): m/z calcd for C$_{23}$H$_{27}$ClN$_6$O (M+H)$^+$ 439.2008, found 439.2009.

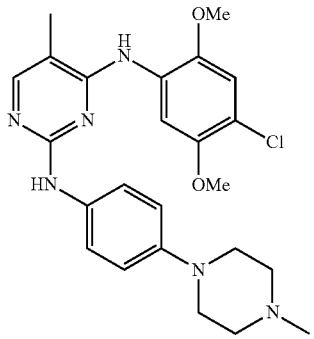

5-Methyl-N$^4$-(4-chloro-2,5-dimethoxyphenyl)-N$^2$-[4-(4-methylpiperazin-1-yl)phenyl]pyrimidine-2,4-diamine (SG2-072-01): This was obtained as an off-white solid (29 mg, 39%) from SG2-068 (50 mg) and 4-(4-methylpiperazino) aniline (31 mg) using the general method x. Mp: 252° C. (dec). HPLC: 94% [t$_R$=13.5 min, 35% MeOH, 65% water (with 0.1% TFA), 20 min]. $^1$H NMR (400 MHz, DMSO-d$_6$): δ 8.69 (s, 1H, disappeared on D$_2$O shake), 7.83 (s, 1H), 7.74 (s, 1H), 7.60 (s, 1H, disappeared on D$_2$O shake), 7.35 (d, J=9.0 Hz, 2H), 7.16 (s, 1H), 6.72 (d, J=9.0 Hz, 2H), 3.77 (s, 3H), 3.62 (s, 3H), 3.02-2.95 (m, 4H), 2.45-2.40 (m, 4H), 2.19 (s, 3H), 2.05 (s, 3H). HPLC-MS (ESI+): m/z 469.2 [20%, (M$^{35}$Cl+H)$^+$], 236.2 [20%, (M$^{37}$Cl+2H)$^{2+}$], 235.2 [60%, (M$^{35}$Cl+2H)$^{2+}$]. LC-MS (ESI+): 469.2 [100%, (M$^{35}$Cl+H)$^+$]. HRMS (ESI+): m/z calcd for C$_{24}$H$_{29}$ClN$_6$O$_2$ (M+H)$^+$ 469.2113, found 469.2115.

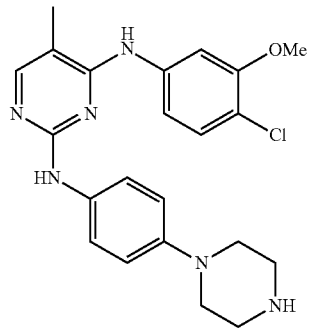

5-Methyl-N$^4$-(4-chloro-3-methoxyphenyl)-N$^2$-[4-(piperazin-1-yl)phenyl]pyrimidine-2,4-diamine (SG2-081-01): This was obtained as a light yellow solid (26 mg, 35%) from SG1-173-01 (50 mg) and tert-butyl 4-(4-aminophenyl)piperazine-1-carboxylate (49 mg) using the general method x. Mp: 245° C. (dec). HPLC: 98% [t$_R$=12.5 min, 35% MeOH, 65% water (with 0.1% TFA), 20 min]. $^1$H NMR (400 MHz, DMSO-d$_6$): δ 8.73 (s, 1H, disappeared on D$_2$O shake), 8.28 (s, 1H, disappeared on D$_2$O shake), 7.85 (s, 1H), 7.48 (d, J=2.0 Hz, 1H), 7.46-7.40 (m, 3H), 7.26 (d, J=8.6 Hz, 1H), 6.76 (d, J=9.0 Hz, 2H), 3.71 (s, 3H), 2.95-2.87 (m, 4H), 2.83-2.77 (m, 4H), 2.07 (s, 3H). HPLC-MS (ESI+): m/z 425.2 [25%, (M$^{35}$Cl+H)$^+$], 214.2 [40%, (M$^{37}$Cl+2H)$^{2+}$], 213.2 [100%, (M$^{35}$Cl+2H)$^{2+}$]. LC-MS (ESI+): 427.2 [30%, (M$^{37}$Cl+H)$^+$], 425.2 [100%, (M$^{35}$Cl+H)$^+$]. HRMS (ESI+): m/z calcd for C$_{22}$H$_{25}$ClN$_6$O (M+H)$^+$ 425.1851, found 425.1861.

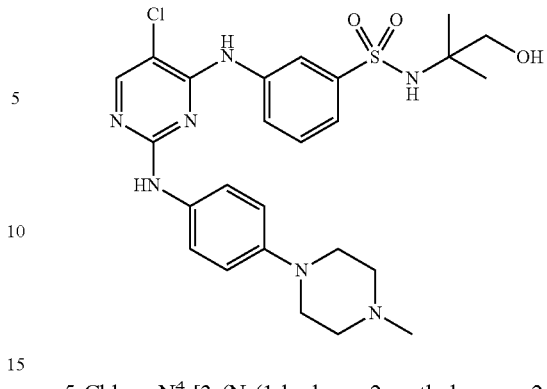

5-Chloro-N$^4$-[3-(N-(1-hydroxy-2-methylpropan-2-yl)sulfamoyl)phenyl]-N$^2$-[4-(4-methylpiperazin-1-yl)phenyl]pyrimidine-2,4-diamine (SG2-085-01): This was obtained as a light yellow solid (31 mg, 44%) from SG2-082 (50 mg) and 4-(4-methylpiperazino)aniline (24 mg) using the general method x. Mp: 258° C. (dec). HPLC: 93% [t$_R$=6.7 min, 35% MeOH, 65% water (with 0.1% TFA), 20 min]. $^1$H NMR (400 MHz, DMSO-d$_6$): δ 9.07 (s, 2H, disappeared on D$_2$O shake), 8.12 (s, 1H), 8.07 (brs, 1H), 8.00 (br d, J=7.0 Hz, 1H), 7.55 (d, J=7.9 Hz, 1H), 7.49 (t, J=7.9 Hz, 1H), 7.43-7.34 (m, 3H; 1H disappeared on D$_2$O shake), 6.79 (d, J=8.9 Hz, 2H), 4.78 (t, J=5.8 Hz, 1H, disappeared on D$_2$O shake), 3.19 (d, J=5.8 Hz, 2H), 3.07-2.96 (m, 4H), 2.46-2.37 (m, 4H), 2.19 (s, 3H), 1.01 (s, 6H). HPLC-MS (ESI+): m/z 548.3 [40%, (M$^{37}$Cl+H)$^+$], 546.3 [100%, (M$^{35}$Cl+H)$^+$], 274.6 [50%, (M$^{37}$Cl+2H)$^{2+}$], 273.7 [100%, (M$^{35}$Cl+2H)$^{2+}$]. LC-MS (ESI+): 548.2 [40%, (M$^{37}$Cl+H)$^+$], 546.2 [100%, (M+H)$^+$]. HRMS (ESI+): m/z calcd for C$_{25}$H$_{32}$ClN$_7$O$_3$S (M+H)±546.2049, found 546.2056.

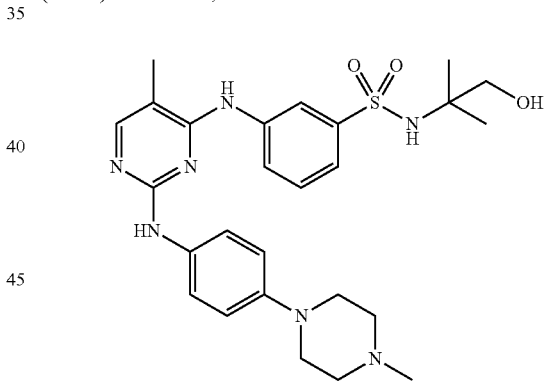

5-Methyl-N$^4$-[3-(N-(1-hydroxy-2-methylpropan-2-yl)sulfamoyl)phenyl]-N$^2$-[4-(4-methylpiperazin-1-yl)phenyl]pyrimidine-2,4-diamine (SG2-087-01): This was obtained as a yellow solid (15 mg, 21%) from SG2-083-02 (50 mg) and 4-(4-methylpiperazino)aniline (26 mg) using the general method x. Mp: 273° C. (dec). HPLC: 93% [t$_R$=11.7 min, 30% MeOH, 70% water (with 0.1% TFA), 20 min]. $^1$H NMR (400 MHz, DMSO-d$_6$): δ 8.70 (s, 1H, disappeared on D$_2$O shake), 8.50 (s, 1H, disappeared on D$_2$O shake), 8.12 (s, 2H), 7.87 (s, 1H), 7.48-7.43 (m, 4H), 7.38 (s, 1H, disappeared on D$_2$O shake), 6.80 (d, J=9.1 Hz, 2H), 4.78 (t, J=5.9 Hz, 1H, disappeared on D$_2$O shake), 3.20 (d, J=5.9 Hz, 2H), 3.05-2.97 (m, 4H), 2.44-2.40 (m, 4H), 2.19 (s, 3H), 2.09 (s, 3H), 1.02 (s, 6H). HPLC-MS (ESI+): m/z 526.2 [60%, (M+H)$^+$], 263.7 [100%, (M+2H)$^{2+}$]. LC-MS (ESI+): 526.3 [100%, (M+H)$^+$]. HRMS (ESI+): m/z calcd for C$_{26}$H$_{35}$N$_7$O$_3$S (M+H)$^+$ 526.2595, found 526.2611.

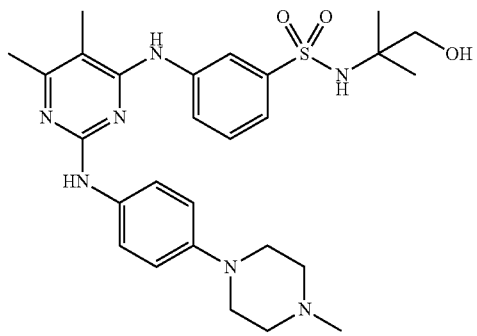
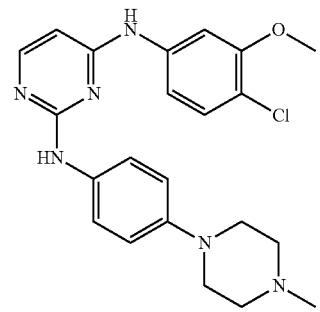

5,6-Dimethyl-$N^4$-[3-(N-(1-hydroxy-2-methylpropan-2-yl)sulfamoyl)phenyl]-$N^2$-[4-(4-methylpiperazin-1-yl)phenyl]pyrimidine-2,4-diamine (SG2-088-01): This was obtained as a yellow oil (14 mg, 20%) from SG2-084-02 (50 mg) and 4-(4-methylpiperazino)aniline (25 mg) using the general method x. HPLC: 94% [$t_R$=7.7 min, 35% MeOH, 65% water (with 0.1% TFA), 20 min]. $^1$H NMR (400 MHz, DMSO-$d_6$): δ 8.65 (s, 1H, disappeared on $D_2O$ shake), 8.43 (s, 1H, disappeared on $D_2O$ shake), 8.07-7.97 (m, 2H), 7.49-7.41 (m, 4H), 7.34 (s, 1H, disappeared on $D_2O$ shake), 6.77 (d, J=9.1 Hz, 2H), 4.77 (t, J=5.9 Hz, 1H, disappeared on $D_2O$ shake), 3.19 (d, J=5.9 Hz, 2H), 3.02-2.94 (m, 4H), 2.44-2.38 (m, 4H), 2.25 (s, 3H), 2.19 (s, 3H), 2.09 (s, 3H), 1.01 (s, 6H). HPLC-MS (ESI+): m/z 540.4 [20%, (M+H)$^+$], 270.7 [100%, (M+2H)$^{2+}$]. LC-MS (ESI+): 540.3 [100%, (M+H)$^+$], 270.6 [20%, (M+2H)$^{2+}$]. HRMS (ESI+): m/z calcd for $C_{27}H_{37}N_7O_3S$ (M+H)$^+$ 540.2751, found 540.2746.

$N^4$-[4-Chloro-3-methoxyphenyl]-$N^2$-[4-(4-methylpiperazin-1-yl)phenyl]pyrimidine-2,4-diamine (MA1-094B): This was obtained as a white solid (47 mg, 44%) from MA1-092 (100 mg) and 4-(4-methylpiperazino)aniline (48 mg) using the general method x. Mp: 231° C. (dec). HPLC: 92% [$t_R$=8.4 min, 40% MeOH, 60% water (with 0.1% TFA), 20 min]. $^1$H NMR (400 MHz, DMSO-$d_6$): δ 9.42 (s, 1H, disappeared on $D_2O$ shake), 8.91 (s, 1H, disappeared on $D_2O$ shake), 7.98 (d, J=5.7 Hz, 1H), 7.48 (d, J=9.0 Hz, 2H), 7.44 (d, J=2.2 Hz, 1H), 7.35 (brd, J=8.6 Hz, 1H), 7.26 (d, J=8.6 Hz, 1H), 6.86 (d, J=9.0 Hz, 2H), 6.15 (d, J=5.7 Hz, 1H), 3.71 (s, 3H), 3.13-3.03 (m, 4H), 2.61-2.54 (m, 4H), 2.30 (s, 3H). HPLC-MS (ESI+): m/z 425.2 [25%, ($M^{35}Cl$+2H)$^+$], 214.2 [38%, ($M^{37}Cl$+2H)$^{2+}$], 213.2 [100%, ($M^{35}Cl$+2H)$^{2+}$]. LC-MS (ESI+): 427.2 [30%, ($M^{37}Cl$+H)$^+$], 425.2 [100%, ($M^{35}Cl$+H)$^+$]. HRMS (ESI+): m/z calcd for $C_{22}H_{25}ClN_6O$ (M+H)$^+$ 425.1851, found 425.1846.

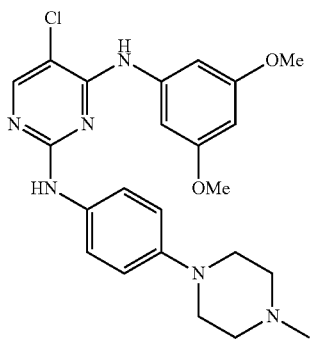
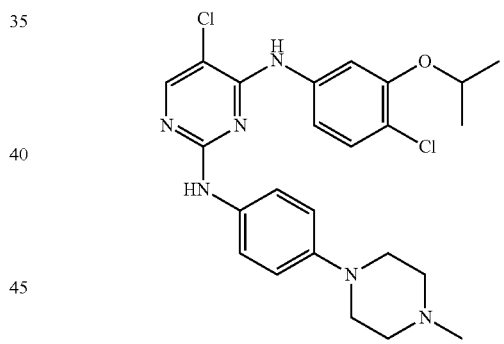

5-Chloro-$N^4$-[3,5-dimethoxyphenyl]-$N^2$-[4-(4-methylpiperazin-1-yl)phenyl]pyrimidine-2,4-diamine (MA1-070): This was obtained as a white solid (44 mg, 58%) from MA1-069 (50 mg) and 4-(4-methylpiperazino)aniline (32 mg) using the general method x. Mp: 201° C. (dec). HPLC: 100% [$t_R$=14.9 min, 35% MeOH, 65% water (with 0.1% TFA), 20 min]. $^1$H NMR (400 MHz, DMSO-$d_6$): δ 9.12 (s, 1H, disappeared on $D_2O$ shake), 8.62 (s, 1H, disappeared on $D_2O$ shake), 8.07 (s, 1H), 7.44 (d, J=9.0 Hz, 2H), 6.91 (brd, J=2.0 Hz, 2H), 6.76 (d, J=9.0 Hz, 2H), 6.25 (t, J=2.0 Hz, 1H), 3.67 (s, 6H), 3.03-2.98 (m, 4H), 2.45-2.40 (m, 4H), 2.20 (s, 3H). HPLC-MS (ESI+): m/z 457.2 [25%, ($M^{37}Cl$+H)$^+$], m/z 455.2 [75%, ($M^{35}Cl$+H)$^+$], m/z 229.2 [38%, ($M^{37}Cl$+2H)$^{2+}$], m/z 228.2 [100%, ($M^{35}Cl$+2H)$^{2+}$]. LC-MS (ESI+): 457.2 [30%, ($M^{37}Cl$+H)$^+$], 455.2 [100%, ($M^{35}Cl$+H)$^+$]. HRMS (ESI+): m/z calcd for $C_{23}H_{27}ClN_6O_2$ (M+H)$^+$ 455.1957, found 455.1942.

5-Chloro-$N^4$-[4-chloro-3-isopropoxyphenyl]-$N^2$-[4-(4-methylpiperazin yl)phenyl]pyrimidine-2,4-diamine (MA1-096-1): This was obtained as a gold-colored solid (38 mg, 52%) from MA1-088 (50 mg) and 4-(4-methylpiperazino) aniline (29 mg) using the general method x. Mp: 212° C. (dec). HPLC: 96% [$t_R$=6.1 min, 50% MeOH, 50% water (with 0.1% TFA), 20 min]. $^1$H NMR (400 MHz, DMSO-$d_6$): δ 9.09 (s, 1H, disappeared on $D_2O$ shake), 8.79 (s, 1H, disappeared on $D_2O$ shake), 8.09 (s, 1H), 7.45-7.34 (m, 4H), 7.29 (d, J=8.6 Hz, 1H), 6.78 (d, J=9.1 Hz, 2H), 4.47 (sextet, 6.0 Hz, 1H), 3.04-2.98 (m, 4H), 2.44-2.39 (m, 4H), 2.19 (s, 3H), 1.24 (d, J=6.0 Hz, 6H). HPLC-MS (ESI+): m/z 489.2 [60%, ($M^{35}Cl^{37}Cl$+2H)$^{2+}$], 487.2 [95%, ($M^{35}Cl^{37}Cl$+2H)$^{2+}$], 245.1 [72% ($MCl^{35}Cl^{37}$+2H)$^{2+}$], 244.2 [100%, ($MCl^{35}Cl^{35}$+2H)$^{2+}$]. LC-MS (ESI+): 489.2 [100%, ($M^{35}Cl^{37}Cl$+H)$^+$], 487.2 [100%, ($M^{35}Cl^{35}Cl$+H)$^+$]. HRMS (ESI+): m/z calcd for $C_{24}H_{28}Cl_2N_6O$ (M+H)$^+$ 487.1774, found 487.1782.

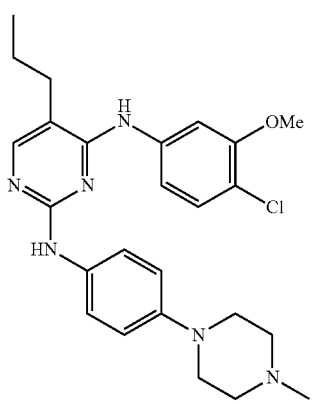

5-Propyl-N⁴-[3-methoxy-4-chlorophenyl]-N²-[4-(4-methylpiperazin-1-yl)phenyl]pyrimidine-2,4-diamine (MA1-096-2): This was obtained as a white solid (41 mg, 55%) from MA1-072 (50 mg) and 4-(4-methylpiperazino)aniline (31 mg) using the general method x. Mp: 250° C. (dec). HPLC: 96% [$t_R$=18.9 min, 40% MeOH, 60% water (with 0.1% TFA), 30 min]. ¹H NMR (400 MHz, DMSO-$d_6$): δ 8.76 (s, 1H, disappeared on D₂O shake), 8.31 (s, 1H, disappeared on D₂O shake), 7.85 (s, 1H), 7.49-7.42 (m, 3H), 7.40-7.35 (m, 1H), 7.28 (d, J=8.6 Hz, 1H), 6.77 (d, J=9.0 Hz, 2H), 3.72 (s, 3H), 3.05-2.96 (m, 4H), 2.52-2.47 (m, 2H, overlapped with the residual DMSO signal) 2.47-2.39 (m, 4H), 2.21 (s, 3H), 1.54 (sextet, J=7.3 Hz, 2H), 0.94 (t, J=7.3 Hz, 3H). HPLC-MS (ESI+): m/z 467.3 [30%, (M³⁵Cl+H)⁺], 235.1 [40%, (M³⁷Cl+2H)²⁺], 234.2 [100%, (M³⁵Cl+2H)²⁺], LC-MS (ESI+): 469.2 [30%, (M³⁷Cl+2H)²⁺], 467.2 [100%, (M³⁵Cl+H)+]. HRMS (ESI+): m/z calcd for C₂₅H₃₁ClN₆O (M+H)⁺ 467.2321, found 467.2302.

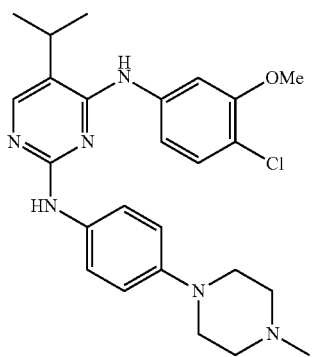

5-Methylethyl-N⁴-[3-methoxy-4-chlorophenyl]-N²-[4-(4-methylpiperazin-1-yl)phenyl]pyrimidine-2,4-diamine (MA1-096-3): This was obtained as a white solid (19 mg, 26%) from MA1-073 (50 mg) and 4-(4-methylpiperazino)aniline (36 mg) using the general method x. Mp: 212° C. (dec). HPLC: 99% [$t_R$=15.2 min, 40% MeOH, 60% water (with 0.1% TFA), 20 min]. ¹H NMR (400 MHz, DMSO-$d_6$): δ 8.75 (s, 1H, disappeared on D₂O shake), 8.33 (s, 1H, disappeared on D₂O shake), 7.95 (s, 1H), 7.45-7.41 (m, 3H), 7.36 (d, J=8.6, 2.0 Hz, 1H), 7.26 (d, J=8.6 Hz, 1H), 6.75 (d, J=9.1 Hz, 2H), 3.69 (s, 3H), 3.14 (septet, J=6.8 Hz, 1H), 3.03-2.95 (m, 4H), 2.46-2.40 (m, 4H), 2.20 (s, 3H), 1.19 (d, J=6.8 Hz, 6H). HPLC-MS (ESI+): m/z 467.3 [20%, (M³⁵Cl+H)⁺], 235.2 [30%, (M³⁷Cl+2H)²⁺], 234.3 [100%, (M³⁵Cl+2H)²⁺]. LC-MS (ESI+): 469.2 [35%, (M³⁵Cl+H)⁺], 467.2 [100%, (M³⁵Cl+H)⁺], 234.1 [25%, (MCl³⁵+2H)²⁺]. HRMS (ESI+): m/z calcd for C₂₅H₃₁ClN₆O (M+H)⁺ 467.2321 found 467.2344.

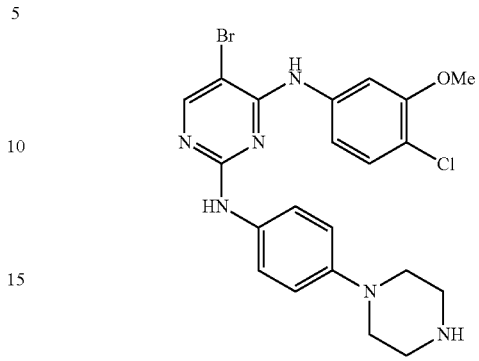

5-Bromo-N⁴-[4-chloro-3-methoxyphenyl]-N²-[4-(piperazin-1-yl)phenyl]pyrimidine-2,4-diamine (MA2-012): Trifluoroacetic acid (4 mL of freshly prepared 50% solution in DCM) was added to MA2-010 (280 mg) in a 20 mL microwave vial equipped with a magnetic stirrer bar. The reaction mixture was stirred at room temperature for 30 h at which point HPLC-MS confirmed the complete consumption of starting material. The mixture was diluted with DCM (100 mL) and water (30 mL). Triethylamine (ca. 5.5 mL) was added slowly to this mixture until a pH was 11. The mixture was transferred to a separatory funnel and separated. The aqueous layer was further extracted with DCM (50 mL). Combined organic layers were evaporated, dried (Na₂SO₄) and evaporated to provide the title compound (190 mg, 83%) as a dark gray to black solid. Mp: 268° C. (dec). HPLC: 98% [$t_R$=11.6 min, 40% MeOH, 60% water (with 0.1% TFA), 20 min]. ¹H NMR (400 MHz, DMSO-$d_6$): δ 9.17 (s, 1H, disappeared on D₂O shake), 8.62 (s, 1H, disappeared on D₂O shake), 8.19 (s, 1H), 7.44-7.40 (m, 3H), 7.33 (s, 2H), 6.80 (d, J=9.0 Hz, 2H), 3.72 (s, 3H), 3.10-3.00 (m, 8H). HPLC-MS (ESI+): m/z 491.1 [38%, (M⁸¹Br+H)⁺], 489.1 [45%, (M⁷⁹Br+H)⁺], 245.2 [40%, (M⁷⁹Br+2H)²⁺]. LC-MS (ESI+): 491.1 [100%, (M⁸¹Br+H)⁺], 489.1 [75%, (M⁷⁹Br+H)⁺]. HRMS (ESI+): m/z calcd for C₂₁H₂₂BrClN₆O (M+H)⁺ 489.0800, found 489.0793.

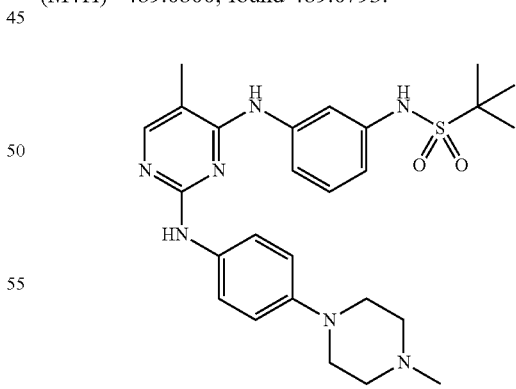

5-Methyl-N⁴-[3-(1,1-dimethylethyl)sulfonamidophenyl]-N²-[4-(4-methylpiperazin-1-yl)phenyl]pyrimidine-2,4-diamine (MA2-014): This was obtained as a green solid (41 mg, 48%) from MA2-008 (60 mg) and 4-(4-methylpiperazino)aniline (32 mg) using the general method x. Mp: 173° C. (dec). HPLC: 99% [$t_R$=5.9 min, 40% MeOH, 60% water (with 0.1% TFA), 20 min]. ¹H NMR (400 MHz, DMSO-$d_6$):

δ 9.56 (s, 1H, disappeared on D$_2$O shake), 8.57 (s, 1H, disappeared on D$_2$O shake), 8.29 (s, 1H, disappeared on D$_2$O shake), 7.82 (s, 1H), 7.54 (s, 1H), 7.51-7.43 (m, 3H), 7.19 (t, J=8.2 Hz, 1H), 6.97 (d, J=8.2 Hz, 1H), 6.78 (d, J=8.7 Hz, 2H), 3.08-2.97 (m, 4H), 2.53-2.47 (m, 4H, appeared from the solvent signal on D$_2$O shake), 2.30 (brs, 3H), 2.06 (s, 3H), 1.26 (s, 9H). HPLC-MS (ESI+): m/z 510.3 [15%, (M+H)$^+$], 255.7 [100%, (M+2H)$^{2+}$]. LC-MS (ESI+): 510.3 [100%, (M+H)$^+$]. HRMS (ESI+): m/z calcd for C$_{26}$H$_{35}$N$_7$O$_2$S (M+H)$^+$ 510.2646, found 510.2637.

8.73 (s, 1H, disappeared on D$_2$O shake), 8.25 (s, 1H, disappeared on D$_2$O shake), 7.84 (s, 1H), 7.48-7.36 (m, 4H), 7.26 (d, J=8.6 Hz, 1H), 6.77 (d, J=9.1 Hz, 2H), 3.91 (q, J=6.9 Hz, 2H), 3.04-2.97 (m, 4H), 2.46-2.40 (m, 4H), 2.20 (s, 3H), 2.07 (s, 3H), 1.28 (t, J=6.9 Hz, 3H). HPLC-MS (ESI+): m/z 453.2 [30%, (M$^{35}$Cl+H)$^+$], 228.2 [38%, (M$^{37}$Cl+2H)$^{2+}$], 227.2 [100%, (M$^{35}$Cl+2H)$^{2+}$]. LC-MS (ESI+): 455.2 [30%, (M$^{37}$Cl+H)$^+$], 453.2 [100%, (M$^{35}$Cl+H)$^+$]. HRMS (ESI+): m/z calcd for C$_{24}$1-129ClN$_6$O (M+H)$^+$ 453.2164, found 453.2150.

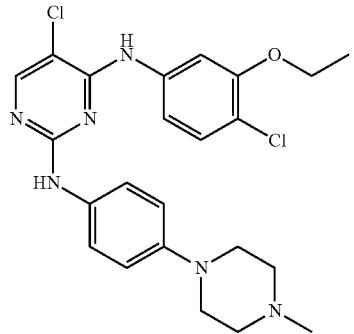

5-Chloro-N$^4$-(4-chloro-3-ethoxyphenyl)-N$^2$-[4-(4-methylpiperazin yl)phenyl]pyrimidine-2,4-diamine (MA2-024-1): This was obtained as a white solid (45 mg, 62%) from MA2-016-1 (50 mg) and 4-(4-methylpiperazino)aniline (30 mg) using the general method x. Mp: 228° C. (dec). HPLC: 99% [t$_R$=16.3 min, 40% MeOH, 60% water (with 0.1% TFA), 20 min]. $^1$H NMR (400 MHz, DMSO-d$_6$): δ 9.11 (s, 1H, disappeared on D$_2$O shake), 8.81 (s, 1H, disappeared on D$_2$O shake), 8.10 (s, 1H), 7.43 (d, J=2.0 Hz, 1H), 7.41-7.33 (m, 3H), 7.31 (d, J=8.6 Hz, 1H), 6.79 (d, J=9.0 Hz, 2H), 3.97-3.87 (m, 2H), 3.08-3.00 (m, 4H), 2.48-2.42 (m, 4H), 2.21 (s, 3H), 1.30 (t, J=6.9 Hz, 3H). HPLC-MS (ESI+): m/z 475.3 [65%, (M$^{35}$Cl$^{37}$Cl+H)$^+$], 473.2 [100%, M$^{35}$Cl$^{35}$Cl+H)$^+$], 238.2 [53%, (M$^{37}$Cl$^{35}$Cl+2H)$^{2+}$], 237.2 [83%, (M$^{35}$Cl$^{35}$Cl+2H)$^{2+}$]. LC-MS (ESI+): 475.2 [60%, (M$^{35}$Cl$^{37}$Cl+H)$^+$], 473.2 [100%, (M$^{35}$Cl$^{35}$Cl+H)$^+$], HRMS (ESI+): m/z calcd for C$_{23}$H$_{26}$Cl$_2$N$_6$O (M+H)$^+$ 473.1618, found 473.1629.

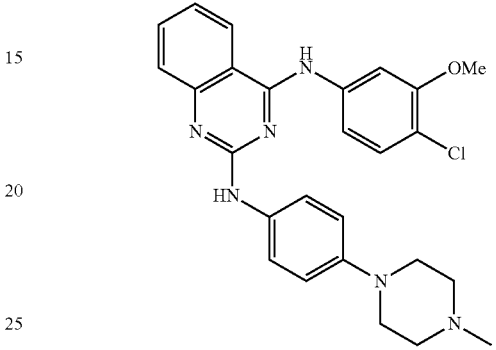

N$^4$-(4-Chloro-3-methoxyphenyl)-N$^2$-[4-(4-methylpiperazin-1-yl)phenyl]quinazoline-2,4-diamine (MA2-032): This was obtained as a green solid (37 mg, 50%) from MA2-030 (50 mg) and 4-(4-methylpiperazino)aniline (29 mg) using the general method x. Mp: 188° C. (dec). HPLC: 96% [t$_R$=4.9 min, 50% MeOH, 50% water (with 0.1% TFA), 20 min]. $^1$H NMR (400 MHz, DMSO-d$_6$): δ 9.58 (s, 1H, disappeared on D$_2$O shake), 8.97 (s, 1H, disappeared on D$_2$O shake), 8.28 (dd, J=8.2, 0.8 Hz, 1H), 7.73-7.62 (m, 5H), 7.44 (d, J=8.4 Hz, 1H), 7.36 (d, J=9.1 Hz, 1H), 7.25 (ddd, J=8.2, 7.0, 1.2 Hz, 1H), 6.87 (d, J=9.0 Hz, 2H), 3.82 (s, 3H), 3.12-3.04 (m, 4H), 2.59-2.50 (m, 4H), 2.28 (s, 3H). HPLC-MS (ESI+): m/z 477.3 [15%, (M$^{37}$Cl+H)$^+$], 475.3 [40%, (M$^{35}$Cl+H)$^+$], 238.3 [100%, (M$^{35}$Cl+2H)$^{2+}$]. LC-MS (ESI+): 477.2 [30%, (M$^{37}$Cl+H)$^+$], 475.2 [100%, (M$^{35}$Cl+H)+], 238.1 [30%, (M$^{35}$Cl+2H)$^{2+}$]. HRMS (ESI+): m/z calcd for C$_{26}$H$_{27}$ClN$_6$O (M+H)$^+$ 475.2008, found 475.2023.

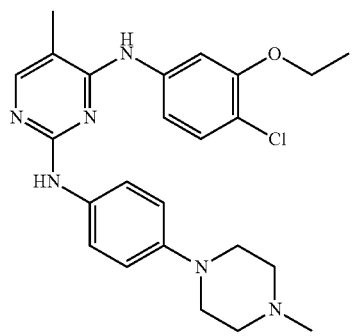

5-Methyl-N$^4$-(4-chloro-3-ethoxyphenyl)-N$^2$-[4-(4-methylpiperazin-1-yl)phenyl]pyrimidine-2,4-diamine (MA2-024-2): This was obtained as a white solid (16 mg, 22%) from MA2-016-2 (50 mg) and 4-(4-methylpiperazino)aniline (32 mg) using the general method x. Mp: 214° C. (dec). HPLC: 97% [t$_R$=12.7 min, 40% MeOH, 60% water (with 0.1% TFA), 20 min]. $^1$H NMR (400 MHz, DMSO-d$_6$): δ

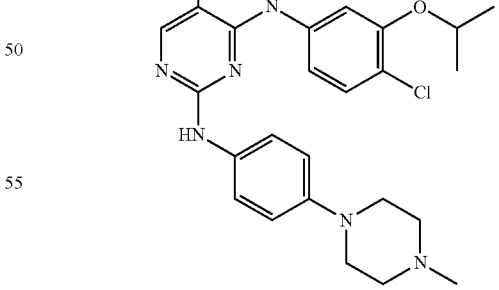

5-Methyl-N$^4$-[4-chloro-3-(1-methylethoxy)phenyl]-N$^2$-[4-(4-methylpiperazin-1-yl)phenyl]pyrimidine-2,4-diamine (MA2-031): This was obtained as a gray solid (7 mg, 9%) from MA1-090 (50 mg) and 4-(4-methylpiperazino)aniline (31 mg) using the general method x. Mp: 264° C. (dec). HPLC: 97% [t$_R$=9.1 min, 45% MeOH, 55% water (with 0.1% TFA), 20 min]. $^1$H NMR (400 MHz, DMSO-d$_6$): δ

8.77 (s, 1H, disappeared on D$_2$O shake), 8.25 (s, 1H, disappeared on D$_2$O shake), 7.87 (s, 1H), 7.53-7.42 (m, 4H), 7.28 (d, J=8.6 Hz, 1H), 6.82 (d, J=8.8 Hz, 2H), 4.46 (septet, J=6.0 Hz, 1H), 3.20-3.05 (brs, 4H), 2.86-2.71 (brs, 4H), 2.45 (s, 3H), 2.09 (s, 3H), 1.26 (d, J=6.0 Hz, 6H). HPLC-MS (ESI+): m/z 467.2 [30%, (M$^{35}$Cl+H)$^+$], 235.0 [40%, (M$^{37}$Cl+2H)$^{2+}$], 234.3 [100%, (M$^{35}$Cl+2H)$^{2+}$]. LC-MS (ESI+): 469.2 [30%, (M$^{37}$Cl+H)$^+$], 467.2 [100%, (M$^{35}$Cl+H)$^+$]. HRMS (ESI+): m/z calcd for C$_{25}$H$_{31}$ClN$_6$O (M+H)$^+$ 467.2321, found 467.2329.

(with 0.1% TFA), 20 min]. $^1$H NMR (400 MHz, DMSO-d$_6$): δ 9.69 (brs, 1H, disappeared on D$_2$O shake), 8.61 (s, 1H, disappeared on D$_2$O shake), 8.31 (s, 1H, disappeared on D$_2$O shake), 7.85 (s, 1H), 7.55 (d, J=8.1 Hz, 1H), 7.51-7.44 (m, 3H), 7.25 (t, J=8.1 Hz, 1H), 6.89 (d, J=8.1 Hz, 1H), 6.79 (d, J=8.9 Hz, 2H), 3.05-2.99 (m, 4H), 2.99 (s, 3H), 2.47-2.40 (m, 4H), 2.21 (s, 3H), 2.09 (s, 3H). HPLC-MS (ESI+): m/z 468.3 [20%, (M+H)$^+$], 234.8 [100%, (M+2H)$^{2+}$]. LC-MS (ESI+): 468.2 [100%, (M+H)$^+$]. HRMS (ESI+): m/z calcd for C$_{23}$H$_{29}$N$_7$O$_2$S (M+H)$^+$ 468.2176, found 468.2161.

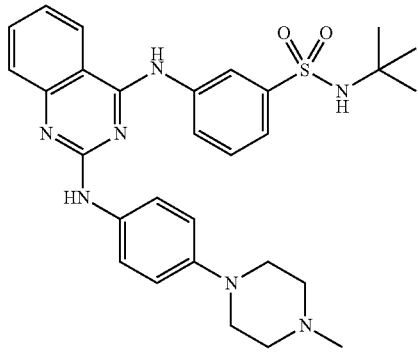

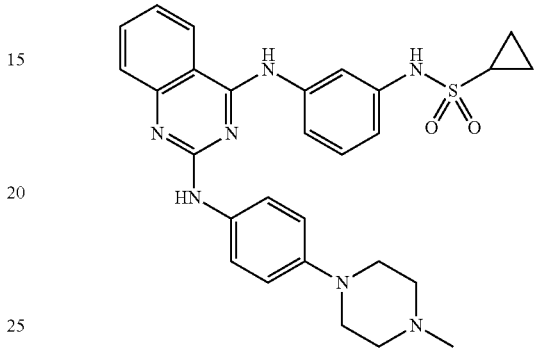

N$^4$-([3-(1,1-dimethylethyl)sulfamoyl]phenyl)-N$^2$-[4-(4-methylpiperazin-1-yl)phenyl]quinazoline-2,4-diamine (MA2-034): This was obtained as a green solid (11 mg, 16%) from MA2-033 (50 mg) and 4-(4-methylpiperazino) aniline (24 mg) using the general method x. Mp: 229° C. (dec). HPLC 99% [t$_R$=13.4 min, 45% MeOH, 55% water (with 0.1% TFA), 20 min]; $^1$H NMR (400 MHz, DMSO-d$_6$) δ 9.76 (s, 1H, disappeared on D$_2$O shake), 8.92 (s, 1H, disappeared on D$_2$O shake), 8.44-8.37 (m, 2H), 8.36-8.28 (1H, s, disappeared on D$_2$O shake), 7.74-7.63 (m, 4H), 7.56-7.53 (m, 2H), 7.45 (d, J=8.5 Hz, 1H), 7.26 (t, J=7.6 Hz, 1H), 6.89 (d, J=9.1 Hz, 2H), 3.12-3.03 (m, 4H), 2.48-2.44 (m, 4H, overlapped by residual DMSO signal), 2.23 (s, 3H), 1.15 (s, 9H). HPLC-MS (ESI+) m/z 273.7 [100%, (M+2H)$^{2+}$], 546.2 [40%, (M+H)$^+$]; LC-MS 546.3 [100%, (M+H)$^+$], 273.6 [10%, (M+2H)$^{2+}$], 245.6 [40%, (M-tBu+2H)$^{2+}$]; HRMS (ESI+) m/z calculated for C$_{29}$H$_{35}$N$_7$O$_2$S (M+H)$^+$ 546.2646, found 546.2626.

N$^4$-(3-Cyclopropylsulfonamido)phenyl-N$^2$-[4-(4-methylpiperazin yl)phenyl]quinazoline-2,4-diamine (MA2-047): This was obtained as a green solid (26 mg, 38%) from MA2-038 (50 mg) and 4-(4-methylpiperazino)aniline (26 mg) using the general method x. Mp: 294° C. (dec). HPLC: 99% [t$_R$=10.9 min, 40% MeOH, 60% water (with 0.1% TFA), 20 min]. $^1$H NMR (400 MHz, DMSO-d$_6$): δ 9.73 (s, 1H, disappeared on D$_2$O shake), 9.59 (s, 1H, disappeared on D$_2$O shake), 8.73 (s, 1H, disappeared on D$_2$O shake), 8.35 (d, J=7.7 Hz, 1H), 7.81-7.74 (brd, 2H), 7.66 (brd, J=8.2 Hz, 2H), 7.62 (t, J=7.7 Hz, 1H), 7.41 (d, J=8.3 Hz, 1H), 7.30 (t, J=8.3 Hz, 1H), 7.21 (t, J=7.7 Hz, 1H), 6.98 (d, J=7.7 Hz, 1H), 6.85 (d, J=9.1 Hz, 2H), 3.10-2.98 (m, 4H), 2.72-2.59 (m, 1H), 2.48-2.44 (m, 4H, appeared from the solvent signal on D$_2$O shake), 2.22 (s, 3H), 1.04-0.86 (m, 4H). HPLC-MS (ESI+): m/z 530.2 [40%, (M+H)$^+$], 265.7 [100%, (M+2H)$^{2+}$]. LC-MS (ESI+): 530.2 [100%, (M+H)$^+$], 265.6 [100%, (M+2H)$^{2+}$]. HRMS (ESI+): m/z calcd for C$_{24}$H$_{13}$N$_7$O$_2$S (M+H)$^+$ 530.2333, found 530.2316.

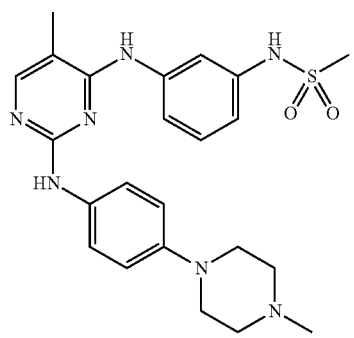

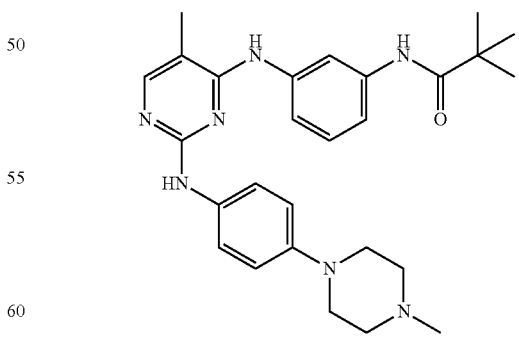

5-Methyl-N$^4$-(3-methylsulfonamidophenyl)-N$^2$-[4-(4-methylpiperazin-1-yl)phenyl]pyrimidine-2,4-diamine (MA2-046): This was obtained as a white solid (42 mg, 56%) from MA2-035 (50 mg) and 4-(4-methylpiperazino) aniline (30 mg) using the general method x. Mp: 198° C. (dec). HPLC: 96% [t$_R$=4.4 min, 35% MeOH, 65% water 5-Methyl-N$^4$-[3-(2,2-dimethylpropanamido)phenyl]-N$^2$-[4-(4-methylpiperazin-1-yl)phenyl]pyrimidine-2,4-diamine (MA2-052-1): This was obtained as a beige solid (33 mg, 45%) from MA2-042-1 (50 mg) and 4-(4-methylpiperazino) aniline (30 mg) using the general method x. Mp: 273° C.

(dec). HPLC: 99% [$t_R$=6.6 min, 40% MeOH, 60% water (with 0.1% TFA), 20 min]. $^1$H NMR (400 MHz, DMSO-$d_6$): δ 9.16 (s, 1H), 8.70 (s, 1H, disappeared on $D_2O$ shake), 8.26 (s, 1H, disappeared on $D_2O$ shake), 7.85 (t, J=1.9 Hz, 1H), 7.83 (s, 1H), 7.49 (d, J=9.0 Hz, 2H), 7.42 (d, J=8.0 Hz, 1H), 7.32 (d, J=8.0 Hz, 1H), 7.22 (t, J=8.0 Hz, 1H), 6.72 (d, J=9.0 Hz, 2H), 3.03-2.96 (m, 4H), 2.49-2.45 (m, 4H), 2.24 (s, 3H), 2.08 (s, 3H), 1.21 (s, 9H). HPLC-MS (ESI+): m/z 474.3 [30%, (M+H)$^+$], 237.8 [100%, (M+2H)$^{2+}$]. LC-MS (ESI+): 474.3 [100%, (M+H)$^+$], 273.7 [35%, (M+2H)$^{2+}$]. HRMS (ESI+): m/z calcd for $C_{27}H_{35}N_7O$ (M+H)$^+$ 474.2976, found 474.2974.

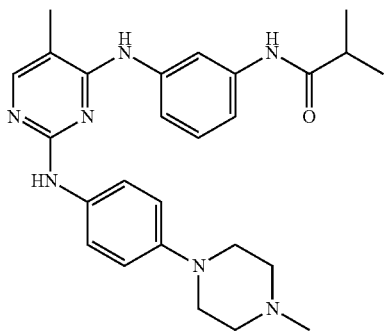

5-Methyl-N$^4$-[3-(2-methylpropanamido)phenyl]-N$^2$-[4-(4-methylpiperazin-1-yl)phenyl]pyrimidine-2,4-diamine (MA2-052-2): This was obtained as a beige solid (32 mg, 43%) from MA2-042-2 (47 mg) and 4-(4-methylpiperazino) aniline (30 mg) using the general method x. Mp: 259° C. (dec). HPLC: 99% [$t_R$=5.1 min, 40% MeOH, 60% water (with 0.1% TFA), 20 min]. $^1$H NMR (400 MHz, DMSO-$d_6$): δ 9.84 (s, 1H), 8.75 (s, 1H, disappeared on $D_2O$ shake), 8.27 (s, 1H, disappeared on $D_2O$ shake), 7.87 (s, 1H), 7.82 (s, 1H), 7.52 (d, J=9.0 Hz, 2H), 7.37 (d, J=8.0 Hz, 1H), 7.31 (d, J=8.0 Hz, 1H), 7.20 (t, J=8.0 Hz, 1H), 6.75 (d, J=9.0 Hz, 2H), 3.19-3.04 (brs, 4H), 2.95-2.80 (brs, 4H), 2.59 (septet, J=6.8 Hz, 6H), 2.52 (s, 3H), 2.06 (s, 3H), 1.06 (d, J=6.8 Hz, 6H). HPLC-MS (ESI+): m/z 460.3 [20%, (M+H)$^+$], 230.8 [100%, (M+2H)$^{2+}$]. LC-MS (ESI+): 460.3 [100%, (M+H)$^+$], 230.6 [15%, (M+2H)$^{2+}$]. HRMS (ESI+): m/z calcd for $C_{26}H_{33}N_7O$ (M+H)$^+$ 460.2819, found 460.2805.

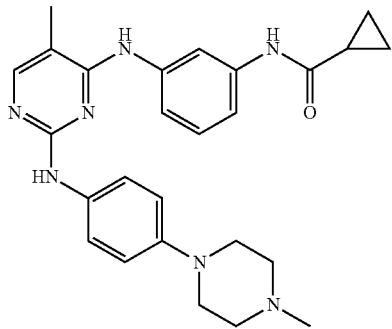

5-Methyl-N$^4$-[3-(cyclopropylcarboxamido)phenyl]-N$^2$-[4-(4-methylpiperazin-1-yl)phenyl]pyrimidine-2,4-diamine (MA2-052-3): This was obtained as a beige solid (27 mg, 38%) from MA2-042-3 (47 mg) and 4-(4-methylpiperazino) aniline (30 mg) using the general method x. Mp: 227° C. (dec). HPLC: 99% [$t_R$=4.3 min, 40% MeOH, 60% water (with 0.1% TFA), 20 min]. $^1$H NMR (400 MHz, DMSO-$d_6$): δ 10.14 (s, 1H, 50% reduced on $D_2O$ shake), 8.66 (s, 1H, disappeared on $D_2O$ shake), 8.24 (s, 1H, disappeared on $D_2O$ shake), 7.84 (s, 1H), 7.81 (s, 1H), 7.48 (d, J=9.1 Hz, 2H), 7.35-7.27 (m, 2H), 7.20 (t, J=8.0 Hz, 1H), 6.72 (d, J=9.1 Hz, 2H), 3.01-2.94 (m, 4H), 2.47-2.40 (m, 4H), 2.22-2.18 (brs, 3H), 2.06 (s, 3H), 1.82-1.72 (m, 1H), 0.79-0.73 (m, 4H). HPLC-MS (ESI+): m/z 458.2 [30%, (M+H)$^+$], 229.7 [100%, (M+2H)$^{2+}$]. LC-MS (ESI+): 458.3 [100%, (M+H)$^+$], 229.6 [10%, (M+2H)$^{2+}$]. HRMS (ESI+): m/z calcd for $C_{26}H_{311\setminus170}$ (M+H)$^+$ 458.2663, found 458.2647.

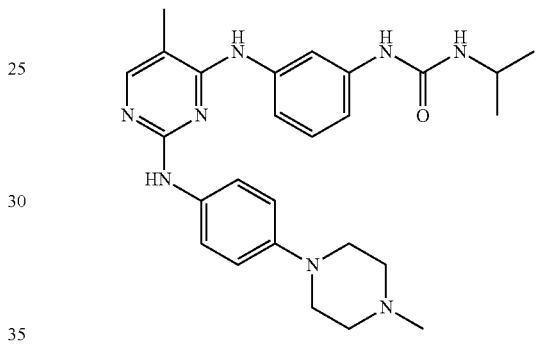

5-Methyl-N$^4$-(3-[3-(methylethyl)ureido]phenyl)-N$^2$-[4-(4-methylpiperazin-1-yl)phenyl]pyrimidine-2,4-diamine (MA2-082-2): Dry THF (1.5 mL) was added to an oven-dried reaction tube 5 mL Ace pressure tube. Argon was bubbled through the solvent for 15 min and PdCl$_2$(dppf) (10.6 mg, 0.1 eq.) and 4-(4-methylpiperazino)aniline (24 mg) were added sequentially. The mixture was then stirred at room temperature for about 2 minutes. Finally, the 2-chloropyrimidine MA2-058-2 (40 mg) and KO$^t$Bu (32 mg, 2.4 eq.) were added. The pressure tube was heated in a oil bath (100° C.) and stirred for 11 h. The reaction mixture was filtered through a pad of celite and purified by chromatography eluting with MeOH-DCM to provide the title compound as a yellow solid (32 mg, 54%). Mp: 268° C. (dec). HPLC: 98% [$t_R$=5.0 min, 40% MeOH, 60% water (with 0.1% TFA), 20 min]. $^1$H NMR (400 MHz, DMSO-$d_6$): δ 8.68 (s, 1H, 60% reduced on $D_2O$ shake), 8.30 (s, 1H, 20% reduced on $D_2O$ shake), 8.18 (s, 1H, 55% reduced on $D_2O$ shake), 7.81 (s, 1H), 7.60 (s, 1H), 7.51 (d, J=9.0 Hz, 2H), 7.21 (s, 1H), 7.17-7.11 (m, 2H), 6.74 (d, J=9.0 Hz, 2H), 6.08 (d, J=7.3 Hz, 1H, 85% reduced on $D_2O$ shake), 3.73 (m, 1H), 3.02-2.96 (m, 4H), 2.46-2.39 (m, 4H), 2.21 (s, 3H), 2.07 (s, 3H), 1.08 (d, J=6.5 Hz, 6H). HPLC-MS (ESI+): m/z 475.3 [30%, (M+H)$^+$], 238.2 [100%, (M+H)$^{2+}$]. LC-MS (ESI+): 475.3 [100%, (M+H)$^+$]. HRMS (ESI+): m/z calcd for $C_{26}H_{341\setminus180}$ (M+H)$^+$ 475.2928, found 475.2910.

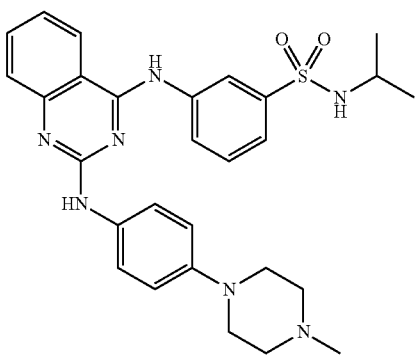

N⁴-(3-[(1-Methylethyl)sulfamoyl]phenyl)-N²-[4-(4-methylpiperazin-1-yl)phenyl]quinazoline-2,4-diamine (MA2-085): This was obtained as a yellow solid (59 mg, 41%) from MA2-084 (50 mg) and 4-(4-methylpiperazino) aniline (25 mg) using the general method x. Mp: 225° C. (dec). HPLC: 100% [$t_R$=7.0 min, 45% MeOH, 55% water (with 0.1% TFA), 20 min]. ¹H NMR (400 MHz, DMSO-d₆): δ 9.78 (s, 1H, disappeared on D₂O shake), 8.94 (s, 1H, disappeared on D₂O shake), 8.49 (brd, J=7.6 Hz, 1H), 8.40 (d, J=8.3 Hz, 1H), 8.25 (brs, 1H), 7.77-7.62 (m, 4H; 1H disappeared on D₂O shake), 7.58 (t, J=7.6 Hz, 1H), 7.53 (d, J=7.6 Hz, 1H), 7.45 (d, 0.1=8.3 Hz, 1H), 7.26 (t, J=7.6 Hz, 1H), 6.88 (d, J=9.0 Hz, 2H), 3.27 (septet, J=6.6 Hz, 1H), 3.11-3.00 (m, 4H), 2.48-2.42 (m, 4H), 2.22 (s, 3H), 1.00 (d, J=6.6 Hz, 6H). HPLC-MS (ESI+): m/z 532.2 [50%, (M+H)⁺], 266.7 [100%, (M+2H)²⁺]. LC-MS (ESI+): 532.2 [100%, (M+H)⁺], 266.6 [50%, (M+2H)²⁺]. HRMS (ESI+): m/z calcd for C₂₈H₃₃N₇O₂S (M+H)⁺ 532.2489, found 532.2478.

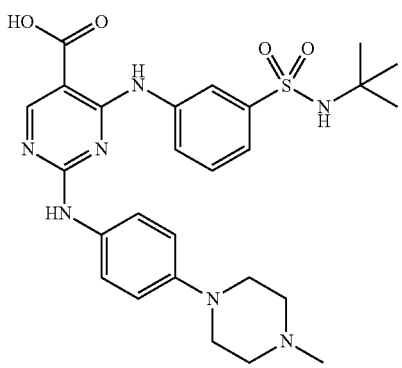

5-Carboxy-N⁴-(3-[N-(1,1-dimethylethyl)sulfamoyl]phenyl)-N²-[4-(4-methylpiperazin-1-yl)phenyl]pyrimidine-2,4-diamine (SG2-086-01): To a solution of RJ1-066-01 (40 mg, 0.070 mmol) in THF/H₂O (1.5:1, 2.5 mL) was added 1 M NaOH solution (0.140 mL). The mixture was stirred overnight at room temperature. The reaction mixture was concentrated under reduced pressure and the crude paste was purified via HPLC eluting with 55% MeOH and 45% water (with 0.1% TFA) to provide the title compound as a yellow solid (12 mg, 32%). Mp: 199° C. (dec). HPLC: 88% [$t_R$=6.7 min, 45% MeOH, 55% water (with 0.1% TFA), 20 min]. ¹H NMR at 80° C. (400 MHz, DMSO-d₆): δ 10.57 (s, 1H), 9.39 (s, 1H), 8.69 (s, 1H), 8.05 (d, J=7.7 Hz, 1H), 7.92 (s, 1H), 7.59-7.44 (m, 4H), 7.22 (s, 1H), 6.94 (d, J=9.0 Hz, 2H), 3.40-3.25 (m, 4H, partly overlapped by water signal), 2.50- 2.45 (m, 4H, overlapped by residual DMSO solvent signal), 2.86 (s, 3H), 1.13 (s, 9H). HPLC-MS (ESI+): m/z 270.7 [100%, (M+2H)²⁺], 540.3 [20%, (M+H)⁺]. LC-MS (ESI+): 540.2 [100%, (M+H)⁺]. HRMS (ESI+): m/z calcd for C₂₆H₃₃N₇O₄S (M+H)⁺ 540.2388, found 540.2406.

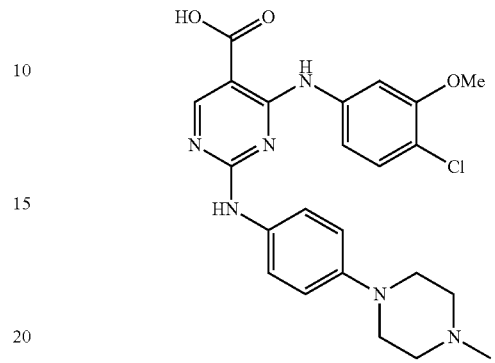

5-Carboxy-N⁴-(4-chloro-3-methoxyphenyl)-N²-[4-(4-methylpiperazin yl)phenyl]pyrimidine-2,4-diamine (SG2-102): To a solution of RJ1-064-01 (40 mg, 0.080 mmol) in THF/H₂O (1.5:1, 2.5 mL) was added 1 M NaOH solution (0.480 mL). The mixture was stirred for 29 h at 50° C. The solvent was removed, water (1 mL) was added, and the mixture acidified to pH 2 by addition of 1 M HCl. The mixture was concentrated under reduced pressure to provide the product as a light yellow solid (74 mg). Mp: 219° C. (dec). HPLC: 99% [$t_R$=6.7 min, 45% MeOH, 55% water (with 0.1% TFA), 20 min]. ¹H NMR at 80° C. (400 MHz, DMSO-d₆): δ 10.43 (s, 1H, disappeared on D₂O shake), 9.41 (s, 1H, disappeared on D₂O shake), 8.66 (s, 1H), 7.47 (d, J=9.0 Hz, 2H), 7.39 (s, 1H), 7.30 (d, J=8.7 Hz, 1H), 7.24 (d, J=8.7 Hz, 1H), 6.90 (d, J=9.0 Hz, 2H), 3.72 (s, 3H), 3.18-3.12 (m, 4H, overlapped by water signal), 2.50-2.46 (m, 4H, overlapped by residual DMSO solvent signal), 2.83 (s, 3H). HPLC-MS (ESI+): m/z 469.3 [50%, (M³⁵Cl+H)⁺], 236.2 [40%, (M³⁷Cl+2H)²⁺], 235.2 [100%, (M³⁵Cl+2H)²⁺]. LC-MS (ESI+): 471.2 [30%, (M³⁷Cl+H)⁺]. 469.2 [100%, (M³⁵Cl+H)⁺]. HRMS (ESI+): m/z calcd for C₂₃H₂₅ClN₆O₃ (M+H)⁺ 469.1794, found 469.1741.

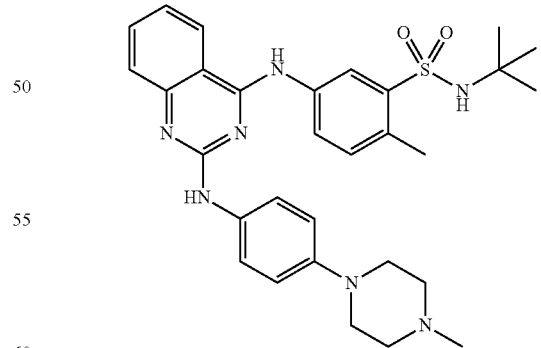

N⁴-(4-Methyl-3-(N-1,1-dimethylethyl)sulfamoyl]phenyl)-N²-[4-(4-methylpiperazin-1-yl)phenyl]quinazoline-2,4-diamine (SG2-120): This was obtained as a yellow solid (30 mg, 43%) from SG2-115 (50 mg) and 4-(4-methylpiperazino)aniline (24 mg) using the general method x. Mp: 241° C. (dec). HPLC: 99% [$t_R$=6.7 min, 50% MeOH, 50% water (with 0.1% TFA), 20 min]. $^1$H NMR (400 MHz, DMSO-$d_6$): δ 9.69 (s, 1H, disappeared on D$_2$O shake), 8.88 (s, 1H, disappeared on D$_2$O shake), 8.36 (d, J=8.1 Hz, 1H), 8.32 (br d, J=8.6 Hz, 1H), 8.28 (br s, 1H), 7.66 (br d, J=9.1 Hz, 2H), 7.62 (t, J=7.6 Hz, 1H), 7.55 (s, 1H, disappeared on D$_2$O shake), 7.41 (d, J=8.1 Hz, 1H), 7.32 (d, J=8.6 Hz, 1H), 7.22 (t, J=7.6 Hz, 1H), 6.86 (d, J=9.1 Hz, 2H), 3.08-3.01 (m, 4H), 2.57 (s, 3H), 2.46-2.41 (m, 4H), 2.20 (s, 3H), 1.13 (s, 9H). HPLC-MS (ESI+): m/z 560.2 [20%, (M+H)$^+$], 280.7 [100%, (M+2H)$^{2+}$]. LC-MS (ESI+): 560.3 [100%, (M+H)$^+$], 280.6 [30%, (M+2H)$^{2+}$], 252.6 [60%, (M+2H-tBu)$^{2+}$]. HRMS (ESI+): m/z calcd for C$_{30}$H$_{37}$N$_7$O$_2$S (M+H)$^+$ 560.2802, found 560.2784.

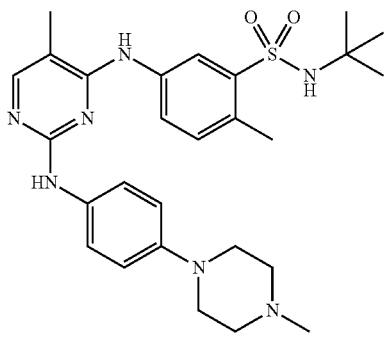

5-Methyl-N$^4$-(4-methyl-[3-(N-1,1-dimethylethyl)sulfamoyl]phenyl)-N$^2$-[4-(4-methylpiperazin-1-yl)phenyl]pyrimidine-2,4-diamine (SG2-121): This was obtained as a red solid (25 mg, 32%) from SG2-108 (52 mg) and 4-(4-methylpiperazino)aniline (27 mg) using the general method x. Mp: 268° C. (dec). HPLC: 98% [t$_R$=11.4 min, 40% MeOH, 60% water (with 0.1% TFA), 20 min]. $^1$H NMR (400 MHz, DMSO-$d_6$): δ 8.66 (s, 1H, disappeared on D$_2$O shake), 8.44 (s, 1H, disappeared on D$_2$O shake), 8.11 (d, J=1.9 Hz, 1H), 8.02 (dd, J=8.2, 1.9 Hz, 1H), 7.83 (s, 1H), 7.47 (s, 1H, disappeared on D$_2$O shake), 7.44 (d, J=9.1 Hz, 2H), 7.25 (d, J=8.2 Hz, 1H), 6.78 (d, J=9.1 Hz, 2H), 3.04-2.96 (m, 4H), 2.54 (s, 3H), 2.45-2.38 (m, 4H), 2.19 (s, 3H), 2.07 (s, 3H), 1.09 (s, 9H). HPLC-MS (ESI+): m/z 524.2 [20%, (M+H)$^+$], 262.8 [100%, (M+2H)$^{2+}$]. LC-MS (ESI+): 524.3 [100%, (M+H)+], 262.6 [10%, (M+2H)$^{2+}$], 234.6 [40%, (M+2H-tBu)$^{2+}$]. HRMS (ESI+): m/z calcd for C$_{27}$H$_{37}$N$_7$O$_2$S (M+H)$^+$ 524.2802, found 524.2809.

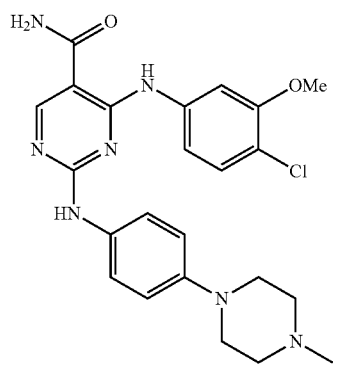

5-Carbamoyl-N$^4$-(4-chloro-3-methoxyphenyl)-N$^2$-[4-(4-methylpiperazin-1-yl)phenyl]pyrimidine-2,4-diamine (SG2-135): This was obtained as a brown thin film (14 mg, 20%) from SG2-132 (48 mg) and 4-(4-methylpiperazino)aniline (29 mg) using the general method x. Mp: 242° C. (dec). HPLC: 86% [t$_R$=7.8 min, 30% MeOH, 70% water (with 0.1% TFA), 20 min]. $^1$H NMR at 80° C. (400 MHz, DMSO-$d_6$): δ 11.45 (s, 1H, disappeared on D$_2$O shake), 9.07 (s, 1H, disappeared on D$_2$O shake), 8.65 (s, 1H), 7.46-7.33 (m, 5H; 2H disappeared on D$_2$O shake), 7.28-7.15 (m, 2H), 6.83 (d, J=9.0 Hz, 2H), 3.70 (s, 3H), 3.12-3.01 (m, 4H, overlapped by water signal, but partly visible upon D$_2$O shake), 2.50-2.45 (m, 4H, overlapped by residual DMSO solvent signal), 2.24 (s, 3H). HPLC-MS (ESI+): m/z 468.3 [40%, (M$^{35}$Cl+H)$^+$], 235.8 [40%, (M$^{37}$Cl+2H)$^{2+}$], 234.7 [100%, (M$^{35}$Cl+2H)$^{2+}$]. LC-MS (ESI+): 470.2 [30%, (M$^{37}$Cl+H)$^+$], 468.2 [100%, (M$^{35}$Cl+H)$^+$]. HRMS (ESI+): m/z calcd for C$_{23}$H$_{26}$ClN$_7$O$_2$ (M+H)$^+$ 468.1909, found 468.1913.

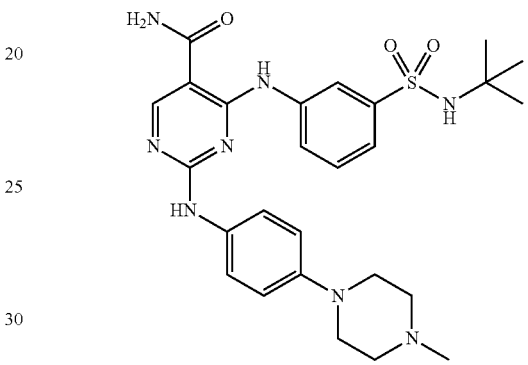

5-Carbamoyl-N$^4$-(3-[N-(1,1-dimethylethyl)sulfamoyl]phenyl)-N$^2$-[4-(4-methylpiperazin-1-yl)phenyl]pyrimidine-2,4-diamine (SG2-142-01): This was obtained as a yellow solid (14 mg, 20%) from SG2-139-01 (50 mg) and 4-(4-methylpiperazino)aniline (25 mg) using the general method x. Mp: 200° C. (dec). HPLC: 92% [t$_R$=11.4 min, 40% MeOH, 60% water (with 0.1% TFA), 20 min]. $^1$H NMR at 80° C. (400 MHz, DMSO-$d_6$): δ 11.65 (s, 1H, disappeared on D$_2$O shake), 9.09 (s, 1H, disappeared on D$_2$O shake), 8.68 (s, 1H), 8.08 (d, J=7.5 Hz, 1H), 7.88 (s, 1H), 7.54-7.41 (m, 6H; 2H disappeared on D$_2$O shake), 7.22 (s, 1H, disappeared on D$_2$O shake), 6.87 (d, J=9.0 Hz, 2H), 3.13-3.07 (m, 4H, partly overlapped by water signal), 2.50-2.45 (m, 4H, overlapped by residual DMSO solvent signal), 2.24 (s, 3H), 1.13 (s, 9H). HPLC-MS (ESI+): m/z 539.2 [50%, (M+H)$^+$], 270.2 [100%, (M+2H)$^{2+}$]. LC-MS (ESI+): 539.3 [100%, (M+H)$^+$]. HRMS (ESI+): m/z calcd for C$_{26}$H$_{34}$N$_8$O$_3$S (M+H)$^+$ 539.2547, found 539.2545.

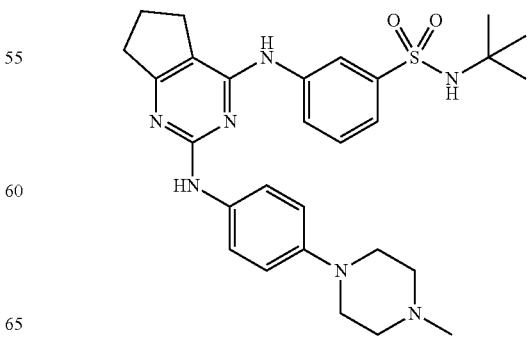

N⁴-(3-[N-(1,1-Dimethylethyl)sulfamoyl]phenyl)-N²-[4-(4-methylpiperazin-1-yl)phenyl]-6,7-dihydro-5H-cyclopenta[d]pyrimidine-2,4-diamine (MA3-006-1): This was obtained as a white solid (13 mg, 19%) from MA2-098-1 (50 mg) and 4-(4-methylpiperazino)aniline (25 mg) using the general method x. Mp: 281° C. (dec). HPLC: 98% [$t_R$=19.5 min, 40% MeOH, 60% water (with 0.1% TFA), 40 min]. ¹H NMR (400 MHz, DMSO-$d_6$): δ 8.78 (s, 1H, disappeared on $D_2O$ shake), 8.76 (s, 1H, disappeared on $D_2O$ shake), 8.19 (d, J=7.1 Hz, 1H), 8.11 (brs, 1H), 7.56 (brs, 1H, disappeared on $D_2O$ shake), 7.49 (d, J=9.0 Hz, 2H), 7.46-7.39 (m, 2H), 6.82 (d, J=9.0 Hz, 2H), 3.05-2.98 (m, 4H), 2.75 (t, J=7.7 Hz, 2H), 2.70 (t, J=7.7 Hz, 2H), 2.47-2.42 (m 4H), 2.21 (s, 3H), 2.00 (quint, J=7.7 Hz, 2H), 1.10 (s, 9H). HPLC-MS (ESI+): m/z 536.3 [30%, (M+H)⁻¹], 268.7 [100%, (M+2H)²⁺]. LC-MS (ESI+): 536.3 [100%, (M+H)⁺], 268.7 [15%, (M+2H)²⁺], 240.6 [40%, (M+3H)²⁺]. HRMS (ESI+): m/z calcd for $C_{28}H_{37}N_7O_2S$ (M+H)⁺ 536.2802, found 536.2798.

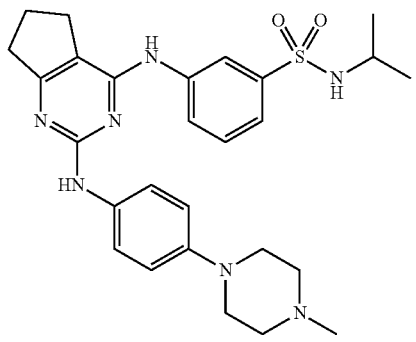

N⁴-(3-[N-(1-Methylethyl)sulfamoyl]phenyl)-N²-[4-(4-methylpiperazin-1-yl)phenyl]-6,7-dihydro-5H-cyclopenta[d]pyrimidine-2,4-diamine (MA3-006-2): This was obtained as a white solid (19 mg, 27%) from MA2-098-2 (50 mg) and 4-(4-methylpiperazino)aniline (26 mg) using the general method x. Mp: 223° C. (dec). HPLC: 98% [$t_R$=10.9 min, 40% MeOH, 60% water (with 0.1% TFA), 20 min]. ¹H NMR (400 MHz, DMSO-$d_6$): δ 8.79 (s 1H, disappeared on $D_2O$ shake), 8.76 (s 1H, disappeared on $D_2O$ shake), 8.28 (d, J=7.9 Hz, 1H), 8.04 (s, 1H), 7.61 (d, J=6.5 Hz, 1H, disappeared on $D_2O$ shake), 7.50 (d, J=9.0 Hz, 2H), 7.46 (d, J=8.0 Hz, 1H), 7.40 (d, J=7.8 Hz, 1H), 6.83 (d, J=9.0 Hz, 2H), 3.23 (oct, J=6.5 Hz, 1H), 3.06-2.97 (m, 4H), 2.76 (t, J=7.5 Hz, 2H), 2.71 (t, J=7.5 Hz, 2H), 2.46-2.42 (m, 4H), 2.22 (s, 3H), 2.01 (quint, J=7.5 Hz, 2H), 0.97 (d, J=6.5 Hz, 6H). HPLC-MS (ESI+): m/z 522.3 [30%, (M+H)⁺], 261.7 [100%, (M+2H)²⁺]. LC-MS (ESI+): 522.3 [100%, (M+H)⁺], 261.6 [30%, (M+2H)²⁺]. HRMS (ESI+): m/z calcd for $C_{27}H_{35}N_7O_2S$ (M+H)⁺ 522.2646, found 522.2627.

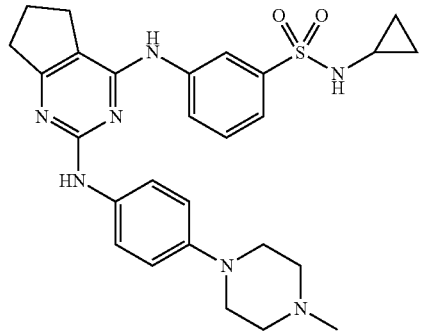

N⁴-(3-[N-Cyclopropylsulfamoyl]phenyl)-N²-[4-(4-methylpiperazin-1-yl)phenyl]-6,7-dihydro-5H-cyclopenta[d]pyrimidine-2,4-diamine (MA3-006-3): This was obtained as off white solid (21 mg, 29%) from MA2-098-3 (50 mg) and 4-(4-methylpiperazino)aniline (26 mg) using the general method x. Mp: 227° C. (dec). HPLC: 99% [$t_R$=7.6 min, 40% MeOH, 60% water (with 0.1% TFA), 20 min]. ¹H NMR (400 MHz, DMSO-$d_6$): δ 8.85 (s, 1H, disappeared on $D_2O$ shake), 8.79 (s, 1H, disappeared on $D_2O$ shake), 8.38 (d, J=8.0 Hz, 1H), 7.96 (s, 1H), 7.93 (brs, 1H disappeared on $D_2O$ shake), 7.51 (d, J=8.0 Hz) overlapping 7.49 (d, J=9.0 Hz, 2H), 7.40 (d, J=7.8 Hz, 1H), 6.83 (d, J=9.1 Hz, 2H), 3.06-3.00 (m, 4H), 2.77 (t, J=7.3 Hz, 2H), 2.72 (t, J=7.3 Hz, 2H), 2.48-2.41 (m, 4H), 2.21 (s, 3H), 2.15 (m, 1H), 2.07-1.96 (quintet, J=7.3 Hz, 2H), 0.54-0.45 (m, 2H), 0.44-0.38 (m, 2H). HPLC-MS (ESI+): m/z 520.3 [30%, (M+H)⁺], 260.7 [100%, (M+2H)²⁻¹]. LC-MS (ESI+): 520.2 [100%, (M+H)⁺], 260.6 [35%, (M+2H)²⁺]. HRMS (ESI+): m/z calcd for $C_{27}H_{33}N_7O_2S$ (M+H)⁺ 520.2489, found 520.2488.

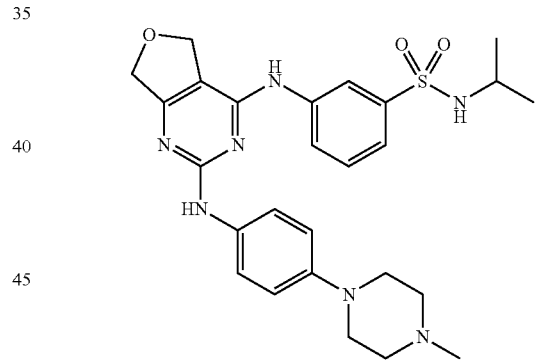

N⁴-(3-[N-(1-Methylethyl)sulfamoyl]phenyl)-N²-[4-(4-methylpiperazin-1-yl)phenyl]-5,7-dihydrofuro[3,4-d]pyrimidine-2,4-diamine (MA3-012-2): This was obtained as a white solid (14 mg, 20%) from MA3-002-2 (50 mg) and 4-(4-methylpiperazino)aniline (26 mg) using the general method x. Mp: 254° C. (dec). HPLC: 97% [$t_R$=5.6 min, 40% MeOH, 60% water (with 0.1% TFA), 20 min]. ¹H NMR (400 MHz, DMSO-$d_6$): δ 8.95 (s, 1H, 45% reduced on $D_2O$ shake), 8.72 (s, 1H, disappeared on $D_2O$ shake), 8.22-8.18 (m, 1H), 7.95 (s, 1H), 7.52-7.44 (m, 4H), 7.34 (d, J=6.9 Hz, 1H, disappeared on $D_2O$ shake), 6.86 (d, J=8.9 Hz, 2H), 4.96 (s, 2H), 4.74 (s, 2H), 3.31 (oct, J=6.5 Hz, 1H), 3.16-3.10 (m, 4H, appeared from water signal on $D_2O$ shake), 2.65-2.52 (m, 4H), 2.33 (s, 3H), 1.01 (d, J=6.5 Hz, 6H). HPLC-MS (ESI+): m/z 524.3 [35%, (M+H)⁺], 262.7 [100%, (M+2H)²⁺]. LC-MS (ESI+): 524.2 [100%, (M+H)⁺]. HRMS (ESI+): m/z calcd for $C_{26}H_{33}N_7O_3S$ (M+H)⁺ 524.2438, found 524.2448.

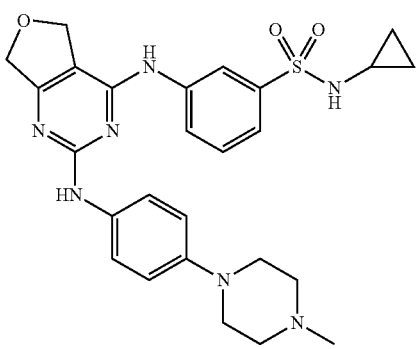

N[4]-(3-[N-Cyclopropylsulfamoyl]phenyl)-N[2]-[4-(4-methylpiperazin-1-yl)phenyl]-5,7-dihydrofuro[3,4-d]pyrimidine-2,4-diamine (MA3-012-3): This was obtained as off white solid (15 mg, 22%) from MA3-002-3 (50 mg) and 4-(4-methylpiperazino)aniline (26 mg) using the general method x. Mp: 221° C. (dec). HPLC: 95% [$t_R$=7.4 min, 35% MeOH, 65% water (with 0.1% TFA), 20 min]. $^1$H NMR (400 MHz, dmso): $^1$H NMR (400 MHz, DMSO-$d_6$) δ 10.13 (s, 1H), 9.24 (s, 1H, 70% reduced on $D_2O$ shake), 9.13 (s, 1H, disappeared on $D_2O$ shake), 8.40 (brd, J=8.0 Hz, 1H), 7.97 (d, J=2.5 Hz, 1H, disappeared on $D_2O$ shake), 7.90 (s, 1H), 7.55 (d, J=9.1 Hz, 2H), 7.51 (d, J=8.0) 7.48-7.41 (m, 1H), 6.93 (d, J=9.1 Hz, 2H), 4.97 (s, 2H), 4.76 (s, 2H), 3.69 (s, 2H), 3.48 (s, 2H), 3.16 (s, 2H), 2.95 (s, 2H), 2.83 (s, 3H), 2.09-2.13 (m, 1H) 0.52-0.45 (m, 2H), 0.45-0.36 (m, 2H). HPLC-MS (ESI+): m/z 522.3 [65%, (M+H)$^+$], 261.8 [100%, (M+2H)$^{2+}$]. LC-MS (ESI+): 522.3 [100%, (M+H)$^+$]. HRMS (ESI+): m/z calcd for $C_{26}H_{31}N_7O_3S$ (M+H)$^+$ 522.2282, found 522.2288.

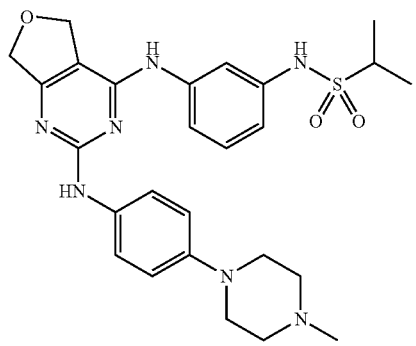

N[4]-(3-[(1-Methylethyl)sulfonamido]phenyl)-N[2]-[4-(4-methylpiperazin-1-yl)phenyl]-5,7-dihydrofuro[3,4-d]pyrimidine-2,4-diamine (MA3-018): This was obtained as a white solid (27 mg, 38%) from MA3-016-2 (50 mg) and 4-(4-methylpiperazino)aniline (26 mg) using the general method x. Mp: 258° C. (dec). HPLC: 99% [$t_R$=5.2 min, 35% MeOH, 65% water (with 0.1% TFA), 20 min]. $^1$H NMR (400 MHz, DMSO-$d_6$): δ 9.74 (s, 1H, disappeared on $D_2O$ shake), 8.94 (s, 1H, disappeared on $D_2O$ shake), 8.89 (s, 1H, disappeared on $D_2O$ shake), 7.69 (d, J=8.0 Hz, 1H), 7.49 (d, J=9.0 Hz, 2H), 7.40 (s, 1H), 7.22 (t, J=8.0 Hz, 1H), 6.89 (dd, J=8.0, 1.2 Hz, 1H), 6.83 (d, J=9.0 Hz, 2H), 4.93 (s, 2H), 4.73 (s, 2H), 3.25 (septet, J=6.8 Hz, 1H), 3.08-2.99 (m, 4H), 2.46-2.40 (m, 4H), 2.21 (s, 3H), 1.24 (d, J=6.8 Hz, 6H). HPLC-MS (ESI+): m/z 524.3 [40%, (M+H)$^+$], 262.8 [100%, (M+2H)$^{2+}$]. LC-MS (ESI+): 524.2 [100%, (M+H)$^+$]. HRMS (ESI+): m/z calcd for $C_{26}H_{33}N_7O_3S$ (M+H)$^+$ 524.2438, found 524.2435.

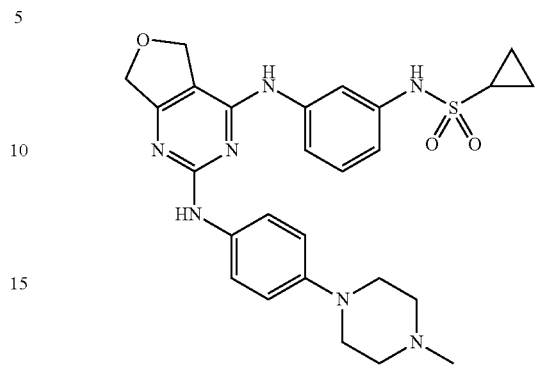

N[4]-[3-(Cyclopropylsulfonamido)phenyl]-N[2]-[4-(4-methylpiperazin-1-yl)phenyl]-5,7-dihydrofuro[3,4-d]pyrimidine-2,4-diamine (MA3-022): This was obtained as a white solid (19 mg, 28%) from MA3-016-3 (50 mg) and 4-(4-methylpiperazino)aniline (26 mg) using the general method x. Mp: 234° C. (dec). HPLC: 93% [$t_R$=14.9 min, 5-95% gradient MeOH-water (with 0.1% TFA), 25 min]. $^1$H NMR (400 MHz, DMSO-$d_6$): δ 9.19 (s, 1H, disappeared on $D_2O$ shake), 9.03 (s, 1H, disappeared on $D_2O$ shake), 8.43 (d, J=7.6 Hz, 1H, disappeared on $D_2O$ shake), 7.96 (d, J=2.2 Hz, 1H), 7.88 (s, 1H), 7.56-7.41 (m, 4H), 6.86 (d, J=9.0 Hz, 2H), 4.96 (s, 2H), 4.75 (s, 2H), 3.09-3.00 (m, 4H), 2.47-2.41 (m, 4H), 2.21 (s, 3H), 2.15-2.07 (m, 1H), 0.52-0.45 (m, 2H), 0.44-0.36 (m, 2H). HPLC-MS (ESI+): m/z 522.2 [40%, (M+H)$^+$], 261.7 [100%, (M+2H)$^{2+}$]. LC-MS (ESI+): 522.2 [100%, (M+H)$^+$]. HRMS (ESI+): m/z calcd for $C_{26}H_{31}N_7O_3S$ (M+H)$^+$ 522.2282, found 522.2298.

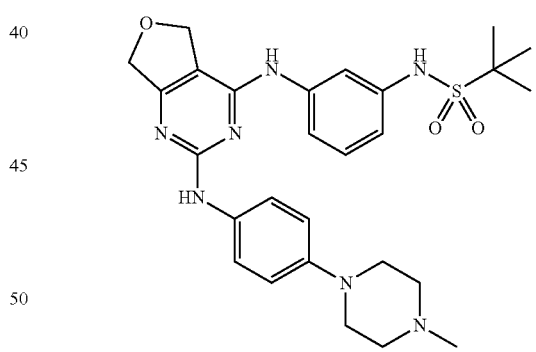

N[4]-(3-[(1,1-Dimethylethyl)sulfonamido]phenyl)-N[2]-[4-(4-methylpiperazin-1-yl)phenyl]-5,7-dihydrofuro[3,4-d]pyrimidine-2,4-diamine (MA3-023): This was obtained as a white solid (37 mg, 53%) from MA3-016-1 (50 mg) and 4-(4-methylpiperazino)aniline (25 mg) using the general method x. Mp: 211° C. (dec). HPLC: 98% [$t_R$=7.4 min, 35% MeOH, 65% water (with 0.1% TFA), 20 min]. $^1$H NMR (400 MHz, DMSO-$d_6$): δ 9.61 (s, 1H, disappeared on $D_2O$ shake), 8.92 (s, 1H, disappeared on $D_2O$ shake), 8.88 (s, 1H, disappeared on $D_2O$ shake), 7.68 (d, J=8.0 Hz, 1H), 7.49 (d, J=9.0 Hz, 2H), 7.46 (s, 1H), 7.19 (t, J=8.0 Hz, 1H), 7.01-6.89 (m, 1H), 6.83 (d, J=9.0 Hz, 2H), 4.92 (s, 2H), 4.73 (s, 2H), 3.08-2.99 (m, 4H), 2.48-2.42 (m, 4H), 2.22 (s, 3H), 1.28 (s, 9H). HPLC-MS (ESI+): m/z 538.3 [40%, (M+H)$^+$], 269.8 [100%, (M+2H)$^{2+}$]. LC-MS (ESI+): 538.3 [100%, (M+H)$^+$]. HRMS (ESI+): m/z calcd for C$_{27}$H$_{35}$N$_7$O$_3$S (M+H)$^+$ 538.2595, found 538.2613.

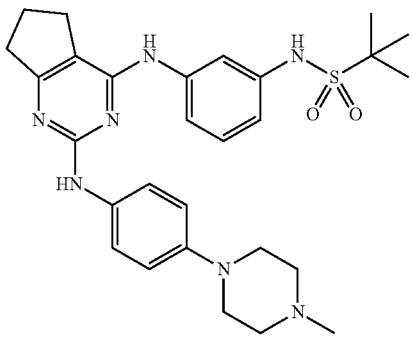

N$^4$-(3-[(1,1-Dimethylethyl)sulfonamido]phenyl)-N$^2$-[4-(4-methylpiperazin-1-yl)phenyl]-6,7-dihydro-5H-cyclopenta[d]pyrimidine-2,4-diamine (MA3-024-1): This was obtained as a white solid (9 mg, 13%) from MA3-014-1 (50 mg) and 4-(4-methylpiperazino)aniline (25 mg) using the general method x. Mp: 248° C. (dec). HPLC: 98% [t$_R$=12.8 min, 40% MeOH, 60% water (with 0.1% TFA), 20 min]. $^1$H NMR (400 MHz, DMSO-d$_6$): δ 9.56 (s, 1H, disappeared on D$_2$O shake), 8.64 (s, 1H, disappeared on D$_2$O shake), 8.55 (s, 1H, disappeared on D$_2$O shake), 7.62 (d, J=8.1 Hz, 1H), 7.54 (s, 1H), 7.51 (d, J=9.0 Hz, 2H), 7.17 (t, J=8.1 Hz, 1H), 6.97-6.90 (m, 1H), 6.81 (d, J=9.0 Hz, 2H), 3.05-2.98 (m, 4H), 2.74 (d, J=7.5 Hz, 2H), 2.69 (d, J=7.5 Hz, 2H), 2.47-2.41 (m, 4H), 2.21 (s, 3H), 2.00 (quint, J=7.5 Hz, 2H), 1.28 (s, 9H). HPLC-MS (ESI+): m/z 536.4 [40%, (M+H)$^+$], 268.7 [100%, (M+1H)$^{2+}$]. LC-MS (ESI+): 536.3 [100%, (M+H)$^+$], 208.8 [100%, (M-$^t$Bu+3H)$^{2+}$]. HRMS (ESI+): m/z calcd for C$_{28}$H$_{37}$N$_7$O$_3$S (M+H)$^+$ 536.2802, found 536.2807.

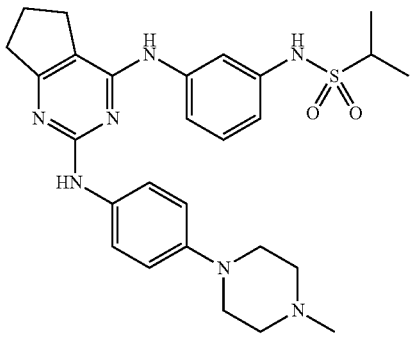

N$^4$-(3-[(1-Methylethyl)sulfonamido]phenyl)-N$^2$-[4-(4-methylpiperazin-1-yl)phenyl]-6,7-dihydro-5H-cyclopenta[d]pyrimidine-2,4-diamine (MA3-024-2): This was obtained as off white solid (10 mg, 14%) from MA3-014-2 (50 mg) and 4-(4-methylpiperazino)aniline (26 mg) using the general method x. Mp: 273° C. (dec). HPLC: 99% [t$_R$=7.7 min, 40% MeOH, 60% water (with 0.1% TFA), 20 min]. $^1$H NMR (400 MHz, DMSO-d$_6$): δ 9.68 (s, 1H, disappeared on D$_2$O shake), 8.64 (s, 1H, disappeared on D$_2$O shake), 8.56 (s, 1H, disappeared on D$_2$O shake), 7.62 (d, J=8.1 Hz, 1H), 7.51 (d, J=9.0 Hz, 2H), 7.48 (s, 1H), 7.20 (t, J=8.1 Hz, 1H), 6.86 (d, J=8.1 Hz, 1H), 6.81 (d, J=9.0 Hz, 2H), 3.24 (septet, J=6.8 Hz, 1H), 3.03 (s, 4H), 2.74 (t, J=7.4 Hz, 2H), 2.70 (t, J=7.4 Hz, 2H), 2.48 (s, 4H, partially overlapped by residual DMSO solvent signal), 2.24 (s, 3H), 2.00 (quintet, J=7.4 Hz, 2H), 1.24 (d, J=6.8 Hz, 6H). HPLC-MS (ESI+): HPLC-MS (ESI+): m/z 522.3 [20%, (M+H)$^+$], 261.8 [100%, (M+2H)$^{2+}$]. LC-MS (ESI+): 522.3 [100%, (M+H)$^+$], 261.6 [12%, (M+2H)$^{24}$]. HRMS (ESI+): m/z calcd for C$_{27}$H$_{35}$N$_7$O$_2$S (M+H)$^+$ 522.2646, found 522.2631.

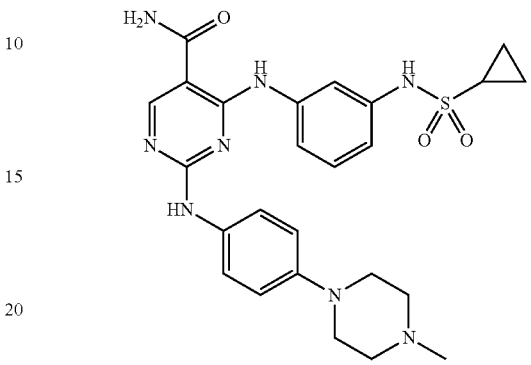

5-Carbamoyl-N$^4$-[3-(cyclopropanesulfonamido)phenyl]-N$^2$-[4-(4-methylpiperazin-1-yl)phenyl]pyrimidine-2,4-diamine (SG2-147): This was obtained as a yellow oil (26 mg, 37%) from SG2-140-01 (50 mg) and 4-(4-methylpiperazino)aniline (26 mg) using the general method x. HPLC: 94% [t$_R$=6.7 min, 35% MeOH, 65% water (with 0.1% TFA), 20 min]. $^1$H NMR at 80° C. (400 MHz, DMSO-d$_6$): δ 11.39 (s, 1H, disappeared on D$_2$O shake), 9.38-9.30 (brs, 1H, disappeared on D$_2$O shake), 8.97 (s, 1H, disappeared on D$_2$O shake), 8.64 (s, 1H), 7.62 (d, J=8.1 Hz, 1H), 7.46 (d, J=9.0 Hz, 2H), 7.42-7.35 (brs, 2H, disappeared on D$_2$O shake), 7.30 (s, 1H), 7.22 (t, J=8.1 Hz, 1H), 6.98 (d, J=8.1 Hz, 1H), 6.85 (d, J=9.0 Hz, 2H), 3.13-3.07 (m, 4H), 2.63-2.54 (m, 1H), 2.50-2.45 (m, 4H, overlapped by residual DMSO solvent signal), 2.23 (s, 3H), 1.01-0.87 (m, 4H). HPLC-MS (ESI+): m/z 523.2 [40%, (M+H)$^+$], 262.3 [100%, (M+2H)$^{2+}$]. HPLC-MS (ESI-): m/z 521.1 [100%, (M-H)$^-$]. LC-MS (ESI+): 523.2 [100%, (M+H)$^+$]. HRMS (ESI+): m/z calcd for C$_{25}$H$_{30}$N$_8$O$_3$S (M+H)$^+$ 523.2234, found 539.2226.

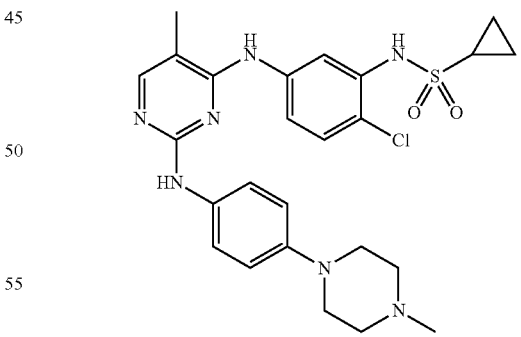

5-Methyl-N$^4$-[4-chloro-(3-cyclopropanesulfonamido)phenyl]-N$^2$-[4-(4-methylpiperazin-1-yl)phenyl]pyrimidine-2,4-diamine (SG2-180): This was obtained as a light brown solid (29 mg, 41%) from SG2-163 (50 mg) and 4-(4-methylpiperazino)aniline (26 mg) using the general method x. Mp: 202° C. (dec). HPLC: 98% [t$_R$=8.9 min, 40% MeOH, 60% water (with 0.1% TFA), 20 min]. $^1$H NMR (400 MHz, DMSO-d$_6$): δ 9.48-9.38 (brs, 1H, disappeared on D$_2$O shake), 8.64 (s, 1H, disappeared on D$_2$O shake), 8.39 (s, 1H, disappeared on D$_2$O shake), 7.86 (s, 1H), 7.81 (dd, J=8.8, 2.4 Hz, 1H), 7.73 (d, J=2.4 Hz, 1H), 7.43 (d, J=9.0 Hz, 2H), 7.36 (d, J=8.8 Hz, 1H), 6.81 (d, J=9.0 Hz, 2H), 3.06-2.96 (m, 4H), 2.65-2.56 (m, 1H), 2.46-2.40 (m, 4H), 2.20 (s, 3H), 2.07 (s, 3H), 0.96-0.82 (m, 4H). HPLC-MS (ESI+): m/z 528.2 [10%, (M$^{35}$Cl+H)$^+$], 265.7 [50%, (M$^{37}$Cl+2H)$^{2+}$], 264.7 [100%, (M$^{35}$Cl+2H)$^{2+}$]. LC-MS (ESI+): 530.2 [30%, (M$^{37}$Cl+H)$^+$], 528.2 [100%, (M$^{35}$Cl+H)$^+$], 265.8 [15%, (M$^{37}$Cl-2H)$^{2+}$], 264.6 [40%, (M$^{35}$Cl+2H)$^{2+}$]. HRMS (ESI+): m/z calcd for C$_{26}$H$_{30}$ClN$_7$O$_2$S (M+H)$^+$ 528.1943, found 528.1948.

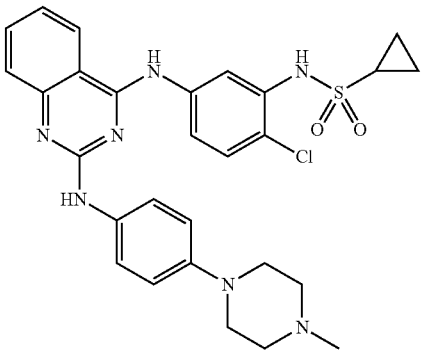

N$^4$-[4-chloro-(3-cyclopropanesulfonamido)phenyl]-N$^2$-[4-(4-methylpiperazin-1-yl)phenyl]quinazoline-2,4-diamine (SG2-181): This was obtained as a yellow solid (30 mg, 43%) from SG2-164 (50 mg) and 4-(4-methylpiperazino)aniline (23 mg) using the general method x. Mp: 236° C. (dec). HPLC: 99% [t$_R$=6.5 min, 45% MeOH, 55% water (with 0.1% TFA), 20 min]. $^1$H NMR (400 MHz, DMSO-d$_6$): δ 9.67 (s, 1H, disappeared on D$_2$O shake), 9.49 (brs, 1H, disappeared on D$_2$O shake), 8.80 (s, 1H, disappeared on D$_2$O shake), 8.33 (d, J=8.0 Hz, 1H), 8.10 (brd, J=8.7 Hz, 1H), 7.89 (d, J=2.5 Hz, 1H), 7.70-7.57 (m, 3H), 7.42 (d, J=8.0 Hz, 2H), 7.22 (t, J=8.0 Hz, 1H), 6.87 (d, J=9.0 Hz, 2H), 3.10-3.01 (m, 4H), 2.73-2.61 (m, 1H), 2.48-2.43 (m, 4H), 2.21 (s, 3H), 1.01-0.87 (m, 4H). HPLC-MS (ESI+): m/z 564.2 [50%, (M$^{35}$Cl+H)$^+$], 283.7 [40%, (M$^{37}$Cl+2H)$^{2+}$], 282.7 [100%, (M$^{35}$Cl+2H)$^{2+}$]. LC-MS (ESI+): 566.2 [40%, (M$^{37}$Cl+H)$^+$], 564.2 [100%, (M$^{35}$Cl+H)$^+$], 283.6 [20%, (M$^{37}$Cl+2H)$^{2+}$], 282.6 [60%, (M$^{35}$Cl+2H)$^{2+}$]. HRMS (ESI+): m/z calcd for C$_{28}$H$_{30}$ClN$_7$O$_2$S (M+H)$^+$ 564.1943, found 564.1939.

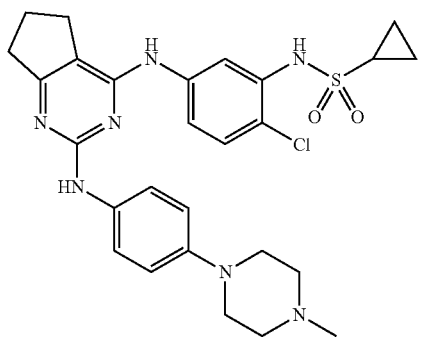

N$^4$-[4-Chloro-3-(cyclopropanesulfonamido)phenyl]-N$^2$-[4-(4-methylpiperazin-yl)phenyl]-6,7-dihydro-5H-cyclopenta[d]pyrimidine-2,4-diamine (SG2-182): This was obtained as a brown solid (11 mg, 16%) from SG2-165 (50 mg) and 4-(4-methylpiperazino)aniline (24 mg) using the general method x. Mp: 192° C. (dec). HPLC: 90% [t$_R$=9.4 min, 40% MeOH, 60% water (with 0.1% TFA), 20 min]. $^1$H NMR (400 MHz, DMSO-d$_6$): δ 9.50-9.40 (brs, 1H, disappeared on D$_2$O shake), 8.72 (s, 1H, disappeared on D$_2$O shake), 8.64 (s, 1H, disappeared on D$_2$O shake), 7.91 (dd, J=8.6, 2.5 Hz, 1H), 7.72 (d, J=2.5 Hz, 1H), 7.46 (d, J=9.0 Hz, 2H), 7.33 (d, J=8.6 Hz, 1H), 6.83 (d, J=9.0 Hz, 2H), 3.08-2.97 (m, 4H), 2.74 (t, J=7.4 Hz, 2H), 2.68 (t, J=7.4 Hz, 2H), 2.62-2.54 (m, 1H), 2.46-2.40 (m, 4H), 2.21 (s, 3H), 1.99 (quintet, J=7.4 Hz, 2H), 0.95-0.84 (m, 4H). HPLC-MS (ESI+): m/z 554.2 [20%, (M$^{35}$Cl+H)$^+$], 278.3 [50%, (M$^{37}$Cl+2H)$^{2+}$], 277.7 [100%, (M$^{35}$Cl+2H)$^{2+}$]. LC-MS (ESI+): 574.2 [40%, (M$^{37}$Cl+H)$^+$], 554.2 [100%, (M$^{35}$Cl+H)$^+$], 277.6 [50%, (M$^{35}$Cl+2H)$^{2+}$]. HRMS (ESI+): m/z calcd for C$_{27}$H$_{32}$ClN$_7$O$_2$S (M+H)$^+$ 554.2099, found 554.2094.

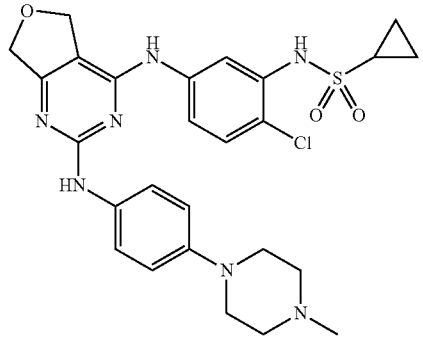

N$^4$-[4-chloro-3-(cyclopropanesulfonamido)phenyl]-N$^2$-[4-(4-methylpiperazin-1-yl)phenyl]-5,7-dihydrofuro[3,4-d]pyrimidine-2,4-diamine (SG2-183): This was obtained as a brown solid (17 mg, 25%) from SG2-166 (50 mg) and 4-(4-methylpiperazino)aniline (24 mg) using the general method x. Mp: 190° C. (dec). HPLC: 94% [t$_R$=6.1 min, 40% MeOH, 60% water (with 0.1% TFA), 20 min]. $^1$H NMR (400 MHz, DMSO-d$_6$): δ 9.50-9.35 (brs, 1H, disappeared on D$_2$O shake), 9.00 (s, 1H, disappeared on D$_2$O shake), 8.95 (s, 1H, disappeared on D$_2$O shake), 7.94 (brd, J=8.9 Hz, 1H), 7.63 (d, J=2.5 Hz, 1H), 7.44 (d, J=9.0 Hz, 2H), 7.34 (d, J=8.9 Hz, 1H), 6.85 (d, J=9.0 Hz, 2H), 4.93 (s, 2H), 4.72 (s, 2H), 3.09-3.00 (m, 4H), 2.63-2.53 (m, 1H), 2.46-2.40 (m, 4H), 2.21 (s, 3H), 0.98-0.81 (m, 4H). HPLC-MS (ESI+): m/z 558.2 [25%, (M$^{37}$Cl+H)$^+$], 556.2 [70%, (M$^{35}$Cl+H)$^+$], 279.4 [45%, (M$^{37}$Cl+2H)$^{2+}$], 278.6 [100%, (M$^{35}$Cl+2H)$^{2+}$]. LC-MS (ESI+): 558.2 [40%, (M$^{35}$Cl+H)$^+$], 556.2 [100%, (M$^{35}$Cl+H)$^+$]. HRMS (ESI+): m/z calcd for C$_{26}$H$_{30}$ClN$_7$O$_3$S (M+H)$^+$ 556.1892, found 556.1900.

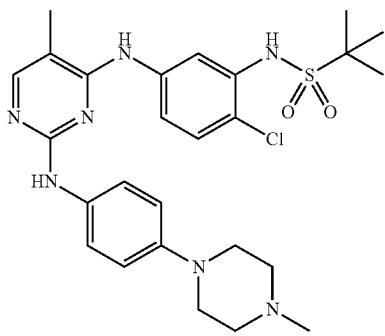

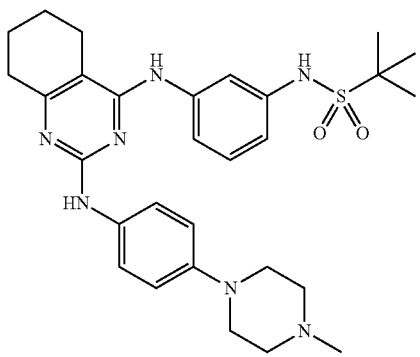

5-Methyl-$N^4$-(4-chloro-[3-(1,1-dimethylethylsulfonamido)]phenyl)-$N^2$-[4-(4-methylpiperazin-1-yl)phenyl]pyrimidine-2,4-diamine (SG3-014): This was obtained as an off-white solid (35 mg, 50%) from SG3-012 (50 mg) and 4-(4-methylpiperazino)aniline (25 mg) using the general method x. Mp: 274° C. (dec). HPLC: 98% [$t_R$=8.4 min, 40% MeOH, 60% water (with 0.1% TFA), 20 min]. $^1$H NMR (400 MHz, DMSO-$d_6$): δ 9.40-9.25 (brs, 1H, disappeared on $D_2O$ shake), 8.62 (s, 1H, disappeared on $D_2O$ shake), 8.40 (s, 1H, disappeared on $D_2O$ shake), 7.85 (s, 1H), 7.84 (d, J=2.2 Hz, 2H), 7.76 (dd, J=8.8, 2.2 Hz, 1H), 7.43 (d, J=9.0 Hz, 2H), 7.32 (d, J=8.8 Hz, 1H), 6.80 (d, J=9.0 Hz, 2H), 3.07-2.96 (m, 4H), 2.46-2.41 (m, 4H), 2.20 (s, 3H), 2.07 (s, 3H), 1.30 (s, 9H). HPLC-MS (ESI+): m/z 544.3 [20%, ($M^{35}Cl+H)^+$], 273.6 [50%, ($M^{37}Cl+2H)^{2+}$], 272.7 [100%, ($M^{35}Cl+2H)^{2+}$]. LC-MS (ESI+): 212.6 [50%, ($M^{35}Cl-SO_2tBu+2H)^{2+}$], 272.6 [20%, ($M^{35}Cl+2H)^{2+}$], 544.2 [100%, ($M^{35}Cl+H)^+$]. HRMS (ESI+): m/z calcd for $C_{26}H_{34}ClN_7O_2S$ $(M+H)^+$ 544.2256, found 544.2242.

$N^4$-(3-[(1,1-Dimethylethyl)sulfonamido]phenyl)-$N^4$-[4-(4-methylpiperazin-1-yl)phenyl]-5,6,7,8-tetrahydroquinazoline-2,4-diamine (MA3-068-1): This was obtained as off white solid (24 mg, 35%) from MA3-064-1 (50 mg) and 4-(4-methylpiperazino)aniline (24 mg) using the general method x. Mp: 242° C. (dec). HPLC: 100% [$t_R$=6.8 min, 45% MeOH, 55% water (with 0.1% TFA), 20 min]. $^1$H NMR (400 MHz, DMSO-$d_6$): δ 9.57 (s, 1H, disappeared on $D_2O$ shake), 8.54 (s, 1H, disappeared on $D_2O$ shake), 8.15 (s, 1H, disappeared on $D_2O$ shake), 7.52 (s, 1H), 7.49 (d, J=9.0 Hz, 2H), 7.44 (d, J=8.1 Hz, 1H), 7.19 (t, J=8.1 Hz, 1H), 6.97 (d, J=8.1 Hz, 1H), 6.76 (d, J=9.0 Hz, 2H), 3.05-3.00 (m, 4H), 2.57-2.45 (m, 8H, overlapped by residual DMSO solvent signal), 2.29-2.23 (brs, 3H), 1.80-1.72 (m, 4H), 1.28 (s, 9H). HPLC-MS (ESI+): m/z 550.3 [20%, $(M+H)^+$], 275.8 [100%, $(M+2H)^{2+}$]. LC-MS (ESI+): 550.3 [100%, $(M+H)^+$]. HRMS (ESI+): m/z calcd for $C_{29}H_{39}N_7O_3S$ $(M+H)^+$ 550.2959, found 550.2969.

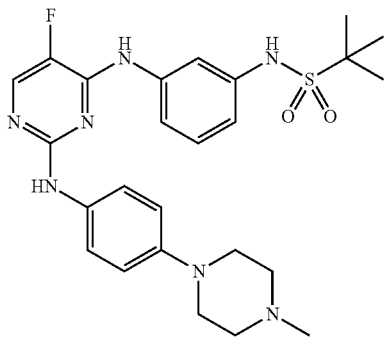

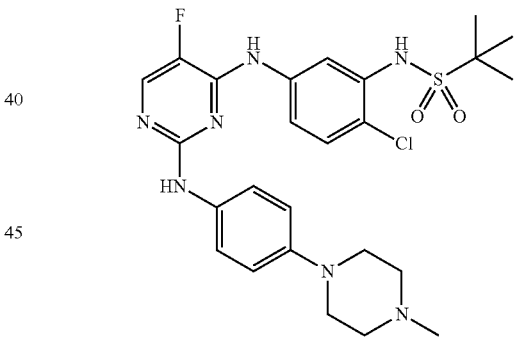

5-Fluoro-$N^4$-(3-[(1,1-dimethylethyl)sulfonamido]phenyl)-$N^2$-[4-(4-methylpiperazin-1-yl)phenyl]pyrimidine-2,4-diamine (MA3-066): This was obtained as a gray solid (45 mg, 62%) from MA3-061 (50 mg) and 4-(4-methylpiperazino)aniline (27 mg) using the general method x. Mp: 217° C. (dec). HPLC: 99% [$t_R$=6.5 min, 35% MeOH, 65% water (with 0.1% TFA), 20 min]. $^{19}$F NMR (376 MHz, DMSO-$d_6$): δ −165.02 (s). $^1$H NMR (400 MHz, DMSO-$d_6$): δ 9.60 (s, 1H, disappeared on $D_2O$ shake), 9.38 (s, 1H, disappeared on $D_2O$ shake), 8.82 (s, 1H, disappeared on $D_2O$ shake), 8.05 (d, $J_{HF}$=3.7 Hz, 1H), 7.66 (d, J=9.0 Hz, 1H), 7.58 (s, 1H), 7.46 (d, J=9.1 Hz, 2H), 7.21 (t, J=8.1 Hz, 1H), 7.01-6.95 (m, 1H), 6.83 (d, J=9.1 Hz, 2H), 3.07-3.00 (m, 4H), 2.48-2.41 (m, 4H), 2.21 (s, 3H), 1.28 (s, 9H). HPLC-MS (ESI+): m/z 514.3 [80%, $(M+H)^+$], 257.7 [100%, $(M+2H)^{2+}$]. LC-MS (ESI+): 514.2 [100%, $(M+H)^+$]. HRMS (ESI+): m/z calcd for $C_{25}H_{32}N_7O_2S$ $(M+H)^+$ 514.2395, found 514.2394.

5-Fluoro-$N^4$-(4-chloro-[3-(1,1-dimethylethylsulfonamido)]phenyl)-$N^2$-[4-(4-methylpiperazin-1-yl)phenyl]pyrimidine-2,4-diamine (MA3-072): This was obtained as a white solid (28 mg, 40%) from MA3-070 (50 mg) and 4-(4-methylpiperazino)aniline (24 mg) using the general method x. Mp: 236° C. (dec). HPLC: 99% [$t_R$=7.1 min, 40% MeOH, 60% water (with 0.1% TFA), 20 min]. $^{19}$F NMR (376 MHz, DMSO-$d_6$): δ −164.93 (s). $^1$H NMR (400 MHz, DMSO-$d_6$): δ 9.51 (s, 1H, disappeared on $D_2O$ shake), 9.40-9.25 (brs, 1H, disappeared on $D_2O$ shake), 8.89 (s, 1H, 80% reduced on $D_2O$ shake), 8.08 (d, J=3.7 Hz, 1H), 7.90 (d, J=8.8 Hz, 1H), 7.87 (d, J=2.4 Hz, 1H), 7.44 (d, J=9.0 Hz, 2H), 7.36 (d, J=8.8 Hz, 1H), 6.86 (d, J=9.0 Hz, 2H), 3.09-3.01 (m, 4H), 2.49-2.40 (m, 4H), 2.22 (s, 3H), 1.31 (s, 9H). HPLC-MS (ESI+): m/z 550.2 [30%, $(M^{37}Cl+H)^+$], 548.2 [88%, $(M^{35}Cl+H)^+$], 275.7 [42%, $(M^{37}Cl+2H)^{2+}$], 274.7 [100%, $(M^{35}Cl+2H)^{2+}$]. LC-MS (ESI+): 550.2 [35%, (M$^{37}$Cl+H)$^+$], 548.2 [100%, (M$^{35}$Cl+H)$^+$]. HRMS (ESI+): m/z calcd for C$_{25}$H$_{31}$N$_2$O$_3$S (M+H)$^+$ 548.2005, found 550.2020.

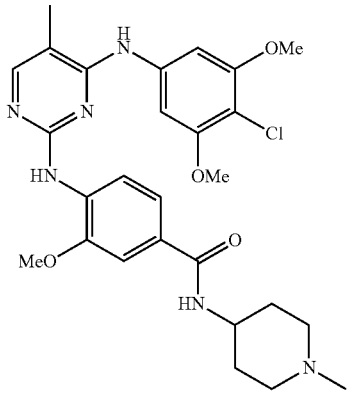

5-Methyl-N$^4$-(4-chloro-3,5-dimethoxyphenyl)-N$^2$-[4-(1-methylpiperidin-4-ylcarbamoyl)-2-methoxyphenyl]pyrimidine-2,4-diamine (SG3-026-02): This was obtained as a clear thin film (21 mg, 24%) from SG3-067 (50 mg) and SG3-016 (42 mg) using the general method x, except the mixture was heated in a microwave reactor at 160° C. for 3×15 minutes.

HPLC: 97% [t$_R$=7.5 min, 40% MeOH, 60% water (with 0.1% TFA), 20 min]. $^1$H NMR (400 MHz, DMSO-d$_6$): δ 8.52 (s, 1H, disappeared on D$_2$O shake), 8.31 (d, J=8.4 Hz, 1H), 8.13 (d, J=7.5 Hz, 1H), 7.98 (s, 1H), 7.67 (s, 1H, disappeared on D$_2$O shake), 7.45 (d, J=1.7 Hz, 1H), 7.36 (dd, J=8.4, 1.7 Hz, 1H), 7.22 (s, 2H), 3.90 (s, 3H), 3.85-3.73 (m, 1H), 3.75 (s, 6H), 3.05-2.87 (brs, 2H), 2.40-2.28 (brs, 3H), 2.12 (s, 3H), 1.87-1.77 (brd, J=10.9 Hz, 2H), 1.72-1.57 (m, 2H). HPLC-MS (ESI+): m/z 541.3 [10%, (M$^{35}$Cl+H)$^+$], 271.9 [50%, (M$^{37}$Cl+2H)$^{2+}$], 271.2 [100%, (M$^{35}$Cl+2H)$^{2+}$]. LC-MS (ESI+): 541.2 [100%, (M$^{35}$Cl+H)$^+$], 271.1 [40%, (M$^{35}$Cl+2H)$^{2+}$]. HRMS (ESI+): m/z calcd for C$_{27}$H$_{33}$ClN$_6$O$_4$ (M+H)$^+$ 541.2325, found 541.2313.

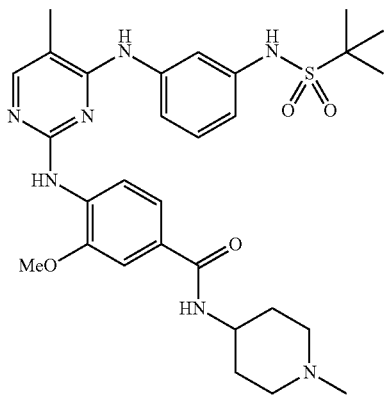

5-Methyl-N$^4$-([3-(1,1-dimethylethylsulfonamido)]phenyl)-N$^2$-[4-(1-methylpiperidin-4-ylcarbamoyl)-2-methoxyphenyl]pyrimidine-2,4-diamine (SG3-059): This was obtained as a white solid (27 mg, 33%) from SG3-053 (50 mg) and SG3-016 (42 mg) using the general method x. Mp: 269° C. (dec). HPLC: 99% [t$_R$=9.3 min, 40% MeOH, 60% water (with 0.1% TFA), 20 min]. $^1$H NMR (400 MHz, DMSO-d$_6$): δ 9.65 (s, 1H, disappeared on D$_2$O shake), 8.47 (s, 1H, disappeared on D$_2$O shake), 8.40 (d, J=8.6 Hz, 1H), 8.04 (d, J=7.7 Hz, 1H), 7.95 (s, 1H), 7.92 (s, 1H), 7.60 (s, 1H, disappeared on D$_2$O shake), 7.43 (s, 1H), 7.38 (d, J=8.6 Hz, 1H), 7.26 (d, J=7.9 Hz, 1H), 7.22 (t, J=7.9 Hz, 1H), 6.99 (d, J=7.9 Hz, 1H), 3.90 (s, 3H), 3.78-3.65 (m, 1H), 2.84-2.74 (brd, J=10.3 Hz, 2H), 2.18 (s, 3H), 2.11 (s, 3H), 2.03-1.90 (brt, J=10.7 Hz, 2H), 1.80-1.70 (brd, J=10.7 Hz, 2H), 1.64-1.51 (m, 2H), 1.30 (s, 9H). HPLC-MS (ESI+): m/z 582.4 [20%, (M+H)$^+$], 291.8 [100%, (M+2H)$^{2+}$]. LC-MS (ESI+): 604.3 [30%, (M+Na)$^+$], 582.3 [100%, (M+H)$^+$], 291.6 [70%, (M+2H)$^{2+}$]. HRMS (ESI+): m/z calcd for C$_{29}$H$_{39}$N$_7$O$_4$S(M+H)$^+$ 582.2857, found 582.2869.

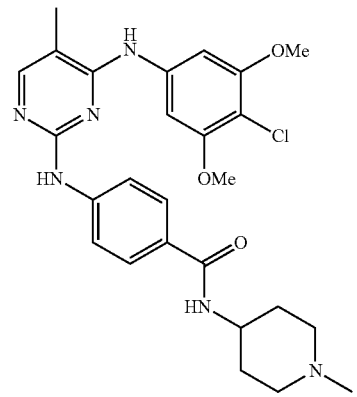

5-Methyl-N$^4$-(4-chloro-3,5-dimethoxyphenyl)-N$^2$-[4-(1-methylpiperidin-4-ylcarbamoyl)phenyl]pyrimidine-2,4-diamine (SG3-064): This was obtained as an off-white solid (32 mg, 40%) from SG3-067 (50 mg) and SG3-051 (37 mg) using the general method x. Mp: 203° C. (dec). HPLC: 95% [t$_R$=12.4 min, 37.5% MeOH, 62.5% water (with 0.1% TFA), 20 min]. $^1$H NMR at 40° C. (400 MHz, DMSO-d$_6$): δ 9.18 (s, 1H, disappeared on D$_2$O shake), 8.34 (s, 1H, reduced by 50% on D$_2$O shake), 7.96 (s, 1H), 7.84 (d, J=7.8 Hz, 1H), 7.72 (d, J=8.9 Hz, 2H), 7.66 (d, J=8.9 Hz, 2H), 7.15 (s, 2H), 3.75 (s, 6H), 3.71-3.63 (m, 1H), 2.78-2.70 (brd, J=11.6 Hz, 2H), 2.15 (s, 3H), 2.12 (s, 3H), 1.93 (t, J=11.6 Hz, 2H), 1.73 (brd, J=12.3, 3.4 Hz, 2H), 1.56 (qd, J=12.3, 3.4 Hz, 2H). HPLC-MS (ESI+): m/z 511.2 [20%, (M$^{35}$Cl+H)$^+$], 257.1 [40%, (M$^{37}$Cl+2H)$^{2+}$], 256.3 [100%, (M$^{35}$Cl+2H)$^{2+}$]. LC-MS (ESI+): 513.2 [35%, (M$^{37}$Cl+H)$^+$], 511.2 [100%, (M$^{35}$Cl+H)$^+$], 257.1 [20%, (M$^{37}$Cl+2H)$^{2+}$], 256.1 [50%, (M$^{35}$Cl+2H)$^{2+}$]. HRMS (ESI+): m/z calcd for C$_{26}$H$_{31}$ClN$_6$O$_3$ (M+H)$^+$ 511.2219, found 511.2208.

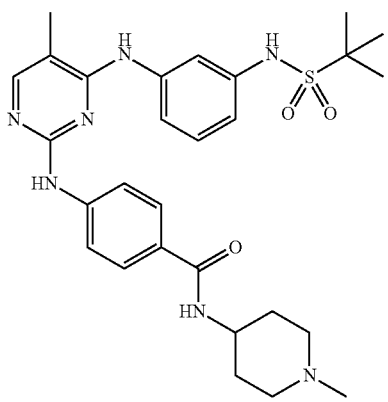

5-Methyl-$N^4$-([3-(1,1-dimethylethylsulfonamido)]phenyl)-$N^2$-[4-O-methylpiperidin-4-ylcarbamoyl)phenyl]pyrimidine-2,4-diamine (SG3-065): This was obtained as a light brown solid (47 mg, 60%) from SG3-053 (50 mg) and SG3-051 (33 mg) using the general method x. Mp: 252° C. (dec). HPLC: 95% [$t_R$=6.8 min, 40% MeOH, 60% water (with 0.1% TFA), 20 min]. $^1$H NMR (400 MHz, DMSO-$d_6$): δ 9.61 (s, 1H, disappeared on D$_2$O shake), 9.16 (s, 1H, reduced by 75% on D$_2$O shake), 8.45 (s, 1H, reduced by 50% on D$_2$O shake), 7.92 (s, 1H), 7.91 (brs, 1H), 7.70 (d, J=8.7 Hz, 2H), 7.63 (d, J=8.7 Hz, 2H), 7.48 (d, J=7.9 Hz, 1H), 7.47 (s, 1H), 7.23 (t, J=7.9 Hz, 1H), 7.02 (d, J=7.9 Hz, 1H), 3.75-3.61 (m, 1H), 2.78-2.70 (d, J=10.3 Hz, 2H), 2.13 (s, 3H), 2.09 (s, 3H), 1.90 (t, J=11.7 Hz, 2H), 1.75-1.65 (brd, J=10.3 Hz, 2H), 1.54 (qd, J=11.7, 3.5 Hz, 2H), 1.26 (s, 9H). HPLC-MS (ESI+): m/z 552.3 [20%, (M+H)$^+$], 276.7 [100%, (M+2H)$^{2+}$]. HPLC-MS (ESI−): m/z 550.3 [100%, (M+H)$^+$]. LC-MS (ESI+): 574.3 [40%, (M+Na)$^+$], 552.3 [100%, (M+H)$^+$], 276.6 [50%, (M+2H)$^{2+}$]. HRMS (ESI+): m/z calcd for $C_{28}H_{37}N_7O_3S$ (M+H)$^+$ 552.2751, found 552.2759.

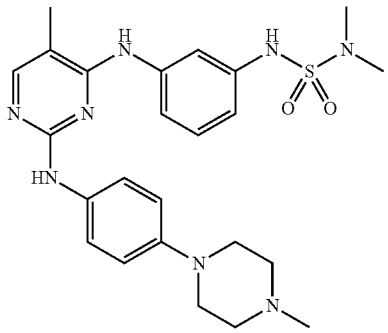

5-Methyl-$N^4$-([3-(N,N-dimethylsulfamoylamino)]phenyl)-$N^2$-[4-(4-methylpiperazin-1-yl)phenyl]pyrimidine-2,4-diamine (SG3-043A): This was obtained from SG3-038 (50 mg) and 4-(4-methylpiperazino)aniline (28 mg) using the general method x. The residue was purified via HPLC eluting with gradient 5-95% MeOH and water (with 0.1% TFA) to provide the title compound as a clear thin film (11 mg, 15%). HPLC: 99% [$t_R$=7.6 min, 35% MeOH, 65% water (with 0.1% TFA), 20 min]. $^1$H NMR at 80° C. (400 MHz, DMSO-$d_6$): δ 9.55 (s, 1H, disappeared on D$_2$O shake), 9.17 (brs, 1H, disappeared on D$_2$O shake), 8.98 (brs, 1H, disappeared on D$_2$O shake), 7.80 (s, 1H), 7.41-7.31 (m, 4H), 7.24 (t, J=8.0 Hz, 1H), 7.04 (d, J=8.0 Hz, 1H), 6.88 (d, J=9.1 Hz, 2H), 3.25-3.10 (m, 4H, overlapped by water signal), 2.86 (s, 3H), 2.72 (s, 6H), 2.49-2.45 (m, 4H, overlapped by residual DMSO solvent signal), 2.14 (s, 3H). HPLC-MS (ESI+): m/z 497.3 [20%, (M+H)$^+$], 249.2 [100%, (M+2H)$^{2+}$]. LC-MS (ESI+): 497.2 [100%, (M+H)$^+$]. HRMS (ESI+): m/z calcd for $C_{24}H_{32}N_8O_2S$ (M+H)$^+$ 497.2442, found 497.2439.

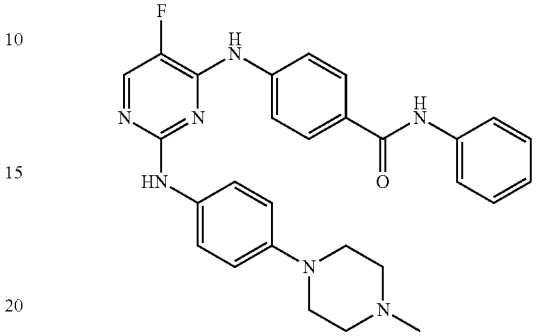

5-Fluoro-$N^4$-(phenylbenzamide)-$N^2$-[4-(4-methylpiperazin-1-yl)phenyl]pyrimidine-2,4-diamine (SG3-073): This was obtained as a yellow solid (29 mg, 40%) from SG3-071 (50 mg) and 4-(4-methylpiperazino)aniline (28 mg) using the general method x. Mp: 240° C. (dec). HPLC: 99% [$t_R$=9.4 min, 35% MeOH, 65% water (with 0.1% TFA), 20 min]. $^1$H NMR (400 MHz, DMSO-$d_6$): δ 10.14 (s, 1H, disappeared on D$_2$O shake), 9.59 (s, 1H, disappeared on D$_2$O shake), 9.06 (s, 1H, disappeared on D$_2$O shake), 8.13 (d, J=3.4 Hz, 1H), 8.02 (d, J=8.6 Hz, 2H), 7.92 (d, J=8.6 Hz, 2H), 7.79 (d, J=7.7 Hz, 2H), 7.48 (d, J=8.8 Hz, 2H), 7.35 (t, J=7.7 Hz, 2H), 7.10 (t, J=7.7 Hz, 1H), 6.89 (d, J=8.8 Hz, 2H), 3.11-3.03 (m, 4H), 2.48-2.41 (m, 4H), 2.21 (s, 3H). $^{19}$F NMR (376 MHz, DMSO-$d_6$): δ −164.70. HPLC-MS (ESI+): m/z 498.3 [80%, (M+H)$^+$], 249.7 [100%, (M+2H)$^2$]. LC-MS (ESI+): 498.2 [100%, (M+H)$^+$]. HRMS (ESI+): m/z calcd for $C_{28}H_{28}FN_7O$ (M+H)$^+$ 498.2412, found 498.2412.

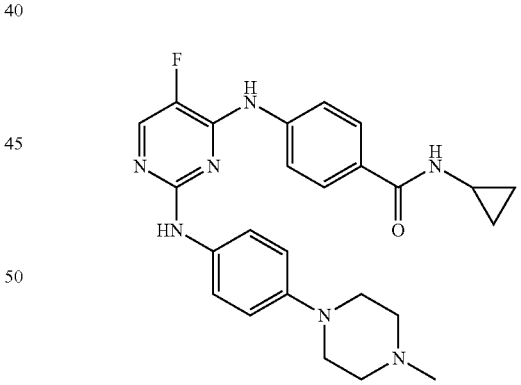

5-Fluoro-$N^4$-(cyclopropylbenzamide)-$N^2$-[4-(4-methylpiperazin-1-yl)phenyl]pyrimidine-2,4-diamine (SG3-081): This was obtained as a yellow solid (34 mg, 45%) from SG3-076 (50 mg) and 4-(4-methylpiperazino)aniline (31 mg) using the general method x. Mp: 240° C. (dec). HPLC: 99% [$t_R$=5.6 min, 35% MeOH, 65% water (with 0.1% TFA), 20 min]. $^1$H NMR (400 MHz, DMSO-$d_6$): δ 9.48 (s, 1H, disappeared on D$_2$O shake), 9.02 (s, 1H, reduced by 35% on D$_2$O shake), 8.33 (d, J=4.1 Hz, 1H), 8.10 (d, J=3.7 Hz, 1H), 7.91 (d, J=8.8 Hz, 2H), 7.76 (d, J=8.8 Hz, 2H), 7.46 (d, J=9.0 Hz, 2H), 6.86 (d, J=9.0 Hz, 2H), 3.09-3.02 (m, 4H), 2.87-2.79 (m, 1H), 2.48-2.42 (m, 4H), 0.73-0.65 (m, 2H), 0.58-

0.52 (m, 2H). $^{19}$F NMR (376 MHz, DMSO-d$_6$): δ −164.84. HPLC-MS (ESI+): m/z 462.3 [80%, (M+H)$^+$], 231.8 [100%, (M+2H)$^{2+}$]. LC-MS (ESI+): 462.2 [100%, (M+H)$^+$]. HRMS (ESI+): m/z calcd for C$_{25}$H$_{28}$FN$_7$O (M+H)$^+$ 462.2412, found 462.2389.

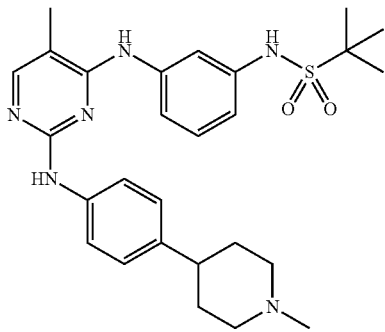

5-Methyl-N$^4$-[3-(1,1-dimethylethylsulfonamido)phenyl]-N$^2$-[4-(1-methylpiperidin-4-yl)phenyl]pyrimidine-2,4-diamine (SG3-082): This was obtained as a yellow oil (28 mg, 40%) from SG3-053 (50 mg) and SG3-079 (27 mg) using the general method x. HPLC: 98% [t$_R$=15.7 min, 35% MeOH, 65% water (with 0.1% TFA), 20 min]. $^1$H NMR (400 MHz, DMSO-d$_6$): δ 9.61 (s, 1H, disappeared on D$_2$O shake), 8.75 (s, 1H, disappeared on D$_2$O shake), 8.35 (s, 1H, disappeared on D$_2$O shake), 7.87 (s, 1H), 7.57-7.52 (m, 3H), 7.48 (d, J=8.1 Hz, 1H), 7.22 (t, J=8.1 Hz, 1H), 7.05-6.98 (m, 3H), 2.88-2.81 (brd, J=11.3 Hz, 2H), 2.39-2.26 (m, 1H), 2.18 (s, 3H), 2.09 (s, 3H), 1.93 (td, J=12.0, 2.6 Hz, 2H), 1.74-1.53 (m, 4H), 1.28 (s, 9H). HPLC-MS (ESI+): m/z 509.3 [20%, (M+H)$^+$], 255.2 [100%, (M+2H)$^{2+}$]. LC-MS (ESI+): 531.3 [20%, (M+Na)$^+$]. 509.3 [100%, (M+H)$^+$], 195.1 [50%, (M-SO$_2$tBu+2H)$^{2+}$]. HRMS (ESI+): m/z calcd for C$_{27}$H$_{36}$N$_6$O$_2$S (M+H)$^+$ 509.2693, found 509.2664.

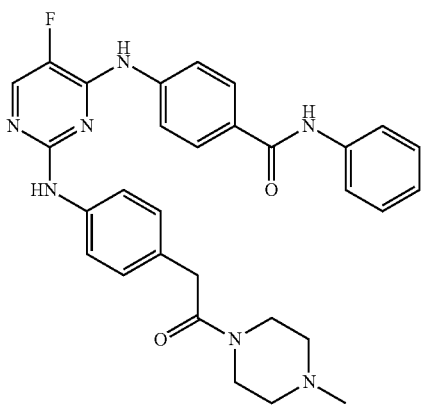

5-Fluoro-N$^4$-(phenylbenzamide)-N$^2$-(4-[2-(4-methylpiperazin-1-yl) oxoethyl]phenyl)pyrimidine-2,4-diamine (SG3-075): This was prepared using the reported procedure of Aliagas-Martin et al$^2$ from SG3-071 (50 mg), 2-(4-aminophenyl)acetic acid (22 mg), TBTU (37 mg), 1-methylpiperazine (10.67 μL), and DIPEA (67 μL) to give the title compound as a yellow solid (22 mg, 33%, 3 steps). HPLC: 98% [t$_R$=5.6 min, 45% MeOH, 45% water (with 0.1% TFA), 20 min]. $^1$H NMR (400 MHz, DMSO-d$_6$): δ 10.13 (s, 1H, disappeared on D$_2$O shake), 9.64 (s, 1H, disappeared on D$_2$O shake), 9.29 (s, 1H, disappeared on D$_2$O shake), 8.17 (d, J=3.4 Hz, 1H), 8.01 (d, J=8.7 Hz, 2H), 7.92 (d, J=8.7 Hz, 2H), 7.77 (d, J=7.9 Hz, 2H), 7.58 (d, J=8.4 Hz, 2H), 7.33 (t, J=7.9 Hz, 2H), 7.13-7.04 (m, 3H), 3.62 (s, 2H), 3.47-3.40 (m, 4H), 2.21-2.12 (m, 4H), 2.09 (s, 3H). $^{19}$F NMR (376 MHz, DMSO-d$_6$): δ −163.62. HPLC-MS (ESI+): m/z 540.2 [80%, (M+H)$^+$], 270.7 [100%, (M+2H)$^{2+}$]. HPLC-MS (ESI−): m/z 538.3 [100%, (M−H)$^-$]. LC-MS (ESI+): 562.2 [40%, (M+Na)$^+$], 540.2 [100%, (M+H)$^+$]. HRMS (ESI+): m/z calcd for C$_{30}$H$_{30}$FN$_7$O$_2$ (M+H)$^+$ 540.2517, found 540.2519.

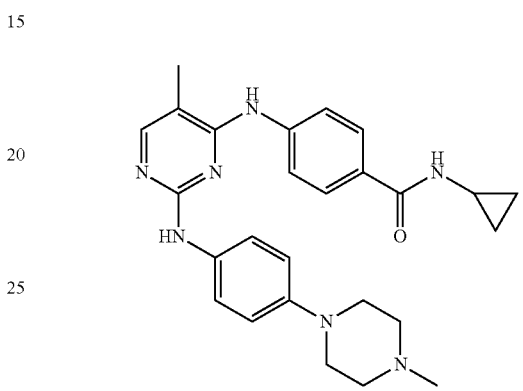

5-Methyl-N$^4$-(cyclopropylbenzamide)-N$^2$-[4-(4-methylpiperazin-1-yl)phenyl]pyrimidine-2,4-diamine (SG3-087-01): This was obtained as a light yellow solid (35 mg, 47%) from SG3-083 (50 mg) and 4-(4-methylpiperazino)aniline (31 mg) using the general method x. HPLC: 98% [t$_R$=7.7 min, 35% MeOH, 65% water (with 0.1% TFA), 20 min]. $^1$H NMR (400 MHz, DMSO-d$_6$): δ 8.65 (s, 1H, disappeared on D$_2$O shake), 8.29 (s, 1H, disappeared on D$_2$O shake), 8.20 (d, J=3.3 Hz, 1H), 7.87 (s, 1H), 7.82 (d, J=8.8 Hz, 2H), 7.75 (d, J=8.8 Hz, 2H), 7.45 (d, J=9.0 Hz, 2H), 6.80 (d, J=9.0 Hz, 2H), 3.07-3.00 (m, 4H), 2.88-2.78 (m, 1H), 2.49-2.43 (m, 4H, overlapped by residual DMSO solvent signal), 2.22 (s, 3H), 2.10 (s, 3H), 0.71-0.64 (m, 2H), 0.59-0.52 (m, 2H). HPLC-MS (ESI+): m/z 458.3 [20%, (M+H)$^+$], 229.7 [100%, (M+2H)$^{2+}$]. LC-MS (ESI+): 458.3 [100%, (M+H)$^+$]. HRMS (ESI+): m/z calcd for C$_{26}$H$_{31}$N$_7$O (M+H)$^+$ 458.2663, found 458.2667.

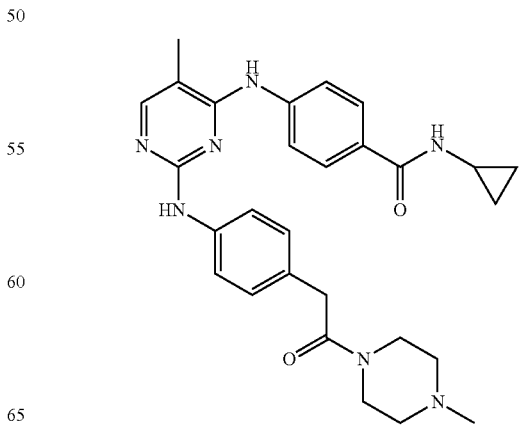

5-Methyl-N⁴-(cyclopropylbenzamide)-N²-(4-[2-(4-methylpiperazin-1-yl)-2-oxoethyl]phenyl)pyrimidine-2,4-diamine (SG3-092): This was prepared using the reported procedure of Aliagas-Martin et al[2] from SG3-083 (50 mg), 2-(4-aminophenyl)acetic acid (25 mg), TBTU (63 mg), 1-methylpiperazine (18.30 μL), and DIPEA (115 μL) to give the title compound as a light yellow thin film (20 mg, 25%, 3 steps). HPLC: 96% [$t_R$=8.0 min, 35% MeOH, 65% water (with 0.1% TFA), 20 min]. ¹H NMR (400 MHz, DMSO-$d_6$): δ 9.02 (s, 1H, disappeared on $D_2O$ shake), 8.42 (s, 1H, disappeared on $D_2O$ shake), 8.30 (d, J=4.1 Hz, 1H, reduced by 50% on $D_2O$ shake), 7.92 (s, 1H), 7.84 (d, J=8.8 Hz, 2H), 7.77 (d, J=8.8 Hz, 2H), 7.59 (d, J=8.6 Hz, 2H), 7.03 (d, J=8.6 Hz, 2H), 3.60 (s, 2H), 3.46-3.40 (m, 4H), 2.87-2.78 (m, 1H), 2.22-2.17 (m, 2H), 2.17-2.13 (m, 2H), 2.11 (s, 6H), 0.71-0.63 (m, 2H), 0.60-0.53 (m, 2H). HPLC-MS (ESI+): m/z 500.3 [20%, (M+H)⁺], 250.8 [100%, (M+2H)²⁺]. HPLC-MS (ESI−): m/z 498.3 [100%, (M−H)⁻]. LC-MS (ESI+): 1021.5 [100%, (2M+Na)⁺], 522.2 [100%, (M+Na)⁺], 500.3 [100%, (M+H)⁺]. HRMS (ESI+): m/z calcd for $C_{28}H_{33}N_7O_2$ (M+H)⁺ 500.2768, found 500.2787.

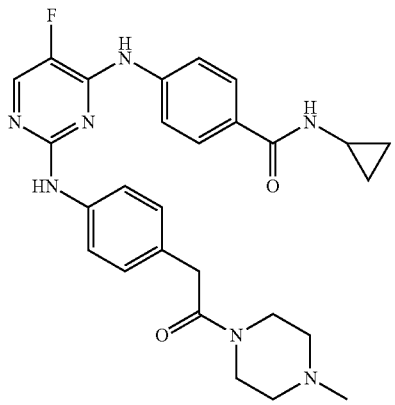

5-Fluoro-N⁴-(cyclopropylbenzamide)-N²-(4-[2-(4-methylpiperazin-1-yl)-2-oxoethyl]phenyl)pyrimidine-2,4-diamine (SG3-094): This was prepared using the reported procedure of Aliagas-Martin et al[e] from SG3-076 (50 mg), 2-(4-aminophenyl)acetic acid (25 mg), TBTU (63 mg), 1-methylpiperazine (18.08 μL), and DIPEA (113 μL) to give the title compound as a light yellow thin film (20 mg, 25%, 3 steps). HPLC: 96% [$t_R$=7.3 min, 35% MeOH, 65% water (with 0.1% TFA), 20 min]. ¹H NMR (400 MHz, DMSO-$d_6$): δ 9.54 (s, 1H, disappeared on $D_2O$ shake), 9.25 (s, 1H, disappeared on $D_2O$ shake), 8.32 (d, J=3.7 Hz, 1H, reduced by 20% on $D_2O$ shake), 8.14 (d, J=3.6 Hz, 1H), 7.90 (d, J=8.8 Hz, 2H), 7.76 (d, J=8.8 Hz, 2H), 7.57 (d, J=8.6 Hz, 2H), 7.08 (d, J=8.6 Hz, 2H), 3.62 (s, 2H), 3.47-3.40 (m, 4H), 2.86-2.77 (m, 1H), 2.23-2.14 (m, 4H), 2.11 (s, 3H), 0.71-0.64 (m, 2H), 0.59-0.52 (m, 2H). ¹⁹F NMR (376 MHz, DMSO-$d_6$): δ −163.73. HPLC-MS (ESI+): m/z 504.3 [40%, (M+H)⁺], 252.8 [100%, (M+2H)²⁺]. LC-MS (ESI+): 526.2 [30%, (M+Na)⁺], 504.2 [100%, (M+H)⁺]. HRMS (ESI+): m/z calcd for $C_{27}H_{30}N_7O_2$ (M+H)⁺ 504.2518, found 504.2509.

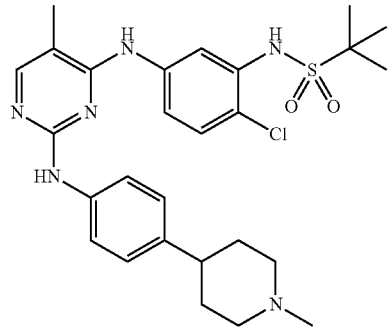

5-Methyl-N⁴-(4-chloro-[3-(1,1-dimethylethylsulfonamido)]phenyl)-N²-[4-(1-methylpiperidin-4-yl)phenyl]pyrimidine-2,4-diamine (SG3-111): This was obtained as an off-white solid (30 mg, 43%) from SG3-012 (50 mg) and SG3-079 (24 mg) using the general method x. Mp: 238° C. (dec). HPLC: 97% [$t_R$=11.0 min, 40% MeOH, 60% water (with 0.1% TFA), 20 min]. ¹H NMR (400 MHz, DMSO-$d_6$): δ 8.82 (s, 1H, disappeared on $D_2O$ shake), 8.46 (s, 1H, disappeared on $D_2O$ shake), 7.88 (s, 1H), 7.84 (d, J=2.6 Hz, 1H), 7.73 (dd, J=8.8, 2.6 Hz, 1H), 7.52 (d, J=8.6 Hz, 2H), 7.34 (d, J=8.8 Hz, 1H), 7.04 (d, J=8.6 Hz, 2H), 2.93-2.84 (brd, J=11.4 Hz, 2H), 2.41-2.30 (m, 1H), 2.22 (s, 3H), 2.08 (s, 3H), 2.07-1.97 (brt, 0.1=11.4 Hz, 2H), 1.74-1.55 (m, 4H), 1.30 (s, 9H). HPLC-MS (ESI+): m/z 543.3 [20%, (M³⁵Cl+H)⁺], 273.2 [40%, (M³⁷Cl+2H)²⁺], 272.3 [100%, (M³⁵Cl+2H)²⁺]. LC-MS (ESI+): 545.2 [40%, (M³⁷Cl+H)⁺], 543.2 [100%, (M³⁵Cl+H)⁺], 212.1 [50%, (M³⁵Cl—SO₂tBu+2H)²⁺]. HRMS (ESI+): m/z calcd for $C_{27}H_{35}ClN_6O_2S$ (M+H)⁺ 543.2304, found 543.2302.

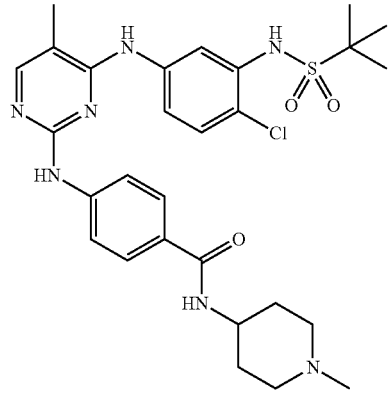

5-Methyl-N⁴-(4-chloro-[3-(1,1-dimethylethylsulfonamido)]phenyl)-N²-[4-(1-methylpiperidin-4-ylcarbamoyl)phenyl]pyrimidine-2,4-diamine (SG3-112): This was obtained as an off-white solid (30 mg, 40%) from SG3-012 (50 mg) and SG3-051 (30 mg) using the general method x. Mp: 231° C. (dec). HPLC: 97% [$t_R$=8.6 min, 40% MeOH, 60% water (with 0.1% TFA), 20 min]. ¹H NMR (400 MHz, DMSO-$d_6$): δ 9.21 (s, 1H, disappeared on $D_2O$ shake), 8.56 (s, 1H, disappeared on $D_2O$ shake), 7.95 (s, 1H), 7.94 (d, J=8.0 Hz, 1H, reduced by 30% on $D_2O$ shake), 7.81 (d, J=2.4 Hz, 1H), 7.78 (dd, J=8.7, 2.4 Hz, 1H), 7.70 (d, J=9.2 Hz, 2H), 7.68 (d, J=9.2 Hz, 2H), 7.38 (d, J=8.7 Hz, 1H), 3.77-3.64 (m, 1H), 2.82-2.74 (brd, J=11.5 Hz, 2H), 2.17 (s, 3H), 2.11 (s, 3H), 2.03-1.92 (brt, J=11.5 Hz, 2H), 1.73 (dd, J=12.6, 3.4 Hz, 2H), 1.56 (qd, J=12.6, 3.4 Hz, 2H), 1.30 (s, 9H). HPLC-MS (ESI+): m/z 586.3 [25%, (M³⁵Cl+H)⁺], 294.4 [40%, (M³⁷Cl+2H)²⁺], 293.7 [100%, (M³⁵Cl+2H)²⁺]. LC-MS (ESI+): 610.2 [400%, (M³⁷Cl+Na)⁺], 608.2 [60%, (M³⁵Cl+Na)⁺], 588.2 [40%, (M³⁷Cl+H)⁺], 586.2 [100%, (M³⁵Cl+H)⁺]. HRMS (ESI+): m/z calcd for $C_{28}H_{36}ClN_7O_3S$ (M+H)⁺ 586.2362, found 586.2358.

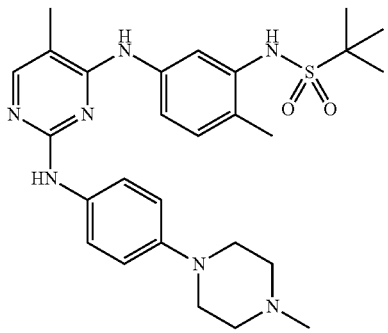

5-Methyl-N⁴-(4-methyl-[3-(1,1-dimethylethylsulfonamido)]phenyl)-N²-[4-(4-methylpiperazin-1-yl)phenyl]pyrimidine-2,4-diamine (SG3-127): This was obtained as a light yellow thin film (31 mg, 44%) from SG3-126 (50 mg) and 4-(4-methylpiperazino)aniline (26 mg) using the general method x. HPLC: 97% [$t_R$=7.4 min, 40% MeOH, 60% water (with 0.1% TFA), 20 min]. ¹H NMR (400 MHz, DMSO-d₆): δ 8.82 (s, 1H, disappeared on D₂O shake), 8.54 (s, 1H, disappeared on D₂O shake), 8.22 (s, 1H, reduced by 50% on D₂O shake), 7.80 (s, 1H), 7.64 (s, 1H), 7.56 (d, J=8.2 Hz, 1H), 7.45 (d, J=8.9 Hz, 2H), 7.09 (d, J=8.2 Hz, 1H), 6.77 (d, J=8.9 Hz, 2H), 3.06-2.94 (m, 4H), 2.46-2.40 (m, 4H), 2.32 (s, 3H), 2.20 (s, 3H), 2.06 (s, 3H), 1.29 (s, 9H). HPLC-MS (ESI+): m/z 524.3 [20%, (M+H)⁺], 262.8 [100%, (M+2H)²⁺]. LC-MS (ESI+): 524.3 [100%, (M+H)⁺], 202.6 [40%, (M-SO₂tBu+2H)²⁺]. HRMS (ESI+): m/z calcd for $C_{27}H_{37}N_7O_2S$ (M+H)⁺ 524.2802, found 524.2813.

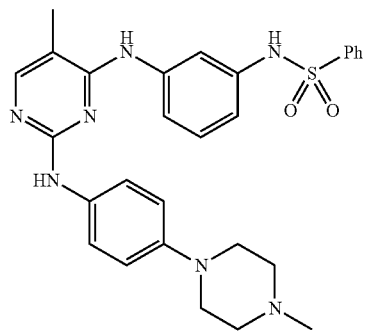

5-Methyl-N⁴-([3-phenylsulfonamido]phenyl)-N²-[4-(4-methylpiperazin-1-yl)phenyl]pyrimidine-2,4-diamine (MA4-012-1): This was obtained as a gray solid (21 mg, 30%) from MA4-006-1 (50 mg) and 4-(4-methylpiperazino)aniline (26 mg) using the general method x. Mp: 276° C. (dec). HPLC: 98% [$t_R$=7.4 min, 40% MeOH, 60% water (with 0.1% TFA), 20 min]. ¹H NMR (400 MHz, DMSO-d₆): 10.27 (s, 1H, 80% reduced on D₂O shake on D₂O shake), 8.63 (s, 1H, 80% reduced on D₂O shake on D₂O shake), 8.29 (s, 1H, disappeared on D₂O shake on D₂O shake), 7.82 (s, 1H), 7.79-7.77 (m, 2H), 7.62-7.56 (m, 1H), 7.54 (d, J=7.9 Hz, 1H), 7.48 (d, J=9.0 Hz, 2H), 7.45-7.41 (m, 3H), 7.12 (t, J=8.0 Hz, 1H), 6.80 (d, J=9.0 Hz, 2H), 6.75 (d, J=7.9 Hz, 1H), 3.10-2.91 (m, 4H), 2.58-2.51 (m, 4H, overlapped by the residual DMSO solvent signal) 2.27 (s, 3H, visible on D₂O shake), 2.06 (s, 3H)). HPLC-MS (ESI+): m/z 530.3 [20%, (M+H)⁺], 265.8 [100%, (M+2H)²⁺]. HPLC-MS (ESI-): m/z 528.3 [100%, (M-H)⁻]. LC-MS (ESI+): 552.2 [15%, (M+Na)⁺], 530.2 [100%, (M+H)⁺], 265.6 [5%, (M+2H)²⁺]. HRMS (ESI+): m/z calcd for $C_{28}H_{31}N_7O_2S$ (M+H)⁺ 530.2333, found 530.2317.

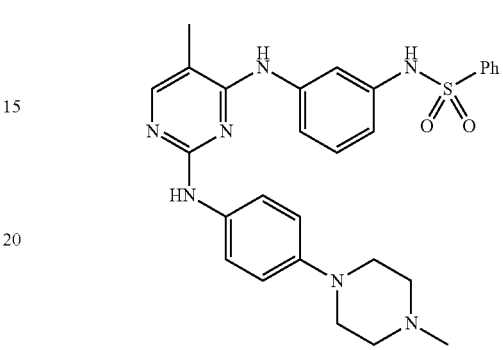

5-Methyl-N⁴-([3-phenylsulfonamido]phenyl)-N²-[4-(4-methylpiperazin-1-yl)phenyl]pyrimidine-2,4-diamine (MA4-012-1): This was obtained as a gray solid (21 mg, 30%) from MA4-006-1 (50 mg) and 4-(4-methylpiperazino)aniline (26 mg) using the general method x. Mp: 276° C. (dec). HPLC: 98% [$t_R$=7.4 min, 40% MeOH, 60% water (with 0.1% TFA), 20 min]. ¹H NMR (400 MHz, DMSO-d₆): 10.27 (s, 1H, 80% reduced on D₂O shake on D₂O shake), 8.63 (s, 1H, 80% reduced on D₂O shake on D₂O shake), 8.29 (s, 1H, disappeared on D₂O shake on D₂O shake), 7.82 (s, 1H), 7.79-7.77 (m, 2H), 7.62-7.56 (m, 1H), 7.54 (d, J=7.9 Hz, 1H), 7.48 (d, J=9.0 Hz, 2H), 7.45-7.41 (m, 3H), 7.12 (t, J=8.0 Hz, 1H), 6.80 (d, J=9.0 Hz, 2H), 6.75 (d, J=7.9 Hz, 1H), 3.10-2.91 (m, 4H), 2.58-2.51 (m, 4H, overlapped by the residual DMSO solvent signal) 2.27 (s, 3H, visible on D₂O shake), 2.06 (s, 3H)). HPLC-MS (ESI+): m/z 530.3 [20%, (M+H)⁺], 265.8 [100%, (M+2H)²⁺]. HPLC-MS (ESI-): m/z 528.3 [100%, (M-H)⁻]. LC-MS (ESI+): 552.2 [15%, (M+Na)⁺], 530.2 [100%, (M+H)⁺], 265.6 [5%, (M+2H)²⁺]. HRMS (ESI+): m/z calcd for $C_{28}H_{31}N_7O_2S$ (M+H)⁺ 530.2333, found 530.2317.

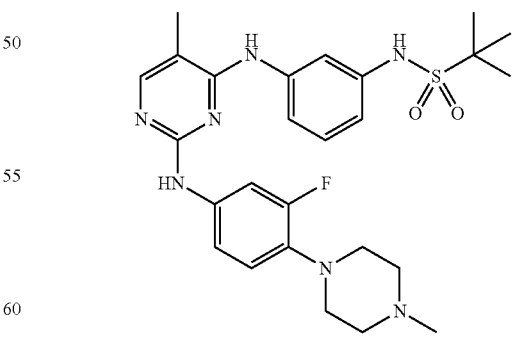

5-Methyl-N⁴-[3-(1,1-dimethylethyl)sulfonamidophenyl]-N²-[4-(4-methylpiperazin-1-0)-3-fluorophenyl]pyrimidine-2,4-diamine (MA4-022-1): This was obtained as a grayish white solid (31 mg, 42%) from SG3-053 (50 mg) and MA4-020 (30 mg) using the general method x. Mp: 233° C.

(dec). HPLC: 99% [$t_R$=10.0 min, 40% MeOH, 60% water (with 0.1% TFA), 20 min]. $^{19}$F NMR (376 MHz, DMSO-$d_6$): δ −122.41 (dd, J=15.5, 10.1 Hz). $^1$H NMR (400 MHz, DMSO-$d_6$): δ 9.61 (s, 1H, disappeared on D$_2$O shake), 8.93 (s, 1H, 80% reduced on D$_2$O shake), 8.41 (s, 1H, 80% reduced on D$_2$O shake), 7.88 (s, 1H), 7.63 (dd, J=15.6, 2.1 Hz, 1H), 7.50-45 (m, 2H), 7.47 (d, J=2.0 Hz, 1H), 7.27-7.19 (m, 2H), 7.03-6.96 (m, 1H), 6.85 (t, J=9.4 Hz, 1H), 2.94-2.85 (m, 4H), 2.47-2.41 (m, 4H), 2.21 (s, 3H), 2.09 (s, 3H), 1.27 (s, 9H). HPLC-MS (ESI+): m/z 528.3 [40%, (M+H)$^+$], m/z 264.8 [100%, (M+2H)$^{2+}$]. LC-MS (ESI+): 528.2 [100%, (M+H)$^+$], 204.6 [30%, (M+2H-SO$_2$$^t$Bu)$^{2+}$]. HRMS (ESI+): m/z calcd for C$_{26}$H$_{34}$FN$_7$O$_2$S (M+H)$^+$ 528.2552, found 528.2560.

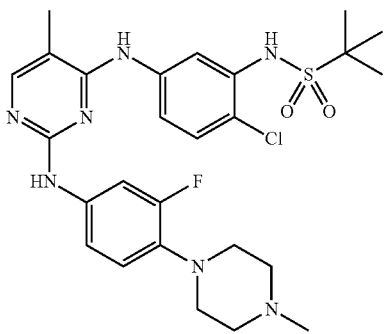

5-Methyl-N$^4$-(4-chloro-[3-(1,1-dimethylethylsulfonamido)]phenyl)-N$^2$-[4-(4-methylpiperazin-1-0)-3-fluorophenyl]pyrimidine-2,4-diamine (MA4-022-2): This was obtained as a white solid (35 mg, 49%) from SG3-012 (50 mg) and MA4-020 (27 mg) using the general method x. Mp: 206° C. (dec). HPLC: 97% [$t_R$=10.9 min, 40% MeOH, 60% water (with 0.1% TFA), 20 min]. $^{19}$F NMR (376 MHz, DMSO-$d_6$): δ −122.56 (dd, J=14.9, 10.3 Hz). $^1$H NMR (400 MHz, DMSO-$d_6$): δ 9.37 (s, 1H, disappeared on D$_2$O shake), 8.99 (s, 1H, 90% reduced on D$_2$O shake), 8.53 (s, 1H, 80% reduced on D$_2$O shake), 7.91 (s, 1H), 7.80-7.76 (m, 2H), 7.62 (d, J=15.9 Hz, 1H), 7.36 (d, J=9.3 Hz, 1H), 7.24 (dd, J=8.5, 2.1 Hz, 1H), 6.89 (t, J=9.3 Hz, 1H), 2.95-2.86 (m, 4H), 2.46-2.40 (s, 4H, partially overlapped by residual DMSO solvent signal), 2.22 (s, 3H), 2.10 (s, 3H), 1.31 (s, 9H). HPLC-MS (ESI+): m/z 562.3 [40%, (M+H)$^+$], m/z 282.7 [100%, (M$^{37}$Cl+2H)$^{2+}$], m/z 281.7 [50%, (M$^{35}$Cl+2H)$^{2+}$]. LC-MS (ESI+): m/z 564.3 [40%, (M$^{37}$Cl+H)$^+$], 562.3 [100%, (M$^{35}$Cl+H)$^+$]. HRMS (ESI+): m/z calcd for C$_{26}$H$_{33}$FN$_7$O$_2$S (M+H)$^+$ 562.2162, found 562.2171.

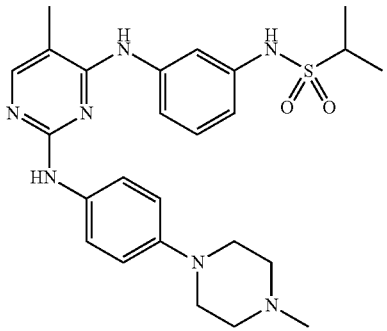

5-Methyl-N$^4$-(3-[(1-methylethyl)sulfonamido]phenyl)-N$^2$-[4-(4-methylpiperazin-1-yl)phenyl]pyrimidine-2,4-diamine (MA4-026): This was obtained as a green solid (32 mg, 44%) from MA4-008 (50 mg) and 4-(4-methylpiperazino)aniline (28 mg) using the general method x. Mp: 212° C. (dec). HPLC: 98% [$t_R$=6.6 min, 40% MeOH, 60% water (with 0.1% TFA), 20 min]. $^1$H NMR (400 MHz, DMSO-$d_6$): δ 9.71 (s, 1H, disappeared on D$_2$O shake), 8.59 (s, 1H, disappeared on D$_2$O shake), 8.32 (s, 1H, disappeared on D$_2$O shake), 7.84 (s, 1H), 7.52 (d, J=8.6 Hz, 1H), 7.50 (brs, 1H), 7.48 (d, J=9.1 Hz, 2H), 7.23 (t, J=8.6 Hz, 1H), 6.91 (brd, J=8.6 Hz, 1H), 6.79 (d, J=9.1 Hz, 2H), 3.27 (septet, J=6.8 Hz, 1H), 3.04-2.97 (m, 4H), 2.47-2.40 (m, 4H), 2.21 (s, 3H), 2.08 (s, 3H), 1.23 (d, J=6.8 Hz, 6H). HPLC-MS (ESI+): m/z 496.3 [35%, (M+H)$^+$], 248.7 [100%, (M+2H)$^{2+}$]. LC-MS (ESI+): 496.2 [100%, (M+H)$^+$]. HRMS (ESI+): m/z calcd for C$_{25}$H$_{33}$N$_7$O$_2$S (M+H)$^+$ 496.2489, found 496.2480.

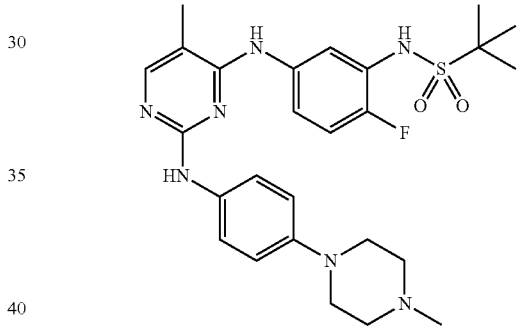

5-Methyl-N$^4$-(4-fluoro-3-[(1,1-dimethylethyl)sulfonamido]phenyl)-N$^2$-[4-(4-methylpiperazin-1-yl)phenyl]pyrimidine-2,4-diamine (MA4-034): This was obtained as a white solid (29 mg, 42%) from MA4-025 (50 mg) and 4-(4-methylpiperazino)aniline (26 mg) using the general method x. Mp: 240° C. (dec). HPLC: 99% [$t_R$=9.5 min, 40% MeOH, 60% water (with 0.1% TFA), 20 min]. $^{19}$F NMR (376 MHz, DMSO-$d_6$): δ −129.73 (s). 9.51 (s, 1H, disappeared on D$_2$O shake), 8.64 (s, 1H, disappeared on D$_2$O shake), 8.33 (s, 1H, disappeared on D$_2$O shake), 7.84 (d, J=0.7 Hz, 1H), 7.70 (dd, J=7.3, 2.6 Hz, 1H), 7.68-7.63 (m, 1H), 7.45 (d, J=9.0 Hz, 2H), 7.17 (dd, J=10.0, 9.1 Hz, 1H), 6.80 (d, J=9.0 Hz, 2H), 3.08-2.97 (m, 4H), 2.47-2.43 (m, 4H), 2.22 (s, 3H), 2.07 (s, 3H), 1.29 (s, 9H). HPLC-MS (ESI+): m/z 528.3 [20%, (M+H)$^+$], 264.7 [100%, (M+2H)$^{2+}$]. LC-MS (ESI+): 528.3 [100%, (M+H)$^+$], 204.6 [50%, (M+2H-SO$_2$$^t$Bu)$^{2+}$]. HRMS (ESI+): m/z calcd for C$_{26}$H$_{34}$N$_7$FO$_2$S (M+H)$^+$ 528.2552, found 528.2532.

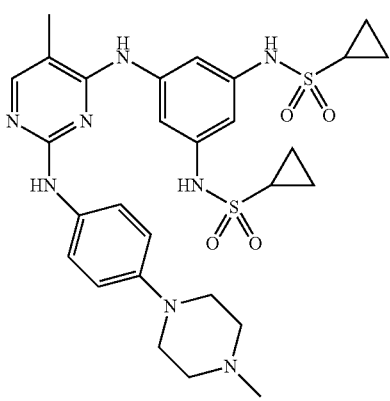

5-Methyl-N$^4$-[3,5-bis-(cyclopropylsulfonamido)phenyl]-N$^2$-[4-(4-methylpiperazin-1-yl)phenyl]pyrimidine-2,4-diamine (MA4-084): This was obtained as a white solid (26 mg, 39%) from MA4-056 (50 mg) and 4-(4-methylpiperazino)aniline (21 mg) using the general method x. Mp: 265° C. (dec). HPLC: 100% [$t_R$=16.8 min, gradient MeOH-water (with 0.1% TFA), 5-95% over 35 min.]. $^1$H NMR (400 MHz, DMSO-d$_6$): δ 9.75 (s, 2H, disappeared on D$_2$O shake), 8.45 (s, 1H, disappeared on D$_2$O shake), 8.42 (s, 1H, disappeared on D$_2$O shake), 7.86 (s, 1H), 7.47 (d, J=9.1 Hz, 2H), 7.29 (brs, 2H), 6.95 (t, J=1.9 Hz, 1H), 6.81 (d, J=9.1 Hz, 2H), 3.02-2.95 (m, 4H), 2.61 (ddd, J=12.8, 7.9, 4.8 Hz, 2H), 2.47-2.41 (m, 4H, overlapped by residual DMSO solvent signal), 2.24 (s, 3H), 2.07 (s, 3H), 1.03-0.96 (m, 4H), 0.96-0.88 (m, 4H). HPLC-MS (ESI+): m/z 613.3 [25%, (M+H)$^+$], 307.2 [100%, (M+2H)$^{2+}$]. LC-MS (ESI+): 635.2 [20%, (M+Na)$^+$], 613.2 [100%, (M+H)$^+$], 307.2 [20%, (M+2H)$^{2+}$]. HRMS (ESI+): m/z calcd for C$_{28}$H$_{36}$N$_8$O$_4$S$_2$ (M+H)$^+$ 613.2374, found 613.2356.

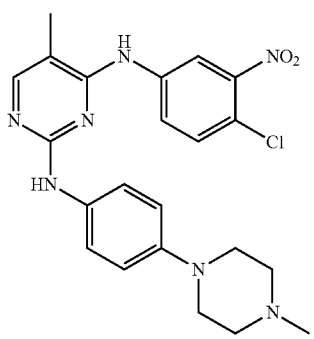

5-Methyl-N$^4$-(4-chloro-3-nitrophenyl)-N$^2$-[4-(4-methylpiperazin-1-yl)phenyl]pyrimidine-2,4-diamine (SG3-155): A mixture of SG3-149 (450 mg, 1.50 mmol), 4-(4-methylpiperazino)aniline (288 mg, 1.50 mmol), 20 drops of 4 M HCl, and EtOH (9 mL) was heated in a microwave reactor at 160° C. for 15 minutes. The reaction mixture was diluted with EtOAc (40 mL). The precipitates were filtered, washed with EtOAc (5 mL, saturated NaHCO$_3$ (80 mL), and hexanes (80 mL) then dried under high vacuum to provide the title compound as a green solid (569 mg, 83%). Mp: >300° C. HPLC: 99% [$t_R$=7.0 min, 40% MeOH, 60% water (with 0.1% TFA), 20 min]. $^1$H NMR (400 MHz, DMSO-d$_6$): δ 8.86 (s, 1H, disappeared on D$_2$O shake), 8.68 (s, 1H, disappeared on D$_2$O shake), 8.53 (d, J=2.3 Hz, 1H), 8.11-8.03 (brd, J=8.9 Hz, 1H), 7.92 (s, 1H), 7.61 (d, J=8.9 Hz, 1H), 7.38 (d, J=8.9 Hz, 2H), 6.79 (d, J=8.9 Hz, 2H), 3.05-3.00 (m, 4H), 2.46-2.41 (m, 4H), 2.20 (s, 3H), 2.09 (s, 3H). HPLC-MS (ESI+): m/z 454.3 [20%, (M$^{35}$Cl+H)$^+$], 228.7 [40%, (M$^{37}$Cl+2H)$^{2+}$], 227.7 [100%, (M$^{35}$Cl+2H)$^{2+}$]. LC-MS (ESI+): 456.2 [300%, (M$^{35}$Cl+H)$^+$], 454.2 [100%, (M$^{35}$Cl+H)$^+$]. HRMS (ESI+): m/z calcd for C$_{22}$H$_{24}$ClN$_7$O$_2$ (M+H)$^+$ 454.1753, found 454.1735.

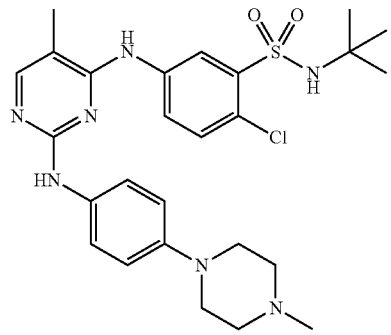

5-Methyl-N$^4$-(4-chloro-3-[N-(1,1-dimethylethyl)sulfamoyl]phenyl)-N$^2$-[4-(4-methylpiperazin-1-yl)phenyl]pyrimidine-2,4-diamine (SG3-158): This was obtained as a light brown solid (37 mg, 52%) from SG3-145 (50 mg) and 4-(4-methylpiperazino)aniline (25 mg) using the general method x. Mp: 265° C. (dec). HPLC: 97% [$t_R$=7.8 min, 40% MeOH, 60% water (with 0.1% TFA), 20 min]. $^1$H NMR (400 MHz, DMSO-d$_6$): δ 8.75 (s, 1H, disappeared on D$_2$O shake), 8.61 (s, 1H, disappeared on D$_2$O shake), 8.23 (d, J=2.5 Hz, 1H, coupling visible upon D$_2$O shake), 8.22 (brd, J=8.6 Hz, 1H, coupling visible upon D$_2$O shake), 7.88 (s, 1H), 7.65 (s, 1H, disappeared on D$_2$O shake), 7.45 (d, J=8.6 Hz, 1H), 7.43 (d, J=9.0 Hz, 2H), 6.82 (d, J=9.0 Hz, 2H), 3.05-2.99 (m, 4H), 2.46-2.40 (s, 4H), 2.20 (s, 3H), 2.08 (s, 3H), 1.12 (s, 9H). HPLC-MS (ESI+): m/z 544.3 [20%, (M$^{35}$Cl+H)$^+$], 273.8 [50%, (M$^{37}$Cl+2H)$^{2+}$], 272.8 [100%, (M$^{35}$Cl+2H)$^{2+}$]. LC-MS (ESI+): 546.2 [100%, (M$^{37}$Cl+H)+], 544.2 [100%, (M$^{35}$Cl+H)$^+$], 244.6 [20%, (M+2H-tBu)$^{2+}$]. HRMS (ESI+): m/z calcd for C$_{26}$H$_{34}$ClN$_7$O$_2$S (M+H)$^+$ 544.2256, found 544.2256.

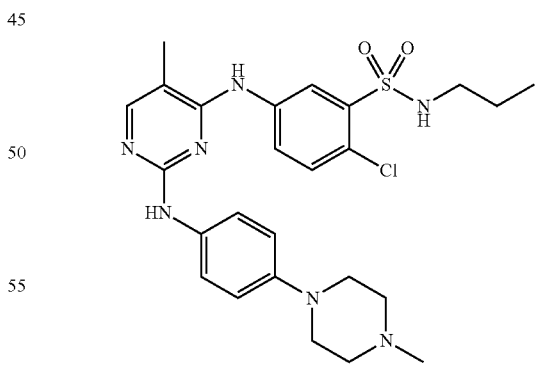

5-Methyl-N$^4$-[4-chloro-(3-propanesulfonamido)phenyl]-N$^2$-[4-(4-methylpiperazin-1-yl)phenyl]pyrimidine-2,4-diamine (SG3-170): To a solution of SG3-156 (100 mg, 0.236 mmol) and triethylamine (0.098 mL, 0.708 mmol) in pyridine (0.4 mL) was added propane sulfonyl chloride (0.077 mL, 0.650 mmoL). The crude mixture was purified via column chromatography using DCM/MeOH (0-10%) to provide a mixture of the title compound and bis-sulfonylation product (57 mg). The mixture was dissolved in THF/MeOH (4:1, 1.2 mL) and treated with 1 M NaOH (0.6 mL). The solution was stirred at 50° C. for 2 h. The crude mixture was purified via preparative TLC using DCM/MeOH 15% and afforded the title product as a light yellow solid (8 mg, 6%). Mp: 208° C. (dec). HPLC: 96% [$t_R$=6.1 min, 40% MeOH, 60% water (with 0.1% TFA), 20 min]. $^1$H NMR (400 MHz, DMSO-$d_6$): δ 9.43 (brs, 1H, disappeared on D$_2$O shake), 8.66 (s, 1H, disappeared on D$_2$O shake), 8.40 (s, 1H, disappeared on D$_2$O shake), 7.85 (s, 1H), 7.80 (dd, J=8.8, 2.4 Hz, 1H), 7.68 (d, J=2.4 Hz, 1H), 7.43 (d, J=9.0 Hz, 2H), 7.36 (d, J=8.8 Hz, 1H), 6.80 (d, J=9.0 Hz, 2H), 3.10-2.97 (m, 6H), 2.47-2.42 (m, 4H, overlapped by residual DMSO solvent signal), 2.21 (s, 3H), 2.07 (s, 3H), 1.72 (sextet, J=7.5 Hz, 2H), 0.92 (t, J=7.5 Hz, 3H). HPLC-MS (ESI+): m/z 530.3 [20%, (M$^{35}$Cl+H)$^+$], 266.7 [40%, (M$^{37}$Cl+2H)$^{2+}$], 265.8 [100%, (M$^{35}$Cl+2H)$^{2+}$]. LC-MS (ESI+): 532.2 [35%, (M$^{37}$Cl+H)$^+$]. 530.2 [100%, (M$^{35}$Cl+H)$^+$]. HRMS (ESI+): m/z calcd for C$_{25}$H$_{32}$ClN$_7$O$_2$S (M+H)*530.2099, found 530.2081.

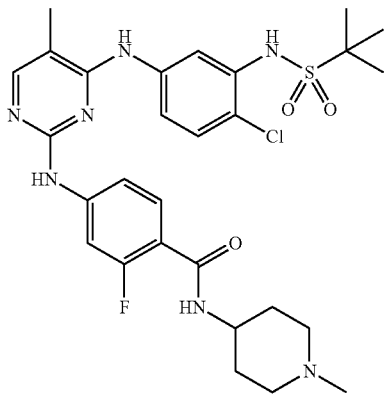

5-Methyl-N$^4$-(4-chloro-[3-(1,1-dimethylethylsulfonamido)]phenyl)-N$^2$-[3-fluoro-4-(1-methylpiperidin-4-ylcarbamoyl)phenyl]pyrimidine-2,4-diamine (SG3-179): This was obtained as an off-white solid (20 mg, 26%) from SG3-012B3 (50 mg) and SG3-153 (32 mg) using the general method x. The resulting mixture was further purified via preparative TLC using DCM/MeOH 15% and afforded the title product as an off-white solid (20 mg, 26%). Mp: 252° C. (dec). HPLC: 98% [$t_R$=9.7 min, 40% MeOH, 60% water (with 0.1% TFA), 20 min]. $^1$H NMR (400 MHz, DMSO-$d_6$): δ 9.44 (s, 1H, disappeared on D$_2$O shake), 8.63 (s, 1H, disappeared on D$_2$O shake), 7.97 (s, 1H), 7.82-7.71 (m, 4H), 7.41 (t, J=8.6 Hz, 2H), 7.39 (d, J=8.8 Hz, 2H), 7.32 (dd, J=8.6, 2.0 Hz, 1H), 3.77-3.65 (brs, 1H), 2.85-2.73 (brs, 2H), 2.22 (s, 3H), 2.15-2.07 (brs, 2H), 2.11 (s, 3H), 1.82-1.72 (brd, J=12.5 Hz, 2H), 1.61-1.47 (m, 2H), 1.30 (s, 9H). $^{19}$F NMR (376 MHz, DMSO-$d_6$): 45-112.33. HPLC-MS (ESI+): m/z 604.3 [25%, (M$^{35}$Cl+H)$^+$], 303.3 [50%, (M$^{37}$Cl+2H)$^{2+}$], 302.8 [100%, (M$^{35}$Cl+2H)$^{2+}$]. LC-MS (ESI+): 606.2 [40%, (M$^{37}$Cl+H)$^+$]. 604.2 [100%, (M$^{35}$Cl+H)$^+$]. HRMS (ESI+): m/z calcd for C$_{28}$H$_{35}$ClFN$_7$O$_3$S (M+H)$^+$ 604.2267, found 604.2251.

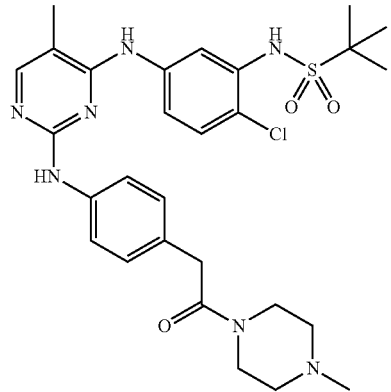 [SMILES: Cc1cnc(Nc2ccc(CC(=O)N3CCN(C)CC3)cc2)nc1Nc1ccc(Cl)c(NS(=O)(=O)C(C)(C)C)c1]

5-Methyl-N$^4$-(4-chloro-[3-(1,1-dimethylethylsulfonamido)]phenyl)-N$^2$-(4-[2-(4-methylpiperazin-1-yl)-2-oxoethyl]phenyl)pyrimidine-2,4-diamine (SG3-180): This was obtained as an off-white solid (25 mg, 33%) from SG3-012B3 (50 mg) and SG3-144 (30 mg) using the general method x. Mp: 246° C. (dec). HPLC: 95% [$t_R$=9.6 min, 40% MeOH, 60% water (with 0.1% TFA), 20 min]. $^1$H NMR (400 MHz, DMSO-$d_6$): δ 9.27 (s, 1H, disappeared on D$_2$O shake), 8.82 (s, 1H, disappeared on D$_2$O shake), 8.45 (s, 1H, disappeared on D$_2$O shake), 7.88 (s, 1H), 7.80 (s, 1H), 7.77 (d, J=8.8 Hz, 1H), 7.52 (d, J=8.4 Hz, 2H), 7.31 (d, J=8.8 Hz, 1H), 7.01 (d, J=8.4 Hz, 2H), 3.57 (s, 2H), 3.46-3.38 (m, 4H), 2.22-2.13 (m, 4H), 2.10 (s, 3H), 2.07 (s, 3H), 1.29 (s, 9H). HPLC-MS (ESI+): m/z 586.3 [25%, (M$^{35}$Cl+H)$^+$], 294.4 [40%, (M$^{37}$Cl+2H)$^{2+}$], 293.7 [100%, (M$^{35}$Cl+2H)$^{2+}$]. LC-MS (ESI+): 610.2 [35%, (M$^{37}$Cl+Na)$^+$], 608.2 [100%, (M$^{35}$Cl+Na)$^+$], 588.2 [35%, (M$^{37}$Cl+H)$^+$], 586.2 [90%, (M$^{35}$Cl+H)$^+$]. HRMS (ESI+): m/z calcd for C$_{28}$H$_{36}$ClN$_7$O$_3$S (M+H)$^+$ 586.2362, found 586.2356.

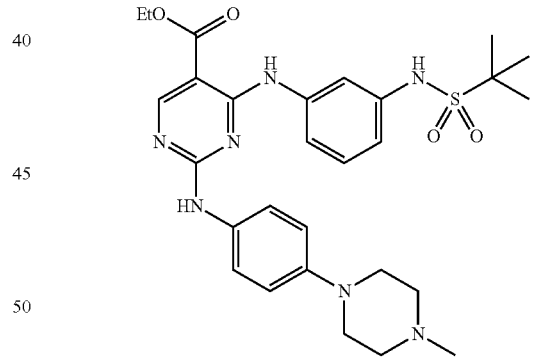

5-Ethoxycarbonyl-N$^4$-(3-[(1,1-dimethylethyl)sulfonamido]phenyl)-N$^2$-[4-(4-methylpiperazin-1-yl)phenyl]pyrimidine-2,4-diamine (MA4-062): This was obtained as a white solid (58 mg, 42%) from MA4-048 (100 mg) and 4-(4-methylpiperazino)aniline (46 mg) using the general method x. Mp: 232° C. (dec). HPLC: 99% [$t_R$=7.3 min, 55% MeOH, 45% water (with 0.1% TFA), 20 min]. $^1$H NMR at 70° C. 10.09 (s, 1H, disappeared on D$_2$O shake on D$_2$O shake), 9.38 (s, 2H, disappeared on D$_2$O shake on D$_2$O shake), 8.69 (s, 1H), 7.61 (d, J=7.5 Hz, 1H), 7.46 (d, J=9.0 Hz, 2H), 7.34 (brs, 1H, disappeared on D$_2$O shake on D$_2$O shake), 7.23 (t, J=8.1 Hz, 1H), 7.09 (d, J=8.6 Hz, 1H), 6.86 (d, 0.1=9.1 Hz, 2H), 4.34 (q, J=7.0 Hz, 2H), 3.14-3.09 (m, 4H, overlapped with residual water signals), 2.57-2.53 (m, 3H, overlapped by residual DMSO solvent signal), 2.28 (s, 3H), 1.35 (t, J=7.0 Hz, 3H), 1.31 (s, 9H). HPLC-MS (ESI+): m/z 568.3 [80%, (M+H)$^+$], 284.8 [100%, (M+2H)$^{2+}$]. LC-MS (ESI+): 568.3 [100%, (M+H)$^+$]. HRMS (ESI+): m/z calcd for $C_{28}H_{37}N_7O_4S$ (M+H)$^+$ 568.2701, found 568.2698.

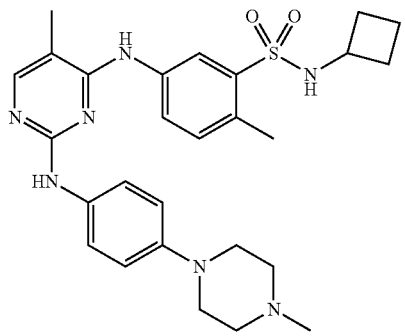 [SMILES: Cc1ccc(Nc2nc(Nc3ccc(N4CCN(C)CC4)cc3)ncc2C)cc1S(=O)(=O)NC1CCC1]

5-Methyl-N$^4$-(4-methyl-[3-(N-cyclobutyl)sulfamoyl]phenyl)-N$^2$-[4-(4-methylpiperazin yl)phenyl]pyrimidine-2,4-diamine (MA4-088): This was obtained as a white solid (36 mg, 51%) from MA4-082 (50 mg) and 4-(4-methylpiperazino)aniline (26 mg) using the general method x. Mp: 246° C. (dec). HPLC: 100% [t$_R$=7.4 min, 40% MeOH, 60% water (with 0.1% TFA), 20 min]. $^1$H NMR (400 MHz, DMSO-d$_6$): δ 8.71 (s, 1H, 85% reduced on D$_2$O shake), 8.47 (s, 1H, 85% reduced on D$_2$O shake on D$_2$O shake), 8.03 (d, J=7.3 Hz, 1H, disappeared on D$_2$O shake), 8.02 (s, 1H), 7.98 (d, J=8.6 Hz, 1H), 7.85 (d, J=0.7 Hz, 1H), 7.45 (d, J=9.0 Hz, 2H), 7.28 (d, J=8.6 Hz, 1H), 6.79 (d, J=9.0 Hz, 2H), 3.55 (pentet, J=7.9 Hz, 1H), 3.08-2.97 (m, 4H), 2.55 (s, 3H), 2.47-2.39 (m, 4H), 2.22 (s, 3H), 2.09 (s, 3H), 1.92-1.76 (m, 4H), 1.49-1.32 (m, 2H). HPLC-MS (ESI+): m/z 522.3 [38%, (M+H)$^+$], 261.7 [100%, (M+2H)$^{2+}$]. LC-MS (ESI+): 522.3 [100%, (M+H)$^+$], 261.6 [30%, (M+2H)$^{2+}$]. HRMS (ESI+): m/z calcd for $C_{27}H_{35}N_7O_2S$ (M+H)$^+$ 522.2646, found 522.2643.

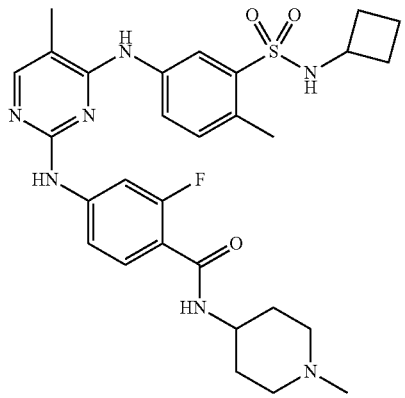 [SMILES: Cc1ccc(Nc2nc(Nc3ccc(C(=O)NC4CCN(C)CC4)c(F)c3)ncc2C)cc1S(=O)(=O)NC1CCC1]

5-Methyl-N$^4$-(4-methyl-[3-(N-cyclobutyl)sulfamoyl]phenyl)-N$^2$-[3-fluoro-4-(1-methylpiperidin-4-ylcarbamoyl)phenyl]pyrimidine-2,4-diamine (MA4-089): This was obtained as a white solid (11 mg, 14%) from MA4-082 (50 mg) and SG3-153 (34 mg) using the general method x. However, reverse phase chromatography (using $C_{18}$ as the stationary phase and gradient of 5-95% methanol-water as eluent, 35 min) was required to purify the product. Mp: 235° C. (dec). HPLC: 98% [t$_R$=11.7 min, 37.5% MeOH, 62.5% water (with 0.1% TFA), 20 min]. $^1$H NMR (400 MHz, DMSO-d$_6$): δ 9.47 (s, 1H, disappeared on D$_2$O shake), 8.67 (s, 1H, disappeared on D$_2$O shake), 7.96 (d, 1H, J=2.3 Hz, in D$_2$O shake), 7.94 (d, J=2.3 Hz, 1H, in D$_2$O shake), 7.91 (dd, J=8.2, 2.3 Hz, 1H, in D$_2$O shake), 7.75 (m, 1H, in D$_2$O shake), 7.69 (brs, disappeared on D$_2$O shake), 7.41 (t, J=8.6 Hz, 1H), 7.35 (d, 0.1=8.2 Hz, 1H, in D$_2$O shake), 7.32 (dd, J=8.6, 1.9 Hz, 1H, in D$_2$O shake), 3.78-3.69 (m, 1H), 3.55 (sextet, J=8.1 Hz, 1H), 2.70 (brd, J=11.0 Hz, 2H), 2.15 (s, 3H), 2.13 (s, 3H), 1.96 (t, J=11.0 Hz, 3H), 1.90-1.74 (m, 7H), 1.57-1.35 (m, 6H). HPLC-MS (ESI+): m/z 582.4 [20%, (M+H)$^+$], 291.7 [100%, (M+2H)$^{2+}$]. LC-MS (ESI+): 604.3 [30%, (M+Na)$^+$], 582.3 [100%, (M+H)$^+$], 291.6 [15%, (M+2H)$^{2+}$]. HRMS (ESI+): m/z calcd for $C_{29}H_{36}FN_7O_3S$ (M+H)+582.2657, found 582.2654.

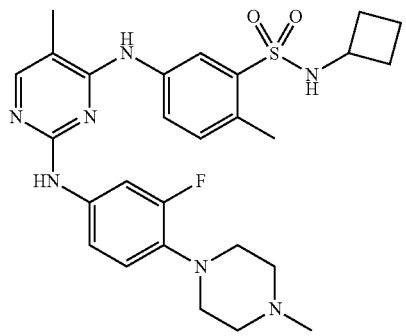 [SMILES: Cc1ccc(Nc2nc(Nc3ccc(N4CCN(C)CC4)c(F)c3)ncc2C)cc1S(=O)(=O)NC1CCC1]

5-Methyl-N$^4$-(4-methyl-[3-(N-cyclobutyl)sulfamoyl]phenyl)-N$^2$-[4-(4-methylpiperazin-1-yl)-3-fluorophenyl]pyrimidine-2,4-diamine (MA4-090): This was obtained as a white solid (46 mg, 63%) from MA4-082 (50 mg) and MA4-020 (28 mg) using the general method x. Mp: 245° C. (dec). HPLC: 99% [t$_R$=8.8 min, 40% MeOH, 60% water (with 0.1% TFA), 20 min]. $^1$H NMR (400 MHz, DMSO-d$_6$): S. HPLC-MS (ESI+): m/z 540.3 [35%, (M+H)$^+$], 279.8 [100%, (M+2H)$^{2+}$]. $^{19}$F NMR (376 MHz, DMSO-d$_6$) δ −122.39 (d, J=11.1 Hz). $^1$H NMR (400 MHz, DMSO-d$_6$): δ 8.99 (s, 1H, disappeared on D$_2$O shake), 8.55 (s, 1H, disappeared on D$_2$O shake), 8.02-7.92 (m, 3H, 1H disappeared on D$_2$O shake), 7.89 (s, 1H), 7.57 (dd, J=15.7, 2.1 Hz, 1H), 7.29 (d, J=8.3 Hz, 1H), 7.23 (dd, J=8.7, 1.9 Hz, 1H), 6.87 (t, J=9.5 Hz, 1H), 3.6-3.46 (sextet, J=8.0 Hz, 1H), 2.92-2.85 (m, 4H), 2.54 (s, 3H), 2.46-2.39 (m, 4H, overlapped by the residual DMSO solvent signal), 2.19 (s, 3H), 2.09 (s, 3H), 1.88-1.74 (m, 4H), 1.47-1.30 (m, 2H). HPLC-MS (ESI+): m/z 540.3 [38%, (M+H)$^+$], 270.8 [100%, (M+2H)$^{2+}$]. LC-MS (ESI+): 540.3 [100%, (M+H)±], 270.6 [25%, (M+2H)$^{2+}$]. HRMS (ESI+): m/z calcd for $C_{27}H_{34}N_7O_2S$ (M+H)$^+$ 540.2552, found 540.2552.

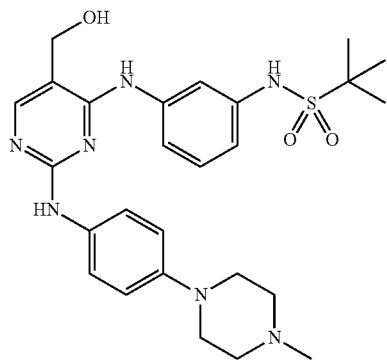 [SMILES: CN1CCN(c2ccc(Nc3ncc(CO)c(Nc4cccc(NS(=O)(=O)C(C)(C)C)c4)n3)cc2)CC1]

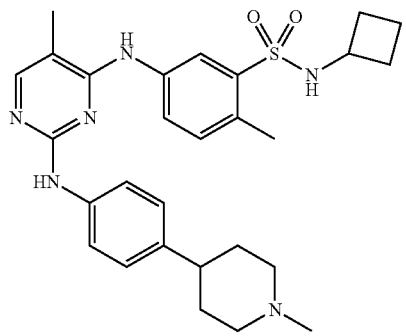 [SMILES: Cc1ccc(Nc2nc(Nc3ccc(C4CCN(C)CC4)cc3)ncc2C)cc1S(=O)(=O)NC1CCC1]

5-Hydroxymethyl-$N^4$-(3-[(1,1-dimethylethyl)sulfonamido]phenyl)-$N^2$-[4-(4-methylpiperazin-1-yl)phenyl]pyrimidine-2,4-diamine (MA4-094): The ethyl ester MA4-062 (0.047 g) and dry THF (2 mL) were added to an oven dried 10 mL round bottom flask, MA4-062 under an atmosphere of argon. The mixture was cooled to ice-water temperature and lithium aluminum hydride (0.331 mL of a 1M solution in THF) was slowly added. The mixture was stirred for 1 h, and additional lithium aluminum hydride (0.497 mL of a 1M solution in THF) was added after which the flask was warmed to room temperature and stirred for a further 1.5 h. At this stage TLC and HPLC-MS analysis showed only traces of remaining starting material so the reaction mixture was cooled to −16° C. (using NaCl in ice-water) and carefully quenched with cold water (1 mL). Subsequently, the reaction mixture was basified using NaOH (2 mL of 10% aq. solution) and filtered. The resulting residue was partitioned between ethyl acetate (50 mL) and water (50 mL). The organic layer was evaporated under reduced pressure and the resulting residue purified by chromatography ($SiO_2$) eluting with using ethyl acetate and hexane to provide the title compound as a white solid (21 mg, 49%). Mp: 222° C. (dec). HPLC: 99% [$t_R$=7.9 min, 35% MeOH, 65% water (with 0.1% TFA), 20 min]. $^1$H NMR (400 MHz, DMSO-$d_6$): 9.59 (s, 1H, disappeared on $D_2O$ shake on $D_2O$ shake), 8.76 (s, 1H, disappeared on $D_2O$ shake on $D_2O$ shake), 8.35 (s, 1H, disappeared on $D_2O$ shake on $D_2O$ shake), 7.92 (s, 1H), 7.60 (d, J=8.3 Hz, 1H), 7.49 (d, J=9.0 Hz, 2H), 7.43 (s, 1H), 7.21 (t, J=8.1 Hz, 1H), 6.98 (dd, J=8.1, 2.0 Hz, 1H), 6.82 (d, J=9.0 Hz, 2H), 5.23 (t, J=5.4 Hz, 1H, disappeared on $D_2O$ shake on $D_2O$ shake), 4.46 (d, J=5.4 Hz, 2H), 3.10-2.98 (m, 4H), 2.46-2.40 (m, 4H), 2.22 (s, 3H), 1.28 (s, 9H). HPLC-MS (ESI+): m/z 526.3 [20%, (M+H)$^+$], 263.8 [100%, (M+2H)$^{2+}$]. LC-MS (ESI+): 548.2 [10%, (M+Na)$^+$], 526.3 [100%, (M+H)$^+$], 203.2 [10%, (M+2H-$SO_2$Bu)$^{2+}$].. HRMS (ESI+): m/z calcd for $C_{28}H_{35}N_7O_3S$ (M+H)$^+$ 526.2595, found 526.2585.

5-Methyl-$N^4$-(4-methyl-[3-(N-cyclobutyl)sulfamoyl]phenyl)-$N^2$-[4-(1-methylpiperidin-4-yl)phenyl]pyrimidine-2,4-diamine (MA4-100): This was obtained as a white solid (29 mg, 41%) from MA4-082 (50 mg) and SG3-079 (26 mg) using the general method x. Mp: 219° C. (dec). HPLC: 100% [$t_R$=7.1 min, 40% MeOH, 60% water (with 0.1% TFA), 20 min]. $^1$H NMR (400 MHz, DMSO-$d_6$): 8.90 (s, 1H, 85% reduced on $D_2O$ shake), 8.53 (s, 1H, 85% reduced on $D_2O$ shake on $D_2O$ shake), 8.05-7.96 (m, 3H, 1H disappeared on $D_2O$ shake), 7.89 (s, 1H), 7.54 (d, J=8.6 Hz, 2H), 7.30 (d, J=7.8 Hz, 1H), 7.03 (d, 0.1=8.6 Hz, 2H), 3.6-3.49 (m, 2H), 2.99 (brd, J=9.1 Hz, 2H), 2.56 (s, 3H), 2.47-2.36 (m, 1H), 2.32 (s, 3H), 2.21-2.15 (m, 1H), 2.11 (s, 3H), 1.93-1.59 (m, 8H), 1.49-1.37 (m, 2H). HPLC-MS (ESI+): m/z 521.4 [20%, (M+H)$^+$], 261.3 [100%, (M+2H)$^{2+}$]. LC-MS (ESI+): 521.3 [100%, (M+H)$^+$], 261.1 [25%, (M+2H)$^{2+}$]. HRMS (ESI+): m/z calcd for $C_{28}H_{36}N_6O_2S$ (M+H)$^+$ 521.2693, found 521.2690

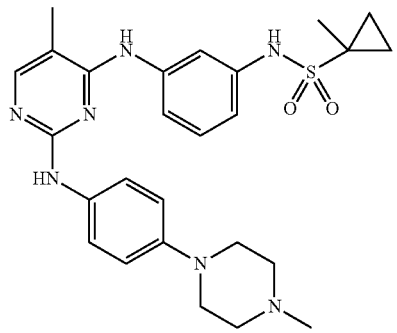 [SMILES: Cc1cnc(Nc2ccc(N3CCN(C)CC3)cc2)nc1Nc1cccc(NS(=O)(=O)C2(C)CC2)c1]

5-Methyl-$N^4$-(3-[(1-methylcyclopropyl)sulfonamido]phenyl)-$N^2$-[4-(4-methylpiperazin-1-yl)phenyl]pyrimidine-2,4-diamine (MA4-102): This was obtained as a white solid (47 mg, 68%) from MA4-098 (50 mg) and 4-(4-methylpiperazino)aniline (26 mg) using the general method x. Mp: 222° C. (dec). HPLC: 99% [$t_R$=8.6 min, 35% MeOH, 65% water (with 0.1% TFA), 20 min]. $^1$H NMR (400 MHz, DMSO-$d_6$): 9.72 (s, 1H, disappeared on $D_2O$ shake), 8.56 (s, 1H, disappeared on $D_2O$ shake), 8.32 (s, 1H, 85% reduced on $D_2O$ shake on $D_2O$ shake), 7.84 (s, 1H), 7.60-7.53 (m, 2H), 7.48 (d, J=9.1 Hz, 2H), 7.23 (t, J=8.3 Hz, 1H), 6.94 (dd, J=8.0, 1.9 Hz, 1H), 6.79 (d, J=9.1 Hz, 2H), 3.06-2.97 (m, 4H), 2.46-2.40 (m, 4H), 2.21 (s, 3H), 2.08 (d, J=0.6 Hz, 3H), 1.40 (s, 3H), 1.16-1.10 (m, 2H), 0.75-0.68 (m, 2H). HPLC-MS (ESI+): m/z 508.6 [25%, (M+H)$^+$], 254.9 [100%, (M+2H)$^{2+}$]. LC-MS (ESI+): 508.3 [100%, (M+H)$^+$], 254.6 [10%, (M+2H)$^{2+}$]. HRMS (ESI+): m/z calcd for $C_{26}H_{33}N_7O_2S$ (M+H)$^+$ 508.2489, found 508.2487.

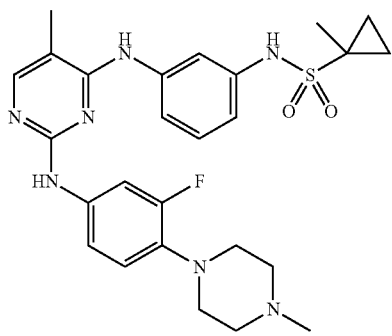 [SMILES: Cc1cnc(Nc2ccc(N3CCN(C)CC3)c(F)c2)nc1Nc1cccc(NS(=O)(=O)C2(C)CC2)c1]

5-Methyl-N⁴-[3-(N-1-methylcyclopropyl)sulfamoyl]phenyl]-N²-[4-(4-methylpiperazin-1-yl)-3-fluorophenyl]pyrimidine-2,4-diamine (MA4-103): This was obtained as a white solid (25 mg, 34%) from MA4-098 (50 mg) and MA4-020 (30 mg) using the general method x. The product was purified by column chromatography (SiO₂, eluting with DCM-MeOH, 0-12%) and triturated from ethanol. Mp: 286° C. (dec). HPLC: 99% [t$_R$=11.9 min, 35% MeOH, 65% water (with 0.1% TFA), 20 min]. ¹⁹F NMR (376 MHz, DMSO-d₆): δ −122.39 (dd, J=15.6, 9.5 Hz). ¹H NMR (400 MHz, DMSO-d₆): δ 9.74 (s, 1H, disappeared on D₂O shake), 8.90 (s, 1H, disappeared on D₂O shake), 8.42 (s, 1H, disappeared on D₂O shake), 7.89 (s, 1H), 7.64 (dd, J=15.6, 2.4 Hz, 1H), 7.53 (d, J=8.3 Hz, 1H), 7.45 (s, 1H), 7.26 (d, J=8.3 Hz, 1H), 7.23 (t, J=8.6 Hz, 1H), 6.96 (d, J=9.3 Hz, 1H), 6.85 (t, J=9.8 Hz, 1H), 2.92-2.87 (m, 4H), 2.46-2.39 (m, 4H), 2.21 (s, 3H), 2.10 (s, 3H), 1.39 (s, 3H), 1.14-1.10 (m, 2H), 0.73-0.69 (m, 2H). HPLC-MS (ESI+): m/z 526.3 [20%, (M+H)⁺], m/z 263.7 [100%, (M+2H)²⁺]. LC-MS (ESI+): 526.3 [100%, (M+H)⁺], 263.6 [10%, (M+2H)²⁺]. HRMS (ESI+): m/z calcd for C₂₆H₃₂FN₇O₂S (M+H)⁺ 526.2395, found 526.2401.

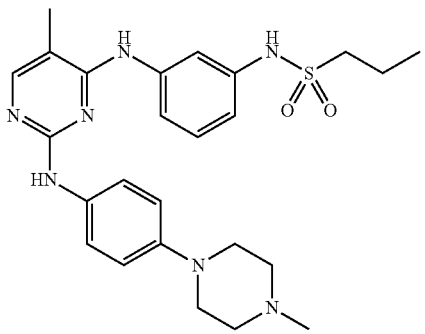 [SMILES: CCCS(=O)(=O)Nc1cccc(Nc2nc(Nc3ccc(N4CCN(C)CC4)cc3)ncc2C)c1]

5-Methyl-N⁴-[(3-propylsulfonamido)phenyl]-N²-[4-(4-methylpiperazin-1-yl)phenyl]pyrimidine-2,4-diamine (MA4-108): A mixture of MA4-106 (60 mg, 0.154 mmol) and dry pyridine (1 mL) in a 5 mL round bottom flask was cooled using an ice-bath. 1-Propanesulfonyl chloride (22 mg, 0.154 mmol, 17.4 µL) was added via a 20 µL Hamilton syringe. After 30 minutes, the ice bath was removed and the mixture was stirred for an additional 3.5 h at rt. Water (10 mL) was added and the mixture was extracted using ethyl acetate (2×15 mL). The organic layer was dried (Na₂SO₄) and the solvent evaporated. The residue was purified via chromatography (SiO₂, Isolera-4) eluting with a gradient mixture (0-12%) of DCM-MeOH to provide the title compound as a brown solid (24 mg, 31%). Mp: 289° C. (dec).

HPLC: 97% [t$_R$=7.6 min, 35% MeOH, 65% water (with 0.1% TFA), 20 min]. ¹H NMR (400 MHz, DMSO-d₆): δ 9.73 (s, 1H, disappeared on D₂O shake), 8.60 (s, 1H, disappeared on D₂O shake), 8.31 (s, 1H, disappeared on D₂O shake), 7.84 (d, J=0.8 Hz, 1H), 7.53 (dd, J=8.2, 2.2 Hz, 1H), 7.50-7.45 (m, 3H), 7.24 (t, J=8.1 Hz, 1H), 6.89 (ddd, J=8.1, 2.1, 0.8 Hz, 1H), 6.79 (d, J=9.1 Hz, 2H), 3.10-3.04 (m, 2H), 3.04-2.94 (m, 4H), 2.47-2.40 (m, 4H), 2.22 (s, 3H), 2.08 (s, 3H), 1.69 (sextet, J=7.4 Hz 2H), 0.91 (t, J=7.4 Hz 2H). HPLC-MS (ESI+): m/z 496.3 [25%, (M+H)⁺], 248.8 [100%, (M+2H)²⁺]. LC-MS (ESI+): 496.2 [100%, (M+H)⁺]. HRMS (ESI+): m/z calcd for C₂₅H₃₃N₇O₂S (M+H)⁺ 496.2489, found 496.2498.

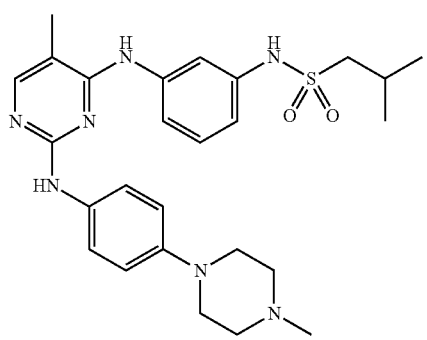 [SMILES: Cc1cnc(Nc2ccc(N3CCN(C)CC3)cc2)nc1Nc1cccc(NS(=O)(=O)CC(C)C)c1]

5-Methyl-N⁴-[13-(2-methylpropyl)sulfonamido)phenyl]-N²-[4-(4-methylpiperazin yl)phenyl]pyrimidine-2,4-diamine (MA4-116): This was obtained as a beige solid (24 mg, 30%) from MA4-106 (60 mg) and isobutanesulfonyl chloride (27 mg, 0.17 mmol, 22.1 µL) using the same method as described for the synthesis of MA4-108. Mp: 218° C. (dec). HPLC: 99% [t$_R$=6.8 min, 40% MeOH, 60% water (with 0.1% TFA), 20 min]. ¹H NMR (400 MHz, DMSO-d₆): δ 9.73 (s, 1H, disappeared on D₂O shake), 8.60 (s, 1H, disappeared on D₂O shake), 8.32 (s, 1H, 85% reduced on D₂O shake), 7.84 (d, 0.8 Hz, 1H), 7.52 (dd, J=8.1, 1.0 Hz, 1H), 7.50-7.44 (m, 3H), 7.25 (t, J=8.1 Hz, 1H), 6.89 (ddd, J=8.1, 2.1, 0.9 Hz, 1H), 6.78 (d, J=9.1 Hz, 2H), 3.04-2.99 (m, 4H), 2.98 (d, J=6.6 Hz, 2H), 2.47-2.39 (m, 4H), 2.21 (s, 3H), 2.18-2.11 (m, 1H), 2.09 (s, 3H), 0.97 (d, J=6.6 Hz, 6H). HPLC-MS (ESI+): m/z 510.3 [25%, (M+H)⁺], 255.8 [100%, (M+2H)²⁺]. LC-MS (ESI+): 510.3 [100%, (M+H)⁺]. HRMS (ESI+): m/z calcd for C₂₆H₃₅N₇O₂S (M+H)⁺ 510.2646, found 510.2660.

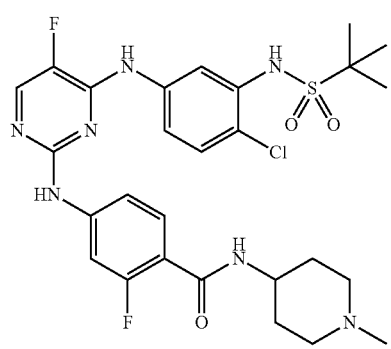 [SMILES: CN1CCC(NC(=O)c2ccc(Nc3ncc(F)c(Nc4ccc(Cl)c(NS(=O)(=O)C(C)(C)C)c4)n3)cc2F)CC1]

5-Fluoro-N⁴-(4-chloro-[3-(1,1-dimethylethylsulfonamido)]phenyl)-N²-[3-fluoro-4-(1-methylpiperidin-4-ylcarbamoyl)phenyl]pyrimidine-2,4-diamine (MA4-144-1): This was prepared from MA3-070B2 (86 mg) and SG3-153 (50 mg) using the general method x. Purification by column chromatography and crystallization from ethanol gave the title compound as a white solid (27 mg, 22%). Mp: 241° C. (dec). HPLC: 100% [$t_R$=6.3 min, 50% MeOH, 50% water (with 0.1% TFA), 20 min]. $^{19}$F NMR (376 MHz, DMSO-$d_6$): δ −112.31 (dd, J=13.9, 8.3 Hz), −161.95 (s). $^1$H NMR (400 MHz, DMSO-$d_6$): δ 9.72 (s, 1H, disappeared on D$_2$O shake), 9.67 (s, 1H, disappeared on D$_2$O shake), 9.36 (s, 1H, disappeared on D$_2$O shake), 8.22 (d, J=3.6 Hz, 1H), 7.90 (brd, J=7.8 Hz, 1H), 7.83 (dd, J=7.4, 2.9 Hz, 1H, 20% reduced on D$_2$O shake), 7.78 (d, J=2.6 Hz, 1H), 7.76 (dd, J=14.2, 1.8 Hz, 1H), 7.48 (t, J=8.6 Hz, 1H), 7.42 (d, J=8.8 Hz, 1H), 7.39 (dd, J=8.7, 2.0 Hz, 1H), 3.77-3.63 (m, 1H), 2.74 (d, J=13.0 Hz, 2H), 2.18 (s, 3H), 2.06-1.94 (m, 2H), 1.82-1.72 (m, 2H), 1.60-1.47 (m, 2H), 1.32 (s, 9H). HPLC-MS (ESI+): m/z 610.3 [30%, (M$^{37}$Cl+H)$^+$], 608.3 [100%, (M$^{35}$Cl+H)$^+$], 305.8 [20%, (M$^{37}$Cl+2H)$^{2+}$], 304.8 [60%, (M$^{35}$Cl+2H)$^{2+}$]. LC-MS (ESI+): δ 30.2 [20%, (M+Na)$^+$], 610.2 [40%, (M$^{37}$Cl+H)$^+$], 608.2 [100%, (M$^{35}$Cl+H)$^+$]. HRMS (ESI+): m/z calcd for C$_{27}$H$_{32}$ClF$_2$N$_7$O$_3$S (M+H)$^+$ 608.2017, found 608.2008.

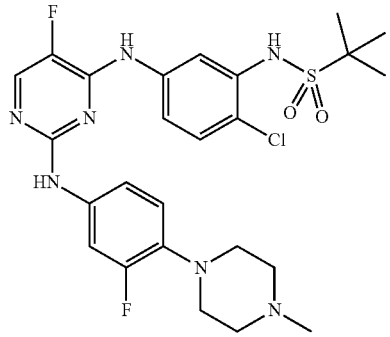 [SMILES: CN1CCN(c2ccc(Nc3ncc(F)c(Nc4ccc(Cl)c(NS(=O)(=O)C(C)(C)C)c4)n3)cc2F)CC1]

5-Fluoro-N$^4$-(4-chloro-[3-(1,1-dimethylethylsulfonamido)]phenyl)-N$^4$-[4-(4-methylpiperazin-1-yl)-3-fluorophenyl]pyrimidine-2,4-diamine (MA4-144-2): This was obtained as a white solid (34 mg, 42%) from MA3-070B2 (62 mg) and MA4-020 (30 mg) using the general method x. Mp: 244° C. (dec). HPLC: 97% [$t_R$=11.8 min, 40% MeOH, 60% water (with 0.1% TFA), 20 min]. $^{19}$F NMR (376 MHz, DMSO-$d_6$): 5-122.33 (dd, J=14.7, 10.2 Hz), −163.76 (s). $^1$H NMR (400 MHz, DMSO-$d_6$): δ 9.61 (s, 1H, disappeared on D$_2$O shake), 9.35 (s, 1H, disappeared on D$_2$O shake), 9.21 (s, 1H, disappeared on D$_2$O shake), 8.14 (d, J=3.6 Hz, 1H), 7.94-7.88 (m, 2H), 7.81 (d, J=2.5 Hz, 1H), 7.60 (dd, J=15.4, 1.9 Hz, 1H), 7.38 (d, J=8.8 Hz, 1H), 7.26 (dd, J=8.7, 1.9 Hz, 1H), 6.94 (t, J=9.8 Hz, 1H), 2.95-2.88 (m, 4H), 2.47-2.42 (m, 4H, partially overlapped by residual DMSO signal), 2.22 (s, 3H), 1.32 (s, 9H). HPLC-MS (ESI+): m/z 568.3 [30%, (M$^{37}$Cl+H)$^+$], 566.2 [100%, (M$^{35}$Cl+H)$^+$], 284.7 [40%, (M$^{37}$Cl+2H)$^{2+}$], 283.7 [95%, (M$^{35}$Cl+2H)$^{2+}$]. LC-MS (ESI+): 568.3 [100%, (M$^{37}$Cl+H)$^+$], 566.2 [100%, (M$^{35}$Cl+H)$^+$]. HRMS (ESI+): m/z calcd for C$_{25}$H$_{30}$ClF$_2$N$_7$O$_2$S (M+H)$^+$ 566.1911, found 566.1901.

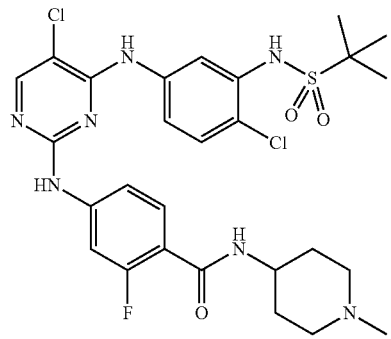 [SMILES: CN1CCC(NC(=O)c2ccc(Nc3ncc(Cl)c(Nc4ccc(Cl)c(NS(=O)(=O)C(C)(C)C)c4)n3)cc2F)CC1]

5-Chloro-N$^4$-(4-chloro-[3-(1,1-dimethylethylsulfonamido)]phenyl)-N$^2$-[3-fluoro-4-(1-methylpiperidin-4-ylcarbamoyl)phenyl]pyrimidine-2,4-diamine (MA4-146-1): This was obtained as a white solid (27 mg, 22%) from MA4-142 (69 mg) and SG3-153 (35 mg) using the general method x. Mp: 229° C. (dec). HPLC: 100% [$t_R$=10.9 min, 50% MeOH, 50% water (with 0.1% TFA), 20 min]. $^{19}$F NMR (376 MHz, DMSO-$d_6$): δ −112.29 (dd, J=14.1, 8.4 Hz). $^1$H NMR (400 MHz, DMSO-$d_6$): δ 9.76 (s, 1H, disappeared on D$_2$O shake), 9.41 (s, 1H, disappeared on D$_2$O shake), 9.23 (s, 1H, disappeared on D$_2$O shake), 8.25 (s, 1H), 7.82 (dd, J=7.6, 2.5 Hz, 1H, 45% reduced on D$_2$O shake), 7.73 (d, J=2.4 Hz, 1H), 7.66 (dd, J=14.1, 1.0 Hz, 1H), 7.60 (dd, J=8.9, 1.2 Hz, 1H), 7.45 (d, J=8.7 Hz, 1H), 7.43 (t, J=8.5 Hz, 1H), 7.34 (dd, J=8.7, 1.7 Hz, 1H), 3.75-3.65 (m, 1H), 2.73 (d, J=10.7 Hz, 2H), 2.18 (s, 3H), 2.01 (t, J=9.5 Hz, 2H), 1.76 (dd, J=12.3, 3.3 Hz, 2H), 1.60-1.48 (m, 2H), 1.31 (s, 9H). HPLC-MS (ESI+): m/z 626.2 [95%, (M$^{35}$Cl$^{37}$Cl+H)$^+$], 624.2 [100%, (M$^{35}$Cl$^{35}$Cl+H)$^+$], 313.7 [65%, (M$^{35}$Cl$^{37}$Cl+2H)$^{2+}$], 312.7 [85%, (M$^{35}$Cl$^{35}$Cl+2H)$^{2+}$]. LC-MS (ESI+): δ 48.2 [30%, (M$^{37}$Cl$^{35}$Cl+Na)$^+$], 646.2 [35%, (M$^{35}$Cl$^{35}$Cl+Na)$^+$], 626.2 [70%, (M$^{37}$Cl$^{35}$Cl+H)$^+$], 624.2 [100%, (M$^{35}$Cl$^{35}$Cl+H)$^+$]. HRMS (ESI+): m/z calcd for C$_{27}$H$_{32}$C$_{12}$FN$_7$O$_3$S (M+H)$^+$ 624.1721, found 624.1737.

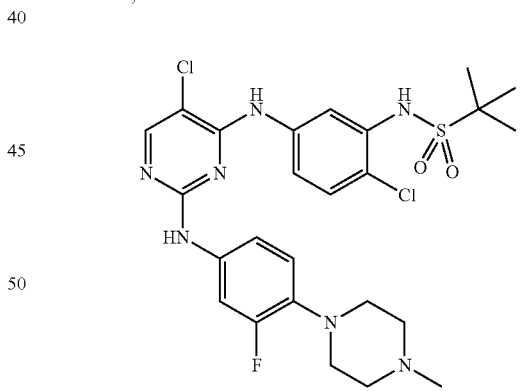

5-Chloro-N$^4$-(4-chloro-[3-(1,1-dimethylethylsulfonamido)]phenyl)-N$^2$-[4-(4-methylpiperazin-1-yl)-3-fluorophenyl]pyrimidine-2,4-diamine (MA4-146-2): This was prepared from MA4-142 (75 mg) and MA4-020 (35 mg) using the general method x. Purification by chromatography (eluting with MeOH-DCM, 0-10%) and crystallization from ethanol gave the title compound as a light brown solid (36 mg, 37%). Mp: 224 (dec). HPLC: 99% [$t_R$=7.4 min, 45% MeOH, 55% water (with 0.1% TFA), 20 min]. $^{19}$F NMR (376 MHz, DMSO-$d_6$): δ −122.31 (dd, J=14.6, 10.4 Hz), −163.76 (s). $^1$H NMR (400 MHz, DMSO-$d_6$): δ 9.39 (s, 1H, disappeared on D$_2$O shake), 9.32 (s, 1H, 80% reduced on D$_2$O shake), 9.10 (s, 1H, 90% reduced on D$_2$O shake), 8.16 (s, 1H), 7.76 (s, 1H), 7.61 (d, J=9.1 Hz, 1H), 7.50 (d, J=16.0 Hz, 1H), 7.40 (d, J=8.7 Hz, 1H), 7.20 (d, J=8.7 Hz, 1H), 6.88 (t, J=9.5 Hz, 1H), 2.96-2.85 (m, 4H), 2.47-2.41 (m, 4H), partially overlapped by residual DMSO signal), 2.22 (s, 3H), 1.30 (s, 9H). HPLC-MS (ESI+): m/z 584.3 [70%, (M$^{35}$Cl$^{37}$Cl+H)$^+$], 582.2 [100%, (M$^{35}$Cl$^{35}$Cl+H)$^+$], 292.7 [65%, (M$^{37}$Cl$^{35}$Cl+2H)$^{2+}$], 291.7 [45%, (M$^{35}$Cl$^{35}$Cl+2H)$^{2+}$]. LC-MS (ESI+): 584.2 [70%, (M$^{37}$Cl$^{35}$Cl+H)$^+$], 582.2 [100%, (M$^{35}$Cl$^{35}$Cl+H)$^+$]. HRMS (ESI+): m/z calcd for C$_{25}$H$_{30}$Cl$_2$FN$_7$O$_2$S (M+H)$^+$ 582.1616, found 582.1633.

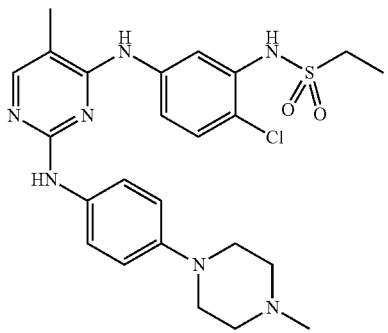 [SMILES: CCS(=O)(=O)Nc1cc(Nc2nc(Nc3ccc(N4CCN(C)CC4)cc3)ncc2C)ccc1Cl]

5-Methyl-N$^4$-(4-chloro-[3-(ethylsulfonamido)]phenyl)-N$^2$-[4-(4-methylpiperazin yl)phenyl]pyrimidine-2,4-diamine (SG4-013): This was obtained as an off-white solid (21 mg, 30%) from SG4-012 (50 mg) and 4-(4-methylpiperazino)aniline (26 mg) using the general method x. Mp: 104-106° C. (dec). HPLC: 98% [t$_R$=7.1 min, 35% MeOH, 65% water (with 0.1% TFA), 20 min]. $^1$H NMR (400 MHz, DMSO-d$_6$): δ 9.40 (s, 1H, disappeared on D$_2$O shake), 8.65 (s, 1H, disappeared on D$_2$O shake), 8.39 (s, 1H, disappeared on D$_2$O shake), 7.85 (s, 1H), 7.81 (d, J=8.6 Hz, 1H), 7.67 (d, J=2.4 Hz, 1H), 7.43 (d, J=9.0 Hz, 2H), 7.35 (d, J=8.6 Hz, 1H), 6.80 (d, J=9.0 Hz, 2H), 3.09 (q, J=7.3 Hz, 2H), 3.05-2.98 (m, 4H), 2.45-2.40 (m, 4H), 2.20 (s, 3H), 2.07 (s, 3H), 1.24 (t, J=7.3 Hz, 3H). HPLC-MS (ESI+): m/z 516.3 [15%, (M$^{35}$Cl+H)$^+$], 259.8 [100%, (M$^{37}$Cl+2H)$^{2+}$], 258.8 [35%, (M$^{35}$Cl+2H)$^{2+}$]. HPLC-MS (ESI−): m/z 514.1 [50%, (M−H)$^−$]. LC-MS (ESI+): 518.2 [35%, (M$^{37}$Cl+H)$^+$], 516.2 [100%, (M$^{35}$Cl+H)$^+$]. HRMS (ESI+): m/z calcd for C$_{24}$H$_{30}$ClN$_7$O$_2$S (M+H)+516.1943, found 516.1961.

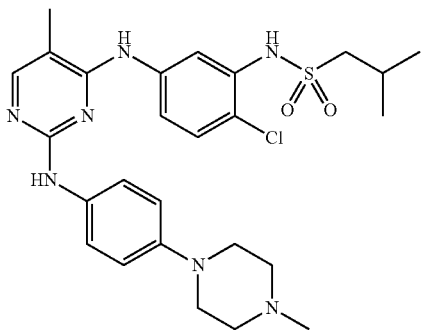 [SMILES: Cc1cnc(Nc2ccc(N3CCN(C)CC3)cc2)nc1Nc1ccc(Cl)c(NS(=O)(=O)CC(C)C)c1]

5-Methyl-N$^4$-(4-chloro-[3-(2-methylpropylsulfonamido)]phenyl)-N$^2$-[4-(4-methylpiperazin-1-yl)phenyl]pyrimidine-2,4-diamine (SG4-025): This was obtained as an off-white solid (26 mg, 47%) from SG4-018 (50 mg) and 4-(4-methylpiperazino)aniline (19 mg) using the general method x. Mp: 224° C. (dec). HPLC: 99% [t$_R$=8.9 min, 40% MeOH, 60% water (with 0.1% TFA), 20 min]. $^1$H NMR (400 MHz, DMSO-d$_6$): δ 9.42 (s, 1H, disappeared on D$_2$O shake), 8.65 (s, 1H, disappeared on D$_2$O shake), 8.40 (s, 1H, disappeared on D$_2$O shake), 7.85 (s, 1H), 7.78 (dd, J=8.8, 2.2 Hz, 1H), 7.70 (d, J=2.2 Hz, 1H), 7.43 (d, J=9.0 Hz, 2H), 7.36 (d, J=8.8 Hz, 1H), 6.80 (d, J=9.0 Hz, 2H), 3.05-2.99 (m, 4H), 2.96 (d, J=6.6 Hz, 2H), 2.46-2.41 (m, 4H), 2.21 (s, 3H), 2.15 (octet, J=6.6 Hz, 1H), 2.07 (s, 3H), 0.97 (d, J=6.6 Hz, 6H). HPLC-MS (ESI+): m/z 544.3 [20%, (M$^{35}$Cl+H)$^+$], 273.5 [40%, (M$^{35}$Cl+2H)$^{2+}$], 272.8 [100%, (M$^{37}$Cl+2H)$^{2+}$]. LC-MS (ESI+): 546.2 [35%, (M$^{37}$Cl+H)+], 544.2 [100%, (M$^{35}$Cl+H)+]. HRMS (ESI+): m/z calcd for C$_{26}$H$_{34}$ClN$_7$O$_2$S (M+H)+544.2276, found 544.2256.

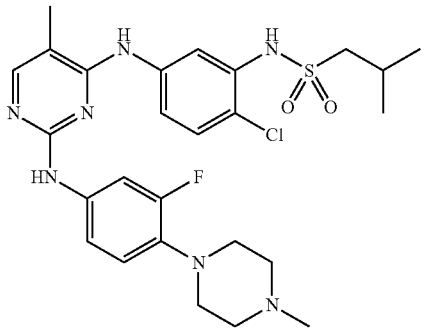 [SMILES: Cc1cnc(Nc2ccc(N3CCN(C)CC3)c(F)c2)nc1Nc1ccc(Cl)c(NS(=O)(=O)CC(C)C)c1]

5-Methyl-N$^4$-(4-chloro-[3-(2-methylpropylsulfonamido)]phenyl)-N$^2$-[4-(4-methylpiperazin-1-yl)-3-fluorophenyl]pyrimidine-2,4-diamine (SG4-027): This was obtained as a white solid (17 mg, 30%) from SG4-018 (50 mg) and MA4-020 (21 mg) using the general method x. Mp: 222° C. (dec). HPLC: 99% [t$_R$=10.4 min, 40% MeOH, 60% water (with 0.1% TFA), 20 min]. $^1$H NMR (400 MHz, DMSO-d$_6$): δ 9.43 (s, 1H, disappeared on D$_2$O shake), 8.98 (s, 1H, disappeared on D$_2$O shake), 8.50 (s, 1H, disappeared on D$_2$O shake), 7.90 (d, J=0.6 Hz, 1H), 7.75 (dd, J=8.8, 2.3 Hz, 1H), 7.62 (d, J=2.3 Hz, 1H), 7.60 (dd, J=15.3, 2.2 Hz, 1H), 7.38 (d, J=8.8 Hz, 1H), 7.23 (dd, J=8.6, 2.2 Hz, 1H), 6.87 (dd, J=9.8, 9.1 Hz, 1H), 2.98 (d, J=6.6 Hz, 2H), 2.93-2.85 (m, 4H), 2.46-2.38 (m, 4H), 2.20 (s, 3H), 2.15 (octet, J=6.6 Hz, 1H), 2.09 (s, 3H), 0.97 (d, J=6.6 Hz, 6H). $^{19}$F NMR (376 MHz, DMSO-d$_6$): δ −122.51 (dd, J=15.5, 10.1 Hz). HPLC-MS (ESI+): m/z 562.3 [10%, (M$^{35}$Cl+H)$^+$], 282.3 [40%, (M$^{37}$Cl+2H)$^{2+}$], 281.8 [100%, (M$^{35}$Cl+2H)$^{2+}$]. HPLC-MS (ESI−): m/z 560.2 [100%, (M−H)$^−$]. LC-MS (ESI+): 564.2 [35%, (M$^{37}$Cl+H)+], 562.2 [100%, (M$^{35}$Cl+H)$^+$]. HRMS (ESI+): m/z calcd for C$_{26}$H$_{33}$ClFN$_7$O$_2$S (M+H)$^+$ 562.2162, found 562.2158.

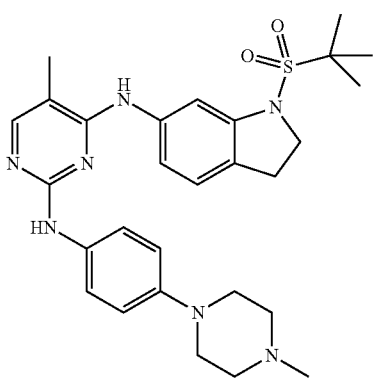 [SMILES: Cc1cnc(Nc2ccc(N3CCN(C)CC3)cc2)nc1Nc1ccc2c(c1)N(S(=O)(=O)C(C)(C)C)CC2]

5-Methyl-N⁴(1-(1,1-dimethylethylsulfonyl)indolin-6-yl)-N²-[4-(4-methylpiperazin-1-yl)phenyl]pyrimidine-2,4-diamine (SG4-031): This was obtained as a white solid (36 mg, 52%) from SG4-024 (50 mg) and 4-(4-methylpiperazino)aniline (25 mg) using the general method x. Mp: 204° C. (dec). HPLC: 98% [$t_R$=10.7 min, 40% MeOH, 60% water (with 0.1% TFA), 20 min]. ¹H NMR (400 MHz, DMSO-$d_6$): δ 8.53 (s, 1H, disappeared on D₂O shake), 8.25 (s, 1H, disappeared on D₂O shake), 7.79 (s, 1H), 7.47 (dd, J=8.1, 1.5 Hz, 1H), 7.45 (d, J=9.1 Hz, 2H), 7.35 (d, J=1.5 Hz, 1H), 7.13 (d, J=8.1 Hz, 1H), 6.75 (d, J=9.1 Hz, 2H), 4.04 (t, J=8.4 Hz, 2H), 3.08 (t, J=8.4 Hz, 2H), 3.03-2.95 (m, 4H), 2.46-2.40 (m, 4H), 2.20 (s, 3H), 2.05 (s, 3H), 1.34 (s, 9H). HPLC-MS (ESI+): m/z 536.3 [10%, (M+H)⁺], 268.8 [100%, (M+2H)²⁺]. LC-MS (ESI+): 558.3 [15%, (M+Na)⁺], 536.3 [100%, (M+H)⁺]. HRMS (ESI+): m/z calcd for C₂₈H₃₇N₇O₂S (M+H)⁺ 536.2802, found 536.2789.

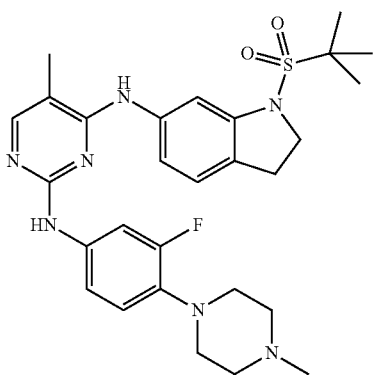 [SMILES: Cc1cnc(Nc2ccc(N3CCN(C)CC3)c(F)c2)nc1Nc1ccc2c(c1)N(S(=O)(=O)C(C)(C)C)CC2]

5-Methyl-N⁴(1-(1,1-dimethylethylsulfonyl)indolin-6-yl)-N²-[4-(4-methylpiperazin-1-yl)-3-fluorophenyl]pyrimidine-2,4-diamine (SG4-032): This was obtained as an off-white solid (27 mg, 38%) from SG4-024 (50 mg) and MA4-020 (27 mg) using the general method x. Mp: 181-185° C. (dec). HPLC: 98% [$t_R$=11.1 min, 40% MeOH, 60% water (with 0.1% TFA), 20 min]. ¹H NMR (400 MHz, DMSO-$d_6$): δ 8.87 (s, 1H, disappeared on D₂O shake), 8.35 (s, 1H, disappeared on D₂O shake), 7.84 (s, 1H), 7.60 (dd, J=15.8, 2.3 Hz, 1H), 7.39 (dd, J=8.1, 1.7 Hz, 1H), 7.30 (d, J=1.7 Hz, 1H), 7.20 (dd, J=8.7, 1.9 Hz, 1H), 7.15 (d, J=8.1 Hz, 1H), 6.82 (t, J=9.4 Hz, 2H), 4.04 (t, J=8.4 Hz, 2H), 3.08 (t, J=8.4 Hz, 2H), 2.92-2.84 (m, 4H), 2.48-2.41 (m, 4H), 2.20 (s, 3H), 2.07 (s, 3H), 1.33 (s, 9H). ¹⁹F NMR (376 MHz, DMSO-$d_6$): δ -122.65 (dd, J=15.6, 10.1 Hz). HPLC-MS (ESI+): m/z 554.3 [10%, (M+H)⁺], 277.8 [100%, (M+2H)²⁺]. HPLC-MS (ESI-): m/z 552.4 [100%, (M-H)⁻]. LC-MS (ESI+): 554.3 [100%, (M+H)⁺], 217.6 [30%, (M-SO₂tBu+2H)²⁺]. HRMS (ESI+): m/z calcd for C₂₈H₃₆FN₇O₂S (M+H)⁺ 554.2708, found 554.2703.

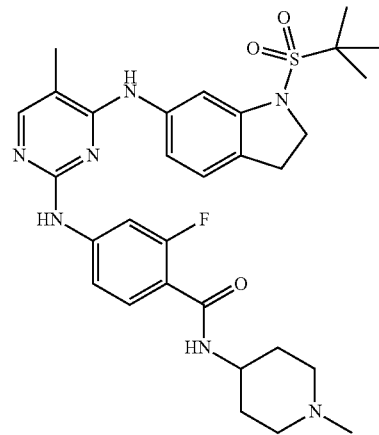 [SMILES: Cc1cnc(Nc2ccc(C(=O)NC3CCN(C)CC3)c(F)c2)nc1Nc1ccc2c(c1)N(S(=O)(=O)C(C)(C)C)CC2]

5-Methyl-N⁴(1-(1,1-dimethylethylsulfonyl)indolin-6-yl)-N²-[3-fluoro-4-(1-methylpiperidin-4-ylcarbamoyl)phenyl]pyrimidine-2,4-diamine (SG4-033): This was obtained as an off-white solid (16 mg, 21%) from SG4-024 (50 mg) and SG3-153 (33 mg) using the general method x. Mp: 240° C. (dec). HPLC: 99% [$t_R$=12.1 min, 40% MeOH, 60% water (with 0.1% TFA), 20 min]. ¹H NMR (400 MHz, DMSO-$d_6$): δ 9.37 (s, 1H, disappeared on D₂O shake), 8.48 (s, 1H, disappeared on D₂O shake), 7.91 (d, J=0.8 Hz, 1H), 7.73 (dd, J=14.7, 1.9 Hz, 1H), 7.68 (dd, J=7.6, 3.8 Hz, 1H, disappeared on D₂O shake), 7.38 (t, J=8.6 Hz, 1H), 7.34-7.26 (m, 3H), 7.19 (d, J=8.0 Hz, 1H), 4.06 (t, J=8.4 Hz, 2H), 3.72-3.60 (m, 1H), 3.10 (t, J=8.4 Hz, 2H), 2.68 (d, J=11.3 Hz, 2H), 2.13 (s, 3H), 2.09 (s, 3H), 1.94 (t, J=11.3 Hz, 2H), 1.73 (dd, J=12.4, 3.4 Hz, 2H), 1.50 (qd, J=12.4, 3.4 Hz, 2H), 1.32 (s, 9H). ¹⁹F NMR (376 MHz, DMSO-$d_6$): δ -112.31--112.43 (m). HPLC-MS (ESI+): m/z 596.3 [10%, (M+H)⁺], 298.7 [100%, (M+2H)²⁺]. LC-MS (ESI+): δ 18.3 [20%, (M+Na)⁺], 596.3 [100%, (M+H)⁺], 238.1 [35%, (M-SO₂tBu+2H)²⁺]. HRMS (ESI+): m/z calcd for C₃₀H₃₈FN₇O₃S (M+H)⁺ 596.2814, found 596.2811.

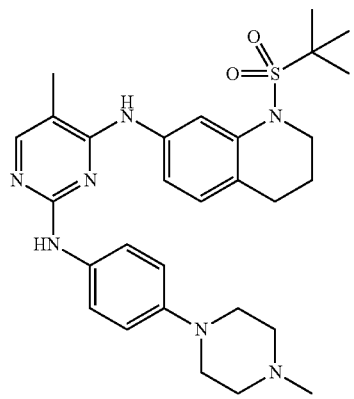 [SMILES: Cc1cnc(Nc2ccc(N3CCN(C)CC3)cc2)nc1Nc1ccc2c(c1)N(S(=O)(=O)C(C)(C)C)CCC2]

5-Methyl-N⁴(1-(1,1-dimethylethylsulfonyl)-1,2,3,4-tetrahydroquinolin-7-yl)-N²-[4-(4-methylpiperazin-1-yl)phenyl]pyrimidine-2,4-diamine (SG4-038): This was obtained as a white solid (22 mg, 32%) from SG4-026 (50 mg) and 4-(4-methylpiperazino)aniline (24 mg) using the general method x. Mp: 218° C. (dec). HPLC: 97% [$t_R$=11.3 min, 40% MeOH, 60% water (with 0.1% TFA), 20 min]. $^1$H NMR (400 MHz, DMSO-$d_6$): δ 8.47 (s, 1H, disappeared on D$_2$O shake), 8.27 (s, 1H, disappeared on D$_2$O shake), 7.80 (d, J=0.8 Hz, 1H), 7.66 (d, J=1.9 Hz, 1H), 7.45 (d, J=9.1 Hz, 2H), 7.28 (dd, J=8.2, 1.9 Hz, 1H), 7.04 (d, J=8.2 Hz, 1H), 6.74 (d, J=9.1 Hz, 2H), 3.69-3.60 (m, 2H), 3.03-2.95 (m, 4H), 2.78 (t, J=6.7 Hz, 2H), 2.45-2.39 (m, 4H), 2.19 (s, 3H), 2.05 (s, 3H), 1.94 (quintet, J=6.7 Hz, 2H), 1.32 (s, 9H). HPLC-MS (ESI+): m/z 550.3 [20%, (M+H)$^+$], 275.8 [100%, (M+2H)$^{2+}$]. HPLC-MS (ESI−): m/z 548.3 [100%, (M−H)$^−$]. LC-MS (ESI+): 550.3 [100%, (M+H)$^+$], 215.6 [20%, (M−SO$_2$tBu+2H)$^{2+}$]. HRMS (ESI+): m/z calcd for C$_{29}$H$_{39}$N$_7$O$_2$S (M+H)$^+$ 550.2959, found 550.2941.

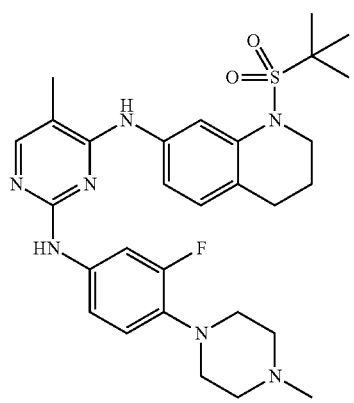 [SMILES: Cc1cnc(Nc2ccc(N3CCN(C)CC3)c(F)c2)nc1Nc1ccc2c(c1)N(S(=O)(=O)C(C)(C)C)CCC2]

5-Methyl-N$^4$(1-(1,1-dimethylethylsulfonyl)-1,2,3,4-tetrahydroquinolin-7-yl)-N$^2$-[4-(4-methylpiperazin-1-yl)-3-fluorophenyl]pyrimidine-2,4-diamine (SG4-039-01): This was obtained as a yellow foam (21 mg, 29%) from SG4-026 (50 mg) and MA4-020 (26 mg) using the general method x. Mp: 237° C. (dec). HPLC: 96% [$t_R$=12.3 min, 40% MeOH, 60% water (with 0.1% TFA), 20 min]. $^1$H NMR (400 MHz, DMSO-$d_6$): δ 8.82 (s, 1H, disappeared on D$_2$O shake), 8.37 (s, 1H, disappeared on D$_2$O shake), 7.84 (d, J=0.7 Hz, 1H), 7.60 (dd, J=15.5, 2.1 Hz, 1H), 7.59 (d, J=1.9 Hz, 1H), 7.25 (dd, J=8.2, 2.1 Hz, 1H), 7.21 (dd, J=8.4, 1.9 Hz, 1H), 7.06 (d, J=8.4 Hz, 1H), 6.81 (dd, J=9.4, 9.1 Hz, 1H), 3.68-3.60 (m, 2H), 2.91-2.84 (m, 4H), 2.78 (t, J=6.7 Hz, 2H), 2.46-2.38 (m, 4H), 2.19 (s, 3H), 2.07 (s, 3H), 1.94 (quintet, J=6.7 Hz, 2H), 1.31 (s, 9H). $^{19}$F NMR (376 MHz, DMSO-$d_6$): δ −122.60 (dd, J=15.3, 10.2 Hz). HPLC-MS (ESI+): m/z 568.3 [15%, (M+H)$^+$], 284.7 [100%, (M+2H)$^{2+}$]. HPLC-MS (ESI−): m/z 566.2 [100%, (M−H)$^−$]. LC-MS (ESI+): 568.3 [100%, (M+H)$^+$], 224.6 [10%, (M−SO$_2$tBu+2H)$^{2+}$]. HRMS (ESI+): m/z calcd for C$_{29}$H$_{38}$FN$_7$O$_2$S (M+H)$^+$ 568.2864, found 568.2867.

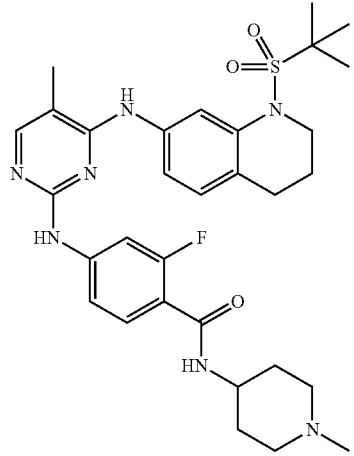 [SMILES: Cc1cnc(Nc2ccc(C(=O)NC3CCN(C)CC3)c(F)c2)nc1Nc1ccc2c(c1)N(S(=O)(=O)C(C)(C)C)CCC2]

5-Methyl-N$^4$(1-(1,1-dimethylethylsulfonyl)-1,2,3,4-tetrahydroquinolin-7-yl)-N$^2$-[3-fluoro-4-(1-methylpiperidin-4-ylcarbamoyl)phenyl]pyrimidine-2,4-diamine (SG4-043): A mixture of SG4-026 (50 mg), SG3-153 (32 mg), 3 drops of 4 M HCl, and EtOH (1 mL) in a 2-mL microwave vial was heated in a oil bath at 100° C. for 15 h. Sodium bicarbonate (ca. 100 mg) was added to the mixture, stirred for 30 min at room temperature, and concentrated under reduced pressure. The crude mixture was purified via preparative TLC using DCM/MeOH 10% and afforded the title product as a light yellow solid (43 mg, 56%). Mp: 242° C. (dec). HPLC: 98% [$t_R$=12.6 min, 40% MeOH, 60% water (with 0.1% TFA), 20 min]. $^1$H NMR (400 MHz, DMSO-$d_6$): δ 9.33 (s, 1H, disappeared on D$_2$O shake), 8.50 (s, 1H, disappeared on D$_2$O shake), 7.91 (s, 1H), 7.72 (dd, J=14.8, 1.7 Hz, 1H), 7.70 (brs, 1H), 7.54 (d, J=1.8 Hz, 1H), 7.39 (t, J=8.5 Hz, 1H), 7.31 (dd, J=8.5, 1.7 Hz, 1H), 7.23 (dd, J=8.2, 1.8 Hz, 1H), 7.10 (d, J=8.2 Hz, 1H), 3.74-3.60 (m, 3H), 2.79 (t, J=6.5 Hz, 2H), 2.70 (d, J=11.1 Hz, 2H), 2.15 (s, 3H), 2.09 (s, 3H), 2.05-1.90 (m, 4H), 1.73 (dd, J=12.5, 3.8 Hz, 2H), 1.51 (qd, J=12.5, 3.8 Hz, 2H), 1.30 (s, 9H). $^{19}$F NMR (376 MHz, DMSO-$d_6$): δ −112.28-.−112.37 (m) HPLC-MS (ESI+): m/z 610.4 [20%, (M+H)$^+$], 305.7 [100%, (M+2H)$^{2+}$]. HPLC-MS (ESI−): m/z 608.3 [100%, (M−H)$^−$]. LC-MS (ESI+): δ 32.3 [50%, (M+Na)$^+$], 610.3 [100%, (M+H)$^+$]. HRMS (ESI+): m/z calcd for C$_{31}$H$_{40}$FN$_7$O$_3$S (M+H)$^+$610.2970, found 610.2966.

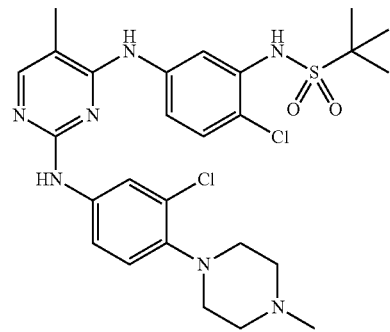 [SMILES: Cc1cnc(Nc2ccc(N3CCN(C)CC3)c(Cl)c2)nc1Nc1ccc(Cl)c(NS(=O)(=O)C(C)(C)C)c1]

5-Methyl-N$^4$-(4-chloro-[3-(1,1-dimethylethylsulfonamido)]phenyl)-N$^2$-[4-(4-methylpiperazin-1-yl)-3-chlorophenyl]pyrimidine-2,4-diamine (SG4-046): This was obtained from SG3-012 (50 mg) and SG4-030 (29 mg) using the general method y. Further trituration using EtOH/hexanes of the isolated product give the title compound as a light yellow solid (18 mg, 25%). HPLC: 99% [$t_R$=6.4 min, 45% MeOH, 55% water (with 0.1% TFA), 20 min]. $^1$H NMR (400 MHz, DMSO-$d_6$): δ 9.33 (s, 1H, disappeared on D$_2$O shake), 8.99 (s, 1H, disappeared on D$_2$O shake), 8.52 (s, 1H, disappeared on D$_2$O shake), 7.90 (s, 1H), 7.83 (d, J=1.7 Hz, 1H), 7.75 (d, J=2.0 Hz, 1H), 7.71 (d, J=8.9 Hz, 1H), 7.41 (dd, J=8.8, 2.0 Hz, 1H), 7.35 (d, J=8.8 Hz, 1H), 7.00 (d, J=8.9 Hz, 1H), 2.91-2.82 (m, 4H), 2.46-2.40 (m, 4H, overlapped by residual DMSO solvent), 2.22 (s, 3H), 2.08 (s, 3H), 1.29 (s, 9H). HPLC-MS (ESI+): m/z 578.3 (20%, M$^{35}$Cl$^{35}$Cl+H)$^+$], 290.7 [80%, (M$^{35}$Cl$^{37}$Cl+2H)$^{2+}$]289.8 [100%, M$^{35}$Cl$^{35}$Cl+2H)$^{2+}$]. HPLC-MS (ESI-): m/z 578.2 [80%, (M$^{35}$Cl$^{37}$Cl-H)$^-$], 576.2 [100%, (M$^{35}$Cl$^{35}$Cl-H)$^-$]. LC-MS (ESI+): 580.2 [70%, (M$^{35}$Cl$^{37}$Cl+H)$^+$], 578.2 [100%, (M$^{35}$Cl$^{35}$Cl+H)$^+$]. HRMS (ESI+): m/z calcd for C$_{26}$H$_{33}$Cl$_2$N$_7$O$_2$S (M+H)+578.1866, found 578.1847.

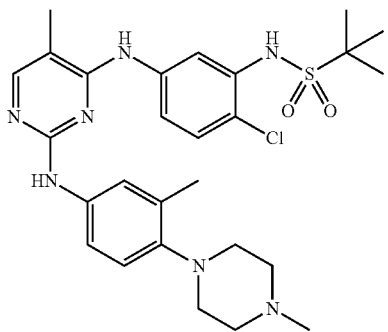 [SMILES: Cc1cc(Nc2ncc(C)c(Nc3ccc(Cl)c(NS(=O)(=O)C(C)(C)C)c3)n2)ccc1N1CCN(C)CC1]

5-Methyl-N$^4$-(4-chloro-[3-(1,1-dimethylethylsulfonamido)]phenyl)-N$^2$-[14-(4-methylpiperazin-1-yl)-3-methylphenyl]pyrimidine-2,4-diamine (SG4-047): This was obtained from SG3-012 (50 mg) and SG4-037 (26 mg) using the general method y. Further trituration using DCM/hexanes of the isolated product give the title compound as an off-white solid (39 mg, 55%). HPLC: 96% [$t_R$=13.2 min, 40% MeOH, 60% water (with 0.1% TFA), 20 min]. $^1$H NMR (400 MHz, DMSO-$d_6$): δ 9.33 (s, 1H, disappeared on D$_2$O shake), 8.69 (s, 1H, disappeared on D$_2$O shake), 8.45 (s, 1H, disappeared on D$_2$O shake), 7.87 (s, 1H), 7.79 (d, J=2.0 Hz, 1H), 7.75 (dd, J=8.8, 1.6 Hz, 1H), 7.43 (d, J=1.6 Hz, 1H), 7.32 (d, J=8.8 Hz, 1H), 7.31 (d, J=8.6 Hz, 1H), 6.87 (d, J=8.6 Hz, 1H), 2.79-2.71 (m, 4H), 2.47-2.38 (m, 4H, overlapped by residual DMSO solvent), 2.22 (s, 3H), 2.09 (s, 3H), 2.07 (s, 3H), 1.30 (s, 9H). HPLC-MS (ESI+): m/z 558.3 [15%, (M$^{35}$Cl+H)$^+$], 280.7 [35%, (M$^{37}$Cl+2H)$^{2+}$], 279.7 [100%, (M$^{35}$Cl+2H)$^{2+}$]. HPLC-MS (ESI-) m/z 556.2 [100%, ($^{35}$Cl-H)$^-$]. LC-MS (ESI+): 560.2 [35%, (M$^{37}$Cl+H)$^+$], 558.2 [100%, (M$^{35}$Cl+H)$^+$], 219.6 [40%, (M-SO$_2$tBu+2H)$^{2+}$]. HRMS (ESI+): m/z calcd for C$_{27}$H$_{36}$ClN$_7$O$_2$S (M+H)$^+$ 558.2412, found 558.2412.

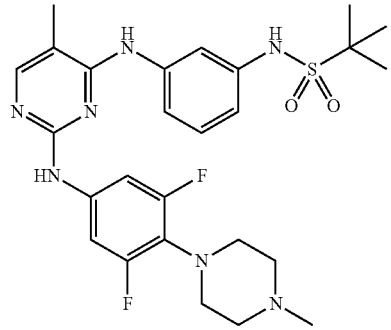 [SMILES: Cc1cnc(Nc2cc(F)c(N3CCN(C)CC3)c(F)c2)nc1Nc1cccc(NS(=O)(=O)C(C)(C)C)c1]

5-Methyl-N$^4$-[3-(1,1-dimethylethyl)sulfonamidophenyl]-N$^2$-[4-(4-methylpiperazin-1-yl)-3,5-difluorophenyl]pyrimidine-2,4-diamine (MA5-006-1): This was obtained as a white white solid (31 mg, 42%) from SG3-053 (50 mg) and MA4-182-1 (32 mg) using the general method x. Mp: 201° C. (dec). HPLC: 100% [$t_R$=8.3 min, 40% MeOH, 60% water (with 0.1% TFA), 20 min]. $^{19}$F NMR (376 MHz, DMSO-$d_6$): δ -119.83 (d, J=12.2 Hz). $^1$H NMR (400 MHz, DMSO-$d_6$): δ 9.62 (s, 1H, disappeared on D$_2$O shake), 9.20 (s, 1H, disappeared on D$_2$O shake), 8.49 (s, 1H, 80% reduced on D$_2$O shake), 7.91 (d, J=0.8 Hz, 1H), 7.43 (dd, J=8.0, 1.1 Hz, 1H), 7.40-7.35 (m, 2H), 7.34 (brs, 1H), 7.23 (t, J=8.0 Hz, 1H), 7.03 (dd, J=8.0, 1.1 Hz, 1H), 3.05-2.95 (m, 4H), 2.46-2.39 (m, 4H), 2.24 (s, 3H), 2.10 (s, 3H), 1.27 (s, 9H). HPLC-MS (ESI+): m/z 546.3 [20%, (M+H)$^+$], 273.7 [100%, (M+2H)$^{2+}$]. HPLC-MS (ESI-): m/z 544.2 [100%, (M-H)$^-$]. LC-MS (ESI+): 546.3 [100%, (M+H)$^+$]. HRMS (ESI+): m/z calcd for C$_{26}$H$_{33}$F$_2$N$_7$O$_2$S (M+H)$^+$546.2457, found 546.2468.

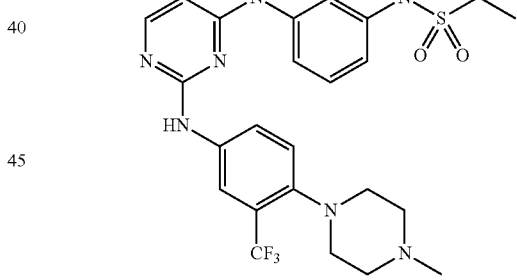

5-Methyl-N$^4$-[13-(1,1-dimethylethyl)sulfonamidophenyl]-N$^2$-[4-(4-methylpiperazin-1-yl)-3-trifluoromethylphenyl]pyrimidine-2,4-diamine (MA5-006-2): This was obtained as a white solid (31 mg, 38%) from SG3-053 (50 mg) and MA4-182-2 (36 mg) using the general method x. Mp: 208° C. (dec). HPLC: 99% [$t_R$=15.5 min, 40% MeOH, 60% water (with 0.1% TFA), 20 min]. $^{19}$F NMR (376 MHz, DMSO-$d_6$): δ -59.08 (s). $^1$H NMR (400 MHz, DMSO-$d_6$): δ 9.61 (s, 1H, disappeared on D$_2$O shake), 9.13 (s, 1H, disappeared on D$_2$O shake), 8.42 (s, 1H, disappeared on D$_2$O shake), 7.97 (dd, J=8.8, 2.3 Hz, 1H), 7.91 (brs, 2H), 7.52-7.48 (m, 2H), 7.37 (d, J=8.8 Hz, 1H), 7.20 (t, J=8.4 Hz, 1H), 7.00 (d, J=8.4 Hz, 1H), 2.87-2.75 (m, 4H), 2.55-2.42 (m, 4H, partially overlapped with the residual DMSO signal), 2.26 (brs, 3H), 2.11 (s, 3H), 1.27 (s, 9H). HPLC-MS (ESI+): m/z 578.3 [30%, (M+H)$^+$], 289.8 [100% (M+

2H)²⁺]. LC-MS (ESI+): 578.2 [100%, (M+H)⁺]. HRMS (ESI+): m/z calcd for $C_{27}H_{34}F_3N_7O_2S$ (M+H)⁺ 578.2520, found 578.2510.

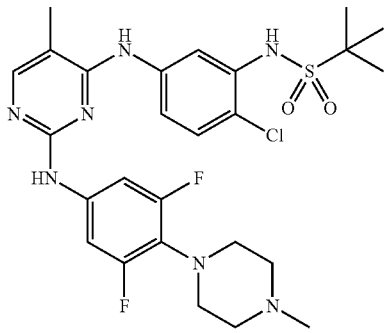 [SMILES: Cc1cnc(Nc2cc(F)c(N3CCN(C)CC3)c(F)c2)nc1Nc1ccc(Cl)c(NS(=O)(=O)C(C)(C)C)c1]

5-Methyl-$N^4$-(4-chloro-[3-(1,1-dimethylethylsulfonamido)]phenyl)-$N^2$-[4-(4-methylpiperazin-1-yl)-3,5-difluorophenyl]pyrimidine-2,4-diamine (MA5-008-1): This was obtained as a beige solid (44 mg, 56%) from SG3-012 (50 mg) and MA4-182-1 (29 mg) using the general method x. Mp: 190° C. (dec). HPLC: 100% [$t_R$=6.6 min, 45% MeOH, 55% water (with 0.1% TFA), 20 min]. ¹⁹F NMR (376 MHz, DMSO-d₆): δ −119.89 (d, J=11.8 Hz). ¹H NMR (400 MHz, DMSO-d₆): δ 9.37 (s, 1H, disappeared on D₂O shake), 9.26 (s, 1H, disappeared on D₂O shake), 8.62 (s, 1H, disappeared on D₂O shake), 7.95 (s, 1H), 7.73 (dd, J=8.6, 2.1 Hz, 1H), 7.70 (d, J=2.3 Hz, 1H), 7.41-7.31 (m, 3H), 3.08-2.99 (m, 4H), 2.55-2.45 (m, 4H, overlapped by the residual DMSO signal), 2.27 (brs, 3H), 2.11 (s, 3H), 1.32 (s, 9H). HPLC-MS (ESI+): m/z 581.3 [20%, (M³⁵Cl+H)⁺], 291.4 [40%, (M³⁷Cl+2H)²⁺], 290.7 [100%, (M³⁵Cl+2H)²⁺]. HPLC-MS m/z 580.3 [30%, (M³⁷Cl−H)⁻], 578.3 [100%, (M³⁵Cl−H)⁻]. LC-MS (ESI+): 582.2 [35%, (M³⁷Cl+H)⁺], 580.2 [100%, (M³⁵Cl+H)+]. HRMS (ESI+): m/z calcd for $C_{26}H_{32}ClF_2N_7O_2S$ (M+H)⁺ 580.2068, found 580.2074.

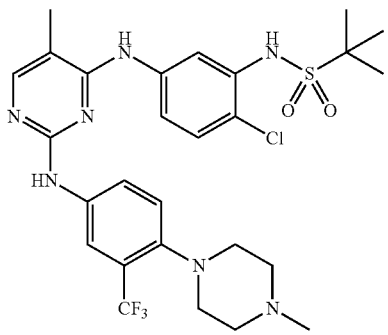 [SMILES: Cc1cnc(Nc2ccc(N3CCN(C)CC3)c(C(F)(F)F)c2)nc1Nc1ccc(Cl)c(NS(=O)(=O)C(C)(C)C)c1]

5-Methyl-$N^4$-(4-chloro-[3-(1,1-dimethylethylsulfonamido)]phenyl)-$N^2$-[4-(4-methylpiperazin-1-yl)-3-trifluoromethylphenyl]pyrimidine-2,4-diamine (MA5-008-2): This was obtained as a beige solid (34 mg, 43%) from SG3-012 (50 mg) and MA4-182-2 (33 mg) using the general method x. Mp: 188° C. (dec). HPLC: 98% [$t_R$=4.7 min, 50% MeOH, 50% water (with 0.1% TFA), 20 min]. ¹⁹F NMR (376 MHz, DMSO-d₆): δ −59.20 (s). ¹H NMR (400 MHz, DMSO-d₆): δ 9.36 (s, 1H, disappeared on D₂O shake), 9.24 (s, 1H, disappeared on D₂O shake), 8.57 (s, 1H, disappeared on D₂O shake), 7.99 (brs, 1H), 7.95 (s, 1H), 7.91 (dd, J=8.8, 2.0 Hz, 1H), 7.83-7.75 (m, 2H), 7.41 (d, J=8.8 Hz, 1H), 7.33 (d, J=8.6 Hz, 1H), 2.94-2.88 (m, 4H), 2.68-2.48 (m, 4H, partially overlapped with the residual DMSO signal), 2.46 (s, 3H, completely overlapped by the residual DMSO signal), 2.12 (s, 3H), 1.32 (s, 9H). HPLC-MS (ESI+): m/z 614.3 [5%, (M³⁷Cl+H)+], 612.3 [20%, (M³⁵Cl+H)⁺], 307.6 [40%, (M³⁷Cl+2H)²⁺], 306.7 [100%, (M³⁵Cl+2H)²⁺]. HPLC-MS (ESI−): m/z 612.3 [30%, (M³⁷Cl−H)⁻], 610.3 [100%, (M³⁵Cl−H)⁻]. LC-MS (ESI+): δ 14.2 [35%, (M³⁷Cl+H)⁺], 612.2 [100%, (M³⁵Cl+H)⁺], 246.1 [30%, (M-SO₂tBu+2H)²⁺]. HRMS (ESI+): m/z calcd for $C_{27}H_{33}ClF_3N_7O_2S$ (M+H)⁺ 612.2130, found 612.2113.

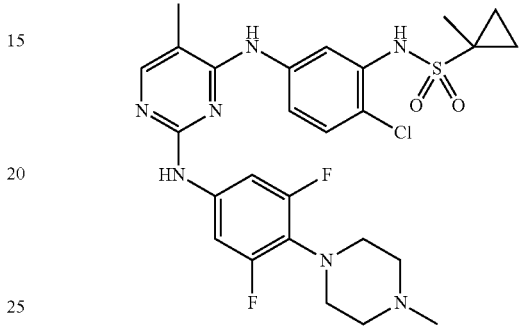

5-Methyl-$N^4$-(4-chloro-3-[(1-methylcyclopropyl)sulfonamido]phenyl)-$N^2$-[4-(4-methylpiperazin-1-yl)-3,5-difluorophenyl]pyrimidine-2,4-diamine (MA5-016-1): This was obtained as a white solid (26.5 mg, 36%) from MA5-014 (50 mg) and MA4-182-1 (29 mg) using the general method x. Mp: 260° C. (dec). HPLC: 97% [$t_R$=8.0 min, 40% MeOH, 60% water (with 0.1% TFA), 20 min]. ¹⁹F NMR (376 MHz, DMSO-d₆): δ −119.88 (d, J=12.2 Hz). ¹H NMR (400 MHz, DMSO-d₆): δ 9.51 (s, 1H, disappeared on D₂O shake), 9.25 (s, 1H, disappeared on D₂O shake), 8.61 (s, 1H, disappeared on D₂O shake), 7.95 (s, 1H), 7.73 (d, J=8.3 Hz, 1H), 7.59 (d, J=2.5 Hz, 1H), 7.43-7.32 (m 3H), 3.11-2.96 (m, 4H), 2.42-2.37 (m, 4H), 2.20 (s, 3H), 2.11 (s, 3H), 1.48 (s, 3H), 1.10-1.06 (m, 2H), 0.77-0.74 (m, 2H). HPLC-MS (ESI+): m/z 580.3 [30%, (M³⁷Cl+H)⁺], 578.2 [50%, (M³⁵Cl+H)⁺], 290.7 [40%, (M³⁷Cl+2H)²⁴], 289.7 [100%, (M³⁵Cl+2H)²⁺]. LC-MS (ESI+): 578.2 [100%, (M+H)⁺]. HRMS (ESI+): m/z calcd for $C_{26}H_{30}ClF_2N_7O_2S$ (M+H)⁺ 578.1911, found 578.1938.

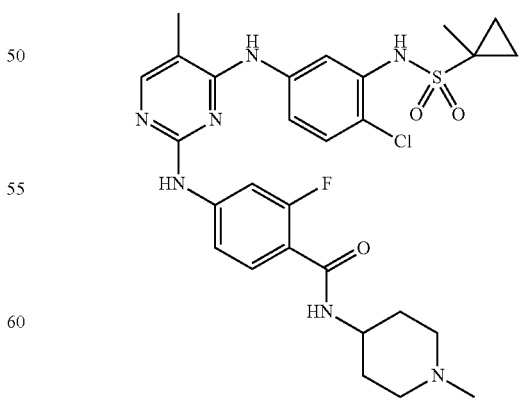

5-Methyl-$N^4$-(4-chloro-3-[(1-methylcyclopropyl)sulfonamido]phenyl)-$N^2$-[3-fluoro-4-(1-methylpiperidin-4-ylcarbamoyl)phenyl]pyrimidine-2,4-diamine (MA5-018): This was obtained as a white solid (28 mg, 47%) from MA5-014 (50 mg) and SG3-153 (26 mg) using the general method x. Mp: 191° C. (dec). HPLC: 98% [$t_R$=6.7 min, 40% MeOH, 60% water (with 0.1% TFA), 20 min]. $^{19}$F NMR (376 MHz, DMSO-$d_6$): δ −112.38 (dd, J=13.6, 8.5 Hz). $^1$H NMR (400 MHz, DMSO-$d_6$): δ 9.61 (brs, 1H, disappeared on D$_2$O shake), 9.47 (s, 1H, disappeared on D$_2$O shake), 8.66 (s, 1H, disappeared on D$_2$O shake), 8.00 (d, J=0.7 Hz, 1H), 7.90 (brd, J=7.4 Hz, 1H), 7.80 (dd, J=8.8, 2.6 Hz, 1H), 7.78 (dd, J=14.4, 2.0 Hz, 1H), 7.65 (d, J=2.5 Hz, 1H), 7.46-7.42 (m, 3H), 7.37 (dd, J=8.5, 2.0 Hz, 1H), 3.80-3.79 (m, 1H), 3.05-2.91 (m, 2H), 2.50-2.45 (m, 1H), 2.39-2.29 (m, 4H), 2.13 (d, J=0.7 Hz, 3H), 1.88-1.81 (m, 2H), 1.69-1.61 (m, 2H), 1.48 (s, 3H), 1.10-1.06 (m, 2H), 0.79-0.75 (m, 2H). HPLC-MS (ESI+): m/z 604.2 [10%, (M$^{37}$Cl+H)$^+$], 602.2 [40%, (M$^{35}$Cl+H)$^+$], 302.4 [40%, (M$^{37}$Cl+2H)$^{2+}$], 301.6 [100%, (M$^{35}$Cl+2H)$^{2+}$]. HPLC-MS (ESI−): m/z 602.3 [35%, (M$^{37}$Cl−H$^−$], 600.3 [100%, (M$^{35}$Cl−H)$^−$]. LC-MS (ESI+): δ 24.2 [30%, (M$^{35}$Cl+Na)$^+$], 604.2 [30%, (M$^{37}$Cl+H)$^+$], 602.2 [100%, (M$^{35}$Cl+H)$^+$], 301.6 [20%, (M$^{35}$Cl+2H)$^{2+}$]. HRMS (ESI+): m/z calcd for C$_{28}$H$_{33}$ClFN$_7$O$_3$S (M+H)+602.2111, found 602.2081.

Synthesis of the Pyrimidine-A-Ring Intermediates 3

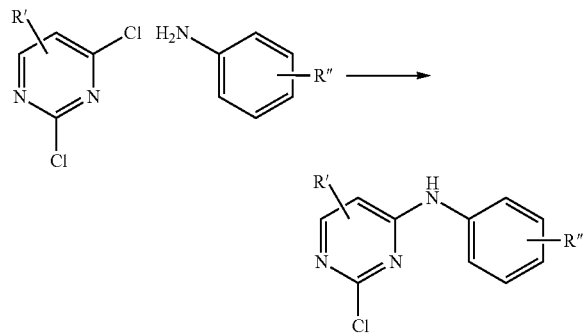

Procedure A: A mixture of substituted 2,4-dichloropyrimidine (1.0 equiv.) and substituted aniline (1.15 equiv.) in MeOH/water (1:1.5, 0.2 M) was stirred at 45° C. The reaction time is indicated below. Upon cooling to ambient temperature, the desired product precipitated and was filtered, washed with MeOH/water (1:1.5, 20 mL), and dried.

Procedure B: A mixture of substituted 2,4-dichloropyrimidine (1.0 equiv.), and substituted aniline (1.0-1.05 equiv.), and DIPEA (1.2 equiv.) in isopropanol (0.1 M) was stirred and heated at reflux. The reaction time, work-up, and product isolation procedure are described below.

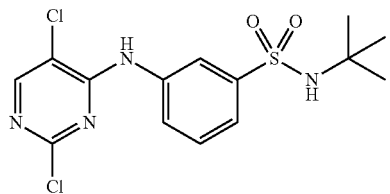 [SMILES: CC(C)(C)NS(=O)(=O)c1cccc(Nc2nc(Cl)ncc2Cl)c1]

2,5-Dichloro-N$^4$-(3-[N-(1,1-dimethylethyl)sulfamoyl]phenyl)pyrimidin-4-amine (SG1-149): This was prepared from 2,4,5-trichloropyrimidine (0.100 g) and SG1-137 (0.031 g) using procedure A (reaction time, 21 h) to give the title compound as a white solid (0.190 g, 93%). Mp: 172-173° C. $^1$H NMR (400 MHz, DMSO-$d_6$): δ 9.79 (s, 1H, disappeared on D$_2$O shake), 8.42 (s, 1H), 8.07 (s, 1H), 7.77 (d, J=8.2 Hz, 1H), 7.64-7.52 (m, 3H; 1H disappeared on D$_2$O shake), 1.11 (s, 9H). HPLC-MS (ESI+): m/z 773.1 [30%, (M$^{35}$Cl$^{35}$Cl+M$^{35}$Cl$^{37}$Cl+Na)$^+$], 377.1 [70%, (M$^{35}$Cl$^{37}$Cl+H)$^+$], 375.1 [100%, (M$^{35}$Cl$^{35}$Cl+H)$^+$].

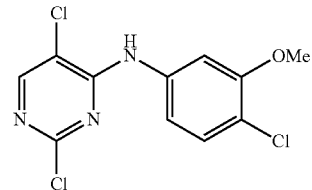 [SMILES: COc1cc(Nc2nc(Cl)ncc2Cl)ccc1Cl]

2,5-Dichloro-N$^4$-(4-chloro-3-methoxyphenyl)pyrimidin-4-amine (SG1-168): This was prepared from 2,4,5-trichloropyrimidine (0.500 g), 4-chloro-3-methoxyaniline (0.451 g), and DIPEA (0.570 mL) using procedure B (reaction time, 12 h). The solvent was removed and EtOAc (20 mL) was added. The organic layer was extracted with water (20 mL). The aqueous layer was re-extracted with EtOAc (20 mL). The organic layers were combined and washed with water and brine (20 mL each), dried (Na$_2$SO$_4$) and concentrated under reduced pressure. The resulting dark purple oil was triturated using EtOAc/hexanes to give the title compound as a light purple solid (0.680 g, 82%). Mp: 136-138° C. $^1$H NMR (400 MHz, DMSO-$d_6$): δ 9.57 (s, 1H, disappeared on D$_2$O shake), 8.41 (s, 1H), 7.49 (d, J=2.2 Hz, 1H), 7.41 (d, J=8.6 Hz, 1H), 7.28 (dd, J=8.6, 2.2 Hz, 1H), 3.82 (s, 3H). HPLC-MS (ESI+): m/z 308.1 [40%, (M$^{35}$Cl$^{37}$Cl$^{37}$Cl+H)$^+$], 306.1 [98%, (M$^{35}$Cl$^{35}$Cl$^{37}$Cl+H)$^+$], 304.0 [100%, (M$^{35}$Cl$^{35}$Cl$^{35}$Cl+H)$^+$].

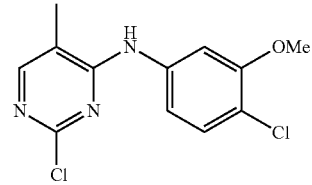 [SMILES: COc1cc(Nc2nc(Cl)ncc2C)ccc1Cl]

2-Chloro-N$^4$-(4-chloro-3-methoxyphenyl)-5-methylpyrimidin-4-amine (SG1-173-01):

This was prepared from 2,4-dichloro-5-methylpyrimidine (1.00 g), 4-chloro-3-methoxyaniline (1.02 g), and DIPEA (1.28 mL) using procedure B (reaction time, 13 h). The solvent was removed and EtOAc (40 mL) was added. The organic layer was extracted with water (40 mL). The aqueous layer was re-extracted with EtOAc (40 mL). The organic layers were combined, washed with water and brine (40 mL each), dried (Na$_2$SO$_4$), and concentrated under reduced pressure. The resulting residue was purified via column chromatography (SiO$_2$) eluting with hexanes/EtOAc (0:10 to 4:6 v/v) to give the title compound as an off-white solid (0.530 g, 30%). Mp: 132-134° C. $^1$H NMR (400 MHz, DMSO-$d_6$): δ 8.90 (s, 1H, disappeared on D$_2$O shake), 8.07 (s, 1H), 7.54 (s, 1H), 7.38 (d, J=8.7 Hz, 1H), 7.33 (d, J=8.7 Hz, 1H), 3.83 (s, 3H), 2.16 (s, 3H). HPLC-MS (ESI+): m/z 286.1 [70%, (M$^{35}$Cl$^{37}$Cl+H)+], 284.1 [100%, (M$^{35}$Cl$^{35}$Cl+H)$^+$].

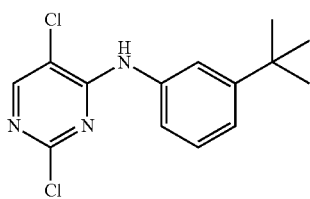 [SMILES: CC(C)(C)c1cccc(Nc2nc(Cl)ncc2Cl)c1]

2,5-Dichloro-N⁴-(3-tert-butylphenyl)pyrimidin-4-amine (SG1-175): A solution of 2,4,5-trichloropyrimidine (1.00 g), 3-(tert-butyl)aniline (0.813 mg), and DIPEA (5.70 mL) in EtOH (5 mL) was heated at reflux for 14 h. The mixture was concentrated under reduced pressure. The residue was dissolved in EtOAc (50 mL) and washed with water (2×50 mL) and brine (50 mL). The organic layer was dried (Na$_2$SO$_4$) and concentrated under reduced pressure to give the title compound as a brown solid (1.545 g, 96%). Mp: 107-110° C. $^1$H NMR (400 MHz, DMSO-d$_6$): δ 9.48 (s, 1H, disappeared on D$_2$O shake), 8.35 (s, 1H), 7.62 (t, J=1.9 Hz, 1H), 7.41 (ddd, J=7.8, 1.9, 1.0 Hz, 1H), 7.29 (t, J=7.8 Hz, 1H), 7.19 (ddd, J=7.8, 1.9, 1.0 Hz, 1H), 1.27 (s, 9H). HPLC-MS (ESI+): m/z 300.1 [10%, (MCl$^{37}$Cl$^{37}$+H)⁺], 298.1 [65%, (M$^{35}$Cl$^{37}$Cl+H)⁺], 296.1 [100%, (M$^{35}$Cl$^{35}$Cl+H)⁺].

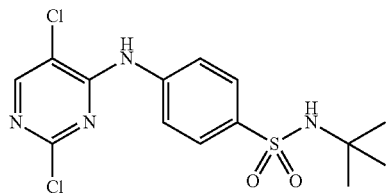 [SMILES: CC(C)(C)NS(=O)(=O)c1ccc(Nc2nc(Cl)ncc2Cl)cc1]

2,5-Dichloro-N⁴-(4[N-(1,1-dimethylethyl)sulfamoyl] phenyl)pyrimidin-4-amine (SG1-182): This was prepared from 2,4,5-trichloropyrimidine (0.500 g) and SG1-177 (0.715 g) using procedure A (stirred for 4 d). The crude solid was purified via flash chromatography (SiO$_2$) eluting with hexanes/EtOAc (0:10 to 4:6 v/v) to provide the title compound as a tangerine-colored solid (0.590 g, 58%). Mp: 180-181° C. $^1$H NMR (400 MHz, DMSO-d$_6$): δ 9.73 (s, 1H, disappeared on D$_2$O shake), 8.46 (s, 1H), 7.80 (s, 4H), 7.48 (s, 1H, disappeared on D$_2$O shake), 1.09 (s, 9H). HPLC-MS (ESI+): m/z 773.1 [10%, (MCl$^{35}$Cl$^{37}$+M$^{35}$Cl$^{35}$Cl+Na)⁺], 379.1 [10%, (MCl$^{37}$Cl$^{37}$+H)⁺], 377.1 [70%, (MCl$^{35}$Cl$^{37}$+H)⁺], 375.1 [100%, (M$^{35}$Cl$^{35}$Cl+H)⁺].

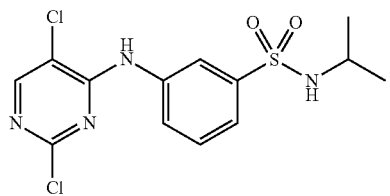

2,5-Dichloro-N⁴-(3-[N-(methylethyl)sulfamoyl]phenyl) pyrimidin-4-amine (SG2-003): This was prepared from 2,4,5-trichloropyrimidine (0.550 g) and SG1-147 (0.740 g) using procedure A (reaction time, 22.5 h) to give the title compound as a white solid (0.948 g, 88%). Mp: 153-155° C. $^1$H NMR (400 MHz, DMSO-d$_6$): δ 9.79 (s, 1H, disappeared on D$_2$O shake), 8.42 (s, 1H), 8.07 (s, 1H), 7.83 (d, J=6.3 Hz, 1H), 7.62-7.53 (m, 311; 1H, disappeared on D$_2$O shake), 3.30 (septet, J=6.6 Hz, 1H), 0.95 (d, J=6.6 Hz, 6H). HPLC-MS (ESI+): m/z 745.0 [10%, (MCl$^{35}$Cl$^{37}$+M$^{35}$Cl$^{35}$Cl+Na)⁺], 365.0 [15%, (M$^{37}$Cl$^{37}$Cl+H)⁺], 363.0 [75%, (M$^{35}$Cl$^{37}$Cl+H)⁺], 361.0 [100%, (M$^{35}$Cl$^{37}$Cl+H)+].

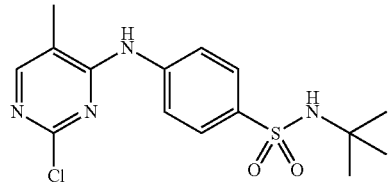 [SMILES: Cc1cnc(Cl)nc1Nc1ccc(S(=O)(=O)NC(C)(C)C)cc1]

2-Chloro-N⁴-(4-[N-(1,1-dimethylethyl)sulfamoyl]phenyl)-5-methylpyrimidin-4-amine (SG2-007): This was prepared from 2,4-dichloro-5-methylpyrimidine (0.500 g) and SG1-177 (0.805 g) using procedure A (reaction time, 22.5 h). The resulting residue was purified via column chromatography (SiO$_2$) eluting with hexanes/EtOAc (3:7 to 5:5 v/v) to give the title compound as an off-white solid (0.541 g, 50%). Mp: 281° C. (dec). $^1$H NMR (400 MHz, DMSO-d$_6$): δ 9.07 (s, 1H, disappeared on D$_2$O shake), 8.13 (s, 1H), 7.85 (d, J=9.0 Hz, 2H), 7.77 (d, J=9.0 Hz, 2H), 7.42 (s, 1H, disappeared on D$_2$O shake), 2.19 (s, 3H), 1.08 (s, 9H). HPLC-MS (ESI+): m/z 731.1 [10%, (2M$^{35}$Cl+H)⁺], 357.1 [40%, (M$^{37}$Cl+H)⁺], 355.1 [100%, (M$^{35}$Cl+H)⁴].

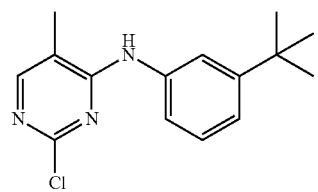 [SMILES: Cc1cnc(Cl)nc1Nc1cccc(C(C)(C)C)c1]

2-Chloro-N⁴-[3-(1,1-dimethylethyl)phenyl]-5-methylpyrimidin-4-amine (SG2-013): A solution of 2,4-dichloro-5-methylpyrimidine (0.500 g), 3-(tert-butyl)aniline (0.458 mg), and DIPEA (3.21 mL) in EtOH (2.5 mL) was heated at reflux for 24 h. The mixture was concentrated under reduced pressure. The resulting residue was dissolved in EtOAc (25 mL), washed with water (2×25 mL) and brine (25 mL). The organic layer was dried (Na$_2$SO$_4$) and concentrated under reduced pressure to give the title compound as an off-white solid (0.564 g, 67%). Mp: 174-175° C. $^1$H NMR (400 MHz, DMSO-d$_6$): δ 8.80 (s, 1H, reduced by 50% on D$_2$O shake), 8.01 (s, 1H), 7.65 (t, J=1.9 Hz, 1H), 7.47 (ddd, J=7.8, 1.9, 1.0 Hz, 1H), 7.26 (t, J=7.8 Hz, 1H), 7.12 (ddd, J=7.8, 1.9, 1.0 Hz, 1H), 2.15 (s, 3H), 1.27 (s, 9H). HPLC-MS (ESI+): m/z 278.1 [40%, (M$^{37}$Cl+H)⁺], 276.1 [100%, (M$^{35}$Cl+H)⁺].

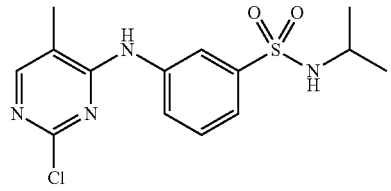 [SMILES: Cc1cnc(Cl)nc1Nc1cccc(S(=O)(=O)NC(C)C)c1]

2-Chloro-N⁴-(3-[N-(methylethyl)sulfamoyl]phenyl)-5-methylpyrimidin-4-amine (SG2-014): This was prepared from 2,4-dichloro-5-methylpyrimidine (0.500 g) and SG1-

147 (0.755 g) using procedure A (reaction time, 10 d) to give the title compound as an off-white solid (0.600 g, 57%). Mp: 192-194° C. $^1$H NMR (400 MHz, DMSO-d$_6$): δ 9.12 (s, 1H, disappeared on D$_2$O shake), 8.10 (t, J=1.8 Hz, 1H, coupling visible upon D$_2$O shake), 8.06 (d, J=0.8 Hz, 1H, coupling visible upon D$_2$O shake), 7.92 (ddd, J=7.9, 1.8, 1.0 Hz, 1H), 7.57 (d, J=6.8 Hz, 1H, disappeared on D$_2$O shake), 7.56 (t, J=7.9 Hz, 1H), 7.49 (dt, J=7.9, 1.8 Hz, 1H), 3.28 (septet, J=6.8 Hz, 1H), 2.17 (s, 3H), 0.95 (d, J=6.8 Hz, 6H). HPLC-MS (ESI+): m/z 681.2 [10%, (2M$^{35}$Cl+H)$^+$], 343.1 [40%, (M$^{37}$Cl+H)+]. 341.1 [100%, (M$^{35}$Cl+H)$^+$].

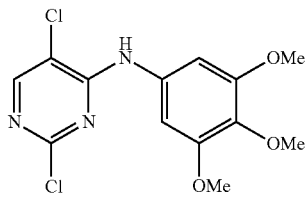

2,5-Dichloro-N$^4$-(3,4,5-trimethoxyphenyl)pyrimidin-4-amine (SG2-047): This was prepared from 2,4,5-trichloropyrimidine (0.367 g), 3,4,5-trimethoxyaniline (0.385 g), and DIPEA (0.420 mL) using procedure B (reaction time, 14 h). The precipitate filtered and washed with water (2×10 mL), hexanes (2×10 mL), and dried to give the title compound as an off-white solid (0.642 g, 97%). Mp: 236° C. (dec). $^1$H NMR (400 MHz, DMSO-d$_6$): δ 9.41 (s, 1H, disappeared on D$_2$O shake), 8.36 (s, 1H), 7.04 (s, 2H), 3.75 (s, 6H), 3.64 (s, 3H). HPLC-MS (ESI+): m/z 681.1 [40%, (M$^{35}$Cl+M$^{37}$Cl+Na)$^+$], 332.1 [60%, (M$^{35}$Cl$^{37}$Cl+H)$^+$], 330.1 [100%, (M$^{35}$Cl$^{35}$Cl+H)$^+$].

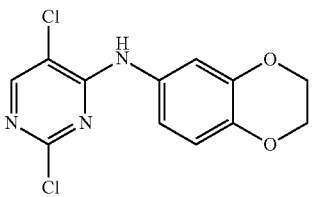 [SMILES: Clc1ncc(Cl)c(Nc2ccc3c(c2)OCCO3)n1]

2,5-Dichloro-N$^4$-(2,3-dihydrobenzo[b][1,4]dioxin-6-yl)pyrimidin-4-amine (SG2-048): This was prepared from 2,4,5-trichloropyrimidine (0.367 g), 2,3-dihydrobenzo[b][1,4]dioxin-6-amine (0.318 g), and DIPEA (0.420 mL) using procedure B (reaction time, 14 h). The solvent was removed and EtOAc (20 mL) was added. The organic layer was washed with water (20 mL). The aqueous layer was re-extracted with EtOAc (20 mL). The organic layers were combined and washed with water and brine (20 mL each), dried (Na$_2$SO$_4$), and concentrated under reduced pressure to give the title compound as a dark brown oil (0.635 g, 107%, 90% purity based on $^1$H NMR), which was used for the next step without purification. $^1$H NMR (400 MHz, DMSO-d$_6$): δ 9.36 (s, 1H, disappeared on D$_2$O shake), 8.31 (s, 1H), 7.10 (d, J=2.5 Hz, 1H), 6.98 (dd, J=8.7, 2.5 Hz, 1H), 6.84 (d, J=8.7 Hz, 1H), 4.23 (s, 4H). HPLC-MS (ESI+): m/z 300.1 [70%, (M$^{35}$Cl$^{37}$Cl+H)$^+$], 298.1 [100%, (M$^{35}$Cl$^{35}$Cl+H)$^+$].

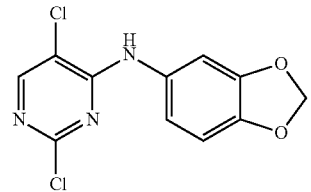 [SMILES: Clc1ncc(Cl)c(Nc2ccc3c(c2)OCO3)n1]

2,5-Dichloro-N$^4$-(Benzo[d][1,3]dioxol-5-yl)pyrimidin-4-amine (SG2-049): This was prepared from 2,4,5-trichloropyrimidine (0.367 g), benzo[d][1,3]dioxol-5-amine (0.288 g), and DIPEA (0.420 mL) using procedure B (reaction time, 14 h). The mixture was concentrated under reduced pressure. The resulting solid was washed with water (3×10 mL), hexanes (1×10 mL), water (1×10 mL), and dried to give the title compound as a brown solid (0.642 g, 97%). Mp: 197° C. (dec). $^1$H NMR (400 MHz, DMSO-d$_6$): δ 9.43 (s, 1H, disappeared on D$_2$O shake), 8.31 (s, 1H), 7.13 (s, 1H), 6.98-6.87 (m, 2H), 6.03 (s, 2H). HPLC-MS (ESI+): m/z 286.1 [70%, (M$^{35}$Cl$^{37}$Cl+H)±], 284.1 [100%, (M$^{35}$Cl$^{35}$Cl+H)$^+$].

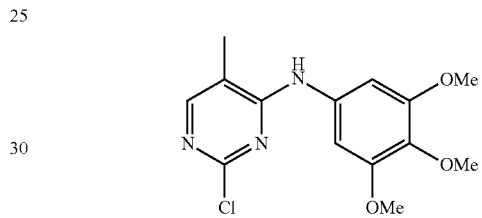

2-Chloro-N$^4$-(3,4,5-trimethoxyphenyl)-5-methylpyrimidin-4-amine (SG2-050): This was prepared from 2,4-dichloro-5-methylpyrimidine (0.326 g), 3,4,5-trimethoxyaniline (0.385 g), and DIPEA (0.420 mL) using procedure B (reaction time, 14 h). The mixture was concentrated under reduced pressure. The resulting solid was washed with MeOH (1×5 mL), water (2×10 mL), hexanes (1×10 mL), and dried to give the title compound as an off-white solid (0.360 g, 58%). Mp: 222° C. (dec). $^1$H NMR (400 MHz, DMSO-d$_6$): δ 8.75 (s, 1H, reduced by 70% on D$_2$O shake), 8.02 (d, J=0.7 Hz, 1H), 7.09 (s, 2H), 3.75 (s, 6H), 3.63 (s, 1H), 2.14 (s, 3H). HPLC-MS (ESI+): m/z 312.2 [20%, (M$^{37}$Cl+H)+], 310.1 [100%, (M$^{35}$Cl+H)$^+$].

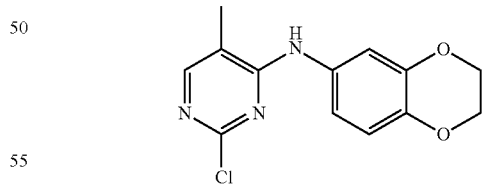

2-Chloro-N$^4$-(2,3-dihydrobenzo[b][1,4]dioxin-6-yl)-5-methylpyrimidin-4-amine (SG2-051): This was prepared from 2,4-dichloro-5-methylpyrimidine (0.326 g), 2,3-dihydrobenzo[b][1,4]dioxin-6-amine (0.318 g), and DIPEA (0.420 mL) using procedure B (reaction time, 14 h). The solvent was removed and EtOAc (20 mL) was added. The organic layer was extracted with water (20 mL). The aqueous layer was re-extracted with EtOAc (20 mL). The organic layers were combined and washed with water and brine (20 mL each), dried (Na$_2$SO$_4$), concentrated under reduced pressure to give the title compound as a dark brown oil (0.590 g, 106%, 90% purity based on $^1$H NMR), which was used for the next step without purification. $^1$H NMR (400 MHz, DMSO-d$_6$): δ 8.68 (s, 1H, disappeared on D$_2$O shake), 7.96 (d, J=0.9 Hz, 1H), 7.18 (d, J=2.5 Hz, 1H), 7.01 (dd, J=8.7, 2.5 Hz, 1H), 6.82 (d, J=8.7 Hz, 1H), 4.34-4.15 (m, 4H), 2.10 (s, 3H). HPLC-MS (ESI+): m/z 280.1 [30%, (M$^{37}$Cl+H)$^+$], 278.1 [100%, (M$^{35}$Cl+H)$^+$].

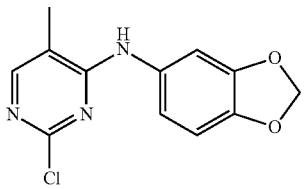 [SMILES: Cc1cnc(Cl)nc1Nc1ccc2c(c1)OCO2]

2-Chloro-N$^4$-(Benzo[d][1,3]dioxol-5-yl)-5-methylpyrimidin-4-amine (SG2-052): This was prepared from 2,4-dichloro-5-methylpyrimidine (0.326 g), benzo[d][1,3]dioxol-5-amine (0.288 g), and DIPEA (0.420 mL) using procedure B (reaction time, 14 h). The solvent was removed. The solid obtained was poured into water/MeOH (10:1, 20 mL) and the mixture was sonicated. The precipitate filtered and washed with water (3×10 mL), hexanes (1×10 mL), water (1×10 mL), then dried to give the title compound as a dark grey solid (0.425 g, 81%). Mp: 134° C. (dec). $^1$H NMR (400 MHz, DMSO-d$_6$): δ 8.76 (s, 1H, disappeared on D$_2$O shake), 7.97 (s, J=0.9 Hz, 1H), 7.20 (d, J=2.1 Hz, 1H), 6.97 (dd, J=8.4, 2.1 Hz, 1H), 6.89 (d, J=8.4 Hz, 1H), 6.01 (s, 2H), 2.11 (d, J=0.7 Hz, 3H). HPLC-MS (ESI+): m/z 266.1 [40%, (M$^{37}$Cl+H)±], 264.1 [100%, (M$^{35}$Cl+H)$^+$].

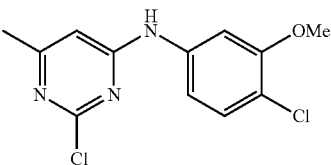 [SMILES: COc1cc(Nc2cc(C)nc(Cl)n2)ccc1Cl]

2-Chloro-N$^4$-(4-chloro-3-methoxyphenyl)-6-methylpyrimidin-4-amine (SG2-053-01): This was prepared from 2,4-dichloro-6-methylpyrimidine (0.326 g), 4-chloro-3-methoxyaniline (0.331 mg), and DIPEA (0.420 mL) using procedure B (reaction time, 3 d). Ethyl acetate (15 mL) was added to the mixture which was then washed with water (15 mL). The aqueous layer was re-extracted with EtOAc (15 mL). The organic layers were combined, washed with water and brine (15 mL each), dried (Na$_2$SO$_4$), and concentrated under reduced pressure. The resulting residue was purified via column chromatography (SiO$_2$) eluting with hexanes/EtOAc (2:8 to 3:4 v/v) to give the title compound as an off-white solid (0.334 g, 59%). Mp: 168-169° C. $^1$H NMR (400 MHz, DMSO-d$_6$): δ 10.02 (s, 1H, disappeared on D$_2$O shake), 7.44 (d, J=1.7 Hz, 1H), 7.36 (d, J=8.6 Hz, 1H), 7.17 (dd, J=8.6, 1.7 Hz, 1H), 6.59 (s, 1H), 3.83 (s, 3H), 2.28 (s, 3H). HPLC-MS (ESI+): m/z 286.1 [70%, (M$^{35}$Cl$^{37}$Cl+H)$^+$], 284.1 [100%, (M$^{35}$Cl$^{35}$Cl+H)$^+$].

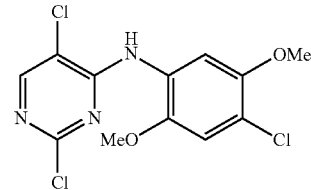 [SMILES: COc1cc(Nc2nc(Cl)ncc2Cl)c(OC)cc1Cl]

2,5-Dichloro-N$^4$-(4-chloro-2,5-dimethoxyphenyl)pyrimidin-4-amine (SG2-059): This was prepared from 2,4,5-trichloropyrimidine (0.367 g), 4-chloro-2,5-dimethoxyaniline (0.394 g), and DIPEA (0.420 mL) using procedure B (reaction time, 14 h). The precipitate was filtered, washed with isopropanol (2×10 mL), water (2×10 mL), hexanes (1×10 mL), and dried to give the title compound as an off-white solid (0.622 g, 93%). Mp: 195-198° C. $^1$H NMR (400 MHz, CDCl3): δ 8.46 (s, 1H), 8.21 (s, 1H), 8.09 (s, 1H, disappeared on D$_2$O shake), 6.95 (s, 1H), 3.95 (s, 3H), 3.91 (s, 3H). HPLC-MS (ESI+): m/z 338.0 [30%, (M$^{35}$Cl$^{37}$Cl$^{37}$Cl+H)$^+$]. 336.0 [90%, (M$^{35}$Cl$^{35}$Cl$^{37}$Cl+H)$^+$], 334.0 [100%, (M$^{35}$Cl$^{35}$Cl$^{35}$Cl+H)+].

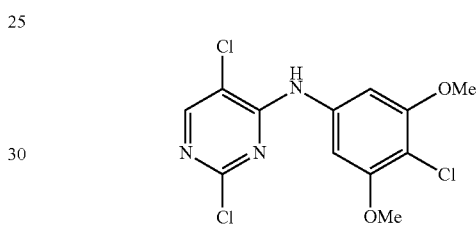

2,5-Dichloro-N$^4$-(4-chloro-3,5-dimethoxyphenyl)pyrimidin-4-amine (SG2-066): This was prepared from 2,4,5-trichloropyrimidine (0.183 g), SG2-062-01 (0.197 g), and DIPEA (0.210 mL) using procedure B (reaction time, 14.5 h). The precipitate was filtered, washed with isopropanol (1×10 mL), water (2×10 mL), isopropanol (1×10 mL), hexanes (1×10 mL), and dried to give the title compound as an off-white solid (0.315 g, 94%). Mp: 252° C. (dec). $^1$H NMR (400 MHz, DMSO-d$_6$): δ 9.55 (s, 1H, disappeared on D$_2$O shake), 8.42 (s, 1H), 7.23 (s, 2H), 3.81 (s, 6H). HPLC-MS (ESI+): m/z 356.0 [40%, (M$^{35}$Cl$^{35}$Cl$^{35}$Cl+Na)$^+$], 338.0 [30%, (MCl$^{35}$Cl$^{37}$Cl$^{37}$+H)±], 336.0 [95%, (M$^{35}$Cl$^{35}$Cl$^{37}$Cl+H)$^+$], 334.1 [100%, (M$^{35}$Cl$^{35}$Cl$^{35}$Cl+H)$^+$].

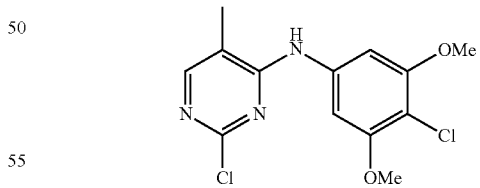

2-Chloro-N$^4$-(4-chloro-3,5-dimethoxyphenyl)-5-methylpyrimidin-4-amine (SG2-067): This was prepared from 2,4-dichloro-5-methylpyrimidine (0.163 g), SG2-062-01 (0.197 g), and DIPEA (0.210 mL) using procedure B (reaction time, 1.5 d). The precipitate was filtered, washed with isopropanol (1×10 mL), water (2×10 mL), isopropanol (1×10 mL), hexanes (1×10 mL), and dried to give the title compound as a white solid (0.174 g, 55%). Mp: 237-238° C. $^1$H NMR (400 MHz, DMSO-d$_6$): δ 8.89 (s, 1H, disappeared on D$_2$O shake), 8.08 (s, 1H), 7.29 (s, 2H), 3.81 (s, 6H), 2.17

(s, 3H). HPLC-MS (ESI+): m/z 316.1 [60%, (M$^{35}$Cl$^{37}$Cl+H)$^+$], 314.1 [100%, (M$^{35}$Cl$^{35}$Cl+H)$^+$].

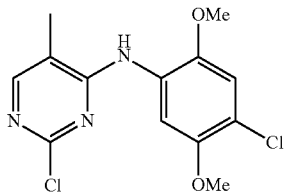 [SMILES: COc1cc(Nc2nc(Cl)ncc2C)c(OC)cc1Cl]

2-Chloro-N$^4$-(4-chloro-2,5-dimethoxyphenyl)-5-methylpyrimidin-4-amine (SG2-068): This was prepared from 2,4-dichloro-5-methylpyrimidine (0.326 g), 4-chloro-2,5-dimethoxyaniline (0.394 g), and DIPEA (0.420 mL) using procedure B (reaction time, 5 d). The precipitate was filtered, washed with isopropanol (1×10 mL), water (2×10 mL), isopropanol (1×10 mL), hexanes (1×10 mL), and dried to give the title compound as an off-white solid (0.284 g, 45%). Mp: 184-185° C. $^1$H NMR (400 MHz, DMSO-d$_6$): δ 8.44 (s, 1H, disappeared on D$_2$O shake), 8.01 (s, 1H), 7.46 (s, 1H), 7.21 (s, 1H), 3.78 (s, 3H), 3.75 (s, 3H), 2.12 (s, 3H). HPLC-MS (ESI+): m/z 316.1 [60%, (M$^{35}$Cl$^{37}$Cl+H)$^+$], 314.1 [100%, (M$^{35}$Cl$^{35}$Cl+H)$^+$].

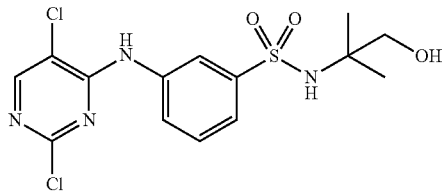 [SMILES: CC(C)(CO)NS(=O)(=O)c1cccc(Nc2nc(Cl)ncc2Cl)c1]

2,5-Dichloro-N$^4$(3-[N-(1-hydroxy-2-methylpropan-2-yl)sulfamoyl]phenyl)pyrimidin-4-amine (SG2-082): This was prepared from 2,4,5-trichloropyrimidine (0.183 g) and SG2-079 (0.281 g) using procedure A (reaction time, 16 h) to give the title compound as a white solid (0.318 g, 81%). Mp: 183-186° C. $^1$H NMR (400 MHz, DMSO-d$_6$): δ 9.78 (s, 1H, disappeared on D$_2$O shake), 8.42 (s, 1H), 8.06 (s, 1H), 7.79 (d, J=7.9 Hz, 1H), 7.62 (d, J=7.9 Hz, 1H), 7.56 (t, J=7.9 Hz, 1H), 7.33 (s, 1H, disappeared on D$_2$O shake), 4.75 (t, J=5.8 Hz, 1H, disappeared on D$_2$O shake), 3.20 (d, J=5.8 Hz, 2H), 1.03 (s, 6H). HPLC-MS (ESI+): m/z 805.1 [50%, (M$^{35}$Cl$^{35}$Cl+M$^{35}$Cl$^{37}$Cl+Na)$^+$], 803.1 [30%, (2M$^{35}$Cl$^{35}$Cl+Na)$^+$], 413.0 [30%, (M$^{35}$Cl$^{35}$Cl+Na)$^+$], 393.1 [60%, (M$^{35}$Cl$^{37}$Cl+H)$^+$], 391.1 [100%, (M$^{35}$Cl$^{35}$Cl+H)$^+$].

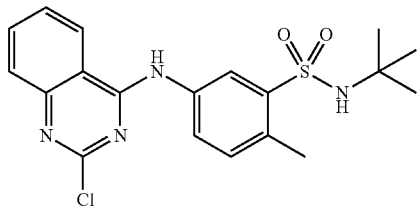 [SMILES: Cc1ccc(Nc2nc(Cl)nc3ccccc23)cc1S(=O)(=O)NC(C)(C)C]

2-Chloro-N$^4$-(4-methyl-[3-(N-1,1-dimethylethyl)sulfamoyl]phenyl)quinazoline-4-amine (SG2-115): This was prepared from MA2-028 (0.199 g), SG2-100 (0.218 g), and DIPEA (0.210 mL) using procedure B (reaction time, 15 min). Water (6 mL) was added and the precipitate filtered, washed with water (3×10 mL), hexanes (3×10 mL), and dried to give the title compound as a yellow solid (0.315 g, 78%). Mp: 197-199° C. $^1$H NMR (400 MHz, DMSO-d$_6$): δ 10.35 (s, 1H, disappeared on D$_2$O shake), 8.56 (d, J=8.2 Hz, 1H), 8.30 (d, J=2.3 Hz, 1H), 7.95 (dd, J=8.3, 2.3 Hz, 1H), 7.88 (ddd, J=8.2, 7.0, 1.1 Hz, 1H), 7.71 (dd, J=8.2, 1.1 Hz, 1H), 7.65 (ddd, J=8.2, 7.0, 1.1 Hz, 1H), 7.52 (s, 1H, disappeared on D$_2$O shake), 7.41 (d, J=8.3 Hz, 1H), 2.57 (s, 3H), 1.13 (s, 9H). HPLC-MS (ESI+): m/z 407.1 [30%, (M$^{37}$Cl+H)$^+$], 405.1 [100%, (M$^{35}$Cl+H)$^+$].

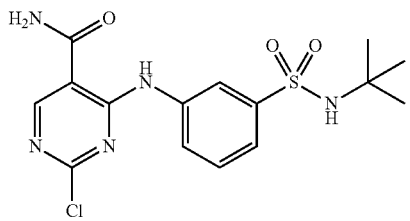 [SMILES: CC(C)(C)NS(=O)(=O)c1cccc(Nc2nc(Cl)ncc2C(N)=O)c1]

2-Chloro-N$^4$-(3-[N-(1,1-dimethylethyl)sulfamoyl]phenyl)-5-carbamoylpyrimidin-4-amine (SG2-139-01): This was prepared from SG2-138 (0.192 g) and SG1-137 (0.228 g) using procedure A (reaction time, 13.5 h). The resulting residue was purified via column chromatography (SiO$_2$) eluting with hexanes/EtOAc (2:8 to 6:4 v/v) to give the title compound as a white solid (0.105 g, 27%). Mp: 243° C. (dec). $^1$H NMR (400 MHz, DMSO-d$_6$): δ 11.65 (s, 1H, disappeared on D$_2$O shake), 8.80 (s, 1H), 8.47 (s, 1H, disappeared on D$_2$O shake), 8.10 (s, 1H), 8.01 (s, 1H, disappeared on D$_2$O shake), 7.83-7.75 (m, 1H), 7.59-7.53 (m, 3H; 1H disappeared on D$_2$O shake), 1.11 (s, 9H). HPLC-MS (ESI+): m/z 769.1 [40%, (2M$^{37}$Cl+H)$^+$], 767.1 [100%, (2M$^{35}$Cl+H)+], 386.1 [40%, (M$^{37}$Cl+H)$^+$], 384.1 [100%, (M$^{35}$Cl+H)$^+$].

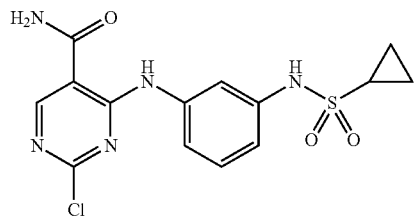 [SMILES: NC(=O)c1cnc(Cl)nc1Nc1cccc(NS(=O)(=O)C2CC2)c1]

2-Chloro-N$^4$-[3-(Cyclopropanesulfonamido)phenyl]-5-carboxamoylpyrimidin-4-amine (SG2-140-01): This was prepared from SG2-138 (0.192 g) and RJ1-025 (0.212 g) using procedure A (reaction time, 13.5 h). The resulting residue was purified via column chromatography (SiO$_2$) eluting with hexanes/EtOAc (3:7 to 5:5 v/v) to give the title compound as an off-white solid (0.097 g, 26%). Mp: 239° C. (dec). $^1$H NMR (400 MHz, DMSO-d$_6$): δ 11.52 (s, 1H, disappeared on D$_2$O shake), 9.84 (s, 1H, disappeared on D$_2$O shake), 8.77 (s, 1H), 8.44 (s, 1H, disappeared on D$_2$O shake), 7.97 (s, 1H, disappeared on D$_2$O shake), 7.55 (s, 1H), 7.40-7.21 (m, 2H), 7.03-6.95 (m, 1H), 2.71-2.63 (m, 1H), 1.02-0.90 (m, 4H). HPLC-MS (ESI+): m/z 737.1 [20%, (M$^{37}$Cl+M$^{35}$Cl+H)$^+$], 735.1 [30%, (2M$^{35}$Cl+H)$^+$], 370.1 [40%, (M$^{37}$Cl+H)$^+$], 368.1 [100%, (M$^{35}$Cl+H)$^+$].

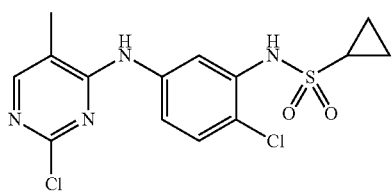 [SMILES: Cc1cnc(Cl)nc1Nc1ccc(Cl)c(NS(=O)(=O)C2CC2)c1]

2-Chloro-N⁴-[4-chloro-3-(cyclopropanesulfonamido)phenyl]-5-methylpyrimidin-4-amine (SG2-163): This was prepared from 2,4-dichloro-5-methylpyrimidine (0.082 g), SG2-159 (0.123 g), and DIPEA (0.210 mL) using procedure B (reaction time, 22.5 h). Water (10 mL) was added and the precipitate filtered, washed with water (3×10 mL), hexanes (1×10 mL), and dried to give the title compound as an off-white solid (0.099 g, 53%). Mp: 218-219° C. $^1$H NMR (400 MHz, DMSO-d$_6$): δ 9.46 (s, 1H, disappeared on D$_2$O shake), 9.00 (s, 1H, disappeared on D$_2$O shake), 8.08 (d, J=0.8 Hz, 1H), 7.86 (d, J=2.5 Hz, 1H), 7.57 (dd, J=8.8, 2.5 Hz, 1H), 7.48 (d, J=8.8 Hz, 1H), 2.75-2.65 (m, 1H), 2.16 (s, 3H), 1.04-0.90 (m, 4H). HPLC-MS (ESI+): m/z 375.1 [70%, (M$^{35}$Cl$^{37}$Cl+H)$^+$], 373.1 [100%, (M$^{35}$Cl$^{35}$Cl+H)$^+$].

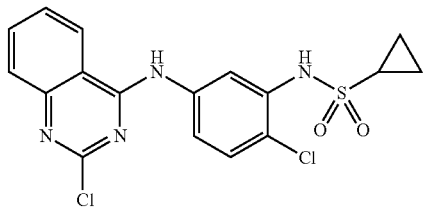 [SMILES: O=S(=O)(Nc1cc(Nc2nc(Cl)nc3ccccc23)ccc1Cl)C1CC1]

2-Chloro-N⁴-[4-chloro-3-(cyclopropanesulfonamido)phenyl]-quinazoline-4-amine (SG2-164): This was prepared from MA2-028 (0.099 g), SG2-159 (0.123 g), and DIPEA (0.210 mL) using procedure B (reaction time, 14 h). Water (5 mL) was added and the precipitate filtered and washed with water (3×10 mL), hexanes (1×10 mL), and dried to give the title compound as a yellow solid (0.125 g, 61%). Mp: 253-256° C. $^1$H NMR (400 MHz, DMSO-d$_6$): δ 10.31 (s, 1H, disappeared on D$_2$O shake), 9.54 (s, 1H, disappeared on D$_2$O shake), 8.57 (d, J=8.5 Hz, 1H), 8.02 (d, J=2.5 Hz, 1H), 7.90 (ddd, J=8.4, 7.1, 1.5 Hz, 1H), 7.76 (dd, J=8.4, 1.5 Hz, 1H), 7.73 (dd, J=8.4, 1.5 Hz, 1H), 7.66 (ddd, J=8.4, 7.1, 1.5 Hz, 1H), 7.56 (d, J=8.5 Hz, 1H), 2.78-2.69 (m, 1H), 1.06-0.91 (m, 4H). HPLC-MS (ESI+): m/z 411.1 [70%, (M$^{35}$Cl$^{37}$Cl+H)$^+$], 409.1 [100%, (M$^{35}$Cl$^{35}$Cl+H)$^+$].

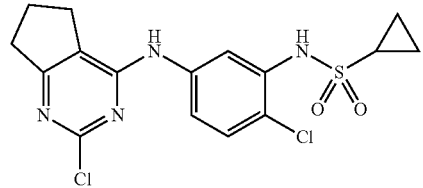 [SMILES: O=S(=O)(Nc1cc(Nc2nc(Cl)nc3c2CCC3)ccc1Cl)C1CC1]

2-Chloro-N⁴-[4-Chloro-3-(cyclopropanesulfonamido)phenyl]-6,7-dihydro-5H-cyclopenta[d]pyrimidine-4-amine (SG2-165): This was prepared from MA2-092 (0.095 g), SG2-159 (0.123 g), and DIPEA (0.210 mL) using procedure B (reaction time, 1.5 d). Water (5 mL) was added and the precipitate filtered, washed with water (3×10 mL), hexanes (1×10 mL), and dried to give the title compound as a light brown solid (0.099 g, 50%). Mp: 237° C. (dec). $^1$H NMR (400 MHz, DMSO-d$_6$): δ 9.45 (brs, 1H, disappeared on D$_2$O shake), 9.27 (s, 1H, disappeared on D$_2$O shake), 7.87 (d, J=2.4 Hz, 1H), 7.60 (dd, J=8.8, 2.4 Hz, 1H), 7.46 (d, J=8.8 Hz, 1H), 2.80 (t, J=7.6 Hz, 4H), 2.74-2.64 (m, 1H), 2.05 (quintet, J=7.6 Hz, 2H), 1.02-0.89 (m, 4H). HPLC-MS (ESI+): m/z 401.1 [60%, (M$^{35}$Cl$^{37}$Cl+H)$^+$], 399.1 [100%, (M$^{35}$Cl$^{35}$Cl+H)$^+$].

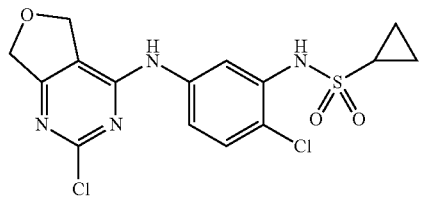 [SMILES: O=S(=O)(Nc1cc(Nc2nc(Cl)nc3c2COC3)ccc1Cl)C1CC1]

2-Chloro-N⁴-[4-chloro-3-(cyclopropanesulfonamido)phenyl]-(5,7-dihydrofuro[3,4-d]pyrimidine-4-amine) (SG2-166): This was prepared from MA2-096 (0.095 g), SG2-159 (0.123 g), and DIPEA (0.210 mL) using procedure B (reaction time, 14 h). Water (5 mL) was added and the precipitate filtered, washed with water (3×10 mL), hexanes (1×10 mL), and dried to give the title compound as a light brown solid (0.160 g, 80%). Mp: 252° C. (dec). $^1$H NMR (400 MHz, DMSO-d$_6$): δ 9.69 (s, 1H, disappeared on D$_2$O shake), 9.49 (s, 1H, disappeared on D$_2$O shake), 7.82 (d, J=2.5 Hz, 1H), 7.61 (dd, J=8.8, 2.5 Hz, 1H), 7.50 (d, J=8.8 Hz, 1H), 4.98 (s, 2H), 4.84 (s, 2H), 2.73-2.63 (m, 1H), 1.05-0.86 (m, 4H). HPLC-MS (ESI−) m/z 401.0 [70%, (M$^{35}$Cl$^{37}$Cl−H)$^-$], 399.0 [100%, (M$^{35}$Cl$^{35}$Cl−H)$^-$].

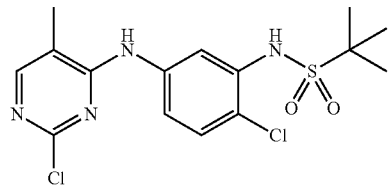 [SMILES: Cc1cnc(Cl)nc1Nc1ccc(Cl)c(NS(=O)(=O)C(C)(C)C)c1]

2-Chloro-N⁴-(4-chloro-[3-(1,1-dimethylethylsulfonamido)]phenyl) methylpyrimidin-4-amine (SG3-012): This was prepared from 2,4-dichloro-5-methylpyrimidine (0.082 g), SG3-105 (0.131 g), and DIPEA (0.210 mL) using procedure B (reaction time, 20 h at reflux, 1.5 d at 120° C.). Water (5 mL) was added and the precipitate filtered, washed with water (2×5 mL), hexanes (2×5 mL), and dried to give the title compound as a light brown solid (0.101 g, 52%). Mp: 274° C. (dec). $^1$H NMR (400 MHz, DMSO-d$_6$): δ 9.33 (s, 1H, disappeared on D$_2$O shake), 8.99 (s, 1H, disappeared on D$_2$O shake), 8.07 (s, 1H), 7.92 (d, J=2.4 Hz, 1H), 7.56 (brd, J=8.7 Hz, 1H), 7.44 (d, J=8.7 Hz, 1H), 2.16 (s, 3H), 1.32 (s, 9H). HPLC-MS (ESI+): m/z 391.1 [70%, (M$^{35}$Cl$^{37}$Cl+H)$^+$], 389.1 [100%, (M$^{35}$Cl$^{35}$Cl+H)$^+$].

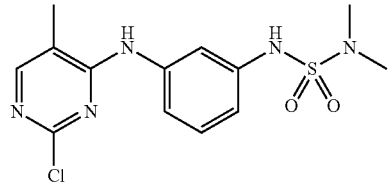 [SMILES: Cc1cnc(Cl)nc1Nc1cccc(NS(=O)(=O)N(C)C)c1]

2-Chloro-$N^4$-([3-(N,N-dimethylsulfamoylamino)]phenyl)-5-methylpyrimidin-4-amine (SG3-038): A mixture of 2,4-dichloro-5-methylpyrimidine (0.163 g), SG3-033-01 (0.215 g), and DIPEA (0.420 mL) in isopropanol (1 mL) was stirred and heated at reflux for 3 d. The solvent was removed and the resulting oil was purified via column chromatography (SiO$_2$) eluting with hexanes/EtOAc (3:7 to 6:4 v/v) to give the title compound as a brown solid (0.172 g, 50%). Mp: 270° C. (dec). $^1$H NMR (400 MHz, DMSO-d$_6$): δ 9.85 (brs, 1H, disappeared on D$_2$O shake), 8.85 (s, 1H, disappeared on D$_2$O shake), 8.03 (s, 1H), 7.52 (s, 1H), 7.31-7.18 (m, 2H), 6.93 (dt, J=6.8, 2.1 Hz, 1H), 2.71 (s, 6H), 2.15 (s, 3H). HPLC-MS (ESI+): m/z 344.1 [40%, (M$^{37}$Cl+H)$^+$], 342.2 [100%, (M$^{35}$Cl+H)$^+$].

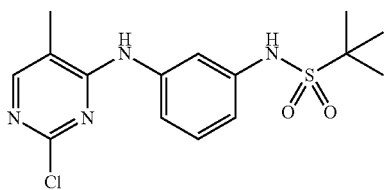 [SMILES: Cc1cnc(Cl)nc1Nc1cccc(NS(=O)(=O)C(C)(C)C)c1]

2-Chloro-$N^4$-[3-(1,1-dimethylethylsulfonamido)phenyl]-5-methylpyrimidin-4-amine (SG3-053): A mixture of 2,4-dichloro-5-methylpyrimidine (0.326 g), MA2-010 (0.457 g), and DIPEA (0.836 mL) in isopropanol (2 mL) was stirred and heated at reflux for 3 d. The solvent was removed and the resulting oil was purified via column chromatography (SiO$_2$) eluting with hexanes/EtOAc (1:9 to 1:1 v/v) to give the title compound as a brown solid (0.420 g, 59%). Mp: 258° C. (dec). $^1$H NMR (400 MHz, DMSO-d$_6$): δ 9.66 (s, 1H, reduced by 70% on D$_2$O shake), 8.88 (s, reduced by 50% on D$_2$O shake), 8.03 (d, J=0.9 Hz, 1H), 7.58 (t, J=1.8 Hz, 1H), 7.26 (dt, J=8.0, 1.8 Hz, 1H), 7.22 (t, J=8.0 Hz, 1H), 6.99 (dt, J=8.0, 1.8 Hz, 1H), 2.14 (s, 3H), 1.28 (s, 9H). HPLC-MS (ESI+): m/z 357.1 [40%, (M$^{37}$Cl+H)$^+$], 355.1 [100%, (M$^{35}$Cl+H)$^+$].

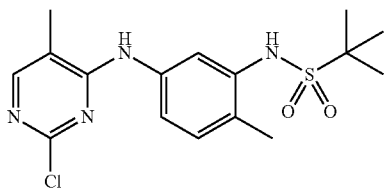

2-Chloro-$N^4$-(4-methyl-[3-(1,1-dimethylethylsulfonamido)]phenyl)-5-methylpyrimidin-4-amine (SG3-126): A mixture of 2,4-dichloro-5-methylpyrimidine (0.163 g), SG3-124 (0.242 g), and DIPEA (0.420 mL) in isopropanol (1 mL) was stirred and heated at 120° C. for 3.5 d. Water (5 mL) was added and the precipitate filtered, washed with water (2×10 mL), hexanes (2×10 mL), and dried to give the title compound as a yellow solid (0.297 g, 81%). Mp: 246° C. (dec). $^1$H NMR (400 MHz, DMSO-d$_6$): δ 8.86 (s, 1H, disappeared on D$_2$O shake), 8.84 (s, 1H, disappeared on D$_2$O shake), 8.01 (d, J=0.8 Hz, 1H), 7.73 (d, J=2.2 Hz, 1H), 7.34 (dd, J=8.3, 2.2 Hz, 1H), 7.15 (d, 0.1=8.3 Hz, 1H), 2.30 (s, 3H), 2.14 (s, 3H), 1.32 (s, 9H). HPLC-MS (ESI+): m/z 759.3 [10%, (2M$^{35}$Cl+Na)$^+$], 371.2 [40%, (M$^{37}$Cl+H)$^+$], 369.2 [100%, (M$^{35}$Cl+H)$^+$].

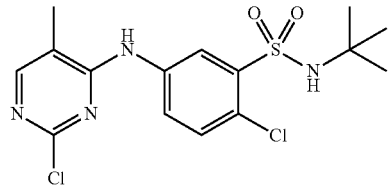 [SMILES: Cc1cnc(Cl)nc1Nc1ccc(Cl)c(S(=O)(=O)NC(C)(C)C)c1]

2-Chloro-$N^4$-(4-chloro-[3-(N-1,1-dimethylethyl)sulfamoyl]phenyl)-5-methylpyrimidin-4-amine (SG3-145): A mixture of 2,4-dichloro-5-methylpyrimidine (0.163 g), SG3-142-01 (0.262 g), and DIPEA (0.420 mL) in isopropanol (1 mL) was stirred and heated at 120° C. for 3 d, 130° C. for 3 d, and 140° C. for 3 d. The solvent was removed and the resulting oil was purified via column chromatography (SiO$_2$) eluting with hexanes/EtOAc (0:10 to 3:7 v/v) to give the title compound as a yellow solid (0.241 g, 62%). Mp: 282° C. (dec). $^1$H NMR (400 MHz, DMSO-d$_6$): δ 9.19 (s, 1H, reduced by 50% on D$_2$O shake), 8.34 (d, J=2.7 Hz, 1H), 8.11 (d, J=0.9 Hz, 1H), 7.95 (dd, J=8.7, 2.7 Hz, 1H), 7.66 (s, 1H, reduced by 40% on D$_2$O shake), 7.60 (d, J=8.7 Hz, 1H), 2.17 (s, 3H), 1.12 (s, 9H). HPLC-MS (ESI+): m/z 779.1 [20%, (M$^{35}$Cl$^{37}$Cl+M$^{35}$Cl$^{35}$Cl+H)$^+$], 391.1 [80%, (M$^{35}$Cl$^{37}$Cl+H)$^+$], 389.1 [100%, (M$^{35}$Cl$^{35}$Cl+H)$^+$].

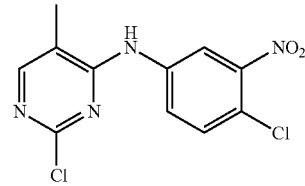 [SMILES: Cc1cnc(Cl)nc1Nc1ccc(Cl)c([N+](=O)[O-])c1]

2-Chloro-$N^4$-(4-chloro-3-nitrophenyl)-5-methylpyrimidin-4-amine (SG3-149): A mixture of 2,4-dichloro-5-methylpyrimidine (4.00 g), 4-chloro-3-nitroaniline (4.23 g), and DIPEA (10.26 mL) in isopropanol (12 mL) in a 10-mL Ace pressure tube was stirred and heated at 160° C. for 6 d. The solvent was removed and the resulting oil was purified via column chromatography (SiO$_2$) eluting with hexanes/EtOAc (0:10 to 1:1 v/v) to give the title compound as a yellow solid (3.623 g, 49%). Mp: 251° C. (dec). $^1$H NMR (400 MHz, DMSO-d$_6$): δ 9.28 (s, 1H, disappeared on D$_2$O shake), 8.47 (d, J=2.4 Hz, 1H), 8.17 (s, 1H), 8.05 (dd, J=8.8, 2.4 Hz, 1H), 7.76 (d, J=8.8 Hz, 1H), 2.19 (s, 3H). HPLC-MS (ESI+): m/z 301.1 [60%, (M$^{35}$Cl$^{37}$Cl+H)$^+$], 299.1 [100%, (M$^{35}$Cl$^{35}$Cl+H)$^+$].

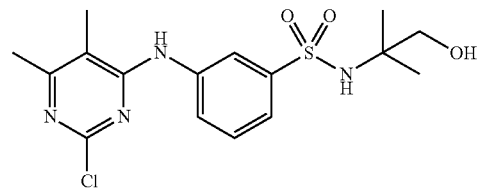 [SMILES: Cc1nc(Cl)nc(Nc2cccc(S(=O)(=O)NC(C)(C)CO)c2)c1C]

2-Chloro-$N^4$(3-[N-(1-hydroxy-2-methylpropan-2-yl)sulfamoyl]phenyl)-5,6-dimethylpyrimidin-4-amine (SG2-084): This was prepared from RJ1-008 (0.177 g) and SG2-079 (0.281 g) using procedure A (reaction time, 16 h at 80° C.) to give the title compound as a white solid (0.318 g, 81%). The solvent was removed under reduced pressure and the resulting residue was purified via column chromatography (SiO$_2$) eluting with hexanes/EtOAc (0:10 to 4:6 v/v) to give the title compound as an off-white solid (0.060 g, 16%; 78% purity based on HPLC-MS) which was used in the next step without further purification. $^1$H NMR (400 MHz, DMSO-d$_6$): 9.02 (s, 1H), 8.05 (s, 1H), 7.88-7.80 (m, 2H), 7.51 (brs, 1H), 7.31 (s, 1H), 3.19 (d, J=2.9 Hz, 2H), 2.33 (s, 3H), 2.16 (s, 3H), 1.15 (s, 6H). HPLC-MS (ESI+): m/z 387.2 [35%, (M$^{37}$Cl+H)$^+$], 385.1 [100%, (M$^{35}$Cl+H)$^+$].

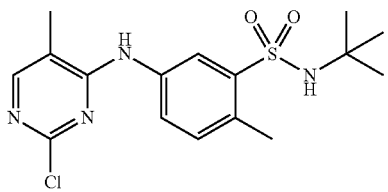 [SMILES: Cc1ccc(Nc2nc(Cl)ncc2C)cc1S(=O)(=O)NC(C)(C)C]

2-Chloro-N$^4$-(4-methyl-[3-(N-1,1-dimethylethyl)sulfamoyl]phenyl) methylpyrimidin-4-amine (SG2-108): This was prepared from 2,4-dichloro-5-methylpyrimidine (0.163 g) and SG2-100 (0.279 g) using procedure A (reaction time; 17 h at 45° C., 2.5 h at 80° C.) to give the title compound as an off-white solid (0.135 g, 37%; 65% purity based on HPLC-MS) which was used in the next step without further purification. $^1$H NMR (400 MHz, DMSO-d$_6$): δ 9.05 (s, 1H), 8.15 (d, J=2.3 Hz, 1H), 8.05 (d, J=0.8 Hz, 1H), 7.76 (dd, J=8.3, 2.3 Hz, 1H), 7.46 (s, 1H), 7.33 (d, J=8.3 Hz, 1H), 2.54 (s, 3H), 2.16 (s, 3H), 1.11 (s, 9H). HPLC-MS (ESI+): m/z 737.3 [10%, (2M$^{35}$Cl+H)$^+$], 371.2 [35%, (M$^{37}$Cl+H)$^+$], 369.1 [100%, (M$^{35}$Cl+H)$^+$].

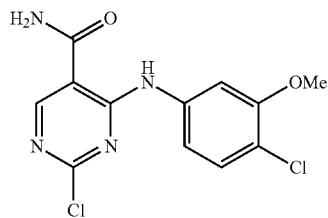 [SMILES: COc1cc(Nc2nc(Cl)ncc2C(N)=O)ccc1Cl]

2-Chloro-N$^4$-(4-chloro-3-methoxyphenyl)-5-carbamoylpyrimidin-4-amine (SG2-132): This was prepared from SG2-138 (0.096 g) and 4-chloro-3-methoxyaniline (0.079 g) using procedure B (reaction time, 12.5 h). Water (2 mL) was added and the precipitate was filtered, washed with water (1×10 mL) and hexanes (1×10 mL), and dried to give the title compound as a brown solid (0.110 g, 49%; 52% purity based on HPLC-MS) and used in the next step without further purification. HPLC-MS (ESI+): m/z 315.0 [30%, (M$^{37}$Cl+H)$^+$], 313.0 [40%, (M$^{35}$Cl+H)$^+$].

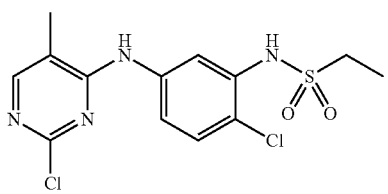 [SMILES: CCS(=O)(=O)Nc1cc(Nc2nc(Cl)ncc2C)ccc1Cl]

2-Chloro-N$^4$-(4-chloro-[3-(ethylsulfonamido)]phenyl)-5-methylpyrimidin-4-amine (SG4-012): A mixture of 2,4-dichloro-5-methylpyrimidine (0.326 g), SG4-009 (0.469 g), and DIPEA (0.836 mL) in isopropanol (1 mL) in a 2-mL microwave vial was stirred and heated at 140° C. for 3 d. Water (50 mL) was added and the precipitate was filtered, washed with water (2×50 mL) and hexanes (1×10 mL), and dried to give the title compound as an off-white solid (0.568 g, 79%). $^1$H NMR (400 MHz, DMSO-d$_6$): δ 9.42 (s, 1H, disappeared on D$_2$O shake), 9.00 (s, 1H, disappeared on D$_2$O shake), 8.08 (s, 1H), 7.81 (d, J=1.7 Hz, 1H), 7.52 (d, J=8.6, 1.7 Hz, 1H), 7.46 (d, J=8.6 Hz, 1H), 3.18 (q, J=7.3 Hz, 2H), 2.16 (s, 3H), 1.28 (t, J=7.3 Hz, 3H). HPLC-MS (ESI+): m/z 363.1 [80%, (M$^{35}$Cl$^{37}$Cl+H)$^+$], 361.1 [100%, (M$^{35}$Cl$^{35}$Cl+H)$^+$].

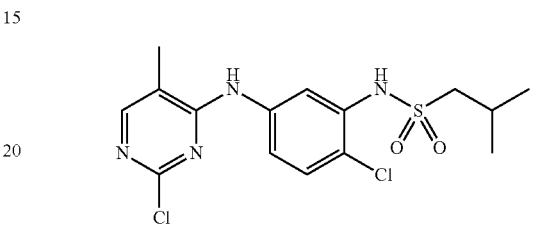

2-Chloro-N$^4$-(4-chloro-[3-(2-methylpropylsulfonamido)]phenyl)-5-methylpyrimidin-4-amine (SG4-018): A mixture of 2,4-dichloro-5-methylpyrimidine (0.081 g), SG4-016 (0.135 g), and DIPEA (0.210 mL) in isopropanol (0.25 mL) in a 2-mL microwave vial was stirred and heated at 140° C. for 3 d. The solvent was removed and the resulting oil was purified via column chromatography (SiO$_2$) eluting with EtOAc/hexanes (1:9 to 4:6 v/v) to give the title compound as an off-white solid (0.085 g, 44%). $^1$H NMR (400 MHz, DMSO-d$_6$): δ 9.46 (s, 1H, disappeared on D$_2$O shake), 9.00 (s, 1H, reduced by 40% on D$_2$O shake), 8.08 (d, J=0.8 Hz, 1H), 7.80 (d, J=2.4 Hz, 1H), 7.54 (dd, J=8.8, 2.4 Hz, 1H), 7.47 (d, J=8.8 Hz, 1H), 3.06 (d, J=6.5 Hz, 2H), 2.25-2.12 (m, 1H) overlapping 2.16 (s, 3H), 1.01 (d, J=6.5 Hz, 6H). HPLC-MS (ESI+): m/z 391.1 [80%, (M$^{35}$Cl$^{37}$Cl+H)$^+$], 389.1 [100%, (M$^{35}$Cl$^{35}$Cl+H)$^+$].

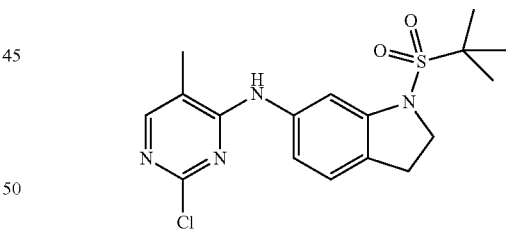

1-(tert-Butylsulfonyl)-N-(2-chloro-5-methylpyrimidin-4-yl)indolin-6-amine (SG4-024): A mixture of 2,4-dichloro-5-methylpyrimidine (0.163 g), SG4-020 (0.254 g), and DIPEA (0.418 mL) in isopropanol (0.5 mL) in a 2-mL microwave vial was stirred and heated at 140° C. for 3 d. The solvent was removed and the resulting oil was purified via column chromatography (SiO$_2$) eluting with EtOAc/hexanes (0:10 to 4:6 v/v) to give the title compound as an off-white foam (0.308 g, 81%). $^1$H NMR (400 MHz, DMSO-d$_6$): δ 8.85 (s, 1H, disappeared on D$_2$O shake), 8.00 (s, 1H), 7.57 (d, J=1.7 Hz, 1H), 7.17 (d, J=8.1 Hz, 1H), 7.10 (dd, J=8.1, 1.7 Hz, 1H), 4.05 (t, J=8.5 Hz, 2H), 3.07 (t, J=8.5 Hz, 2H), 2.13 (s, 3H), 1.39 (s, 9H). HPLC-MS (ESI+): m/z 381.2 [35%, (M$^{35}$Cl+H)$^+$].

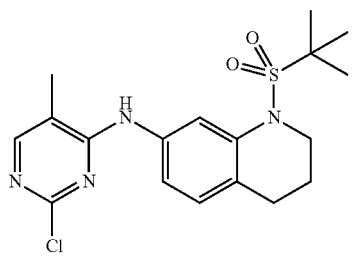 [SMILES: Cc1cnc(Cl)nc1Nc1ccc2c(c1)N(S(=O)(=O)C(C)(C)C)CCC2]

1-(tert-butylsulfonyl)-N-(2-chloro-5-methylpyrimidin-4-yl)-1,2,3,4-tetrahydroquinolin-7-amine (SG4-026): A mixture of 2,4-dichloro-5-methylpyrimidine (0.163 g), SG4-023 (0.268 g), and DIPEA (0.418 mL) in isopropanol (0.5 mL) in a 2-mL microwave vial was stirred and heated at 140° C. for 3 d. The solvent was removed and the resulting oil was purified via column chromatography (SiO$_2$) eluting with EtOAc/hexanes (0:10 to 4:6 v/v) to give the title compound as a white foam (0.314 g, 80%). $^1$H NMR (400 MHz, DMSO-d$_6$): δ 8.82 (s, 1H, reduced by 70% on D$_2$O shake), 8.00 (d, J=0.9 Hz, 1H), 7.79 (d, J=2.1 Hz, 1H), 7.14 (dd, J=8.3, 2.1 Hz, 1H), 7.08 (d, J=8.3 Hz, 1H), 3.65 (brs, 2H), 2.77 (t, J=6.7 Hz, 2H), 2.13 (d, J=0.8 Hz, 3H), 1.90 (quintet, J=6.7 Hz, 2H), 1.43 (s, 9H). HPLC-MS (ESI+): m/z 397.2 [35%, (M$^{37}$Cl+H)$^+$], 395.2 [100%, (M$^{35}$Cl+H)$^+$].

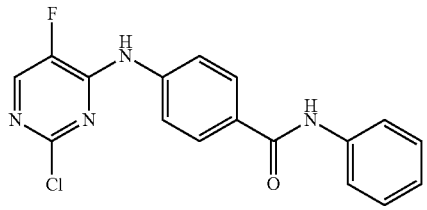 [SMILES: O=C(Nc1ccccc1)c1ccc(Nc2nc(Cl)ncc2F)cc1]

2-Chloro-N$^4$-(phenylbenzamide)-5-fluoropyrimidin-4-amine (SG3-071): A mixture of 2,4-dichloro-5-fluoropyrimidine (0.167 g), SG3-063 (0.212 g), and DIPEA (0.418 mL) in isopropanol (1 mL) was stirred and heated at 85° C. for 3 d. The mixture was concentrated under reduced pressure. The resulting oil was purified via column chromatography (SiO$_2$) eluting with EtOAc/hexanes (0:10 to 1:1 v/v) to give the title compound as a yellow solid (0.262 g, 77%). $^1$H NMR (400 MHz, DMSO-d$_6$): δ 10.27 (s, 1H, disappeared on D$_2$O shake), 10.18 (s, 1H, reduced by 60% on D$_2$O shake), 8.41 (d, J=3.4 Hz, 1H), 7.98 (d, J=8.8 Hz, 2H), 7.87 (d, J=8.8 Hz, 2H), 7.78 (d, J=7.6 Hz, 2H), 7.35 (d, J=7.6 Hz, 2H), 7.09 (t, J=7.64 Hz, 1H). $^{19}$F NMR (376 MHz, DMSO-d$_6$): δ −152.79. HPLC-MS (ESI+): m/z 709.2 [80%, (M$^{37}$Cl$^{35}$Cl+H)$^+$], 707.1 [80%, (2M$^{35}$Cl+H)$^+$], 344.2 [35%, (M$^{37}$Cl+H)$^+$], 343.2 [100%, (M$^{35}$Cl+H)$^+$].

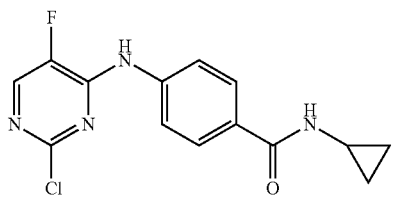 [SMILES: O=C(NC1CC1)c1ccc(Nc2nc(Cl)ncc2F)cc1]

2-Chloro-N$^4$-(cyclopropylbenzamide)-5-fluoropyrimidin-4-amine (SG3-076): A mixture of 2,4-dichloro-5-fluoropyrimidine (0.167 g), SG3-067 (0.176 g), and DIPEA (0.418 mL) in isopropanol (1 mL) was stirred and heated at 85° C. for 15 h. The mixture was concentrated under reduced pressure. The resulting oil was purified via column chromatography (SiO$_2$) eluting with EtOAc/hexanes (0:10 to 1:1 v/v) to give the title compound as a yellow solid (0.205 g, 67%). $^1$H NMR (400 MHz, DMSO-d$_6$): δ 10.19 (s, 1H, disappeared on D$_2$O shake), 8.39 (d, J=3.4 Hz, 1H, reduced by 40% on D$_2$O shake), 8.37 (d, J=4.2 Hz, 1H), 7.82 (d, J=8.9 Hz, 2H), 7.78 (d, J=8.9 Hz, 2H), 2.88-2.78 (m, 1H), 0.74-0.65 (m, 2H), 0.59-0.52 (m, 2H). $^{19}$F NMR (376 MHz, DMSO-d$_6$): δ −152.93. HPLC-MS (ESI+): m/z 637.2 [20%, (M$^{37}$Cl$^{35}$Cl+Na)$^+$], 635.2 [25%, (2M$^{35}$Cl+Na)$^+$], 615.2 [20%, (M$^{37}$Cl$^{35}$Cl+H)$^+$], 613.2 [25%, (2M$^{35}$Cl+H)$^+$], 309.2 [35%, (M$^{37}$Cl+H)$^+$], 307.1 [100%, (M$^{35}$Cl+H)$^+$].

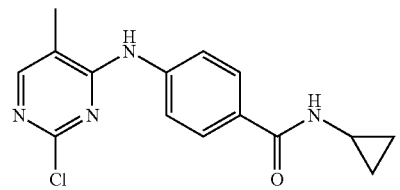 [SMILES: Cc1cnc(Cl)nc1Nc1ccc(C(=O)NC2CC2)cc1]

2-Chloro-N$^4$-(cyclopropylbenzamide)-5-methylpyrimidin-4-amine (SG3-083): A mixture of 2,4-dichloro-5-methylpyrimidine (0.163 g), SG3-067 (0.176 g), and DIPEA (0.418 mL) in isopropanol (1 mL) was stirred and heated at 120° C. for 3 d. Water (5 mL) was added and the precipitate filtered and washed with water (1×10 mL), isopropanol (1×1 mL), hexanes (1×20 mL), then dried to give the title compound as a white solid (0.175 g, 58%). $^1$H NMR (400 MHz, DMSO-d$_6$): δ 9.01 (s, 1H), 8.35 (d, J=4.1 Hz, 1H), 8.09 (d, J=0.8 Hz, 1H), 7.79 (d, J=8.8 Hz, 2H), 7.71 (d, J=8.8 Hz, 2H), 2.86-2.76 (m, 1H), 2.17 (s, 3H), 0.70-0.64 (m, 2H), 0.58-0.50 (m, 2H). HPLC-MS (ESI+): m/z 605.2 [25%, (2M$^{35}$Cl+H)$^+$], 305.2 [35%, (M$^{37}$Cl+H)$^+$], 303.2 [100%, (M$^{35}$Cl+H)$^+$].

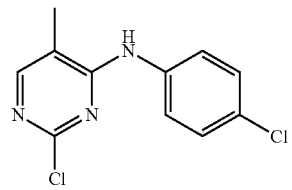 [SMILES: Cc1cnc(Cl)nc1Nc1ccc(Cl)cc1]

2-Chloro-N$^4$-(4-chlorophenyl)-5-methylpyrimidin-4-amine (SG3-139): A mixture of 2,4-dichloro-5-methylpyrimidine (0.326 g), 4-chloroaniline (0.255 g), and DIPEA (0.836 mL) in isopropanol (2 mL) was stirred and heated at 120° C. for 3 d. The mixture was concentrated under reduced pressure. The resulting oil was purified via column chromatography (SiO$_2$) eluting with EtOAc/hexanes (0:10 to 3:7 v/v) to give the title compound as a light yellow solid (0.405 g, 80%). $^1$H NMR (400 MHz, DMSO-d$_6$): δ 8.93 (s, 1H, disappeared on D$_2$O shake), 8.06 (s, 1H), 7.66 (d, J=8.9 Hz, 2H), 7.41 (d, J=8.9 Hz, 2H), 2.15 (s, 3H). HPLC-MS (ESI+): m/z 256.1 [70%, (M$^{35}$Cl$^{37}$Cl+H)$^+$], 254.1 [100%, (M$^{35}$Cl$^{35}$Cl+H)$^+$].

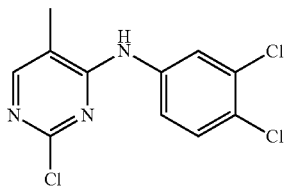 [SMILES: Cc1cnc(Cl)nc1Nc1ccc(Cl)c(Cl)c1]

2-Chloro-N[4]-(3,4-dichlorophenyl)-5-methylpyrimidin-4-amine (SG3-140): A mixture of 2,4-dichloro-5-methylpyrimidine (0.326 g), 3,4-dichloroaniline (0.324 g), and DIPEA (0.836 mL) in isopropanol (2 mL) was stirred and heated at 120° C. for 3 d. The mixture was concentrated under reduced pressure. The resulting oil was purified via column chromatography (SiO$_2$) eluting with EtOAc/hexanes (0:10 to 3:7 v/v) to give the title compound as a light yellow solid (0.331 g, 57%). $^1$H NMR (400 MHz, CDCl$_3$): δ 9.01 (s, 1H, disappeared on D$_2$O shake), 8.11 (s, 1H), 8.01 (d, J=2.3 Hz, 1H), 7.71 (dd, J=8.8, 2.3 Hz, 1H), 7.61 (d, J=8.8 Hz, 1H), 2.16 (s, 3H). HPLC-MS (ESI+): m/z 290.0 [90%, (M$^{35}$Cl$^{35}$Cl$^{37}$Cl+H)$^+$], 288.0 [100%, (M$^{35}$Cl$^{35}$Cl$^{35}$Cl+H)$^+$].

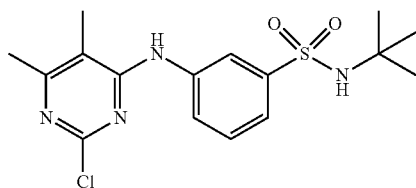 [SMILES: Cc1nc(Cl)nc(Nc2cccc(S(=O)(=O)NC(C)(C)C)c2)c1C]

N-tert-Butyl-3-(2-chloro-5,6-dimethylpyrimidin-4-ylamino)benzenesulfonamide (RJ1-010): A mixture of RJ1-008 (0.500 g, 2.82 mmol), 3-amino-N-tert-butylbenzenesulfonamide (SG1-137) (0.74 g, 3.24 mmol), MeOH (5 mL), and water (7.5 mL) was heated to reflux at 40° C. The reflux temperature was raised to 80° C. and the reaction was further heated for 26 hours. Upon cooling to ambient temperature, the precipitate which formed was then filtered and washed with water (50 mL) to yield RJ1-010 as an off-white solid (0.649 g, 62%). m.p.=232° C. (decomposed). $^1$H NMR (400 MHz, DMSO-d$_6$) δ 8.99 (s, 1H), 8.05 (s, 1H), 7.82-7.78 (m, 1H), 7.53-7.50 (m, 3H), 2.33 (s, 3H), 2.16 (s, 3H), 1.11 (s, 9H). LRMS (ESI+) m/z 369.2 (M$^{35}$Cl+H)$^+$, 371.2 (M$^{37}$Cl+H)$^+$; (ESI−) m/z 367.2 (M$^{35}$Cl−H)$^-$, 369.2 (M$^{37}$Cl−H)$^-$; HRMS (ESI+) m/z calculated for C$_{16}$H$_{21}$ClN$_4$O$_2$S (M+H)$^+$ 369.11465, found 369.11431.

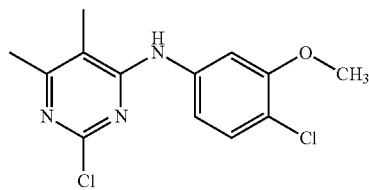

2-Chloro-N-(4-chloro-3-methoxyphenyl)-5,6-dimethylpyrimidin-4-amine (RJ1-034): A mixture of RJ1-008 (0.354 g, 2.0 mmol), 4-chloro-3-methoxyaniline (0.331 g, 2.1 mmol), DIPEA (0.42 mL, 2.4 mmol), and iPrOH (2 mL) was added to a 5 mL microwave vial which was then sealed and placed in a hot oil bath at 85° C. with stirring. After 23.5 hours, DMAP (0.024 g, 0.2 mmol) was added as no significant reaction was observed by TLC or LC/MS. After 3.5 days, the vial was removed from the oil bath and the reaction mixture was concentrated before being dissolved in EtOAc (20 mL) and washed with water (20 mL). The aqueous layer was re-extracted with EtOAc (20 mL). The combined organic layers were washed with water (20 mL), brine (20 mL), dried over sodium sulfate, and concentrated. The residue was then dissolved in EtOAc and purified via flash chromatography, and the desired product was collected at hexane/EtOAc 22-25% to give RJ1-034 as a yellow-orange solid (0.117 g, 20%). m.p.=162° C. (decomposed). $^1$H NMR (400 MHz, DMSO-d$_6$) δ 8.78 (s, 1H), 7.49 (d, J=2.3 Hz, 1H), 7.35 (d, J=8.6 Hz, 1H), 7.28 (dd, J=8.6, 2.3 Hz, 1H), 3.82 (s, 3H), 2.32 (s, 3H), 2.14 (s, 3H). LRMS (ESI+) m/z 298.1 (M$^{35}$Cl+H)+, 300.0 (M$^{37}$Cl+H)$^+$; HRMS (ESI+) m/z calculated for C$_{13}$H$_{13}$Cl$_2$N$_3$O (M+H)$^+$ 298.05084, found 298.04992.

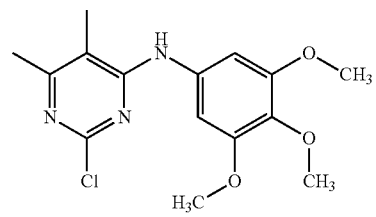

2-Chloro-5,6-dimethyl-N-(3,4,5-trimethoxyphenyl)pyrimidin-4-amine (RJ1-037): A mixture of RJ1-008 (0.354 g, 2.0 mmol), 3,4,5-trimethoxyaniline (0.385 g, 2.1 mmol), DIPEA (0.42 mL, 2.4 mmol) and iPrOH (2 mL) was added to a 5 mL microwave vial which was then sealed and placed in a hot oil bath at 85° C. with stirring for 3.5 days. At this point, a large amount of yellow-white precipitate was observed in the vial so the reaction mixture was filtered and the solid washed with MeOH (2×10 mL) and water (10 mL) before being left to dry in vacuo to give RJ1-037 as an off-white solid (0.232 g, 36%). m.p.=214-217° C. $^1$H NMR (400 MHz, DMSO-d$_6$) δ 8.61 (s, 1H), 7.04 (s, 2H), 3.74 (s, 6H), 3.63 (s, 3H), 2.30 (s, 3H), 2.12 (s, 3H). LRMS (ESI+) m/z 324.2 (M$^{35}$Cl+H)$^+$, 326.2 (M$^{37}$Cl+H)$^+$; HRMS (ESI+) m/z calculated for C$_{15}$H$_{18}$ClN$_3$O$_3$ (M+H)$^+$ 324.11095, found 324.11200.

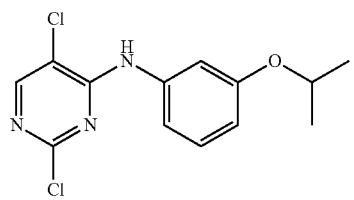 [SMILES: CC(C)Oc1cccc(Nc2nc(Cl)ncc2Cl)c1]

2,5-Dichloro-N-(3-isopropoxyphenyl)pyrimidin-4-amine (RJ1-048): A mixture of 2,4,5-trichloropyrimidine (0.367 g, 2.0 mmol), 3-isopropoxyaniline (0.310 mL, 2.1 mmol), DIPEA (0.420 mL, 2.4 mmol), and iPrOH (2 mL) was added to a 5 mL microwave vial which was then sealed and placed in a hot oil bath with stirring at 85° C. for 1.5 hours. MeOH was added and the reaction mixture was then evaporated under reduced pressure to give a whitish-yellow solid. This solid was then dissolved in EtOAc (20 mL) and washed with water (20 mL). The aqueous layer was re-extracted with EtOAc (20 mL) and the combined organic layers were washed with water (20 mL), brine (20 mL), dried over sodium sulfate and concentrated to yield RJ1-048 as a caramel-colored product (0.521 g, 87%). m.p.=100° C. (decomposed). $^1$H NMR (400 MHz, DMSO-$d_6$) δ 9.44 (s, 1H), 8.37 (s, 1H), 7.27-7.20 (m, 2H), 7.15-7.10 (m, 1H), 6.70 (dd, J=8.1, 2.1 Hz, 1H), 4.63-4.44 (m, 1H), 1.27 (d, J=6.0 Hz, 6H). LRMS (ESI+) m/z 298.1 (MCl$^{35}$Cl$^{35}$+H)$^+$, 300.1 (MCl$^{35}$Cl$^{37}$+H)$^+$, 302.1 (MCl$^{37}$Cl$^{37}$+H)$^+$; (ESI−) m/z 296.0 (MCl$^{35}$Cl$^{35}$−H)$^-$, 298.0 (MCl$^{35}$Cl$^{37}$−H)$^-$, 300.0 (MCl$^{37}$Cl$^{37}$−H)$^-$. HRMS (ESI+) m/z calculated for $C_{13}H_{13}Cl_2N_3O$ (M+H)$^+$ 298.05084, found 298.05025.

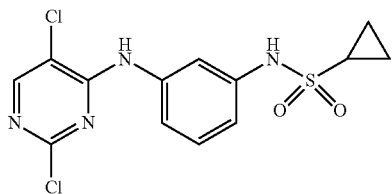 [SMILES: O=S(=O)(Nc1cccc(Nc2nc(Cl)ncc2Cl)c1)C1CC1]

N-(3-(2,5-Dichloropyrimidin-4-ylamino)phenyl)cyclopropanesulfonamide (RJ1-050): A mixture of 2,4,5-trichloropyrimidine (0.200 g, 1.09 mmol), N-(3-aminophenyl)cyclopropanesulfonamide (RJ1-025) (0.266 g, 1.25 mmol), MeOH (2 mL), and water (3 mL) was added to a 5 mL microwave vial which was then sealed and placed in a hot oil bath with stirring at 45° C. for 21 hours. At this point, the vial was removed and allowed to cool to ambient temperature before the reaction mixture was filtered and washed with a solution of MeOH (20 mL) and water (30 mL) to yield RJ1-050 as a beige solid product (0.273 g, 70%). m.p.=197° C. (decomposed). $^1$H NMR (400 MHz, DMSO-$d_6$) δ 9.84 (s, 1H), 9.60 (s, 1H), 8.38 (s, 1H), 7.52 (s, 1H), 7.39-7.20 (m, 2H), 7.00 (d, J=6.8 Hz, 1H), 2.67 (s, 1H), 1.05-0.89 (m, 4H). LRMS (ESI+) m/z 359.1 (MCl$^{35}$Cl$^{35}$+H)$^+$, 361.1 (MCl$^{35}$Cl$^{37}$+H)$^+$, 363.1 (MCl$^{37}$Cl$^{37}$+H)$^+$; (ESI−) m/z 357.1 (MCl$^{35}$Cl$^{35}$−H)$^-$, 359.1 (MCl$^{35}$Cl$^{37}$−H)$^-$, 361.1 (MCl$^{37}$Cl$^{37}$−H)$^-$; HRMS (ESI+) m/z calculated for $C_{13}H_{12}Cl_2N_4O_2S$ (M+H)$^+$ 359.01308, found 359.01276.

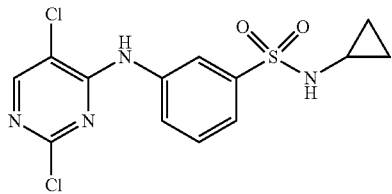 [SMILES: O=S(=O)(NC1CC1)c1cccc(Nc2nc(Cl)ncc2Cl)c1]

N-Cyclopropyl-3-(2,5-dichloropyrimidin-4-ylamino)benzenesulfonamide (RJ1-052): A mixture of 2,4,5-trichloropyrimidine (0.100 g, 0.545 mmol), 3-amino-N-cyclopropylbenzenesulfonamide (RJ1-042) (0.133 g, 0.627 mmol), MeOH (1 mL), and water (1.5 mL) was allowed to react and worked up following the same procedure used to make RJ1-050 to provide RJ1-052 as a white solid product (0.138 g, 70%). m.p.=185° C. (decomposed). $^1$H NMR (400 MHz, DMSO-$d_6$) δ 9.85 (s, 1H), 8.45 (s, 1H), 8.10 (m, 1H), 7.98 (d, J=2.1 Hz, 1H), 7.90-7.84 (m, 1H), 7.67-7.56 (m, 2H), 2.18 (dt, J=9.4, 3.2 Hz, 1H), 0.49 (ddd, J=27.4, 9.5, 5.2 Hz, 4H). LRMS (ESI+) m/z 359.1 (MCl$^{35}$Cl$^{35}$+H)$^+$, 361.1 (MCl$^{35}$Cl$^{37}$+H)$^+$, 363.1 (MCl$^{37}$Cl$^{37}$+H)$^+$; (ESI−) m/z 357.0 (MCl$^{35}$Cl$^{35}$−H)$^-$, 359.0 (MCl$^{35}$Cl$^{37}$−H)$^-$, 361.0 (MCl$^{37}$Cl$^{37}$−H)$^-$; HRMS (ESI+) m/z calculated for $C_{13}H_{12}Cl_2N_4O_2S$ (M+H)$^+$ 359.01308, found 359.01277.

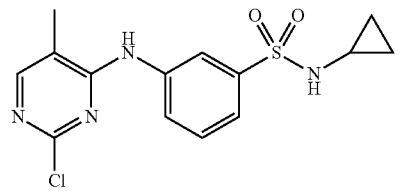 [SMILES: Cc1cnc(Cl)nc1Nc1cccc(S(=O)(=O)NC2CC2)c1]

3-(2-Chloro-5-methylpyrimidin-4-ylamino)-N-cyclopropylbenzenesulfonamide (RJ1-046): A mixture of RJ1-042 (0.300 g, 1.41 mmol), 2,4-dichloro-5-methylpyrimidine (0.200 g, 1.23 mmol), MeOH (2 mL), and water (3 mL) was allowed to react and worked up following the same procedure used to make RJ1-050, with the exception that the reaction was run for 23 hours, to provide RJ1-046 as a yellow-white product (0.216 g, 52%). m.p.=192° C. (decomposed). $^1$H NMR (400 MHz, DMSO-$d_6$) δ 9.17 (s, 1H), 8.15-8.08 (m, 2H), 7.95 (d, J=6.1 Hz, 2H), 7.59 (t, J=7.9 Hz, 1H), 7.51 (d, J=7.8 Hz, 1H), 2.28 (s, 1H), 2.18 (s, 3H), 0.46 (ddd, J=11.5, 7.4, 4.7 Hz, 4H). LRMS (ESI+) m/z 339.1 (M$^{35}$Cl+H)$^+$, 341.2 (M$^{37}$Cl+H)$^+$; HRMS (ESI+) m/z calculated for $C_{14}H_{15}ClN_4O_2S$ (M+H)$^+$ 339.06770, found 339.06769.

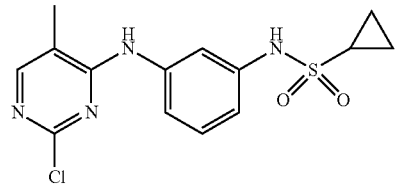 [SMILES: Cc1cnc(Cl)nc1Nc1cccc(NS(=O)(=O)C2CC2)c1]

N-(3-(2-Chloro-5-methylpyrimidin-4-ylamino)phenyl)cyclopropanesulfonamide (RJ1-032): A mixture of 2,4-dichloro-5-methylpyrimidine (0.200 g, 1.23 mmol), RJ1-025 (0.300 g, 1.41 mmol), MeOH (2.0 mL) and water (3.0 mL) was heated to reflux overnight in a hot oil bath at 45° C. with stirring. The next day, the flask was removed and allowed to cool to ambient temperature before being evaporated under reduced pressure. The residue was dissolved in MeOH and the desired product collected via filtration, to provide RJI-032 (0.200 g, 48%) as a white solid. m.p.=211° C. (decomposed). $^1$H NMR (400 MHz, DMSO-$d_6$) δ 9.79 (s, 1H), 8.96 (s, 1H), 8.05 (s, 1H), 7.57 (s, 1H), 7.33 (d, J=7.5 Hz, 1H), 7.27 (t, J=8.0 Hz, 1H), 6.94 (d, J=7.7 Hz, 1H), 2.71-2.62 (m, 1H), 2.16 (s, 3H), 1.01-0.82 (m, 4H). LRMS (ESI+) m/z 339.1 (M+H)$^+$; (ESI−) m/z 337.1 (M−H)$^-$.

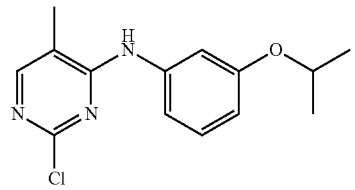 [SMILES: Cc1cnc(Cl)nc1Nc1cccc(OC(C)C)c1]

2-Chloro-N-(3-isopropoxyphenyl)-5-methylpyrimidin-4-amine (RJ1-058): A mixture of 2,4-dichloro-5-methylpyrimidine (0.326 g, 2.0 mmol), 3-isopropoxyaniline (0.310 mL, 2.1 mmol), DIPEA (0.420 mL, 2.4 mmol), and iPrOH (2 mL) was allowed to react and worked up following the same procedure used to make RJ1-048, with the exception that no MeOH was added before workup and that the reaction was run overnight for 19.5 hours. The residue was then purified via flash chromatography, and the desired product RJ1-058 was collected at hexanes/EtOAc 15-20% as a flaky caramel-colored solid (0.242 g, 44%). m.p.=127-128° C. $^1$H NMR (400 MHz, DMSO-d$_6$) δ 8.76 (s, 1H), 8.03 (s, 1H), 7.30 (t, J=2.2 Hz, 1H), 7.25-7.13 (m, 2H), 6.64 (ddd, J=8.0, 2.4, 1.1 Hz, 1H), 4.59-4.50 (m, 1H), 2.15 (d, J=0.6 Hz, 3H), 1.27 (d, J=6.0 Hz, 6H). LRMS (ESI+) m/z 278.1 (M$^{35}$Cl+H)$^+$, 280.1 (M$^{37}$Cl+H)$^+$; HRMS (ESI+) m/z calculated for C$_{14}$H$_{16}$ClN$_3$O (M+H)$^+$ 278.10547, found 278.10860.

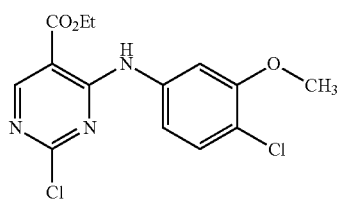 [SMILES: CCOC(=O)c1cnc(Cl)nc1Nc1ccc(Cl)c(OC)c1]

Ethyl 2-chloro-4-(4-chloro-3-methoxyphenylamino)pyrimidine-5-carboxylate (RJ1-061): A mixture of ethyl 2,4-dichloropyrimidine-5-carboxylate (0.442 g, 2.0 mmol), 4-chloro-3-methoxyaniline (0.331 g, 2.1 mmol), DIPEA (0.42 mL, 2.4 mmol), and iPrOH (2 mL) was added to a 5 mL microwave vial which was then sealed and placed in a hot oil bath with stirring at 85° C. overnight for 17 hours. At this point, a brown solid had formed and this was then washed with iPrOH (10 mL), water (10 mL), iPrOH (10 mL), and hexanes (10 mL) to yield RJ1-061 as a brown solid (0.570 g, 83%). m.p.=119° C. (decomposed). $^1$H NMR (400 MHz, DMSO-d$_6$) δ 10.27 (s, 1H), 8.81 (s, 1H), 7.48 (d, J=2.3 Hz, 1H), 7.43 (d, J=8.6 Hz, 1H), 7.28 (dd, J=8.6, 2.3 Hz, 1H), 4.37 (q, J=7.1 Hz, 2H), 3.85 (s, 3H), 1.34 (t, J=7.1 Hz, 31-1). LRMS (ESI+) m/z 342.1 (MCl$^{35}$Cl$^{35}$+H)$^+$, 344.0 (MCl$^{35}$Cl$^{37}$+H)$^+$, 346.0 (MCl$^{37}$Cl$^{37}$+H)$^+$; (ESI−) m/z 339.3 (MCl$^{35}$Cl$^{35}$−H)$^−$; HRMS (ESI+) m/z calculated for C$_{14}$H$_{13}$Cl$_2$N$_3$O$_3$ (M+H)$^+$ 342.04067, found 342.04100.

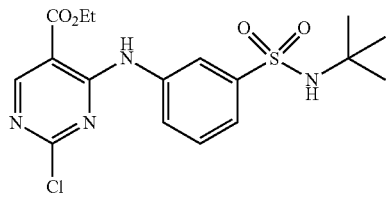 [SMILES: CCOC(=O)c1cnc(Cl)nc1Nc1cccc(S(=O)(=O)NC(C)(C)C)c1]

Ethyl 4-(3-(N-tert-butylsulfamoyl)phenylamino)-2-chloropyrimidine-5-carboxylate (RJ1-063-01): A mixture of ethyl 2,4-dichloropyrimidine-5-carboxylate (0.221 g, 1.0 mmol), 3-amino-N-tert-butylbenzenesulfonamide SG1-137 (0.265 g, 1.15 mmol), MeOH (2 mL), and water (3 mL) was reacted and worked up following the same procedure used to make RJ1-050, with the exception that the reaction was run for 17 hours, to yield a tan solid. The solid was then purified via flash chromatography eluting with hexanes/EtOAc to provide RJ1-063-01 as a white flaky solid (0.211 g, 51%). m.p.=161° C. (decomposed). $^1$H NMR (400 MHz, DMSO-d$_6$) δ 10.35 (s, 1H), 8.82 (s, 1H), 8.11 (t, J=1.9 Hz, 1H), 7.80-7.72 (m, 1H), 7.63 (dt, J=7.8, 1.5 Hz, 1H), 7.61-7.55 (m, 2H), 4.38 (q, J=7.1 Hz, 2H), 1.34 (t, J=7.1 Hz, 3H), 1.11 (s, 9H). LRMS (ESI+) m/z 413.1 (M$^{35}$Cl+H)$^+$, 415.1 (M$^{37}$Cl+H)$^+$; (ESI−) m/z 411.1 (M$^{35}$Cl−H)$^−$; HRMS (ESI+) m/z calculated for C$_{17}$H$_{21}$ClN$_4$O$_4$S (M+H)$^+$ 413.10448, found 413.10573.

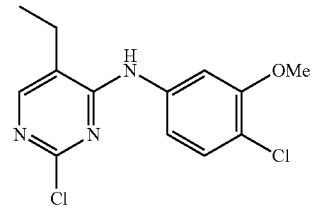

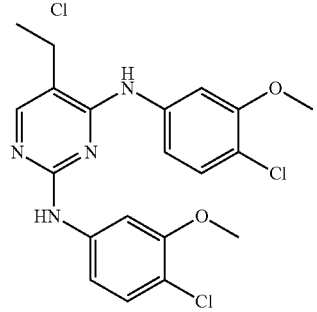

2-Chloro-5-ethyl-N$^4$-(3-methoxy-4-chlorophenyl)pyrimidin-4-amine (MA1-025) and 5-Ethyl-N$^4$,N$^2$-bis-[4-chloro-3-methoxyphenyl]pyrimidine-2,4-diamine (MA1-025B): This was prepared from MA1-012 (0.531 g) and 3-methoxy-4-chloroaniline (0.473 g) using procedure A (reaction time, 16 h) to give the title compound as a white solid (0.202 g, 23%). Mp: 143-144° C. $^1$H NMR (400 MHz, DMSO-d$_6$): δ 8.93 (s, 1H, disappeared on D$_2$O shake), 8.07 (s, 1H), 7.53 (d, J=2.3 Hz, 1H), 7.37 (d, J=8.6 Hz, 1H), 7.31 (dd, J=8.6, 2.3 Hz, 1H), 3.83 (s, 3H), 2.61 (q, J=7.4 Hz, 2H), 1.17 (t, J=7.4 Hz, 3H). HPLC-MS (ESI+): m/z 300.1 [70%, (M$^{37}$Cl$^{35}$Cl+H)$^+$], m/z 298.1 [100%, (M$^{35}$Cl$^{35}$Cl+H)$^+$]. Further elution gave the bis-addition side product MA1-025B (109 mg, 9%) as a yellow solid, Mp: 201° C. (dec). HPLC: 99% [t$_R$=8.1 min, 65% MeOH, 35% water (with 0.1% TFA), 20 min]. $^1$H NMR (400 MHz, DMSO-d$_6$): δ 9.20 (s, 1H, disappeared on D$_2$O shake), 8.48 (s, 1H, 40% reduced on D$_2$O shake), 7.97 (s, 1H), 7.56 (d, J=2.3 Hz, 1H), 7.43 (d, J=2.3 Hz, 1H), 7.38 (dd, J=8.6, 2.3 Hz, 1H), 7.32 (d, J=8.7 Hz, 1H) 7.29 (dd, J=8.6, 2.3 Hz, 1H), 7.15 (d, J=8.7 Hz, 1H), 3.74 (s, 3H), 3.60 (s, 3H), 2.57 (q, J=7.4 Hz, 2H), 1.18 (t, J=7.4 Hz, 3H). HPLC-MS (ESI+): m/z 421.1 [70%, (M$^{37}$Cl$^{35}$Cl+H)$^+$], 419.2 [100%, (M$^{35}$Cl$^{35}$Cl+H)$^+$]. LC-MS (ESI+): 421.1 [70%, (M$^{37}$Cl$^{35}$Cl+H)$^+$], 419.1 [100%, (M$^{35}$Cl$^{35}$Cl+H)$^+$]. HRMS (ESI+): m/z calcd for C$_{20}$H$_{20}$Cl$_2$N$_4$O$_2$ (M+H)$^+$ 419.1036, found 419.1035.

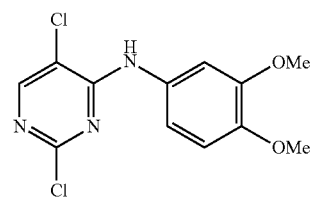 [SMILES: COc1ccc(Nc2nc(Cl)ncc2Cl)cc1OC]

2,5-Dichloro-N$^4$-(3,4-dimethoxyphenyl)pyrimidin-4-amine (MA1-059): This was prepared from 2,4,5-trichloropyrimidine (0.367 g) and 3,4-dimethoxyaniline (0.322 g) using procedure B (reaction time, 2 h) to give the title compound as a gray solid (0.540 g, 90%). Mp: 130° C. (dec).

¹H NMR (400 MHz, DMSO-d₆): δ 9.42 (s, 1H, disappeared on D₂O shake), 8.33 (s, 1H), 7.21 (d, J=2.4 Hz, 1H), 7.12 (dd, J=8.7, 2.4 Hz, 1H), 6.97 (d, J=8.7 Hz, 1H), 3.76 (s, 3H), 3.74 (s, 3H). HPLC-MS (ESI+): m/z 623.1 [20%, (M³⁵Cl³⁵Cl+M³⁵Cl³⁷Cl+Na)⁺], 302.1 [70%, (M³⁵Cl³⁷Cl+H)⁺], 300.1 [100%, (M³⁵Cl³⁵Cl+H)⁺].

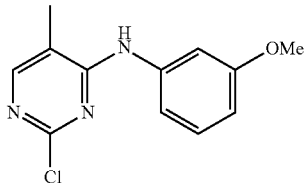

2-Chloro-5-methyl-N⁴-(3-methoxyphenyl)pyrimidin-4-amine (MA1-060): This was prepared from 2,4-dichloro-5-methylpyrimidine (0.326 g) and 3-methoxyaniline (0.258 g) using procedure B (reaction time, 72 h) to give the title compound as a white solid (0.342 g, 68%). Mp: 104-106° C. ¹H NMR (400 MHz, DMSO-d₆): δ 8.80 (s, 1H, disappeared on D₂O shake), 8.06 (d, J=0.9 Hz, 1H), 7.34-7.32 (m, 1H), 7.28-7.24 (m, 2H), 6.72-6.67 (m, 1H), 3.76 (s, 3H), 2.17 (d, J=0.8 Hz, 3H). HPLC-MS (ESI+): m/z 352.2 [40%, (M³⁷Cl+H)⁺], 350.2 [100%, (M³⁵Cl+H)⁺].

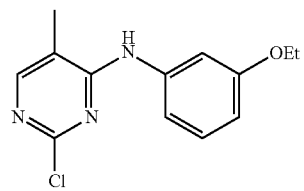 [SMILES: CCOc1cccc(Nc2nc(Cl)ncc2C)c1]

2-Chloro-5-methyl-N⁴-(3-ethoxyphenyl)pyrimidin-4-amine (MA1-061): This was prepared from 2,4-dichloro-5-methylpyrimidine (0.326 g) and 3-ethoxyaniline (0.288 g) using procedure B (reaction time, 72 h) to give the title compound as an off white solid (0.332 g, 63%). Mp: 114° C. (dec). ¹H NMR (400 MHz, DMSO-d₆): δ 8.78 (s, 1H disappeared on D₂O shake), 8.05 (d, J=0.8 Hz, 1H), 7.33-7.31 (m, 1H), 7.27-7.21 (m, 2H), 6.70-6.64 (m, 1H), 4.02 (q, J=7.0 Hz, 2H), 2.17 (d, J=0.6 Hz, 3H), 1.34 (t, J=7.0 Hz, 3H). HPLC-MS (ESI+): m/z 266.2 [40%, (M³⁷Cl+H)⁺], 264.2 [100%, (M³⁵Cl+H)⁺].

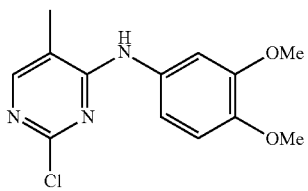 [SMILES: COc1ccc(Nc2nc(Cl)ncc2C)cc1OC]

2-Chloro-5-methyl-N⁴-(3,4-dimethoxyphenyl)pyrimidin-4-amine (MA1-062): This was prepared from 2,4-dichloro-5-methylpyrimidine (0.326 g) and 3,4-dimethoxyaniline (0.322 g) using procedure B (reaction time, 72 h) to give the title compound as a beige solid (0.341 g, 61%). Mp: 192° C. (dec). ¹H NMR (400 MHz, DMSO-d₆): δ 8.75 (s, 1H, 1H disappeared on D₂O shake), 7.99 (d, J=0.9 Hz, 1H), 7.26 (d, J=2.4 Hz, 1H), 7.17 (dd, J=8.7, 2.4 Hz, 1H), 6.95 (d, J=8.7 Hz, 1H), 3.75 (s, 3H), 3.745 (s, 3H), 2.14 (d, J=0.9 Hz, 3H). HPLC-MS (ESI+): m/z 282.2 [40%, (M³⁷Cl+H)⁺], 380.2 [100%, (M³⁵Cl+H)⁺].

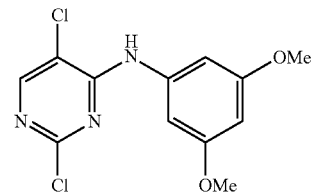

2,5-Dichloro-N⁴-(3,5-dimethoxyphenyl)pyrimidin-4-amine (MA1-069): This was prepared from 2,4,5-trichloropyrimidine (0.326 g) and 3,5-dimethoxyaniline (0.306 g) using procedure B (reaction time, 10 min) to give the title compound as a white solid (0.512 g, 85%). Mp: 150-151° C. ¹H NMR (400 MHz, DMSO-d₆): δ 9.39 (s, 1H, disappeared on D₂O shake), 8.40 (s, 1H), 6.93 (d, J=2.2 Hz, 2H), 6.34 (t, J=2.2 Hz, 1H), 3.74 (s, 6H). HPLC-MS (ESI+): m/z 302.1 [70%, (M³⁷Cl³⁵Cl+H)⁺], 300.1 [100%, (M³⁵Cl³⁵Cl+H)⁺].

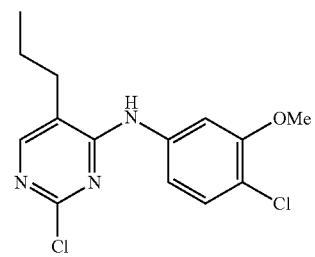 [SMILES: CCCc1cnc(Cl)nc1Nc1ccc(Cl)c(OC)c1]

2-Chloro-5-propyl-N⁴-(3-methoxy-4-chlorophenyl)pyrimidin-4-amine (MA1-072): This was prepared from MA1-039 (0.262 g) and 3-methoxy-4-chloroaniline (0.227 g) using procedure B (reaction time, 67 h) to give the title compound as a white solid (0.116 g, 27%). Mp: 142-142° C. ¹H NMR (400 MHz, DMSO-d₆): δ 10.04 (s, 1H, disappeared on D₂O shake), 8.43 (s, 1H), 7.66 (s, 1H), 7.31 (s, 1H), 7.30 (s, 1H), 3.82 (s, 3H), 2.54 (t, J=7.5 Hz, 2H), 1.58 (sextet, J=7.5 Hz, 2H), 0.92 (t, J=7.5 Hz, 3H). HPLC-MS (ESI+): m/z 314.1 [70%, (M³⁵Cl³⁷Cl+H)⁺], 312.1 [100%, (M³⁵Cl³⁵Cl+H)⁺].

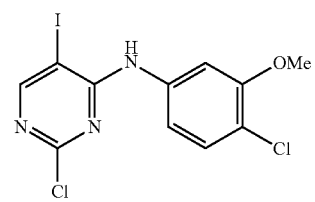 [SMILES: COc1cc(Nc2nc(Cl)ncc2I)ccc1Cl]

2-Chloro-5-iodo-N⁴-(3-methoxy-4-chlorophenyl)pyrimidin-4-amine (MA1-092): This was prepared from 2,4-dichloro-5-iodopyrimdine (0.550 g) and 3-methoxy-4-chloroaniline (0.315 g) using procedure B (reaction time, 1 h) to give the title compound as a gray solid (0.708 g, 90%). Mp: 190-192° C. (dec). ¹H NMR (400 MHz, DMSO-d₆): δ 8.94 (s, 1H, disappeared on D₂O shake), 8.59 (s, 1H), 7.43 (d, J=2.3 Hz, 1H), 7.41 (d, J=8.6 Hz, 1H), 7.21 (dd, J=8.6, 2.3 Hz, 1H), 3.84 (s, 3H). HPLC-MS (ESI+): m/z 397.9 [78%, (M³⁵Cl³⁷Cl+H)⁺], 395.9 [100%, (M³⁵Cl³⁵Cl+H)+].

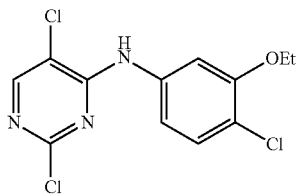 [SMILES: CCOc1cc(Nc2nc(Cl)ncc2Cl)ccc1Cl]

2,5-Dichloro-N⁴-(4-chloro-3-ethoxyphenyl)pyrimidin-4-amine (MA2-016-1): This was prepared from 2,4-dichloro-5-methylpyrimidine (0.116 g), 4-chloro-3-ethoxyaniline (0.108 g), and DIPEA (0.121 mL) using procedure B (reaction time, 2 h). The product precipitated when the reaction was cooled to room temperature. The reaction mixture was vigorously shaken after water (5 mL) was added. Finally the product was filtered using a sintered funnel and rinsed with water (3×10 mL) and hexane (3×10 mL). The title compound was obtained as a white solid (0.156 g, 78%). Mp: 102-104° C. ¹H NMR (400 MHz, DMSO-d₆): δ 9.57 (s, 1H, disappeared on D₂O shake), 8.42 (s), 7.48 (d, J=2.3 Hz, 1H), 7.42 (d, J=8.6 Hz, 1H), 7.26 (dd, J=8.6, 2.3 Hz, 1H), 4.11 (q, J=7.0 Hz, 2H), 1.38 (t, J=7.0 Hz, 3H). HPLC-MS (ESI+): m/z 342.0 [20%, (M³⁵Cl³⁷Cl+Na)⁺], 320.0 [70%, (M³⁵Cl³⁷Cl+H)⁺], 318.1 [100%, (M³⁵Cl³⁵Cl+H)⁺].

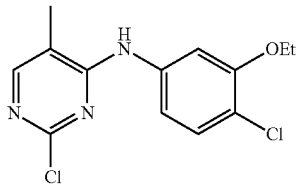 [SMILES: CCOc1cc(Nc2nc(Cl)ncc2C)ccc1Cl]

2-Chloro-5-methyl-As-(4-chloro-3-ethoxyphenyl)pyrimidin-4-amine (MA2-016-2): This was prepared from 2,4-dichloro-5-methylpyrimidine (0.103 g), 4-chloro-3-ethoxyaniline (0.108 g), and DIPEA (0.121 mL) using procedure B (reaction time, 3 days). The product precipitated when the reaction cooled to room temperature. The title compound MA2-016-2 was obtained, in same way as that used to isolate MA2-016-1 as a gray-white solid (0.154 g, 82%). Mp: 180° C. (dec). ¹H NMR (400 MHz, DMSO-d₆): δ 8.90 (s, 1H, disappeared on D₂O shake), 8.09 (s, 1H), 7.55 (d, J=2.1 Hz, 1H), 7.39 (d, J=8.6 Hz, 1H), 7.30 (dd, J=8.6, 2.1 Hz, 1H), 4.11 (q, J=6.9 Hz, 2H), 2.18 (s, 3H), 1.39 (t, J=6.9 Hz, 3H). HPLC-MS (ESI+): m/z 300.1 [70%, (M³⁵Cl³⁷Cl+H)⁺], 298.2 [100%, (M³⁵Cl³⁵Cl+H)⁺].

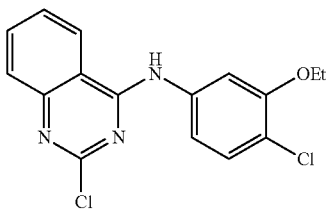 [SMILES: CCOc1cc(Nc2nc(Cl)nc3ccccc23)ccc1Cl]

2-Chloro-N⁴-(4-chloro-3-ethoxyphenyl)quinazoline-4-amine (MA2-030): This was prepared from MA2-028 (0.398 g), 4-chloro-3-ethoxyaniline (0.315 g), and DIPEA (0.418 mL) using procedure B (reaction time, 18 h). Water (6 mL) was added and the precipitated product was filtered, washed with water (3×10 mL), hexanes (3×10 mL), and dried to give the title compound MA2-030 as a gray solid (0.633 g, 99%). Mp: 265° C. (dec). ¹H NMR (400 MHz, DMSO-d₆): δ 10.25 (s, 1H, disappeared on D₂O shake), 8.58 (d, J=7.7 Hz, 1H), 7.91 (ddd, J=8.2, 7.0, 1.2 Hz, 1H), 7.77-7.74 (m, 2H), 7.68 (ddd, J=8.2, 7.0, 1.2 Hz, 1H), 7.51-7.45 (m, 2H), 3.89 (s, 3H). HPLC-MS (ESI+): m/z 322.1 [70%, (M³⁵Cl³⁷Cl+H)⁺], 320.1 [100%, (M³⁵Cl³⁵Cl+H)⁺].

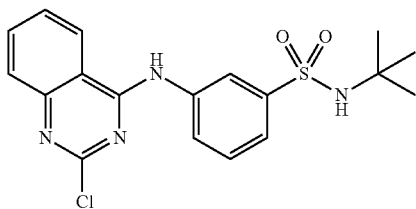 [SMILES: CC(C)(C)NS(=O)(=O)c1cccc(Nc2nc(Cl)nc3ccccc23)c1]

2-Chloro-N⁴-([3-(N-1,1-dimethylethyl)sulfamoyl]phenyl)quinazoline-4-amine (MA2-033): This was prepared from MA2-028 (0.070 g), SG1-137 (0.080 g), and DIPEA (0.067 mL) using procedure B (reaction time, 2 h) and isolated in the same way as MA2-030 give the title compound MA2-033 as a gray solid (0.104 g, 76%). Mp: 286° C. (dec). ¹H NMR (400 MHz, DMSO-d₆): δ 10.43 (s, 1H, disappeared on D₂O shake), 8.60 (d, J=8.3 Hz, 1H), 8.28 (s, 1H), 8.06 (ddd, J=9.2, 4.8, 3.1 Hz, 1H), 7.96-7.88 (m, 1H), 7.75 (d, J=8.4 Hz, 1H), 7.72-7.66 (m, 1H), 7.65-7.62 (m, 2H), 7.60 (s, 1H, disappeared on D₂O shake), 1.15 (s, 9H). HPLC-MS (ESI+): m/z 393.1 [40%, (M³⁵Cl³⁷Cl+H)⁺], 391.1 [100%, (M³⁵Cl³⁵Cl+H)⁺].

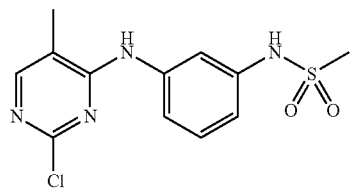 [SMILES: Cc1cnc(Cl)nc1Nc1cccc(NS(C)(=O)=O)c1]

2-Chloro-5-methyl-N⁴-[3-(methanesulfonamido)phenyl]pyrimidin-4-amine (MA2-035): This was prepared from 2,4-dichloro-5-methylpyrimidine (0.326 g), N-(3-aminophenyl)methanesulfonamide (0.372 g) and DIPEA (0.418 mL) using procedure B (reaction time, 48 h) and isolated in the same way as MA2-030 to give the title compound MA2-035 as a gray solid (0.374 g, 100%). Mp: 191-193° C. ¹H NMR (400 MHz, DMSO-d₆): δ 9.85 (s, 1H, disappeared on D₂O shake), 8.95 (s, 1H, disappeared on D₂O shake), 8.06 (d, J=0.9 Hz, 1H), 7.54 (t, J=1.9 Hz, 1H), 7.35 (dd, J=8.4, 1.5 Hz, 1H), 7.30 (t, J=8.0 Hz, 1H), 6.91 (ddd, J=7.8, 2.0, 1.1 Hz, 1H), 3.05 (s, 3H), 2.17 (s, 3H). HPLC-MS (ESI+): m/z 315.2 [40%, (M³⁵Cl³⁷Cl+H)⁺], 313.1 [100%, (M³⁵Cl³⁵Cl+H)⁺].

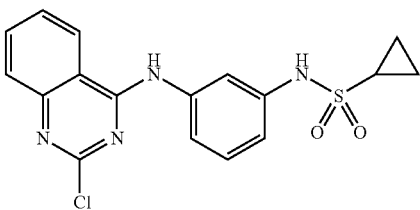 [SMILES: O=S(=O)(Nc1cccc(Nc2nc(Cl)nc3ccccc23)c1)C1CC1]

2-Chloro-N⁴-[3-(cyclopropanesulfonamido)phenyl]quinazoline-4-amine (MA2-038): This was prepared from MA2-028 (0.199 g), RJ-025 (0.212 g), and DIPEA (0.1 mL) using procedure B (reaction time, 16 h) and isolated in the same way as MA2-030 to give the title compound MA2-038 as a gray solid (0.374 g, 100%). Mp: 198-203° C. ¹H NMR (400 MHz, DMSO-$d_6$): δ ¹H NMR (400 MHz, dmso) δ 10.25 (s, 1H, disappeared on $D_2O$ shake), 9.87 (s, 1H disappeared on $D_2O$ shake), 8.57 (d, J=8.3 Hz, 1H), 7.93-7.84 (m, 1H), 7.73-7.70 (m, 2H), 7.68-7.62 (m, 1H), 7.53 (dd, J=8.1, 1.0 Hz, 1H), 7.35 (t, J=8.1 Hz, 1H), 7.06-6.99 (m, 1H), 2.73-2.66 (m, 1H), 1.03-0.92 (m, 4H). HPLC-MS (ESI+): m/z 377.1 [40%, (M³⁵Cl³⁷Cl+H)⁺], 375.1 [100%, (M³⁵Cl³⁵Cl+H)⁺].

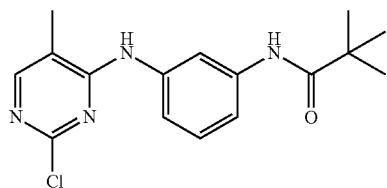 [SMILES: Cc1cnc(Cl)nc1Nc1cccc(NC(=O)C(C)(C)C)c1]

2-Chloro-5-methyl-N⁴-[3-(2,2-dimethylpropanamido)phenyl]pyrimidin-4-amine (MA2-042-1): This was prepared from MA2-040-1 (0.192 g), 2,4-dichloro-5-methylpyrimidine (0.163 g), and DIPEA (0.192 mL) using procedure B (reaction time, 48 h) and isolated in the same way as MA2-030 give the title compound MA2-042-1 as a gray solid (0.241 g, 76%). Mp: 178° C. (dec). ¹H NMR (400 MHz, DMSO-$d_6$): δ 9.22 (s, 1H, 10% reduced on $D_2O$ shake), 8.86 (s, 1H, 80% reduced on $D_2O$ shake), 8.02 (s, 1H), 7.85 (brs, 1H), 7.37 (d, J=7.8 Hz, 1H), 7.30 (d, J=7.8 Hz, 1H), 7.25 (t, J=7.8 Hz, 1H), 2.14 (s, 3H), 1.21 (s, 9H). HPLC-MS (ESI+): m/z 321.2 [40%, (M³⁵Cl³⁷Cl+H)⁺], 319.2 [100%, (M³⁵Cl³⁵Cl+H)⁺].

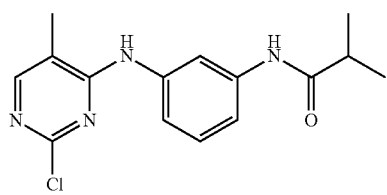 [SMILES: Cc1cnc(Cl)nc1Nc1cccc(NC(=O)C(C)C)c1]

2-Chloro-5-methyl-N⁴-[3-(2-methylpropanamido)phenyl]pyrimidin-4-amine (MA2-042-2): This was prepared from MA2-040-2 (0.178 g), 2,4-dichloro-5-methylpyrimidine (0.163 g), and DIPEA (0.192 mL) using procedure B (reaction time, 48 h) and isolated in the same way as MA2-030 to give the title compound MA2-042-2 as a gray solid (0.233 g, 77%). Mp: 186-189° C. ¹H NMR (400 MHz, DMSO-$d_6$): δ 9.87 (s, 1H, 50% reduced on $D_2O$ shake), 8.88 (s, 1H, disappeared on $D_2O$ shake), 8.03 (s, 1H), 7.87 (s, 1H), 7.38-7.23 (m, 3H), 2.60 (septet, J=6.8 Hz, 1H), 2.16 (s, 3H), 1.10 (d, J=6.8 Hz, 6H). HPLC-MS (ESI+): m/z 307.1 [40%, (M³⁵Cl³⁷Cl+H)⁺], 305.2 [100%, (M³⁵Cl³⁵Cl+H)⁺].

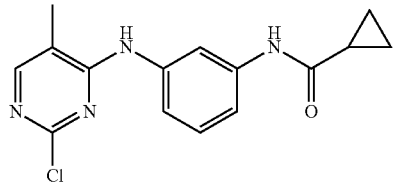 [SMILES: Cc1cnc(Cl)nc1Nc1cccc(NC(=O)C2CC2)c1]

2-Chloro-5-methyl-N⁴-[3-(cyclopropanecarboxamido)phenyl]pyrimidin-4-amine (MA2-042-3): This was prepared from MA2-040-3 (0.176 g), 2,4-dichloro-5-methylpyrimidine (0.163 g), and DIPEA (0.192 mL) using procedure B (reaction time, 48 h) and isolated in the same way as MA2-030 to give the title compound MA2-042-2 to give the title compound MA2-042-3 as a gray solid (0.219 g, 72%). Mp: 230-232° C. ¹H NMR (400 MHz, DMSO-$d_6$): δ 10.22 (s, 1H, 40% reduced on $D_2O$ shake), 8.87 (s, 1H, disappeared on $D_2O$ shake), 8.03 (d, J=0.7 Hz, 1H), 7.85 (s, 1H), 7.35-7.24 (m, 3H), 2.15 (s, 3H), 1.80 (quintet, J=6.2 Hz, 1H), 0.79 (d, J=6.2 Hz, 4H). HPLC-MS (ESI+): m/z 305.1 [40%, (M³⁵Cl³⁷Cl+H)⁺], 303.2 [100%, (M³⁵Cl³⁵Cl+H)⁺].

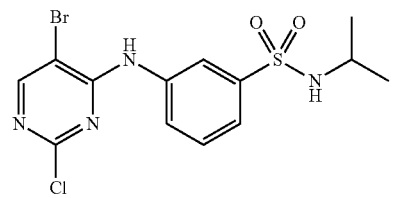 [SMILES: CC(C)NS(=O)(=O)c1cccc(Nc2nc(Cl)ncc2Br)c1]

2-Chloro-5-bromo-N⁴-(3-[N-(1,1-dimethylethyl)sulfamoyl]phenyl)-pyrimidin-4-amine (MA1-001): This was prepared from 2-chloro-5-bromopyrimidine (0.401 g) and SG1-147 (0.434 g) using procedure A (reaction time, 16 h) to give the title compound as a white solid (0.482 g, 68%). Mp: 212° C. (dec). ¹H NMR (400 MHz, DMSO-$d_6$): 9.59 (s, 1H, disappeared on $D_2O$ shake), 8.52 (s, 1H), 8.06-8.03 (m, 1H), 7.83-7.78 (m, 1H), 7.63-7.58 (m, 3H, 1H disappeared on $D_2O$ shake), 3.30 (octet, J=6.5 Hz, 1H), 0.97 (d, J=6.5 Hz, 6H). HPLC-MS (ESI+): m/z 409.0 [40%, (M⁸¹Br³⁷Cl+H)⁺], 407.0 [100%, (M⁷⁹Br³⁷Cl+H and M⁸¹Br³⁵Cl)⁺], 405.1 [100%, (M⁷⁹Br³⁵Cl+H)⁺].

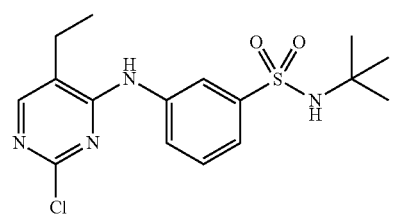 [SMILES: CCc1cnc(Cl)nc1Nc1cccc(S(=O)(=O)NC(C)(C)C)c1]

2-Chloro-5-ethyl-N⁴-(3-[N-(1,1-dimethylethyl)sulfamoyl]phenyl)pyrimidin-4-amine (MA1-017): This was prepared from MA1-012 (0.354 g) and SG1-137 (0.457 g) using procedure A (reaction time, 16 h) to give the title compound as a white solid (0.318 g, 43%). Mp: 209-210° C. ¹H NMR (400 MHz, DMSO-d$_6$): δ 9.16 (s, 1H, disappeared on D$_2$O shake), 8.14-8.07 (m, 2H), 7.90-7.81 (m, 1H), 7.59-7.52 (m, 3H, 1H disappeared on D$_2$O shake), 2.64 (q, J=7.4 Hz, 2H), 1.19 (t, J=7.4 Hz, 3H), 1.13 (s, 9H). HPLC-MS (ESI+): m/z 371.2 [40%, (M$^{37}$Cl+H)$^+$], 369.2 [100%, (M$^{35}$Cl+H)$^+$].

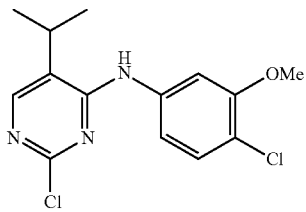 [SMILES: COc1cc(Nc2nc(Cl)ncc2C(C)C)ccc1Cl]

2-Chloro-5-methylethyl-N$^4$-[3-methoxy-4-chlorophenyl]-pyrimidin-4-amine (MA1-073): This was prepared from MA1-039 (0.262 g) and 3-methoxy-4-chloroaniline (0.227 g) using procedure B (reaction time, 36 h) and isolated in the same way as MA2-030 to give the title compound MA1-073 as a white solid (0.097 g, 31%). Mp: 230° C. (dec). $^1$H NMR (400 MHz, DMSO-d$_6$): δ 10.05 (s, 1H, 70% on D$_2$O shake), 8.50 (s, 1H), 7.69 (s, 1H), 7.31 (d, J=8.4 Hz, 1H), 7.29 (d, J=8.4 Hz, 1H), 3.82 (s, 3H), 3.08 (dt, J=13.8, 6.9 Hz, 1H), 1.24 (d, J=6.9 Hz, 6H). HPLC-MS (ESI+): m/z 314.1 [20%, (M$^{35}$Cl$^{37}$Cl+H)$^+$], 312.1 [100%, (M$^{35}$Cl$^{35}$Cl+H)$^+$].

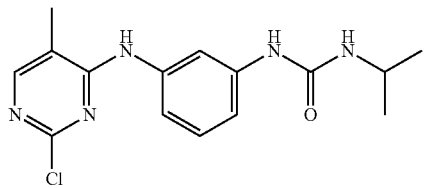 [SMILES: Cc1cnc(Cl)nc1Nc1cccc(NC(=O)NC(C)C)c1]

2-Chloro-5-methyl-N$^4$-(3-[3-(methylethyl)ureido]phenyl)-pyrimidin-4-amine (MA2-058-2): This was prepared from MA2-056-2 (0.193 g) and 2,4-dichloro-5-methylpyrimidine (0.163 g) using procedure B (reaction time, 48 h) and isolated in the same way as MA2-030 to give the title compound MA2-058-2 as a white solid (0.263 g, 82%). Mp: 248° C. (dec). $^1$H NMR (400 MHz, DMSO-d$_6$): δ 8.80 (s, 1H, 80% reduced on D$_2$O shake), 8.30 (s, 1H), 8.02 (d, J=0.8 Hz, 1H), 7.62 (s, 1H), 7.23-7.11 (m, 3H), 6.02 (d, J=7.5 Hz, 1H, 20% reduced on D$_2$O shake), 3.77-3.71 (m, 1H), 2.15 (s, 3H), 1.09 (d, J=6.5 Hz, 6H). HPLC-MS (ESI+): m/z 322.2 [40%, (M$^{37}$Cl+H)$^+$], 320.2 [100%, (M$^{35}$Cl+H)$^+$].

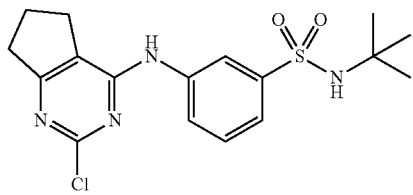 [SMILES: CC(C)(C)NS(=O)(=O)c1cccc(Nc2nc(Cl)nc3c2CCC3)c1]

2-Chloro-N$^4$-(3-[N-(1,1-dimethylethyl)sulfamoyl]phenyl)-6,7-dihydro-5H-cyclopenta[d]pyrimidine-4-amine (MA2-098-1): This was prepared from MA2-092 (0.189 g) and SG1-137 (0.228 g) using procedure B (reaction time, 3 days) and isolated in the same way as MA2-030 to give the title compound MA2-098-1 as a white solid (0.197 g, 52%). Mp: 230° C. (dec). $^1$H NMR (400 MHz, DMSO-d$_6$): δ 9.39 (s, 1H, disappeared on D$_2$O shake), 8.13 (brd, J=1.8 Hz, 1H), 7.94 (dt, J=7.5, 1.8 Hz, 1H), 7.58-7.48 (m, 3H, 1H disappeared on D$_2$O shake), 2.83 (t, J=7.6 Hz, 4H), 2.08 (quintet, J=7.6 Hz, 2H), 1.13 (s, 9H). HPLC-MS (ESI+): m/z 383.2 [40%, (M$^{37}$Cl+H)$^+$], 381.2 [100%, (M$^{35}$Cl+H)$^+$].

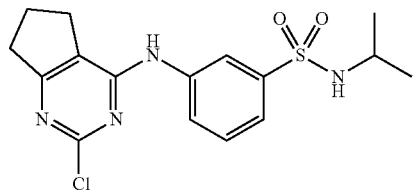 [SMILES: CC(C)NS(=O)(=O)c1cccc(Nc2nc(Cl)nc3c2CCC3)c1]

2-Chloro-N$^4$-(3-[N-(1-methylethyl)sulfamoyl]phenyl)-6,7-dihydro-5H-cyclopenta[d]pyrimidine-4-amine (MA2-098-2): This was prepared from MA2-092 (0.189 g) and SG1-147 (0.214 g) using procedure B (reaction time, 3 days) and isolated in the same way as MA2-030 to give the title compound MA2-098-2 as a white solid (0.220 g, 60%). Mp: 212° C. (dec). $^1$H NMR (400 MHz, DMSO-d$_6$): δ 9.41 (s, 1H, disappeared on D$_2$O shake), 8.13 (t, J=1.9 Hz, 1H), 8.01-7.98 (m, 1H), 7.57 (t, J=8.1 Hz, 1H), 7.58 (d, J=7.2 Hz, 1H), 3.3-3.26 (m, 1H, partially overlapped by residual DMSO solvent signal), 2.83 (t, J=7.7 Hz, 4H), 2.08 (quintet, J=7.7 Hz, 2H), 0.97 (d, J=6.5 Hz, 6H). HPLC-MS (ESI+): m/z 369.2 [40%, (M$^{37}$Cl+H)$^+$], 367.1 [100%, (M$^{35}$Cl+H)$^+$].

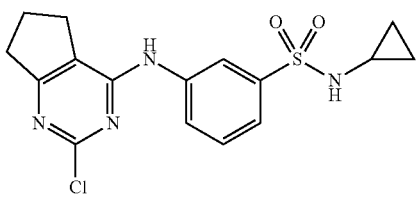 [SMILES: O=S(=O)(NC1CC1)c1cccc(Nc2nc(Cl)nc3c2CCC3)c1]

2-Chloro-N$^4$-(3-(N-cyclopropylsulfamoyl)phenyl)-6,7-dihydro-5H-cyclopenta[d]pyrimidine-4-amine (MA2-098-3): This was prepared from MA2-092 (0.189 g) and RJ1-025 (0.212 g) using procedure B (reaction time, 3 days) and isolated in the same way as MA2-030 to give the title compound MA2-098-3 as a white solid (0.198 g, 54%). Mp: 216° C. (dec). $^1$H NMR (400 MHz, DMSO-d$_6$): δ 9.44 (s, 1H, disappeared on D$_2$O shake), 8.15 (t, J=1.9 Hz, 1H), 8.01 (dd, J=8.0, 1.3 Hz, 1H), 7.95 (d, J=2.4 Hz, 1H, disappeared on D$_2$O shake), 7.59 (t, J=8.0 Hz, 1H), 7.49 (8.01 (dd, J=8.0, 1.3 Hz, 1H)), 2.83 (t, J=7.6 Hz, 4H), 2.2-2.14 (m, 1H), 2.08 (quintet, J=7.8 Hz, 2H), 0.56-0.48 (m, 2H), 0.47-0.38 (m, 2H). HPLC-MS (ESI+): m/z 367.1 [40%, (M$^{37}$Cl+H)$^+$], 365.1 [100%, (M$^{35}$Cl+H)$^+$].

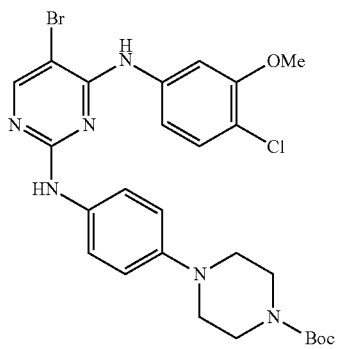 [SMILES: COc1cc(Nc2nc(Nc3ccc(N4CCN(C(=O)OC(C)(C)C)CC4)cc3)ncc2Br)ccc1Cl]

5-Bromo-N⁴-[4-chloro-3-methoxyphenyl]-N²-(4-[14-(1,1-dimethylethoxy)carbonylpiperazin-1-yl]phenyl)pyrimidine-2,4-diamine (MA2-010): This was obtained by stirring MA2-004 (0.698 g) and 4-(4-tert-butoxycarbonylpiperazino)aniline (0.555 g) in isopropanol (4 mL) at 85° C. (oil bath) for 24 h. The reaction mixture was allowed to cool to room temperature and diluted with water (50 mL) which led to the precipitation of product. The crude product was filtered and washed with water (4×10 mL) and hexane (4×10 mL) to provide MA2-010 as a grey solid (0.960 g, 81%). Mp: 194-195° C. ¹H NMR (400 MHz, DMSO-d₆ acquired at 70° C.): δ 8.92 (s, 1H, disappeared on D₂O shake), 8.41 (s, 1H, disappeared on D₂O shake), 8.17 (s, 1H), 7.43-7.37 (m, 3H), 7.34-7.28 (m, 2H), 6.82 (d, J=9.0 Hz, 2H), 3.75 (s, 3H), 3.50-3.45 (m, 4H), 3.06-3.00 (m, 4H), 1.44 (s, 9H). HPLC-MS (ESI+): m/z 591.2 [100%, (M⁸¹Br³⁵Cl+H)⁺ and (M⁷⁹Br³⁷Cl+H)⁺], 589.2 [70%, (M⁷⁹B³⁵Cl+H)⁺].

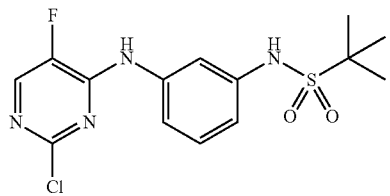 [SMILES: CC(C)(C)S(=O)(=O)Nc1cccc(Nc2nc(Cl)ncc2F)c1]

2-Chloro-5-fluoro-N⁴-(3-[(1,1-dimethylethyl)sulfonamido]phenyl)-pyrimidin-4-amine (MA3-061): This was prepared from 2-chloro-5-fluoro-pyrimidine (0.084 g) and MA3-010 (0.114 g) using procedure B (reaction time, 3 days) and isolated in the same way as MA2-030 to give the title compound MA3-061 as a white solid (0.147 g, 81%). Mp: 194-196° C. ¹H NMR (400 MHz, DMSO-d₆): δ 10.05 (s, 1H, disappeared on D₂O shake), 9.73 (s, 1H, disappeared on D₂O shake), 8.33 (d, J=3.4 Hz, 1H), 7.71 (s, 1H), 7.37 (d, J=8.0 Hz, 1H), 7.27 (t, J=8.0 Hz, 1H), 7.02 (d, J=8.0 Hz, 1H), 1.30 (s, 9H). HPLC-MS (ESI+): m/z 361.1 [40%, (M³⁷Cl+H)⁺], 359.1 [100%, (M³⁵Cl+H)⁺].

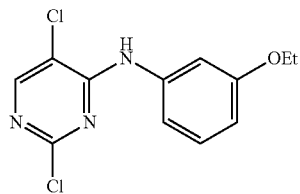 [SMILES: CCOc1cccc(Nc2nc(Cl)ncc2Cl)c1]

2,5-Dichloro-N⁴-(3-ethoxyphenyl)pyrimidin-4-amine (MA1-058): This was prepared from 2,4,5-trichloropyrimidine (0.367 g) and 3-ethoxyaniline (0.288 g) using procedure B (reaction time, 2 h) and isolated in the same way as MA2-030 to give the title compound MA1-058 as a white solid (0.168 g, 91%). Mp: 89-91° C. ¹H NMR (400 MHz, DMSO-d₆): δ 9.46 (s, 1H, disappeared on D₂O shake), 8.39 (s, 1H), 7.27 (t, J=8.2 Hz, 1H), 7.24 (t, J=2.1 Hz, 1H), 7.17 (d, with unresolved fine coupling, J=8.2 Hz, 1H), 6.74 (ddd, J=8.2, 2.4, 0.8 Hz, 1H), 4.02 (q, J=7.0 Hz, 2H), 1.34 (t, J=7.0 Hz, 3H). HPLC-MS (ESI+): m/z 286.1 [70%, (M³⁵Cl³⁷Cl+H)⁺], 284.1 [100%, (M³⁵Cl³⁵Cl+H)⁺].

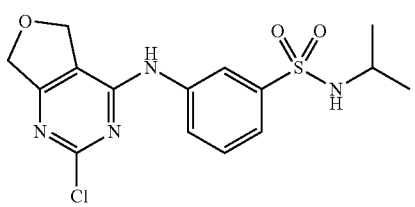 [SMILES: CC(C)NS(=O)(=O)c1cccc(Nc2nc(Cl)nc3c2COC3)c1]

2-Chloro-N⁴-(3-[N-(1-methylethyl)sulfamoyl]phenyl)-5,7-dihydrofuro[3,4-d]pyrimidine-4-amine (MA3-002-2): This was prepared from MA2-096 (0.096 g) and SG1-147 (0.107 g) using procedure B (reaction time, 18 h, reaction temperature 100° C.) and isolated in the same way as MA2-030 to give the title compound MA3-002-2 as a white solid (0.168 g, 91%). Mp: 268° C. ¹H NMR (400 MHz, DMSO-d₆): δ 9.81 (s, 1H, disappeared on D₂O shake), 8.07 (t, J=1.8 Hz, 1H), 7.95 (ddd, J=8.1, 1.8, 1.0 Hz, 1H), 7.60 (d, J=7.2 Hz, disappeared on D₂O shake, 1H), 7.58 (t, J=8.0 Hz, 1H), 7.50 (ddd, J=8.1, 1.8, 1.1 Hz, 1H), 4.99 (t, J=2.5 Hz, 2H), 4.85 (t, J=2.5 Hz, 2H), 3.28 (quint, J=6.5 Hz, 1H), 0.95 (d, J=6.5 Hz, 6H). HPLC-MS (ESI+): m/z 371.1 [40%, (M³⁷Cl+H)⁺], 369.2 [100%, (M³⁵Cl+H)⁺].

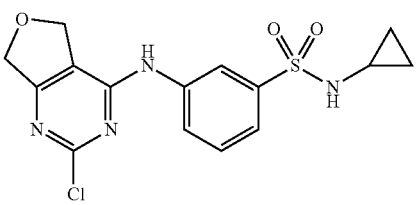 [SMILES: O=S(=O)(NC1CC1)c1cccc(Nc2nc(Cl)nc3c2COC3)c1]

2-Chloro-N⁴-(3-[N-cyclopropylsulfamoyl]phenyl)-5,7-dihydrofuro[3,4-d]pyrimidine-4-amine (MA3-002-3): This was prepared from MA2-096 (0.096 g) and RJ1-042 (0.212 g) using procedure B (reaction time, 18 h, reaction temperature 100° C.) and isolated in the same way as MA2-030 to give the title compound MA3-002-3 as a white solid (0.165 g, 90%). Mp: 208° C. (dec). ¹H NMR (400 MHz, DMSO-d₆): δ 9.86 (s, 1H, disappeared on D₂O shake), 8.10 (s, 1H), 8.00 (d with unresolved fine coupling, J=8.2, Hz, 1H), 7.96 (d, J=2.3 Hz, 1H, disappeared on D₂O shake), 7.62 (t, J=8.0 Hz, 1H), 7.52 (d, J=8.0 Hz, 1H), 5.02 (s, 2H), 4.87 (s, 2H), 2.22-2.12 (m, 1H), 0.56-0.48 (m, 2H), 0.47-0.38 (m, 2H). HPLC-MS (ESI+): m/z 757.1 [20%, (2M³⁷Cl+Na)⁺], 755.1 [30%, (2M³⁵Cl+Na)⁺], 369.1 [40%, (M³⁷Cl+H)⁺], 367.1 [100%, (M³⁵Cl+H)⁺].

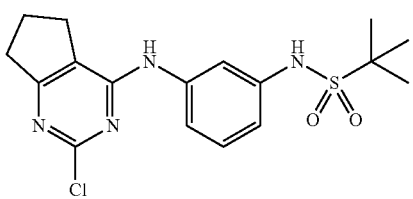 [SMILES: CC(C)(C)S(=O)(=O)Nc1cccc(Nc2nc(Cl)nc3c2CCC3)c1]

2-Chloro-N⁴-(3-[(1,1-dimethylethyl)sulfonamido]phenyl)-6,7-dihydro-5H-cyclopenta[d]pyrimidine-4-amine (MA3-014-1): This was prepared from MA2-092 (0.095 g) and MA3-010 (0.114 g) using procedure B (reaction time, 3 days) and isolated in the same way as MA2-030 to give the title compound MA3-014-1 as a white solid (0.110 g, 52%). Mp: 217° C. (dec). ¹H NMR (400 MHz, DMSO-d₆): δ 9.65 (s, 1H, 80% reduced on D₂O shake), 9.14 (s, 1H, 85% reduced on D₂O shake), 7.59 (s, 1H), 7.34 (d, J=8.0 Hz, 1H), 7.21 (t, J=8.0 Hz, 1H), 6.96 (d, J=8.0 Hz, 1H), 2.78 (t, J=7.7 Hz, 4H), 2.04 (quint, J=7.7 Hz, 2H), 1.28 (s, 9H). HPLC-MS (ESI+): m/z 383.2 [40%, (M³⁷Cl+H)⁺], 381.2 [100%, (M³⁵Cl+H)⁺].

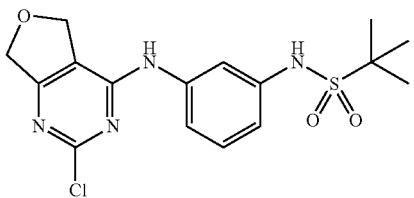 [SMILES: CC(C)(C)S(=O)(=O)Nc1cccc(Nc2nc(Cl)nc3c2COC3)c1]

2-Chloro-N⁴-(3-[(1,1-dimethylethyl)sulfonamido]phenyl)-5,7-dihydrofuro[3,4-d]pyrimidine-4-amine (MA3-016-1): This was prepared from MA2-096 (0.096 g) and MA3-010 (0.114 g) using procedure B (reaction time, 2 days) and isolated in the same way as MA2-030 to give the title compound MA3-016-1 as a white solid (0.138 g, 69%). Mp: 194° C. (dec). ¹H NMR (400 MHz, DMSO-d₆): δ 9.73 (s, 1H, disappeared on D₂O shake), 9.60 (s, 1H, disappeared on D₂O shake), 7.57 (s, 1H), 7.38 (d, J=8.0 Hz, 1H), 7.26 (t, J=8.0 Hz, 1H), 7.01 (d, J=8.0 Hz, 1H), 4.96 (s, 2H), 4.84 (s, 2H), 1.30 (s, 9H). HPLC-MS (ESI+): m/z 385.2 [40%, (M³⁷Cl+H)⁺], 383.2 [100%, (M³⁵Cl+H)⁺].

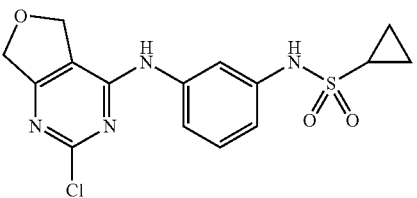 [SMILES: O=S(=O)(Nc1cccc(Nc2nc(Cl)nc3c2COC3)c1)C1CC1]

2-Chloro-N⁴-[3-(cyclopropylsulfonamido)phenyl]-5,7-dihydrofuro[3,4-d]pyrimidine-4-amine (MA3-016-3): This was prepared from MA2-096 (0.096 g) and RJ1-025 (0.106 g) using procedure B (reaction time, 2 days) and isolated in the same way as MA2-030 to give the title compound MA3-016-3 as a white solid (0.129 g, 70%). Mp: 237° C. (dec). ¹H NMR (400 MHz, DMSO-d₆): δ 9.86 (s, 1H, disappeared on D₂O shake), 8.10 (t, J=1.9 Hz, 1H), 8.00 (ddd, J=8.1, 2.1, 0.9 Hz, 1H), 7.98 (d, J=2.3 Hz, 1H, disappeared on D₂O shake), 7.63 (t, J=8.1 Hz, 1H), 7.53 (ddd, J=8.1, 2.1, 0.9 Hz, 1H), 5.02 (t, J=2.5 Hz, 2H), 4.87 (t, J=2.5 Hz, 2H), 2.21-2.15 (m, 1H), 0.55-0.47 (m, 2H), 0.47-0.39 (m, 2H). HPLC-MS (ESI+): m/z 369.1 [40%, (M³⁷Cl+H)⁺], 367.1 [100%, (M³⁵Cl+H)⁺].

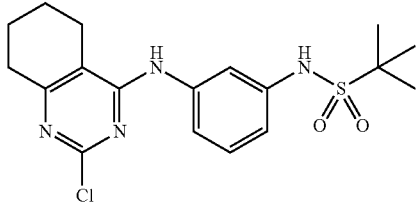 [SMILES: CC(C)(C)S(=O)(=O)Nc1cccc(Nc2nc(Cl)nc3c2CCCC3)c1]

2-Chloro-N⁴-(3-[(1,1-dimethylethyl)sulfonamido]phenyl)-5,6,7,8-tetrahydroquinazoline-4-amine (MA3-064-1): This was prepared from MA2-10 (0.114 g) and MA3-034 (0.102 g) using procedure B (reaction time, 4 days). The volatiles were evaporated under the reduced pressure and the product was purified via column chromatography (SiO₂) eluting with hexanes/EtOAc (1:9 to 1:2 v/v) to give the title compound MA3-064-1 as a gray solid (0.087 g, 44%). Mp: 265° C. (dec). ¹H NMR (400 MHz, DMSO-d₆): δ 9.67 (s, 1H, disappeared on D₂O shake), 8.73 (s, 1H, disappeared on D₂O shake), 7.56 (s, 1H), 7.26-7.22 (m, 2H), 7.02-6.98 (m, 1H), 2.62 (t, J=6.1 Hz, 2H), 2.47-2.43 (m, 2H, partially overlapped by residual DMSO solvent signal), 1.81-1.73 (m, 4H), 1.30 (s, 9H). ¹H NMR (400 MHz, CD₃OD) δ 7.73-7.70 (m, 1H), 7.27-7.24 (m, 2H), 7.11-7.05 (m, 1H), 4.63 (s, 1H), 2.69 (t, J=6.0 Hz, 3H), 2.55 (t, J=6.0 Hz, 2H), 1.92-1.86 (m, 4H), 1.39 (s, 19H). HPLC-MS (ESI+): m/z 397.2 [40%, (M³⁷Cl+H)⁺], 395.2 [100%, (M³⁵Cl+H)⁺].

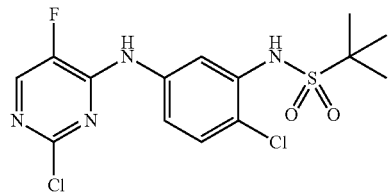 [SMILES: CC(C)(C)S(=O)(=O)Nc1cc(Nc2nc(Cl)ncc2F)ccc1Cl]

2-Chloro-5-fluoro-N⁴-(4-chloro-[3-(1,1-dimethylethylsulfonamido)]phenyl)pyrimidine-4-amine (MA3-070): This was prepared from SG3-010 (0.043 g) and 2,4-dichloro-5-fluoropyrimidine (0.027 g) using procedure B (reaction time, 4 h) and isolated in the same way as MA2-030 to give the title compound MA3-070 as a white solid (0.054 g, 86%). Mp: 223° C. (dec). ¹⁹F NMR (376 MHz, DMSO-d₆): δ −152.98 (s). ¹H NMR (400 MHz, DMSO-d₆): δ 10.17 (s, 1H, disappeared on D₂O shake), 9.34 (s, 1H, disappeared on D₂O shake), 8.36 (d, J=3.4 Hz, 1H), 8.03 (d, J=2.6 Hz, 1H), 7.63 (dd, J=8.8, 2.6 Hz, 1H), 7.49 (d, J=8.8 Hz, 1H), 1.34 (s, 9H). HPLC-MS (ESI+): m/z 807.1 [30%, (2M³⁵Cl³⁵Cl+Na)⁺], 395.1 [70%, (M³⁵Cl³⁷Cl+H)⁺], 393.1 [100%, (M³⁵Cl³⁵Cl+H)⁺].

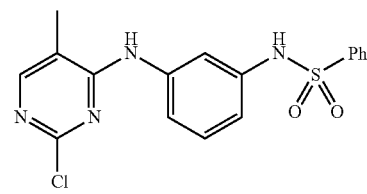 [SMILES: Cc1cnc(Cl)nc1Nc1cccc(NS(=O)(=O)c2ccccc2)c1]

2-Chloro-5-methyl-N⁴-([3-phenylsulfonamido]phenyl)pyrimidine-4-amine (MA4-006-1): This was prepared from MA3-092 (0.124 g) and 2,4-dichloro-5-methylpyrimidine (0.082 g) using procedure B (reaction time, 2.5 days) and isolated in the same way as MA2-030 to give the title compound MA4-006-1 as a beige solid (0.128 g, 69%). Mp: 199° C. (dec). ¹H NMR (400 MHz, DMSO-$d_6$): δ 10.36 (s, 1H, disappeared on D$_2$O shake), 8.85 (s, 1H), 8.05 (d, J=0.9 Hz, 1H), 7.85-7.80 (m, 2H), 7.63-7.58 (t, J=7.4 Hz with fine coupling, 1H), 7.57-7.52 (m, 3H), 7.30 (ddd, J=8.0, 2.0, 0.9 Hz, 1H), 7.18 (t, J=8.0 Hz, 1H), 6.81 (ddd, J=8.0, 2.0, 0.9 Hz, 1H), 2.14 (d, J=0.7 Hz, 3H). HPLC-MS (ESI+): m/z 777.2 [10%, (2M³⁵Cl+Na)⁺], 377.1 [40%, (M³⁷Cl+H)⁺], 375.2 [100%, (M³⁵Cl+H)⁺].

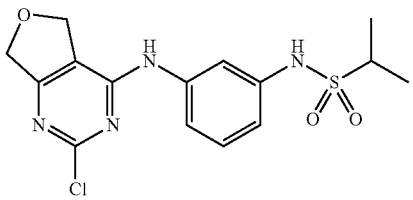 [SMILES: CC(C)S(=O)(=O)Nc1cccc(Nc2nc(Cl)nc3c2COC3)c1]

2-Chloro-N⁴-(3-[(1-methylethyl)sulfonamido]phenyl)-5,7-dihydrofuro[3,4-d]pyrimidine-4-amine (MA3-016-2): This was prepared from MA2-096 (0.096 g) and MA3-004 (0.107 g) using procedure B (reaction time, 2 days) and isolated in the same way as MA2-030 to give the title compound MA3-016-2 as a white solid (0.121 g, 66%). Mp: 241° C. (dec). ¹H NMR (400 MHz, DMSO-$d_6$): 9.88 (s, 1H, disappeared on D$_2$O shake), 9.62 (s, 1H, disappeared on D$_2$O shake), 7.54 (s, 1H), 7.36 (d, J=8.0 Hz, 1H), 7.29 (t, J=8.0 Hz, 1H), 6.94 (d, J=8.0 Hz, 1H), 4.97 (s, 2H), 4.84 (s, 2H), 3.33-3.24 (m, 1H, appeared from the overlapping water signal on D$_2$O shake) 1.26 (d, J=6.7 Hz, 6H). HPLC-MS (ESI+): m/z 761.2 [13%, (M³⁵Cl+M³⁷Cl+Na)⁺], 759.2 [12%, (2M³⁵Cl+Na)⁺], 371.1 [40%, (M³⁷Cl+H)⁺], 369.2 [100%, (M³⁵Cl+H)⁺].

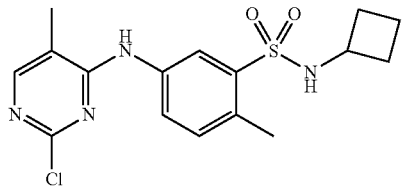 [SMILES: Cc1ccc(Nc2nc(Cl)ncc2C)cc1S(=O)(=O)NC1CCC1]

2-Chloro-5-methyl-N⁴-(4-methyl-[3-(N-cyclobutyl)sulfamoyl]phenyl)-pyrimidine-4-amine (MA4-082): This was prepared from MA4-080 (0.736 g) and 2,4-dichloro-5-methylpyrimidine (0.499 g) using procedure B (reaction time, 3.5 days) and isolated in the same way as MA2-030 to give the title compound MA4-082 as a yellow solid (0.558 g, 50%). Mp: 237° C. (dec). ¹H NMR (400 MHz, DMSO-$d_6$): δ 9.09 (s, 1H, disappeared on D$_2$O shake), 8.10 (d, J=2.1 Hz, 1H), 8.08 (t, J=0.9 Hz, 1H), 7.97 (d, J=8.3 Hz, 1H, disappeared on D$_2$O shake), 7.78 (dd, J=8.2, 2.2 Hz, 1H), 7.36 (d, J=8.2 Hz, 1H), 3.62-3.56 (m, 1H), 2.56 (s, 3H), 2.17 (s, 3H), 1.93-1.87 (m, 2H), 1.84-1.73 (m, 2H), 1.55-1.37 (m, 2H). HPLC-MS (ESI+): m/z 369.1 [40%, (M³⁷Cl+H)⁺], 367.2 [100%, (M³⁵Cl+H)⁺].

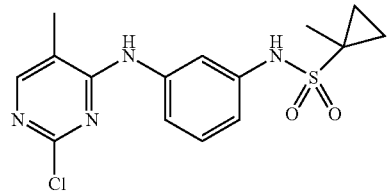 [SMILES: Cc1cnc(Cl)nc1Nc1cccc(NS(=O)(=O)C2(C)CC2)c1]

2-Chloro-5-methyl-N⁴-(3-[(1-methylcyclopropyl)sulfonamido]phenyl)pyrimidine amine (MA4-98): This was prepared from MA4-096 (0.450 g) and 2,4-dichloro methylpyrimidine (0.324 g) using procedure B (reaction time, 2.5 days). The reaction mixture was diluted with ethyl acetate (40 mL) and washed with water (50 mL). The product was purified via column chromatography (SiO$_2$) eluting with hexanes/EtOAc (1:9 to 1:4 v/v) to give the title compound MA4-098 as a yellow solid (0.279 g, 45%). Mp: 215° C. (dec). ¹H NMR (400 MHz, DMSO-$d_6$): δ 9.83 (s, 1H, disappeared on D$_2$O shake), 8.91 (s, 1H, 50% reduced on D$_2$O shake), 8.05 (d, J=0.9 Hz, 1H), 7.59 (t, J=2.0 Hz, 1H), 7.341 (ddd, J=8.0, 2.0, 1.1 Hz, 1H), 7.27 (t, J=8.0 Hz, 1H), 6.98 (ddd, J=8.0, 2.0, 1.1 Hz, 1H), 2.17 (d, J=0.7 Hz, 3H), 1.43 (s, 3H), 1.20-1.14 (m, 2H), 0.77-0.71 (m, 2H). HPLC-MS (ESI+): m/z 355.1 [40%, (M³⁷Cl+H)⁺], 353.1 [100%, (M³⁵Cl+H)⁺].

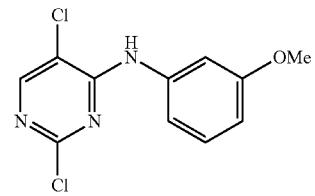 [SMILES: COc1cccc(Nc2nc(Cl)ncc2Cl)c1]

2,5-Dichloro-N⁴-(3-methoxyphenyl)pyrimidine-4-amine (MA1-055-1): This was prepared from m-anisidine (0.246 g) and 2,4,5-trichloropyrimidine (0.367 g) using procedure B (reaction time, 1 h) and isolated in the same way as MA2-030 to give the title compound MA1-055-1 as a white solid (0.476 g, 88%). Mp: 100-101° C. ¹H NMR (400 MHz, DMSO-$d_6$): δ 9.45 (s, 1H, disappeared on D$_2$O shake), 8.38 (s), 7.28 (t, J=8.1 Hz, 1H), 7.24 (t, J=2.1 Hz, 1H), 7.20 (d, with unresolved fine coupling, J=8.1 Hz, 1H), 6.75 (d, with unresolved fine coupling, J=8.1 Hz, 1H), 3.74 (s, 3H). HPLC-MS (ESI+): m/z 272.1 [70%, (M³⁵Cl³⁷Cl+H)⁺], 270.2 [100%, (M³⁵Cl³⁵Cl+H)⁺].

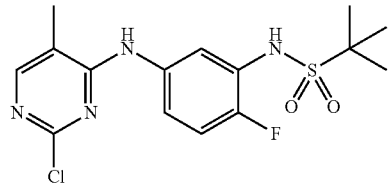 [SMILES: Cc1cnc(Cl)nc1Nc1ccc(F)c(NS(=O)(=O)C(C)(C)C)c1]

2-Chloro-5-methyl-N⁴-(4-fluoro-3-[(1,1-dimethylethyl)sulfonamido]phenyl)pyrimidine-4-amine (MA4-025): This was prepared from MA4-024 (0.2123 g) and 2,4-dichloro-5-methylpyrimidine (0.3082 g) using procedure B (reaction time, 2.5 days) and isolated in the same way as MA2-030 to give the title compound MA4-025 as a yellow solid (0.095 g, 51%). Mp: 268° C. (dec). ¹⁹F NMR (376 MHz, DMSO-d$_6$): δ −127.93 (s). $^1$H NMR (400 MHz, DMSO-d$_6$): δ 9.54 (s, 1H, 90% reduced on D$_2$O shake), 8.94 (s, 1H, 85% reduced on D$_2$O shake), 8.05 (d, J=0.9 Hz, 1H), 7.78 (dd, J=7.3, 2.7 Hz, 1H), 7.47 (ddd, J=9.0, 4.2, 2.7 Hz, 1H), 7.25 (dd, J=10.1, 9.0 Hz, 1H), 2.16 (d, J=0.7 Hz, 3H), 1.32 (s, 9H). HPLC-MS (ESI+): m/z 769.2 [10%, (M$^{37}$Cl+M$^{35}$Cl+Na)$^+$], 767.2 [10%, (2M$^{35}$Cl+Na)$^+$], 375.1 [40%, (M$^{37}$Cl+H)$^+$], 373.2 [100%, (M$^{35}$Cl+H)$^+$].

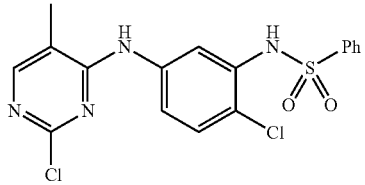 [SMILES: Cc1cnc(Cl)nc1Nc1ccc(Cl)c(NS(=O)(=O)c2ccccc2)c1]

2-Chloro-5-methyl-N$^4$-(4-chloro-[3-phenylsulfonamido]phenyl)pyrimidine-4-amine (MA4-006-2): This was prepared from MA4-002 (0.141 g) and 2,4-dichloro-5-methylpyrimidine (0.082 g) using procedure B (reaction time, 2.5 days) and isolated in the same way as MA2-030 to give the title compound MA4-006-2 as a white solid (0.094 g, 46%). Mp: 214° C. (dec). $^1$H NMR (400 MHz, DMSO-d$_6$): δ 8.84 (s, 1H, disappeared on D$_2$O shake), 8.02 (d, J=0.7 Hz, 1H, disappeared on D$_2$O shake), 7.83-7.80 (m, 2H, 1H disappeared on D$_2$O shake), 7.59 (t, with unresolved fine coupling, J=7.3 Hz, 1H), 7.55-7.50 (m, with unresolved fine coupling, 3H), 7.23 (d, J=8.9 Hz, 1H), 7.16 (t, J=8.0 Hz, 1H), 6.78 (d, with unresolved fine coupling, J=8.0 Hz, 1H), 2.12 (s, 3H). HPLC-MS (ESI+): m/z 841.0 [10%, (2M$^{37}$Cl$^{35}$Cl+Na)$^+$], 411.1 [70%, (M$^{35}$Cl$^{37}$Cl+H)$^+$], 409.1 [100%, (M$^{35}$Cl$^{35}$Cl+H)$^+$].

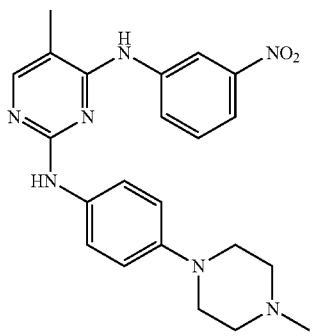

5-Methyl-N$^4$-[3-nitrophenyl]-N$^2$-[4-(4-methylpiperazin-1-yl)phenyl]pyrimidine-2,4-diamine (MA4-104): This was obtained as a yellow solid (1.3 g, 82%) from MA4-092 (1.00 g) and 4-(4-methylpiperazino)aniline (0.723 g) using the general method x. The product was purified by column chromatography (SiO$_2$, eluting with DCM-MeOH, 0-12%). Mp: 194-198° C. HPLC: 99% [t$_R$=7.2 min, 35% MeOH, 65% water (with 0.1% TFA), 20 min]. $^1$H NMR (400 MHz, DMSO-d$_6$): δ 8.84 (s, 1H, disappeared on D$_2$O shake), 8.71 (s, 1H, disappeared on D$_2$O shake), 8.49 (t, J=2.2 Hz, 1H), 8.36 (d, J=8.1 Hz, 1H), 7.93 (d, J=0.8 Hz, 1H), 7.86 (ddd, J=8.1, 2.3, 0.9 Hz, 1H), 7.57 (t, J=8.1 Hz, 1H), 7.44 (d, J=9.0 Hz, 2H), 6.76 (d, J=9.0 Hz, 2H), 3.06-2.97 (m, 4H), 2.48-2.39 (m, 4H), 2.21 (s, 3H), 2.12 (d, J=0.8 Hz, 3H). HPLC-MS (ESI+): m/z 420.3 [20%, (M+H)$^+$], 210.7 [100%, (M+2H)$^{2+}$]. LC-MS (ESI+): m/z 420.2 [100%, (M+H)$^+$]. HRMS (ESI+): m/z calcd for C$_{22}$H$_{25}$N$_7$O$_2$ (M+H)$^+$ 420.2143, found 420.2146.

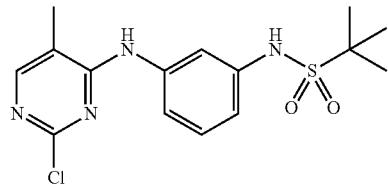

2-Chloro-5-methyl-N$^4$-[3-(1,1-dimethylethyl)sulfonamidophenyl]pyrimidine amine (MA2-008): To a solution of MA2-006 (0.140 g) in DCM (10 mL) was added m-CPBA (65%, 0.093 g) under Argon. After stirring overnight at room temperature, the reaction mixture was diluted with DCM (50 mL) and washed with saturated NaHCO$_3$ (2×25 mL). The organic layer was dried over Na$_2$SO$_4$, concentrated and purified via column chromatography (SiO$_2$) eluting with hexanes/EtOAc (0:10 to 2:8 v/v) to give the title compound MA2-008 as a white solid (0.065 g, 44%). Mp: 254° C. (dec). $^1$H NMR (400 MHz, DMSO-d$_6$): δ 9.68 (s, 1H, 60% reduced on D$_2$O shake), 8.90 (s, 1H, 10% reduced on D$_2$O shake), 8.05 (d, J=0.9 Hz, 1H), 7.60 (t, J=1.9 Hz, 1H), 7.29 (dt, J=8.0, 1.5 Hz, 1H), 7.24 (t, J=8.0 Hz, 1H), 7.02 (ddd, J=8.0, 2.0, 1.5 Hz, 1H), 2.16 (d, J=0.9 Hz, 3H), 1.30 (s, 9H). HPLC-MS (ESI+): m/z 357.1 [40%, (M$^{37}$Cl+H)$^+$], 355.1 [100%, (M$^{35}$Cl+H)$^+$].

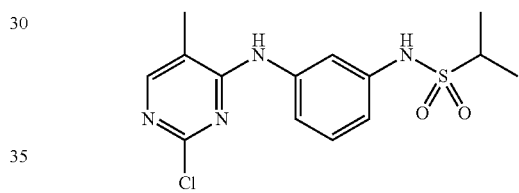

2-Chloro-5-methyl-N$^4$-(3-[(1-methylethyl)sulfonamido]phenyl)pyrimidine-4-amine (MA4-008): This was prepared from MA3-004 (0.107 g) and 2,4-dichloro-5-methylpyrimidine (0.082 g) using procedure B (reaction time, 2.5 days) and isolated in the same way as MA2-030 to give the title compound MA4-008 as a white solid (0.088 g, 52%). Mp: 207° C. (dec). $^1$H NMR (400 MHz, DMSO-d$_6$): δ 9.85 (s, 1H, 85% reduced on D$_2$O shake), 8.94 (s, 1H, 30% reduced on D$_2$O shake), 8.06 (d, J=0.9 Hz, 1H), 7.57 (s, 1H), 7.31-7.26 (m, 2H), 6.98-6.90 (m, 1H), 3.33-3.26 (m, 1H partially overlapped by residual water signal), 2.16 (s, 3H), 1.27 (d, J=6.8 Hz, 6H). HPLC-MS (ESI+): m/z 343.1 [40%, (M$^{37}$Cl+H)$^+$], 341.2 [100%, (M$^{35}$Cl+H)$^+$].

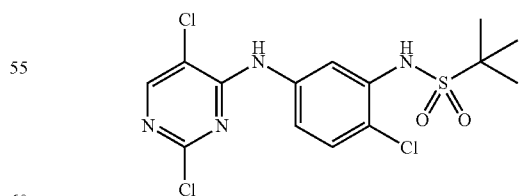

2,5-Dichloro-N$^4$-(4-chloro-[3-(1,1-dimethylethylsulfonamido)]phenyl)pyrimidine amine (MA4-142): This was prepared from SG3-105 (0.263 g) and 2,4,5-trichloropyrimidine (0.183 g) using procedure B (reaction time, 4 h) and isolated in the same way as MA2-030 to give the title compound MA4-025 as a white solid (0.332 g, 81%). Mp: 229-231° C.

¹H NMR (400 MHz, DMSO-d₆): 9.68 (s, 1H, disappeared on D₂O shake), 9.38 (s, 1H, disappeared on D₂O shake), 8.42 (s, 1H), 7.91 (s, 1H), 7.51-7.48 (m, 2H), 1.33 (s, 9H). HPLC-MS (ESI+): m/z 841.1 [50%, (M³⁷Cl³⁵Cl³⁵Cl+ 2H)⁺²], 411.1 [100%, (M³⁷Cl³⁵Cl³⁵Cl+H)⁺], 409.0 [97%, (M³⁵Cl³⁵Cl³⁵Cl+H)⁺].

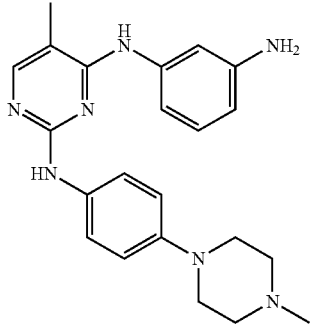 [SMILES: Cc1cnc(Nc2ccc(N3CCN(C)CC3)cc2)nc1Nc1cccc([N+](=O)[O-])c1]

5-Methyl-N⁴-[3-aminophenyl]-N²-[4-(4-methylpiperazin-1-yl)phenyl]pyrimidine-2,4-diamine (MA4-106): In a 3-neck round bottom flask, palladium (10% on carbon) (0.248 g, 0.0.05 eq.) was added to deoxygenated EtOH (20 mL) under Argon. The flask was evacuated and back filled with Argon (twice). Argon gas was evacuated and a balloon of hydrogen was attached to the system. Finally, MA4-104 (1.24 g) was dissolved in DCM (5 mL) and added via a syringe. The reaction mixture was stirred at room temperature for 24 h, filtered using a short plug of celite and concentrated in vacuo. The filtrate was concentrated under reduced pressure to provide the title compound MA4-106 as a gray solid (1.10 g, 96%). Mp: 180° C. (dec). ¹H NMR (400 MHz, CDCl₃) δ: 8.60 (s, 1H, disappeared on D₂O shake), 7.92 (s, 1H, disappeared on D₂O shake), 7.78 (s, 1H), 7.53 (d, J=9.0 Hz, 2H), 6.97 (brs, 1H), 6.94 (t, J=8.0 Hz, 1H), 6.85 (d, J=8.0 Hz, 1H), 6.79 (d, J=9.0 Hz, 2H), 6.29 (d, J=8.0 Hz, 1H), 4.93 (s, 2H, disappeared on D₂O shake), 3.04-2.98 (m, 4H), 2.46-2.41 (m, 4H), 2.21 (s, 3H), 2.05 (s, 3H). HPLC-MS (ESI+): m/z 390.3 [20%, (M+H)⁺], 195.8 [100%, (M+2H)²⁺].

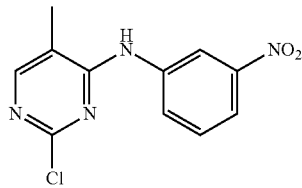 [SMILES: Cc1cnc(Cl)nc1Nc1cccc([N+](=O)[O-])c1]

2-Chloro-5-methyl-N⁴-[3-nitrophenyl]pyrimidine-4-amine (MA4-092): This was prepared from 2,4-dichloro-5-methylpyrimidine (3.26 g) and m-nitroaniline (2.76 g) using procedure B (reaction time 6 days, reaction temperature 155° C.) and isolated in the same way as MA2-030 to give the title compound MA4-092 as a yellow solid (2.46 g, 62%). Mp: 172° C. (dec). ¹H NMR (400 MHz, DMSO-d₆): δ 9.25 (s, 1H, disappeared on D₂O shake), 8.67 (t, J=2.2 Hz, 1H), 8.19 (ddd, J=8.3, 2.2, 0.9 Hz, 1H), 8.17 (d, J=0.9 Hz, 1H), 7.95 (ddd, J=8.2, 2.2, 0.9 Hz, 1H), 7.66 (t, J=8.2 Hz, 1H), 2.22 (d, J=0.9 Hz, 3H). HPLC-MS (ESI+): m/z 287.1 [20%, (M³⁵Cl+Na)⁺], 267.2 [30%, (M³⁷Cl+H)⁺], 265.1 [100%, (M³⁵Cl+H)⁺].

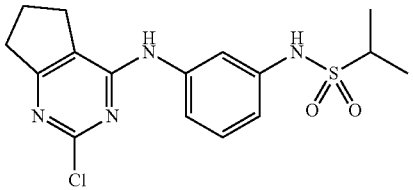 [SMILES: CC(C)S(=O)(=O)Nc1cccc(Nc2nc(Cl)nc3c2CCC3)c1]

2-Chloro-N⁴-(3-[(1-methylethyl)sulfonamido]phenyl)-6,7-dihydro-5H-cyclopenta[d]pyrimidine-4-amine (MA3-014-2): This was prepared from MA2-092 (0.095 g) and MA3-010 (0.114 g) using procedure B (reaction time, 3 days) and isolated in the same way as MA2-030 to give the title compound MA3-016-3 as a white solid (0.114 g, 62%). Mp: 233° C. (dec). ¹H NMR (400 MHz, DMSO-d₆): δ 9.83 (s, 1H, disappeared on D₂O shake), 9.19 (s, 1H disappeared on D₂O shake), 7.57 (t, J=1.9 Hz, 1H), 7.34 (d, with unresolved fine coupling, J=8.0 Hz, 1H), 7.26 (t, J=8.0 Hz, 1H), 6.90 (ddd, J=8.0, 2.0, 1.0 Hz, 1H), 3.33-3.26 (m, 1H), 2.80 (t, J=7.6 Hz, 4H), 2.09-2.03 (m, 2H), 1.26 (d, J=6.8 Hz, 6H). HPLC-MS (ESI+): m/z 369.1 [40%, (M³⁷Cl+H)⁺], 367.1 [100%, (M³⁵Cl+H)⁺].

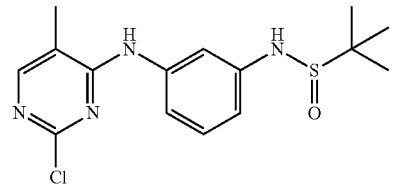 [SMILES: Cc1cnc(Cl)nc1Nc1cccc(NS(=O)C(C)(C)C)c1]

2-Chloro-5-methyl-N⁴-[3-(1,1-dimethylethylsulfinamido)phenyl]pyrimidine-4-amine (MA2-006): The aniline MA1-098 (0.124 g) and DMAP (0.065 g) were dissolved in dry DCM (15 mL) and t-butylsulfinyl chloride (0.074 g) was added via a syringe at room temperature. The reaction mixture was stirred at room temperature for 1 h and then poured onto ice-water (10 mL). The mixture was extracted with DCM (50 mL). The combined organic layers were sequentially washed with NaHCO₃ (50 mL) and brine (20 mL), dried (Na₂SO₄) and evaporated. The residue was purified via column chromatography (SiO₂) eluting with hexanes/EtOAc (0:10 to 2:8 v/v) to give the title compound as a brown solid (0.144 g, 80%). Mp: 135° C. (dec). ¹H NMR (400 MHz, DMSO-d₆): δ 8.82 (s, 1H, 30% reduced on D₂O shake), 8.07 (s, 1H, disappeared on D₂O shake), 8.05 (d, J=0.8 Hz, 1H), 7.43 (t, J=1.8 Hz, 1H), 7.25 (dt, J=8.2, 1.8 Hz, 1H), 7.20 (d, J=8.2 Hz, 1H), 6.83 (dt, J=8.2, 1.8 Hz, 1H), 2.16 (d, J=0.8 Hz, 3H), 1.24 (s, 9H). HPLC-MS (ESI+): m/z 341.2 [40%, (M³⁷Cl+H)⁺], 339.1 [100%, (M³⁵Cl+H)⁺].

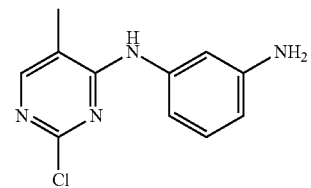 [SMILES: Cc1cnc(Cl)nc1Nc1cccc(N)c1]

2-Chloro-5-methyl-N⁴-[3-(aminophenyl)]pyrimidine-4-amine (MA1-098): This was prepared from MA053 (0.240 g). A mixture of TFA:DCM (2:8, 3 mL) was added to MA1-053 (0.240 g) in a microwave vial equipped with a magnetic stirrer bar. The vial was heated in microwave reactor (Biotage Initiator) at 80° C. for 15 minutes and allowed to cool to room temperature. The DCM was removed under reduced pressure and the residue diluted with ethyl acetate (50 mL), washed with NaHCO$_3$(aq., 20 mL) and water (20 mL). The organic layer was dried (Na$_2$SO$_4$) and evaporated in vacuo. The residue was purified by column chromatography (SiO$_2$, eluting with DCM-MeOH, 0-10%) to provide the title compound MA1-098 as a yellow oil (129 mg, 78%). $^1$H NMR (400 MHz, DMSO-d$_6$): δ 8.59 (s, 1H, 30% reduced on D$_2$O shake), 7.98 (d, J=0.8 Hz, 1H), 6.98 (t, J=8.0 Hz, 1H), 6.77-6.71 (m, 2H), 6.37-6.32 (m, 1H), 5.11 (s, 2H), 2.12 (d, J=0.8 Hz, 3H). HPLC-MS (ESI+): m/z 237.1 [40%, (M$^{37}$Cl+H)$^+$], 235.1 [100%, (M$^{35}$Cl+H)$^+$].

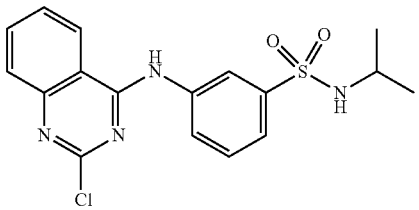 [SMILES: CC(C)NS(=O)(=O)c1cccc(Nc2nc(Cl)nc3ccccc23)c1]

2-Chloro-N$^4$-(3-[N-(1-methylethyl)sulfamoyl]phenyl)quinazoline-4-amine (MA2-084): This was prepared from MA2-028 (0.199 g) and SG3-147 (0.214 g) using procedure B (reaction time, 3 h) and isolated in the same way as MA2-030 to give the title compound MA2-084 as a white solid (0.267 g, 71%). Mp: 220-223° C. (dec). $^1$H NMR (400 MHz, DMSO-d$_6$): δ 10.43 (s, 1H, disappeared on D$_2$O shake), 8.60 (d, J=8.3 Hz, 1H), 8.29 (t, J=1.8 Hz, 1H), 8.10 (d, with unresolved fine coupling, J=8.0 Hz, 1H), 7.93 (ddd, J=8.3, 7.1, 1.2 Hz, 1H), 7.76 (d, J=8.3 Hz, 1H), 7.69 (ddd, J=8.3, 7.1, 1.2 Hz, 1H), 7.66-7.58 (m, 3H, 1H disappeared on D$_2$O shake), 3.39-3.34 (m, 1H, partially overlapped by the residual H$_2$O signal), 1.00 (d, J=6.5 Hz, 6H). HPLC-MS (ESI+): m/z 379.1 [40%, (M$^{37}$Cl+H)$^+$], 377.1 [100%, (M$^{35}$Cl+H)$^+$].

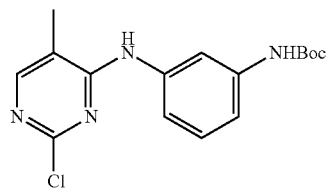

2-Chloro-5-methyl-N$^4$-[3-(1,1-dimethylethyloxycarbonylamino)phenyl]pyrimidine-4-amine (MA1-053): This was prepared from 2,4-dichloro-5-methylpyrimidine (0.326 g) and N-Boc-m-phenylenediamine (0.416 g) using procedure A (reaction time, 16 h) to give the title compound MA1-053 as a white solid (0.315 g, 46%). Mp: 250° C. (dec). $^1$H NMR (400 MHz, DMSO-d$_6$): δ 9.41 (s, 1H, 30% reduced on D$_2$O shake), 8.87 (s, 1H, 90% reduced on D$_2$O shake), 8.03 (d, J=0.8 Hz, 1H), 7.75 (s, 1H), 7.27 (d, J=8.0 Hz, 1H), 7.21 (t, J=8.0 Hz, 1H), 7.13 (d, J=8.0 Hz, 1H), 2.15 (s, 3H), 1.48 (s, 9H). HPLC-MS (ESI+): m/z 337.2 [40%, (M$^{37}$Cl+H)$^+$], 335.2 [100%, (M$^{35}$Cl+H)$^+$].

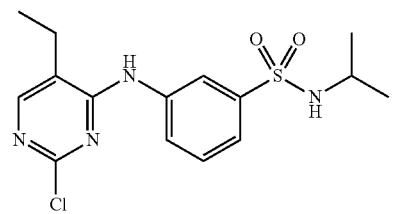 [SMILES: CCc1cnc(Cl)nc1Nc1cccc(S(=O)(=O)NC(C)C)c1]

2-Chloro-5-ethyl-N$^4$-(3-[N-(1,1-dimethylethyl)sulfamoyl]phenyl)pyrimidine-4-amine (MA1-013): This was prepared from MA1-012 (0.106 g) and SG1-147 (0.128 g) using procedure B (reaction time, 16 h) and isolated in the same way as MA2-030 to give the title compound MA1-013 as a white solid (0.099 g, 46%). Mp: 260° C. (dec). $^1$H NMR (400 MHz, DMSO-d$_6$): δ 9.18 (s, 1H), 8.12 (s, 1H), 8.10 (t, J=1.8 Hz, 1H), 7.92 (d, with unresolved fine coupling, J=8.1 Hz, 1H), 7.61-7.55 (m, 2H, 1H disappeared on D$_2$O shake), 7.51 (d, with unresolved fine coupling, J=8.1 Hz, 1H), 3.48-3.40 (m, 1H), 2.64 (q, J=7.4 Hz, 2H), 1.19 (t, J=7.4 Hz, 3H), 0.98 (d, J=6.5 Hz, 6H). HPLC-MS (ESI+): m/z 357.1 [40%, (M$^{37}$Cl+H)$^+$], 355.1 [100%, (M$^{35}$Cl+H)$^+$].

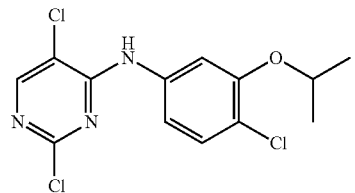 [SMILES: CC(C)Oc1cc(Nc2nc(Cl)ncc2Cl)ccc1Cl]

2,5-Dichloro-N$^4$-[4-chloro-3-isopropoxyphenyl]pyrimidine-4-amine (MA1-088): This was prepared from 2,4,5-trichloropyrimidine (0.115 g) and MA1-086 (0.186 g) using procedure B (reaction time, 1.5 h) to give the title compound as a white solid (0.288 g, 92%). Mp: 120° C. (dec). $^1$H NMR (400 MHz, DMSO-d$_6$): δ 9.55 (s, 1H, disappeared on D$_2$O shake), 8.40 (s, 1H), 7.51 (d, J=2.2 Hz, 1H), 7.40 (d, J=8.6 Hz, 1H), 7.19 (dd, J=8.6, 2.2 Hz, 1H), 4.59 (septet, J=6.0 Hz, 1H), 1.34 (d, J=6.0 Hz, 6H). HPLC-MS (ESI+): HPLC-MS (ESI+): m/z 336.1 [30%, (M$^{37}$Cl$^{37}$Cl$^{35}$Cl+H)$^+$], 334.0 [95%, (M$^{37}$Cl$^{35}$Cl$^{35}$Cl+H)$^+$], 332.1 [100%, (M$^{35}$Cl$^{35}$Cl$^{35}$Cl+H)$^+$].

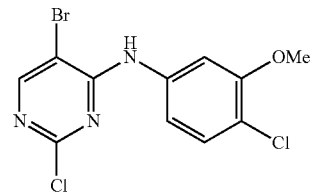

2-Chloro-5-bromo-N$^4$-[4-chloro-3-methoxyphenyl]pyrimidine-4-amine (MA2-004): This was prepared from 5-bromo-2,4-dichloropyrimidine (0.911 g) and 3-methoxy chloroaniline (0.662 g) using procedure B (reaction time, 1h) to give the title compound MA2-004 as a beige solid (1.37 g, 99%). Mp: 224° C. (dec). $^1$H NMR (400 MHz, DMSO-d$_6$): δ 9.33 (s, 1H, disappeared on D$_2$O shake), 8.50 (s, 1H), 7.47 (d, J=2.1 Hz, 1H), 7.42 (d, J=8.6 Hz, 1H), 7.26 (dd, J=8.6, 2.1 Hz, 1H), 3.84 (s, 3H). HPLC-MS (ESI+): m/z 353.9 [10%, (M$^{81}$Br$^{37}$Cl$^{37}$Cl+H)$^+$], 351.9 [40%, ($M^{81}Br^{37}Cl^{35}Cl+H$ and $M^{79}Br^{37}Cl^{37}C_1)^+$], 350.0 [100%, ($M^{79}Br^{37}Cl^{35}Cl+H$ and $M^{81}Br^{35}Cl^{35}C_1)^+$], 348.0 [55%, ($M^{79}Br^{35}Cl^{35}Cl+H)^+$].

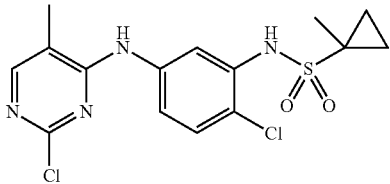 [SMILES: Cc1cnc(Cl)nc1Nc1ccc(Cl)c(NS(=O)(=O)C2(C)CC2)c1]

2-Chloro-5-methyl-$N^4$-(3-[(N-1-methylcyclopropyl)sulfamoyl]-4-chlorophenyl)pyrimidine-4-amine (MA5-014): This was prepared from MA5-010 (0.207 g) and 2,4-dichloro-5-methylpyrimidine (0.129 g) using procedure B (reaction time, 24 h). After evaporation of the volatiles, the crude mixture was directly absorbed on silica and the product was purified via column chromatography ($SiO_2$) eluting with hexanes/EtOAc (2:8 to 1:1 v/v) to give the title compound MA5-014 as a white solid (0.181 g, 59%). Mp: 230° C. (dec). $^1$H NMR (400 MHz, DMSO-$d_6$): δ 9.49 (s, 1H, disappeared on $D_2O$ shake), 8.99 (s, 1H, disappeared on $D_2O$ shake), 8.09 (d, J=0.7 Hz, 1H), 7.89 (d, J=2.4 Hz, 1H), 7.57 (dd, J=8.8, 2.4 Hz, 1H), 7.47 (d, J=8.8 Hz, 1H), 2.18 (s, 3H), 1.50 (s, 3H), 1.14-1.10 (m, 2H), 0.82-0.78 (m, 2H). HPLC-MS (ESI+): m/z 389.1 [70%, ($M^{37}Cl^{35}Cl+H)^+$], 387.1 [100%, ($M^{35}Cl^{35}Cl+H)^+$].

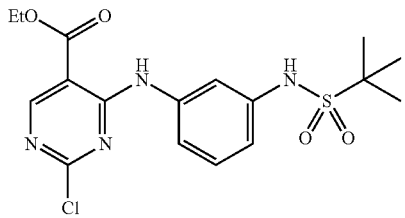 [SMILES: CCOC(=O)c1cnc(Cl)nc1Nc1cccc(NS(=O)(=O)C(C)(C)C)c1]

2-Chloro-5-ethoxycarbonyl-$N^4$-(3-[(1,1-dimethylethyl)sulfonamido]phenyl)pyrimidine-4-amine (MA4-048): This was prepared from MA2-010B2 (0.080 g) and 2,4-dichloro-5-ethoxycarbonylpyrimidine (Combi-Blocks) (0.077 g) using procedure B (reaction time, 16 h) to give the title compound MA4-048 as yellow solid (0.112 g, 76%). Mp: 228° C. (dec). $^1$H NMR (400 MHz, DMSO-$d_6$): δ 10.22 (s, 1H, disappeared on $D_2O$ shake), 9.76 (s, 1H, disappeared on $D_2O$ shake), 8.80 (s, 1H), 7.61 (brs, 1H), 7.36-7.24 (m, 2H), 7.15-7.06 (m, 1H), 4.38 (q, J=7.1 Hz, 2H), 1.36 (t, J=7.1 Hz, 3H), 1.31 (s, 9H). HPLC-MS (ESI+): m/z 415.1 [40%, ($M^{37}Cl+H)^+$], 413.1 [100%, ($M^{35}Cl+H)^+$].

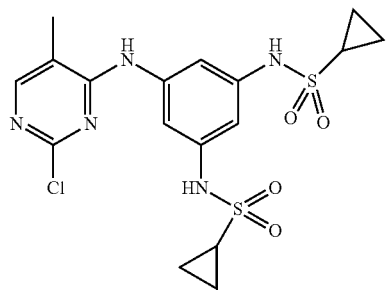 [SMILES: Cc1cnc(Cl)nc1Nc1cc(NS(=O)(=O)C2CC2)cc(NS(=O)(=O)C2CC2)c1]

2-Chloro-5-methyl-$N^4$-[3,5-bis-(cyclopropylsulfonamido)phenyl]pyrimidine-4-amine (MA4-056): This was prepared from the aniline MA4-044 (0.100 g) and 2,4-dichloro-5-methylpyrimidine (0.049 g) using procedure B (reaction time, 3 days). The crude reaction mixture was dissolved in EtOAc (30 mL) and washed with water (20 mL). The title compound was purified (twice) via column chromatography ($SiO_2$) eluting with DCM/MeOH (10:0 to 9:1 v/v) to give the title compound MA4-056 as a yellow solid (0.054 g, 39%). Mp: 228° C. (dec). $^1$H NMR (400 MHz, DMSO-$d_6$): δ 9.88 (s, 2H, disappeared on $D_2O$ shake), 8.99 (s, 1H, disappeared on $D_2O$ shake), 8.07 (d, J=0.9 Hz, 1H), 7.30 (d, J=1.9 Hz, 2H), 6.90 (t, J=1.9 Hz, 1H), 2.71-2.66 (m, 2H), 2.16 (s, 3H), 1.28-1.23 (m, 2H), 1.03-0.95 (m, 6H). HPLC-MS (ESI+): m/z 460.1 [40%, ($M^{37}Cl+H)^+$], 458.1 [100%, ($M^{35}Cl+H)^+$].

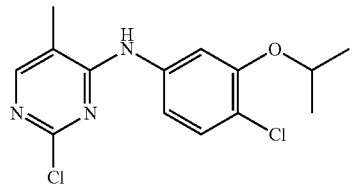 [SMILES: Cc1cnc(Cl)nc1Nc1ccc(Cl)c(OC(C)C)c1]

2-Chloro-$N^4$-[4-chloro-3-isopropoxyphenyl]-5-methylpyrimidine-4-amine (MA1-090): This was prepared from 2,4-dichloro-5-methylpyrimidine (0.163 g) and MA1-086 (0.186 g) using procedure B (reaction time, 2.5 days) to give the title compound as a yellow solid (0.180 g, 58%). $^1$H NMR (400 MHz, DMSO-$d_6$): δ 8.90 (s, 1H), 8.08 (d, J=0.7 Hz, 1H), 7.60 (d, J=2.3 Hz, 1H), 7.37 (d, J=8.6 Hz, 1H), 7.23 (dd, J=8.6, 2.3 Hz, 1H), 4.62-4.51 (m, 1H), 2.17 (d, J=0.7 Hz, 3H), 1.35 (d, J=6.0 Hz, 6H). HPLC-MS (ESI-): m/z 314.1 [60%, ($M^{37}Cl^{35}Cl-H)^+$], 312.1 [95%, ($M^{35}Cl^{35}Cl-H)^+$].

Synthesis of A-Ring and B-Ring Precursors

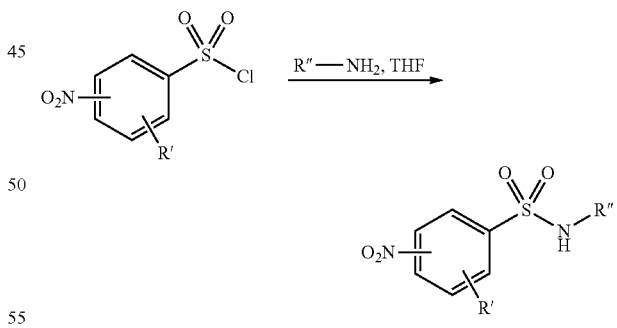

The following nitrobenzenesulfonamides were prepared using the previously reported method.[3]

Method a: To a mixture of nitrobenzenesulfonyl chloride (1.0 equiv.) in THF (0.45 M) was added amine (3.0 equiv.). The solution was stirred at room temperature for 30 min. The pH was adjusted to pH 2 by the addition of HCl (1 M, aq.) at 0° C. The solvent was removed and the resulting solid was triturated using EtOAc/hexanes, washed with water, and dried.

Method a1: Substituted aniline (1 equiv.) was dissolved in dry DCM (0.1M to 1M), pyridine (1.5-5 eq.) and the solution was cooled to 0° C. Arylsulfonylchloride (2.5 equiv.) was added dropwise and the mixture was allowed to warm to room temperature and stirred overnight. The reaction mixture was cooled in an ice-bath and 1M HCl solution was added until pH 7. DCM was added to the mixture and the organic layer was separated, evaporated and dried (Na$_2$SO$_4$) to provide the title compound.

Method b: To a solution of nitroarene (1.0 equiv.) in EtOH or MeOH (deoxygenated with bubbled Argon) was added Pd/C (10%) and hydrazine monohydrate 65% (3.0 equiv.) under Argon. The solution was stirred and heated at reflux for the indicated time. The reaction mixture was filtered over Celite, and the filtrate concentrated under reduced pressure.

Method c: A solution of nitroarene (1.0 equiv.) in MeOH (deoxygenated with bubbled argon) was cooled in an ice-bath and ammonium formate (3 equiv.) was added. After ~5 minutes Pd/C (10%, 0.1 equiv.) was added and reaction was stirred at 0° C. for 30 minutes and at room temperature overnight. The reaction mixture was filtered over Celite, and the filtrate concentrated under reduced pressure. The residue was redissolved in EtOAc and washed with water. The organic layer was separated, dried (Na$_2$SO$_4$) and concentrated to give the product.

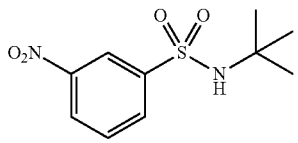

N-(Dimethylethyl)-3-nitrobenzenesulfonamide (SG1-133): This was prepared from 3-nitrobenzenesulfonyl chloride (3.00 g) and tert-butylamine (4.27 mL) using the general method a and provided the title compound as a white solid (2.84 g, 66%). Mp: 103-104° C. (lit.[4] 99-100° C.). $^1$H NMR (400 MHz, CDCl$_3$) δ: 8.74 (t, J=1.9 Hz, 1H), 8.40 (ddd, J=8.0, 1.9, 1.0 Hz, 1H), 8.23 (ddd, J=8.0, 1.9, 1.0 Hz, 1H), 7.72 (t, J=8.0 Hz, 1H), 4.84 (brs, 1H), 1.27 (s, 9H). HPLC-MS (ESI+): m/z 539.1 [40%, (2M+Na)$^+$], 281.0 [45%, (M+Na)+], 276.2 [100%, (M+NH$_4$)$^+$].

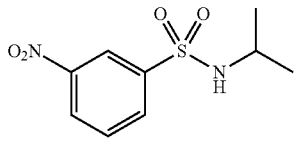

N-Methylethyl-3-nitrobenzenesulfonamide (SG1-143): This was prepared from 3-nitrobenzenesulfonyl chloride (3.00 g) and isopropylamine (3.32 mL) using the general method a and provided the title compound as an off-white solid (2.85 g, 86%). Mp: 64-65° C. (lit.[4] 64-65° C.). $^1$H NMR (400 MHz, DMSO-d$_6$) δ: 8.52 (t, J=1.9 Hz, 1H), 8.45 (ddd, J=8.0, 1.9, 1.0 Hz, 1H), 8.21 (ddd, J=8.0, 1.9, 1.0 Hz, 1H), 7.97 (brd, J=6.8 Hz, 1H, disappeared on D$_2$O shake), 7.88 (t, J=8.0 Hz, 1H), 3.28 (octet, J=6.8 Hz, 1H), 0.94 (d, J=6.8 Hz, 6H). HPLC-MS (ESI+): m/z 511.1 [40%, (2M+Na)$^+$], 267.2 [100%, (M+Na)$^+$].

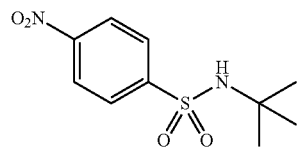

N-Dimethylethyl-4-nitrobenzenesulfonamide (SG1-174): This was prepared from 4-nitrobenzenesulfonyl chloride (10.00 g) and t-butylamine (14.22 mL) using the general method a and provided the title compound as a tangerine solid (10.64 g, 91%). Mp: 103-104° C. (lit.[3] 104-105° C.). $^1$H NMR (400 MHz, CDCl$_3$) δ: 8.34 (d, J=9.0 Hz, 2H), 8.09 (d, J=9.0 Hz, 2H), 5.01 (s, 1H), 1.25 (s, 9H). HPLC-MS (ESI+): m/z 281.1 [100%, (M+Na)$^+$].

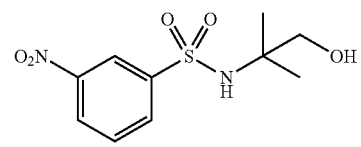

N-(1-Hydroxy-2-methylpropan-2-yl)-3-nitrobenzenesulfonamide (SG2-076): This was prepared from 3-nitrobenzenesulfonyl chloride (1.00 g) and 2-amino-2-methyl-1-propanol (1.21 g) using the general method a to provide the title compound as a white solid (0.510 g, 41%). Mp: 109-111° C. $^1$H NMR (400 MHz, DMSO-d$_6$) δ: 8.59 (t, J=1.9 Hz, 1H), 8.42 (ddd, J=8.0, 1.9, 1.0 Hz, 1H), 8.23 (ddd, J=8.0, 1.9, 1.0 Hz, 1H), 7.85 (t, J=8.0 Hz, 1H), 7.75 (s, 1H, disappeared on D$_2$O shake), 4.78 (t, J=5.7 Hz, 1H, disappeared on D$_2$O shake), 3.18 (d, J=5.7 Hz, 2H), 1.01 (s, 6H). HPLC-MS (ESI+): m/z 571.1 [90%, (2M+Na)$^+$], 297.0 [100%, (M+Na)$^+$].

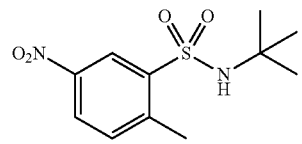

N-(1,1-Dimethylethyl)-2-methyl-5-nitrobenzenesulfonamide (SG2-097): This was prepared from 2-methyl-5-nitrobenzenesulfonyl chloride (2.00 g) and tert-butylamine (2.68 mL) using the general method a to provide the title compound[5] as a light brown solid (2.01 g, 87%). Mp: 128-129° C. (lit.[5] Mp: 127-129° C.). $^1$H NMR (400 MHz, DMSO-d$_6$) δ: 8.58 (d, J=2.5 Hz, 1H), 8.33 (dd, J=8.4, 2.5 Hz, 1H), 7.92 (s, 1H, reduced by 50% on D$_2$O shake), 7.68 (d, J=8.4 Hz, 1H), 2.69 (s, 1H), 1.10 (s, 3H). HPLC-MS (ESI+): m/z 567.2 [60%, (2M+Na)$^+$], 297.0 [100%, (M+Na)$^+$], 290.2 [50%, (M+NH$_4$)$^+$].

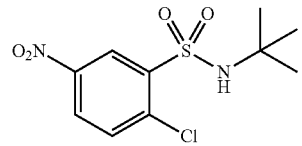

N-(1,1-Dimethylethyl)-2-chloro-5-nitrobenzenesulfonamide (SG3-137): This was prepared from SG3-128 (0.750 g)

and tert-butylamine (0.923 mL) using the general method a to provide the title compound as an off-white solid (0.694 g, 81%). Mp: 202° C. (dec). $^1$H NMR (400 MHz, CDCl$_3$) δ: 8.97 (d, J=2.7 Hz, 1H), 8.34 (dd, J=8.7, 2.7 Hz, 1H), 7.72 (d, J=8.7 Hz, 1H), 5.01 (s, 1H), 1.25 (s, 9H). HPLC-MS (ESI+): m/z 609.1 [50%, (M$^{37}$Cl+M$^{35}$Cl+H)$^+$], 607.1 [80%, (2M$^{35}$Cl+H)$^+$], 317.0 [30%, (M$^{37}$Cl+H)$^+$], 315.1 [100%, (M$^{35}$Cl+H)$^+$].

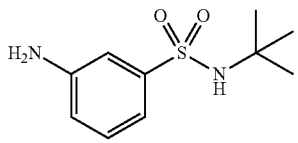 [SMILES: CC(C)(C)NS(=O)(=O)c1cccc([N+](=O)[O-])c1]

3-Amino-N-(dimethylethyl)benzenesulfonamide (SG1-137): This was prepared from SG1-133 (2.50 g), hydrazine monohydrate 65% (1.39 mL), Pd/C (0.500 g), and EtOH (40 mL) using the general method b (reaction time, 3 h) to provide the title compound as a white solid (1.74 g, 79%). Mp: 140° C. $^1$H NMR (400 MHz, DMSO-d$_6$) δ: 7.29 (s, 1H), 7.13 (t, J=7.9 Hz, 1H), 6.99 (t, J=2.0 Hz, 1H), 6.90 (ddd, J=7.9, 2.0, 0.9 Hz, 1H), 6.67 (ddd, J=7.9, 2.0, 0.9 Hz, 1H), 5.50 (s, 2H), 1.07 (s, 9H). HPLC-MS (ESI+): m/z 479.3 [20%, (2M+Na)$^+$], 173.2 [100%, (M-tBu+H)$^{2+}$].

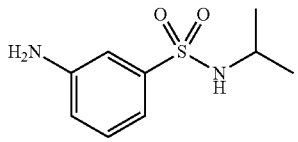 [SMILES: CC(C)NS(=O)(=O)c1cccc([N+](=O)[O-])c1]

3-Amino-N-(methylethyl)benzenesulfonamide (SG1-147): This was prepared from SG1-143 (2.50 g), hydrazine monohydrate 65% (1.47 mL), Pd/C (0.544 g), and EtOH (40 mL) using the general method b (reaction time, 2 h) to provide the title compound as a white solid (1.92 g, 88%). Mp: 94-96° C. $^1$H NMR (400 MHz, DMSO-d$_6$) S: 7.34 (d, J=6.8 Hz, 1H, disappeared on D$_2$O shake), 7.15 (t, J=7.9 Hz, 1H), 6.96 (t, J=2.2 Hz, 1H), 6.86 (ddd, J=7.9, 2.2, 0.8 Hz, 1H), 6.70 (ddd, J=7.9, 2.2, 0.8 Hz, 1H), 5.54 (s, 2H, disappeared on D$_2$O shake), 3.17 (octet, J=6.8 Hz, 1H), 0.92 (d, J=6.8 Hz, 6H). HPLC-MS (ESI+): m/z 429.2 [20%, (2M+H)$^+$], 215.1 [100%, (M+H)$^+$].

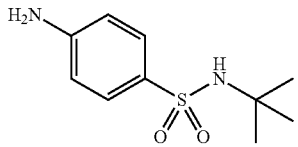 [SMILES: CC(C)(C)NS(=O)(=O)c1ccc([N+](=O)[O-])cc1]

4-Amino-N-(dimethylethyl)benzenesulfonamide (SG1-177): This was prepared from SG1-174 (10.64 g), hydrazine monohydrate 65% (5.92 mL), Pd/C (1.00 g), and EtOH (80 mL) using the general method b (reaction time, 4.5 h) to provide the title compound as a light tangerine solid (8.50 g, 90%). Mp: 122-123° C. $^1$H NMR (400 MHz, DMSO-d$_6$) δ: 7.40 (d, J=8.7 Hz, 2H), 6.98 (s, 1H, disappeared on D$_2$O shake), 6.56 (d, J=8.7 Hz, 2H), 5.83 (s, 2H, disappeared on D$_2$O shake), 1.03 (s, 9H). HPLC-MS (ESI+): m/z 479.3 [100%, (2M+Na)$^+$], 229.2 [25%, (M+H)$^+$], 173.2 [60%, (M-tBu+H)$^+$].

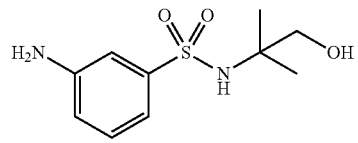 [SMILES: CC(C)(CO)NS(=O)(=O)c1cccc([N+](=O)[O-])c1]

3-Amino-N-(1-hydroxy-2-methylpropan-2-yl)benzenesulfonamide$^6$ (SG2-079): This was prepared from SG2-076 (1.90 g), hydrazine monohydrate 65% (0.995 mL), Pd/C (0.250 g), and EtOH (30 mL) using the general method b (reaction time, 3 h) to provide the title compound as a yellow solid. Mp: 68-71° C. $^1$H NMR (400 MHz, DMSO-d$_6$) δ: 7.13 (t, J=7.8 Hz, 1H), 7.06 (s, 1H, disappeared on D$_2$O shake), 6.99 (t, J=1.9 Hz, 1H), 6.90 (ddd, J=7.8, 1.9, 0.8 Hz, 1H), 6.68 (ddd, J=7.8, 1.9, 0.8 Hz, 1H), 5.50 (s, 2H, disappeared on D$_2$O shake), 4.71 (t, J=5.8 Hz, 1H, disappeared on D$_2$O shake), 3.16 (d, J=5.8 Hz, 2H), 0.99 (s, 6H). HPLC-MS (ESI+): m/z 511.1 [40%, (2M+Na)$^+$], 245.2 [100%, (M+H)$^+$], 173.1 [95%, (M-CMe$_2$CH$_2$OH+H)$^+$].

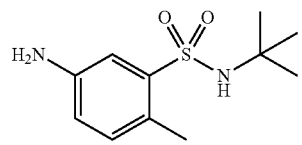 [SMILES: Cc1ccc([N+](=O)[O-])cc1S(=O)(=O)NC(C)(C)C]

5-Amino-N-(1,1-dimethylethyl)-2-methylbenzenesulfonamide (SG2-100): This was prepared from SG2-097 (1.91 g), hydrazine monohydrate (65%, 1.57 mL), palladium (10%) on carbon (0.500 g), and EtOH (35 mL) using the general method b (reaction time, 3 h) to provide the title compound as an off-white solid (1.63 g, 96%). Mp: 136-137° C. $^1$H NMR (400 MHz, DMSO-d$_6$) δ: 7.19 (s, 1H, disappeared on D$_2$O shake), 7.14 (d, J=2.5 Hz, 1H), 6.94 (d, J=8.1 Hz, 1H), 6.60 (dd, J=8.1, 2.5 Hz, 1H), 5.25 (s, 2H, disappeared on D$_2$O shake), 2.36 (s, 3H), 1.07 (s, 9H). HPLC-MS (ESI+): m/z 485.3 [20%, (2M+Na)$^+$], 187.2 [100%, (M-tBu+H)$^{2+}$].

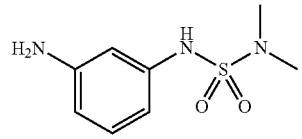

N-(5-Aminophenyl)-3-N,N-dimethylsulfamide (SG3-033-01): This was prepared from SG3-028 (1.40 g), hydrazine monohydrate 65% (1.28 mL), palladium (10%) on carbon (0.250 g), and EtOH (25 mL) using the general method b (reaction time, 1.5 h). The resulting oil was purified via column chromatography (SiO$_2$) eluting with hexanes/EtOAc (1:9 to 1:1 v/v) to give the title compound as an off-white solid (0.941 g, 77%). Mp: 135° C. (dec). $^1$H NMR (400 MHz, DMSO-d$_6$) δ: 9.51 (s, 1H, disappeared on D$_2$O shake), 6.86 (t, J=7.9 Hz, 1H), 6.43 (s, 1H), 6.33 (d, J=7.9 Hz, 1H), 6.22 (d, J=7.9 Hz, 1H), 5.10 (s, 2H, disappeared on D$_2$O shake), 2.66 (s, 6H). HPLC-MS (ESI+): m/z 216.2 [100%, (M+H)$^+$].

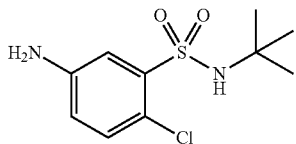 [SMILES: CC(C)(C)NS(=O)(=O)c1cc([N+](=O)[O-])ccc1Cl]

5-Amino-N-(1,1-dimethylethyl)-2-chlorobenzenesulfonamide (SG3-142): A mixture of SG3-137 (0.750 g), iron (III) chloride hexahydrate (0.021 g), charcoal (0.200 g), and MeOH (6 mL) was heated at reflux for 10 min. Hydrazine monohydrate (65%, 0.766 mL) was added and the reaction mixture was further heated at reflux for 2 h. The mixture was filtered over Celite and the filtrate concentrated under reduced pressure. The resulting residue was dissolved in EtOAc (8 mL) and washed with water (1×10 mL) and brine (1×10 mL). The organic layer was dried ($Na_2SO_4$), concentrated under reduced pressure, and the resulting residue purified via column chromatography ($SiO_2$) eluting with hexanes/EtOAc (0:10 to 4:6 v/v) to give the title compound as a yellow solid (0.314 g, 47%). Mp: 223° C. (dec). $^1$H NMR (400 MHz, CDCl$_3$) δ: 7.49 (d, J=2.8 Hz, 1H), 7.25 (d, J=7.8 Hz, 4H), 6.81 (dd, J=7.8, 2.8 Hz, 1H), 4.99 (s, 1H), 1.22 (s, 9H). HPLC-MS (ESI+): m/z 547.2 [20%, (2M+Na)$^+$], 209.1 [40%, (M$^{37}$Cl$_1$-tBu+H)$^{2+}$], 207.1 [100%, (M$^{35}$Cl-tBu+H)$^{2+}$].

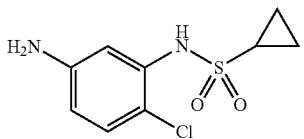

N-(5-Amino-2-chlorophenyl)cyclopropanesulfonamide (SG2-159): This was prepared from SG2-152 (3.23 g), hydrazine monohydrate 65% (3.93 mL), Pd/C (0.750 g), and EtOH (45 mL) using the general method b (reaction time, 8 h) to provide the title compound as an off-white solid (1.86 g, 65%). Mp: 93-94° C. $^1$H NMR (400 MHz, DMSO-d$_6$) δ: 8.18 (s, 1H, disappeared on D$_2$O shake), 7.04 (d, J=8.6 Hz, 1H), 6.68 (d, J=2.7 Hz, 1H), 6.39 (dd, J=8.6, 2.7 Hz, 1H), 5.33 (s, 2H, disappeared on D$_2$O shake), 2.56 (tt, J=7.8, 4.9 Hz, 1H), 0.96-0.83 (m, 4H). HPLC-MS (ESI+): m/z 249.1 [40%, (M$^{37}$Cl+H)$^+$], 247.1 [100%, (M$^{35}$Cl+H)$^+$].

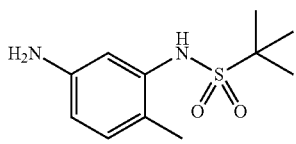

N-(5-Amino-2-methylphenyl)-2-methylpropane-2-sulfonamide (SG3-124): This was prepared from SG3-123 (0.410 g), hydrazine monohydrate (65%, 0.337 mL), Palladium (10%) on carbon (0.100 g), and MeOH (10 mL) using the general method b (reaction time, 15 h). The resulting residue was triturated using EtOAc/hexanes to provide the title compound as an off-white solid (0.338 g, 93%). Mp: 170° C. (dec). $^1$H NMR (400 MHz, CDCl$_3$) δ: 7.17 (d, J=2.1 Hz, 1H), 6.94 (d, J=8.1 Hz, 1H), 6.49 (dd, J=8.1, 2.1 Hz, 1H), 5.91 (s, 1H), 2.20 (s, 3H), 1.42 (s, 9H). HPLC-MS (ESI+): m/z 485.3 [20%, (2M+H)$^+$], 243.2 [100%, (M+H)$^+$].

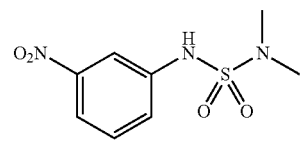

N-(5-Nitrophenyl)-3-N,N-dimethylsulfamide (SG3-028): To a mixture of nitroaniline (1.00 g, 7.24 mmol), pyridine (1.75 mL, 21.72 mmol), and DCM (15 mL) was added dimethylsulfamoyl chloride (1.17 mL, 10.86 mmol). The solution was stirred at room temperature for 3.5 d. The solvent was removed and EtOAc (20 mL) was added. The organic layer was washed with HCl (1 M aq. solution, 2×25 mL), water (2×25 mL), and brine (2×25 mL), dried ($Na_2SO_4$), and concentrated under reduced pressure to give the title compound as a tangerine-colored solid (1.53 g, 86%). Mp: 121-126° C. (dec). $^1$H NMR (400 MHz, DMSO-d$_6$) δ: 10.52 (s, 1H, disappeared on D$_2$O shake), 7.98 (t, J=2.1 Hz, 1H), 7.87 (dt, J=7.8, 2.1 Hz, 1H), 7.59 (t, J=7.8 Hz, 1H), 7.57-7.54 (m, 1H), 2.72 (s, 6H). HPLC-MS (ESI+): m/z 268.1 [100%, (M+Na)$^+$], 246.2 [90%, (M+H)$^+$].

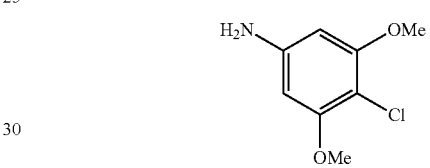

4-Chloro-3,5-dimethoxyaniline (SG2-062-01): This was prepared using the previously reported method.[7] A mixture of 3,5-dimethoxyaniline (2.67 g, 20 mmol), acetic acid (25 mL), and N-chlorosuccinimide (3.37 g, 22 mmol) was stirred at room temperature for 4.5 h. Water (50 mL) and EtOAc (50 mL) were added. The organic layer was washed with brine (1×50 mL), dried ($Na_2SO_4$), and concentrated under reduced pressure. The resulting residue was purified via column chromatography ($SiO_2$) eluting with hexanes/EtOAc (gradient: 100% hexanes to 30% ethyl acetate in hexanes) to give the title compound as a brown solid (0.594 g, 16%). Mp: 153° C. (dec). $^1$H NMR (400 MHz, DMSO-d$_6$) δ: 5.94 (s, 2H), 5.28 (s, 2H, disappeared on D$_2$O shake), 3.69 (s, 6H). HPLC-MS (ESI+): m/z 190.1 [30%, (M$^{37}$Cl+H)$^+$], 188.1 [100%, (M$^{35}$Cl+H)$^+$].

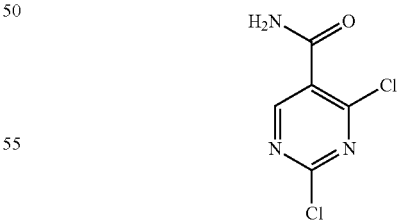

5-Carboxamide-2,4-dichloropyrimidine (SG2-138): To a solution of PE1-028B3 (1.00 g, 4.73 mmol) in DCM (2 mL) was added NH$_4$OH (30% aq. solution, 2.51 mL, 18.92 mmol) slowly at 0° C. Water (1 mL) was added and the mixture stirred for 5 min and the precipitate filtered. The resulting solid was washed with water (1×10 mL) and dried to give the title compound as a pale yellow solid (0.730 g, 80%). Mp: 194° C. (dec). $^1$H NMR (400 MHz, DMSO-d$_6$)

δ: 8.88 (s, 1H), 8.18 (s, 1H), 8.05 (s, 1H). HPLC-MS (ESI+): m/z 216.1 [40%, (M$^{37}$Cl+Na)$^+$], 214.1 [80%, (M$^{35}$Cl+Na)$^+$], 194.1 [60%, (M$^{37}$Cl+H)$^+$], 192.1 [100%, (M$^{35}$Cl+H)$^+$].

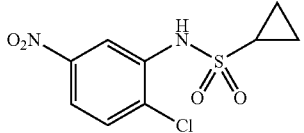 [SMILES: Nc1ccc(Cl)c(NS(=O)(=O)C2CC2)c1]

N-(2-Chloro-5-nitrophenyl)cyclopropanesulfonamide (SG2-152): Cyclopropanesulfonyl chloride (2.66 mL, 26.08 mmol) was added to a mixture of 2-chloro-5-nitroaniline (3.00 g, 17.38 mmol), pyridine (4.21 mL, 52.15 mmol), and DCM (35 mL) in an Ace pressure tube. The mixture was heated at 150° C. for 4 d. The solution was poured into a separatory funnel and EtOAc (50 mL) was added. The organic layer was washed with 1 M HCl (2×25 mL), water (2×25 mL), and brine (2×25 mL), dried (Na$_2$SO$_4$), and concentrated under reduced pressure. The resulting solid was triturated using EtOAc/hexanes and provided the title compound as a tangerine-colored solid (3.23 g, 67%). Mp: 133-137° C. $^1$H NMR (400 MHz, CDCl$_3$) δ: 8.55 (d, J=2.6 Hz, 1H), 7.98 (dd, J=8.8, 2.6 Hz, 1H), 7.60 (d, J=8.8 Hz, 1H), 6.96 (s, 1H, disappeared on D$_2$O shake), 2.57 (tt, J=8.0, 4.8 Hz, 1H), 1.35-1.24 (m, 2H), 1.14-1.03 (m, 2H). HPLC-MS (ESI+): m/z 301.1 [30%, (M$^{37}$Cl+Na)$^+$], 299.1 [100%, (M$^{35}$Cl+Na)$^-$]. HPLC-MS (ESI-): m/z 277.0 [30%, (M$^{37}$Cl-H)$^-$], 275.1 [100%, (m$^{35}$Cl-H)$^-$].

The following anilines were prepared using the previously reported method.[8] Method c: To a mixture of benzoic acid (1.0 equiv.), TBTU (1.1 equiv.), and DCM was added DIPEA (2.0 equiv.). The solution was stirred at room temperature for 30 min followed by the addition of 1-methylpiperidin-4-amine (1.2 equiv.). The reaction mixture was further stirred at room temperature overnight. Work-up and product isolation procedure are described below.

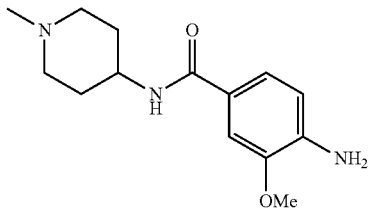 [SMILES: COc1cc(C(=O)NC2CCN(C)CC2)ccc1N]

4-Amino-3-methoxy-N-(1-methylpiperidin-4-yl)benzamide (SG3-016): This was prepared from 4-amino-3-methoxybenzoic acid (1.06 g), TBTU (2.25 g), DIPEA (2.22 mL), 1-methylpiperidin-4-amine (0.960 mL), and DCM (50 mL) using the general method c. Water (50 mL) and DCM (50 mL) were added. The aqueous layer was concentrated under reduced pressure and sodium hydroxide (1 M aq. solution, 50 mL) added. The mixture was extracted with DCM (50 mL). The organic layer was dried (Na$_2$SO$_4$) and concentrated under reduced pressure to give the title compound[9] as an off-white solid (0.987 g, 59%). Mp: 215° C. (dec). $^1$H NMR (400 MHz, DMSO-d$_6$) δ: 7.79 (d, J=7.8 Hz, 1H), 7.29-7.24 (m, 2H), 6.57 (d, J=8.6 Hz, 1H), 5.21 (s, 2H, disappeared on D$_2$O shake), 3.78 (s, 3H), 3.74-3.59 (m, 1H), 2.78-2.70 (brd, J=11.4 Hz, 2H), 2.14 (s, 3H), 1.95-1.84 (brt, J=11.4 Hz, 2H), 1.74-1.65 (brd, J=12.1, 3.3 Hz, 2H), 1.53 (qd, J=12.1, 3.3 Hz, 2H). HPLC-MS (ESI+): m/z 264.2 [100%, (M+H)$^+$].

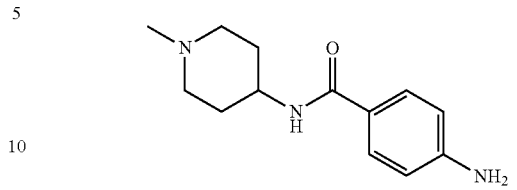

4-Amino-N-(1-methylpiperidin-4-yl)benzamide (SG3-051): This was prepared from 4-aminobenzoic acid (1.00 g), TBTU (2.58 g), DIPEA (2.54 mL), 1-methylpiperidin-4-amine (1.10 mL), and DCM (50 mL) using the general method c. The solvent was removed and the resulting oil was partitioned between water (50 mL) and DCM (50 mL). The aqueous layer was concentrated under reduced pressure, 1 M (50 mL of a 1 M aq. solution) was added, and the mixture stirred at room temperature for 1 h. The resulting precipitate was filtered, washed with water (3×20 mL) and DCM (3×20 mL), and dried (Na$_2$SO$_4$) to give the title compound[9] as an off-white solid (1.41 g, 83%). Mp: 206° C. (dec). $^1$H NMR (400 MHz, DMSO-d$_6$) δ: 7.72 (d, J=7.7 Hz, 1H), 7.56 (d, J=8.6 Hz, 2H), 6.51 (d, J=8.6 Hz, 2H), 5.57 (s, 2H), 3.73-3.59 (m, 1H), 2.78-2.69 (brd, J=11.6 Hz, 2H), 2.14 (s, 3H), 1.94-1.84 (t, J=11.6 Hz, 2H), 1.74-1.64 (d, J=12.2 Hz, 2H), 1.53 (qd, J=12.2, 3.8 Hz, 2H). HPLC-MS (ESI+): m/z 234.2 [100%, (M+H)$^+$].

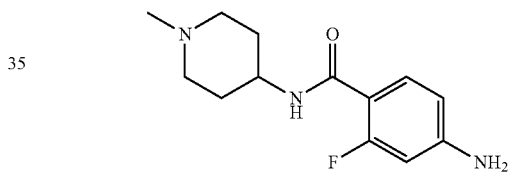

4-Amino-2-fluoro-N-(1-methylpiperidin-4-yl)benzamide (SG3-153): This was prepared from 4-amino-2-fluorobenzoic acid (0.700 g), TBTU (1.59 g), DIPEA (1.57 mL), 1-methylpiperidin-4-amine (0.680 mL), and DCM (18 mL) using the general method c. The solvent was removed and the resulting oil was stirred in NaOH (1 M aq. solution, 50 mL) at room temperature for 30 min. The aqueous layer was extracted with DCM (1×50 mL) and EtOAc (1×50 mL). The organic layers were combined, dried (Na$_2$SO$_4$), and concentrated under reduced pressure. The resulting solid was recrystallized from EtOH/hexanes to provide the title compound as an off-white solid (0.967 g, 85%). Mp: 202° C. (dec). $^1$H NMR (400 MHz, DMSO-d$_6$) δ: 7.41-7.36 (m, 1H), 7.34 (t, J=8.8 Hz, 1H), 6.35 (dd, J=8.5, 2.0 Hz, 1H), 6.25 (dd, J=14.2, 2.0 Hz, 1H), 5.87 (s, 2H, disappeared on D$_2$O shake), 3.71-3.57 (m, 1H), 2.67 (d, J=11.6 Hz, 2H), 2.12 (s, 3H), 1.92 (t, J=10.6 Hz, 2H), 1.70 (d, J=10.6 Hz, 2H), 1.49 (qd, J=11.6, 3.5 Hz, 2H). $^{19}$F NMR (376 MHz, DMSO-d$_6$): δ -112.88. HPLC-MS (ESI+): m/z 252.3 [100%, (M+H)$^+$].

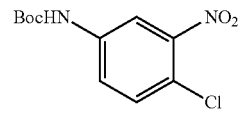

1,1-Dimethylethyl 4-chloro-3-nitrophenylcarbamate (SG3-084): This was prepared using the reported procedure of Sloss et al.[10] 4-Chloro-3-nitroaniline (5.00 g, 28.97 mmol) and di-tert-butyl carbonate (10.12 g, 46.36 mmol) were dissolved in dry THF (20 mL). The mixture was stirred and heated at reflux for 20 h. The solvent was removed and the yellow oil was triturated using EtOAc/hexanes to give the title compound[m] as a yellow solid (6.18 g, 78%). Mp: 103° C. (dec). $^1$H NMR (400 MHz, CDCl$_3$) δ: 8.06 (d, J=2.3 Hz, 1H), 7.46 (dd, J=8.7, 2.3 Hz, 1H), 7.42 (d, J=8.7 Hz, 1H), 6.64 (s, 1H), 1.52 (s, 9H). HPLC-MS (ESI+): m/z 297.1 [30%, (M$^{37}$Cl+H)$^+$], 295.1 [100%, (M$^{35}$Cl+H)$^+$].

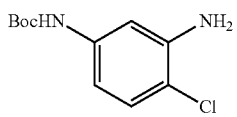

tert-Butyl 3-amino-4-chlorophenylcarbamate (SG3-085): This was prepared using the reported procedure of Sloss et al.[10] The nitroarene SG3-084 (6.18 g, 22.66 mmol), iron(III) chloride hexahydrate (0.183 g, 0.679 mmol), and activated carbon (1 g) were combined in MeOH (50 mL) and stirred at reflux for 10 min. Hydrazine hydrate (6.78 mL, 90.65 mmol) was added slowly and the mixture was stirred at reflux for 1 h. Upon cooling to room temperature, the solution was filtered over a bed of Celite and concentrated under reduced pressure. The resulting residue was dissolved in EtOAc (80 mL) and washed with water (80 mL) and brine (80 mL). The organic layer was dried (Na$_2$SO$_4$) and concentrated under reduced pressure. The resulting solid was triturated using EtOAc/hexanes to give the title compound[m] as a white solid (4.74 g, 86%). Mp: 139-140° C. $^1$H NMR (400 MHz, CDCl$_3$) δ: 7.15 (s, 1H), 7.12 (d, J=8.6 Hz, 1H), 6.57 (dd, J=8.6, 2.5 Hz, 1H), 6.42 (s, 1H, disappeared on D$_2$O shake), 1.50 (s, 9H). HPLC-MS (ESI+): m/z 509.2 [10%, (M$^{37}$Cl+M$^{35}$Cl+H)$^+$], 507.2 [15%, (2M$^{35}$Cl+H)$^+$], 265.1 [10%, (M$^{35}$Cl+H)$^+$], 189.2 [100%, (M$^{37}$C$_1$-tBu+H)$^{2+}$], 187.2 [100%, (M$^{35}$C$_1$-tBu+H)$^{2+}$].

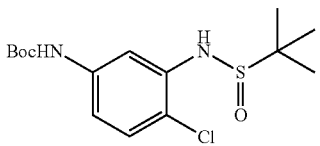 [SMILES: CC(C)(C)OC(=O)Nc1ccc(Cl)c(NS(=O)C(C)(C)C)c1]

1,1-Dimethylethyl 4-chloro-3-(1,1-dimethylethylsulfinamido)phenylcarbamate (SG3-133): To a solution of SG3-085 (2.43 g, 10 mmol) and pyridine (2.42 mL, 30 mmol) in DCM (5 mL) was added a solution of t-butylsulfinyl chloride (1.23 mL, 10 mmol) in DCM (5 mL) dropwise at 0° C. under Argon. The mixture was stirred at 0° C. for 2 h, then warmed to room temperature and further stirred for 5 h. The reaction mixture was diluted with EtOAc (100 mL) and washed with 1 M HCl (1×50 mL), water (1×50 mL), and brine (1×50 mL). The organic layer was dried (Na2SO$_4$) and concentrated under reduced pressure. The resulting residue was purified via column chromatography (SiO$_2$) eluting with hexanes/EtOAc (0:10 to 3:7 v/v) to give the title compound as a light yellow foam (2.81 g, 81%). Mp: 124° C. (dec). $^1$H NMR (400 MHz, CDCl$_3$) δ: 7.41 (d, J=2.4 Hz, 1H), 7.21 (d, J=8.8 Hz, 1H), 6.93 (brd, J=8.8 Hz, 1H), 6.50 (brs, 1H), 6.06 (brs, 1H), 1.51 (s, 9H), 1.35 (s, 9H). HPLC-MS (ESI+): m/z 717.2 [80%, (M$^{37}$Cl+M$^{35}$Cl+H)$^+$], 715.2 [70%, (2M$^{35}$Cl+H)$^+$], 371.2 [50%, (M$^{37}$Cl+H)$^+$], 369.2 [100%, (M$^{35}$Cl+H)$^+$].

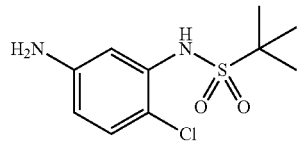 [SMILES: CC(C)(C)S(=O)(=O)Nc1cc(N)ccc1Cl]

N-(5-Amino-2-chlorophenyl)-2-methylpropane-2-sulfonamide (SG3-105): A solution of SG3-088 (1.28 g, 3.52 mmol) in TFA/DCM (1:1, 20 mL) was stirred for 2 h at room temperature. The mixture was concentrated under reduced pressure. The pH was adjusted to pH 12 by the addition of NaOH (1 M, aq.) and extracted with EtOAc (2×20 mL). The combined organic layers were washed with water (1×20 mL) and brine (1×20 mL), dried (Na$_2$SO$_4$), and concentrated under reduced pressure. The resulting solid was triturated using EtOAc/hexanes to provide the title compound as a light brown solid (0.902 g, 97%). Mp: 124-125° C. $^1$H NMR (400 MHz, CDCl$_3$) δ: 7.23 (d, J=2.4 Hz, 1H), 7.11 (d, J=8.6 Hz, 1H), 6.50 (s, 1H), 6.42 (dd, J=8.6, 2.4 Hz, 1H), 1.41 (s, 9H). HPLC-MS (ESI+): m/z 527.2 [30%, (2M$^{37}$Cl+H)$^+$], 525.2 [40%, (2M$^{35}$Cl+H)$^+$], 265.2 [40%, (M$^{37}$Cl+H)$^+$], 263.2 [100%, (M$^{35}$Cl+H)$^+$].

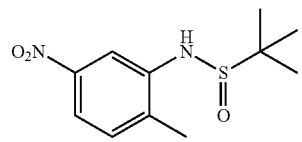 [SMILES: Cc1ccc([N+](=O)[O-])cc1NS(=O)C(C)(C)C]

2-Methyl-N-(2-methyl-5-nitrophenyl)propane-2-sulfinamide (SG3-115): To a solution of 2-methyl-5-nitroaniline (0.152 g, 1 mmol) and pyridine (0.242 mL, 3 mml) in DCM (1 mL) was added a solution of t-butylsulfinyl chloride (0.185 mL, 1.5 mmol) at room temperature under Argon. The mixture was stirred overnight at room temperature. The reaction mixture was diluted with EtOAc (10 mL) and washed with HCl (1 M aq. solution, 1×10 mL), water (1×10 mL), and brine (1×10 mL). The organic layer was dried (Na$_2$SO$_4$) and concentrated under reduced pressure. The resulting residue was purified via column chromatography (SiO$_2$) eluting with hexanes/EtOAc (0:10 to 4:6 v/v) to give the title compound as a light yellow solid (2.81 g, 81%). Mp: 169° C. (dec). $^1$H NMR (400 MHz, CDCl$_3$) δ: 8.02 (d, J=2.2 Hz, 1H), 7.83 (dd, J=8.2, 2.2 Hz, 1H), 7.30 (d, J=8.2 Hz, 1H), 5.37 (s, 1H), 2.36 (s, 3H), 1.39 (s, 9H). HPLC-MS (ESI+): m/z 532.2 [40%, (2M+Na)$^+$], 513.2 [100%, (2 M+H)$^+$], 257.2 [40%, (M+H)$^+$].

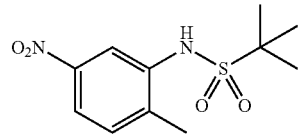 [SMILES: Cc1ccc([N+](=O)[O-])cc1NS(=O)(=O)C(C)(C)C]

2-Methyl-N-(2-methyl-5-nitrophenyl)propane-2-sulfonamide (SG3-123): To a solution of SG3-115 (0.450 g, 1.76 mmol) in DCM (5 mL) was added m-CPBA (65%, 0.433 g, 1.76 mmol) under Argon. The mixture was stirred at room temperature for 14 h. The reaction mixture was diluted with DCM (50 mL) and washed with saturated NaHCO₃ (2×50 mL) and brine (1×50 mL). The organic layer was dried (Na₂SO₄) and concentrated under reduced pressure. The resulting solid was triturated using EtOAc/hexanes to give the title compound as a yellow solid (0.421 g, 88%). Mp: 207° C. (dec). ¹H NMR (400 MHz, CDCl₃) δ: 8.51 (d, J=2.3 Hz, 1H), 7.91 (dd, J=8.4, 2.3 Hz, 1H), 7.34 (d, J=8.4 Hz, 1H), 5.99 (s, 1H), 2.43 (s, 3H), 1.48 (s, 9H). HPLC-MS (ESI+): m/z 567.2 [80%, (2M+Na)⁺], 295.1 [100%, (M+Na)⁺].

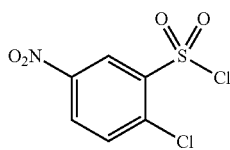 [SMILES: O=[N+]([O-])c1ccc(Cl)c(S(=O)(=O)Cl)c1]

2-Chloro-5-nitrobenzene-1-sulfonyl chloride (SG3-128): SG3-128 was prepared using the method previously reported by Goldfarb and Berk.[11] A mixture of 4-chloronitrobenzene (3.94 g, 25 mmol) and chlorosulfonic acid (8.31 mL, 125 mmol) was stirred and heated overnight at 120° C. The solution was cooled and poured into crushed iced in an ice bath and the precipitate filtered. Recrystallization of the resulting solid from carbon tetrachloride (CAUTION) provided the title compound as a light brown solid (0.342 g, 14%). Mp: 87-88° C. (lit.[11] Mp 85-87° C.). ¹H NMR (400 MHz, CDCl₃) δ: 9.01 (d, J=2.6 Hz, 1H), 8.51 (dd, J=8.7, 2.6 Hz, 1H), 7.88 (d, J=8.7 Hz, 1H).

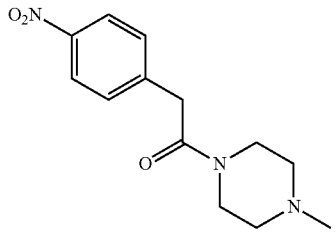 [SMILES: CN1CCN(C(=O)Cc2ccc([N+](=O)[O-])cc2)CC1]

1-(4-Methylpiperazin-1-yl)-2-(4-nitrophenyl)ethanone (SG3-143): To a mixture of 4-nitrophenylacetic acid (5.00 g, 27.60 mmol), carbonyldiimidazole (4.48 g, 27.60 mmol), and THF (28 mL) was added 1-methylpiperazine (3.06 mL, 27.60 mmol). The solution was stirred for 2 h at room temperature. The solvent was removed and EtOAc (100 mL) added and washed with water (2×50 mL). The combined aqueous layers were extracted with EtOAc (2×50 mL) and DCM (1×50 mL). The organic layers were combined, dried (Na₂SO₄), and concentrated under reduced pressure. The resulting solid was recrystallized from EtOH/hexanes to provide the title compound[12] as a tangerine-colored solid (6.017 g, 83%). Mp: 176° C. (dec). ¹H NMR (400 MHz, CDCl₃) δ: 8.19 (d, J=8.8 Hz, 2H), 7.41 (d, J=8.8 Hz, 2H), 3.81 (s, 2H), 3.66 (t, J=5.0 Hz, 2H), 3.50 (t, J=5.0 Hz, 2H), 2.39 (t, J=5.1 Hz, 2H), 2.32 (t, J=5.1 Hz, 2H), 2.29 (s, 3H). HPLC-MS (ESI+): m/z 264.2 [100%, (M+H)⁺].

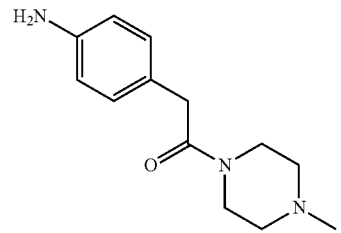

2-(4-Aminophenyl)-1-(4-methylpiperazin-1-yl)ethanone (SG3-144): To a solution of SG3-143 (5.88 g, 22.36 mmol) in MeOH (25 mL, deoxygenated with Argon gas) was added Pd/C (10%, 0.500 g). A balloon of hydrogen gas was attached to the flask via a septum cap. The mixture was stirred at room temperature for 29 h. The reaction mixture was filtered over Celite and the filtrate concentrated under reduced pressure to provide the title compound[12] as a tangerine solid (5.18 g, 99%). Mp: 188° C. (dec). ¹H NMR (400 MHz, CDCl₃) δ: 7.01 (d, J=8.5 Hz, 2H), 6.64 (d, J=8.5 Hz, 2H), 3.65 (t, J=5.0 Hz, 2H), 3.61 (s, 2H), 3.45 (t, J=5.0 Hz, 2H), 2.35 (t, J=5.0 Hz, 2H), 2.25 (s, 3H), 2.20 (t, J=5.0 Hz, 2H). HPLC-MS (ESI+): m/z 467.4 [20%, (2M+H)⁺], 234.2 [100%, (M+H)⁺].

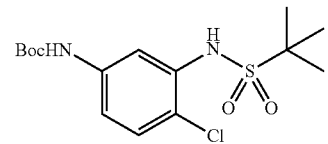 [SMILES: CC(C)(C)OC(=O)Nc1ccc(Cl)c(NS(=O)(=O)C(C)(C)C)c1]

1,1-Dimethylethyl 4-chloro-3-(1,1-dimethylethylsulfonamido)phenylcarbamate (SG3-088): To a solution of SG3-133 (2.80 g, 8.07 mmol) in DCM (30 mL) was added m-CPBA (65%, 2.143 g, 8.07 mmol) under Argon. The mixture was stirred overnight at room temperature. The reaction mixture was diluted with DCM (200 mL) and washed with saturated NaHCO₃ (2×200 mL) and brine (1×200 mL). The organic layer was dried (Na₂SO₄) and concentrated under reduced pressure. The resulting solid was triturated using EtOAc/hexanes to give the title compound as a light yellow solid (2.59 g, 88%). ¹H NMR (400 MHz, CDCl₃) δ: 7.54 (d, J=2.5 Hz, 1H), 7.48 (brd, J=8.9 Hz, 1H), 7.27 (d, J=8.9 Hz, 1H), 6.52 (s, 2H), 1.51 (s, 9H), 1.41 (s, 9H). HPLC-MS (ESI+): m/z 749.2 [80%, (M³⁷Cl+M³⁵Cl+H)⁺], 747.2 [100%, (2M³⁵Cl+H)⁺], 385.2 [50%, (M³⁵Cl+H)⁺].

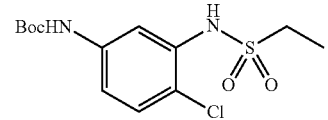 [SMILES: CCS(=O)(=O)Nc1cc(NC(=O)OC(C)(C)C)ccc1Cl]

tert-Butyl 4-chloro-3-(ethylsulfonamido)phenylcarbamate (SG4-008): To a solution of SG3-085 (1.00 g, 4.12 mmol) and pyridine (0.997 mL, 12.36 mmol) in DCM (4 mL) was added ethanesulfonyl chloride (0.584 ml, 6.18 mmol) in DCM (2 mL) at 0° C. The mixture was warmed to room temperature and stirred overnight. The reaction mixture was diluted with EtOAc (40 mL) and washed with HCl (1 M aq. solution, 1×20 mL), water (1×20 mL), and brine (1×20 mL). The organic layer was dried (Na₂SO₄) and concentrated under reduced pressure. The resulting residue was triturated using EtOAc/hexanes to provide the title compound as an off-white solid (1.289 g, 93%). $^1$H NMR (400 MHz, CDCl$_3$) δ: 7.48 (d, J=2.5 Hz, 1H), 7.40 (brd, J=8.6 Hz, 1H), 7.30 (d, J=8.6 Hz, 1H), 6.72 (s, 1H, disappeared on D$_2$O shake), 6.55 (s, 1H, disappeared on D$_2$O shake), 3.14 (q, J=7.4 Hz, 2H), 1.51 (s, 9H), 1.37 (t, J=7.4 Hz, 3H). HPLC-MS (ESI+): m/z 693.2 [60%, (M$^{37}$Cl+M$^{35}$Cl+Na)$^+$], 691.2 [90%, (2M$^{35}$Cl+Na)$^+$], 359.2 [35%, (M$^{37}$Cl+Na)$^+$], 357.2 [100%, (M$^{35}$Cl+Na)$^+$].

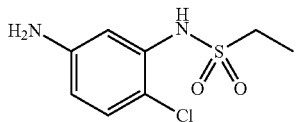

N-(5-Amino-2-chlorophenyl)ethanesulfonamide (SG4-009): A solution of SG4-008 (1.20 g, 3.58 mmol) in TFA/DCM (1:1, 20 mL) was stirred overnight at room temperature. The mixture was concentrated under reduced pressure. The pH was adjusted to pH 8-9 by the addition of NaOH (1 M, aq.) and extracted with EtOAc (2×20 mL). The combined organic layers were washed with water (1×20 mL) and brine (1×20 mL), dried (Na$_2$SO$_4$), and concentrated under reduced pressure. The resulting oil was triturated using EtOAc/hexanes to provide the title compound as a light brown solid (0.776 g, 92%). $^1$H NMR (400 MHz, CDCl$_3$) δ: 7.12 (d, J=8.6 Hz, 1H), 7.02 (d, J=2.7 Hz, 1H), 6.67 (s, 1H), 6.40 (dd, J=8.6, 2.7 Hz, 1H), 3.13 (q, J=7.4 Hz, 2H), 1.36 (t, J=7.4 Hz, 3H). HPLC-MS (ESI+): m/z 237.1 [35%, (M$^{37}$Cl+H)$^+$], 235.1 [100%, (M$^{35}$Cl+H)$^+$].

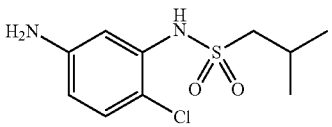 [SMILES: CC(C)CS(=O)(=O)Nc1cc(N)ccc1Cl]

N-(5-Amino-2-chlorophenyl)-2-methylpropane-1-sulfonamide (SG4-016): To a solution of SG3-085 (0.242 g, 1.00 mmol) and pyridine (0.242 mL, 3.00 mmol) in DCM (0.5 mL) was added isobutanesulfonyl chloride (0.156 mL, 1.2 mmol) in DCM (0.5 mL) at 0° C. The mixture was warmed to room temperature and stirred overnight. The reaction mixture was diluted with EtOAc (10 mL) and washed with HCl (1 M aq. solution, 1×5 mL), water (1×5 mL), and brine (1×5 mL). The organic layer was dried (Na$_2$SO$_4$) and concentrated under reduced pressure. The resulting oil was treated with TFA/DCM (1:1, 5 mL) and stirred overnight at room temperature. The mixture was concentrated under reduced pressure. The pH was adjusted to pH 8-9 by the addition of NaHCO$_3$(saturated, aq.) and extracted with EtOAc (1×5 mL). The organic layer was washed with water (1×5 mL) and brine (1×5 mL), dried (Na$_2$SO$_4$), and concentrated under reduced pressure. The resulting brown oil was triturated using EtOAc/hexanes to provide the title compound as an off-white solid (0.135 g, 52%). $^1$H NMR (400 MHz, CDCl$_3$) 67 : 7.16 (d, J=8.6 Hz, 1H), 7.10 (d, J=2.1 Hz, 1H), 6.72 (s, 1H), 6.52 (dd, J=8.6, 2.1 Hz, 1H), 2.98 (d, J=6.7 Hz, 2H), 2.27 (dp, J=13.3, 6.7 Hz, 1H), 1.07 (d, J=6.7 Hz, 7H). HPLC-MS (ESI+): m/z 265.2 [35%, (M$^{37}$Cl+H)$^+$], 263.2 [100%, (M$^{35}$Cl+H)$^+$].

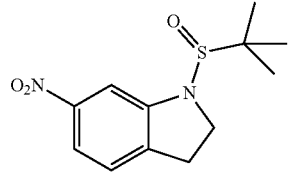 [SMILES: CC(C)(C)S(=O)N1CCc2ccc([N+](=O)[O-])cc21]

1-(tert-Butylsulfinyl)-6-nitroindoline (SG4-017): To a solution of 6-nitroindoline (1.00 g, 6.09 mmol) and pyridine (1.48 mL, 18.27 mmol) in DCM (3 mL) was added a solution of t-butylsulfinyl chloride (0.751 mL, 6.09 mmol) at 0° C. under Argon. The mixture was warmed to room temperature and stirred overnight. The reaction mixture was diluted with EtOAc (50 mL) and washed with HCl (1 M aq. solution, 1×50 mL), water (1×50 mL), and brine (1×50 mL). The organic layer was dried (Na$_2$SO$_4$) and concentrated under reduced pressure. The resulting residue was triturated using EtOAc/hexanes to provide the title compound as a dark yellow solid (1.252 g, 77%). Mp: 108° C. (dec). $^1$H NMR (400 MHz, CDCl$_3$) δ: 7.82 (dd, J=8.1, 2.1 Hz, 1H), 7.67 (d, J=2.1 Hz, 1H), 7.25 (d, J=8.1 Hz, 1H), 4.36 (td, J=10.5, 6.8 Hz, 1H), 3.60 (td, J=10.5, 6.8 Hz, 1H), 3.30 (dddd, J=17.3, 10.5, 6.8, 0.8 Hz, 1H), 3.17 (dddd, J=17.3, 10.5, 6.8, 0.8 Hz, 1H), 1.34 (s, 9H). HPLC-MS (ESI+): m/z 559.3 [70%, (2M+Na)$^+$], 291.2 [100%, (M+H)$^+$].

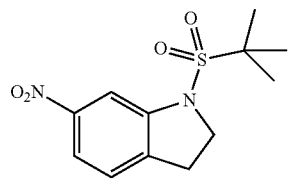 [SMILES: CC(C)(C)S(=O)(=O)N1CCc2ccc([N+](=O)[O-])cc21]

1-(tert-Butylsulfonyl)-6-nitroindoline (SG4-019): To a solution of SG4-017 (1.122 g, 4.18 mmol) in DCM (20 mL) was added m-CPBA (65%, 1.03 g, 4.18 mmol) under Argon. The mixture was stirred overnight at room temperature. The reaction mixture was diluted with DCM (100 mL) and washed with saturated NaHCO$_3$(1×100 mL) and brine (1×100 mL). The organic layer was dried (Na$_2$SO$_4$) and concentrated under reduced pressure. The resulting solid was triturated using EtOAc/hexanes to give the title compound as a yellow solid (1.135 g, 95%). Mp: 113-119° C. $^1$H NMR (400 MHz, CDCl$_3$) δ: 8.14 (d, J=2.1 Hz, 1H), 7.85 (dd, J=8.2, 2.1 Hz, 1H), 7.27 (d, J=8.2 Hz, 1H), 4.22 (t, J=8.6 Hz, 2H), 3.22 (t, J=8.6 Hz, 2H), 1.51 (s, 9H). HPLC-MS (ESI+): m/z 591.3 [70%, (2M+Na)$^+$], 307.2 [100%, (M+Na)$^+$].

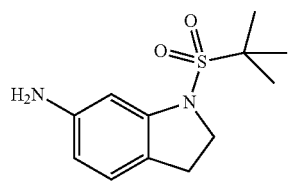 [SMILES: CC(C)(C)S(=O)(=O)N1CCc2ccc(N)cc21]

1-(tert-Butylsulfonyl)indolin-6-amine (SG4-020): To a solution of SG4-019 (1.00 g, 3.517 mmol) in MeOH (25 mL, deoxygenated with Argon gas) was added Pd/C (10%, 0.250 g). A balloon of hydrogen gas was attached to the flask via a septum cap. The mixture was stirred at room temperature for 4 h. The reaction mixture was filtered over Celite and the filtrate concentrated under reduced pressure to provide the title compound as a grey solid (0.833 g, 93%). Mp: 113-116° C. $^1$H NMR (400 MHz, CDCl$_3$) δ: 6.93 (d, J=7.9 Hz, 1H), 6.84 (d, J=2.0 Hz, 1H), 6.34 (dd, J=7.9, 2.0 Hz, 1H4), 4.08 (t, J=8.4 Hz, 2H), 3.00 (t, J=8.4 Hz, 2H), 1.46 (s, 9H). HPLC-MS (ESI+): m/z 255.1 [100%, (M+H)$^+$].

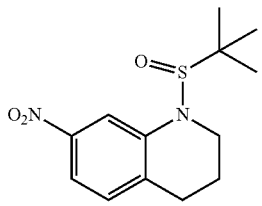 [SMILES: CC(C)(C)S(=O)N1CCCc2ccc([N+](=O)[O-])cc21]

1-(tert-Butylsulfinyl)-7-nitro-1,2,3,4-tetrahydroquinoline (SG4-021): To a solution of 7-nitro-1,2,3,4-tetrahydroquinoline (1.00 g, 5.61 mmol) and pyridine (1.36 mL, 16.84 mmol) in DCM (2.5 mL) was added a solution of t-butylsulfinyl chloride (0.692 mL, 5.61 mmol) at 0° C. under Argon. The mixture was warmed to room temperature and stirred overnight. The reaction mixture was diluted with EtOAc (50 mL) and washed with HCl (1 M aq. solution, 1×50 mL), water (1×50 mL), and brine (1×50 mL). The organic layer was dried (Na$_2$SO$_4$) and concentrated under reduced pressure. The resulting residue was triturated using EtOAc/hexanes to provide the title compound as an orange solid (0.894 g, 56%). $^1$H NMR (400 MHz, CDCl$_3$) δ: 7.88 (d, J=2.2 Hz, 1H), 7.72 (dd, J=8.3, 2.2 Hz, 1H), 7.19 (d, J=8.3 Hz, 1H), 4.19-4.10 (m, 1H), 3.16-3.07 (m, 1H), 2.95-2.79 (m, 2H), 2.08-1.99 (m, 1H), 1.82-1.70 (m, 1H), 1.35 (s, 9H). HPLC-MS (ESI+): m/z 587.3 [70%, (2M+Na)$^+$], 305.1 [100%, (M+Na)$^+$].

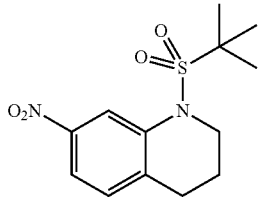

1-(tert-Butylsulfonyl)-7-nitro-1,2,3,4-tetrahydroquinoline (SG4-022): To a solution of SG4-021 (0.873 g, 3.091 mmol) in DCM (15 mL) was added m-CPBA (65%, 0.762 g, 3.091 mmol) under Argon. The mixture was stirred overnight at room temperature. The reaction mixture was diluted with DCM (100 mL) and washed with saturated NaHCO$_3$(1×100 mL) and brine (1×100 mL). The organic layer was dried (Na$_2$SO$_4$) and concentrated under reduced pressure. The resulting solid was triturated using EtOAc/hexanes to give the title compound as a yellow solid (0.903 g, 98%). $^1$H NMR (400 MHz, CDCl$_3$) δ: 8.48 (d, J=2.3 Hz, 1H), 7.85 (dd, J=8.4, 2.3 Hz, 1H), 7.23 (d, J=8.4 Hz, 1H), 3.78 (brs, 2H), 2.94 (t, J=6.8 Hz, 2H), 2.14-2.05 (m, 2H), 1.55 (s, 9H). HPLC-MS (ESI+): m/z 619.3 [100%, (2M+Na)$^+$], 321.2 [80%, (M+Na)$^+$].

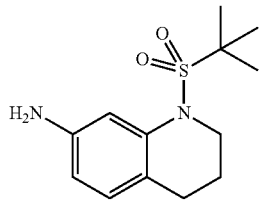 [SMILES: CC(C)(C)S(=O)(=O)N1CCCc2ccc([N+](=O)[O-])cc21]

1-(tert-Butylsulfonyl)-1,2,3,4-tetrahydroquinolin-7-amine (SG4-023): To a solution of SG4-022 (0.750 g, 2.51 mmol) in MeOH (10 mL, deoxygenated with Argon gas) was added Pd/C (10%, 0.200 g). A balloon of hydrogen gas was attached to the flask via a septum cap. The mixture was stirred at room temperature for 4 h. The reaction mixture was filtered over Celite and the filtrate concentrated under reduced pressure to provide the title compound as a light pink solid (0.651 g, 97%). $^1$H NMR (400 MHz, CDCl$_3$) δ: 7.11 (d, J=2.2 Hz, 1H), 6.88 (d, J=8.1 Hz, 1H), 6.45 (dd, J=8.1, 2.2 Hz, 1H), 5.30 (s, 1H), 3.76-3.68 (m, 2H), 2.73 (t, J=6.8 Hz, 2H), 2.01 (quintet, J=6.8 Hz, 2H), 1.46 (s, 9H). HPLC-MS (ESI+): m/z 269.2 [100%, (M+H)$^+$].

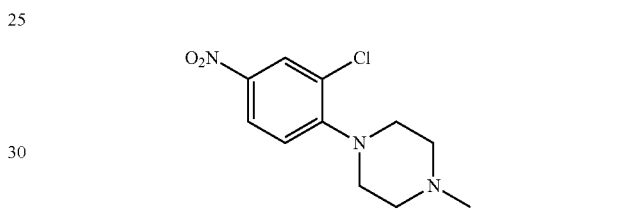

1-(2-Chloro-4-nitrophenyl)-4-methylpiperazine (SG4-029): 3-Chloro-4-fluoronitrobenzene (5.02 g, 28.60 mmol) in a round bottom flask was cooled to 0° C. then treated with 1-methylpiperazine (9.52 mL, 85.80 mmol). The solution was warmed to room temperature and stirred overnight. Water (50 mL) was added and the precipitates were filtered, washed with water (3×25 mL), and air-dried to provide the title compound (WO 2011/120026, page 34) as a yellow solid. Mp: 103-105° C. $^1$H NMR (400 MHz, DMSO-d$_6$) δ: 8.21 (d, J=2.7 Hz, 1H), 8.13 (dd, J=9.0, 2.7 Hz, 1H), 7.27 (d, J=9.0 Hz, 1H), 3.19-3.13 (m, 4H), 2.47-2.45 (m, 4H), 2.22 (s, 3H). HPLC-MS (ESI+): m/z 258.2 [35%, (M$^{37}$Cl+H)$^+$], 256.2 [100%, (M$^{35}$Cl+H)$^+$].

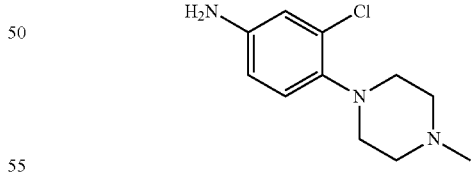

3-Chloro-4-(4-methylpiperazin-1-yl)aniline (SG4-030): To a solution of SG4-029 (2.00 g, 7.82 mmol) in MeOH (32 mL, deoxygenated with Argon gas) was added PtO$_2$ (18 mg, 0.0782 mmol). A balloon of hydrogen gas was attached to the flask via a septum cap. The mixture was stirred at room temperature for 5 h. The reaction mixture was filtered over Celite and the filtrate concentrated under reduced pressure to provide the title compound as a light yellow solid (1.741 g, 98%). $^1$H NMR (400 MHz, DMSO-d$_6$) δ: 6.85 (d, J=8.5 Hz, 1H), 6.59 (d, J=2.6 Hz, 1H), 6.45 (dd, J=8.5, 2.6 Hz, 1H), 5.01 (s, 2H, disappeared on D$_2$O shake), 2.81-2.72 (m, 4H), 2.40 (brs, 4H), 2.18 (s, 3H). HPLC-MS (ESI+): m/z 228.2 [35%, (M$^{37}$Cl+H)$^+$], 226.2 [100%, (M$^{35}$Cl+H)$^+$].

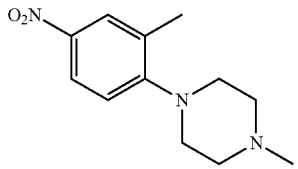 [SMILES: Cc1cc([N+](=O)[O-])ccc1N1CCN(C)CC1]

1-Methyl-4-(2-methyl-4-nitrophenyl)piperazine (SG4-035): 2-Fluoro-5-nitrotoluene (1.00 g, 6.45 mmol) and 1-methylpiperazine (2.15 mL, 19.34 mmol) placed in a 5 mL microwave vial then stirred and heated at reflux. Water (10 mL) was added and the precipitates were filtered, washed with water (3×5 mL), and air-dried to provide the title compound as a yellow solid (1.518 g, 99%). $^1$H NMR (400 MHz, CDCl$_3$) δ: 8.07-8.00 (m, 2H), 7.00 (d, J=9.1 Hz, 1H), 3.12-3.04 (m, 4H), 2.63 (brs, 4H), 2.40 (s, 3H), 2.36 (s, 3H). HPLC-MS (ESI+): m/z 236.2 [100%, (M+H)$^+$].

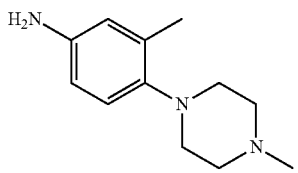

3-Methyl-4-(4-methylpiperazin-1-yl)aniline (SG4-037): To a solution of SG4-035 (2.00 g, 8.50 mmol) in MeOH (35 mL, deoxygenated with Argon gas) was added Pd/C (10%, 0.300 g). A balloon of hydrogen gas was attached to the flask via a septum cap. The mixture was stirred at room temperature for 17 h. The reaction mixture was filtered over Celite and the filtrate concentrated under reduced pressure to provide the title compound as a light brown solid (1.708 g, 98%). $^1$H NMR (400 MHz, CDCl$_3$) δ: 6.89 (d, J=8.3 Hz, 1H), 6.55 (d, J=2.8 Hz, 1H), 6.51 (dd, J=8.3, 2.8 Hz, 1H), 3.45 (s, 2H, disappeared on D$_2$O shake), 2.90-2.83 (m, 4H), 2.57 (brs, 4H), 2.36 (s, 3H), 2.23 (s, 3H). HPLC-MS (ESI+): m/z 206.3 [100%, (M+H)$^+$].

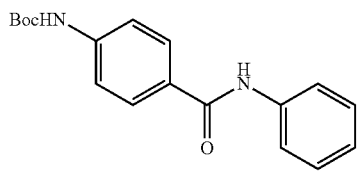 [SMILES: CC(C)(C)OC(=O)Nc1ccc(C(=O)Nc2ccccc2)cc1]

4-(Cert-Butoxycarbonylamino)benzamide (SG3-060): This was prepared using the reported procedure of Rodriguez et al.[13] from Boc-4-Abz-OH (1.00 g), TBTU (1.35 g), aniline (0.384 mL), and triethylamine (2.35 mL) to give the title compound as a white solid (1.009 g, 76%). $^1$H NMR (400 MHz, DMSO-d$_6$): δ 10.04 (s, 1H, reduced by 50% on D$_2$O shake), 9.67 (s, 114, disappeared on D$_2$O shake), 7.86 (d, J=8.8 Hz, 2H), 7.72 (d, J=7.6 Hz, 2H), 7.55 (d, J=8.8 Hz, 2H), 7.30 (d, J=7.6 Hz, 2H), 7.04 (t, J=7.6 Hz, 1H), 1.46 (s, 9H). HPLC-MS (ESI+): m/z 647.3 [100%, (2M+Na)$^+$], 313.2 [100%, (M+H)$^+$].

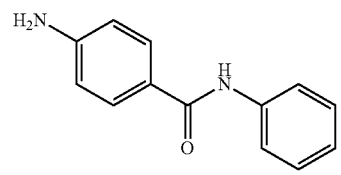 [SMILES: Nc1ccc(C(=O)Nc2ccccc2)cc1]

4-Aminobenzanilide (SG3-063): This was prepared using the reported procedure of Rodriguez et al.[13] from SG3-060 (0.900 g) to give the title compound as a white solid (0.592 g, 97%). $^1$H NMR (400 MHz, DMSO-d$_6$): δ 9.74 (s, 1H, disappeared on D$_2$O shake), 7.73 (d, J=8.0, 1.1 Hz, 2H), 7.70 (d, J=8.7 Hz, 2H), 7.29 (d, J=8.0 Hz, 1H), 7.02 (t, J=8.0 Hz, 1H), 6.58 (d, J=8.7 Hz, 2H), 5.75 (s, 2H, disappeared on D$_2$O shake). HPLC-MS (ESI+): m/z 447.3 [20%, (2M+Na)$^+$], 213.2 [100%, (M+H)$^+$].

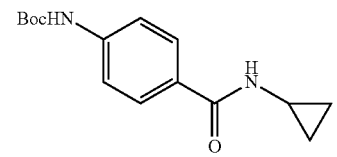 [SMILES: CC(C)(C)OC(=O)Nc1ccc(C(=O)NC2CC2)cc1]

tert-butyl 4-(cyclopropylcarbamoyl)phenylcarbamate (SG3-066): This was prepared using the reported procedure of Rodriguez et al.[13] from Boc-4-Abz-OH (1.00 g), TBTU (1.35 g), cyclopropylamine (0.292 mL), and triethylamine (2.35 mL) to give the title compound as an off-white solid (0.863 g, 74%). $^1$H NMR (400 MHz, DMSO-d$_6$): δ 9.60 (s, 114, disappeared on D$_2$O shake), 8.26 (d, J=4.0 Hz, 1H), 7.70 (d, J=8.7 Hz, 2H), 7.46 (d, J=8.7 Hz, 2H), 2.81-2.72 (m, 1H), 1.45 (s, 9H), 0.69-0.59 (m, 2H), 0.56-0.47 (m, 2H). HPLC-MS (ESI+): m/z 575.3 [70%, (2M+Na)$^+$], 553.3 [70%, (2M+H)$^+$], 277.3 [100%, (M+H)$^+$].

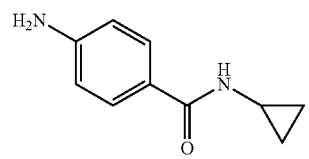 [SMILES: Nc1ccc(C(=O)NC2CC2)cc1]

4-Amino-N-cyclopropylbenzamide (SG3-067): This was prepared using the reported procedure of Rodriguez et al.[13] from SG3-066 (0.800 g) to give the title compound as a yellow solid (0.500 g, 98%). $^1$H NMR (400 MHz, DMSO-d$_6$): δ 7.94 (d, J=3.9 Hz, 1H), 7.52 (d, J=8.7 Hz, 2H), 6.50 (d, J=8.7 Hz, 2H), 5.58 (s, 2H), 2.79-2.71 (m, 1H), 0.66-0.59 (m, 2H), 0.55-0.46 (m, 2H). HPLC-MS (ESI+): m/z 375.3 [20%, (2M+Na)$^+$], 177.2 [100%, (M+H)$^+$].

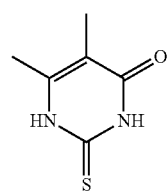

5,6-Dimethyl-2-thioxo-2,3-dihydropyrimidin-4(1H)-one (RJ1-004)[14]: Sodium metal (3.20 g, 0.14 mol) was added to dry EtOH (80 mL) under argon before thiourea (5.30 g, 70 mmol) and ethyl methyl-acetoacetate (10.0 g, 70 mmol) were added to the reaction mixture. The reaction was heated to reflux at 90° C. for three hours. The reaction mixture was cooled to ambient temperature and evaporated under reduced pressure. The product obtained was dissolved in cold water and acetic acid was used to bring the pH down to pH 3-4. The resulting solid was filtered, washed with cold water to provide RJ1-004 as an off-white solid (7.63 g, 70%). m.p.=268° C. (decomposed). $^1$H NMR (400 MHz, DMSO-d$_6$) δ 12.29 (s, 1H), 12.08 (s, 1H), 2.07 (s, 3H), 1.73 (s, 3H). LRMS (ESI+) m/z 157.2 (M+H)$^+$; (ESI−) m/z 155.0 (M−H)$^−$.

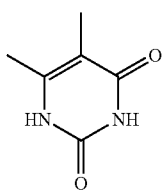

5,6-Dimethylpyrimidine-2,4(1H,3H)-dione (RJ1-006):[15] A mixture of 1a (7.18 g, 46 mmol), chloroacetic acid (50.09 g, 0.530 mol), and water (21.5 mL, 1.20 mol) was heated to reflux under argon at 100° C. for 23 hours. After cooling to ambient temperature, the reaction mixture was quenched with water (250 mL). The precipitate that formed was filtered and washed with water to provide RJ1-006 as a white solid (4.68 g, 73%). m.p.=288° C. (decomposed). $^1$H NMR (400 MHz, DMSO-d$_6$) δ 10.89 (s, 1H), 10.59 (s, 1H), 2.00 (s, 3H), 1.68 (s, 3H). LRMS (ESI+) m/z 141.2 (M+H)$^+$; (ESI−) m/z 139.1 (M−H)$^−$.

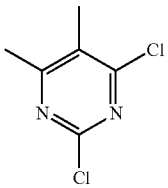

2,4-Dichloro-5,6-dimethylpyrimidine (RJ1-008):[15] A mixture of RJ1-006 (4.00 g, 28.5 mmol), phosphorus(V) oxychloride (60 mL, 0.642 mol), and dimethylformamide (0.08 mL, 1.03 mmol) was heated to reflux at 110° C. for 23 hours. The reaction mixture was then cooled to ambient temperature and evaporated. Toluene (80 mL) was added to the residue and the resulting mixture was concentrated. Cold water with ice (160 mL) was added to the residue, and the mixture was extracted with chloroform (3×60 mL). The combined organic layers were washed with brine (2×150 mL), dried over sodium sulfate, filtered, and concentrated to provide RJ1-008 as a pale yellow solid (4.37 g, 87%). m.p.=68-70° C. $^1$H NMR (400 MHz, CDCl$_3$) δ 2.55 (s, 3H), 2.34 (s, 3H). LRMS (ESI+) m/z 177.1 (MCl$^{35}$Cl$^{35}$+H)$^+$, 179.0 (MCl$^{35}$Cl$^{37}$+H)$^+$, 181.0 (MCl$^{37}$Cl$^{37}$+H)$^+$.

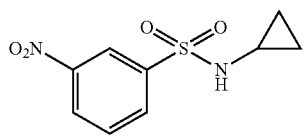

N-Cyclopropyl-3-nitrobenzenesulfonamide (RJ1-016): 3-Nitrobenzenesulfonyl chloride (1.0 g, 4.5 mmol) was added to a round bottom flask followed by dry THF (10 mL) and cyclopropylamine (0.93 mL, 13.5 mmol), both under argon, at ambient temperature with stirring. After thirty minutes, the pH of the reaction mixture was brought down to pH 1 using 4M HCl, and the mixture was evaporated under reduced pressure. The off-white solid was then triturated with EtOAc and hexanes and filtered. The remaining oily residue was diluted with water (10 mL) and extracted with EtOAc (2×10 mL). The organic layer was separated, dried over sodium sulfate, filtered and evaporated, producing a light pink solid. The two crops were determined to be the same by NMR and together give RJ1-016 (0.98 g, 89%). m.p.=123-124° C. $^1$H NMR (400 MHz, DMSO-d$_6$) δ 8.16 (dt, J=2.5, 1.4 Hz, 2H), 7.91 (s, 1H), 7.86 (dd, J=7.8, 1.1 Hz, 1H), 7.57 (t, J=8.0 Hz, 1H), 1.86-1.75 (m, 1H), 0.13 (dd, J=6.9, 4.7 Hz, 2H), 0.03 (dd, J=6.6, 3.3 Hz, 2H). LRMS (ESI+) m/z 243.1 (M+H)$^+$; (ESI−) m/z 241.1 (M−H)$^−$.

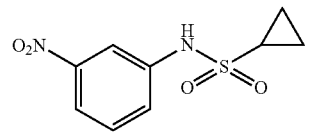

N-(3-Nitrophenyl)cyclopropanesulfonamide (RJ1-020): 3-Nitroaniline (0.100 g, 0.724 mmol) was added to a microwave vial which was then sealed. Dry DCM (3.5 mL), anhydrous pyridine (0.175 mL), and cyclopropanesulfonyl chloride (0.11 mL) were all then added to the sealed tube under argon. The tube was stirred at room temperature for eighteen hours before being concentrated, re-dissolved in DCM, separated via flash chromatography eluting with hexanes/EtOAc to provide RJ1-020 as a yellow-white solid (0.154 g, 88%). m.p.=134-135° C. $^1$H NMR (400 MHz, DMSO-d$_6$) δ 10.36 (s, 1H), 8.10-7.98 (m, 1H), 7.92 (dt, J=6.7, 2.3 Hz, 1H), 7.67-7.55 (m, 2H), 2.80-2.68 (m, 1H), 0.95 (d, J=6.4 Hz, 4H). LRMS (ESI+) m/z 243.1 (M+H)$^+$; (ESI−) m/z 241.1 (M−H)$^−$.

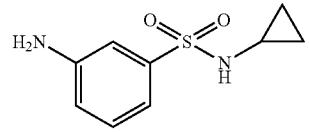 [SMILES: O=[N+]([O-])c1cccc(S(=O)(=O)NC2CC2)c1]

3-Amino-N-cyclopropylbenzenesulfonamide (RJ1-042): To a two-neck round bottom flask was added Pd/C (0.250 g), followed by deoxygenated hydrazine (0.533 mL, 11.1 mmol), and RJ1-016 (0.900 g, 3.72 mmol) dissolved in deoxygenated EtOH (25 mL). The flask was heated to reflux under argon in a hot oil bath at 90° C. with stirring for four hours. After formation of the desired product was confirmed by TLC and LC/MS, the flask was removed from the oil bath and allowed to cool to ambient temperature. The reaction mixture was filtered through a bed of Celite wetted with MeOH using deoxygenated MeOH (3×25 mL, 100 mL). The filtrate was then evaporated under reduced pressure after the Celite and Pd/C had been quenched with water. After evaporation, a white solid precipitated once the flask cooled to ambient temperature, which was identified as the product RJ1-042 (0.757 g, 96%). m.p.=115-118° C. $^1$H NMR (400 MHz, DMSO-d$_6$) δ 7.73 (d, J=2.1 Hz, 1H), 7.20 (t, J=7.9 Hz, 1H), 7.00 (t, J=2.0 Hz, 1H), 6.91-6.86 (m, 1H), 6.75 (ddd, J=8.0, 2.2, 0.8 Hz, 1H), 5.58 (s, 1H), 2.06 (td, J=6.7, 3.2 Hz, 1H), 0.46 (qd, J=7.7, 3.6 Hz, 2H), 0.42-0.36 (m, 2H). LRMS (ESI+) m/z 213.2 (M+H)$^+$; HRMS (ESI+) m/z calculated for C$_9$H$_{12}$N$_2$O$_2$S (M+Na)$^+$235.05117, found 235.05075, (M+H)$^+$ 213.06922, found 213.06890.

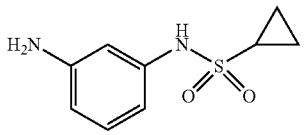 [SMILES: Nc1cccc(NS(=O)(=O)C2CC2)c1]

N-(3-Aminophenyl)cyclopropanesulfonamide (RJ1-025): To a three-neck round bottom flask was added Pd/C (0.500 g), followed by deoxygenated hydrazine (2.4 mL, 11.1 mmol), and RJ1-020 (4.000 g, 16.5 mmol) dissolved in deoxygenated EtOH (120 mL). The mixture was allowed to react following the same procedure as RJ1-042, with the exception that after 25 hours, hydrazine hydrate (1.2 mL, 1.5 equiv.), deoxygenated EtOH (5 mL) and Pd/C (0.250 g) were added to the reaction mixture under argon. The mixture was allowed to react for another 11 hours and worked up in the same manner as RJ1-042 to give a viscous, dark green/yellow material as the final product RJ1-025 (3.482 g, 99%). $^1$H NMR (400 MHz, DMSO-d$_6$) δ 9.35 (s, 1H), 6.89 (t, J=7.9 Hz, 1H), 6.47 (s, 1H), 6.36 (d, J=7.9 Hz, 1H), 6.26 (d, J=9.1 Hz, 1H), 5.13 (s, 2H), 2.58-2.44 (m, 1H), 0.90 (t, J=6.2 Hz, 4H). LRMS (ESI+) m/z 213.1 (M+H)$^+$; (ESI−) m/z 211.2 (M−H)$^-$; HRMS (ESI+) m/z calculated for C$_9$H$_{12}$N$_2$O$_2$S (M+H)$^+$ 213.06922, found 213.07037.

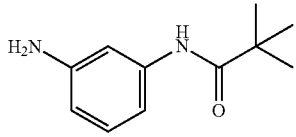

N-(3-Aminophenyl)-1,1-dimethylethylcarboxamide (MA2-040-1): This was prepared from MA2-036-1 (1.100 g), (NH$_4$)$_2$CO$_3$ (0.946 g), Pd/C (0.532 g), and EtOH (12 mL) using the general method c (reaction time, 18 h) to provide the title compound as a light yellow solid (0.750 g, 99%). Mp: 251° C. (dec). $^1$H NMR (400 MHz, DMSO-d$_6$) δ: 8.86 (s, 1H), 6.93 (t, J=2.0 Hz, 1H), 6.88 (t, J=8.0 Hz, 1H), 6.71 (d, with unresolved fine coupling, J=8.0 Hz, 1H) 1H), 6.25 (d, with unresolved fine coupling, J=8.0 Hz, 1H), 4.99 (s, 2H, disappeared on D$_2$O shake), 1.19 (s, 9H). HPLC-MS (ESI+): m/z 193.2 [100%, (M+H)$^+$].

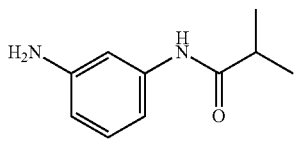

N-(3-Aminophenyl)-1-methylethylcarboxamide (MA2-040-2): This was prepared from MA2-036-2 (1.62 g), (NH$_4$)$_2$CO$_3$ (1.47 g), Pd/C (10%, 0.825 g), and EtOH (12 mL) using the general method c (reaction time, 18 h) to provide the title compound as a white solid (1.10 g, 81%). Mp: 115-117° C. $^1$H NMR (400 MHz, DMSO-d$_6$) δ: 9.49 (s, 1H), 6.92 (s, 1H), 6.88 (t, J=8.0 Hz, 1H), 6.68 (d, J=8.0 Hz, 1H), 6.22 (d, with unresolved fine coupling, J=8.0, 1H), 5.01 (s, 2H, disappeared on D$_2$O shake), 2.59-2.51 (m, 1H), 1.06 (d, J=6.8 Hz, 6H). HPLC-MS (ESI+): m/z 179.2 [100%, (M+H)$^+$].

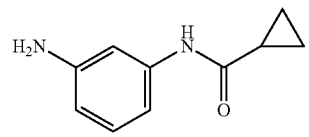

N-(3-Aminophenyl)cyclopropanecarboxamide (MA2-040-3): This was prepared from MA2-036-3 (1.46 g), (NH$_4$)$_2$CO$_3$ (1.34 g), Pd/C (10%, 0.757 g), and EtOH (12 mL) using the general method c (reaction time, 18 h) to provide the title compound as a white solid (1.10 g, 81%). Mp: 126-131° C. $^1$H NMR (400 MHz, DMSO-d$_6$) δ: 9.85 (s, 1H, 70% reduced on D$_2$O shake), 6.92-6.88 (m, 1H), 6.86 (t, J=8.0 Hz, 1H), 6.67 (d, J=8.0 Hz, 1H), 6.24 (d, with unresolved fine coupling, J=8.0 Hz, 1H), 5.02 (s, 2H, disappeared on D$_2$O shake), 1.78-1.71 (m, 1H), 0.78-0.72 (m, 4H). HPLC-MS (ESI+): m/z 177.2 [100%, (M+H)$^+$].

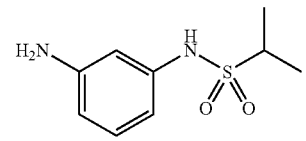

N-(3-Aminophenyl)propane-2-sulfonamide (MA3-004): This was prepared from MA2-086 (2.2 g), (NH$_4$)$_2$CO$_3$ (7 g), Pd/C (10%, 0.956 g), and EtOH (20 mL) using the general method c (reaction time, 18 h) to provide the title compound as a white solid (1.56 g, 81%). Mp: 297° C. (dec). $^1$H NMR (400 MHz, DMSO-d$_6$) δ: 9.41 (s, 1H, disappeared on D$_2$O shake), 6.89 (t, J=8.0 Hz, 1H), 6.47 (t, J=2.1 Hz, 1H), 6.35 (d, with unresolved fine coupling, J=8.0 Hz, 1H), 6.25 (d, with unresolved fine coupling, J=8.0 Hz, 1H), 5.15 (s, 2H, disappeared on D$_2$O shake), 3.18 (septet d, J=6.8 Hz, 6H, J=6.8 Hz, 1H), 1.22 (d, J=6.8 Hz, 6H). HPLC-MS (ESI+): m/z 451.2 [10%, (2M+Na)$^+$], 215.1 [100%, (M+H)$^+$].

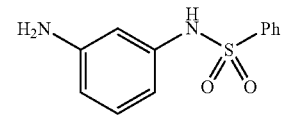

N-(3-Aminophenyl)benzenesulfonamide (MA3-092): This was prepared from MA3-086 (2.17 g, 1 equiv.) and hydrazine monohydrate (1.17 mL, 3 equiv.) using the general method b. The title compound MA3-092 was obtained as a yellow oil which solidified after 1 h (1.83 g, 95%). Mp: 87-90° C. $^1$H NMR (400 MHz, DMSO-d$_6$) δ: 9.95 (s, 1H, disappeared on D$_2$O shake), 7.76 (s, 1H), 7.74 (d, J=1.4 Hz, 1H), 7.63-7.49 (m, 3H), 6.79 (t, J=8.0 Hz, 1H), 6.35 (t, J=1.9 Hz, 1H), 6.22 (d, J=8.0 Hz, 1H), 6.18 (d, J=8.1 Hz, 1H), 5.10 (s, 2H, disappeared on D$_2$O shake). HPLC-MS (ESI+): m/z 249.2 [100%, (M+H)$^+$].

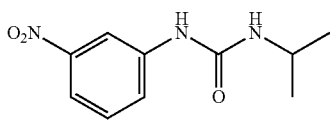 [SMILES: CC(C)NC(=O)Nc1cccc([N+](=O)[O-])c1]

1-Isopropyl-3-(3-nitrophenyl)urea (MA2-054-2): A solution of 3-nitrophenylisocyante (1.15 g) in dry ether (10 mL) was cooled to 0° C. (ice-water bath) and while keeping the reaction under argon, isopropylamine (630 μL, 1.1 equiv.) was added via a Hamilton syringe. The reaction mixture was allowed to warm to room temperature and stirred for 4 h. The precipitate was filtered and washed with hexane (15 mL×3) and dried to provide MA2-054-2 as white powder (1.43 g, 80%). Mp: 162-163° C. $^1$H NMR (400 MHz, DMSO-$d_6$) δ: 8.84 (s, 1H, disappeared on D$_2$O shake), 8.51 (t, J=2.2 Hz, 1H), 7.73 (ddd, J=8.1, 2.3, 0.9 Hz, 1H), 7.59 (ddd, J=8.2, 2.2, 0.9 Hz, 1H), 7.49 (t, J=8.1 Hz, 1H), 6.20 (d, J=7.5 Hz, 1H, 55% reduced on D$_2$O shake), 3.79-3.74 (m, 1H), 1.11 (d, J=6.5 Hz, 6H). HPLC-MS (ESI+): m/z 469.1 [35%, (2M+Na)$^+$], 447.2 [95%, (2M+H)+], 224.2 [100%, (M+H)$^+$].

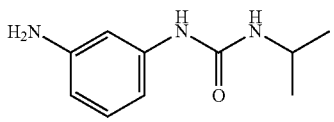

1-(3-Aminophenyl)-3-isopropylurea (MA2-056-2): This was prepared from MA2-054-2 (1.41 g), (NH$_4$)$_2$CO$_3$ (1.34 g), Pd/C (0.757 g), and EtOH (15 mL) using the general method c (reaction time, 3 h) and purified via column chromatography (SiO$_2$) eluting with DCM/EtOAc (10:0 to 10:1 v/v) to provide the title compound MA2-056-2 as a yellow solid (0.661 g, 53%). Mp: 173-175° C. $^1$H NMR (400 MHz, DMSO-$d_6$) δ: 7.95 (s, 1H), 6.81 (t, J=7.9 Hz, 1H), 6.67 (t, J=2.0 Hz, 1H), 6.46 (d, with unresolved fine coupling, J=7.5 Hz, 1H), 6.09 (ddd, J=7.9, 2.0, 0.9 Hz, 1H), 5.86 (d, J=7.5 Hz, 1H), 4.92 (s, 2H), 3.78-3.62 (m, 1H), 1.07 (d, J=6.5 Hz, 6H).

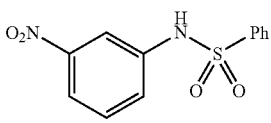 [SMILES: O=[N+]([O-])c1cccc(NS(=O)(=O)c2ccccc2)c1]

N-(3-Nitrophenyl)benzenesulfonamide (MA3-086): This was prepared from m-nitroaniline (1.38 g), pyridine (4.02 mL, 5 eq.) and benzenesulfonyl chloride (4.4 g, 2.5 equiv.) using the general method a1 (reaction time, 16 h). The title compound MA3-086 was obtained as a yellow solid (2.21 g, 79%). Mp: 131° C. (dec). $^1$H NMR (400 MHz, DMSO-$d_6$) δ: 10.96 (s, 1H), 7.94-7.92 (m, 1H), 7.88 (dd, J=7.5, 1.9 Hz, 1H), 7.82-7.79 (m, 2H), 7.64 (t, J=7.3 Hz, 1H), 7.61-7.57 (m, 2H), 7.55-7.51 (m, 2H). HPLC-MS (ESI+): m/z 578.9 [40%, (2M+Na)$^+$], 299.2 [100%, (M+Na)$^+$].

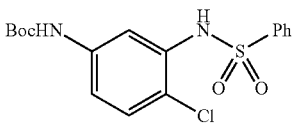 [SMILES: CC(C)(C)OC(=O)Nc1ccc(Cl)c(NS(=O)(=O)c2ccccc2)c1]

tert-Butyl (4-chloro-3-(phenylsulfonamido)phenyl)carbamate (MA3-093): This was prepared in the same manner as SG3-084 using the reported procedure of Sloss et al.[10] from SG3-085 (1.46 g, 1 equiv.) and benzenesulfonyl chloride (0.983 mL, 1.1 equiv.). The resulting residue was purified via column chromatography (SiO$_2$) eluting with hexanes/EtOAc (10:0 to 1:1 v/v) to give the title compound as a white solid (1.64 g, 72%). Mp: 119-121° C. $^1$H NMR (400 MHz, DMSO-$d_6$) δ: 9.90 (s, 1H), 9.57 (s, 1H), 7.73 (brs, 1H), 7.72 (t, J=1.7 Hz, 1H), 7.64 (t, J=7.4 Hz, 1H), 7.56 (brs, 1H), 7.54-7.51 (m, 3H), 7.27 (dd, J=8.8, 2.4 Hz, 1H), 7.23 (d, J=8.8 Hz, 1H), 1.46 (s, 9H). HPLC-MS (ESI): m/z 787.1 [60%, (2M+Na)$^+$], 400.3 [60%, (M+NH$_4$)$^+$].

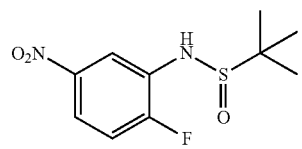 [SMILES: CC(C)(C)S(=O)Nc1cc([N+](=O)[O-])ccc1F]

N-(2-Fluoro-5-nitrophenyl)-2-methylpropane-2-sulfinamide (MA3-094): This was prepared from 2-fluoro-5-nitroaniline (0.781 mg, 1 equiv.) and tert-butylsulfonyl chloride (925 μL, 1.5 equiv.) using the same procedure as for the synthesis of SG3-115. The title compound was obtained as a brown solid (0.671 g, 52%). Mp: 86-89° C. $^1$H NMR (400 MHz, DMSO-$d_6$) δ: 8.31 (s, 1H), 8.13 (dd, J=7.1, 2.8 Hz, 1H), 7.99-7.90 (m, 1H), 7.53 (dd, J=10.3, 9.1 Hz, 1H), 1.27 (s, 9H). HPLC-MS (ESI+): m/z 283.1 [60%, (M+Na)$^+$], 261.1 [100%, (M+H)$^4$].

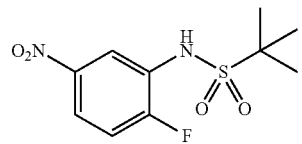 [SMILES: CC(C)(C)S(=O)(=O)Nc1cc([N+](=O)[O-])ccc1F]

N-(2-Fluoro-5-nitrophenyl)-2-methylpropane-2-sulfonamide (MA3-098): This was prepared from MA3-094 (0.632 g, 1 equiv.) and mCPBA (0.658 g, 1.1 equiv.) using the same procedure as for the synthesis of SG3-123. The title compound was obtained as a yellow solid (0.637 g, 95%). Mp: 220° C. (dec). $^1$H NMR (400 MHz, DMSO-$d_6$) δ: 10.20 (s, 1H), 8.38 (dd, J=6.9, 2.8 Hz, 1H), 8.09 (ddd, J=9.1, 4.1, 2.9 Hz, 1H), 7.58 (t, J=9.1 Hz, 1H), 1.30 (s, 9H). HPLC-MS (ESI+): m/z 575.3 [10%, (2M+Na)$^+$], 299.3 [65%, (M+Na)$^+$], 294.2 [55%, (M+NH$_4$)$^+$].

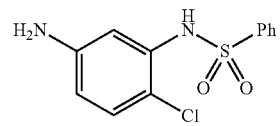 [SMILES: Nc1ccc(Cl)c(NS(=O)(=O)c2ccccc2)c1]

N-(5-Amino-2-chlorophenyl)benzenesulfonamide (MA4-002): This was prepared from MA3-093 (1.57 g, 1 equiv.) and TFA:DCM (1:1, 15 mL) using the same procedure as for the synthesis of MA1-098 (reaction time, 2 h). The title compound was obtained as a yellow solid (1.1 g, 95%). Mp: 155° C. (dec). $^1$H NMR (400 MHz, DMSO-$d_6$) δ: 9.61 (s, 1H, disappeared on D$_2$O shake), 7.73 (s, 1H), 7.72 (d, J=7.4 Hz, 1H), 7.63 (t, J=7.4 Hz, 1H), 7.54 (t, J=7.4 Hz, 2H), 6.93

(d, J=8.6 Hz, 1H), 6.55 (d, J=2.6 Hz, 1H), 6.35 (dd, J=8.6, 2.6 Hz, 1H), 5.35 (s, 2H, disappeared on D₂O shake). HPLC-MS (ESI+): m/z 589.1 [15%, (2M³⁷Cl³⁵Cl+Na)⁺], 587.1 [30%, (2M³⁵Cl³⁵Cl+Na)⁺], 285.1 [40%, (M³⁷Cl+H)⁺], 283.1 [100%, (M³⁵Cl+H)⁺].

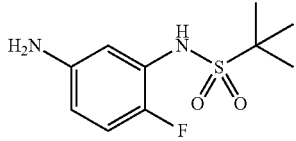

N-(5-Amino-2-fluorophenyl)-2-methylpropane-2-sulfonamide (MA4-024): This was prepared from MA3-098 (0.600 g, 1 equiv.) and hydrazine monohydrate (698 mg, 6 equiv.) and Pd/C (10%, 0.494 g, 0.2 equiv.) using method b (reaction time, 2 h). The title compound was obtained as a pink solid (0.522 g, 91%). Mp: 146° C. (dec). ¹H NMR (400 MHz, DMSO-d₆) δ: 8.91 (brs, 1H, disappeared on D₂O shake), 6.85 (dd, J=10.4, 8.7 Hz, 1H), 6.71 (dd, J=7.0, 2.8 Hz, 1H), 6.31 (ddd, J=8.7, 3.9, 2.8 Hz, 1H), 5.02 (s, 2H, disappeared on D₂O shake), 1.27 (s, 9H). HPLC-MS (ESI+): m/z 493.2 [50%, (2M+H)⁺], 247.2 [100%, (M+H)⁺].

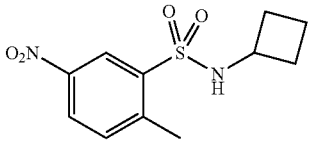 [SMILES: Cc1ccc([N+](=O)[O-])cc1S(=O)(=O)NC1CCC1]

N-Cyclobutyl-2-methyl-5-nitrobenzenesulfonamide (MA4-076): This was prepared from 2-methyl-5-nitrobenzenesulfonyl chloride (1.18 g, 1 equiv.) and cyclobutylamine (0.391 g, 1.1 equiv.) using the general method a1, with pyridine (0.593 g, 1.5 eq.). The crude mixture was purified via column chromatography (SiO₂) eluting with hexanes/EtOAc (1:9 to 1:1 v/v) to give the title compound as a white solid (0.924 g, 68%). Mp: 103-105° C. ¹H NMR (400 MHz, DMSO-d₆) δ: 8.53 (d, J=2.5 Hz, 1H), 8.46 (d, J=8.5 Hz, 1H, disappeared on D₂O shake), 8.36 (dd, J=8.5, 2.5 Hz, 1H), 7.71 (d, J=8.5 Hz, 1H), 3.71-3.58 (m, 1H), 2.70 (s, 3H), 1.96-1.78 (m, 4H), 1.56-1.39 (m, 2H). HPLC-MS (ESI+): m/z 563.1 [25%, (2M+Na)⁺], 293.1 [100%, (M+Na)⁺], 271.2 [10%, (M+H)⁺].

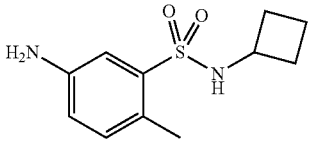

5-Amino-N-cyclobutyl-2-methylbenzenesulfonamide (MA4-080): This was prepared by reduction of MA4-076 according to the general method b. ¹H NMR (400 MHz, DMSO-d₆) δ: 7.74 (d, J=8.8 Hz, 1H, disappeared on D₂O shake), 7.08 (d, J=2.5 Hz, 1H), 6.96 (d, J=8.2 Hz, 1H), 6.63 (dd, J=8.2, 2.5 Hz, 1H), 5.29 (s, 2H, disappeared on D₂O shake), 3.50 (sextet, J=8.2 Hz, 1H), 2.36 (s, 3H), 1.93-1.74 (m, 4H), 1.55-1.36 (m, 2H). HPLC-MS (ESI+): m/z 481.3 [50%, (2M+H)⁺], 241.2 [100%, (M+H)⁺].

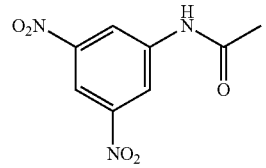 [SMILES: CC(=O)Nc1cc([N+](=O)[O-])cc([N+](=O)[O-])c1]

N-(3,5-Dinitrophenyl)acetamide (MA4-041): This was prepared by refluxing 3,5-dinitroaniline (1 g, 1 equiv.), glacial acetic acid (2.62 g, 8 equiv.) and acetic anhydride (1.08 g, 1.94 equiv.) using the literature procedure. The title compound MA4-041 was obtained as white solid (1.15 g, 94%). ¹H NMR (400 MHz, DMSO-d₆) δ: 10.87 (s, 1H, disappeared on D₂O shake), 8.83 (d, J=2.1 Hz, 2H), 8.49 (t, J=2.1 Hz, 1H), 2.15 (s, 3H). HPLC-MS (ESI+): m/z 248.2 [100%, (M+Na)⁺].

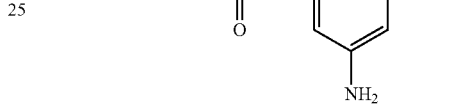

N-(3,5-Diaminophenyl)acetamide (MA4-042): This was prepared by refluxing MA4-041 (1 g, 1 equiv.), hydrazine monohydrate (1.7 g, 8 equiv.) and Pd/C (10%, 0.20 g, 0.04 equiv.) using a reported procedure. The title compound was obtained as a brown oil (0.610 g, 83%). ¹H NMR (400 MHz, DMSO-d₆) δ: 9.30 (s, 1H, 40% reduced on D₂O shake), 6.09 (s, 2H), 5.51 (s, 1H), 4.67 (s, 4H, disappeared on D₂O shake), 1.94 (s, 3H). HPLC-MS (ESI+): m/z 166.2 [100%, (M+H)⁺].

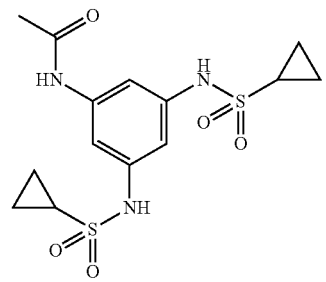 [SMILES: CC(=O)Nc1cc(NS(=O)(=O)C2CC2)cc(NS(=O)(=O)C2CC2)c1]

N-[3,5-Bis(cyclopropanesulfonamido)phenyl]acetamide (MA4-043): This was prepared by stirring MA4-042 (0.165 g, 1 equiv.), cyclopropanesulfonyl chloride (0.422 g, 3 equiv.) and pyridine (0.475 g) in DCM (4 mL) using a reported procedure (0° C. to rt, reaction time 2 h). After work-up the title compound MA4-043 was obtained as a white solid (0.358 g, 96%). ¹H NMR (400 MHz, DMSO-d₆) δ: 10.02 (s, 1H, disappeared on D₂O shake), 9.78 (s, 2H, disappeared on D₂O shake), 7.29 (s, 2H), 6.87 (s, 1H), 2.59-2.52 (m, 2H), 2.01 (s, 3H), 1.00-0.91 (m, 8H). HPLC-MS (ESI+): m/z 747.2 [100%, (2M+H)⁺], 374.2 [65%, (M+H)⁺].

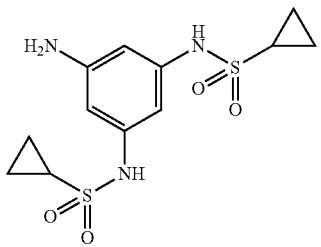 [SMILES: Nc1cc(NS(=O)(=O)C2CC2)cc(NS(=O)(=O)C2CC2)c1]

N,N'-(5-Amino-1,3-phenylene)dicyclopropanesulfonamide (MA4-044): This was prepared by heating MA4-043 (0.033 g, 1 equiv.), in a mixture of HCl (20% aq., 0.435 mL, 2.5 equiv.) and EtOH (0.5 mL) using a reported procedure (sealed tube, 60° C., 4 h). The title compound MA4-044 was obtained as a light green solid (0.023 g, 74%). $^1$H NMR (400 MHz, DMSO-d$_6$) δ: 9.43 (s, 2H, disappeared on D$_2$O shake), 6.38 (t, J=1.9 Hz, 1H), 6.21 (d, J=1.9 Hz, 2H), 5.27 (s, 2H, disappeared on D$_2$O shake), 2.60-2.45 (m, 2H), 0.98-0.88 (m, 8H). HPLC-MS (ESI+): m/z 663.1 [45%, (2M+H)$^+$], 332.2 [100%, (M+H)$^+$].

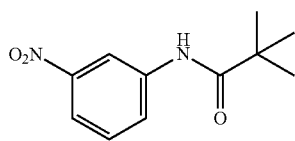

N-(3-Nitrophenyl)pivalamide (MA2-036-1): This was prepared by stirring 3-nitroaniline (1.38 g), pivaloyl chloride (1.30 g, 1.1 equiv.) and triethylamine (1.5 mL, 1.1 equiv.) in DCM using a reported procedure.[16] The title compound was obtained as a white solid (1.67 g, 75%). Mp: 110-113° C. $^1$H NMR (400 MHz, DMSO-d$_6$): δ 9.68 (s, 1H, disappeared on D$_2$O shake), 8.67 (t, J=2.1 Hz, 1H), 8.09 (d, with unresolved fine coupling, J=8.2 Hz, 1H), 7.89 (d, with unresolved fine coupling, J=8.2 Hz, 1H), 7.58 (t, J=8.2 Hz, 1H), 1.24 (s, 9H). HPLC-MS (ESI+): m/z 223.2 [10%, (M+H)$^+$].

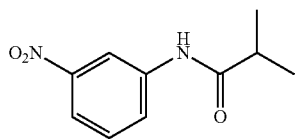

N-(3-Nitrophenyl)isobutyramide (MA2-036-2): This was prepared by stirring 3-nitroaniline (1.38 g), pivaloyl chloride (1.17 g, 1.1 equiv.) and triethylamine (1.5 mL, 1.1 equiv.) in DCM using a reported procedure.[16] The title compound was obtained as a white solid (1.63 g, 80%). Mp: 100-101° C. $^1$H NMR (400 MHz, DMSO-d$_6$): δ 10.33 (s, 1H, disappeared on D$_2$O shake), 8.66 (t, J=2.2 Hz, 1H), 7.93 (ddd, J=8.2, 2.2, 0.9 Hz, 1H), 7.88 (ddd, J=8.2, 2.2, 0.9 Hz, 1H), 7.59 (t, J=8.2 Hz, 1H), 2.60 (septet, J=6.8 Hz, 1H), 1.12 (d, J=6.8 Hz, 6H). HPLC-MS (ESI+): m/z 209.2 [20%, (M+H)$^+$], HPLC-MS (ESI-): m/z 207.1 [30%, (M−H)$^+$].

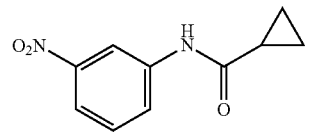 [SMILES: O=C(Nc1cccc([N+](=O)[O-])c1)C1CC1]

N-(3-Nitrophenyl)cyclopropanecarboxamide (MA2-036-3): This was prepared by stirring 3-nitroaniline (1.38 g), pivaloyl chloride (1.15 g, 1.1 equiv.) and triethylamine (1.5 mL, 1.1 equiv.) in DCM using a reported procedure.[16] The title compound was obtained as a gray solid (1.47 g, 71%). $^1$H NMR (400 MHz, DMSO-d$_6$): δ 10.70 (s, 1H, disappeared on D$_2$O shake), 8.64 (t, J=2.2 Hz, 1H), 7.93-7.85 (m, 2H), 7.59 (t, J=8.2 Hz, 1H), 1.79 (quintet, J=6.2 Hz, 1H), 0.85 (d, J=6.2 Hz, 4H). HPLC-MS (ESI+): m/z 207.1 [10%, (M+H)$^+$].

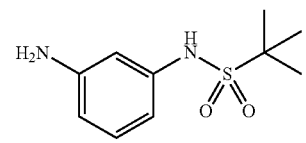

N-(3-Aminophenyl)-2-methylpropane-2-sulfonamide (MA3-010): This was prepared from MA3-009 (0.54 g, 1 equiv.), hydrazine monohydrate (0.314 mL, 3 equiv.) using the general method b. The title compound MA3-010 was obtained as a gray solid (0.362 g, 76%). Mp: 194-195° C. $^1$H NMR (400 MHz, DMSO-d$_6$) δ: 9.28 (s, 1H), 6.86 (t, J=8.0 Hz, 1H), 6.53 (t, J=2.1 Hz, 1H), 6.43 (ddd, J=8.0, 2.1, 0.8 Hz, 1H), 6.23 (ddd, J=8.0, 2.1, 0.8 Hz, 1H), 5.10 (s, 2H), 1.25 (s, 9H). HPLC-MS (ESI+): m/z 479.2 [10%, (2M+Na)$^+$], 229.1 [100%, (M+H)$^+$].

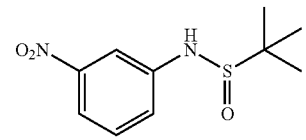 [SMILES: CC(C)(C)S(=O)Nc1cccc([N+](=O)[O-])c1]

N-(3-Nitrophenyl)propane-2-sulfinamide (MA2-044): This was prepared from m-nitroaniline (0.692 mL, 1 equiv.), tert-butylsulfinyl chloride (0.682 mL, 1.1 equiv.) and pyridine (682 mL, 1.1 equiv.) using a reported procedure.[17, 18] The title compound was obtained as yellow oil (0.860 g, 76%). $^1$H NMR (400 MHz, DMSO-d$_6$) δ: 8.61 (s, 1H), 7.91 (t, J=1.9 Hz, 1H), 7.77 (dt, J=7.4, 1.9 Hz, 1H), 7.59-7.49 (m, 2H), 1.26 (s, 9H). HPLC-MS (ESI+): m/z 485.2 [100%, (2M+H)$^+$], 243.1 [65%, (M+H)$^+$].

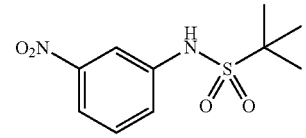 [SMILES: CC(C)(C)S(=O)(=O)Nc1cccc([N+](=O)[O-])c1]

N-(3-Nitrophenyl)-2-methylpropane-2-sulfonamide (MA3-009): This was prepared from MA2-044 (0.745 g, 1 equiv.) and mCPBA (0.795 g, 1.5 equiv.) by the same procedure[17, 18] used to prepare SG3-123. The title compound was obtained as a yellow solid (0.552 g, 70%). $^1$H NMR (400 MHz, DMSO-d$_6$) δ: 10.26 (s, 1H), 8.13 (t, J=2.2 Hz, 1H), 7.91-7.87 (m, 1H), 7.73-7.66 (m, 1H), 7.58 (t, J=8.2 Hz, 1H), 1.30 (s, 9H). HPLC-MS (ESI−): m/z 257.1 [100%, (M−H)$^-$].

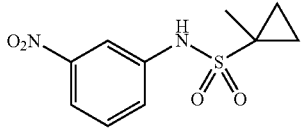 [SMILES: CC1(S(=O)(=O)Nc2cccc([N+](=O)[O-])c2)CC1]

1-Methyl-N-(3-nitrophenyl)cyclopropane-1-sulfonamide (MA4-086): This was prepared by stirring m-nitroaniline (0.414 g, 1 equiv.), 1-methylcyclopropanesulfonyl chloride (0.464 g, 2.5 equiv.) and pyridine (0.982 g, 3 equiv.) in DCM (15 mL) using general method a (reaction time, 16 h). The title compound MA4-086 was obtained as a yellow solid (2.21 g, 79%). $^1$H NMR (400 MHz, DMSO-d$_6$) δ: 10.42 (s, 1H, disappeared on D$_2$O shake), 8.07 (t, J=2.1 Hz, 1H), 7.94 (ddd, J=8.0, 2.1, 1.3 Hz, 1H), 7.66 (ddd, J=8.0, 2.0, 1.3 Hz, 1H), 7.62 (t, J=8.0 Hz, 1H), 1.18-1.11 (m, 2H), 0.86-0.78 (m, 2H). HPLC-MS (ESI+): m/z 535.1 [20%, (2M+Na)$^+$], 279.1 [100%, (M+Na)$^+$], 257.1 [25%, (M+H)$^+$].

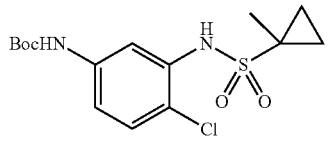 [SMILES: CC(C)(C)OC(=O)Nc1ccc(Cl)c(NS(=O)(=O)C2(C)CC2)c1]

tert-Butyl(4-chloro-3-((1-methylcyclopropane)-1-sulfonamido)phenyl)carbamate (MA5-004): This was prepared by stirring SG3-085 (0.30 g, 1 equiv.), 1-methylcyclopropane sulfonyl chloride (0.287 g, 1.5 equiv.), pyridine (0.299 mL, 3 equiv.) in DCM using method a (0° C. to rt, 5 h). The title compound MA5-004 was obtained as an orange solid (0.380 g, 94%). $^1$H NMR (400 MHz, DMSO-d$_6$) δ: 9.58 (s, 1H, disappeared on D$_2$O shake), 9.39 (s, 1H, disappeared on D$_2$O shake), 7.69 (s, 1H), 7.38-7.28 (m, 2H) 1.47 (brs, 12H), 1.10-1.06 (m, 2H), 0.81-0.77 (m, 2H). HPLC-MS (ESI−): m/z 361.2 [40%, (M$^{37}$Cl−H)$^+$], 359.1 [100%, (M$^{35}$Cl−H)$^+$].

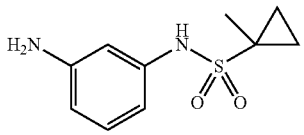

1-Methyl-N-(3-aminophenyl)cyclopropane-1-sulfonamide (MA4-096): This was prepared by refluxing MA4-086 (0.482 g, 1 equiv.), hydrazine-monohydrate (0.565 g, 6 equiv.) and Pd/C (0.200 g) in EtOH (4 mL) using method b (reaction time, 16 h). The title compound MA4-096 was obtained as a yellow solid (0.402 g, 94%). $^1$H NMR (400 MHz, DMSO-d$_6$) δ: 6.88 (t, J=8.0 Hz, 1H), 6.49 (t, J=2.1 Hz, 1H), 6.37 (ddd, J=8.0, 2.1, 0.9 Hz, 1H), 6.25 (ddd, J=8.0, 2.1, 0.9 Hz, 1H), 5.12 (s, 2H, disappeared on D$_2$O shake), 1.37 (s, 3H), 1.11-1.07 (m, 2H), 0.72-0.68 (m, 2H). HPLC-MS (ESI+): m/z 475.2 [10%, (2M+H)$^+$], 227.2 [100%, (M+H)$^+$].

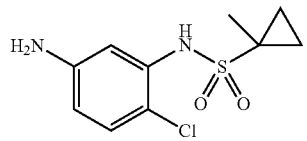 [SMILES: CC1(S(=O)(=O)Nc2cc(N)ccc2Cl)CC1]

N-(5-Amino-2-chlorophenyl)-1-methylcyclopropane-1-sulfonamide (MA5-010): This was prepared from MA3-093 (1.57 g, 1 equiv.) and TFA:DCM (1:1, 15 mL) by the same procedure used to prepare MA1-098 (reaction time, 2 h). The title compound was obtained as a yellow solid (1.1 g, 95%). $^1$H NMR (400 MHz, DMSO-d$_6$) δ: 9.07 (s, 1H, disappeared on D$_2$O shake), 7.04 (d, J=8.5 Hz, 1H), 6.76 (d, J=8.4 Hz, 1H), 6.72 (d, J=2.6 Hz, 1H), 6.40 (dd, J=8.6, 2.6 Hz, 1H), 5.35 (s, 2H, disappeared on D$_2$O shake), 1.44 (s, 3H), 1.10-1.06 (m, 2H), 0.79-0.75 (m, 2H). HPLC-MS (ESI+): m/z 263.1 [40%, (M$^{37}$Cl+H)$^+$], 261.1 [100%, (M$^{35}$Cl+H)$^+$].

1. Holmes, I. P.; Bergman, Y.; Lunniss, G. E.; Nikac, M.; Choi, N.; Hemley, C. F.; Walker, S. R.; Foitzik, R. C.; Ganame, D.; Lessene, R. Fak inhibitors. US2013/0017194A1, 2013.
2. Aliagas-Martin, I.; Burdick, D.; Corson, L.; Dotson, J.; Drummond, J.; Fields, C.; Huang, O. W.; Hunsaker, T.; Kleinheinz, T.; Krueger, E.; Liang, J.; Moffat, J.; Phillips, G.; Pulk, R.; Rawson, T. E.; Ultsch, M.; Walker, L.; Wiesmann, C.; Zhang, B.; Zhu, B. Y.; Cochran, A. G. A class of 2,4-bisanilinopyrimidine Aurora A inhibitors with unusually high selectivity against Aurora B. *J Med Chem* 2009, 52, 3300-7.
3. Lawrence, H. R.; Kazi, A.; Luo, Y.; Kendig, R.; Ge, Y.; Jain, S.; Daniel, K.; Santiago, D.; Guida, W. C.; Sebti, S. M. Synthesis and biological evaluation of naphthoquinone analogs as a novel class of proteasome inhibitors. *Bioorg Med Chem* 2010, 18, 5576-92.
4. Campbell, K. N.; Campbell, B. K.; Salm, E. M. Derivatives of the lower aliphatic amines. *Proc. Indiana Acad. Sci.* 1948, 57, 97-100.
5. Xu, L.; Shu, H.; Liu, Y.; Zhang, S.; Trudell, M. L. Oxidative cyclization of N-alkyl-o-methyl-arenesulfonamides to biologically important saccharin derivatives. *Tetrahedron* 2006, 62, 7902-7910.
6. Goetschi, E.; Wichmann, J.; Woltering, T. J. Pyrazolopyrimidine derivatives. U.S. Pat. No. 7,378,417B2, 2008.
7. Corcoran, J. P. T.; Kalindjian, S. B.; Borthwick, A. D.; Adams, D. R.; Brown, J. T.; Taddei, D. M. A.; Shiers, J. J. Therapeutic Aryl-Amido-Aryl compounds and their use. US Pat. Appl. US2012/0149737A1, 2012.
8. Hollick, J. J.; Jones, S. D.; Flynn, C. J.; Thomas, M. G. Pyrimidine derivatives as protein kinase inhibitors. U.S. Pat. No. 8,563,542B2, 2013.
9. Qin, W. W.; Sang, C. Y.; Zhang, L. L.; Wei, W.; Tian, H. Z.; Liu, H. X.; Chen, S. W.; Hui, L. Synthesis and biological evaluation of 2,4-diaminopyrimidines as selective Aurora A kinase inhibitors. *Eur J Med Chem* 2015, 95, 174-84.
10. Sloss, M. K.; McKenna, J.; Yoon, W. H.; Norris, S.; Robinson, D.; Parnes, J.; Shevlin, G.; Erdman, P.; Hilgraf, R.; Albers, R.; Hegde, S.; Wallace, A.; Chan, H.; Madakamutil, L.; Raymon, H. Pyrazole pyrazine amine compounds as kinase inhibitors, compositions thereof and methods of treatment therewith. US Pat. Appl. US2009/0270418A1, 2009.

11. Goldfarb, A. R.; Berk, B. New Compounds. Derivatives of 2,5-Diaminobenzenesulfonamide. *J. am. Chem. Soc.* 1943, 65, 738-739.
12. Elbaum, D.; Martin, M. W.; Nunes, J. J. Substituted heterocyclic compounds and methods of use. PCT Int. Appl. WO2005/042518A2, 2005.
13. Rodriguez, F.; Rozas, I.; Kaiser, M.; Brun, R.; Nguyen, B.; Wilson, W. D.; Garcia, R. N.; Dardonville, C. New Bis(2-aminoimidazoline) and Bisguanidine DNA Minor Groove Binders with Potent in Vivo Antitrypanosomal and Antiplasmodial Activity. *J. Med. Chem.* 2008,
14. Chi, Y. F.; Kao, Y. S. Pyrimidine Research: The Molecular Rearrangement of 2-Ethylmercapto-4,5-dimethyl-6-thiocyanopyrimidine. *J. Am. Chem. Soc.* 1936, 58, 769-771.
15. Dekhtyar, T.; Gomtsyan, A.; Molla, M. A.; Vasudevan, A.; Ng, T.; Shafeev, M. Diaminopyrimidines useful as inhibitors of the human respiratory syncytial virus (rsv). WO2013/123401A1, 2013.
16. Ueda, S.; Nagasawa, H. Copper-catalyzed synthesis of benzoxazoles via a regioselective C—H functionalization/C—O bond formation under an air atmosphere. *J Org Chem* 2009, 74, 4272-7.
17. Liu, Z.; Page, D.; Tremblay, M.; Walpole, C.; Yang, H. Benzimidazole derivatives, compositions containing them, preparation thereof and uses thereof i. WO2006/033631A1, 2006.
18. Sun, P.; Weinreb, S. M.; Shang, M. tert-Butylsulfonyl (Bus), a New Protecting Group for Amines. *J Org Chem* 1997, 62, 8604-8608.

What is claimed is:

1. A compound of Formula (I):

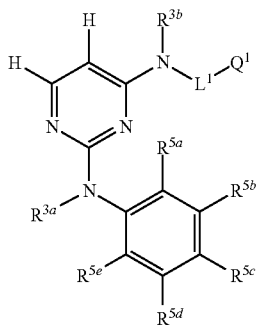

(I)

wherein
$R^{3a}$ and $R^{3b}$ are independently selected from hydrogen and substituted or unsubstituted $C_1$-$C_6$ alkyl;
$L^1$ is selected from a bond or $CH_2$
$Q^1$ is;

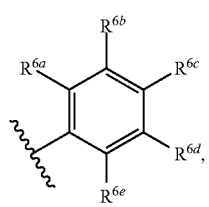

wherein
$R^{6a}$, $R^{6c}$, $R^{6d}$, $R^{6e}$ are independently selected from hydrogen, halogen, hydroxyl, amino, nitro, cyano, isocyano, carboxyl, $(CH_2)_nOR^{3d}$, $(CH_2)_nSR^{3d}$, $(CH_2)_nS(O)R^{3d}$, $(CH_2)_nSO_2R^{3d}$, $(CH_2)_nN(R^{3c})R^{3d}$, $(CH_2)_nC(O)R^{3d}$, $(CH_2)_nN(R^{3c})C(O)R^{3d}$, $(CH_2)_nOC(O)R^{3d}$, $(CH_2)_nC(O)OR^{3d}$, $(CH_2)_nC(O)N(R^{3c})R^{3d}$, $(CH_2)_nN(R^{3c})C(O)N(R^{3c})R^{3d}$, $(CH_2)_nSO_2N(R^{3c})R^{3d}$, $(CH_2)_nN(R^{3c})SO_2R^{3d}$, $(CH_2)_nN(R^{3c})P(O)(R^{3d})_2$, $(CH_2)_nP(O)(N(R^{3c}R^{3d}))_2$, and poly(ethylene oxide);
$R^{6b}$ is $NHSO_2R^{3d}$;
$R^{3d}$ is in each case independently selected from hydrogen, substituted or unsubstituted $C_1$-$C_{10}$ alkyl, substituted or unsubstituted $C_3$-$C_{10}$ cycloalkyl, substituted or unsubstituted $C_6$-$C_{12}$ aryl, and substituted or unsubstituted $C_2$-$C_{10}$ heteroaryl; or wherein any two or more of $R^{3b}$, $R^{6a}$, $R^{6b}$, $R^{6c}$, $R^{6d}$, $R^{6e}$, $R^{3c}$ and $R^{3d}$ together form one or more rings;
$R^{5a}$, $R^{5b}$, $R^{5c}$, $R^{5d}$, and $R^{5e}$ are independently selected from hydrogen, $C_1$-$C_6$ alkyl, $C_1$-$C_6$ alkoxy, $C_3$-$C_{10}$ cycloalkyl, halogen, hydroxy, carboxyl, amino, nitro, cyano, isocyano, $-L^2Q^2$; wherein said $C_1$-$C_6$ alkyl, $C_1$-$C_6$alkoxy and $C_3$-$C_{10}$ cycloalkyl groups are optionally substituted one or more times with a group selected from halogen, hydroxy, carboxyl, amino, nitro, cyano, isocyano, and combinations thereof;
or wherein any two of $R^{5a}$, $R^{5b}$, $R^{5c}$, $R^{5d}$, $R^{5e}$, and $R^{3a}$, together form a ring;
$L^2$ is selected from $(CH_2)_n$, $(CH_2)_nO$, $(CH_2)_nS$, $(CH_2)_nS(O)$, $(CH_2)_nSO_2$, $(CH_2)_nN(R^{3c})$, $(CH_2)_nC(O)$, $(CH_2)_nN(R^{3c})C(O)$, $(CH_2)_nOC(O)$, $(CH_2)_nC(O)O$, $(CH_2)_nC(O)N(R^{3c})$, $(CH_2)_nN(R^{3c})C(O)N(R^{3c})$, $(CH_2)_nSO_2N(R^{3c})$, $(CH_2)_nN(R^{3c})SO_2$, $(CH_2)_n N(R^{3c})P(O)(R^{3c})$, and $(CH_2)_n P(O)N(R^{3c})$;
$R^{3c}$ is in each case independently selected from hydrogen and substituted or unsubstituted $C_1$-$C_6$ alkyl;
$Q^2$ is selected from substituted or unsubstituted alkyl, substituted or unsubstituted aryl, substituted or unsubstituted cycloalkyl, substituted or unsubstituted heteroaryl, and substituted or unsubstituted heterocyclyl or poly(ethylene oxide); or wherein two or more substituents on $Q^2$ form a ring may together with $R^{3a}$ form a ring; and
n in each case is independently selected from 0, 1, 2, 3, 4, 5, 6, 7, 8, 9 and 10;
or a salt thereof.

2. The compound according to claim 1, wherein $R^{3a}$ and $R^{3b}$ are both hydrogen.

3. The compound according to claim 1, wherein $R^{5a}$ and $R^{5e}$ are both hydrogen.

4. The compound according to claim 1, wherein $R^{5b}$ and $R^{5d}$ are hydrogen or halogen.

5. The compound according to claim 1, wherein $R^{5c}$ is $-L^2Q^2$.

6. The compound according to claim 5, wherein $Q^2$ is substituted or unsubstituted heterocyclyl, or poly(ethylene oxide).

7. The compound according to claim 5, wherein $Q^2$ is selected from:

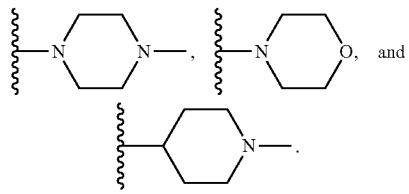

8. The compound according to claim 1, wherein $L^2$ is selected from $(CH_2)_n$, $(CH_2)_nC(O)N(R^{3c})$, $(CH_2)_nN(R^{3c})$, $(CH_2)_nC(O)$, and $(CH_2)_nN(R^{3c})C(O)$.

9. The compound according to claim 8, wherein n is in each case either 0 or 1.

10. A pharmaceutical composition comprising the composition of claim 1 and a pharmaceutically acceptable carrier.

* * * * *

UNITED STATES PATENT AND TRADEMARK OFFICE
CERTIFICATE OF CORRECTION

Page 1 of 10

PATENT NO. : 11,643,396 B2
APPLICATION NO. : 16/894010
DATED : May 9, 2023
INVENTOR(S) : Ernst Schönbrunn et al.

It is certified that error appears in the above-identified patent and that said Letters Patent is hereby corrected as shown below:

On the Title Page

Item (56) References Cited section
On page 2, Column 1, Line 40, delete "afragment-based" and insert -- a fragment-based --
On page 2, Column 2, Line 21, delete "inhibitors" and insert -- inhibitors: --

In the Specification

In Column 2, Line 23, delete "ICso" and insert -- IC$_{50}$ --
In Column 6, Line 2, delete "substitutent" and insert -- substituent --
In Column 7, Line 58, delete "–CN" and insert -- –CN. --
In Column 7, Line 59, delete "represted" and insert -- represented --

In Column 10, Lines 13-25, delete " 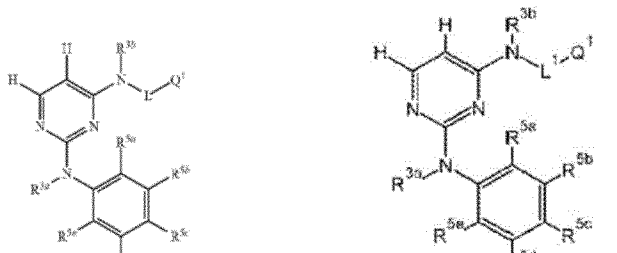 " and insert -- 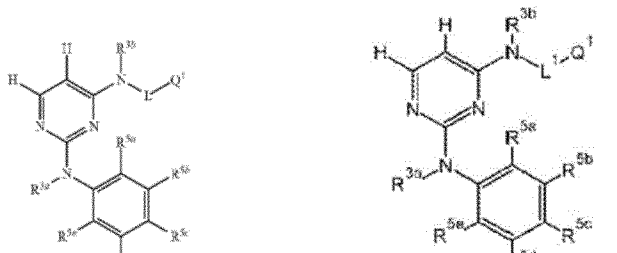 --
In Column 10, Line 53, delete "(CH$_2$)$_n$SO$_2$N(R$^3$)," and insert -- (CH$_2$)$_n$SO$_2$N(R$^{3c}$), --
In Column 11, Line 15, delete "R$^{6d,}$ R$^{6c}$" and insert -- R$^{6d}$, R$^{6e}$ --
In Column 12, Line 8, delete "–C(R6)" and insert -- –C(R$^6$) --
In Column 12, Line 15, delete "(CH$_2$)$_n$S(O) R$^{3d}$," and insert -- (CH$_2$)$_n$S(O)R$^{3d}$, --
In Column 12, Line 47, delete "(CH$_2$)nSR$^{3d}$," and insert -- (CH$_2$)$_n$SR$^{3d}$, --
In Column 14, Line 20, delete "(CH$_2$)$_n$C(O)N(R$^3$)," and insert -- (CH$_2$)$_n$C(O)N(R$^{3c}$), --
In Column 14, Line 54, delete "R$^{3c}$." and insert -- R$^{3e}$. --
In Column 14, Line 56, delete "(CR$^{3e}_2$)$_n$ C(O)," and insert -- (CR$^{3e}_2$)$_n$C(O), --
In Column 14, Line 57, delete "(CR$^{3c}_2$)$_n$N(R$^{3c}$)P(O)(R$^{3c}$)," and insert -- (CR$^{3e}_2$)$_n$N(R$^{3c}$)P(O)(R$^{3c}$), --

Signed and Sealed this
Tenth Day of September, 2024

Katherine Kelly Vidal
*Director of the United States Patent and Trademark Office*

In Column 14, Lines 57-58, delete "$((CR^{3c}_2)_nN(R^{3c})P(O)(R^{3c})$," and insert
-- $(CR^{3e}_2)_nN(R^{3c})P(O)(R^{3c)}$, --
In Column 15, Line 2, delete "$R^{3c}$" and insert -- $R^{3e}$ --
In Column 15, Line 15, delete "$R_4$" and insert -- $R^4$. --
In Column 16, Lines 33-34, delete "$(CH_2)_nN(R^{3c})P(O)(R^{1d})_2$," and insert -- $(CH_2)_nN(R^{3c})P(O)(R^{3d})_2$, --

In Column 18, Lines 43-47, delete " 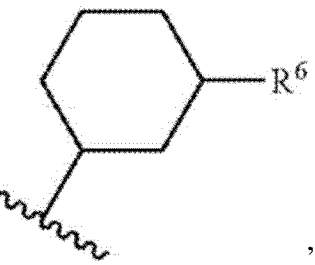 " and insert

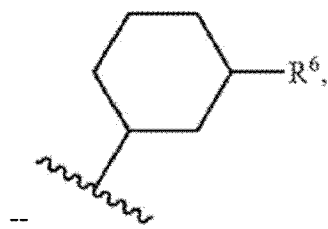

-- --

In Column 19, Line 27, delete "$(CR^{3e}_2)C(O)O$," and insert -- $(CR^{3e}_2),C(O)O$, --
In Column 19, Line 40, delete "$R^{3c}$" and insert -- $R^{3e}$ --
In Column 19, Line 41, delete "$R^{3c}$" and insert -- $R^{3e}$ --
In Column 23, Line 58, delete "$C_1$-$C_6$alkyl, $C_1$-$C_6$alkoxy," and insert -- $C_1$-$C_6$ alkyl, $C_1$-$C_6$ alkoxy, --
In Columns 27-28, approximately Line 13, under comments delete "(μM)" and insert -- μM) --
In Columns 39-40, approximately Line 6, under comments delete "KM" and insert -- μM --

In Columns 41-42, approximately Line 6, delete " 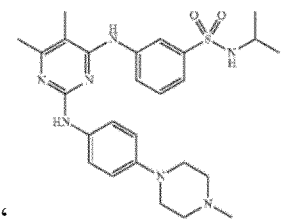 " and insert

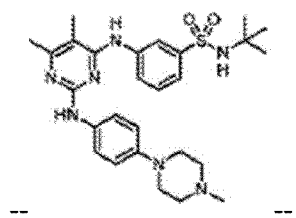

-- --

In Columns 43-44, approximately Line 22, under comments, delete "0050" and insert -- ($IC_{50}$ --
In Columns 47-48, approximately Line 15, delete "438.94" and insert -- 438.91 --
In Columns 67-68, approximately Line 14, delete "MA1-012" and insert -- MA2-012 --

In the Columns 83-84, approximately Line 10, delete " 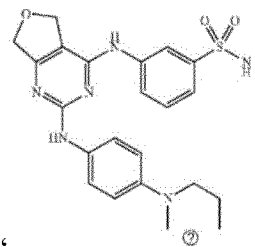 " and insert

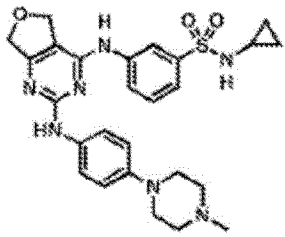 --

In Columns 111-112, approximately Line 5, delete "MM 1.S" and insert -- MM1.S --
In Columns 129-130, approximately Line 9, delete "Prccipitation" and insert -- Precipitation --
In Columns 133-134, approximately Line 4, delete "YL7-164" and insert -- YL7-170-1 --

In Columns 135-136, approximately Line 5, delete " 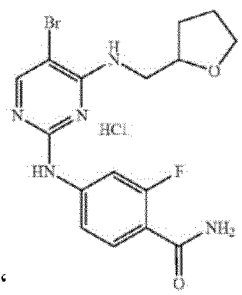 " and insert

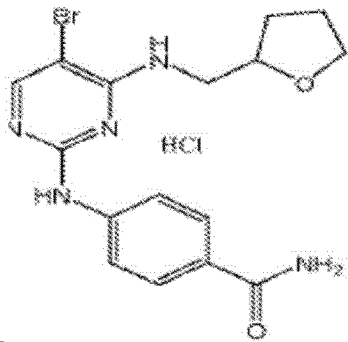 --

In Columns 137-138, approximately Line 6, delete "MH1-006-3" and insert -- MH1-066-3 --

In Columns 139-140, approximately Line 8, delete " 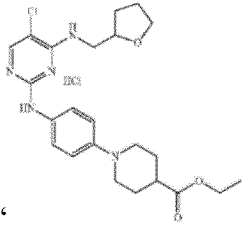 " and insert

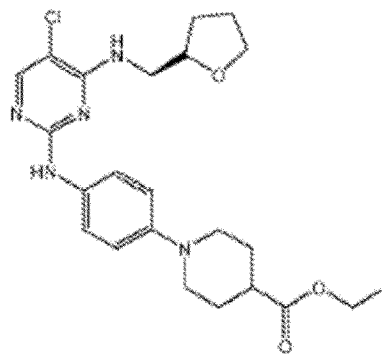
In Columns 139-140, Line 8, delete "406.4" and insert -- 496.4 --
In Columns 139-140, approximately Line 10, delete " 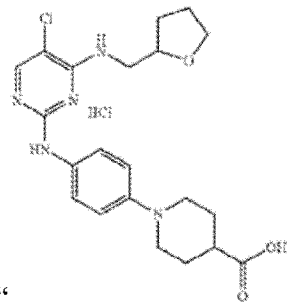 " and insert
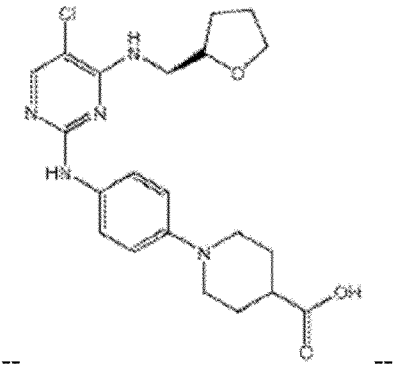
--
In Columns 141-142, approximately Line 4, delete " 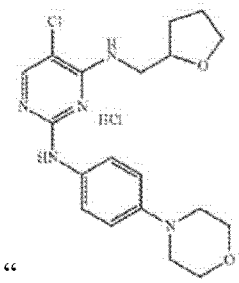 " and insert

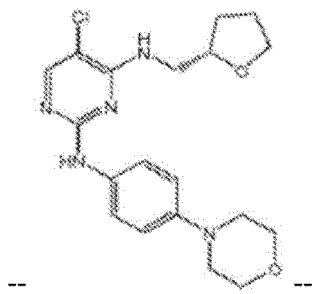

In Columns 141-142, approximately Line 6, delete " 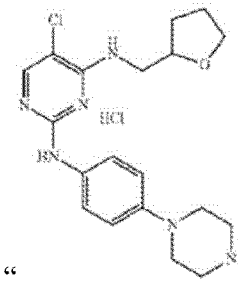 " and insert

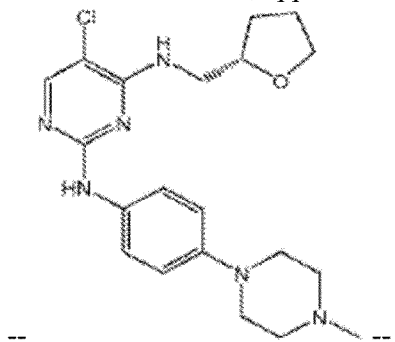

In Columns 143-144, approximately Line 15, delete "0.04" and insert -- 0.14 --
In Column 145, Line 27, delete "Karposi's" and insert -- Kaposi's --
In Column 147, Line 15, delete "cyclophosamide" and insert -- cyclophosphamide --
In Column 147, Line 24, delete "Epstein-Ban" and insert -- Epstein-Barr --
In Column 150, Lines 1-2, delete "cyclophosamide" and insert -- cyclophosphamide --
In Column 150, Line 30, delete "trastuzamab" and insert -- trastuzumab --
In Column 152, Line 20, delete "dianilinopyrimidines" and insert -- diaminopyrimidines --
In Column 153, Line 41, delete "dianilinopyrimidines" and insert -- diaminopyrimidines --
In Column 164, Line 1, delete "(100%, M$^{35}$Cl$^{35}$Cl+H)$^+$]," and insert -- [100%, (M$^{35}$Cl$^{35}$Cl+H)$^+$], --
In Column 164, Line 2, delete "M$^{35}$Cl$^{35}$Cl+2H)$^{2+}$]." and insert -- (M$^{35}$Cl$^{35}$Cl+2H)$^{2+}$]. --
In Column 164, Line 3, delete "(M$^{35}$Cl$^{35}$Cl+H)$^4$]." and insert -- (M$^{35}$Cl$^{35}$Cl+H)$^+$]. --
In Column 164, Line 29, delete "McOH," and insert -- MeOH, --
In Column 164, Line 36, delete "(M$^{35}$Cl+2H)$^2$]." and insert -- (M$^{35}$Cl+2H)$^{2+}$]. --
In Column 166, Line 39, delete "(M$^{35}$Cl+H)$^4$]." and insert -- (M$^{35}$Cl+H)$^+$]. --
In Column 169, Line 42, delete "9.0" and insert -- J=9.0 --
In Column 170, Line 21, delete "δ 70.2" and insert -- 670.2 --
In Column 171, Line 29, delete "(M+H)$^+$ 1," and insert -- (M+H)$^+$], --
In Column 174, Line 4, delete "(M+H)+]," and insert -- (M+H)$^+$], --
In Column 175, Line 15, delete "(100%, M+H)$^+$]." and insert -- [100%, (M+H)$^+$]. --
In Column 175, Line 28, delete "M+H)$^+$ 1." and insert -- M+H)$^+$]. --

CERTIFICATE OF CORRECTION (continued)
U.S. Pat. No. 11,643,396 B2

In Column 175, Line 28, delete "(M+H)+]." and insert -- (M+H)$^+$]. --
In Column 175, Line 29, delete "(M+H)+" and insert -- (M+H)$^+$ --
In Column 175, Line 65, delete "(M+1-1)$^+$]." and insert -- (M+H)$^+$]. --
In Column 178, Line 9, delete "(M+H)+496.2489," and insert -- (M+H)$^+$ 496.2489, --
In Column 180, Line 64, delete "H)$^+$ ];" and insert -- H)$^+$]; --
In Column 181, Line 61, delete "314)," and insert -- --3H), --
In Column 182, Lines 16-17, delete "[4-(4-methylpiperazin yl)" and insert -- [4-(4-methylpiperazin-1-yl) --
In Column 183, Line 30, delete "2.47-2.39" and insert -- 2.472.39 --
In Column 183, Line 32, delete "(M$^{37}$Cl+2H)$^2$]," and insert -- (M$^{37}$Cl+2H)$^{2+}$], --
In Column 183, Line 35, delete "(M$^{35}$Cl+H)$^4$]." and insert -- (M$^{35}$Cl+H)$^+$]. --
In Column 184, Lines 16-17, delete "[4-(4-methylpiperazin yl)" and insert -- [4-(4-methylpiperazin-1-yl) --
In Column 185, Line 30, delete "(WW]," and insert -- (M+H)$^+$], --
In Column 187, Line 48, delete "(M$^{37}$Cl+2H)$^{2\pm}$]," and insert -- (M$^{37}$Cl+2H)2$^+$], --
In Column 188, Line 2, delete "methylpiperazin yl)" and insert -- methylpiperazin-1-yl) --
In Column 189, Line 35, delete "(M$^{37}$Cl+2H)$^{2\pm}$]," and insert -- (M$^{37}$Cl+2H)$^{2+}$], --
In Column 190, Line 60, delete "[4-(4-methylpiperazin yl)" and insert -- [4-(4-methylpiperazin-1-yl) --
In Column 191, Line 57, delete "methylpiperazin yl)" and insert -- methylpiperazin-1-yl) --
In Column 192, Line 1, delete "(M$^{35}$Cl$^{37}$Cl+2H)$^{2\pm}$]," and insert -- (M$^{35}$Cl$^{37}$Cl+2H)$^{2+}$], --
In Column 192, Line 37, delete "C$_{241}$-129ClN$_6$O$_2$" and insert -- C$_{24}$H$_{29}$ClN$_6$O$_2$ --
In Column 192, Line 55, delete "methylpiperazin yl)" and insert -- methylpiperazin-1-yl) --
In Column 192, Line 65, delete "(s, 314)." and insert -- (s, 3H). --
In Column 194, Line 34, delete "(M+H)±546.2049," and insert -- (M+H)$^+$ 546.2049, --
In Column 196, Line 51, delete "methylpiperazin yl)" and insert -- methylpiperazin-1-yl) --
In Column 197, Line 34, delete "(M$^{35}$Cl+H)+]." and insert -- (M$^{35}$Cl+H)$^+$]. --
In Column 199, Line 39, delete "(100%, M$^{35}$Cl$^{35}$Cl+" and insert -- [100%, (M$^{35}$Cl$^{35}$Cl$^+$ --
In Column 200, Line 9, delete "C$_{241}$-129ClN$_6$O" and insert -- C$_{24}$H$_{29}$ClN$_6$O --
In Column 200, Line 43, delete "H)+]," and insert -- H)$^+$], --
In Column 202, Lines 28-29, delete "[4-(4-methylpiperazin yl)" and insert -- [4-(4-methylpiperazin-1-yl) --
In Column 202, Line 46, delete "C$_{24}$H$_{13}$N$_7$O$_2$S" and insert -- C$_{28}$H$_{31}$N$_7$O$_2$S --
In Column 204, Line 20, delete "C$_{26}$H$_{311\backslash 170}$" and insert -- C$_{26}$H$_{31}$N$_7$O --
In Column 204, Line 67, delete "C$_{26}$H$_{341\backslash 180}$" and insert -- C$_{26}$H$_{34}$N$_8$O --
In Column 205, Line 28, delete "0.1=8.3 Hz," and insert -- J=8.3 Hz, --
In Column 206, Line 24, delete "methylpiperazin yl)" and insert -- methylpiperazin-1-yl) --
In Column 207, Line 45, delete "(M+H)+]," and insert -- (M+H)$^+$], --
In Column 209, Line 20, delete "(M+H)$^{-1}$]," and insert -- (M+H)$^+$], --
In Column 209, Line 22, delete "(M+3H)$^{2+}$]." and insert -- (M-$^t$Bu+3H)$^{2+}$]. --
In Column 210, Line 31, delete "(M+2H)$^{2-1}$]." and insert -- (M+2H)$^{2+}$]. --
In Column 213, Line 3, delete "(M+H)$^+$538.2595," and insert -- (M+H)$^+$ 538.2595, --
In Column 214, Line 5, delete "(M+2H)$^{24}$]." and insert -- (M+2H)$^+$]. --
In Column 215, Line 9, delete "(M$^{37}$Cl-2H)$^{2+}$]," and insert -- (M$^{37}$Cl+2H)$^{2+}$], --
In Column 215, Line 10, delete "C$_{26}$H$_{30}$ClN$_7$O$_2$S" and insert -- C$_{25}$H$_{30}$ClN$_7$O$_2$S --

In Column 215, Line 45, delete "(M³⁷Cl+2H)²⁺]," and insert -- (M³⁷Cl+2H)²⁺], --
In Column 216, Line 2, delete "[4-(4-methylpiperazin yl)" and insert -- [4-(4-methylpiperazin-1-yl) --
In Column 217, Line 67, delete "$C_{25}H_{32}N_7O_2S$" and insert -- $C_{25}H_{32}FN_7O_2S$ --
In Column 218, Line 17, delete "-N⁴" and insert -- -N² --
In Column 219, Line 2, delete "$C_{25}H_{31}N_2O_3S$" and insert -- $C_{25}H_{31}N_7O_3S$ --
In Column 220, Line 237, delete "$C_{29}H_{39}N_7O_4S(M+H)^+$" and insert -- $C_{29}H_{39}N_7O_4S$ (M+H)⁺ --
In Column 221, Line 19, delete "-[4-O-" and insert -- -[4-(1- --
In Column 222, Line 37, delete "(M+2H)²]." and insert -- (M+2H)²⁺]. --
In Column 224, Line 12, delete "(M+H)+540.2517," and insert -- (M+H)+ 540.2517, --
In Column 226, Line 28, delete "0.1" and insert -- J --
In Column 228, Line 64, delete "-0)-" and insert -- -yl)- --
In Column 229, Line 33, delete "-0)" and insert -- -yl) --
In Column 232, Line 41, delete "H)+]," and insert -- H)⁺], --

In Column 232, Lines 45-59, delete " 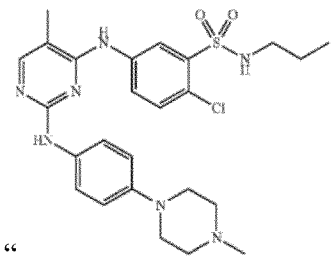 " and insert

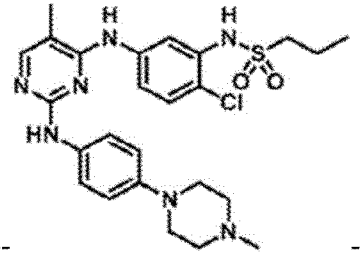 -- --

In Column 233, Line 22, delete "(M³⁷Cl+H)⁺ ]." and insert -- (M³⁷Cl+H)⁺]. --
In Column 233, Line 25, delete "(M+H)*530.2099," and insert -- (M+H)⁺ 530.2099, --
In Column 233, Lines 52-67, delete "DCM/MeOH 15% and afforded the title product as an off-white solid (20 mg, 26%). Mp: 252° C. (dec). HPLC: 98% [t$_R$=9.7 min, 40% MeOH, 60% water (with 0.1% TFA), 20 min]. ¹H NMR (400 MHz, DMSO-d₆): δ 9.44 (s, 1H, disappeared on D₂O shake), 8.63 (s, 1H, disappeared on D2O shake), 7.97 (s, 1H), 7.82-7.71 (m, 4H), 7.41 (t, J=8.6 Hz, 2H), 7.39 (d, J=8.8 Hz, 2H), 7.32 (dd, J=8.6, 2.0 Hz, 1H), 3.77-3.65 (brs, 1H), 2.85-2.73 (brs, 2H), 2.22 (s, 3H), 2.15-2.07 (brs, 2H), 2.11 (s, 3H), 1.82-1.72 (brd, J=12.5 Hz, 2H), 1.61-1.47 (m, 2H), 1.30 (s, 9H). ¹⁹F NMR (376 MHz, DMSO-d₆): 45-112.33. HPLC-MS (ESI+): m/z 604.3 [25%, (M³⁵Cl+H)⁺], 303.3 [50%, (M³⁷Cl+2H)²⁺], 302.8 [100%, (M³⁵Cl+2H)²⁺]. LC-MS (ESI+): 606.2 [40%, (M³⁷Cl+H)⁺ ]. 604.2 [100%, (M³⁵Cl+H)⁺]. HRMS (ESI+): m/z calcd for $C_{28}H_{35}ClFN_7O_3S$ (M+H)+ 604.2267, found 604.2251." and insert same as in Column 233, Line 51, as a continuation of the same paragraph.
In Column 233, Line 63, delete "45-" and insert -- δ- --
In Column 233, Line 65, delete "(M³⁷Cl+H)⁺ ]." and insert -- (M³⁷Cl+H)⁺]. --
In Column 234, Line 66, delete "0.1" and insert -- J --
In Column 235, Line 24, delete "[4-(4-methylpiperazin yl)" and insert -- [4-(4-methylpiperazin-1-yl) --
In Column 236, Line 13, delete "0.1" and insert -- J --

CERTIFICATE OF CORRECTION (continued)
U.S. Pat. No. 11,643,396 B2

In Column 236, Line 23, delete "(M+H)+582.2657," and insert -- (M+H)$^+$ 582.2657, --
In Column 236, Line 50, delete "S." and insert -- δ --
In Column 236, Line 65, delete "(M+H)±]," and insert -- (M+H)$^+$], --
In Column 237, Line 64, delete "(M+2H-SO$_2$Bu)$^{2+}$].." and insert -- (M+2H-SO$_2$$^t$Bu)$^{2+}$]. --
In Column 238, Line 26, delete "0.1" and insert -- J --
In Column 238, Line 33, delete "521.2690" and insert -- 521.2690. --
In Column 239, Line 61, delete "ft." and insert -- rt. --
In Column 240, Line 30, delete "[13-" and insert -- [3- --
In Column 240, Line 31, delete "[4-(4-methylpiperazin yl)" and insert
-- [4-(4-methylpiperazin-1-yl) --
In Column 241, Line 23, delete "δ 30.2" and insert -- 630.2 --
In Column 241, Line 45, delete "N$^4$" and insert -- N$^2$ --.
In Column 241, Line 52, delete "5-" and insert -- δ- --
In Column 242, Line 35, delete "δ 48.2" and insert -- 648.2 --
In Column 242, Line 38, delete "C$_{27}$H$_{32}$C$_{12}$FN$_7$O$_3$S" and insert -- C$_{27}$H$_{32}$Cl$_2$FN$_7$O$_3$S --
In Column 243, Line 30, delete "[4-(4-methylpiperazin yl)" and insert -- [4-(4-methylpiperazin-1-yl) --
In Column 243, Line 51, delete "(M+H)+516.1943," and insert -- (M+H)$^+$ 516.1943, --
In Column 244, Line 21, delete "(M$^{37}$Cl+H)+]," and insert -- (M$^{37}$Cl+H)$^+$], --
In Column 244, Line 22, delete "(M$^{35}$Cl+H)+]." and insert -- (M$^{35}$Cl+H)$^+$]. --
In Column 244, Line 23, delete "(M+H)+544.2276," and insert -- (M+H)$^+$ 544.2276, --
In Column 244, Line 65, delete "(M$^{37}$Cl+H)+]," and insert -- (M$^{37}$Cl+H)$^+$], --
In Column 245, Line 66, delete "5-122.65" and insert -- δ-122.65 --
In Column 246, Line 43, delete "δ 18.3" and insert -- 618.3 --
In Column 248, Line 44, delete "δ 32.3" and insert -- 632.3 --
In Column 248, Line 46, delete "(M+H)$^+$610.2970," and insert -- (M+H)$^+$ 610.2970, --
In Column 249, Lines 15-16, delete "(20%, M$^{35}$Cl$^{35}$Cl+H)$^+$]," and insert -- [20%, (M$^{35}$Cl$^{35}$Cl+H)$^+$], --
In Column 249, Line 16, delete "(M$^{35}$Cl$^{37}$Cl+2H)$^{2+}$]" and insert -- (M$^{35}$Cl$^{37}$Cl+2H)$^{2+}$]. --
In Column 249, Line 17, delete "M$^{35}$Cl$^{35}$Cl+2H)$^{2+}$]." and insert -- (M$^{35}$Cl$^{35}$Cl+2H)$^{2+}$]. --
In Column 249, Line 22, delete "(M+H)+578.1866," and insert -- (M+H)$^+$ 578.1866, --
In Column 249, Line 41, delete "-N$^{2-}$[14-" and insert -- -N$^2$-[4- --
In Column 249, Line 62, delete "($^{35}$Cl-H)$^-$]." and insert -- (M$^{35}$Cl-H)$^-$]. --
In Column 250, Line 19, delete "white white" and insert -- white --
In Column 250, Line 34, delete "(M+H)$^+$546.2457," and insert -- (M+H)$^+$ 546.2457, --
In Column 250, Line 52, delete "[13-" and insert -- [3- --
In Column 251, Line 38, delete "(M$^{35}$Cl+H)+]." and insert -- (M$^{35}$Cl+H)$^+$]. --
In Column 252, Line 5, delete "(M$^{37}$Cl+H)+]," and insert -- (M$^{37}$Cl+H)$^+$], --
In Column 252, Line 8, delete "δ 14.2" and insert -- 614.2 --
In Column 252, Line 43, delete "(M$^{37}$Cl+2H)$^{24}$]," and insert -- (M$^{37}$Cl+2H)$^{2+}$], --
In Column 253, Line 17, delete "(M$^{37}$Cl+2H)$^{2±}$]," and insert -- (M$^{37}$Cl+2H)$^{2+}$] --
In Column 253, Line 19, delete "(M$^{35}$Cl-H)$^-$]," and insert -- (M$^{37}$Cl-H)$^-$], --
In Column 253, Line 20, delete "δ 24.2" and insert -- 624.2 --
In Column 253, Line 23, delete "(M+H)+602.2111," and insert -- (M+H)$^+$ 602.2111, --
In Column 254, Line 66, delete "+H)+], 284.1" and insert -- +H)$^+$], 284.1 --
In Column 255, Line 67, delete "311;" and insert -- 3H; --
In Column 256, Line 4, delete "(M$^{35}$Cl$^{35}$Cl+H)+]." and insert -- (M$^{35}$Cl$^{35}$Cl+H)$^+$]. --

### CERTIFICATE OF CORRECTION (continued)
U.S. Pat. No. 11,643,396 B2

In Column 256, Line 28, delete "$(M^{35}Cl+H)^{4}]$." and insert -- $(M^{35}Cl+H)^{+}]$. --
In Column 257, Line 13, delete "$(M^{37}Cl+H)+]$." and insert -- $(M^{37}Cl+H)^{+}]$. --
In Column 258, Line 22, delete "$(M^{35}Cl^{37}Cl+H)\pm]$," and insert -- $(M^{35}Cl^{37}Cl+H)^{+}]$, --
In Column 258, Line 45, delete "1H)," and insert -- 3H), --
In Column 258, Line 46, delete "$(M^{37}Cl+H)+]$," and insert -- $(M^{37}Cl+H)^{+}]$, --
In Column 259, Line 35, delete "$(M^{37}Cl+H)\pm]$," and insert -- $(M^{37}Cl+H)^{+}]$, --
In Column 260, Line 19, delete "CDCl3):" and insert -- $CDCl_3$): --
In Column 260, Line 23, delete "$(M^{35}Cl^{35}Cl^{35}Cl+H)+]$." and insert -- $(M^{35}Cl^{35}Cl^{35}Cl+H)^{+}]$. --
In Column 260, Line 46, delete "$(MCl^{35}Cl^{37}Cl^{37}+H)\pm]$," and insert -- $(M^{35}Cl^{35}Cl^{35}Cl+H)^{+}]$, --
In Column 262, Line 39, delete "$(2M^{35}Cl+H)+]$," and insert -- $(2M^{35}Cl+H)^{+}]$, --
In Column 265, Line 64, delete "0.1=8.3" and insert -- J=8.3 --
In Column 272, Line 14, delete "$(M^{35}Cl+H)+$," and insert -- $(M^{35}Cl+H)^{+}$, --
In Column 272, Line 15, delete "$C_{13}H_{13}Cl_2N30$" and insert -- $C_{13}H_{13}Cl_2N_3O$ --
In Column 272, Line 41, delete "$(M^{35}Cl+H)^{+}$ ," and insert -- $(M^{35}Cl+H)^{+}$, --
In Column 272, Line 60, delete "stiffing" and insert -- stirring --
In Column 273, Line 5, delete "$(MCl^{35}Cl^{35}+H)^{+}$ ," and insert -- $(MCl^{35}Cl^{35}+H)^{+}$, --
In Column 273, Line 6, delete "$(MCl^{35}Cl^{37}+H)^{+}$ ," and insert -- $(MCl^{35}Cl^{37}+H)^{+}$, --
In Column 273, Line 36, delete "$(MCl^{35}Cl^{35}+H)^{+}$ ," and insert -- $(MCl^{35}Cl^{35}+H)^{+}$, --
In Column 273, Line 37, delete "$(MCl^{35}Cl^{37}+H)^{+}$ ," and insert -- $(MCl^{35}Cl^{37}+H)^{+}$, --
In Column 273, Line 63, delete "$(MCl^{35}Cl^{35}+H)^{+}$ ," and insert -- $(MCl^{35}Cl^{35}+H)^{+}$, --
In Column 273, Line 64, delete "$(MCl^{35}Cl^{37}+H)^{+}$ ," and insert -- $(MCl^{35}Cl^{37}+H)^{+}$, --
In Column 274, Line 23, delete "$(M^{35}Cl+H)^{+}$ ," and insert -- $(M^{35}Cl+H)^{+}$, --
In Column 274, Line 45, delete "RJI-" and insert -- RJ1- --
In Column 275, Line 10, delete "$(M^{35}Cl+H)^{+}$ ," and insert -- $(M^{35}Cl+H)^{+}$, --
In Column 275, Line 38, delete "31-1)." and insert -- 3H). --
In Column 275, Line 38, delete "$(MCl^{35}Cl^{35}+H)^{+}$ ," and insert -- $(MCl^{35}Cl^{35}+H)^{+}$, --
In Column 275, Line 39, delete "$(MCl^{35}Cl^{37}+H)^{+}$ ," and insert -- $(MCl^{35}Cl^{37}+H)^{+}$, --
In Column 276, Line 46, delete "314)," and insert -- 3H), --

In Column 278, Lines 48-57, delete " 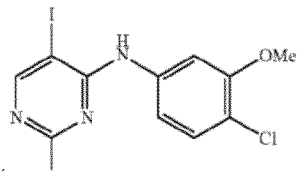 " and insert

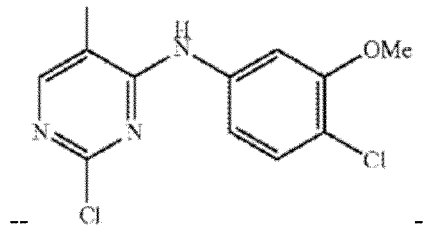

-- --

In Column 278, Line 67, delete "$(M^{35}Cl^{35}Cl+H)+]$." and insert -- $(M^{35}Cl^{35}Cl+H)^{+}]$. --
In Column 279, Line 40, delete "As" and insert -- $N^4$ --
In Column 285, Line 16, delete "[14" and insert -- -[4- --
In Column 297, Line 1, delete "$M^{79}Br^{37}Cl^{37}C_1)^{+}]$," and insert -- $M^{79}Br^{37}Cl^{37}Cl)^{+}]$, --
In Column 297, Line 2, delete "$M^{81}Br^{35}Cl^{35}C_1)^{+}]$," and insert -- $M^{81}Br^{35}Cl^{35}Cl)^{+}]$, --
In Column 298, Line 37, delete "$(M^{37}Cl^{35}Cl-H)^{+}]$," and insert -- $(M^{37}Cl^{35}Cl-H)^{-}]$, --

CERTIFICATE OF CORRECTION (continued)
U.S. Pat. No. 11,643,396 B2

In Column 298, Line 38, delete "H)$^+$]." and insert -- H)$^-$]. --
In Column 299, Line 47, delete "(M+Na)+]," and insert -- (M+Na)$^+$], --
In Column 301, Line 41, delete "S:" and insert -- δ: --
In Column 303, Line 27, delete "(M$^{37}$C$_1$-tBu+H)$^{2+}$]," and insert -- (M$^{37}$Cl-tBu+H)$^{2+}$], --
In Column 305, Line 31, delete "(M$^{35}$Cl+Na) ]." and insert -- (M$^{35}$Cl+Na)$^+$]. --
In Column 305, Line 32, delete "(m$^{35}$Cl H) ]." and insert -- (M$^{35}$Cl H) ]. --
In Column 307, Line 40, delete "(M$^{37}$C$_1$-tBu+" and insert -- (M$^{37}$Cl-tBu+ --
In Column 307, Line 41, delete "(M$^{35}$C$_1$-tBu+H)$^{2+}$]." and insert -- (M$^{35}$Cl-tBu+H)$^{2+}$]. --
In Column 307, Line 60, delete "(Na2SO$_4$)" and insert -- (Na$_2$SO$_4$) --
In Column 308, Line 39, delete "mml)" and insert -- mmol) --
In Column 308, Lines 53-54, delete "(2 M+H)$^+$]," and insert -- (2M+H)$^+$], --
In Column 311, Line 63, delete "67 :" and insert -- δ: --
In Column 313, Line 6, delete "114)," and insert -- 1H), --
In Column 315, Line 3, delete "(M$^{35}$Cl+H)$^+$]." and insert the same on Column 315, Line 2, as a continuation of the same paragraph.
In Column 315, Line 57, delete "(Cert-" and insert -- (tert- --
In Column 315, Line 63, delete "114," and insert -- 1H, --
In Column 316, Line 34, delete "114," and insert -- 1H, --
In Column 317, Line 57, delete "(MCl$^{35}$Cl$^{35}$+H)$^+$ ," and insert -- (MCl$^{35}$Cl$^{35}$+H)$^+$, --
In Column 317, Line 58, delete "(MCl$^{35}$Cl$^{37}$+H)$^+$ ," and insert -- (MCl$^{35}$Cl$^{37}$+H)$^+$, --
In Column 321, Line 21, delete "(2M+H)+]," and insert -- (2M+H)$^+$], --
In Column 322, Line 32, delete "(M+H)$^4$]." and insert -- (M+H)$^+$]. --
In Column 326, Line 15, delete "114)," and insert -- 1H), --
In Column 327, Line 46, delete "(M$^{37}$Cl-H)$^+$]," and insert -- (M$^{37}$Cl-H)$^-$], --
In Column 327, Line 46, delete "(M$^{35}$Cl-H)$^+$]." and insert -- (M$^{35}$Cl-H)$^-$]. --
In Column 329, Line 11, delete "2008," and insert -- 2008, 51, 909-923. --

In the Claims

In Column 330, Line 20, Claim 1, delete "C$_1$-C$_6$alkoxy" and insert -- C$_1$-C$_6$ alkoxy --
In Column 330, Line 27, Claim 1, delete "(CH$_2$)$_n$ C(O)," and insert -- (CH$_2$)$_n$C(O), --
In Column 330, Line 30, Claim 1, delete "(CH$_2$)$_n$ N(R$^{3c}$)P(O)(R$^{3c}$)," and insert -- (CH$_2$)$_n$N(R$^{3c}$)P(O)(R$^{3c}$), --
In Column 330, Line 31, Claim 1, delete "(CH$_2$)$_n$ P(O)N(R$^{3c}$);" and insert -- (CH$_2$)$_n$P(O)N(R$^{3c}$); --